(12) United States Patent
Davies et al.

(10) Patent No.: US 12,286,401 B2
(45) Date of Patent: Apr. 29, 2025

(54) SMALL MOLECULES THAT SENSITIZE HIV-1 INFECTED CELLS TO ANTIBODY DEPENDENT CELLULAR CYTOTOXICITY

(71) Applicants: THE TRUSTEES OF THE UNIVERSITY OF PENNSYLVANIA, Philadelphia, PA (US); VAL-CHUM, LIMITED PARTNERSHIP, Quebec (CA)

(72) Inventors: Melissa Carey Davies, Arlington, MA (US); Amos B. Smith, III, Merion, PA (US); Andres Finzi, Quebec (CA); Shilei Ding, Quebec (CA); Jean-Philippe Chapleau, Quebec (CA)

(73) Assignees: THE TRUSTEES OF THE UNIVERSITY OF PENNSYLVANIA, Philadelphia, PA (US); VAL-CHUM, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 17/263,590

(22) PCT Filed: Jul. 31, 2019

(86) PCT No.: PCT/US2019/044320
§ 371 (c)(1),
(2) Date: Jan. 27, 2021

(87) PCT Pub. No.: WO2020/028482
PCT Pub. Date: Feb. 6, 2020

(65) Prior Publication Data
US 2022/0363639 A1  Nov. 17, 2022

Related U.S. Application Data

(60) Provisional application No. 62/712,283, filed on Jul. 31, 2018.

(51) Int. Cl.
*C07D 211/96* (2006.01)
*A61P 31/18* (2006.01)
(Continued)

(52) U.S. Cl.
CPC ............ *C07D 211/96* (2013.01); *A61P 31/18* (2018.01); *C07D 207/48* (2013.01);
(Continued)

(58) Field of Classification Search
None
See application file for complete search history.

(56) References Cited

U.S. PATENT DOCUMENTS 6,380,243 B1  4/2002  Bloom et al.
6,562,978 B1  5/2003  Mamura et al.
(Continued)

FOREIGN PATENT DOCUMENTS

CN  104945470 A  9/2015
JP  2004-002367 A  1/2004
(Continued)

OTHER PUBLICATIONS

Gunthard et al (JAMA 316:191-210, 2016) (Year: 2016).*
(Continued)

*Primary Examiner* — Craig D Ricci
(74) *Attorney, Agent, or Firm* — BakerHostetler

(57) ABSTRACT

Compounds and methods of treating HIV-1 in a human infected with HIV-1 or preventing HIV-1 infection in a human susceptible to infection with HIV-1 are provided. The compounds are of formula (I), (II), and (IA), wherein $R^1$-$R^7$, X, X', Y, Y', Z, and n are defined herein, and the methods comprises administering therapeutically effective amounts of these compounds to the human.

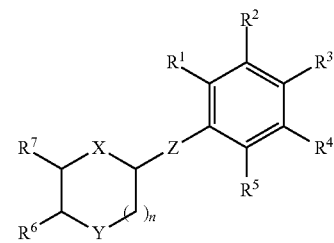

I

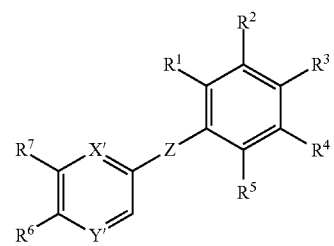

II

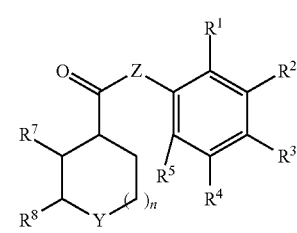

IA

14 Claims, 22 Drawing Sheets

(51) Int. Cl.

| | |
|---|---|
| C07D 207/48 | (2006.01) |
| C07D 211/56 | (2006.01) |
| C07D 211/60 | (2006.01) |
| C07D 215/54 | (2006.01) |
| C07D 241/04 | (2006.01) |
| C07D 265/30 | (2006.01) |
| C07D 309/08 | (2006.01) |
| C07D 401/12 | (2006.01) |
| C07D 403/12 | (2006.01) |
| C07D 413/12 | (2006.01) |

(52) U.S. Cl.
CPC .......... *C07D 211/56* (2013.01); *C07D 211/60* (2013.01); *C07D 215/54* (2013.01); *C07D 241/04* (2013.01); *C07D 265/30* (2013.01); *C07D 309/08* (2013.01); *C07D 401/12* (2013.01); *C07D 403/12* (2013.01); *C07D 413/12* (2013.01)

(56) References Cited

U.S. PATENT DOCUMENTS

| | | | |
|---|---|---|---|
| 8,703,938 | B2 | 4/2014 | Or et al. |
| 2010/0137585 | A1 | 6/2010 | Hayakawa et al. |
| 2010/0261714 | A1 | 10/2010 | Sturino et al. |
| 2011/0257182 | A1 | 10/2011 | Bolea |
| 2012/0010181 | A1 | 1/2012 | Kozlowski et al. |
| 2015/0238489 | A1* | 8/2015 | Huberman ......... A61K 31/4545 514/254.02 |
| 2016/0271137 | A1* | 9/2016 | Koyuncu ............. A61K 31/439 |

FOREIGN PATENT DOCUMENTS

| | | | |
|---|---|---|---|
| WO | 00/12478 | A1 | 3/2000 |
| WO | 02/30891 | A1 | 4/2002 |
| WO | 2005/044797 | A1 | 5/2005 |
| WO | 2011/075747 | A1 | 6/2011 |
| WO | 2015/014960 | A1 | 2/2015 |
| WO | 2016/073847 | A2 | 5/2016 |

OTHER PUBLICATIONS

Bardy et al ("Developing antiviral drugs is not easy—here's why" in The Conversation, Apr. 28, 2021—available online at https://theconversation.com/developing-antiviral-drugs-is-not-easy-heres-why-159512) (Year: 2021).*
Anderson (Chem and Biol 10:787-797, 2003) (Year: 2003).*
Thiel (Nature Biotechnol 2:513-519, 2004) (Year: 2004).*
Grenier et al (ACS Med Chem Lett 11:371-387, 2020) (Year: 2020).*
Adams et al., PHENIX: building new software for automated crystallographic structure determination, Acta. Crystallogr D. Biol. Crystallogr., 2002, 58:1948-1954.
Alkhatib et al., CC CKR5: a RANTES, MIP-1alpha, MIP-1beta receptor as a fusion cofactor for macrophage-tropic HIV-1, Science, 1996, 272:1955-1958.
Allan et al., Major glycoprotein antigens that induce antibodies in AIDS patients are encoded by HTLV-III. Science, 1985, 228:1091-1094.
Alsahafi et al., An Asymmetric Opening of HIV-1 Envelope Mediates Antibody-Dependent Cellular Cytotoxicity. Cell Host Microbe, 2019, 25:578-587 e575.
Alsahafi et al., Effects of the I559P gp41 change on the conformation and function of the human immunodeficiency virus (HIV-1) membrane envelope glycoprotein trimer, PLoS One 10:e0122111, 2015.
Bar et al., Early low-titer neutralizing antibodies impede HIV-1 replication and select for virus escape, PLoS Pathog, 2012, 8:e1002721.

Bell et al., Optimization of novel nipecotic bis(amide) inhibitors of the Rho/MKL 1/SRF transcriptional pathway as potential anti-metastasis agents, Bioorganic & Medicinal Chemistry Letters, 23 (2013) 3826-3832.
Candia et al., Investigation of Platelet Aggregation Inhibitory Activity by Phenyl Amides and Esters of Piperidinecarboxylic Acids, Bioorganic & Medicinal Chemistry, 11 (2003) 1439-1450.
Chemical Abstract Registry Nos. 1791051-57-4, 1790771-23-1, 1791052-66-8, 1791051-52-9, 1789173-55-2, 1791051-44-9, 1791131-30-0, 1795556-01-2, 1090386-40-5, 1389461-12-4, 1581221-42-2, 1581483-50-2, 1595133-31-5, 1595397-17-3, 1787483-83-3, 1787548-92-8, 1791048-57-1, 1789173-47-2, 1789173-81-4, 1790760-39-2, 1790761-22-6, 1790771-29-7, or 1790771-34-4.
Chemical Abstract Registry Nos. 831177-09 4, 915881-32-2, 915889-70-2, 915918-84-2, 1351359-53-9, 1351455-26-9, 1351484-78-0, 1606847-65-7, 1607131-14-5, 915876-85-6, 915914-88-4, 942672-79-9, 942798-66-5, 1197742-12-3, 1484469-72-8, 831236-73-8, 838900-74-6, 847239-99-0, 915873-26-6, 915883-71-5, 915885-78-8, 915900-34-4, 915913-43-8, 947996-20-5, 1000961-30-7, 1030163-64-4, 1030179-32-8, 1030199-26-8, 1583092-54-9 1583392-22-6, 1705934-47-9, 1830593-75-3, 1830593-76-4, and 2184429-45-4.
Chemical Abstract Registry Nos. 832141-35-2, 832141-09-0, 832141-79 4, 947996-40-9, 2184260-45-3, 2184936-47-6, 942672-88-0, 1110954-77-2, 838900-74-6, 847239-99-0, 915871-48-6, 915873-26-6, 915913-43-8, 942755-21-7, 1704631-38-8, 664311-64-2, 948005-90-1, 1091807-00-9, 2135017-95-5, 832137-97-0, 832141-34-1, 832141-37-4, 832141-49-8, 876895-18-0, 876895-24-8, 942672-82-4, 942731-53-5, 1000949-40-5, 1091911-15-7, 1092317-37-7, 1252391-54-0, 1601318-18-6, 1601568-27-7, and 2180573-60-6.
Chemical Abstract Registry Nos. 915873-26-6, 847239-99-0, 915900-34-4, 942889-91-0, 1000961-30-7, 915913-43-8. 832141-09-0, 832141-35-2, 876895-13-5, 892692-13-6, 915881-66-2, 942889-95-4, 948005-82-1, 1428373-32-3, 693233-91-9, 831177-09-4, 832141-37-4, 838900-74-6, 915871-48-6, 915881-32-2, 915883-71-5, 915894-19-8, 942672-88-0, 942858-46-0, 1000949-40-5, 1030199-26-8, 1092317-37-7, 1110954-77-2, and 1351359-53-9.
Chen et al., Structure-Based Design of 3-Carboxy-Substituted 1,2,3,4-Tetrahydroquinolines as Inhibitors of Myeloid Cell Leukemia-1 (Mcl-1), Org. Biomol. Chem., 2016, 14 (24), 5505-5510.
Choe et al., The beta-chemokine receptors CCR3 and CCR5 facilitate infection by primary HIV-1 isolates, Cell, 1996, 85:1135-1148.
Collaborative Computational Project N., The CCP4 suite: programs for protein crystallography, Acta. Crystallogr D. Biol. Crystallogr., 1994, 50:760-763.
Courter et al., Structure-based design, synthesis and validation of CD4-mimetic small molecule inhibitors of HIV-1 entry: conversion of a viral entry agonist to an antagonist, Acc. Chem. Res., 2014, 47:1228-1237.
Davis et al., MOLPROBITY: structure validation and all-atom contact analysis for nucleic acids and their complexes, Nucleic Acids Res., 2004, 32:W615-619.
Decker et al., Antigenic conservation and immunogenicity of the HIV coreceptor binding site, J. Exp. Med., 2005, 201:1407-1419.
Deng et al., Identification of a major co-receptor for primary isolates of HIV-1, Nature, 1996, 381:661-666.
Desormeaux et al., The highly conserved layer-3 component of the HIV-1 gp120 inner domain is critical for CD4-required conformational transitions, J. Virol., 2013, 87:2549-2562.
Ding et al., A Highly Conserved gp120 Inner Domain Residue Modulates Env Conformation and Trimer Stability, J. Virol., 2016, 90(19):8395-409.
Ding et al., A Highly Conserved Residue of the HIV-1 gp120 Inner Domain Is Important for Antibody-Dependent Cellular Cytotoxicity Responses Mediated by Anti-cluster A Antibodies, J. Virol., 2016, 90:2127-2134.
Ding et al., Small Molecule CD4-Mimetics Sensitize HIV-1-infected Cells to ADCC by Antibodies Elicited by Multiple Envelope Glycoprotein Immunogens in Non-Human Primates. AIDS Res Hum Retroviruses, 2016, 33(5):428-431.
Doranz et al., A dual-tropic primary HIV-1 isolate that uses fusin and the beta-chemokine receptors CKR-5, CKR-3, and CKR-2b as fusion cofactors, Cell, 1996, 85:1149-1158.

(56) References Cited

OTHER PUBLICATIONS

Dragic et al., HIV-1 entry into CD4+ cells is mediated by the chemokine receptor CC-CKR-5, Nature, 1996, 381:667-673.
Emsley et al., Coot: model-building tools for molecular graphics, Acta. Crystallogr D. Biol. Crystallogr., 2004, 60:2126-2132.
Feng et al., HIV-1 entry cofactor: functional cDNA cloning of a seven-transmembrane, G protein-coupled receptor, Science, 1996, 272:872-877.
Fenton-May et al., Relative resistance of HIV-1 founder viruses to control by interferon-alpha, Retrovirology, 2013, 10:146.
Finzi et al., Topological layers in the HIV-1 gp120 inner domain regulate gp41 interaction and CD4-triggered conformational transitions, Mol. Cell., 2010, 37:656-667.
Fontaine et al., High expression levels of B lymphocyte stimulator (BLyS) by dendritic cells correlate with HIV-related B-cell disease progression in humans, Blood., 2011, 117:145-155.
Fontaine et al., HIV infection affects blood myeloid dendritic cells after successful therapy and despite nonprogressing clinical disease, J. Infect. Dis., 2009, 199:1007-1018.
Furuta et al., Capture of an early fusion-active conformation of HIV-1 gp41, Nat. Struct. Biol., 1998, 5:276-279.
Haim et al., Contribution of Intrinsic Reactivity of the HIV-1 Envelope Glycoproteins to CD4-Independent Infection and Global Inhibitor Sensitivity, PLoS Pathog., 2011, 7:e1002101.
Haim et al., Soluble CD4 and CD4-mimetic compounds inhibit HIV-1 infection by induction of a short-lived activated state, PLoS Pathog., 2009, 5:e1000360.
He et al., Peptides trap the human immunodeficiency virus type 1 envelope glycoprotein fusion intermediate at two sites, J. Virol., 2003, 77:1666-1671.
Hutchings et al., Pharmacokinetic optimitzation of CCG-203971: Novel inhibitors of the Rho/MRTF/SRF transcriptional pathway as potential antifibrotic therapeutics for systemic scleroderma, Bioorganic & Medicinal Chemistry Letters, 27 (2017) 1744-1749.
Imaeda et al., Discovery of TAK-272: A Novel, Potent, and Orally Active Renin Inhibitor. ACS Med. Chem. Lett., 2016, 7 (10), 933-938.
Kamya et al., Receptor-ligand requirements for increased NK cell polyfunctional potential in slow progressors infected with HIV-1 coexpressing KIR3DL1*h/*y and HLA-B*57, J. Virol., 2011, 85:5949-5960.
Kassa et al., Identification of a Human Immunodeficiency Virus (HIV-1) Envelope Glycoprotein Variant Resistant to Cold Inactivation, 2009, J. Virol., 83(9):4476-88.
Koshiba et al., The prefusogenic intermediate of HIV-1 gp41 contains exposed C-peptide regions, J. Biol. Chem., 2003, 278:7573-7579.
Kwong et al., HIV-1 evades antibody-mediated neutralization through conformational masking of receptor-binding sites, Nature, 2002, 420:678-682.
Kwong et al., Structure of an HIV gp120 envelope glycoprotein in complex with the CD4 receptor and a neutralizing human antibody, Nature, 1998, 393:648-659.
Lack et al., Targeting the Binding Function 3 (BF3) Site of the Human Androgen Receptor through Virtual Screening, J. Med. Chem. 2011, 54, 8563-8573.
Li et al., Discovery of novel xanthine compounds targeting DPP-IV and GPR119 as anti-diabetic agents, European Journal of Medicinal Chemistry 124 (2016) 103e116.
Madani et al., A CD4-mimetic compound enhances vaccine efficacy against stringent immunodeficiency virus challenge, Nat. Commun., 2018, 9:2363.
Madani et al., Activation and Inactivation of Primary Human Immunodeficiency Virus Envelope Glycoprotein Trimers by CD4-Mimetic Compounds, J. Virol., 2017, 91(3):e01880.
Madani et al., Antibodies Elicited by Multiple Envelope Glycoprotein Immunogens in Primates Neutralize Primary Human Immunodeficiency Viruses (HIV-1) Sensitized by CD4-Mimetic Compounds, J. Virol., 2016, 90:5031-5046.
Madani et al., CD4-mimetic small molecules sensitize human immunodeficiency virus to vaccine-elicited antibodies, J. Virol., 2014, 88:6542-6555.
Marcoa et al., Lipophilicity-related inhibition of blood platelet aggregation by nipecotic acid anilides, European Journal of Pharmaceutical Sciences, 22 (2004) 153-164.
Karplus et al., "Linking crystallographic model and data quality", Science, 2012, 336, 1030-1033.
Weiss, "Global Indicators of X-ray data quality", J. Appl. Cryst., 2001, 34, 130-135.
Melillo et al., Small-Molecule CD4-Mimics: Structure-Based Optimization of HIV-1 Entry Inhibition, ACS Med. Chem. Lett., 2016, 7:330-334.
Moody et al., Strain-Specific V3 and CD4 Binding Site Autologous HIV-1 Neutralizing Antibodies Select Neutralization-Resistant Viruses, Cell Host Microbe., 2015, 18:354-362.
Moore et al., Immunological evidence for interactions between the first, second, and fifth conserved domains of the gp120 surface glycoprotein of human immunodeficiency virus type 1, J. Virol., 1994, 68:6836-6847.
Moore et al., Nature of nonfunctional envelope proteins on the surface of human immunodeficiency virus type 1, J. Virol., 2006, 80:2515-2528.
Ochsenbauer et al., Generation of Transmitted/Founder HIV-1 Infectious Molecular Clones and Characterization of Their Replication Capacity in CD4 T Lymphocytes and Monocyte-Derived Macrophages, J. Virol., 2012, 86:2715-2728.
Otwinowski et al., Processing of X-ray diffraction data collected in oscillation mode, Methods Enzymol., 1997, 276:307-326.
Pacheco et al., Residues in the gp41 Ectodomain Regulate HIV-1 Envelope Glycoprotein Conformational Transitions Induced by gp120-Directed Inhibitors, J. Virol., 2017, 91(5):e02219-16.
Parrish et al., Phenotypic properties of transmitted founder HIV-1, Proc. Natl. Acad. Sci. U S A., 2013, 110:6626-6633.
Peretz et al., Functional T cell subsets contribute differentially to HIV peptide-specific responses within infected individuals: correlation of these functional T cell subsets with markers of disease progression, Clin. Immunol., 2007, 124:57-68.
Pereyra et al., The major genetic determinants of HIV-1 control affect HLA class I peptide presentation, Science, 2010, 330:1551-1557.
Prevost et al. Influence of the Envelope gp120 Phe 43 Cavity on HIV-1 Sensitivity to Antibody-Dependent Cell-Mediated Cytotoxicity Responses, J. Virol., vol. 91, No. 7, 2017, e02452.
Rho et al., Characterization of the reverse transcriptase from a new retrovirus (HTLV) produced by a human cutaneous T-cell lymphoma cell line, Virology, 1981, 112:355-360.
Richard et al., BST-2 Expression Modulates Small CD4-Mimetic Sensitization of HIV-1-Infected Cells to Antibody-Dependent Cellular Cytotoxicity, J. Virol., 91, 2017.
Richard et al., CD4 mimetics sensitize HIV-1-infected cells to ADCC, Proc. Natl. Acad. Sci. U. S. A., vol. 112, No. 20, 2015, pp. E2687-E2694 2015.
Richard et al., Co-receptor Binding Site Antibodies Enable CD4-Mimetics to Expose Conserved Anti-cluster A ADCC Epitopes on HIV-1 Envelope Glycoproteins. EBioMedicine 2016, 12:208-218.
Richard et al., Flow cytometry-based assay to study HIV-1 gp120 specific antibody-dependent cellular cytotoxicity responses. J Virol Methods, 2014, 208:107-114.
Richard et al., Small CD4 Mimetics Prevent HIV-1 Uninfected Bystander CD4 + T Cell Killing Mediated by Antibody-dependent Cell-mediated Cytotoxicity. EBioMedicine, 2016, 3:122-134.
Richard et al., Uninfected Bystander Cells Impact the Measurement of HIV-Specific Antibody-Dependent Cellular Cytotoxicity Responses, Mbio., 9, 2018.
Rizzuto et al., A conserved HIV gp120 glycoprotein structure involved in chemokine receptor binding, Science, 1998, 280:1949-1953.
Robey et al., Characterization of envelope and core structural gene products of HTLV-III with sera from AIDS patients, Science, 1985, 228:593-595.

(56) References Cited

OTHER PUBLICATIONS

Robinson et al., Distinct antigenic sites on HIV gp120 identified by a panel of human monoclonal antibodies, Journal of Cellular Biochemistry Supplement, 1992, 16E:Q449.
Tokuhara et al., Discovery of Benzimidazole Derivatives as Orally Active Renin Inhibitors: Optimization of 3,5-Disubstituted Piperidine to Improve Pharmacokinetic Profile, Bioorg. Med. Chem. 2018, 26 (12), 3261-3286.
Trkola et al., CD4-dependent, antibody-sensitive interactions between HIV-1 and its co-receptor CCR-5, Nature, 1996, 384:184-187.
Veillette et al., Conformational evaluation of HIV-1 trimeric envelope glycoproteins using a cell-based ELISA assay, J. Vis. Exp., 2014, 14;(91):51995.
Veillette et al., Interaction with cellular CD4 exposes HIV-1 envelope epitopes targeted by antibody-dependent cell-mediated cytotoxicity, J. Virol., 2014, 88:2633-2644.
Veillette et al., The HIV-1 gp120 CD4-Bound Conformation Is Preferentially Targeted by Antibody-Dependent Cellular Cytotoxicity-Mediating Antibodies in Sera from HIV-1-Infected Individuals, J. Virol., 2015, 89:545-551.
Wu et al., CD4-induced interaction of primary HIV-1 gp120 glycoproteins with the chemokine receptor CCR-5, Nature, 1996, 384:179-183.
Wyatt et al., Involvement of the V1/V2 variable loop structure in the exposure of human immunodeficiency virus type 1 gp120 epitopes induced by receptor binding, J. Virol., 1995, 69:5723-5733.
Wyatt et al., The antigenic structure of the HIV gp120 envelope glycoprotein, Nature, 1998, 393:705-711.
Wyatt et al., The HIV-1 envelope glycoproteins: fusogens, antigens, and immunogens, Science, 1998, 280:1884-1888.
Zhao et al., Identification of N-phenyl-N'-(2,2,6,6-tetramethyl-piperidin-4-yl)-oxalamides as a new class of HIV-1 entry inhibitors that prevent gp120 binding to CD4, Virology, 2005, 339:213-225.
Zoubchenok et al., Histidine 375 Modulates CD4 Binding in HIV-1 CRF01_AE Envelope Glycoproteins, J. Virol., 2017, 91(4):e02151-16.
Chemical Abstract Registry No. 1016518-96-9, C12 H15 Ci N2 O, 3-Piperidinecarboxamide, N-(2-chlorophenyl)-, 1 page.
Chemical Abstract Registry No. 1016733-00-8, C12 H15 Ci N2 O, 3-Piperidinecarboxamide, N-(3-chlorophenyl)-, 1 page.
Chemical Abstract Registry No. 1016840-47-3, C13 H17 Ci N2 O, 3-Piperidinecarboxamide, N-(4-chloro-2-methylphenyl)-, 1 page.
Chemical Abstract Registry No. 1039879-39-4, C12 H15 I N2 O, 3-Piperidinecarboxamide, N-(4-iodophenyl)-, 1 page.
Chemical Abstract Registry No. 1219976-72-3, C12 H15 F N2 O . Ci H, 3-Piperidinecarboxamide, N-(4-fluorophenyl)-, hydrochloride (1 : 1), 1 page.
Chemical Abstract Registry No. 1335041-41-2, Absolute stereochemistry. C12 H15 Cl N2 0, 3- Piperidinecarboxamide, N-(4-chlorophenyl)-, (3S)-, 1 page.
Chemical Abstract Registry No. 1335041-42-3, Absolute stereochemistry. C12 H15 Cl N2 O, 3- Piperidinecarboxamide, N-(4-chlorophenyl)-, (3R), 1 page.
Chemical Abstract Registry No. 1412399-46-2, C13 H17 Ci N2 O, 3-Piperidinecarboxamide, N-(4-chlorophenyl)-3-methyl-, 1 page.
Chemical Abstract Registry No. 1567859-92-0, Absolute stereochemistry. C12 H15 Br N2 O, 3-Piperidinecarboxamide, N-(4-bromophenyl)-, (3R)-, 1 page.
Chemical Abstract Registry No. 1567918-59-5, Absolute stereochemistry. C12 H15 Cl N2 O, 3-Piperidinecarboxamide, N-(3-chlorophenyl)-, (3S)-, 1 page.
Chemical Abstract Registry No. 1567956-04-0, Absolute stereochemistry. C12 H1s I N2 O, 3-Piperidinecarboxamide, N-(4-iodophenyl)-, (3S)-, 1 page.
Chemical Abstract Registry No. 1568027-78-0, Absolute stereochemistry. C12 H1s I N2 O, 3-Piperidinecarboxamide, N-(4-iodophenyl)-, (3R)-, 1 page.
Chemical Abstract Registry No. 1568029-45-7, Absolute stereochemistry. C12 H15 Cl N2 O, 3-Piperidinecarboxamide, N-(2-chlorophenyl)-, 1 page.
Chemical Abstract Registry No. 1568183-11-8, Absolute stereochemistry. C12 H15 F N2 O, 3-Piperidinecarboxamide, N-(4-fluorophenyl)-, (3R)-, 1 page.
Chemical Abstract Registry No. 1568188-33-9, Absolute stereochemistry. C12 H15 CI N2 O, 3-Piperidinecarboxamide, N-(2-chlorophenyl)-, (3S)-, 1 page.
Chemical Abstract Registry No. 1568197-29-4, Absolute stereochemistry. C12 H15 Br N2 O, 3-Piperidinecarboxamide, N-(4-bromophenyl)-, (3S)-, 1 page.
Chemical Abstract Registry No. 1568213-93-3, Absolute stereochemistry. C12 H15 CI N2 O, 3-Piperidinecarboxamide, N-(3-chlorophenyl)-, (3R)-, 1 page.
Chemical Abstract Registry No. 1786638-79-6, Absolute stereochemistry. C13 H17 CI N2 O, 3-Piperidinecarboxamide, N-(4-chloro-2-methylphenyl)-, 1 page.
Chemical Abstract Registry No. 1798630-98-4, C13 H17 CI N2 O, 3-Piperidinecarboxamide, N-(4-chlorophenyl)-1-methyl-, 1 page.
Chemical Abstract Registry No. 1827336-15-1, C13 H17 CI N2 O. Ci H, 3-Piperidinecarboxamide, N-(4-chloro-2-methylphenyl)-, hydrochloride (1 :1), 1 page.
Chemical Abstract Registry No. 1838140-59-2, C12 H15 CI N2 O. Cl H, 3-Piperidinecarboxamide, N-(2-chlorophenyl)-, hydrochloride (1 : 1), 1 page.
Chemical Abstract Registry No. 1839732-47-6, C12 H15 CI N2 O. Cl H, 3-Piperidinecarboxamide, N-(3-chlorophenyl)-, hydrochloride (1 : 1), 1 page.
Chemical Abstract Registry No. 1840479-39-1, C12 H15 I N2 O. Ci H, 3-Piperidinecarboxamide, N-(4-iodophenyl)-, hydrochloride (1 : 1), 1 page.
Chemical Abstract Registry No. 1922099-67-9, C12 H15 CI N2 O. C2 H F3 02, 3-Piperidinecarboxamide, N-(4-chlorophenyl)-, 2,2,2-trifluoroacetate (1 :1), 1 page.
Chemical Abstract Registry No. 1922099-76-0, C13 H15 CI N2 O, 3-Piperidinecarboxamide, N-(4-chlorophenyl)-5-methylene-, 1 page.
Chemical Abstract Registry No. 1922099-77-1, C13 H15 CI N2 O . C2 H F3 02, 3-Piperidinecarboxamide, N-(4-chlorophenyl)-5-methylene-, 2,2,2-trifluoroacetate (1 :1), 1 page.
Chemical Abstract Registry No. 1938433-50-1, Absolute stereochemistry. C12 H15 F N2 O. Cl H, 3-Piperidinecarboxamide, N-(4-fluorophenyl)-, hydrochloride (1 :1), 1 page.
Chemical Abstract Registry No. 1938435-47-2, Absolute stereochemistry. C12 H15 I N2 O. Cl H, 3-Piperidinecarboxamide, N-(4-iodophenyl)-, hydrochloride (1 :1), (3R)-, 1 page.
Chemical Abstract Registry No. 1938602-79-9, Absolute stereochemistry. C12 H15 Ci N2 O. Cl H, 3-Piperidinecarboxamide, N-(2-chlorophenyl)-, hydrochloride (1 :1), 1 page.
Chemical Abstract Registry No. 1938620-29-1, Absolute stereochemistry. C13 H17 CI N2 O. Cl H, 3-Piperidinecarboxamide, N-(4-chloro-2-methylphenyl)-, hydrochloride (1 :1), 1 page.
Chemical Abstract Registry No. 1938924-93-6, Absolute stereochemistry. C12 H1s CI N2 O. Cl H, 3-Piperidinecarboxamide, N-(4-chlorophenyl)-, hydrochloride (1 :1), (3R)-, 1 page.
Chemical Abstract Registry No. 1939009-64-9, Absolute stereochemistry. C12 H15 Br N2 O. Cl H, 3-Piperidinecarboxamide, N-(4-bromophenyl)-, hydrochloride (1 :1), 1 page.
Chemical Abstract Registry No. 1939058-51-1, Absolute stereochemistry. C12 H15 Ci N2 O. Cl H, 3-Piperidinecarboxamide, N-(3-chlorophenyl)-, hydrochloride (1 :1), 1 page.
Chemical Abstract Registry No. 2034144-78-8, C13 H17 Ci N2 O . Cl H, 3-Piperidinecarboxamide, N-(4-chlorophenyl)-3-methyl-, hydrochloride (1 :1), 1 page.
Chemical Abstract Registry No. 2104148-69-6, Absolute stereochemistry. C13 H17 CI N2 O, 3-Piperidinecarboxamide, N-(4-chloro-2-methylphenyl)-, (3S)-, 1 page.
Chemical Abstract Registry No. 2110686-89-8, C13 H17 F N2 O, 1H-Azepine-3-carboxamide, N-(4-fluorophenyl) hexahydro-, 1 page.
Chemical Abstract Registry No. 412293-95-9, C12 H15 CI N2 O . Cl H, 4-Piperidinecarboxamide, N-(4-chlorophenyl)-, hydrochloride (1 : 1), 1 page.
Chemical Abstract Registry No. 599184-18-6, C12 H15 Br N2 O . Cl H, 3-Piperidinecarboxamide, N-(4-bromophenyl)-, hydrochloride (1 : 1), 1 pages.

(56) References Cited

OTHER PUBLICATIONS

Chemical Abstract Registry No. 599184-20-0, C12 H15 Ci N2 O . Cl H, 3-Piperidinecarboxamide, N-(4-chlorophenyl)-, hydrochloride (1 : 1) , 1 page.
Chemical Abstract Registry No. 735258-48-7, C12 H15 Cl N2 O, 4-Piperidinecarboxamide, N-(4-chlorophenyl)-, 1 page.
Chemical Abstract Registry No. 749846-52-4, C12 H15 Br N2 O, 3-Piperidinecarboxamide, N-(4-bromophenyl)-, 1 page.
Chemical Abstract Registry No. 787546-33-2, C12 H15 Cl N2 O, 3-Piperidinecarboxamide, N-(4-chlorophenyl)-, 1 page.
Chemical Abstract Registry No. 851882-97-8, Absolute stereochemistry. C12 H15 F N2 O . Cl H, 3-Piperidinecarboxamide, N-(4-fluorophenyl)-, hydrochloride (1 :1), 1 page.
Chemical Abstract Registry No. 852022-85-6, Absolute stereochemistry. C12 H15 F N2 O, 3-Piperidinecarboxamide, N-(4-fluorophenyl)-, (3S)-, 1 page.
Chemical Abstract Registry No. 883106-66-9, C12 H15 F N2 O, 3-Piperidinecarboxamide, N-(4-fluorophenyl)-, 1 page.

* cited by examiner

SMALL MOLECULES THAT SENSITIZE HIV-1 INFECTED CELLS TO ANTIBODY DEPENDENT CELLULAR CYTOTOXICITY

CROSS-REFERENCE TO RELATED APPLICATIONS

This application is the National Stage Application of International Patent Application No. PCT/US2019/044320, filed Jul. 31, 2019, which claims the benefit of U.S. Provisional Patent Application No. 62/712,283, filed Jul. 31, 2018, both applications of which are incorporated by reference herein.

GOVERNMENT RIGHTS

This invention was made with government support under grant number P01 GM056550 awarded by the National Institutes of Health. The government has certain rights in the invention.

TECHNICAL FIELD

This disclosure relates to compounds and methods of treating and preventing HIV-1.

BACKGROUND

The global AIDS pandemic caused by HIV-1 represents one of the world's leading health problems. Current therapeutic approaches involve combinations of antiretrovirals that only target the inhibition of viral enzymes: reverse transcriptase, protease and integrase. In addition there are two FDA approved entry inhibitors: Enfuvirtide and Maraviroc. Despite the seemingly replete armamentarium for the treatment of HIV, an increase in mutation-derived resistance and issues of drug toxicity, intolerability, and lack of compliance limit current effective therapies. The need to derive novel strategies for the prevention and eradication of HIV-1 in infected individuals remains a worldwide challenge.

Studies demonstrate that antibody-dependent cellular cytotoxicity (ADCC) plays an important role in controlling HIV-1 transmission and disease progression. Conformational changes induced by Env:CD4 binding on the surface of HIV-1 infected cells leads to exposure of conserved CD4-induced (CD4i) epitopes on Env that are recognized by ADCC-mediating antibodies (Abs). Many ADCC-mediating Abs are routinely elicited in HIV-1 infected individuals, but do not have robust viral neutralization effects due to their inability to recognize unbound Env. Thus CD4 binding sensitizes HIV-infected cells to elimination by ADCC. The virus, however, has evolved sophisticated escape mechanisms to avoid such recognition via CD4 downregulation and thereby diminishing the overall amount of Env present on the cell surface.

CD4 mimetics induce the CD4-bound Env conformation and thus sensitize HIV-1 viral particles to ADCC-mediated killing. 1,3-4 CD4 mimetic binding opens the Env trimer to allow binding of co-receptor binding site (CoRBS) antibodies. Binding of CoRBS Abs then further opens Env allowing ADCC-mediating anti-cluster A Ab to bind thus sensitizing infected cells to ADCC.

The development of new approaches aimed at the eradication of HIV-1 infection is critical for altering the course of the global AIDS pandemic. The ability of small molecules to sensitize HIV-1 infected cells to antibody-mediated cellular cytotoxicity (ADCC) bears great promise in controlling HIV-1 transmission and disease progression.

What is needed are novel small molecules that are useful in treating and preventing HIV-1.

SUMMARY

In some embodiments, the disclosure provides methods of treating HIV-1 in a human infected with HIV-1 or preventing HIV-1 infection in a human susceptible to infection with HIV-1 comprising administering to the human a therapeutically effective amount of a compound of formula (I), (II), or (IA):

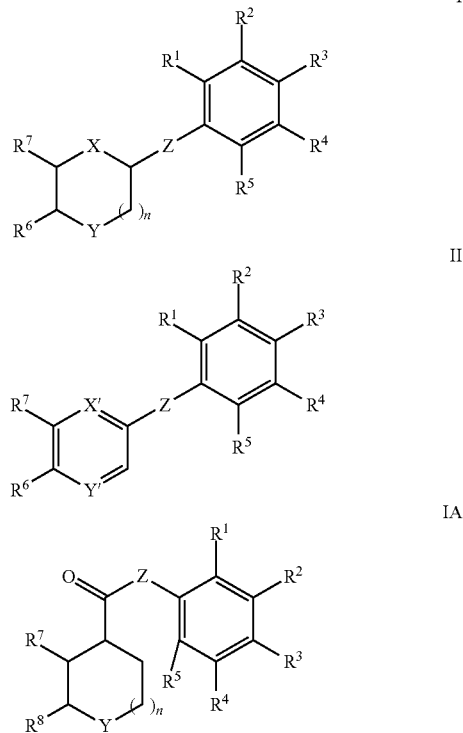

or a pharmaceutically acceptable salt thereof, wherein, n, X, X', Y, Y', Z, and $R^1$ to $R^7$ are defined herein. In some aspects, the compound is of formula (I). In other aspects, the compound is of formula (II). In further aspects, the compound is of formula (IA).

Other aspects and embodiments of the invention will be readily apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific compositions, methods, devices, and systems disclosed. In addition, the drawings are not necessarily drawn to scale.

DETAILED DESCRIPTION OF ILLUSTRATIVE EMBODIMENTS

Figure 1:
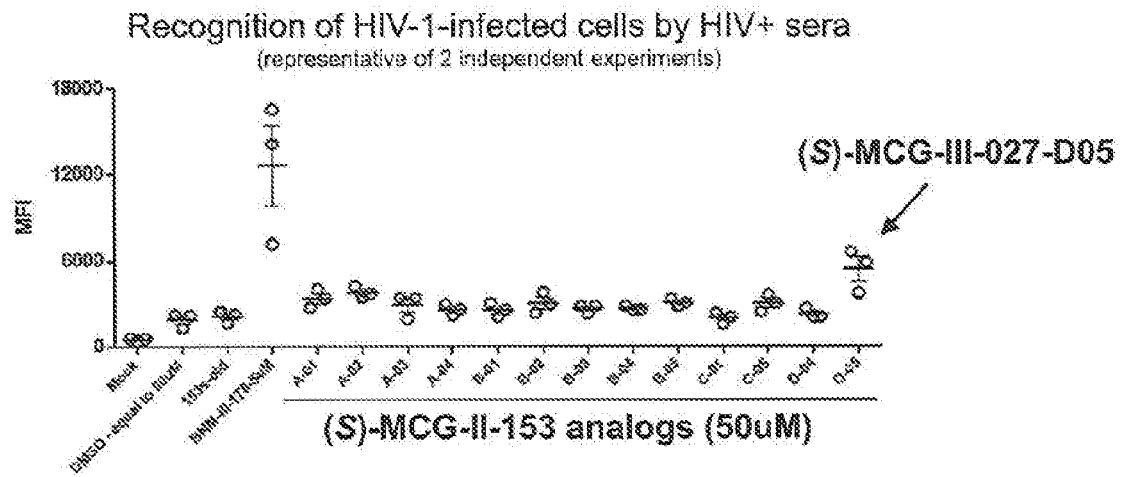
FIG. 1 is a plot of the recognition of HIV-1 infected cells by HIV+ sera as described in Example 32 using compounds of the disclosure shown in Examples 1 and 2.
Figure 2:
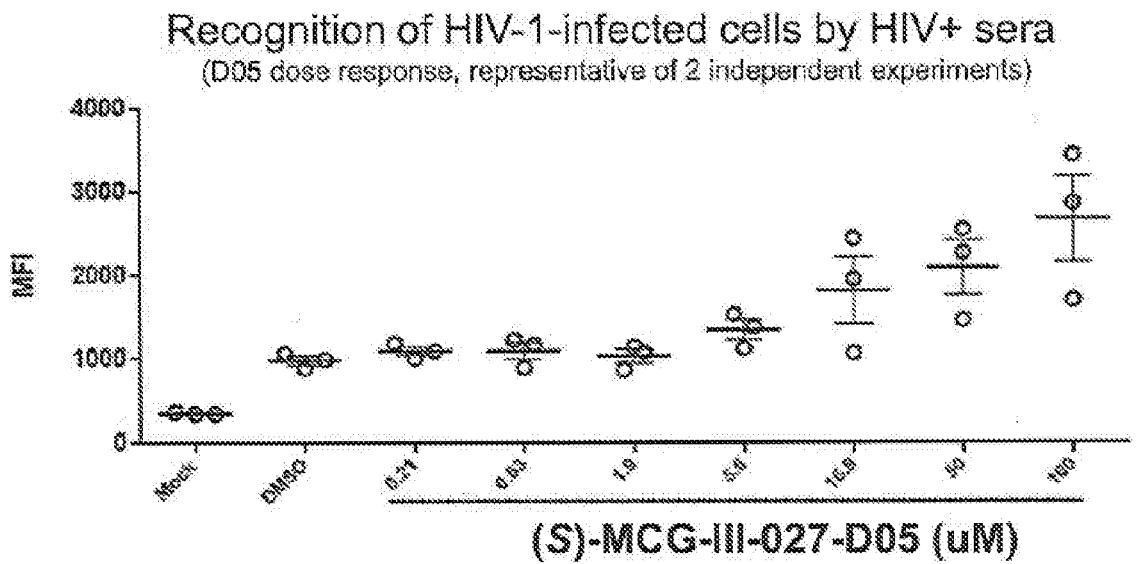
FIG. 2 is a plot of the recognition of HIV-1 infected cells by HIV+ sera as described in Example 32 using varying concentrations of (S)-MCG-III-027-D05 shown in Example 2.
Figure 3:
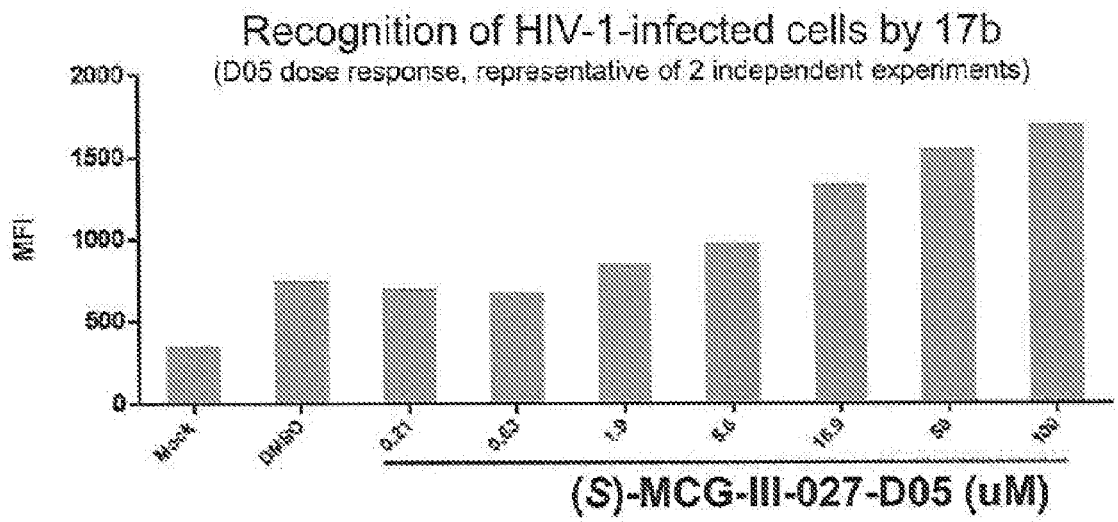
FIG. 3 is a bar graph showing the recognition of HIV-1 infected cells by 17b as described in Example 32 using varying concentrations of (S)-MCG-III-027-D05 shown in Example 2.
Figure 4:
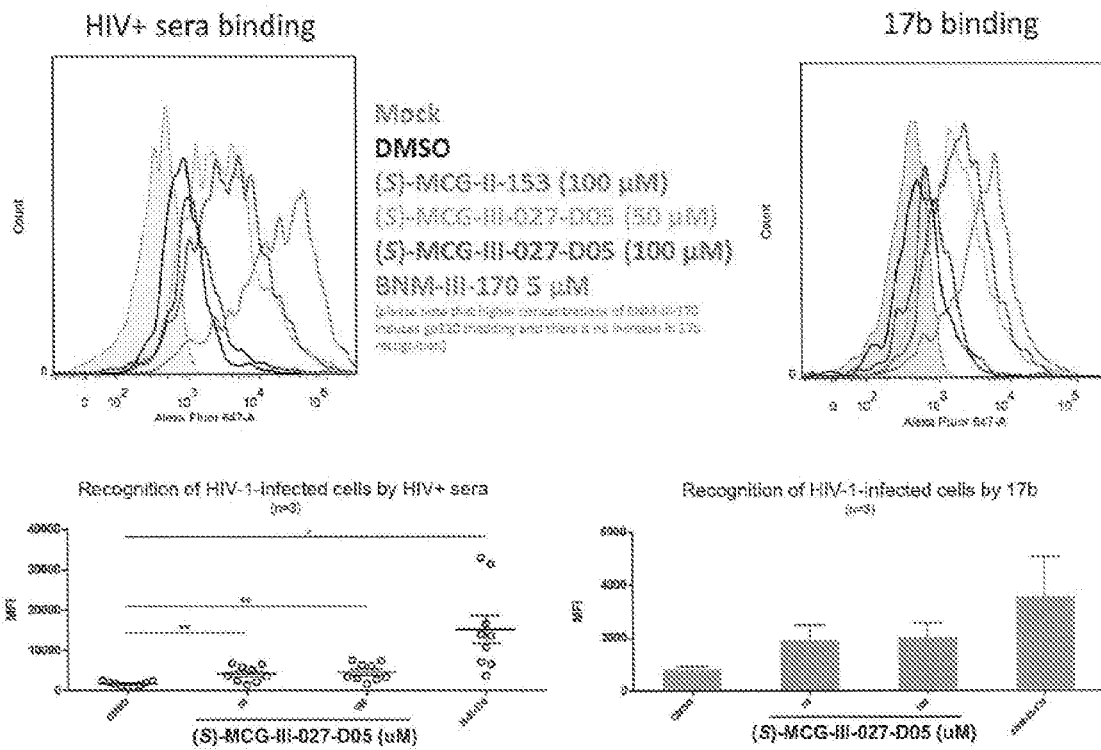
FIG. 4 shows the effect of compounds of the disclosure shown in Example 2 on recognition of primary CD4+ T cells infected with the transmitted/founder CH58 virus by HIV+ sera and 17b as described in Example 32.
Figure 5:
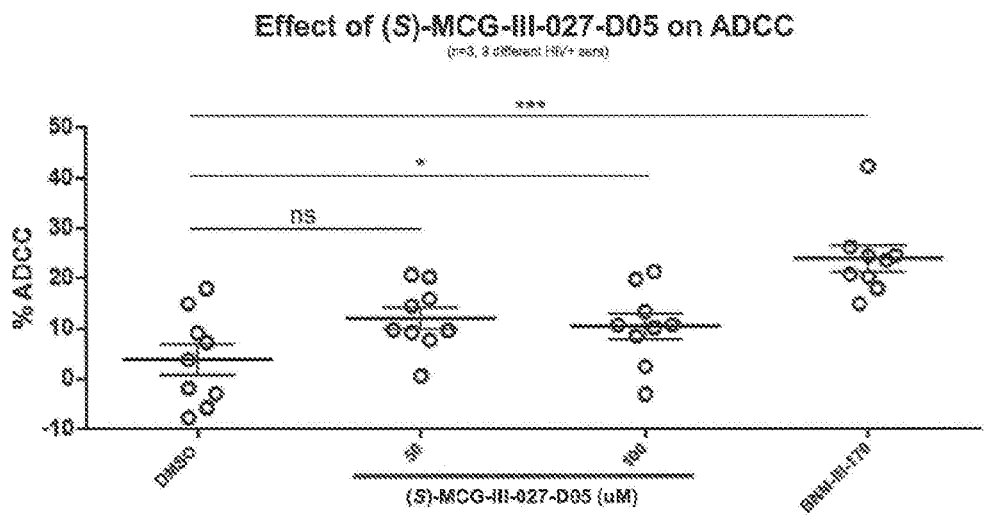
FIG. 5 is a plot showing the effect of (S)-MCG-III-027-D05 shown in Example 2 on ADCC as described in Example 32.

In the present disclosure the singular forms "a", "an" and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

As used herein, while data is given with full disclosure of all significant figures, those of ordinary skill in the art would understand that the data can also be understood when rounded to 1 or 2 decimal places.

When a list is presented, unless stated otherwise, it is to be understood that each individual element of that list and every combination of that list is to be interpreted as a separate embodiment. For example, a list of embodiments presented as "A, B, or C" is to be interpreted as including the embodiments, "A," "B," "C," "A or B," "A or C," "B or C," or "A, B, or C."

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The term "alkyl," when used alone or as part of a substituent group, refers to a straight- or branched-chain alkyl group having from 1 to 12 carbon atoms ("$C_{1-12}$"), preferably 1 to 6 carbons atoms ("$C_{1-6}$"), in the chain. Examples of alkyl groups include methyl (Me, $C_1$alkyl) ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and groups that in light of the ordinary skill in the art and the teachings provided herein would be considered equivalent to any one of the foregoing examples. An alkyl moiety is optionally substituted with one, two, or three substituents selected from halo (F, Cl, Br, or I, preferably F), —OH, —O$C_{1-6}$alkyl, —CN, —NH$_2$, —NH($C_{1-6}$alkyl), —NH($C_{1-6}$alkyl)$_2$, $C_{3-8}$cycloalkyl, heterocyclyl, aryl, or heteroaryl.

The term "haloalkyl," when used alone or as part of a substituent group, refers to an alkyl group as described above having one, two, or three halogen atoms attached to a single carbon atom. Preferably, the halogen is F. In some embodiments, haloalkyl includes perfluoroalkyl groups whereby the alkyl group is terminated with a $CF_3$, $CH_2F$, or $CHF_2$. Examples of alkyl groups include $CF_3$, $CHF_2$, $CH_2F$, $CH_2CF_3$, $CHFCF_3$, $CF_2CF_3$, $CH_2CHF_2$, $CH_2CH_2F$, $CHFCH_3$, $CF_2CH_3$, $CHFCHF_2$, $CF_2CHF_2$, among others, and groups that in light of the ordinary skill in the art and the teachings provided herein would be considered equivalent to any one of the foregoing examples. A haloalkyl moiety is optionally substituted with one, two, or three substituents selected from —OH, —O$C_{1-6}$alkyl, —CN, —NH$_2$, —NH($C_{1-6}$alkyl), —NH($C_{1-6}$alkyl)$_2$, $C_{3-8}$cycloalkyl, heterocyclyl, aryl, or heteroaryl.

The term "aryl" refers to carbocyclic aromatic groups having from 6 to 10 carbon atoms ("$C_{6-10}$") such as phenyl, naphthyl, and the like. An aryl is optionally substituted with one, two, or three substituents selected from halo (F, Cl, Br, or I, preferably F), $C_{1-6}$alkyl, —OH, —O$C_{1-6}$alkyl, $C_{1-6}$haloalkyl, —CN, —NH$_2$, —NHC(O)($C_{1-6}$alkyl), —NH($C_{1-6}$alkyl), —NH($C_{1-6}$alkyl)$_2$, $C_{3-5}$cycloalkyl, heterocyclyl, aryl, or heteroaryl. In some embodiments, the aryl is substituted with one halo. In other embodiments, the aryl is substituted with two halo. In further embodiments, the aryl is substituted with one F and one Cl. In yet further embodiments, the aryl is substituted with two Cl. In still other embodiments, the aryl is substituted with $CF_3$.

"Heteroaryl" refers to a 5- to 18-membered aromatic radical, e.g., C5-18heteroaryl, that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range, e.g., "5 to 18 ring atoms" means that the heteroaryl group may contain 5 ring atoms, 6 ring atoms, etc., up to and including 18 ring atoms. An N-containing heteroaryl moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). A heteroaryl is optionally substituted with one, two, or three substituents selected from halo (F, Cl, Br, or I, preferably F), —OH, $C_{1-6}$alkyl, —O$C_{1-6}$alkyl, —CN, —$NH_2$, —NH($C_{1-6}$alkyl), —N($C_{1-6}$alkyl)$_2$, $C_{3-5}$cycloalkyl, heterocyclyl, aryl, or heteroaryl.

When a range of carbon atoms is used herein, for example, $C_{1-6}$, all ranges, as well as individual numbers of carbon atoms are encompassed. For example, "$C_{1-3}$" includes $C_{1-3}$, $C_{1-2}$, $C_{2-3}$, $C_1$, $C_2$, and $C_3$.

The terms "halogen" and "halo" represent chlorine, fluorine, bromine, or iodine. The term "halo" represents chloro, fluoro, bromo, or iodo.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

The terms "patient" or "subject" as used herein refer to a mammalian animal and are used interchangeably. In some embodiments, the patient or subject is a human. In other embodiments, the patient or subject is a veterinary or farm animal, a domestic animal or pet, or animal normally used for clinical research.

"Treating" any disease or disorder refers, in some embodiments, to ameliorating the disease or disorder (i.e., arresting or reducing the development of the disease or at least one of the clinical symptoms thereof). In some embodiments, "treating" or "treatment" refers to ameliorating at least one physical parameter, which may not be discernible by the subject. In other embodiments, "treating" or "treatment" refers to modulating the disease or disorder, either physically, (e.g., stabilization of a discernible symptom), physiologically, (e.g., stabilization of a physical parameter), or both. In further embodiments, "treating" or "treatment" refers to delaying the onset of the disease or disorder.

As used herein, "HIV" refers human immunodeficiency virus. HIV also refers to any virus that can infect a host cell of a subject through activation of the gp120 or gp41 envelope glycoproteins (Env gps). "HIV" encompasses all strains of HIV-1.

As used herein "gp120" refers to the gp120 envelope glycoprotein, and "Env gps" refers to the complete envelope glycoprotein complex which is a trimer of three gp120s and three gp41s.

"Compounds of the present disclosure," and equivalent expressions, are meant to embrace compounds of the Formulae (I), (II), or (IA) as described herein, which expression includes the pharmaceutically acceptable salts, where the context so permits. Similarly, reference to intermediates, whether or not they themselves are claimed, is meant to embrace their salts, and solvates, where the context so permits.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. Within the present disclosure, any open valency appearing on a carbon, oxygen, or nitrogen atom in any structure described herein indicates the presence of a hydrogen atom. Where a chiral center exists in a structure, but no specific stereochemistry is shown for that center, both enantiomers, separately or as a mixture, are encompassed by that structure. The methods for the determination of stereochemistry and the separation of stereoisomers are well-known in the art.

The disclosure provides compounds that are useful in methods of treating HIV-1 in a human infected with HIV-1 or preventing HIV-1 infection in a human susceptible to infection with HIV-1. These compounds sensitize HIV-1 infected cells to antibody dependent cellular cytotoxicity (ADCC) responses. As such, these compounds may be used in the treatment of HIV-1 infected patients and control HIV-1 transmission and disease progression.

The inventors discovered that these compounds "open" the HIV-1 envelope glycoprotein (Env) trimer and expose CoRBS epitopes. These compounds have HIV-1 specificity, expose Env co-receptor binding site (CoRBS) epitopes at the surface of infected cells, possess ADCC activity, and induce gp120 shedding. These compounds are of formula (I), (II), or (IA). In some embodiments, the compound is of formula (I) or a pharmaceutically acceptable salt thereof. In other embodiments, the compound is of formula (II) or a pharmaceutically acceptable salt thereof. In further embodiments, the compound is of formula (IA) or a pharmaceutically acceptable salt thereof

I

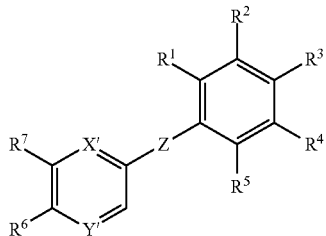

II

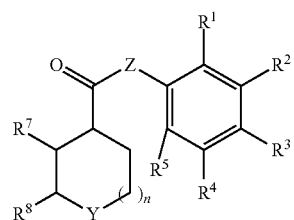

IA

In these compounds, n is 1 or 2. In some embodiments, n is 1. In other embodiments, n is 2.

In the compounds, X is absent, —O—, —N(R¹⁰)—, —CH₂—, or —CH₂CH₂—. In some embodiments, X is absent. In other embodiments, X is —O—. In further embodiments, X is —N(R¹⁰)—. In yet other embodiments, X is —NH—. In still further embodiments, X is —N(C(O)OC₁₋₆alkyl)-, preferably —N(C(O)Omethyl)-, —N(C(O)Oethyl)-, —N(C(O)Opropyl)- (such as N(C(O)O(n-propyl or i-propyl), —N(C(O)O(butyl) (such as —N(C(O)O(n-butyl, i-butyl, or t-butyl)), —N(C(O)O(pentyl)- such as —N(C(O)O(pentyl, i-pentyl, neo-pentyl), or —N(C(O)Ohexyl)- such as (—NC(O)O(n-hexyl, i-hexyl, 3-methyl-pentyl, neo-hexyl, or 2,3-dimethyl-butyl). In other embodiments, X is —CH₂—. In further embodiments, X is —CH₂CH₂—.

Y is —O—, —CH₂—, —NH—, —N(R⁹)—, —N(SO₂R⁹)—, —C(H)(SO₂R⁹)—, —N(C(O)R⁸)—, —N(C(O)NR⁹R¹⁰)—, —N(C(O)R⁸)—, —N(S(O)(=NH)R⁹)—, —N(P(O)R⁹OR¹⁰)—, or —N(C(=NH)NR⁹R¹⁰)— and R⁸ is —OC₁₋₆alkyl, —O—C₁₋₆alk-NH₂, —NH(C₁₋₆alkyl), —N(C₁₋₆alkyl)(C₁₋₆alkyl), —NH—C₁₋₆alk-NH₂, phenyl, or heteroaryl and R⁹ and R¹⁰ are, independently, H, C₁₋₆alkyl, —C(O)OC₁₋₆alkyl, halogenated C₁₋₆alkyl, C₃₋₈cycloalkyl, aryl, or heteroaryl. In some embodiments, Y is —O—. In other embodiments, Y is —NH—. In yet other embodiments, Y is —N(R⁹)—, preferably —N(C₁₋₆alkyl)-, —N(C₃₋₈cycloalkyl)-, —N(aryl)-, or —N(heteroaryl). In further embodiments, Y is —CH₂—. In still other embodiments, Y is —N(SO₂R⁹)—, preferably —N(SO₂C₁₋₆alkyl) such as —NSO₂methyl, —NSO₂ethyl, —NSO₂propyl, —NSO₂butyl, —NSO₂pentyl, or —NSO₂-hexyl; —N(SO₂-aryl)- such as —N(SO₂-optionally substituted phenyl)-; or —N(SO₂-heteroaryl)- such as —N(SO₂-optionally substituted imidazolyl)-. In yet further embodiments, Y is —C(H)(SO₂R⁹)— such as —C(H)(SO₂-aryl)-. In other embodiments, Y is —N(C(O)R⁸)—. In yet further embodiments, Y is —N(C(O)—OC₁₋₆alkyl)- such as —N(C(O)O-methyl)-, —N(C(O)—O-ethyl)-, —N(C(O)O-propyl (such as —N(C(O)O—CH₂CH₂CH₃), —N(C(O)O—CH₂(CH₃)₂)—), —N(C(O)O-butyl)- (such as —N(C(O)O—CH₂CH₂CH₂CH₃), —N(C(O)O—CH₂CH(CH₃)₂)—, —N(C(O)O—CH(CH₃)CH₂CH₃), —N(C(O)O—C(CH₃)₃)—), —N(C(O)O-pentyl)-, or —N(C(O)O— hexyl)-. In still other embodiments, Y is —N(C(O)O-aryl)- such as —N(C(O)O-phenyl)-. In further embodiments, Y is —N(C(O)O-heteroaryl)- such as —N(C(O)O-imidazolyl)-. In other embodiments, Y is —N(C(O)NR⁹R¹⁰)— such as —N(C(O)NH—C₁₋₆alkyl)- including —N(C(O)NH—methyl)-, —N(C(O)NH-ethyl)-, —N(C(O)NH-propyl)- (such as —N(C(O)NHCH₂CH₂CH₃)— or —N(C(O)NHCH(CH₃)₂)—), —N(C(O)NH-butyl)- ((such as —N(C(O)NHCH₂CH₂CH₂CH₃)—, —N(C(O)NHCH₂CH(CH₃)₂)—, or —N(C(O)NHCH(CH₃)₃)—), —N(C(O)NH-pentyl)-, or —N(C(O)NH-hexyl)-; —N(C(O)N(C₁₋₆alkyl)(C₁₋₆alkyl)- including —N(C(O)N(methyl)₂-, —N(C(O)N(methyl)(ethyl))-, —N(C(O)N(ethyl)₂)-, —N(C(O)N(methyl)(propyl))-, —N(C(O)N(ethyl)(propyl))-, —N(C(O)N(propyl)₂)-, —N(C(O)NH(butyl))-, —N(C(O)NH(pentyl))-, —N(C(O)NH(hexyl))-, or —N(C(O)N(methyl)(ethyl))-; or —N(C(O)N(aryl)(aryl))- such as —N(C(O)N(optionally substituted phenyl)(optionally substituted phenyl))-. In still further embodiments, Y is —N(S(O)(=NH)R⁹)— such as —N(S(O)(=NH)aryl)-, preferably —N(S(O)(=NH)(optionally substituted phenyl). In yet other embodiments, Y is —N(P(O)R⁹OR¹⁰)— such as —N(P(O)(aryl)O(aryl))-, preferably, —N(P(O)(optionally substituted phenyl)O(optionally substituted phenyl). In further embodiments, Y is —N(C(=NH)NR⁹R¹⁰)— such as —N(C(=NH)N(aryl)(aryl))-, —N(C(=NH)NH—C₁₋₆alkyl)-, or —N(C(=NH)N(C₁₋₆alkyl)(C₁₋₆alkyl))-, preferably —N(C(=NH)N(optionally substituted phenyl)(optionally substituted phenyl), —N(C(=NH)NH-methyl)-, —N(C(=NH)NH-ethyl)-, —N(C(=NH)NH-propyl)-(such as —N(C(=NH)NH-n-propyl)-, —N(C(=NH)NH-i-propyl)-), —N(C(=NH)NH-butyl)-(such as —N(C(=NH)NH-n-butyl)-, —N(C(=NH)NH-i-butyl)- —N(C(=NH)NH-t-butyl)-), —N(C(=NH)NH-pentyl)-, or —N(C(=NH)NH-hexyl)-. In other embodiments, Y is —N(C(O)—O—C₁₋₆alk-NH₂)—, preferably —N(C(O)—O—CH₂NH₂)—, —N(C(O)—O—CH₂CH₂NH₂)—, —N(C(O)—O-prop-NH₂)—, —N(C(O)—O-but-NH₂)—, —N(C(O)—O-pent-NH₂)—, or —N(C(O)—O-hex-NH₂)—. In still further embodiments, Y is —N(C(O)—NH—C₁₋₆alk-NH₂)—, preferably —N(C(O)—NHCH₂NH₂)—, —N(C(O)—NHCH₂CH₂NH₂)—, —N(C(O)—NH-prop-NH₂)—, —N(C(O)—NH-but-NH₂)—, —N(C(O)—NH-pent-NH₂)—, or —N(C(O)—NH-hex-NH₂)—.

In some preferred embodiments, X is CH₂ and Y is —N(SO₂R⁹)—. In other preferred embodiments, X is CH₂ and Y is —NH—. In further preferred embodiments, X is CH₂ and Y is —N(C(O)OR⁸)—. In yet other preferred embodiments, X is —O— and Y is —N(SO₂R⁹)—. In still further preferred embodiments, X is —O— and Y is —NH—. In other preferred embodiments, X is —N(R¹⁰)— and Y is —N(SO₂R⁹)—. In further preferred embodiments, X and Y are NH. In other preferred embodiments, X is —CH₂— and Y is O. In yet other preferred embodiments, X is CH₂ and Y is —C(O)NH(C₁₋₆alkyl), such as —C(O)NHCH₃, —C(O)NHCH₂CH₃, —C(O)NH-propyl (such as —C(O)NHCH₂CH₂CH₃—, —C(O)NHCH(CH₃)₂), —C(O)NH-butyl (such as —C(O)NHCH(CH₃)CH₂CH₃, —C(O)NHCH₂CH(CH₃)₂, —C(O)NHC(CH₃)₃, —C(O)NHCH₂CH₂CH₂CH₃), —C(O)NH-pentyl (such as —C(O)NHCH₂CH₂CH₂CH₂CH₃, C(O)NHCH₂CH(CH₃)CH₂CH₃, —C(O)NHCH₂C(CH₃)₃), or —C(O)NH-hexyl (such as —C(O)NHCH₂CH₂CH₂CH₂CH₂CH₃, —C(O)NHCH₂CH(CH₃)CH₂CH₂CH₃, —C(O)NHCH₂CH₂CH(CH₃)CH₂CH₃, —C(O)NHC(CH₃)₂CH₂CH₃ or —C(O)NHCH₂CH(CH₃)CH(CH₃)₂.

Z is —C(O)O—, —C(O)C₁₋₆alk-, —C₁₋₆alk-NH—, —C(O)NH—, —OC(O)—, or —NHC(O)—, or —C(O)

NH—. In some embodiments, Z is —C(O)O—. In other embodiments, Z is —C(O)C$_{1-6}$alk- such as —C(O)meth- (—C(O)CH$_2$—), —C(O)eth- (—C(O)CH$_2$CH$_2$—), —C(O)prop-(preferably, —C(O)CH$_2$CH$_2$CH$_2$—, —C(O)CH(CH$_3$)—, —C(O)CH$_2$CH(CH$_3$)—), —C(O)but- (preferably, —C(O)CH$_2$CH$_2$CH$_2$CH$_2$—, —C(O)CH(CH$_3$)CH$_2$CH$_2$—, —C(O)CH(CH$_3$)$_3$—), —C(O)pent-(preferably, —C(O)CH$_2$CH$_2$CH$_2$CH$_2$CH$_2$—, —C(O)CH$_2$CH(CH$_3$)CH$_2$CH$_2$—, —C(O)CH$_2$C(CH$_3$)$_2$CH$_3$—), or —C(O)hex- (preferably, —C(O)CH$_2$CH$_2$CH$_2$CH$_2$CH$_2$CH$_2$—, —C(O)CH$_2$CH(CH$_3$)CH$_2$CH$_2$CH$_2$—. —C(O)CH$_2$CH$_2$CH(CH$_3$)CH$_2$CH$_2$—, —C(O)C(CH$_3$)$_2$CH$_2$CH$_2$— or —C(O)CH$_2$CH(CH$_3$)CH(CH$_3$)CH$_2$—). In further embodiments, Z is —C$_{1-6}$alk-NH— such as -meth-NH (—CH$_2$NH—), -eth-NH (—CH$_2$CH$_2$NH—), -prop-NH— (preferably, —CH$_2$CH$_2$CH$_2$NH—, —CH(CH$_3$)CH$_2$NH—, —CH$_2$CH(CH$_3$)NH—), -but-NH— (preferably, —CH$_2$CH$_2$CH$_2$CH$_2$NH—), -pent-NH-(preferably, —CH$_2$CH$_2$CH$_2$CH$_2$CH$_2$NH—), -hex-NH— (preferably, —CH$_2$CH$_2$CH$_2$—CH$_2$CH$_2$CH$_2$NH—). In still other embodiments, Z is —C(O)NH—. In further embodiments, Z is —OC(O)—. In other embodiments, Z is —NHC(O)—. In yet further embodiments, Z is —C(O)NH—.

$R^1$ to $R^5$ are, independently, H, halogen, C$_{1-6}$alkyl, —OC$_{1-6}$alkyl, C$_{1-6}$haloalkyl, aryl, or heteroaryl, wherein at least one of $R^1$ to $R^5$ is other than H. In some embodiments, at least of $R^1$ to $R^5$ is halogen. In other embodiments, at least one of $R^1$ to $R^5$ is C$_{1-6}$alkyl such as methyl, ethyl, propyl, butyl, pentyl, or hexyl. In further embodiments, at least one of $R^1$ to $R^5$ is —OC$_{1-6}$alkyl such as —O-methyl, —O-ethyl, —O-propyl, —O-butyl, —O— pentyl, or —O-hexyl. In still other embodiments, at least one of $R^1$ to $R^5$ is C$_{1-6}$haloalkyl such as CF$_3$. In yet further embodiments, at least one of $R^1$ to $R^5$ is aryl such as optionally substituted phenyl. In other embodiments, at least one of $R^1$ to $R^5$ is heteroaryl such as optionally substituted imidazolyl. In further embodiments, $R^1$ to $R^5$ are, independently, H, halogen such as F, Cl, or Br, —OC$_{1-6}$alkyl, or C$_{1-6}$haloalkyl such as CF$_3$. In yet other embodiments, $R^1$ to $R^5$ are, independently, H, F, Cl or CF$_3$. In still further embodiments, $R^3$ is Cl and $R^1$, $R^2$, $R^4$, and $R^5$ are H. In other embodiments, $R^3$ is F and $R^1$, $R^2$, $R^4$, and $R^5$ are H. In further embodiments, $R^3$ is Br and $R^1$, $R^2$, $R^4$, and $R^5$ are H. In still other embodiments, $R^3$ is CF$_3$ and $R^1$, $R^2$, $R^4$, and $R^5$ are H. In yet further embodiments, $R^4$ is Cl and $R^1$-$R^3$, and $R^5$ are H. In other embodiments, $R^4$ is Br and $R^1$-$R^3$, and $R^5$ are H. In further embodiments, $R^4$ is F and $R^1$-$R^3$, and $R^5$ are H. In yet other embodiments, $R^4$ is CF$_3$ and $R^1$-$R^3$, and $R^5$ are H. In still other embodiments, $R^4$ is OCH$_3$ and $R^1$-$R^3$, and $R^5$ are H. In other embodiments, $R^5$ is Cl and $R^1$-$R^4$ are H. In further embodiments, $R^5$ is F and $R^1$-$R^4$ are H. In still other embodiments, $R^5$ is CF$_3$ and $R^1$-$R^4$ are H. In yet further embodiments, $R^5$ is OCH$_3$ and $R^1$-$R^4$ are H. In other embodiments, $R^1$, $R^2$, and $R^5$ are H, $R^3$ is Cl and $R^4$ is F. In further embodiments, $R^1$, $R^2$, and $R^5$ are H, $R^3$ is F and $R^4$ is Cl. In still other embodiments, $R^1$, $R^2$, and $R^5$ are H, $R^3$ is Cl and $R^4$ is Br. In yet further embodiments, $R^1$, $R^2$, and $R^5$ are H, $R^3$ is Br and $R^4$ is Cl. In other embodiments, $R^1$, $R^2$, and $R^5$ are H, $R^3$ and $R^4$ are Cl. In further embodiments, $R^1$, $R^2$, and $R^5$ are H, $R^3$ and $R^4$ are F. In still other embodiments, $R^1$, $R^2$, and $R^5$ are H, $R^3$ is CF$_3$ and $R^4$ is F. In yet further embodiments, $R^1$-$R^3$ are H, $R^4$ is F and $R^5$ is Cl. In other embodiments, $R^1$-$R^3$ are H, $R^4$ is Cl and $R^5$ is F.

$R^6$ and $R^7$ are, independently, H or NH$_2$ or fused to form an optionally substituted phenyl ring. In some embodiments, $R^6$ and $R^7$ are H. In further embodiments, $R^6$ and $R^7$ are NH$_2$. In other embodiments, $R^6$ is H and $R^7$ is NH$_2$. In yet further embodiments, $R^7$ is H and $R^6$ is NH$_2$. In still other embodiments, $R^6$ and $R^7$ are fused to form an optionally substituted phenyl ring.

In some preferred embodiments, $R^6$ and $R^7$ are fused to form a phenyl ring, X is —CH$_2$—, and Y is —N(SO$_2$R$^9$)—.

In other preferred embodiments, $R^6$ and $R^7$ are fused to form a phenyl ring, X is —CH$_2$—, and Y is —NH— or —N(C$_{1-6}$alkyl)-.

In some aspects, the compound is of formula (II):

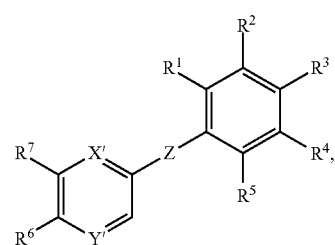

or a pharmaceutically acceptable salt thereof. In these compounds of formula II, X' is —N— or —CH— and Y' is —N— or —CH—. In some embodiments, X' is —N—. In other embodiments, X' is —CH—. In further embodiments, Y' is —N—. In still other embodiments, Y' is —CH—.

In other aspects, the compound is of formula (IA):

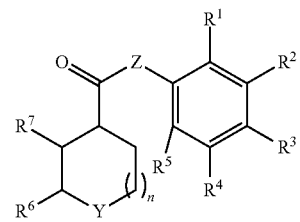

or a pharmaceutically acceptable salt thereof. In these compounds of formula IA, Y, Z, $R^1$-$R^5$, $R^7$, and $R^8$ are defined herein. In some embodiments, Y is —O—, —CH$_2$—, —NH—, —N(R$^9$)—, or —N(SO$_2$R$^9$)—, preferably —N(SO$_2$R$^9$)—.

In some aspects, the compound is of formula (III), wherein $R^1$-$R^5$ and $R^9$ are defined above:

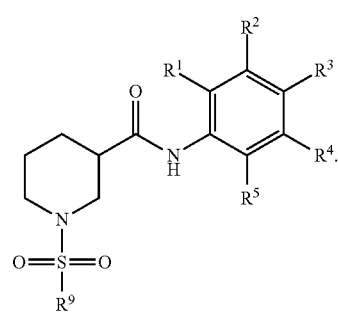

In other aspects, the compound is of formula (IV), wherein $R^1$-$R^5$ and $R^9$ are defined above:

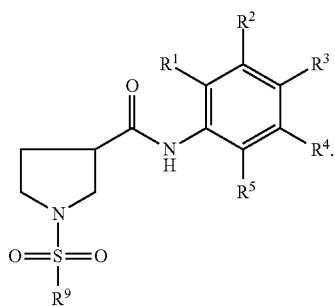

(IV)

In further aspects, the compound is of formula (V), wherein X, Y, Z, n, $R^6$ and $R^7$ are defined above:

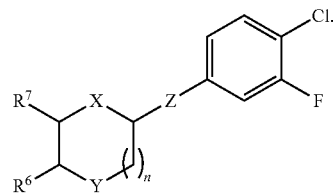

(V)

In yet other aspects, the compound is of formula (VI), wherein $R^1$-$R^5$ and $R^9$ are defined above:

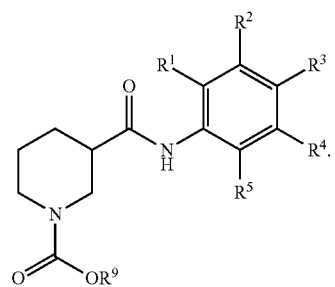

(VI)

In still further aspects, the compound is of formula (VII), wherein $R^1$-$R^5$, $R^9$, and $R^{10}$ are defined above:

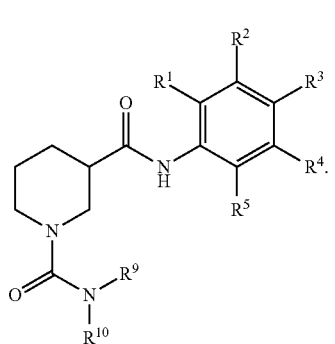

(VII)

In other aspects, the compound is of formula (VIII), wherein $R^1$-$R^5$ and $R^9$ are defined above:

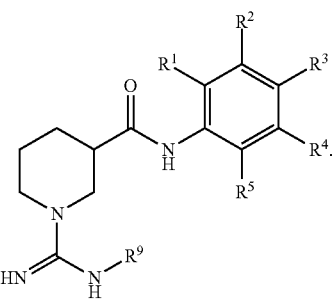

(VIII)

In further aspects, the compound is of formula (IX), wherein $R^1$-$R^5$ and $R^7$ are defined above:

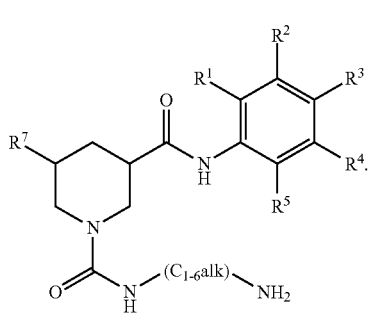

(IX)

In yet other aspects, the compound is of formula (X), wherein $R^1$-$R^5$ and $R^7$ are defined above:

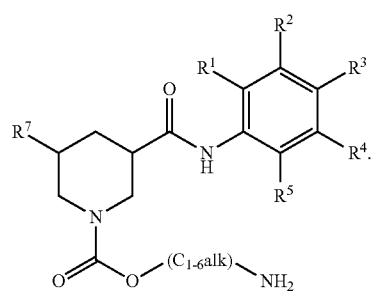

(X)

In still further aspects, the compound is:

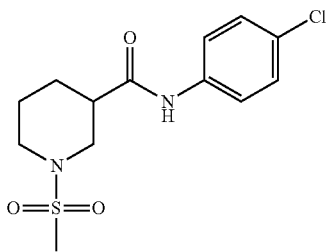

UM0059920

-continued
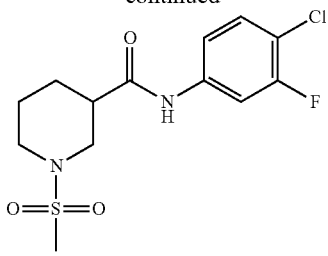
(S)-MCG-III-027-D05
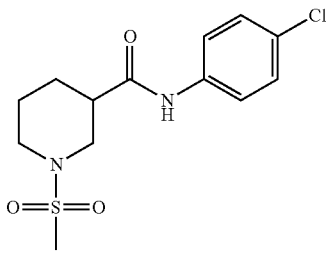
(S)-MCG-II-153
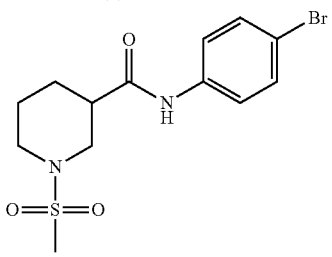
(S)-MCG-III-027-A02
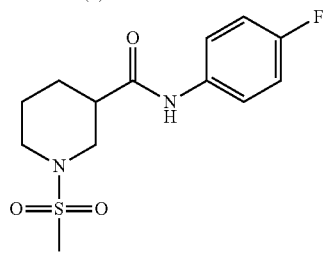
(S)-MCG-III-027-A03
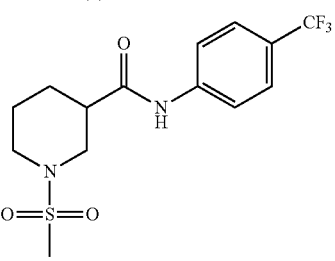
(S)-MCG-III-027-A04
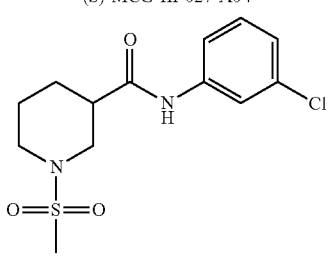
(S)-MCG-III-027-B01
-continued
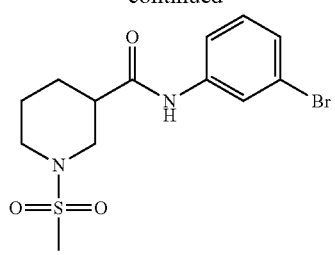
(S)-MCG-III-027-B02
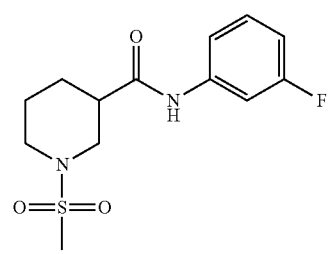
(S)-MCG-III-027-B03
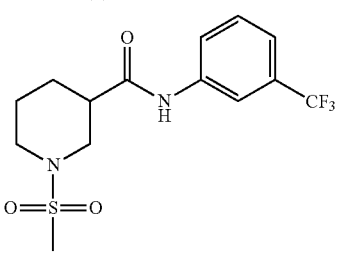
(S)-MCG-III-027-B04
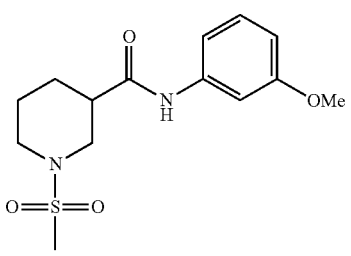
(S)-MCG-III-027-B05
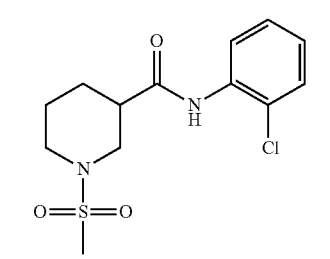
(S)-MCG-III-027-C01
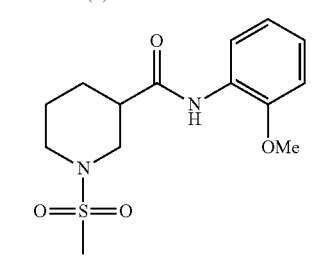
(S)-MCG-III-027-C05

-continued
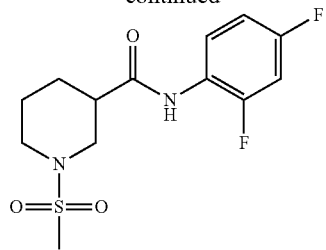
(S)-MCG-III-027-D04
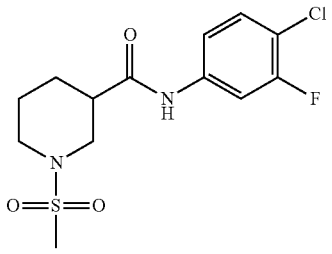
(S)-MCG-III-027-D05
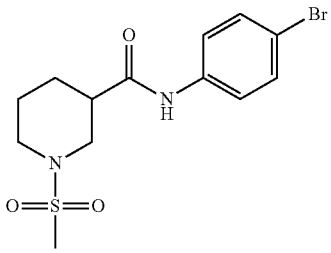
(S)-MCG-III-027-A02
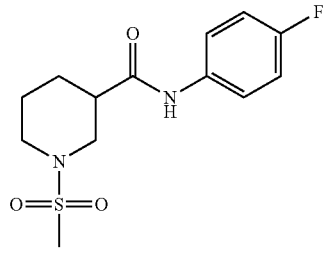
(S)-MCG-III-027-A03
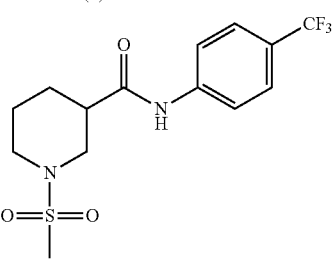
(S)-MCG-III-027-A04
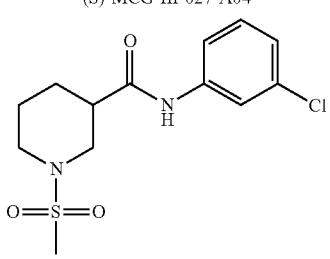
(S)-MCG-III-027-B01
-continued
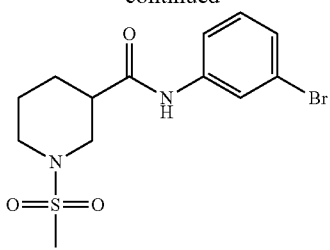
(S)-MCG-III-027-B02
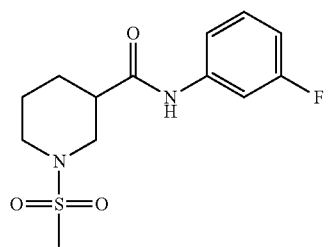
(S)-MCG-III-027-B03
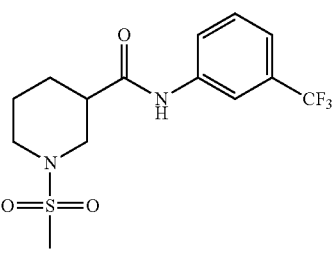
(S)-MCG-III-027-B04
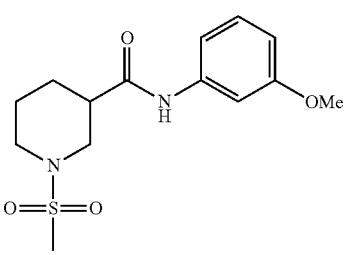
(S)-MCG-III-027-B05
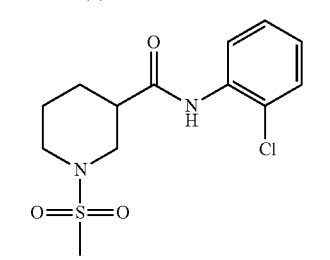
(S)-MCG-III-027-C01
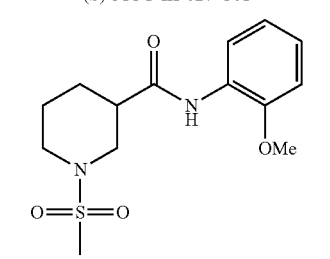
(S)-MCG-III-027-C05

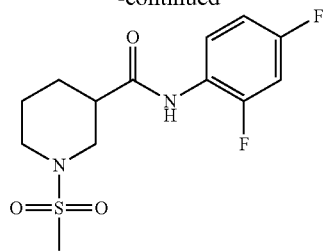
(S)-MCG-III-027-D04
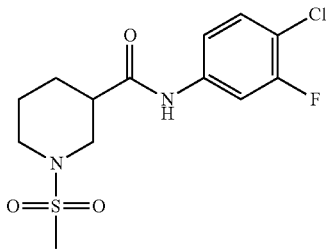
(S)-MCG-III-027-D05
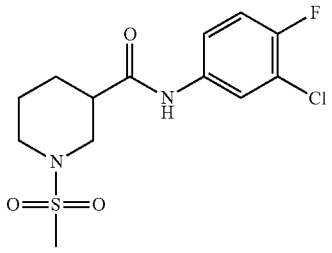
(S)-MCG-III-085-A02
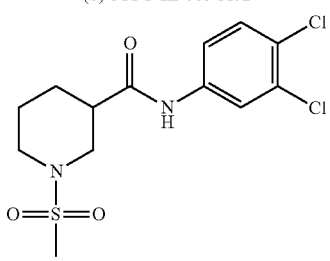
(S)-MCG-III-085-A03
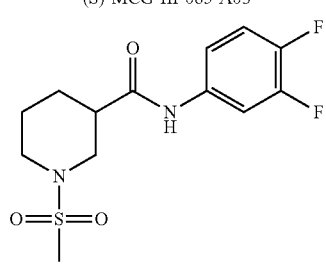
(S)-MCG-III-085-A04
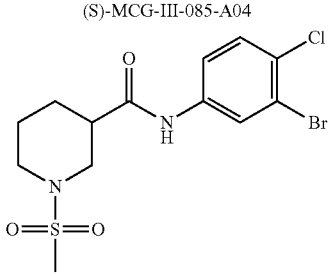
(S)-MCG-III-085-A05
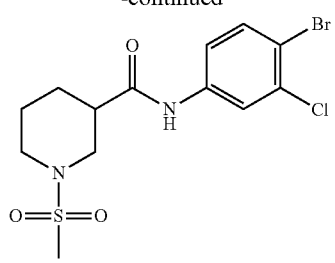
(S)-MCG-III-085-A06
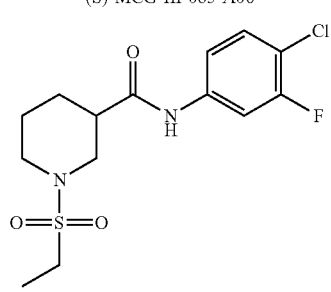
(S)-MCG-III-085-C01
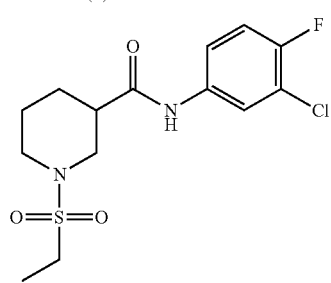
(S)-MCG-III-085-C02
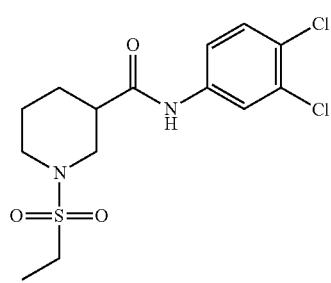
(S)-MCG-III-085-C03
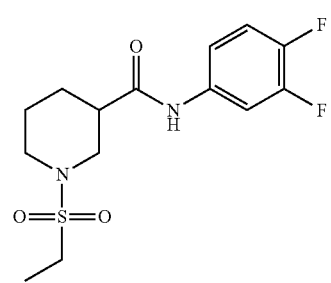
(S)-MCG-III-085-C04

-continued
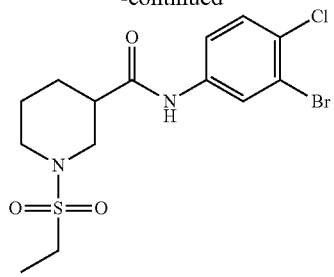
(S)-MCG-III-085-C05
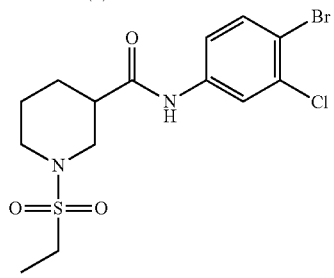
(S)-MCG-III-085-C06
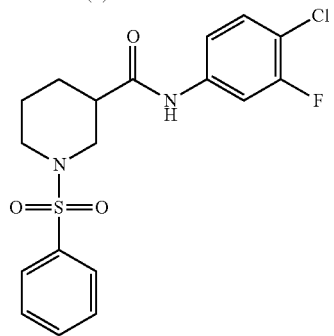
(S)-MCG-III-085-D01
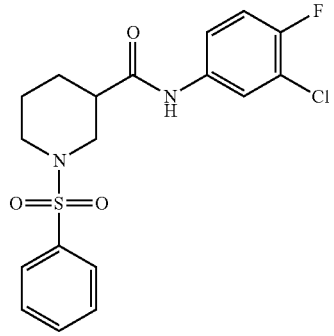
(S)-MCG-III-085-D02
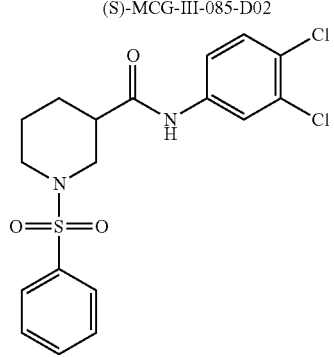
(S)-MCG-III-085-D03
-continued
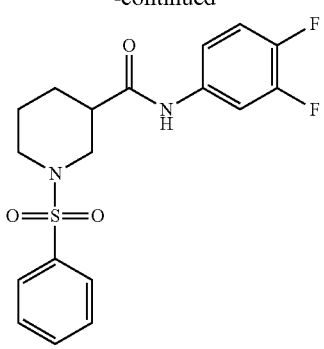
(S)-MCG-III-085-D04
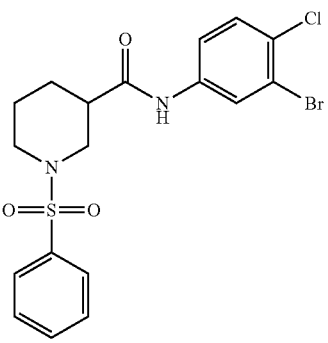
(S)-MCG-III-085-D05
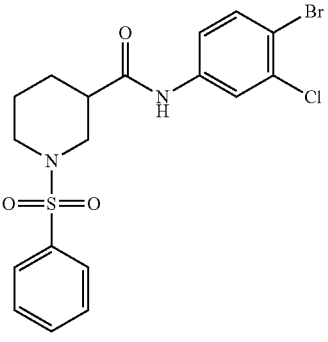
(S)-MCG-III-085-D06
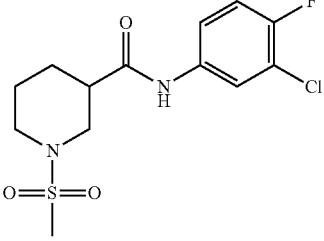
(S)-MCG-III-085-A02
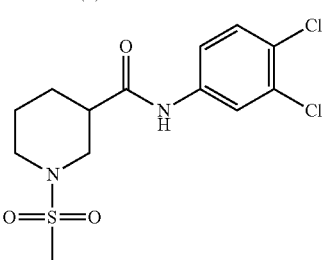
(S)-MCG-III-085-A03

-continued
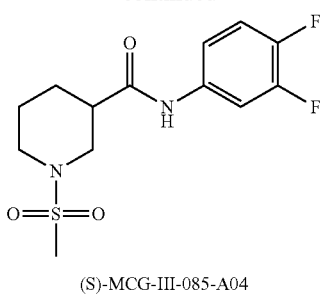
(S)-MCG-III-085-A04
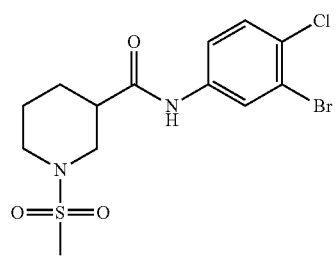
(S)-MCG-III-085-A05
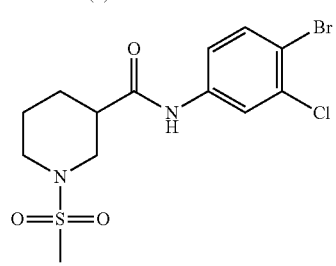
(S)-MCG-III-085-A06
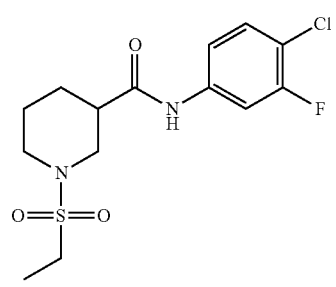
(S)-MCG-III-085-C01
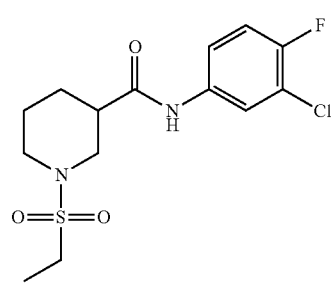
(S)-MCG-III-085-C02
-continued
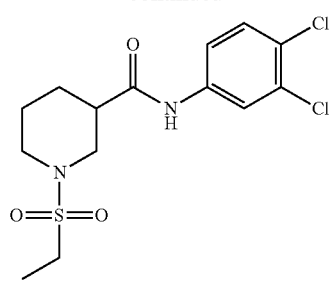
(S)-MCG-III-085-C03
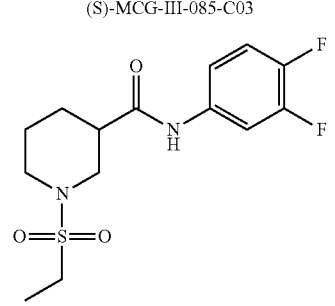
(S)-MCG-III-085-C04
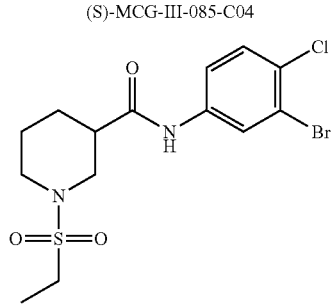
(S)-MCG-III-085-C05
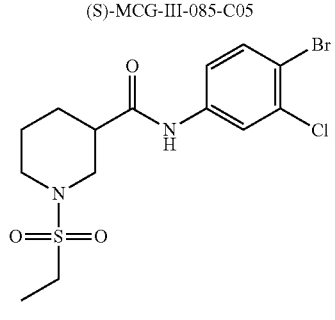
(S)-MCG-III-085-C06
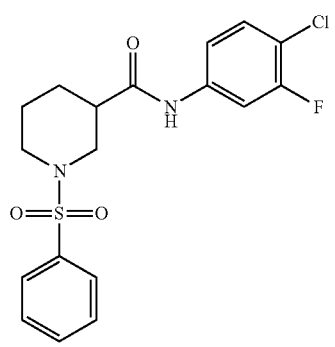
(S)-MCG-III-085-D01

-continued
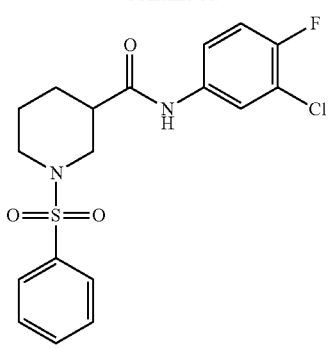
(S)-MCG-III-085-D02
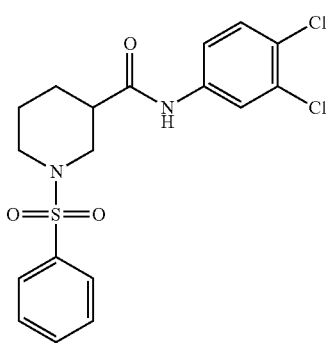
(S)-MCG-III-085-D03
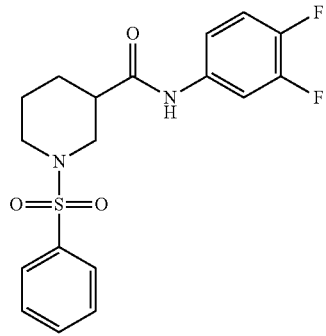
(S)-MCG-III-085-D04
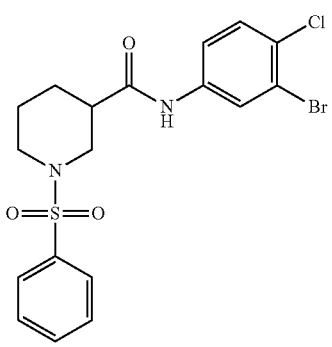
(S)-MCG-III-085-D05
-continued
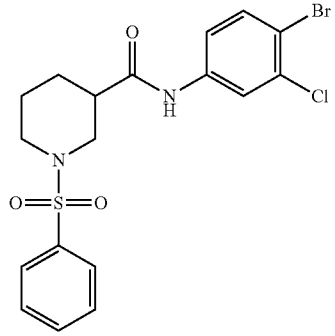
(S)-MCG-III-085-D06
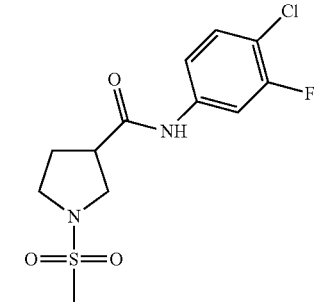
MCG-III-157-A01
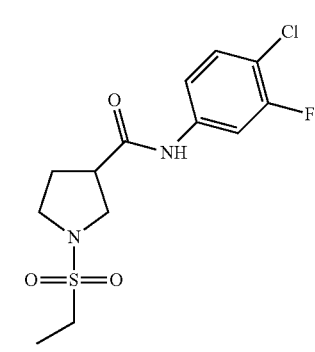
MCG-III-157-A02
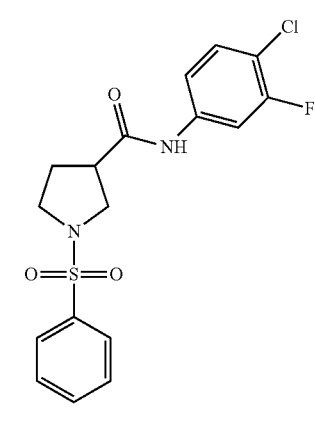
MCG-III-157-A03

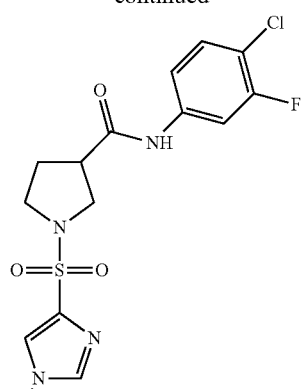
MCG-III-157-A04
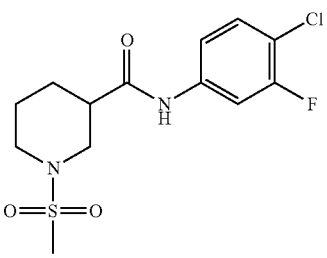
MCG-III-157-B01
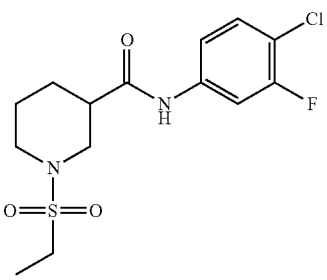
MCG-III-157-B02
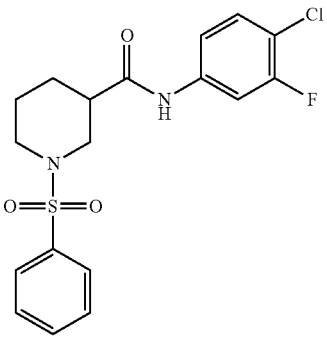
MCG-III-157-B03
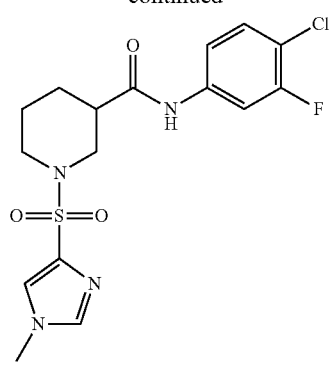
MCG-III-157-B04
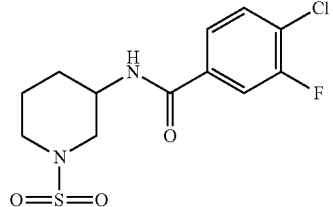
MCG-III-157-C01
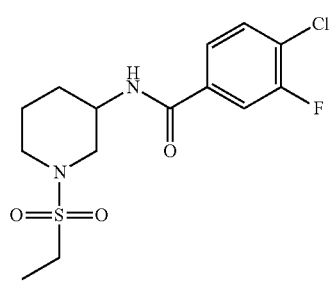
MCG-III-157-C02
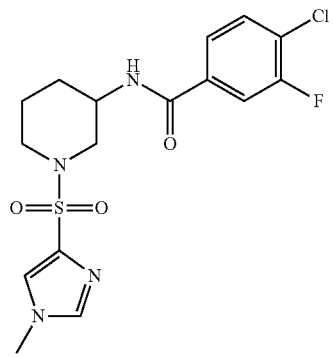
MCG-III-157-C04
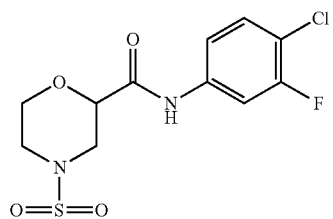
MCG-III-211-A01

-continued
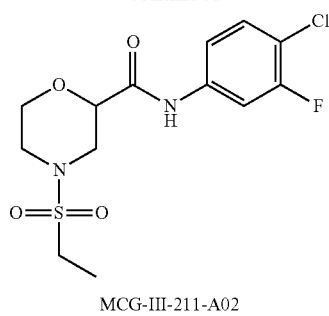
MCG-III-211-A02
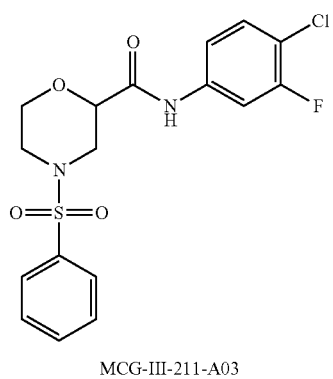
MCG-III-211-A03
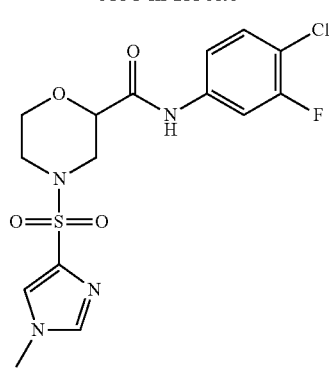
MCG-III-211-A04
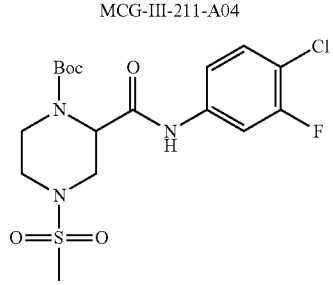
MCG-III-212-A01
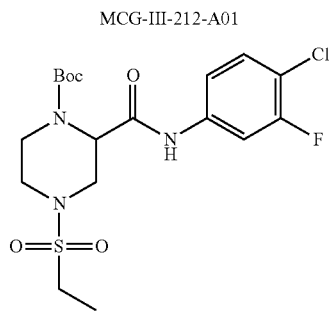
MCG-III-212-A02
-continued
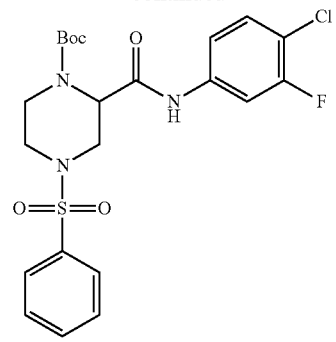
MCG-III-212-A03
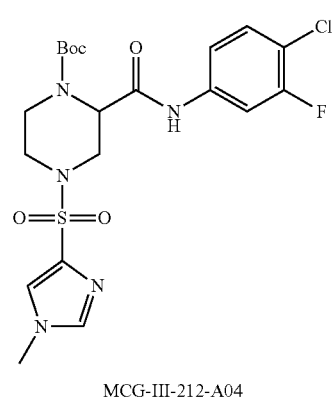
MCG-III-212-A04
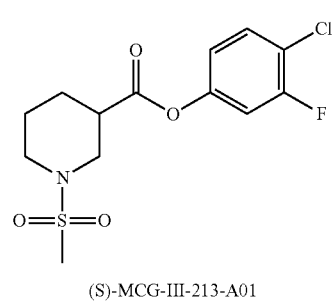
(S)-MCG-III-213-A01
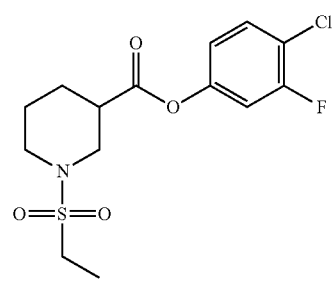
(S)-MCG-III-213-A02

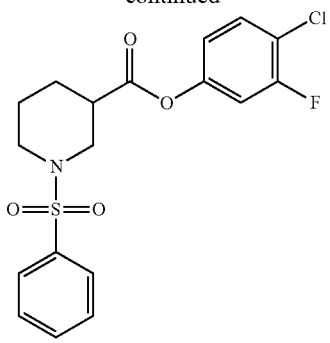
(S)-MCG-III-213-A03
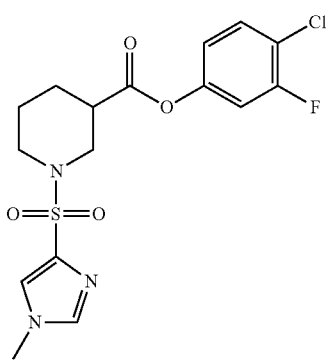
(S)-MCG-III-213-A04
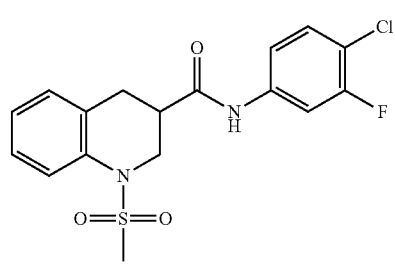
MCG-III-214-A01
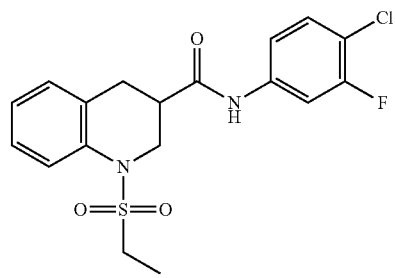
MCG-III-214-A02
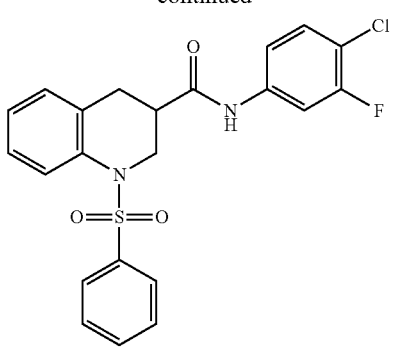
MCG-III-214-A03
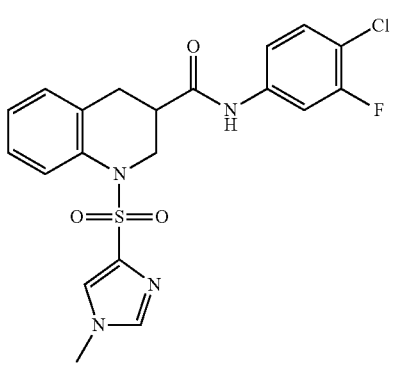
MCG-III-214-A04
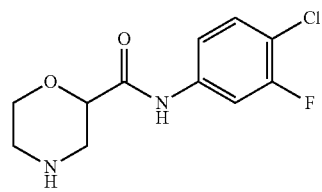
MCG-III-196
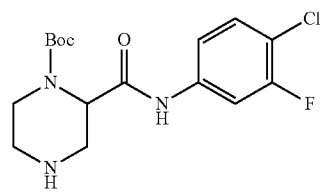
MCG-III-210
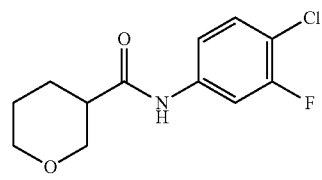
MCG-III-207
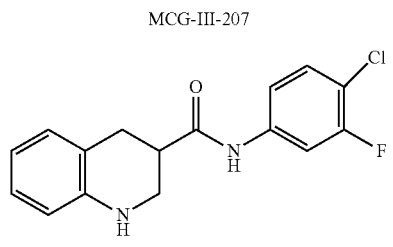
MCG-III-209

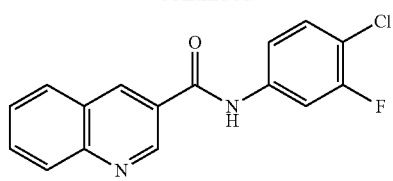
MCG-III-204
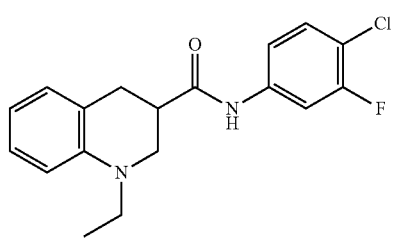
MCG-III-201
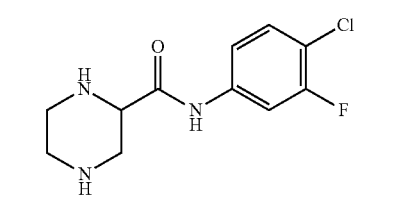
MCG-III-216-A01
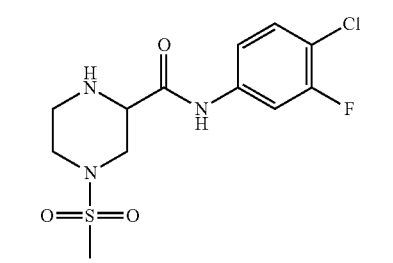
MCG-III-216-A02
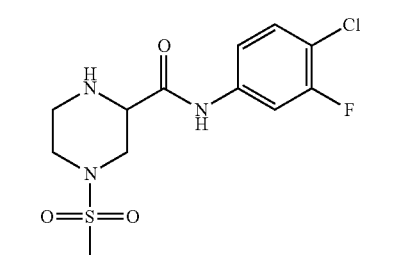
MCG-III-212-A02
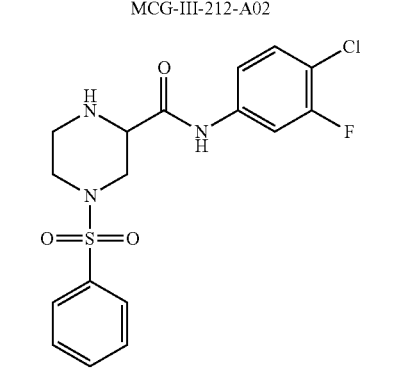
MCG-III-216-A03
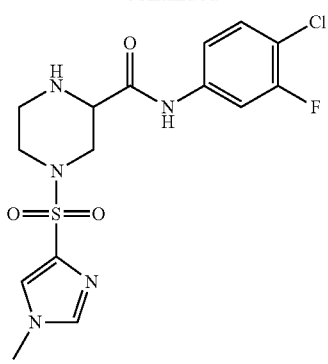
MCG-III-216-A04
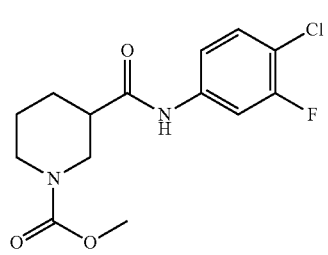
(S)-MCG-III-188-A01
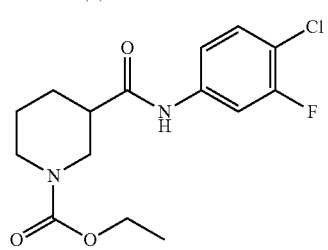
(S)-MCG-III-188-A02
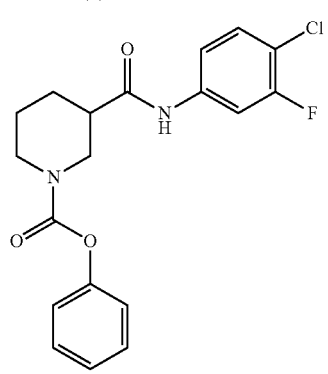
(S)-MCG-III-188-A03
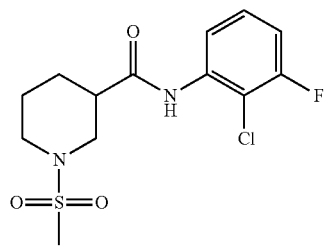
(S)-MCG-IV-024-A01

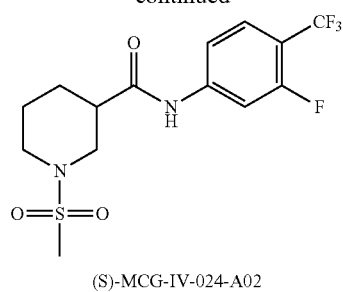
(S)-MCG-IV-024-A02
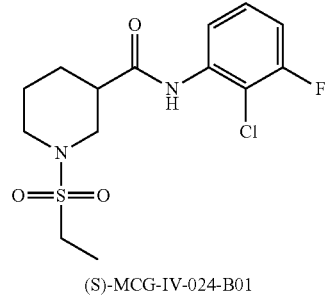
(S)-MCG-IV-024-B01
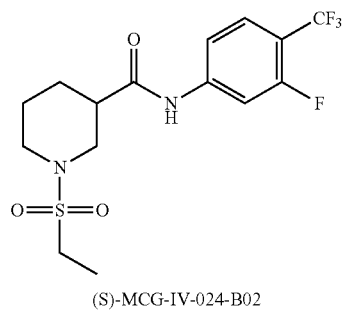
(S)-MCG-IV-024-B02
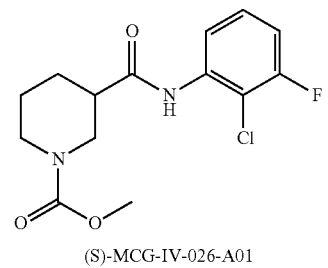
(S)-MCG-IV-026-A01
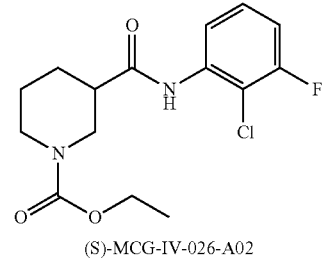
(S)-MCG-IV-026-A02
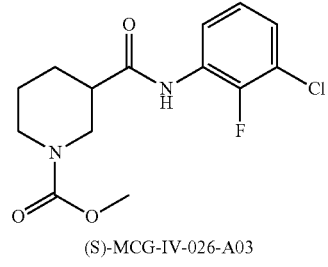
(S)-MCG-IV-026-A03
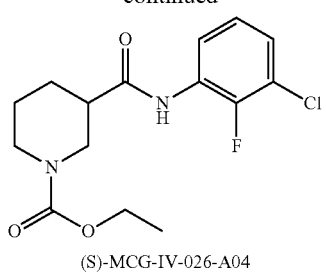
(S)-MCG-IV-026-A04
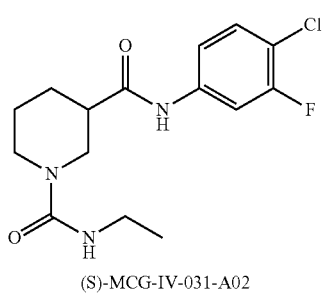
(S)-MCG-IV-031-A02
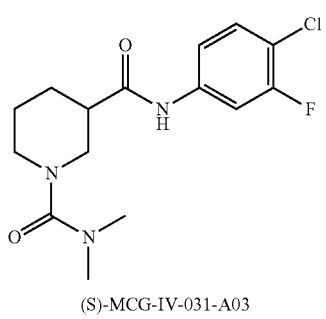
(S)-MCG-IV-031-A03
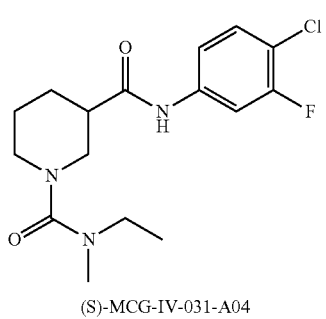
(S)-MCG-IV-031-A04
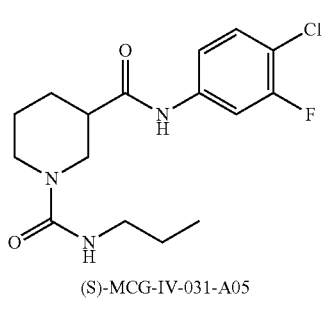
(S)-MCG-IV-031-A05

-continued
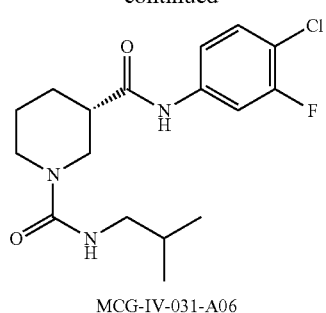
MCG-IV-031-A06
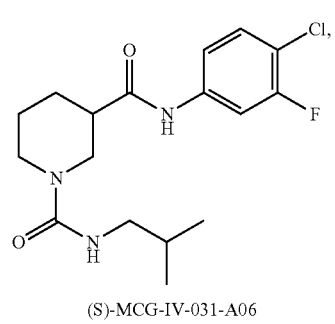
(S)-MCG-IV-031-A06
or a pharmaceutically acceptable salt thereof.
In still further aspects, the compound is:
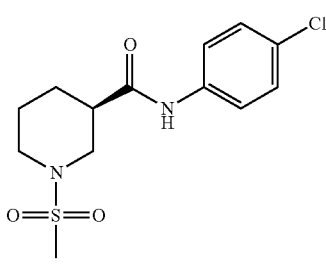
(R)-MCG-II-156
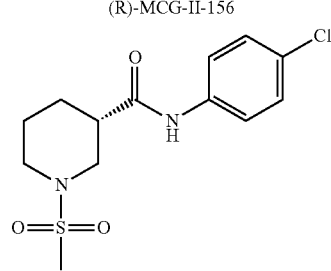
(S)-MCG-II-153
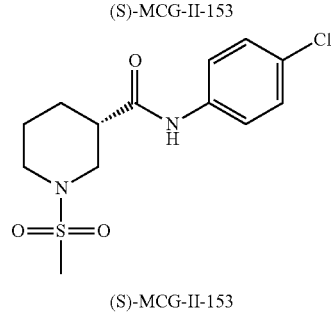
(S)-MCG-II-153
-continued
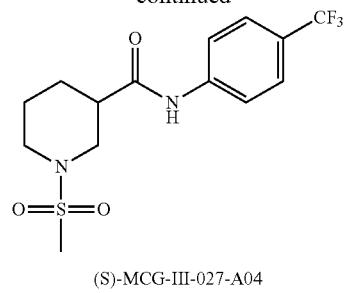
(S)-MCG-III-027-A04
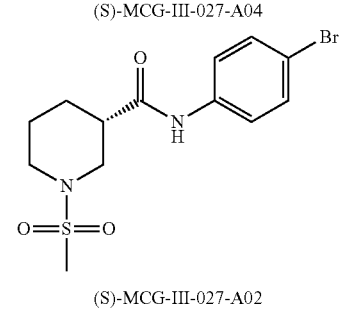
(S)-MCG-III-027-A02
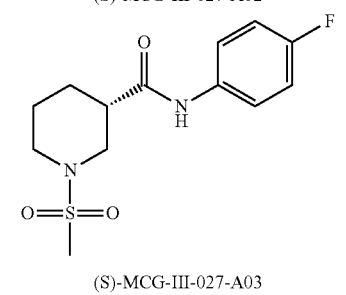
(S)-MCG-III-027-A03
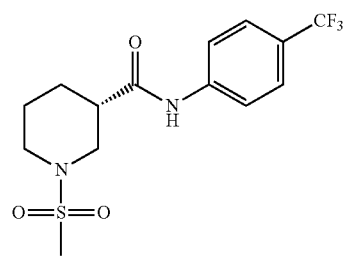
(S)-MCG-III-027-A04
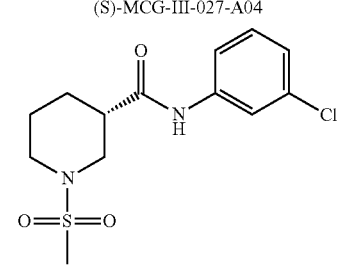
(S)-MCG-III-027-B01
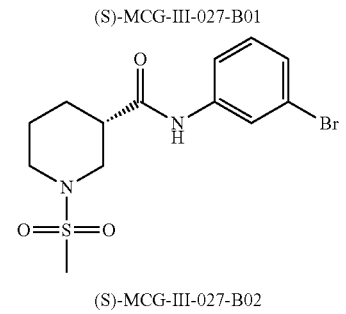
(S)-MCG-III-027-B02

-continued
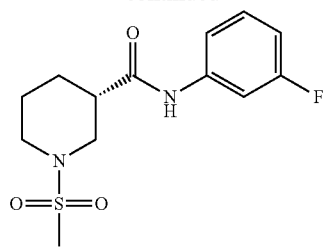
(S)-MCG-III-027-B03
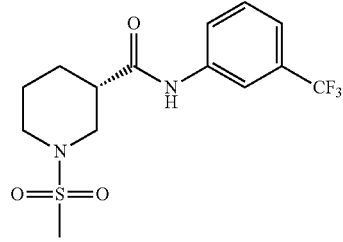
(S)-MCG-III-027-B04
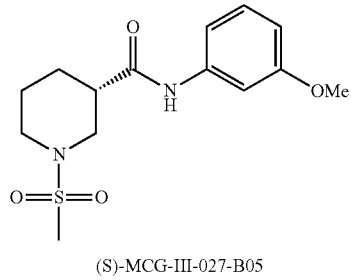
(S)-MCG-III-027-B05
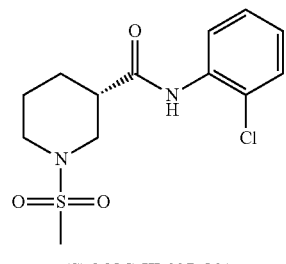
(S)-MCG-III-027-C01
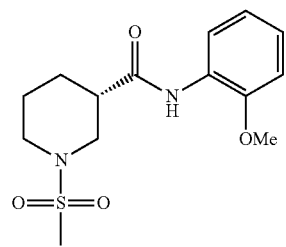
(S)-MCG-III-027-C05
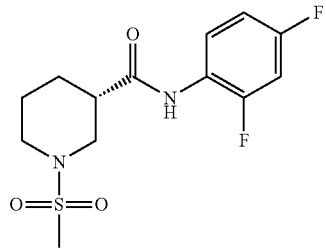
(S)-MCG-III-027-D04
-continued
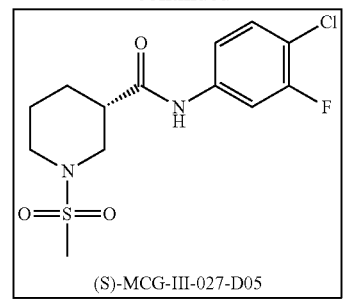
(S)-MCG-III-027-D05
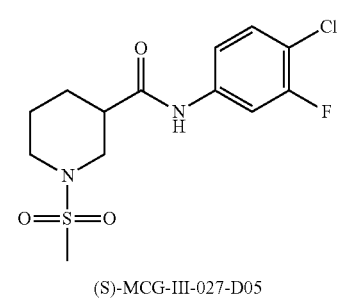
(S)-MCG-III-027-D05
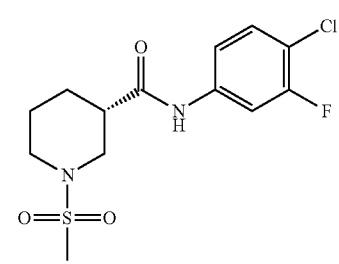
(S)-MCG-III-027-D05
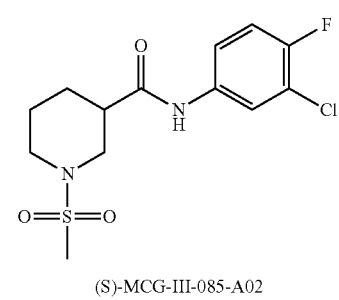
(S)-MCG-III-085-A02
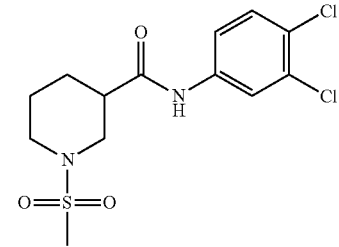
(S)-MCG-III-085-A03

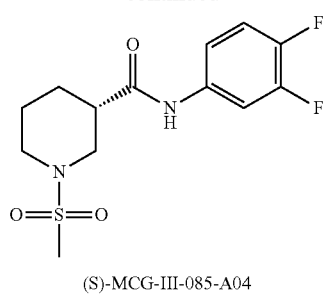
(S)-MCG-III-085-A04
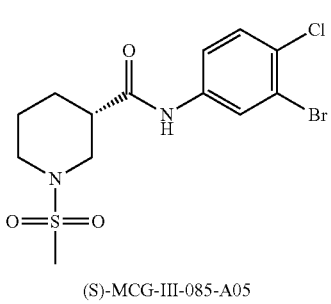
(S)-MCG-III-085-A05
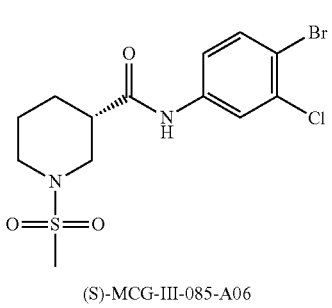
(S)-MCG-III-085-A06
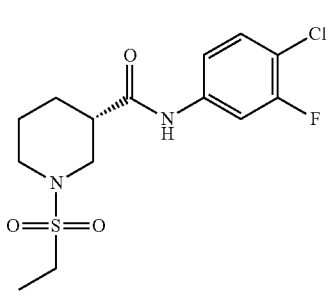
(S)-MCG-III-085-C01
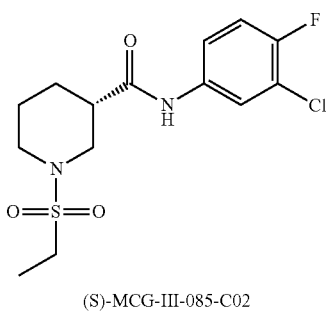
(S)-MCG-III-085-C02
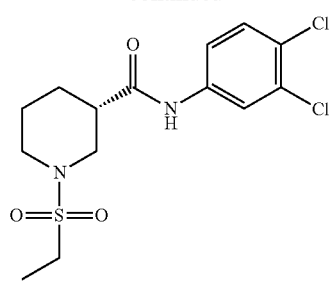
(S)-MCG-III-085-C03
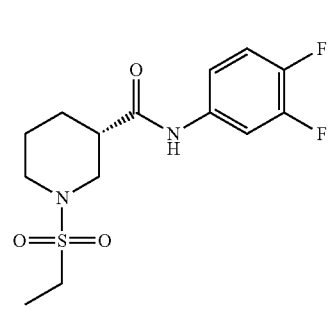
(S)-MCG-III-085-C04
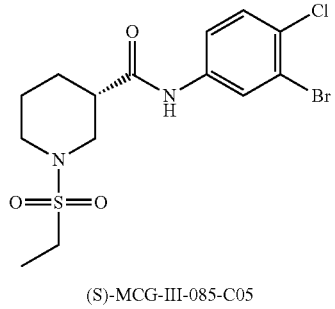
(S)-MCG-III-085-C05
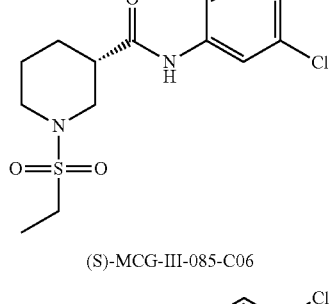
(S)-MCG-III-085-C06
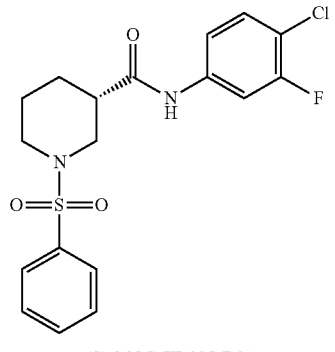
(S)-MCG-III-085-D01

-continued
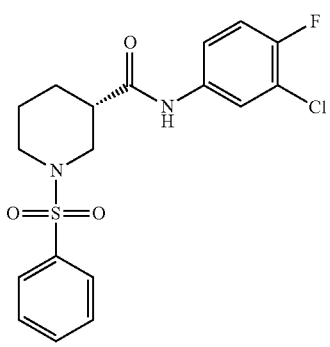
(S)-MCG-III-085-D02
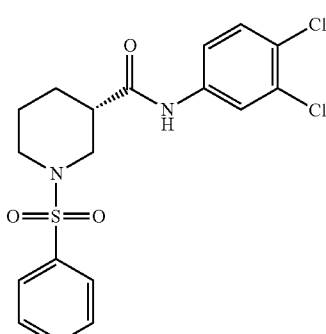
(S)-MCG-III-085-D03
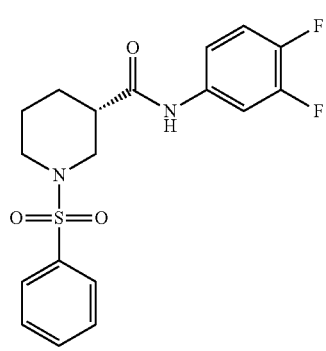
(S)-MCG-III-085-D04
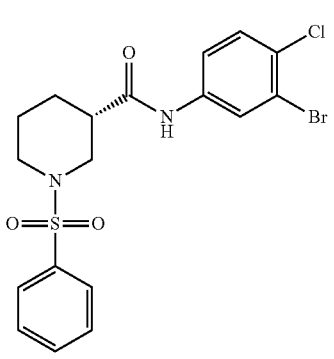
(S)-MCG-III-085-D05
-continued
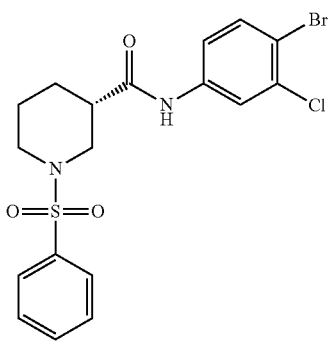
(S)-MCG-III-085-D06
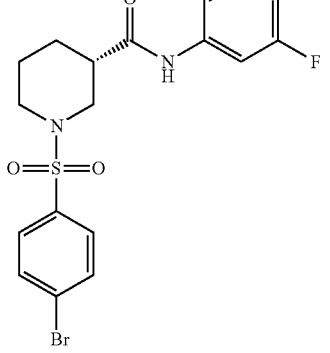
(S)-MCG-III-128
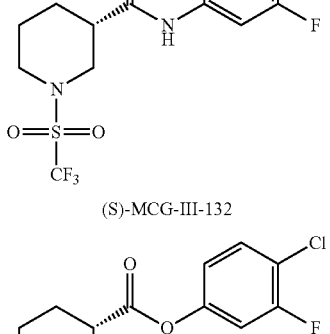
(S)-MCG-III-132
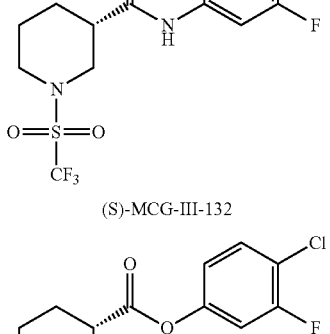
(S)-MCG-III-213-A01
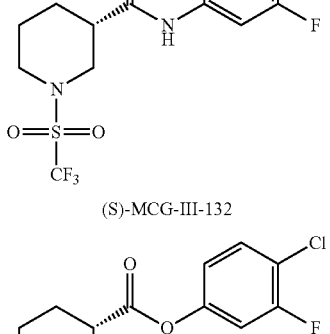
(S)-MCG-III-213-A02

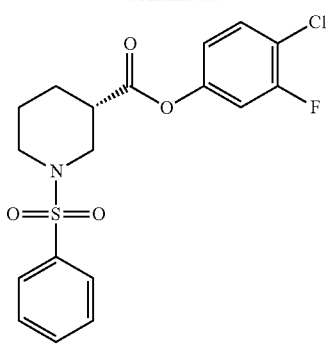
(S)-MCG-III-213-A03
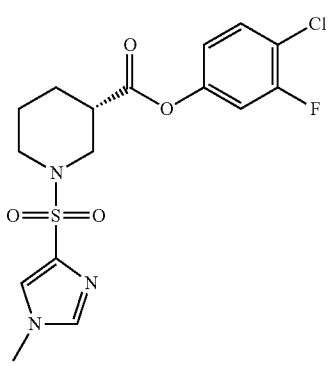
MCG-III-213-A04
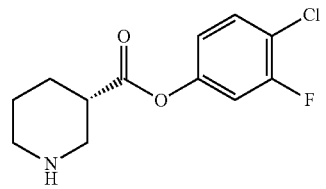
(S)-MCG-III-189
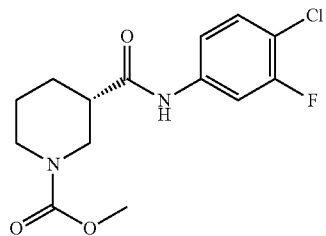
(S)-MCG-III-188-A01
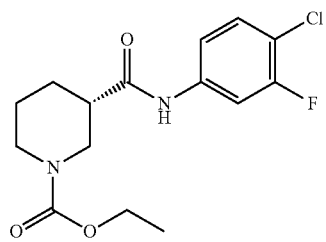
(S)-MCG-III-188-A02
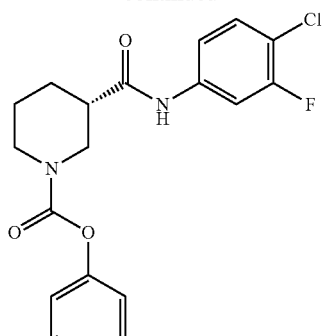
(S)-MCG-III-188-A03
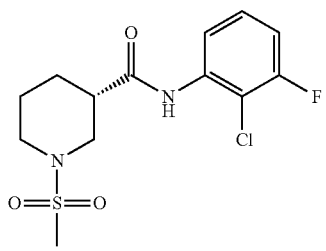
MCG-IV-024-A01
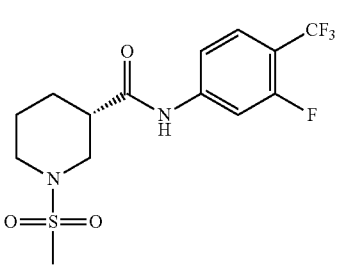
MCG-IV-024-A02
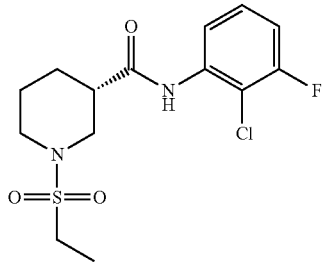
MCG-IV-024-B01
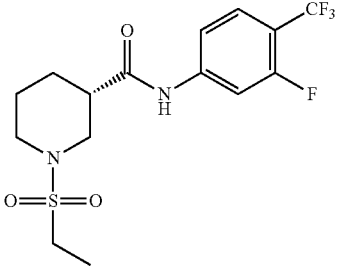
MCG-IV-024-B02

-continued
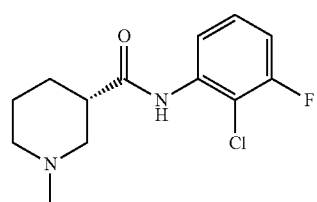
MCG-IV-026-A01
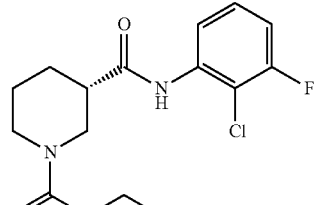
MCG-IV-026-A02
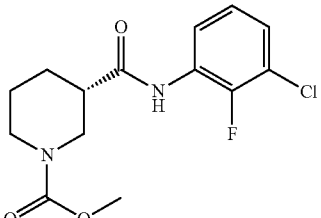
MCG-IV-026-A03
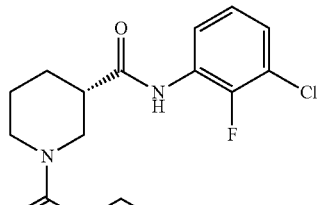
MCG-IV-026-A04
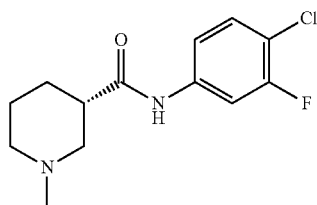
MCG-IV-031-A02
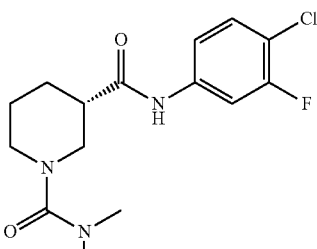
MCG-IV-031-A03
-continued
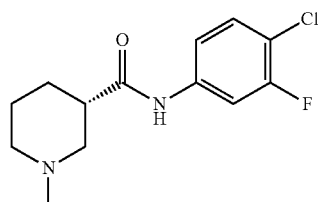
MCG-IV-031-A04
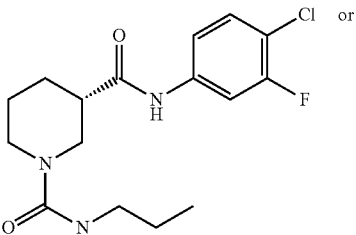
MCG-IV-031-A05
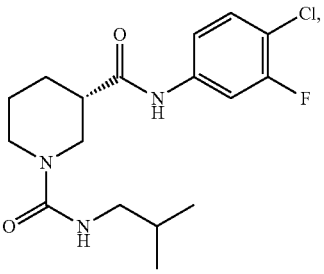
MCG-IV-031-A06
or a pharmaceutically acceptable salt thereof.
In still further aspects, the compound is:
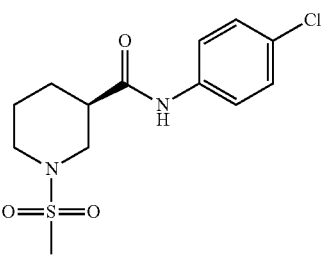
(R)-MCG-II-156
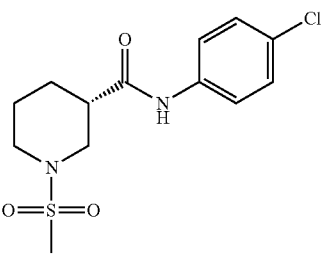
(S)-MCG-II-153

-continued
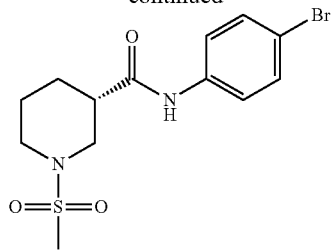
(S)-MCG-III-027-A02
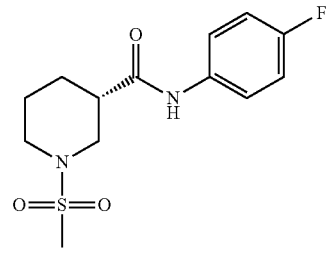
(S)-MCG-III-027-A03
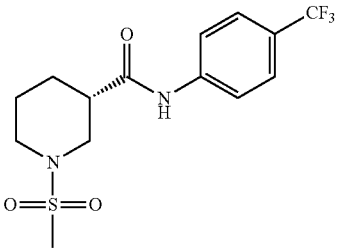
(S)-MCG-III-027-A04
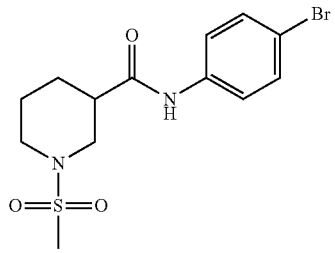
(S)-MCG-III-027-A02
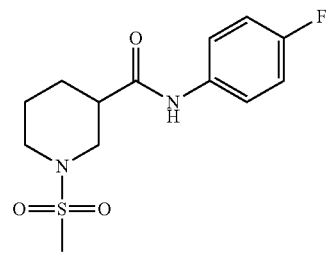
(S)-MCG-III-027-A03
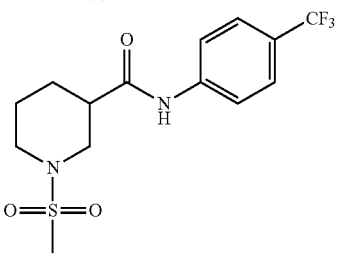
(S)-MCG-III-027-A04
-continued
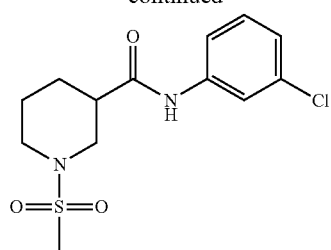
(S)-MCG-III-027-B01
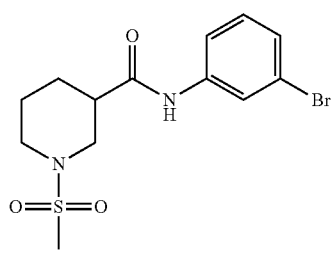
(S)-MCG-III-027-B02
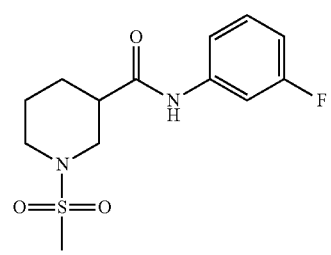
(S)-MCG-III-027-B03
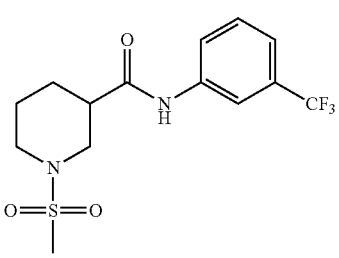
(S)-MCG-III-027-B04
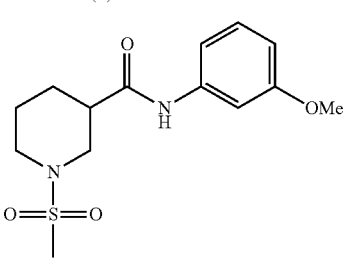
(S)-MCG-III-027-B05
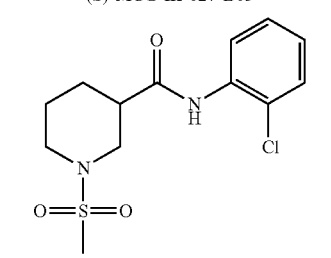
(S)-MCG-III-027-C01

-continued
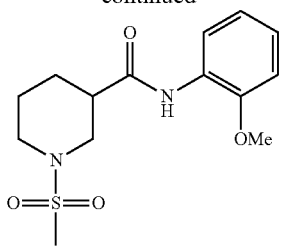
(S)-MCG-III-027-C05
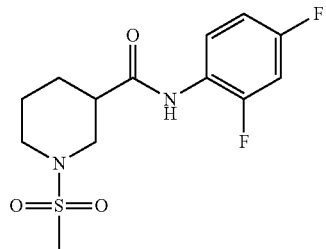
(S)-MCG-III-027-D04
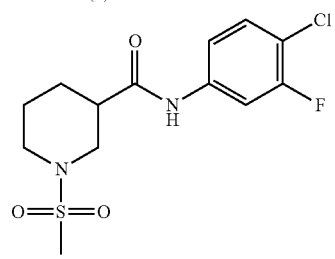
(S)-MCG-III-027-D05
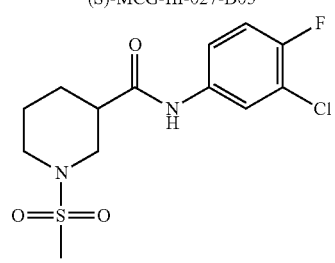
(S)-MCG-III-085-A02
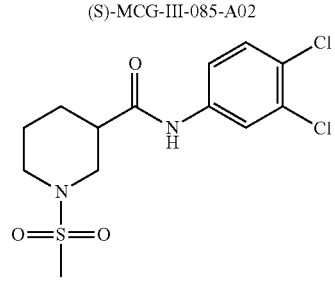
(S)-MCG-III-085-A03
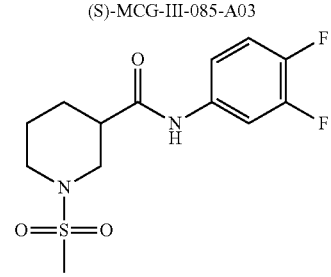
(S)-MCG-III-085-A04
-continued
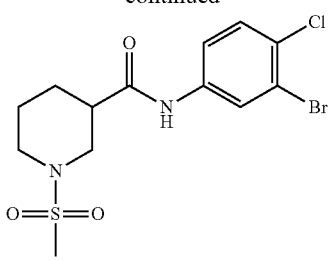
(S)-MCG-III-085-A05
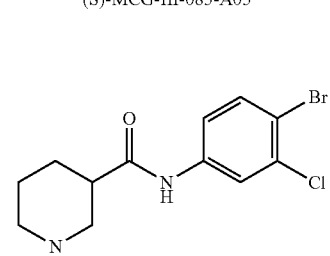
(S)-MCG-III-085-A06
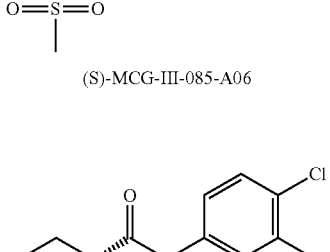
(S)-MCG-III-085-C01
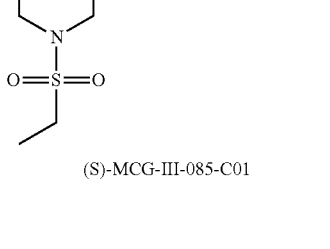
(S)-MCG-III-085-C02
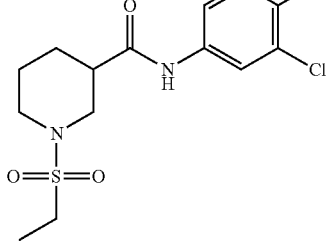
(S)-MCG-III-085-C03

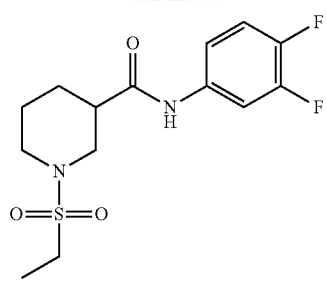
(S)-MCG-III-085-C04
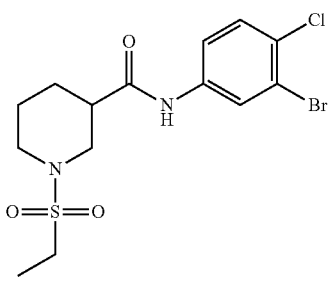
(S)-MCG-III-085-C05
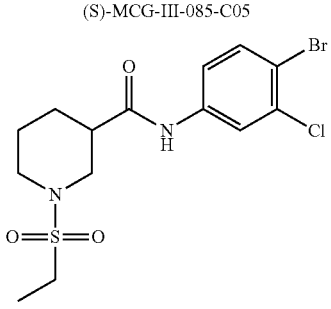
(S)-MCG-III-085-C06
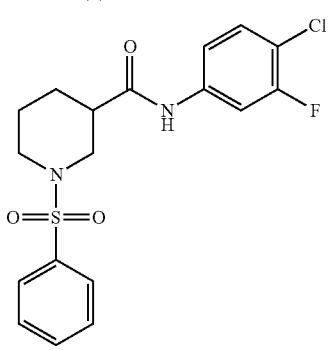
(S)-MCG-III-085-D01
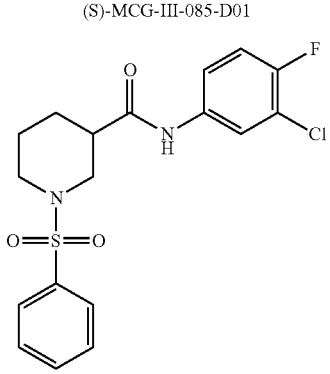
(S)-MCG-III-085-D02
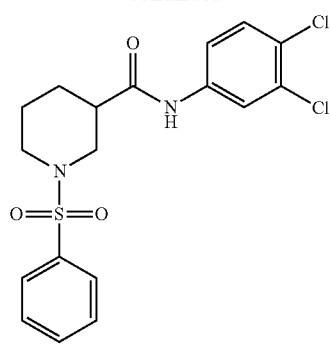
(S)-MCG-III-085-D03
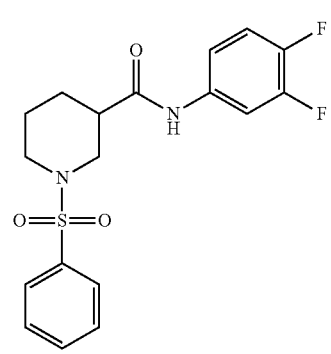
(S)-MCG-III-085-D04
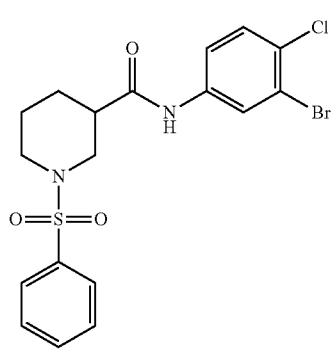
(S)-MCG-III-085-D05
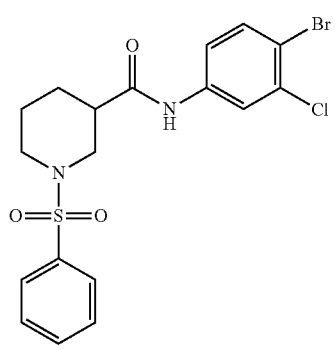
(S)-MCG-III-085-D06

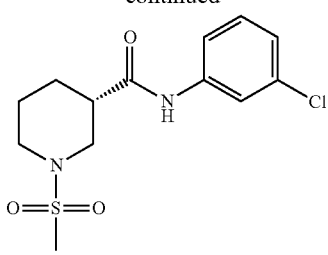
(S)-MCG-III-027-B01
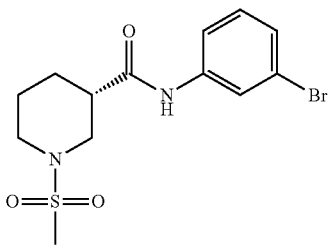
(S)-MCG-III-027-B02
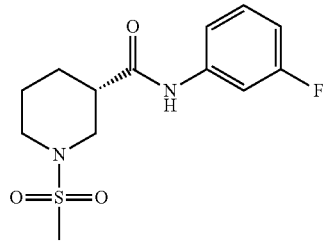
(S)-MCG-III-027-B03
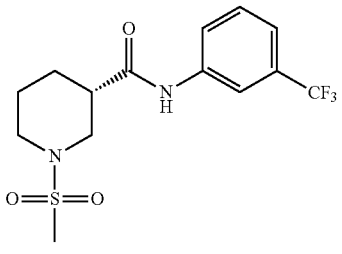
(S)-MCG-III-027-B04
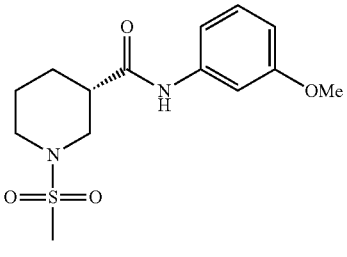
(S)-MCG-III-027-B05
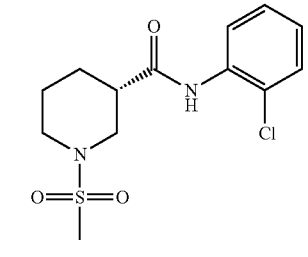
(S)-MCG-III-027-C01
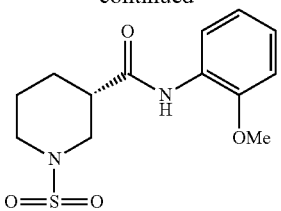
(S)-MCG-III-027-C05
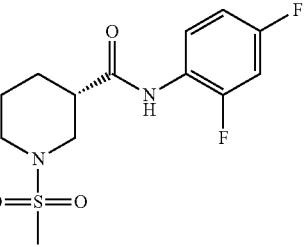
(S)-MCG-III-027-D04
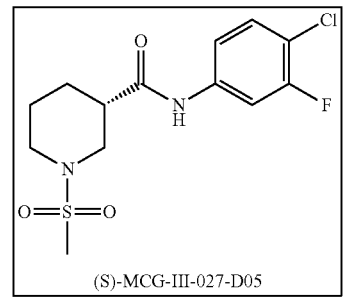
(S)-MCG-III-027-D05
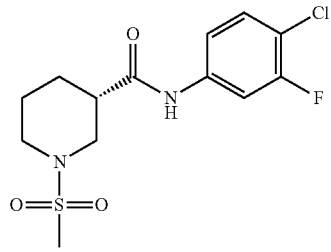
(S)-MCG-III-027-D05
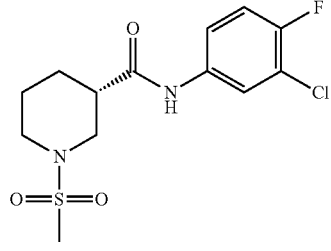
(S)-MCG-III-085-A02
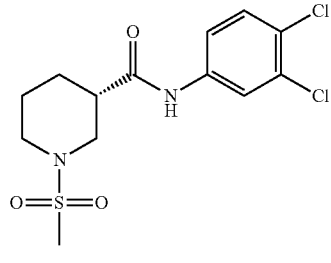
(S)-MCG-III-085-A03

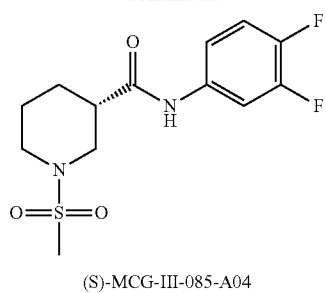
(S)-MCG-III-085-A04
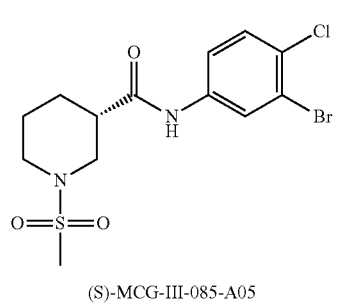
(S)-MCG-III-085-A05
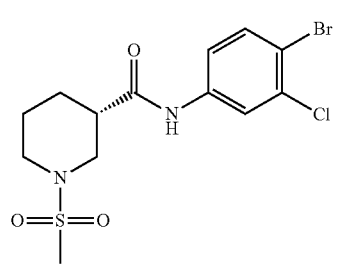
(S)-MCG-III-085-A06
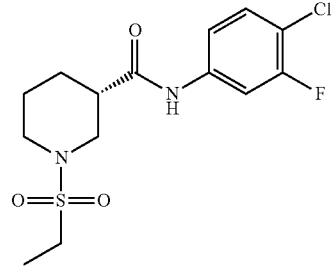
(S)-MCG-III-085-C01
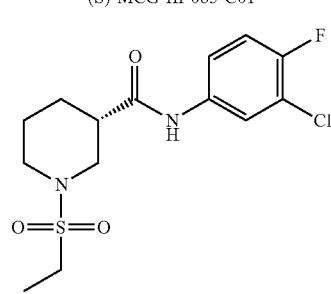
(S)-MCG-III-085-C02
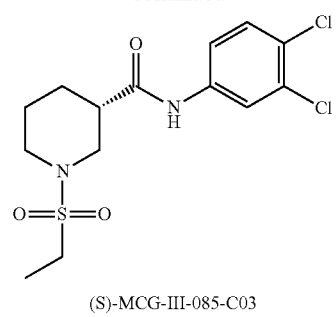
(S)-MCG-III-085-C03
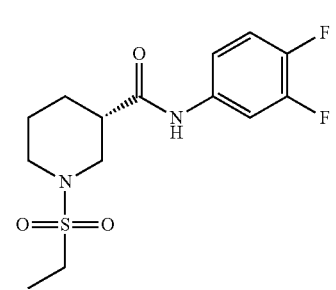
(S)-MCG-III-085-C04
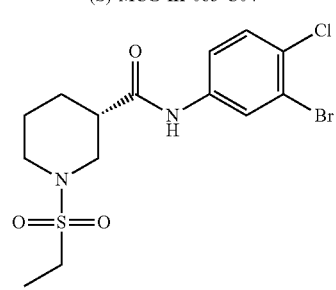
(S)-MCG-III-085-C05
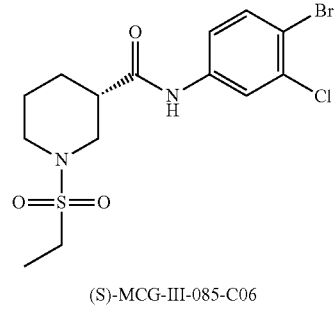
(S)-MCG-III-085-C06
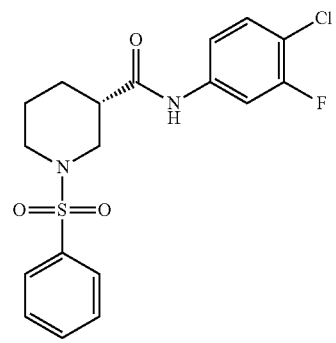
(S)-MCG-III-085-D01

-continued
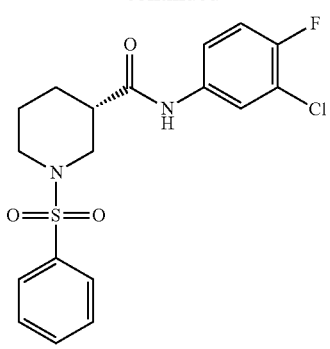
(S)-MCG-III-085-D02
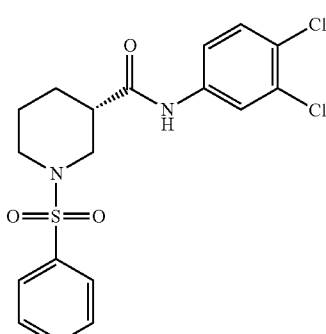
(S)-MCG-III-085-D03
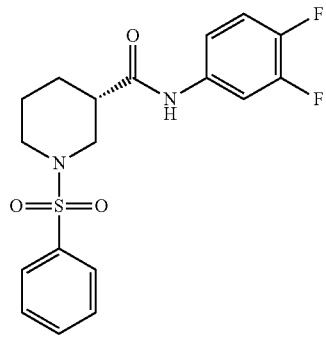
(S)-MCG-III-085-D04
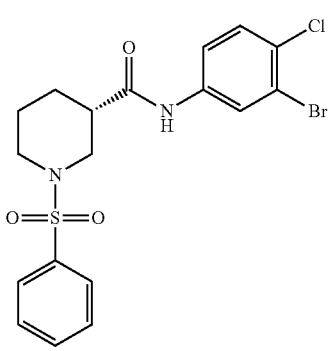
(S)-MCG-III-085-D05
-continued
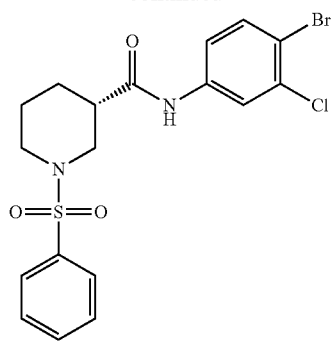
(S)-MCG-III-085-D06
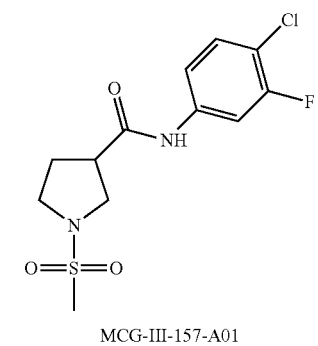
MCG-III-157-A01
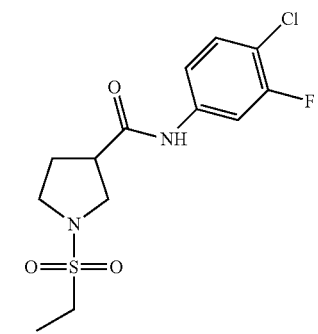
MCG-III-157-A02
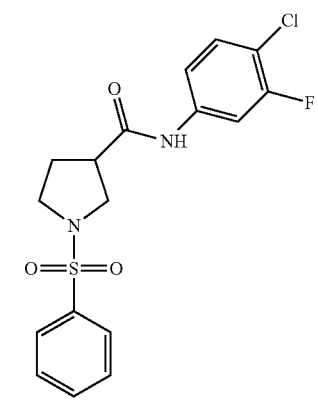
MCG-III-157-A03

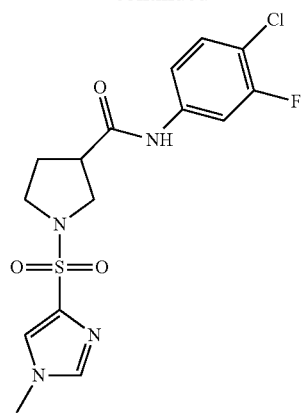
MCG-III-157-A04
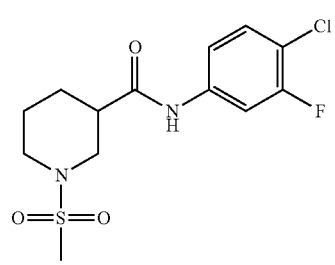
MCG-III-157-B01
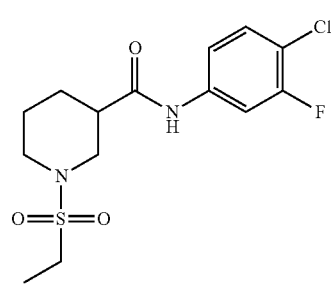
MCG-III-157-B02
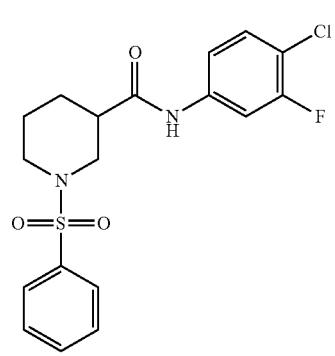
MCG-III-157-B03
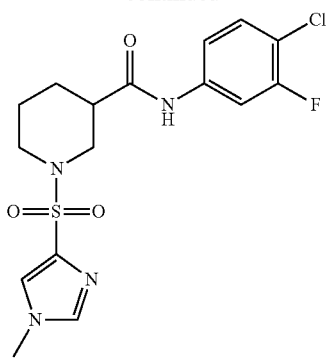
MCG-III-157-B04
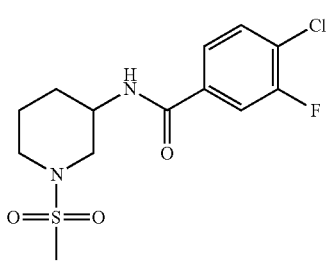
MCG-III-157-C01
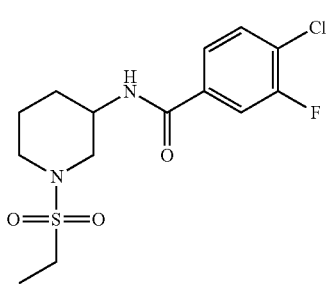
MCG-III-157-C02
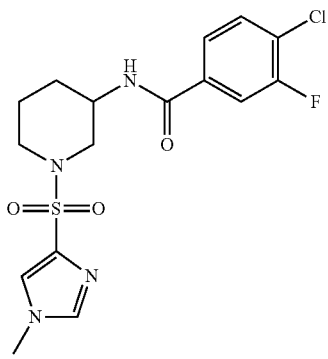
MCG-III-157-C04

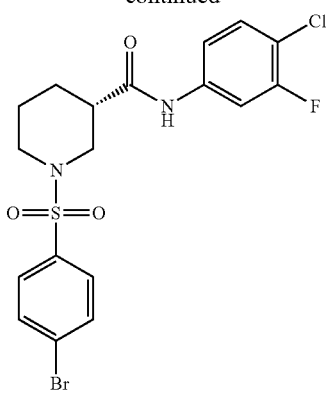
(S)-MCG-III-128
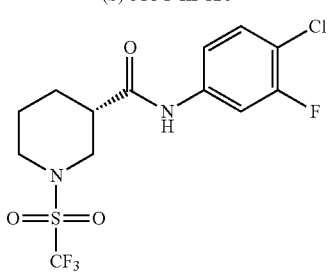
(S)-MCG-III-132
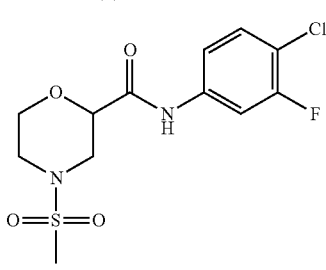
MCG-III-211-A01
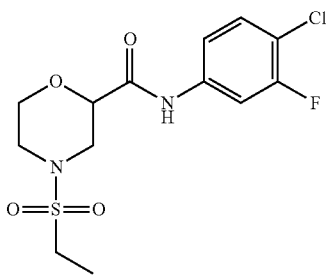
MCG-III-211-A02
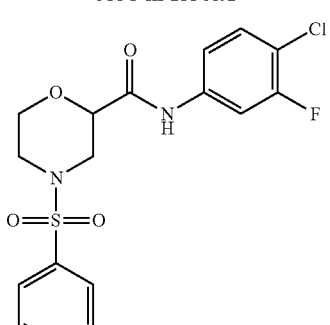
MCG-III-211-A03
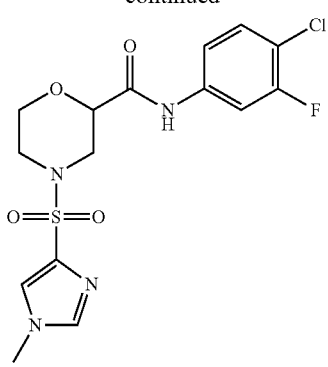
MCG-III-211-A04
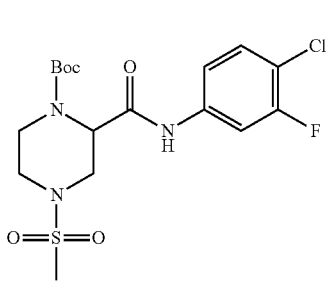
MCG-III-212-A01
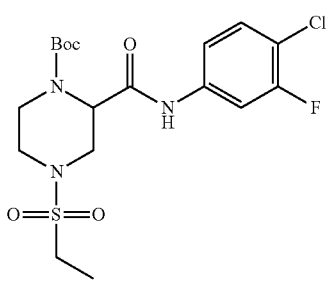
MCG-III-212-A02
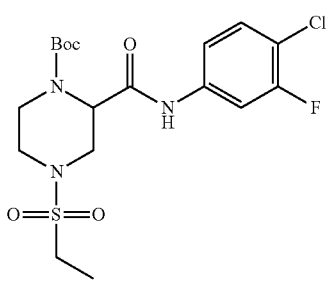
MCG-III-212-A03

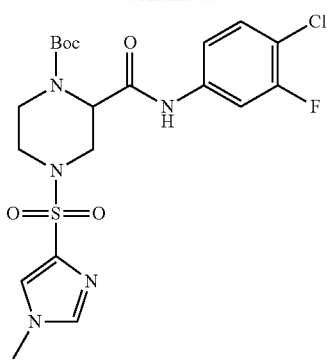
MCG-III-212-A04
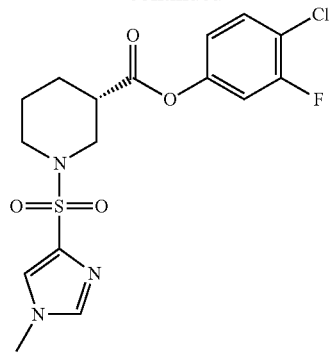
(S)-MCG-III-213-A04
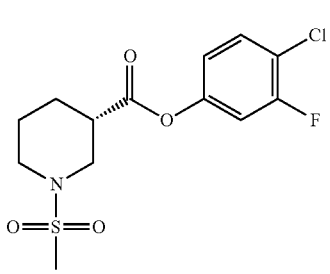
(S)-MCG-III-213-A01
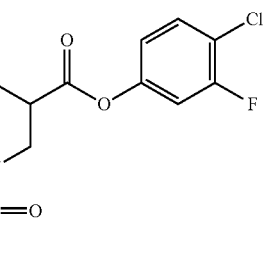
(S)-MCG-III-213-A01
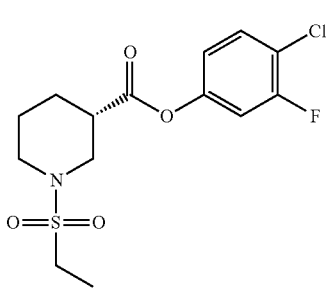
(S)-MCG-III-213-A02
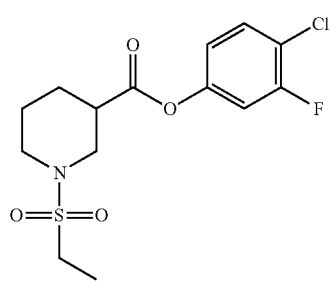
(S)-MCG-III-213-A02
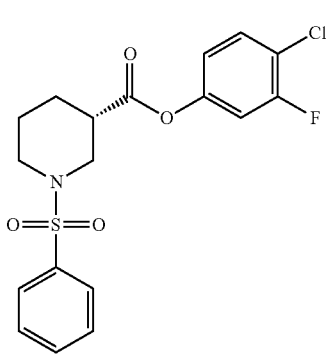
(S)-MCG-III-213-A03
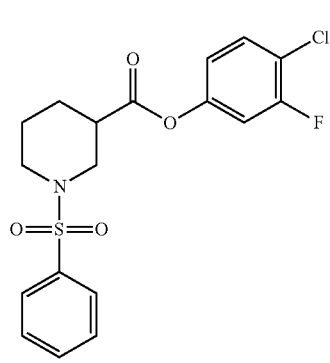
(S)-MCG-III-213-A03

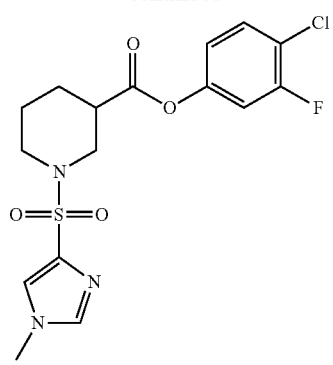
(S)-MCG-III-212-A04
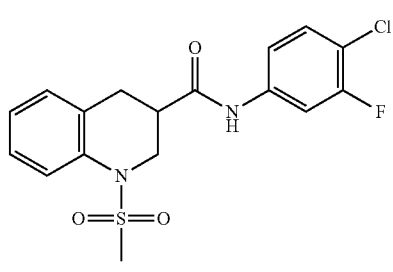
MCG-III-214-A01
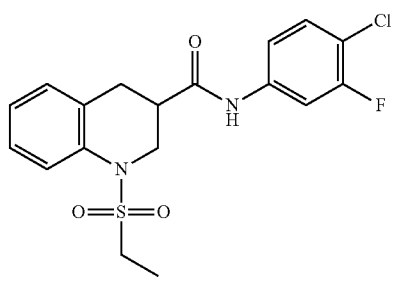
MCG-III-214-A02
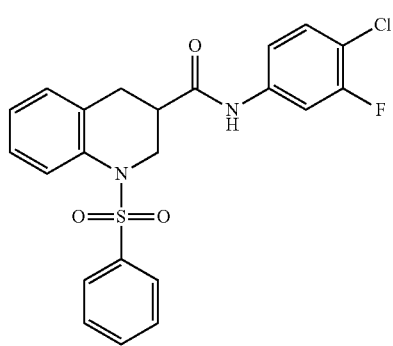
MCG-III-214-A03
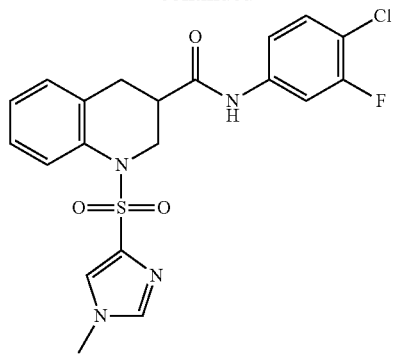
MCG-III-214-A04
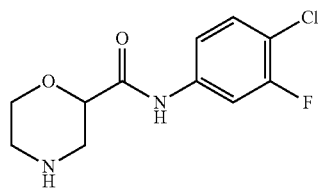
MCG-III-196
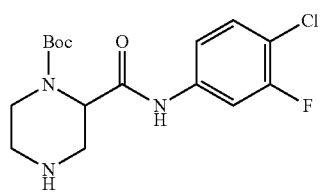
MCG-III-210
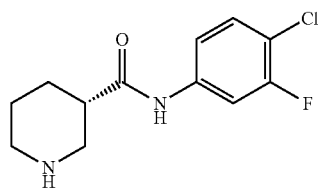
(S)-MCG-III-189
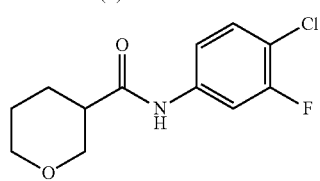
MCG-III-207
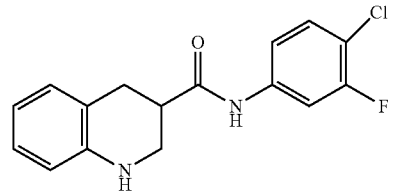
MCG-III-209
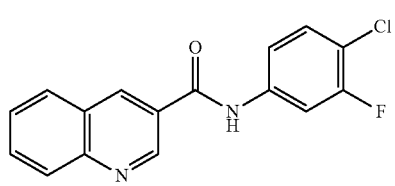
MCG-III-204

-continued
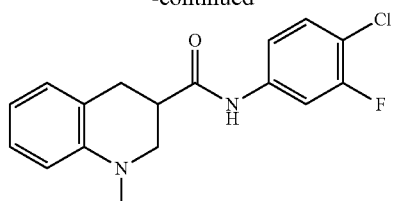
MCG-III-201
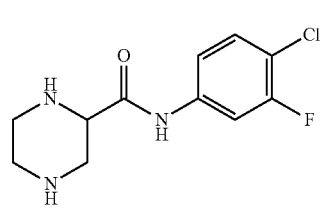
MCG-III-216-A01
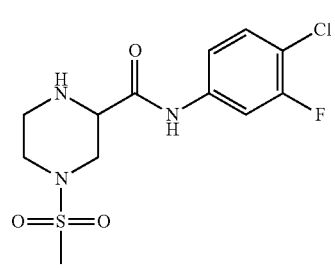
MCG-III-216-A02
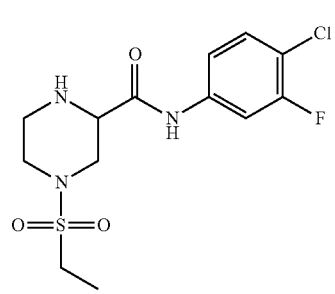
MCG-III-212-A02
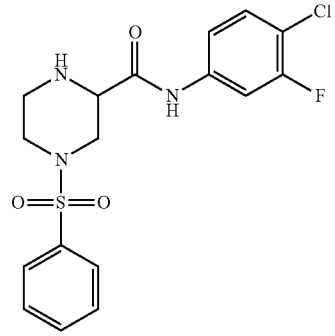
MCG-III-216-A03
-continued
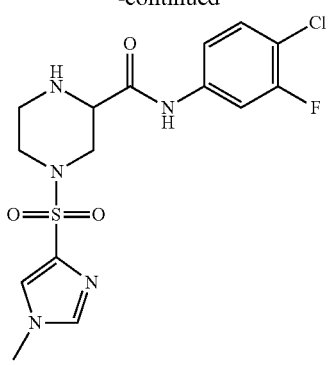
MCG-III-216-A04
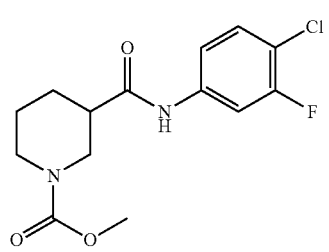
(S)-MCG-III-188-A01
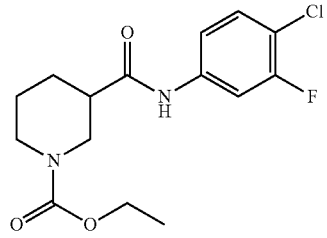
(S)-MCG-III-188-A02
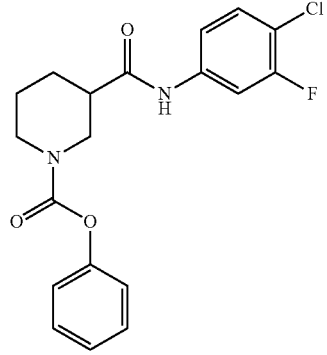
(S)-MCG-III-188-A03
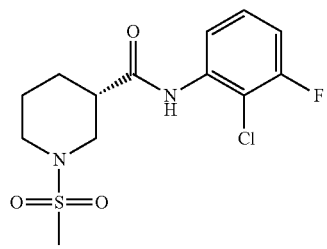
MCG-IV-024-A01

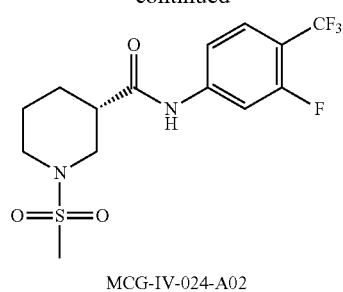
MCG-IV-024-A02
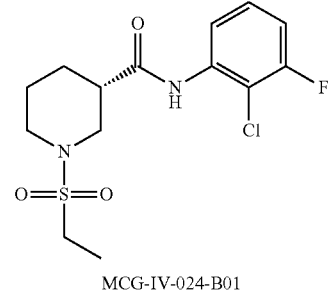
MCG-IV-024-B01
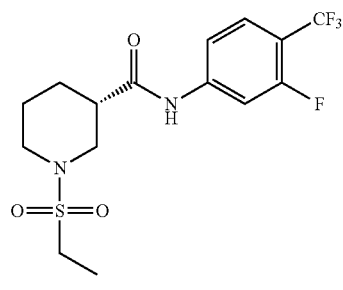
MCG-IV-024-B02
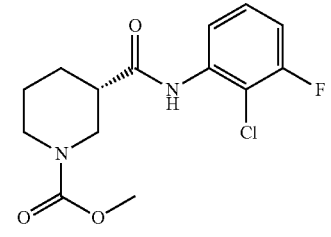
MCG-IV-026-A01
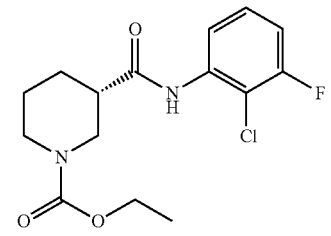
MCG-IV-026-A02
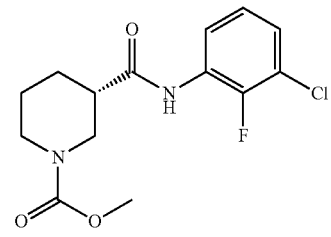
MCG-IV-026-A03
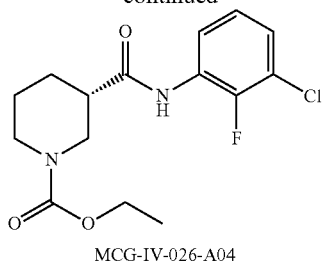
MCG-IV-026-A04
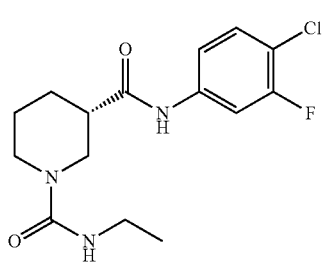
MCG-IV-031-A02
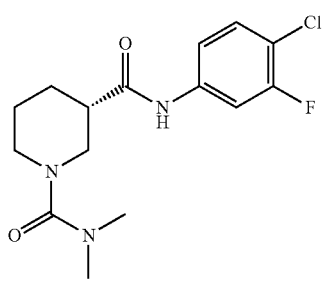
MCG-IV-031-A03
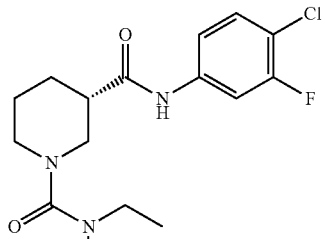
MCG-IV-031-A04
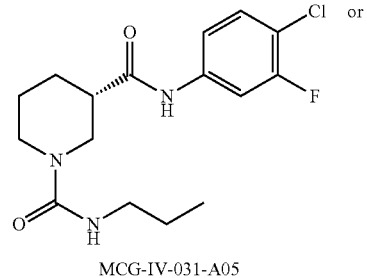
MCG-IV-031-A05
or

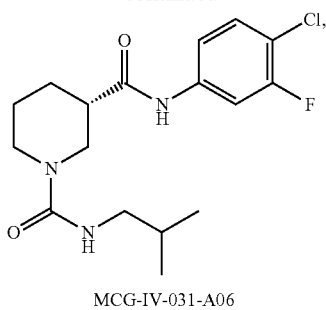
MCG-IV-031-A06
or a pharmaceutically acceptable salt thereof.
In further aspects, the compound that is:
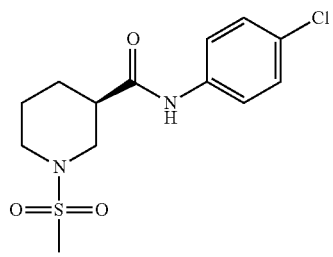
(R)-MCG-II-156
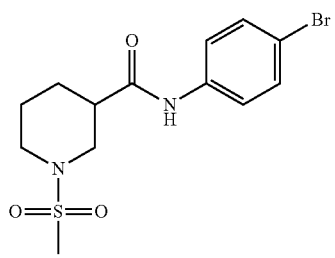
(S)-MCG-III-027-A02
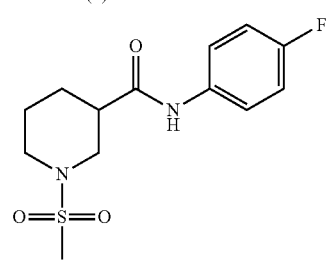
(S)-MCG-III-027-A03
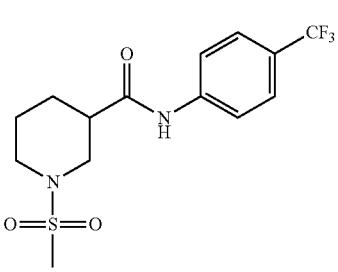
(S)-MCG-III-027-A04
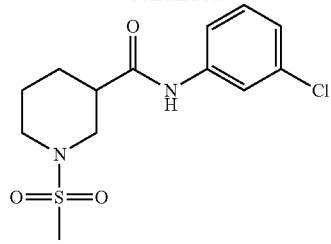
(S)-MCG-III-027-B01
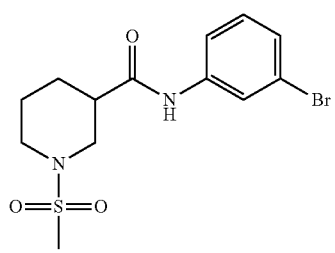
(S)-MCG-III-027-B02
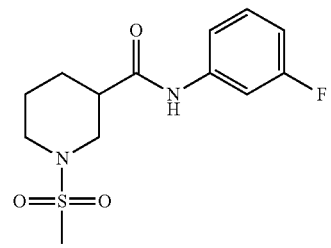
(S)-MCG-III-027-B03
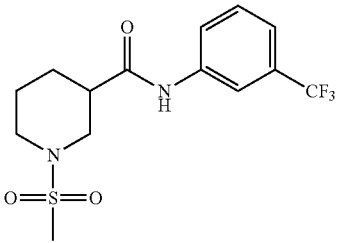
(S)-MCG-III-027-B04
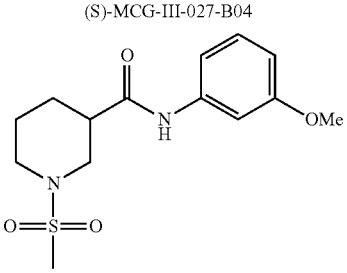
(S)-MCG-III-027-B05

-continued
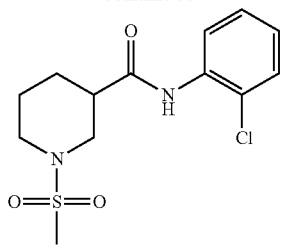
(S)-MCG-III-027-C01
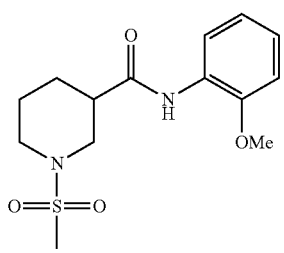
(S)-MCG-III-027-C05
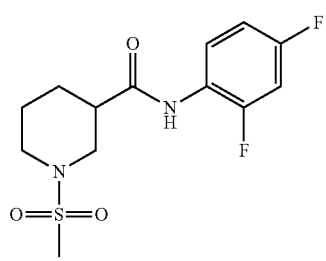
(S)-MCG-III-027-D04
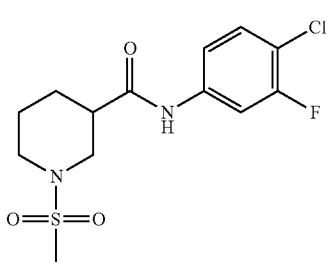
(S)-MCG-III-027-D05
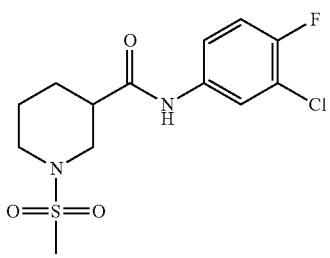
(S)-MCG-III-085-A02
-continued
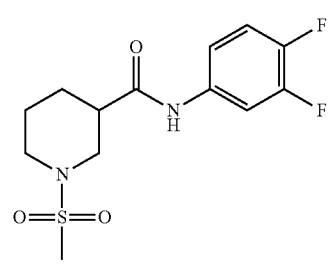
(S)-MCG-III-085-A03
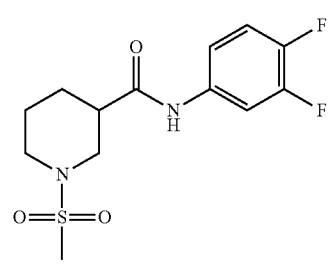
(S)-MCG-III-085-A04
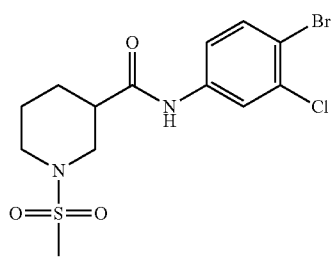
(S)-MCG-III-085-A05
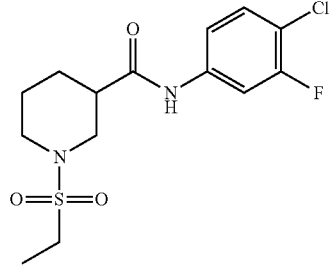
(S)-MCG-III-085-A06
(S)-MCG-III-085-C01

-continued
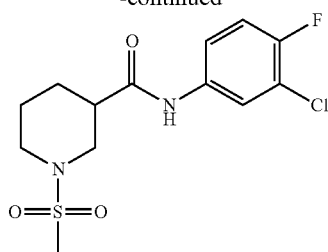
(S)-MCG-III-085-C02
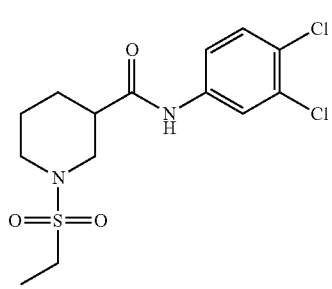
(S)-MCG-III-085-C03
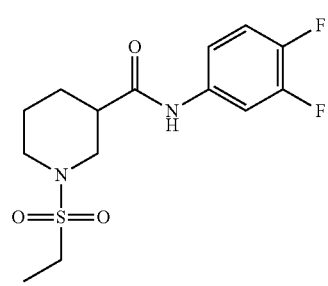
(S)-MCG-III-085-C04
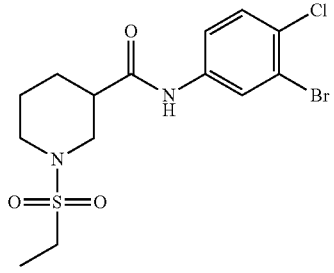
(S)-MCG-III-085-C05
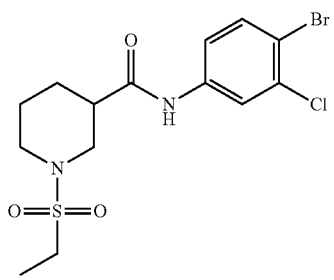
(S)-MCG-III-085-C06
-continued
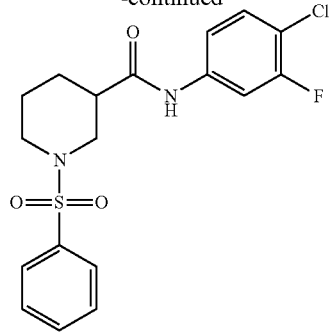
(S)-MCG-III-085-D01
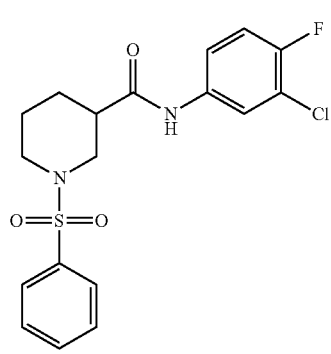
(S)-MCG-III-085-D02
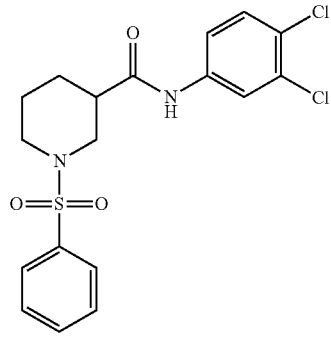
(S)-MCG-III-085-D03
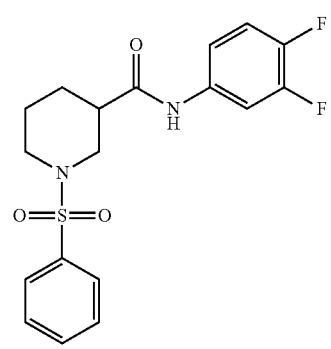
(S)-MCG-III-085-D04

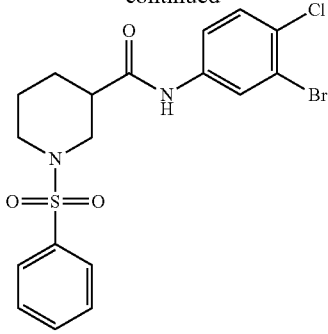
(S)-MCG-III-085-D05
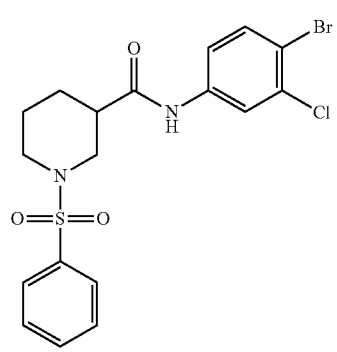
(S)-MCG-III-085-D06
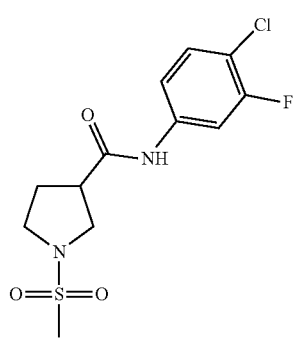
MCG-III-157-A01
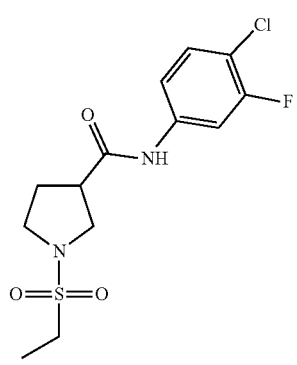
MCG-III-157-A02
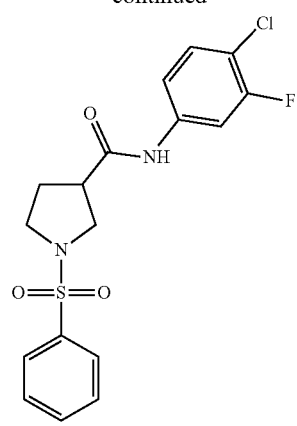
MCG-III-157-A03
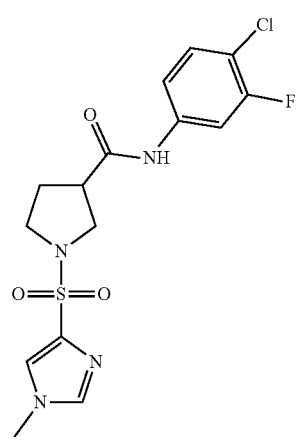
MCG-III-157-A04
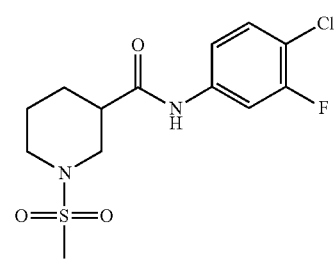
MCG-III-157-B01
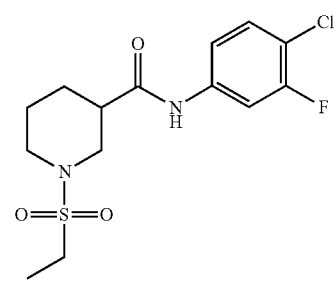
MCG-III-157-B02

-continued
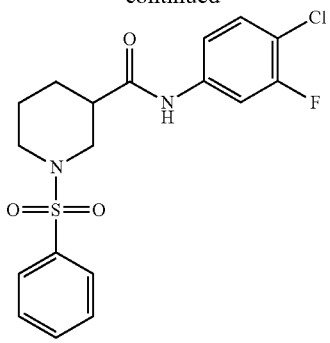
MCG-III-157-B03
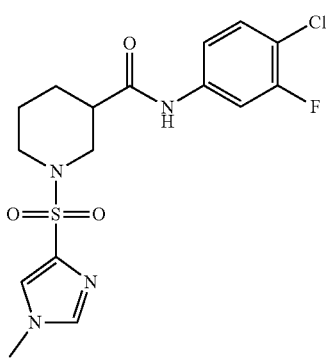
MCG-III-157-B04
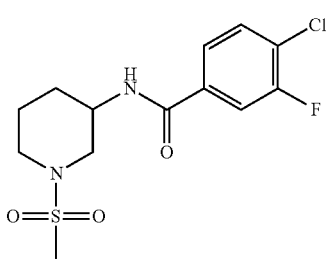
MCG-III-157-C01
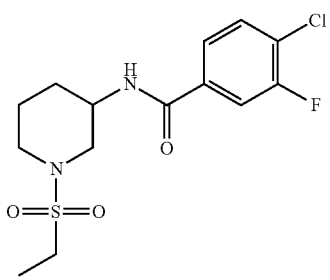
MCG-III-157-C02
-continued
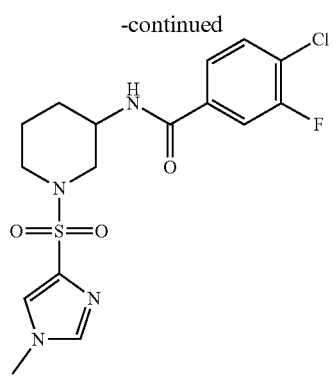
MCG-III-157-C04
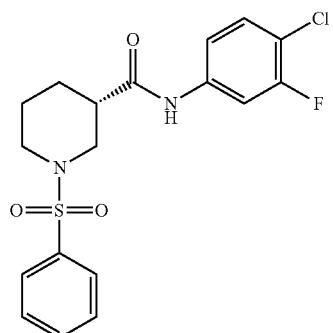
(S)-MCG-III-128
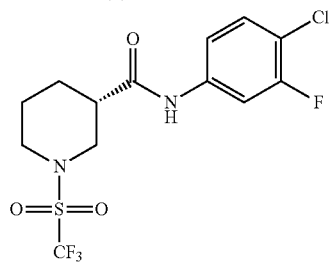
(S)-MCG-III-132
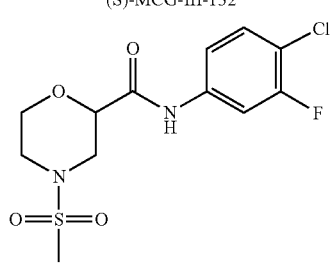
MCG-III-211-A01
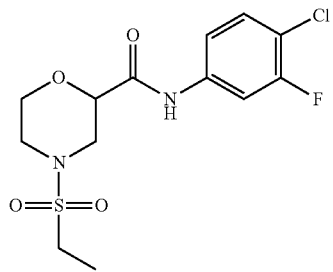
MCG-III-211-A02

83
-continued
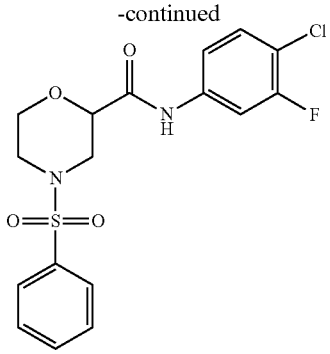
MCG-III-211-A03
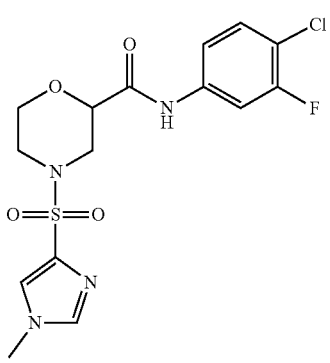
MCG-III-211-A04
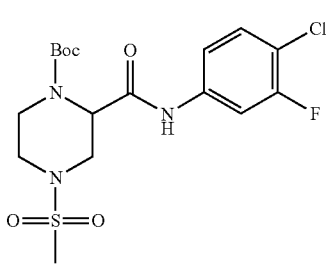
MCG-III-212-A01
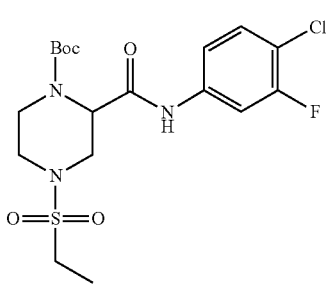
MCG-III-212-A02
84
-continued
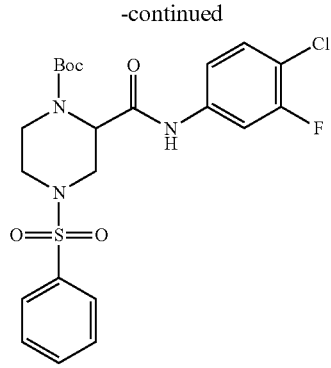
MCG-III-212-A03
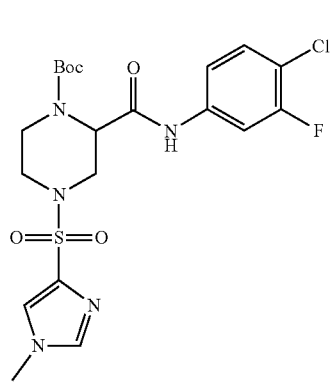
MCG-III-212-A04
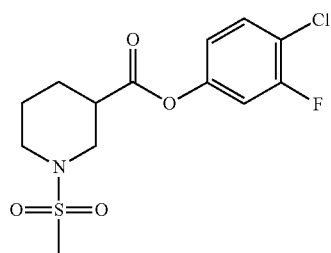
(S)-MCG-III-213-A01
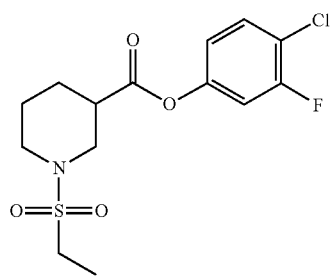
(S)-MCG-III-213-A02

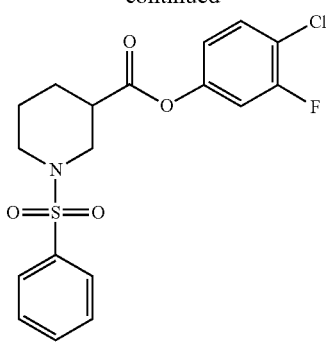
(S)-MCG-III-213-A03
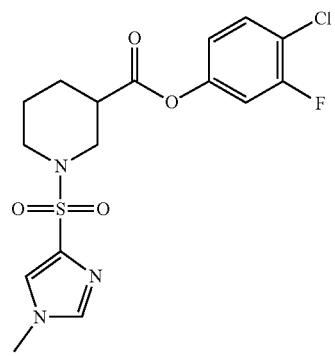
(S)-MCG-III-213-A04
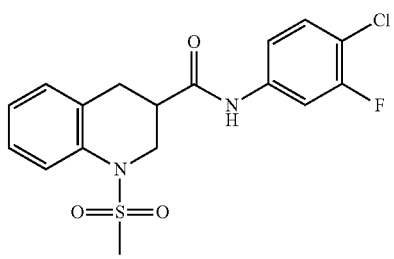
MCG-III-214-A01
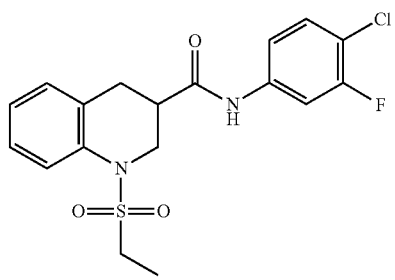
MCG-III-214-A02
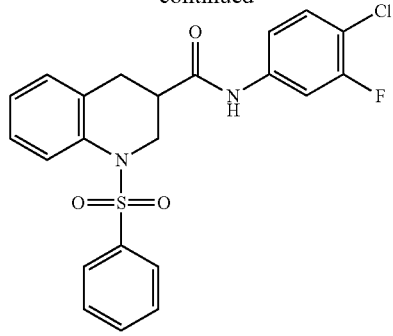
MCG-III-214-A03
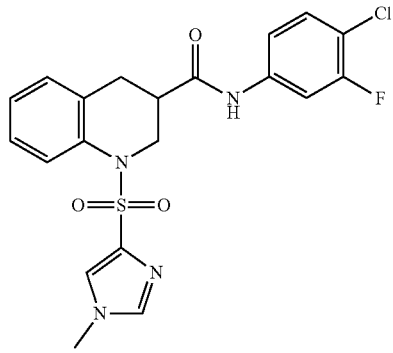
MCG-III-214-A04
MCG-III-196
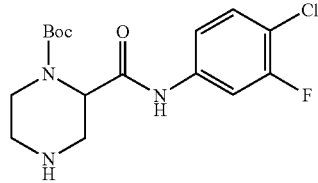
MCG-III-210
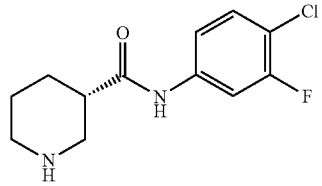
(S)-MCG-III-189
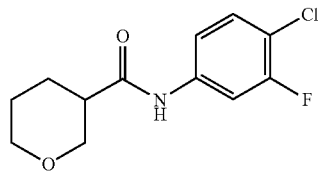
MCG-III-207

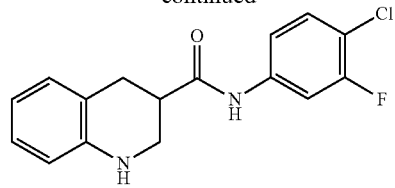
MCG-III-209
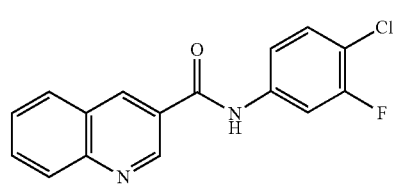
MCG-III-204
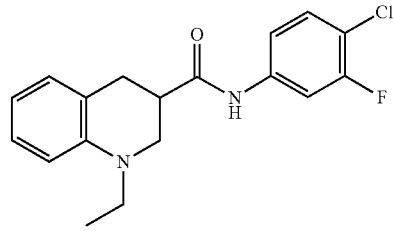
MCG-III-201
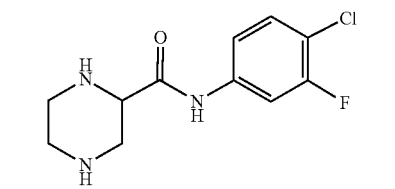
MCG-III-216-A01
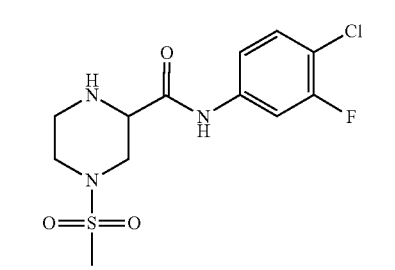
MCG-III-216-A02
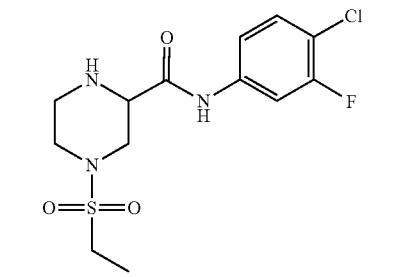
MCG-III-212-A02
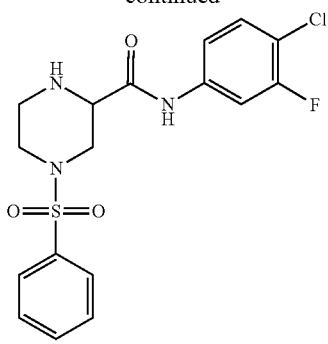
MCG-III-216-A03
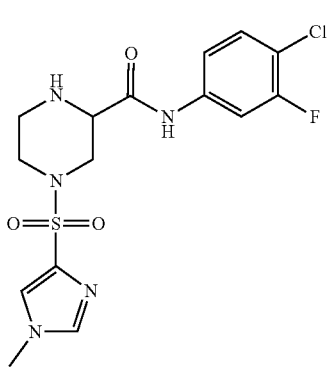
MCG-III-216-A04
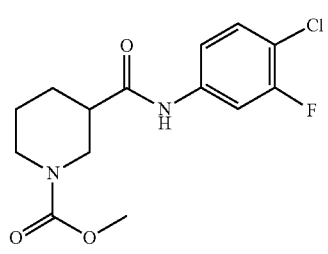
(S)-MCG-III-188-A01
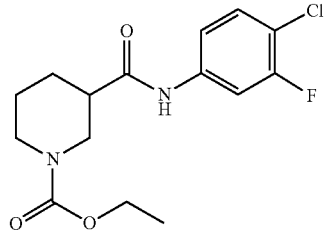
(S)-MCG-III-188-A02

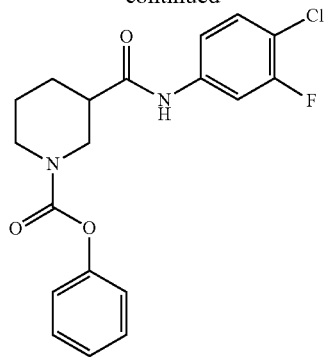
(S)-MCG-III-188-A03
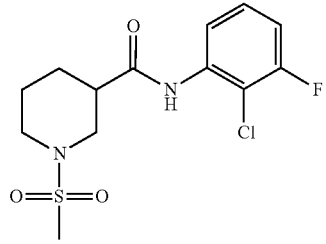
(S)-MCG-IV-024-A01
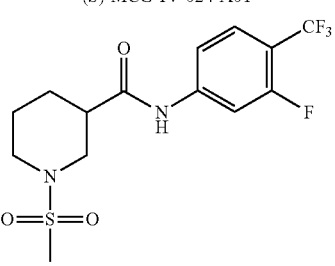
(S)-MCG-IV-024-A02
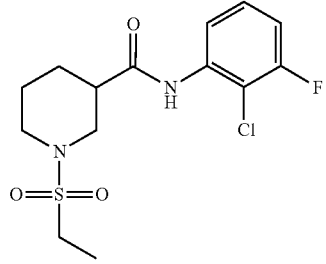
(S)-MCG-IV-024-B01
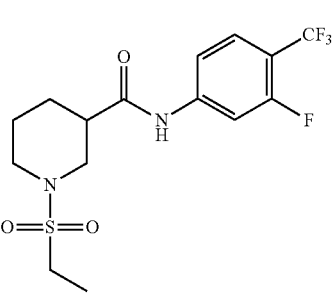
(S)-MCG-IV-024-B02

(S)-MCG-IV-026-A01
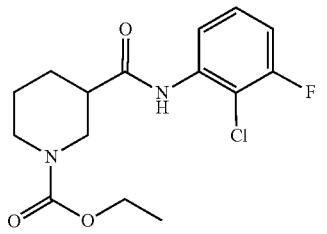
(S)-MCG-IV-026-A02
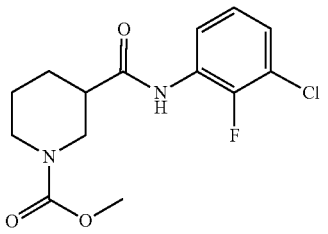
(S)-MCG-IV-026-A03
(S)-MCG-IV-026-A04
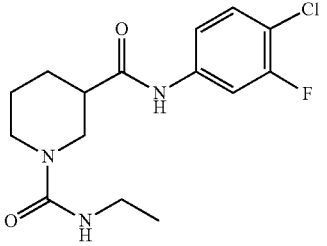
(S)-MCG-IV-031-A02
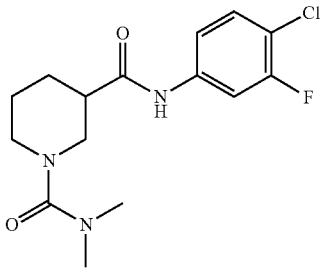
(S)-MCG-IV-031-A03

-continued
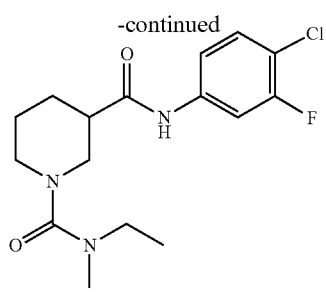
(S)-MCG-IV-031-A04
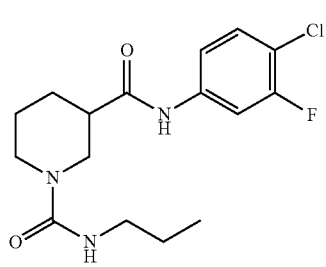
(S)-MCG-IV-031-A05
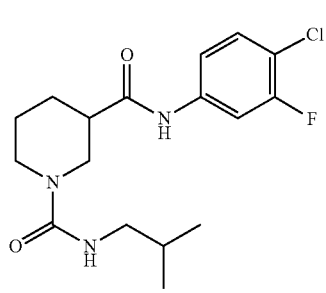
(S)-MCG-IV-031-A06
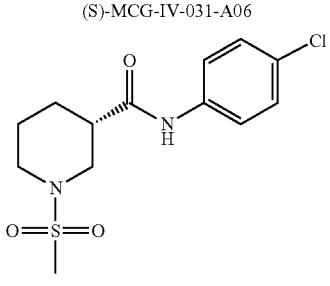
(S)-MCG-II-153
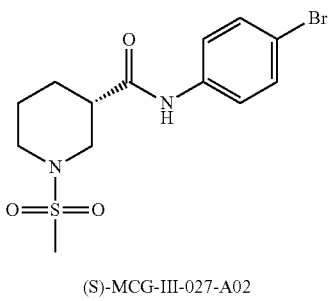
(S)-MCG-III-027-A02
-continued
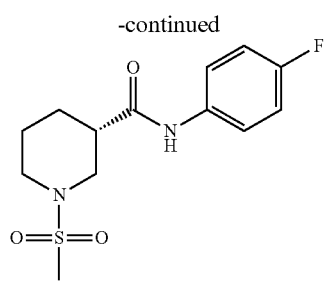
(S)-MCG-III-027-A03
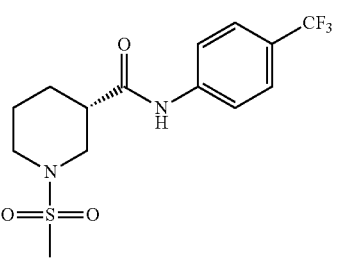
(S)-MCG-III-027-A04
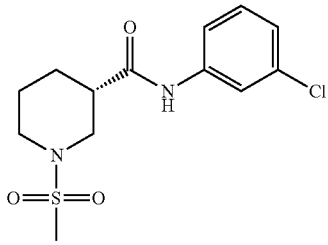
(S)-MCG-III-027-B01
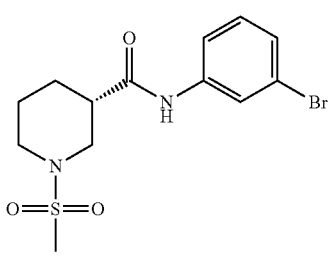
(S)-MCG-III-027-B02
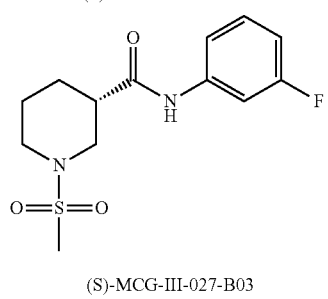
(S)-MCG-III-027-B03

-continued
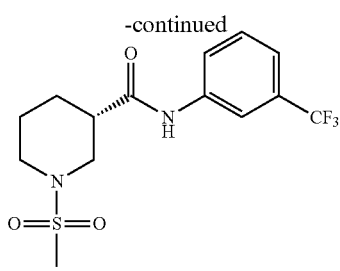
(S)-MCG-III-027-B04
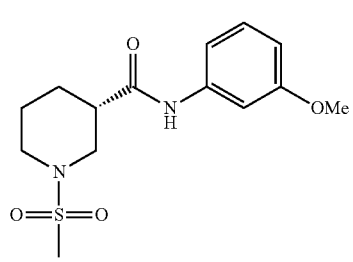
(S)-MCG-III-027-B05
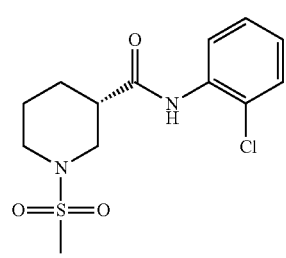
(S)-MCG-III-027-C01
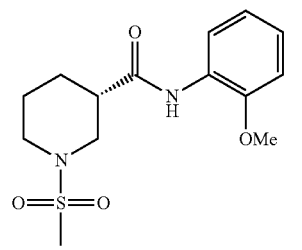
(S)-MCG-III-027-C05
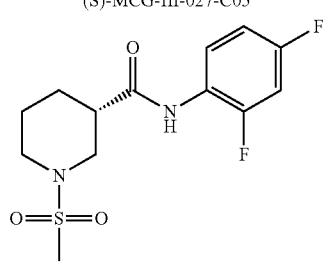
(S)-MCG-III-027-D04
-continued
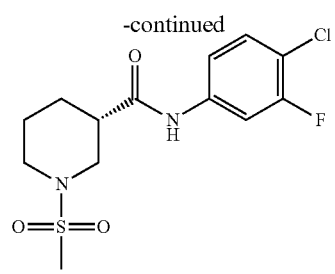
(S)-MCG-III-027-D05
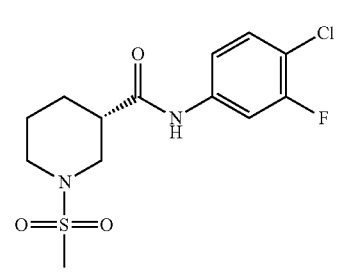
(S)-MCG-III-027-D05
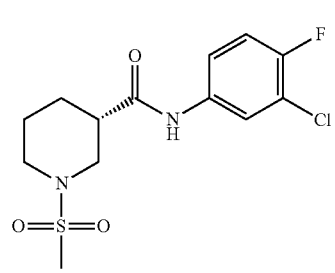
(S)-MCG-III-085-A02
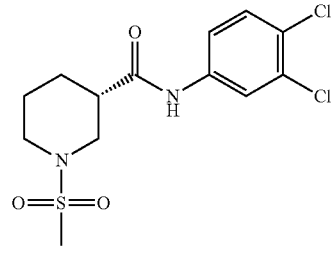
(S)-MCG-III-085-A03
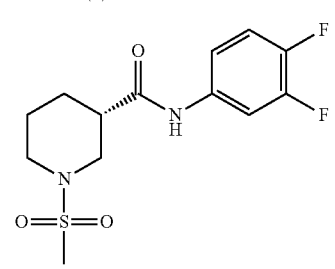
(S)-MCG-III-085-A04

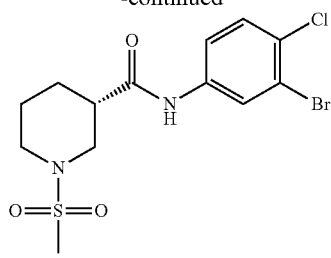
(S)-MCG-III-085-A05
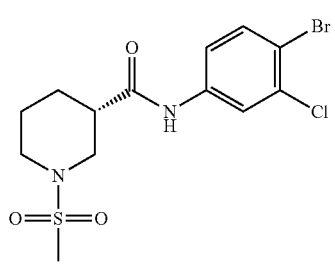
(S)-MCG-III-085-A06
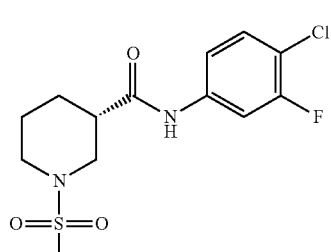
(S)-MCG-III-085-C01
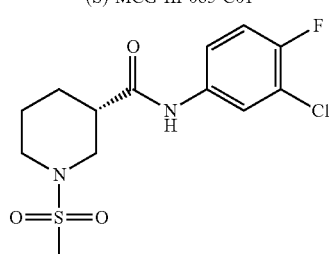
(S)-MCG-III-085-C02
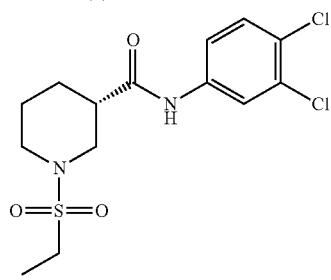
(S)-MCG-III-085-C03
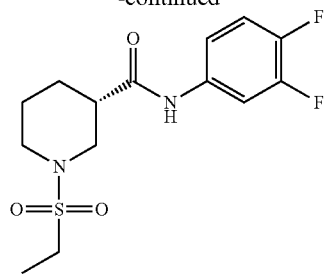
(S)-MCG-III-085-C04
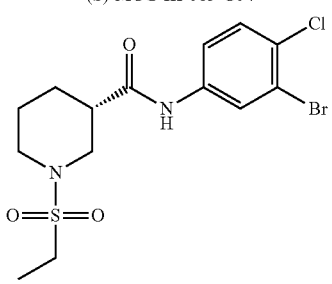
(S)-MCG-III-085-C05
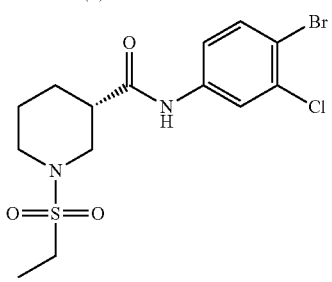
(S)-MCG-III-085-C06
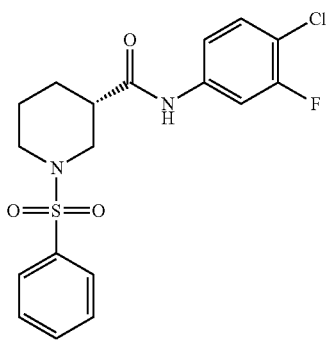
(S)-MCG-III-085-D01
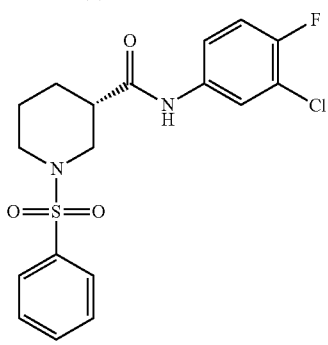
(S)-MCG-III-085-D02

97
-continued
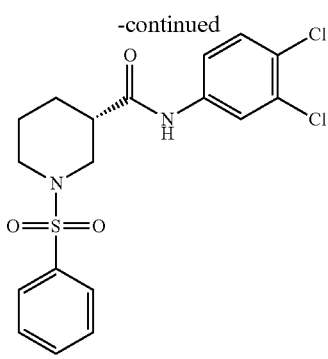
(S)-MCG-III-085-D03
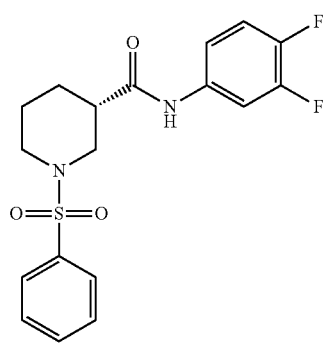
(S)-MCG-III-085-D04
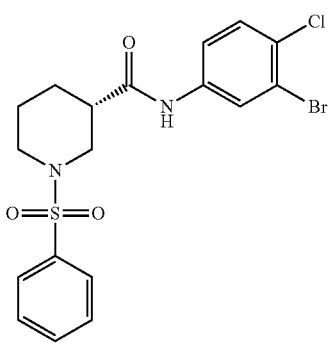
(S)-MCG-III-085-D05
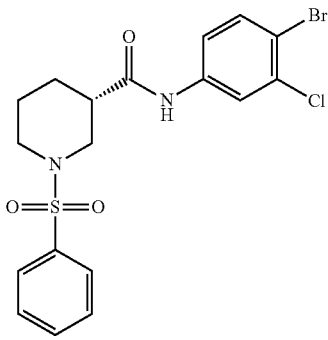
(S)-MCG-III-085-D06
98
-continued
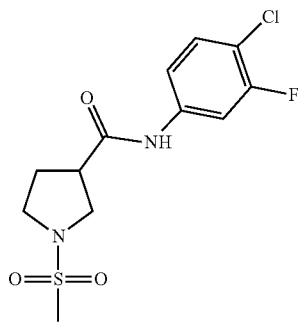
MCG-III-157-A01
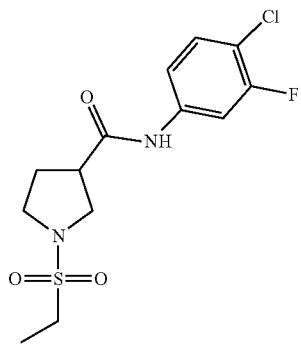
MCG-III-157-A02
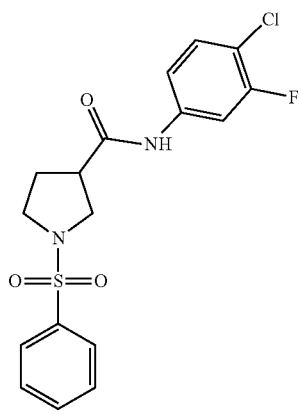
MCG-III-157-A03
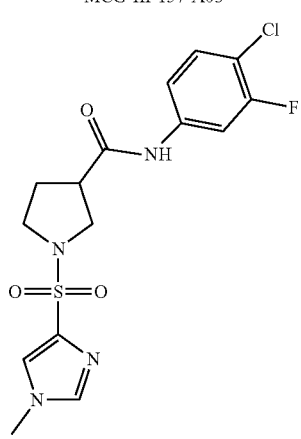
MCG-III-157-A04

-continued
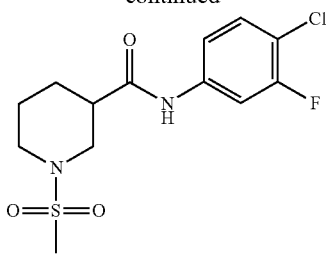
MCG-III-157-B01
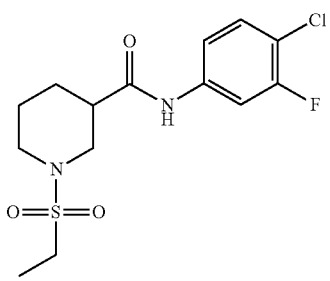
MCG-III-157-B02
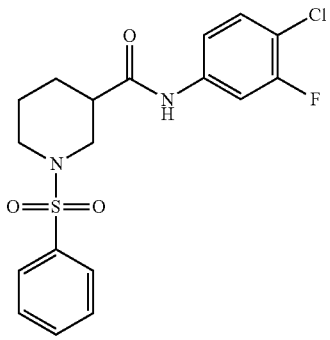
MCG-III-157-B03
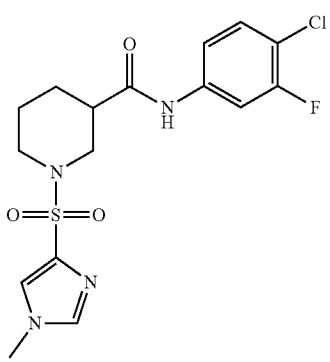
MCG-III-157-B04
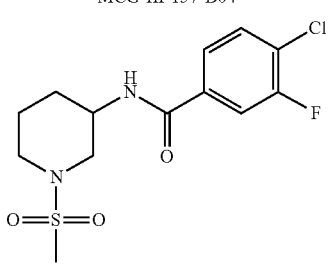
MCG-III-157-C01
-continued
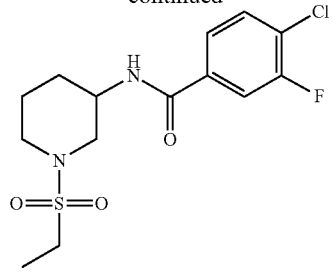
MCG-III-157-C02
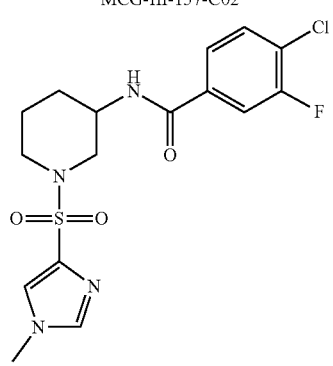
MCG-III-157-C04
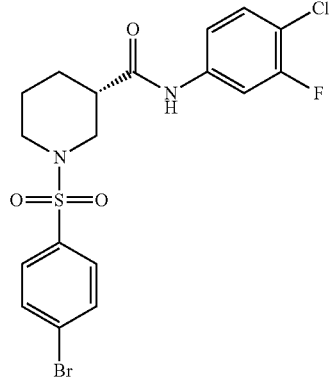
(S)-MCG-III-128
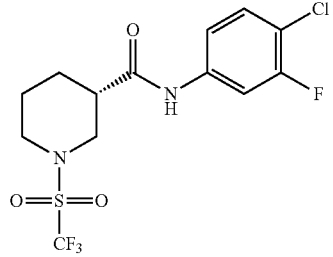
(S)-MCG-III-132
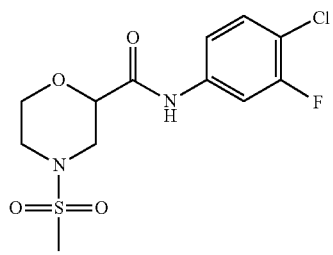
MCG-III-211-A01

-continued
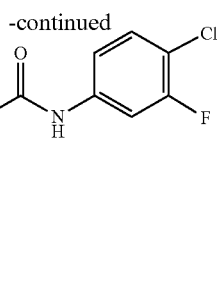
MCG-III-211-A02
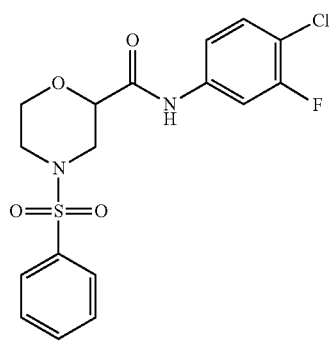
MCG-III-211-A03
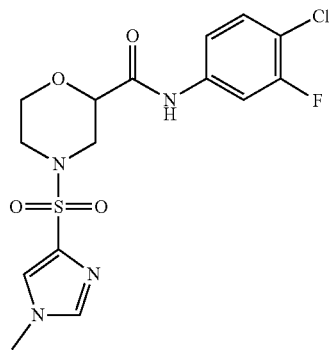
MCG-III-211-A04
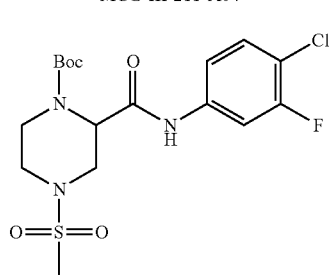
MCG-III-212-A01
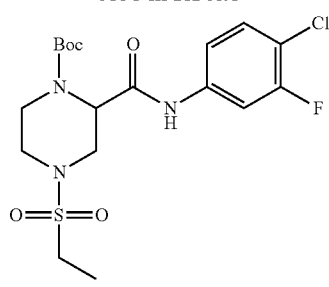
MCG-III-212-A02
-continued
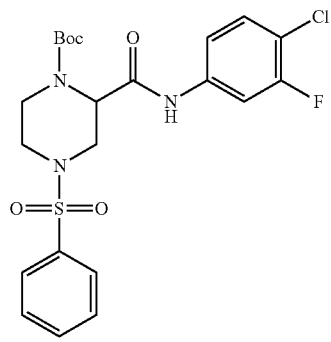
MCG-III-212-A03
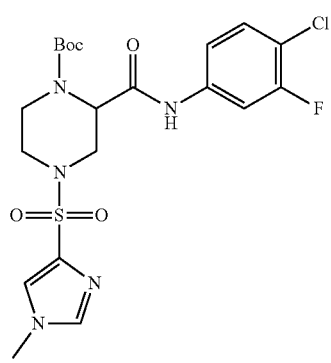
MCG-III-212-A04
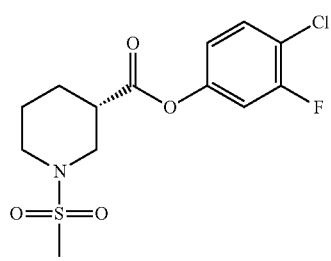
(S)-MCG-III-213-A01
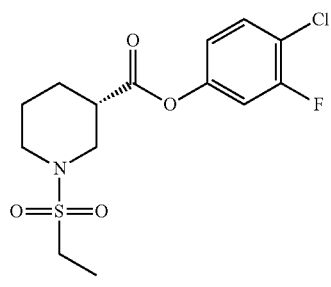
(S)-MCG-III-213-A02

-continued
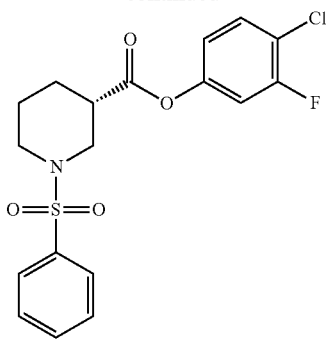
(S)-MCG-III-213-A03
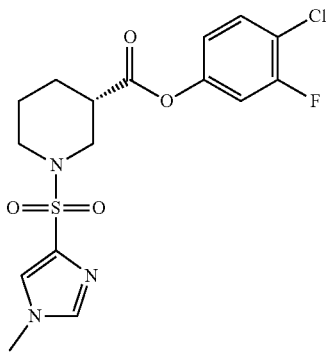
(S)-MCG-III-213-A04
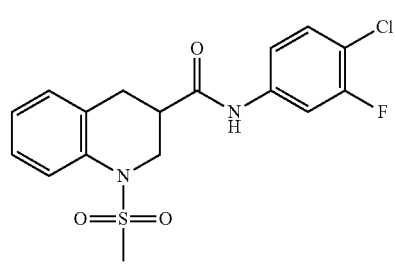
MCG-III-214-A01
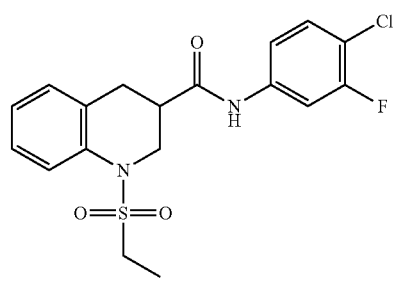
MCG-III-214-A02
-continued
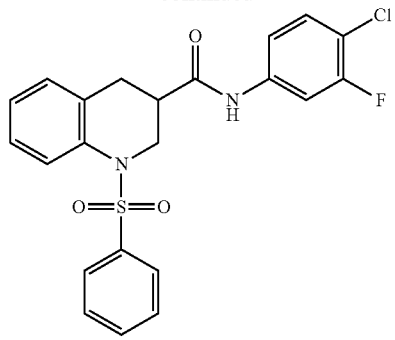
MCG-III-214-A03
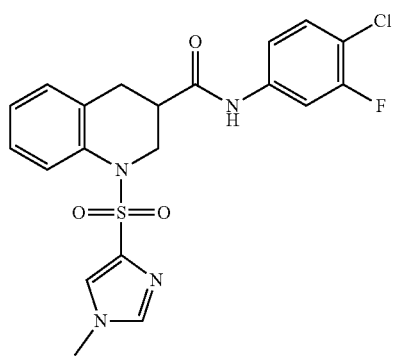
MCG-III-214-A04
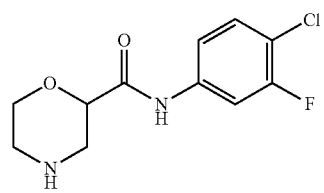
MCG-III-196
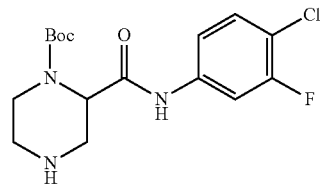
MCG-III-210
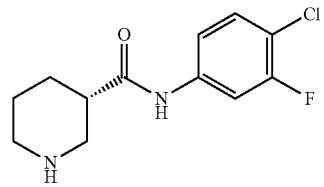
MCG-III-189
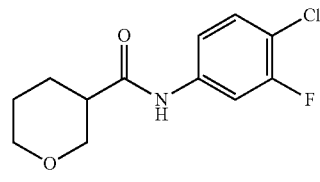
MCG-III-207

-continued
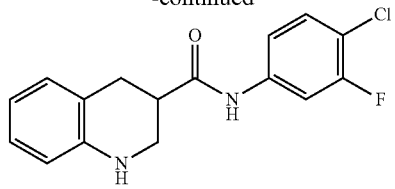
MCG-III-209
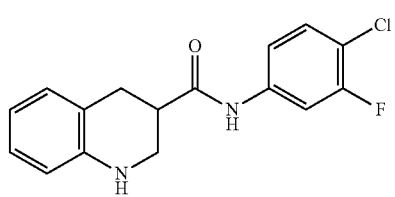
MCG-III-204
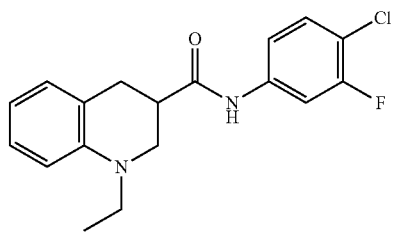
MCG-III-201
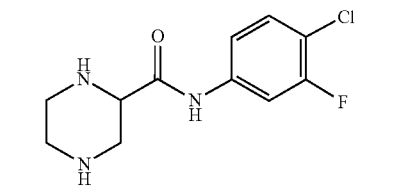
MCG-III-216-A01
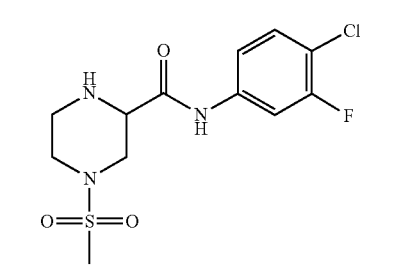
MCG-III-216-A02
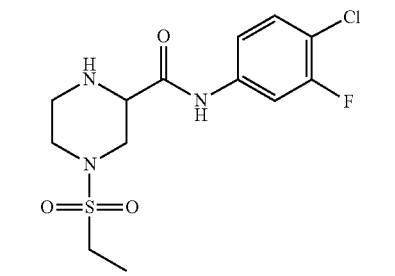
MCG-III-212-A02
-continued
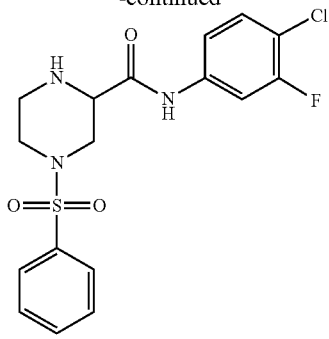
MCG-III-212-A03
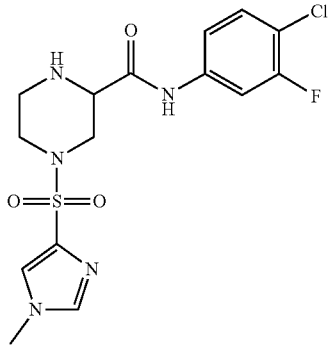
MCG-III-212-A04
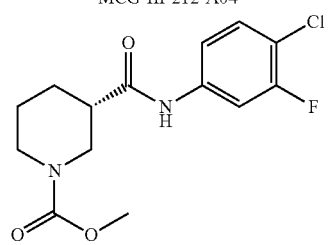
(S)-MCG-III-188-A01
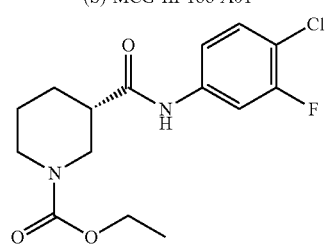
(S)-MCG-III-188-A02
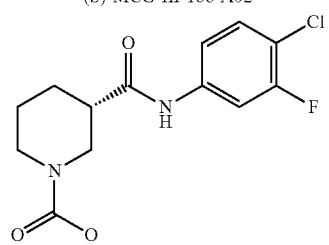
(S)-MCG-III-188-A03

-continued
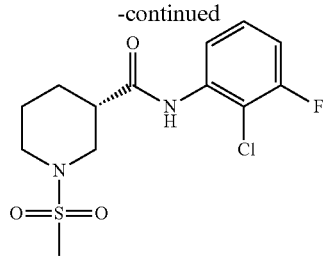
MCG-IV-024-A01
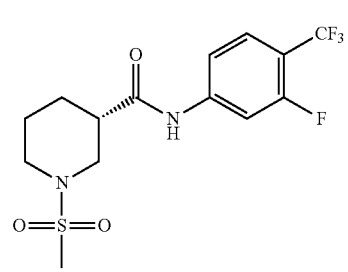
MCG-IV-024-A02
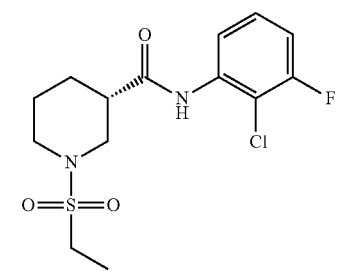
MCG-IV-024-B01
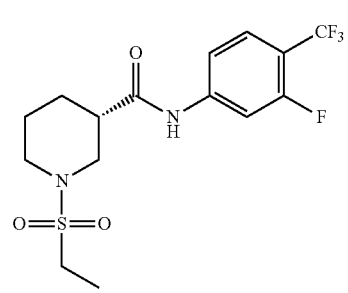
MCG-IV-024-B02
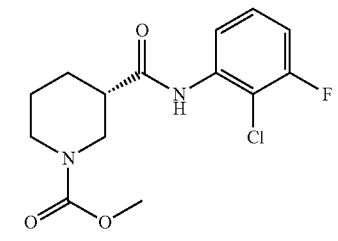
MCG-IV-026-A01
-continued
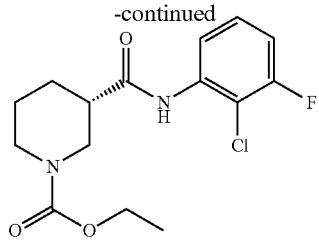
MCG-IV-026-A02
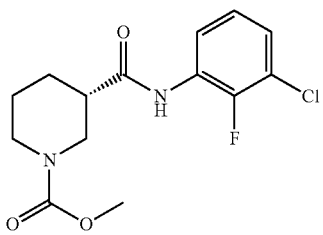
MCG-IV-026-A03
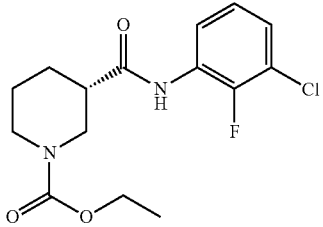
MCG-IV-026-A04
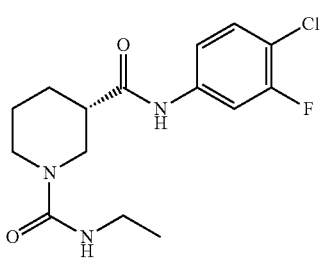
MCG-IV-031-A02
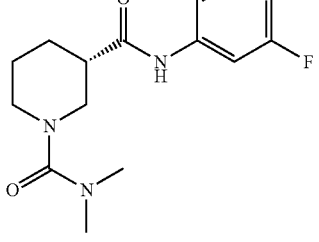
MCG-IV-031-A03

-continued
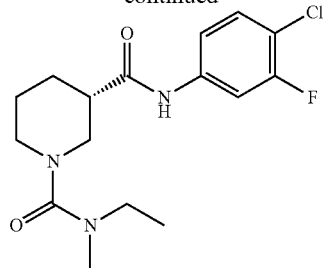
MCG-IV-031-A04
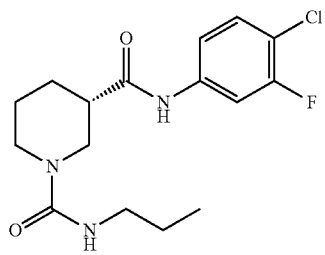
MCG-IV-031-A05
or
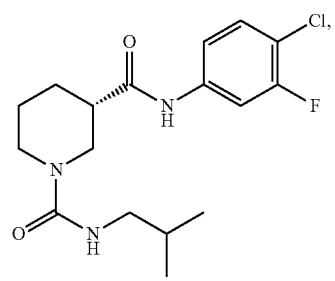
MCG-IV-031-A06
or a pharmaceutically acceptable salt thereof.
In other aspects, the compound is:
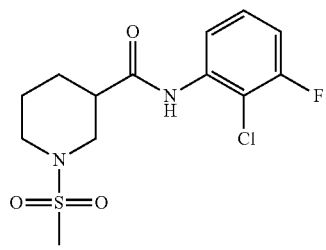
MCG-IV-024-A01
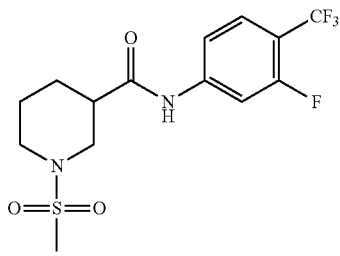
MCG-IV-024-A02
-continued
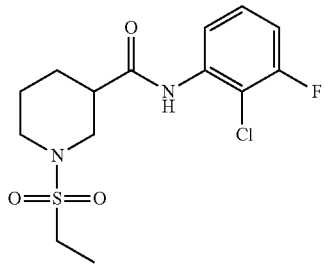
MCG-IV-024-B01
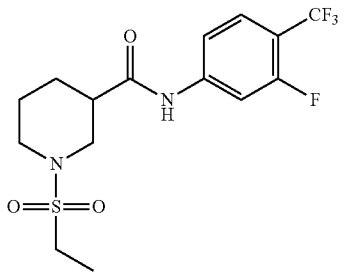
MCG-IV-024-B02
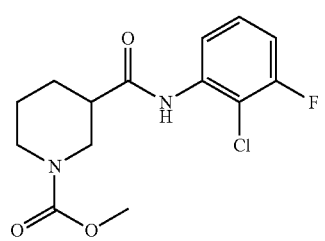
MCG-IV-026-A01
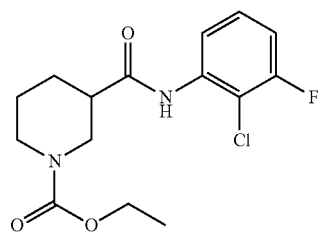
MCG-IV-026-A02
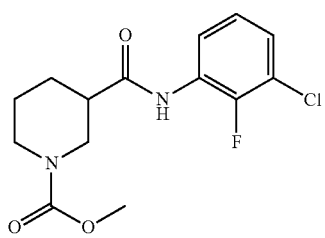
MCG-IV-026-A03
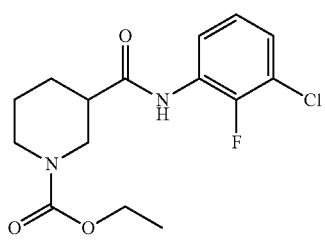
MCG-IV-026-A04

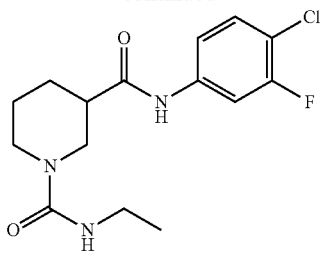
MCG-IV-031-A02
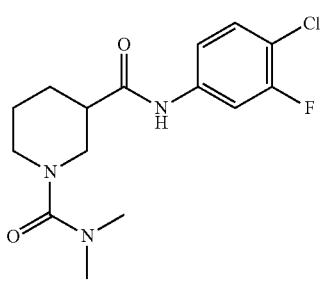
MCG-IV-031-A03
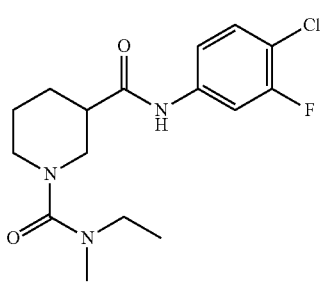
MCG-IV-031-A04
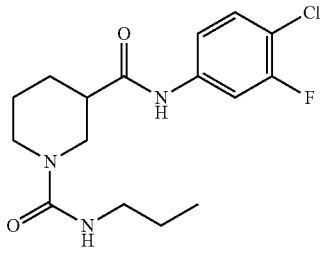
MCG-IV-031-A05
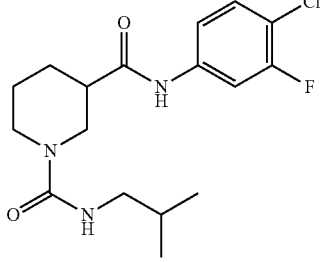
MCG-IV-031-A06
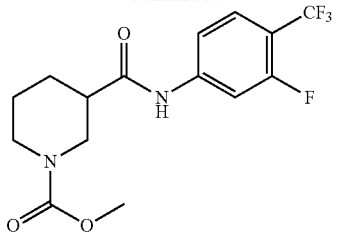
(S)-MCG-IV-050-A01
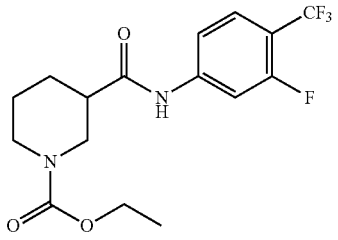
(S)-MCG-IV-050-A02
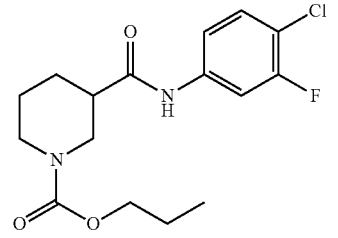
(S)-MCG-IV-058
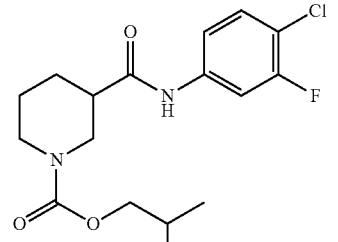
(S)-MCG-IV-061
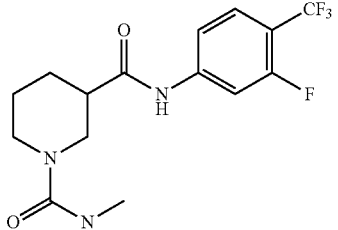
(S)-MCG-IV-063-A01
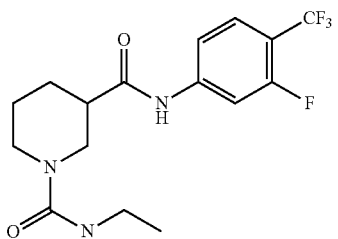
(S)-MCG-IV-063-A02

-continued
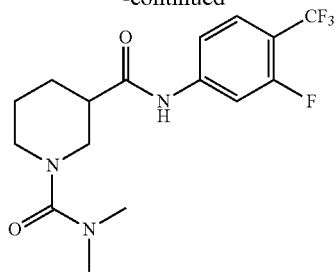
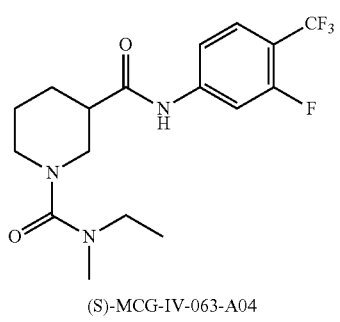
(S)-MCG-IV-063-A04
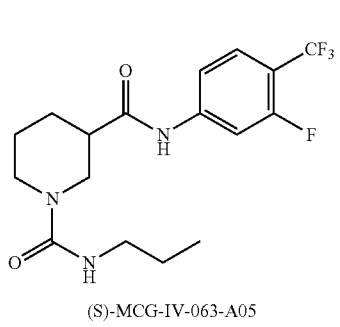
(S)-MCG-IV-063-A05
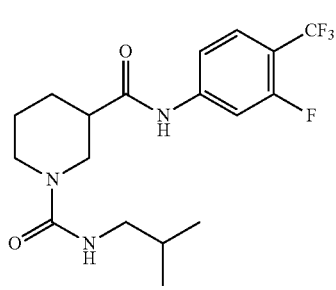
(S)-MCG-IV-063-A06
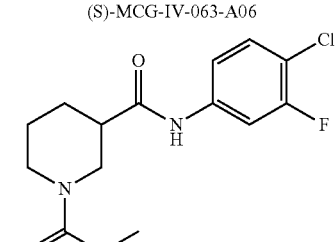
(S)-MCG-IV-053-A01
-continued
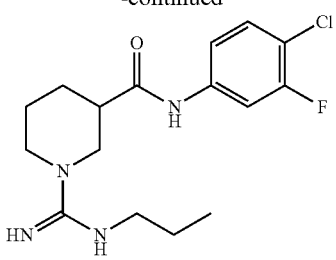
(S)-MCG-IV-053-A05
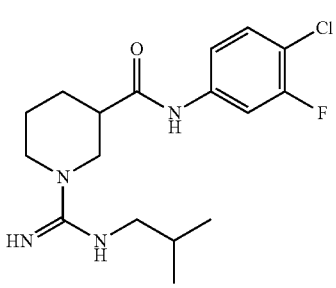
(S)-MCG-IV-053-A06
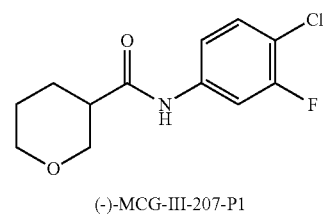
(−)-MCG-III-207-P1
(+)-MCG-III-207-P2
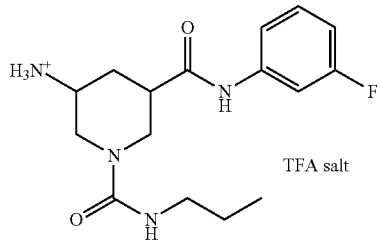
MCG-IV-177
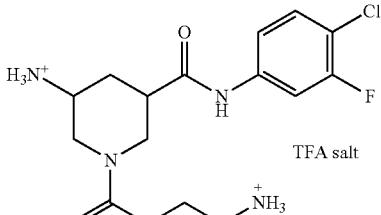
MCG-IV-274

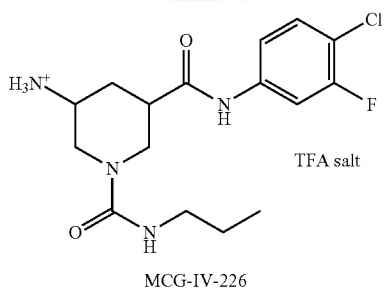
MCG-IV-226
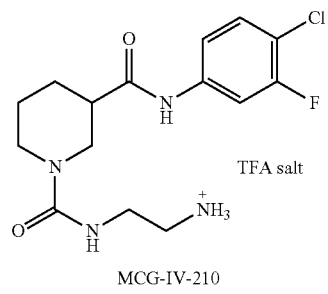
MCG-IV-210
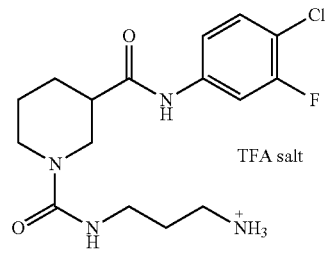
MCG-IV-211
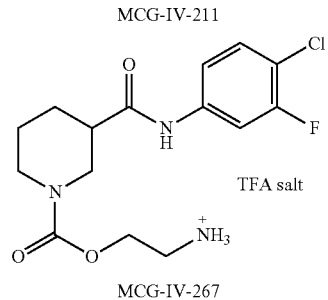
MCG-IV-267
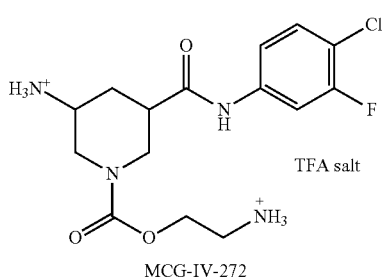
MCG-IV-272
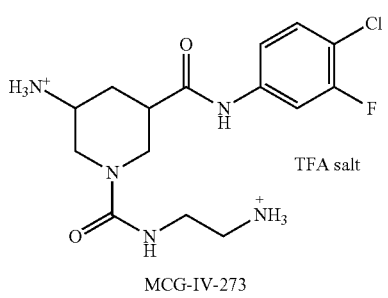
MCG-IV-273
In still further aspects, the compound is:
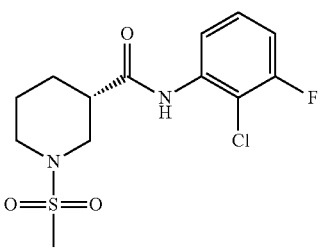
MCG-IV-024-A01
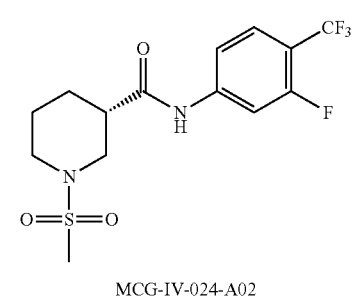
MCG-IV-024-A02
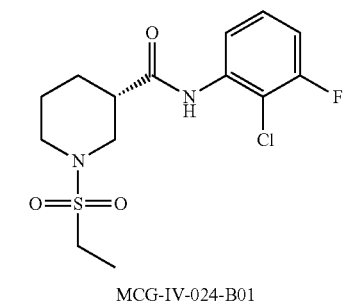
MCG-IV-024-B01
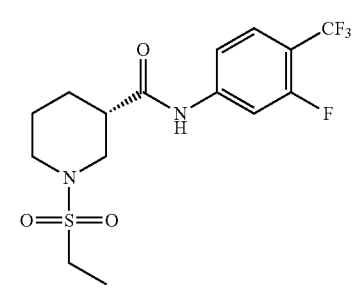
MCG-IV-024-B02
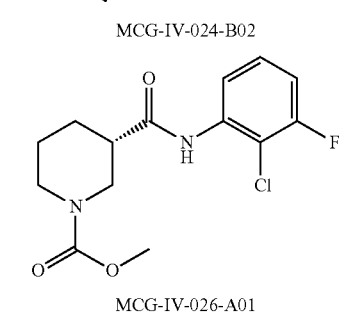
MCG-IV-026-A01

-continued
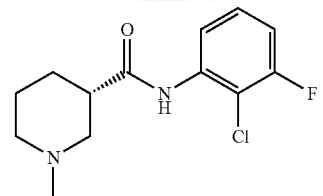
MCG-IV-026-A02
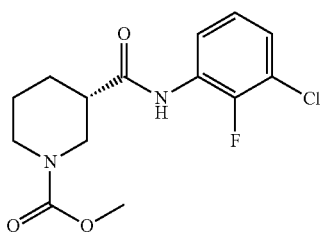
MCG-IV-026-A03
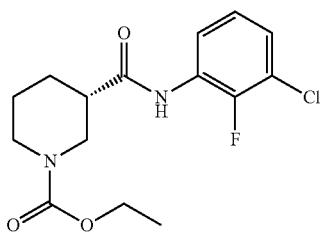
MCG-IV-026-A04
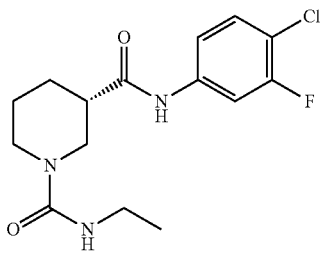
MCG-IV-031-A02
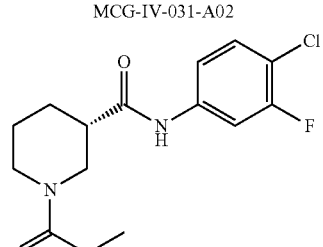
MCG-IV-031-A03
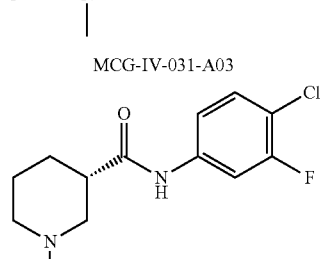
MCG-IV-031-A04
-continued
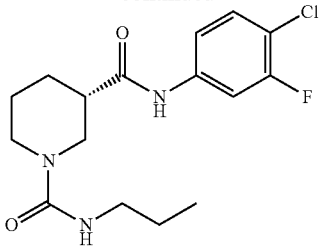
MCG-IV-031-A05
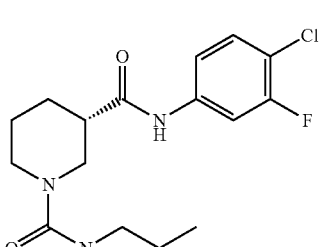
MCG-IV-031-A06
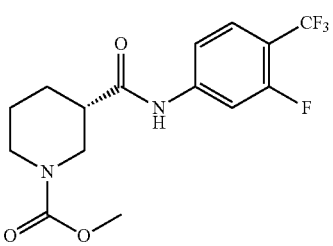
(S)-MCG-IV-050-A01
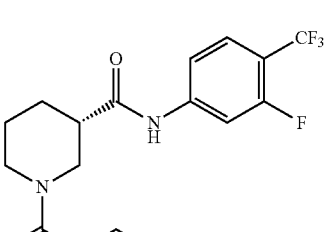
(S)-MCG-IV-050-A02
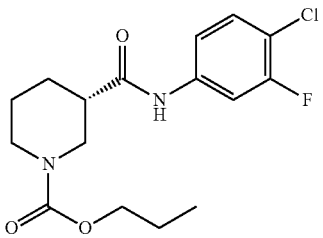
(S)-MCG-IV-058

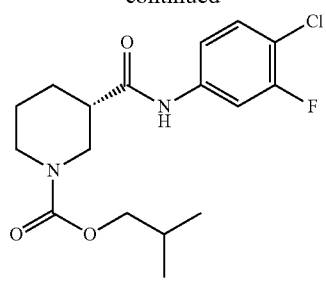
(S)-MCG-IV-061
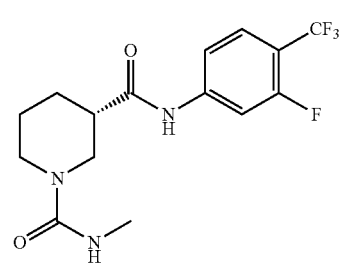
(S)-MCG-IV-063-A01
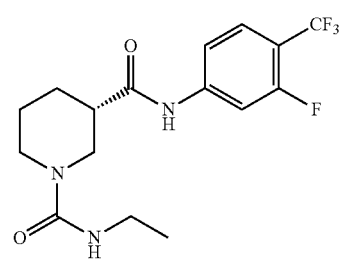
(S)-MCG-IV-063-A02
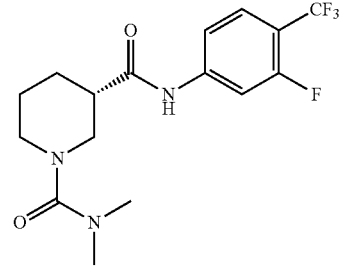
(S)-MCG-IV-063-A03
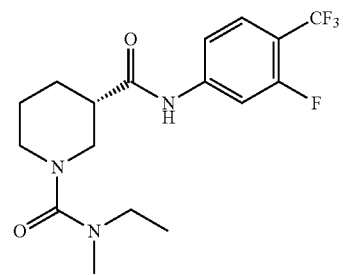
(S)-MCG-IV-063-A04
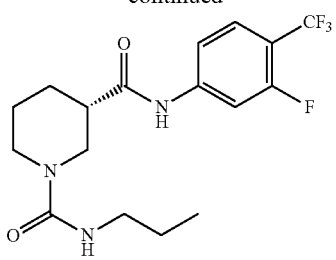
(S)-MCG-IV-063-A05
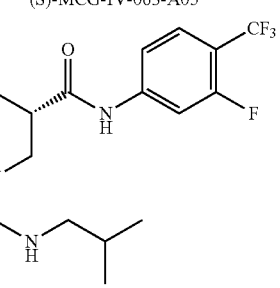
(S)-MCG-IV-063-A06
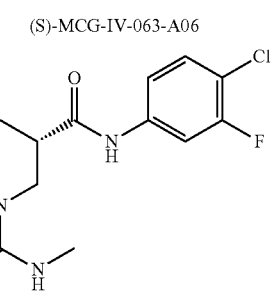
(S)-MCG-IV-053-A01
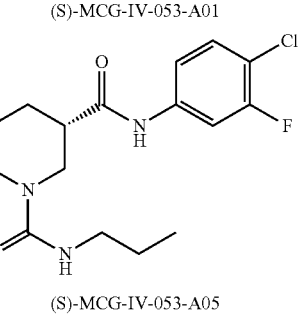
(S)-MCG-IV-053-A05
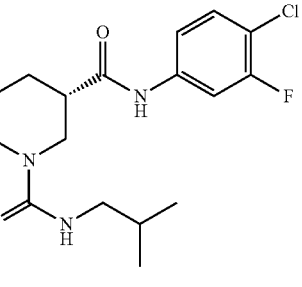
(S)-MCG-IV-053-A06
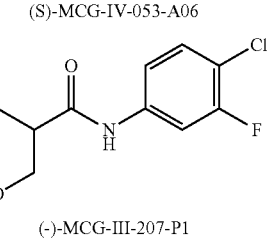
(-)-MCG-III-207-P1

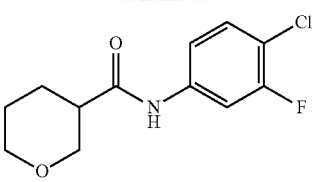

(+)-MCG-III-207-P2

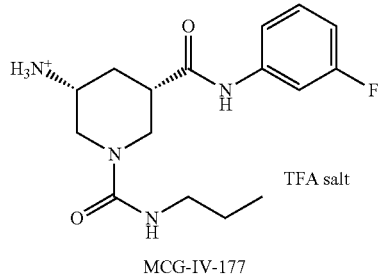

MCG-IV-177

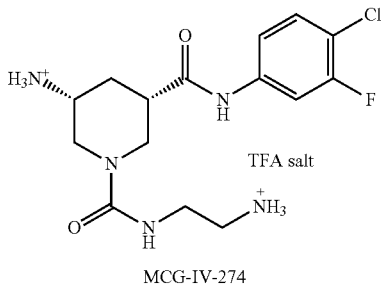

MCG-IV-274

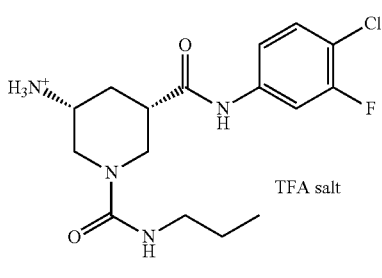

MCG-IV-226

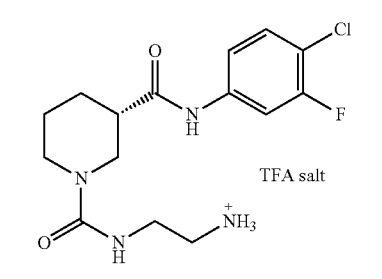

MCG-IV-210

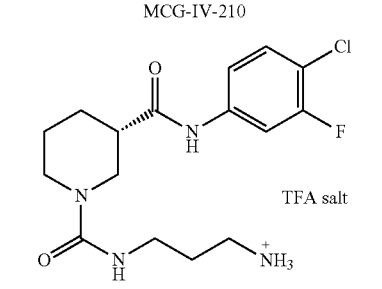

MCG-IV-211

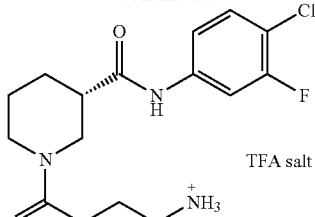

MCG-IV-267

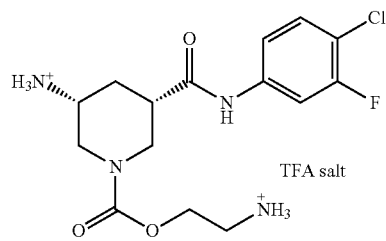

MCG-IV-272

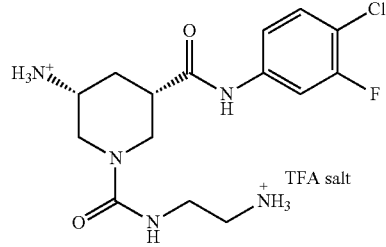

MCG-IV-273

The compounds disclosed herein may be administered to a patient. In some embodiments, the compounds are useful in treating HIV-1 in a human infected with HIV-1. In other embodiments, the compound are useful in preventing HIV-1 infection in a human susceptible to infection with HIV-1. Preferably, a therapeutically effective amount of a compound of formula (I), (II), or (IA) is administered to the subject.

The disclosure also provides pharmaceutical compositions that contain a compound discussed herein in a pharmaceutically acceptable excipient. In some embodiments, a compound described above is present in a single composition. In other embodiments, a compound described above is combined with one or more excipients and/or other therapeutic agents as described below.

The compounds discussed above may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

In some embodiments, pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids.

In other embodiments, pharmaceutically acceptable salts may also be formed from inorganic bases, desirably alkali metal salts including, e.g., sodium, lithium, or potassium, such as alkali metal hydroxides. Examples of inorganic bases include, without limitation, sodium hydroxide, potassium hydroxide, calcium hydroxide, and magnesium hydroxide. Pharmaceutically acceptable salts may also be formed from organic bases, such as ammonium salts, mono-, di-, and trimethylammonium, mono-, di- and triethylammonium, mono-, di- and tripropylammonium, ethyldimethylammonium, benzyldimethylammonium, cyclohexylammonium, benzyl-ammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1 n-butyl piperidinium, 2-methylpiperidinium, l-ethyl-2-methylpiperidinium, mono-, di- and triethanolammonium, ethyl diethanolammonium, n-butylmonoethanolammonium, tris (hydroxymethyl)methylammonium, phenylmono-ethanolammonium, diethanolamine, ethylenediamine, and the like. In one example, the base is selected from among sodium hydroxide, lithium hydroxide, potassium hydroxide, and mixtures thereof.

The disclosure also provides pharmaceutical compositions that contain a compound discussed herein in a pharmaceutically acceptable excipient. The term "pharmaceutically acceptable excipient" as used herein refers to an excipient that is stable and compatible with a patient. In some embodiments, a compound described above is combined with one or more pharmaceutically acceptable excipients and/or other therapeutic agents as described below.

The pharmaceutical compositions include a compound described herein formulated neat or with one or more pharmaceutically acceptable excipients for administration, the proportion of which is determined by the solubility and chemical nature of the compound, chosen route of administration and standard pharmacological practice. The pharmaceutically acceptable excipient may be solid or liquid.

The compound may be administered to a subject by any desirable route, taking into consideration the specific condition for which it has been selected. The compound may, therefore, be delivered orally, by injection, i.e., transdermally, intravenously, subcutaneously, intramuscularly, intravenous, intra-arterial, intraperitoneal, intracavitary, or epiduraly, among others.

Although the compound may be administered alone, it may also be administered in the presence of one or more pharmaceutically acceptable excipient that are physiologically compatible. In some embodiments, the pharmaceutically acceptable excipient is a carrier.

The carrier may be in dry or liquid form and must be pharmaceutically acceptable. Liquid pharmaceutical compositions are typically sterile solutions or suspensions. When liquid carriers are utilized, they are desirably sterile liquids. Liquid carriers are typically utilized in preparing solutions, suspensions, emulsions, syrups and elixirs. In some embodiments, the compound is dissolved a liquid carrier. In some embodiments, the compound is suspended in a liquid carrier. One of skill in the art of formulations would be able to select a suitable liquid carrier, depending on the route of administration. In other embodiments, the liquid carrier includes, without limitation, water, organic solvents, oils, fats, or mixtures thereof. In yet other embodiments, the liquid carrier is water containing cellulose derivatives such as sodium carboxymethyl cellulose. In further embodiments, the liquid carrier is water and/or dimethylsulfoxide. Examples of organic solvents include, without limitation, alcohols such as monohydric alcohols and polyhydric alcohols, e.g., glycols and their derivatives, among others. Examples of oils include, without limitation, fractionated coconut oil, *arachis* oil, corn oil, peanut oil, and sesame oil and oily esters such as ethyl oleate and isopropyl myristate.

Alternatively, the compound may be formulated in a solid carrier. In some embodiments, the composition may be compacted into a unit dose form, i.e., tablet or caplet. In other embodiments, the composition may be added to unit dose form, i.e., a capsule. In further embodiments, the composition may be formulated for administration as a powder. The solid carrier may perform a variety of functions, i.e., may perform the functions of two or more of the pharmaceutically acceptable excipients described below. For example, the solid carrier may also act as a flavoring agent, lubricant, solubilizer, suspending agent, filler, glidant, compression aid, binder, disintegrant, or encapsulating material. Suitable solid carriers include, without limitation, calcium phosphate, dicalcium phosphate, magnesium stearate, talc, starch, sugars (including, e.g., lactose and sucrose), cellulose (including, e.g., microcrystalline cellulose, methyl cellulose, sodium carboxymethyl cellulose), polyvinylpyrrolidine, low melting waxes, ion exchange resins, and kaolin. The solid carrier can contain other suitable pharmaceutically acceptable excipients, including those described below.

Examples of pharmaceutically acceptable excipients which may be combined with the compound include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, the excipients described in the "Handbook of Pharmaceutical Excipients", $5^{th}$ Edition, Eds.: Rowe, Sheskey, and Owen, APhA Publications (Washington, DC), Dec. 14, 2005, which is incorporated herein by reference.

The pharmaceutical composition described herein may be prepared by those skilled in the art. In some embodiments, the pharmaceutical compositions are prepared by combining a compound described herein with a pharmaceutically acceptable excipient.

In some embodiments, a therapeutically effective amount of a compound of formula (I), (II), or (IA) is administered to a subject suffering from or diagnosed as having such a disease, disorder, or condition. A "therapeutically effective amount" means an amount or dose sufficient to generally bring about the desired therapeutic benefit in patients in need of such treatment for the designated disease, disorder, or condition. The "therapeutically effective amount" may also mean the amount of the compound to bind to gp120, sensitize an HIV-1 infect cell to antibody dependent cell-mediated cytotoxicity (ADCC), and/or expose epitopes to Env that are recognized to ADCC-mediating antibodies Therapeutically effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

These therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In some embodiments, the therapeutically effective amount for the first dose is higher than the therapeutically effective amount for one or more of the subsequent doses. In other embodiments, the therapeutically effective amount for the first dose is lower than the therapeutically effective amount for one or more of the subsequent doses.

Also provided herein are kits or packages containing a compound or composition described herein. The kits may be organized to indicate a single formulation or combination of formulations to be taken at each desired time. The composition may also be sub-divided to contain appropriate quantities of the compound. For example, the unit dosage can be packaged compositions, e.g., packeted powders, vials, ampoules, prefilled syringes or sachets containing liquids.

Suitably, the kit contains packaging or a container with the compound formulated for the desired delivery route. Suitably, the kit contains instructions on dosing and an insert regarding the compound. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of the delivery device. Other suitable components to include in such kits will be readily apparent to one of skill in the art, taking into consideration the desired indication and the delivery route. The doses are repeated daily, weekly, or monthly, for a predetermined length of time or as prescribed.

The compound or composition described herein can be a single dose or for continuous or periodic discontinuous administration. For continuous administration, a package or kit can include the compound in each dosage unit (e.g., solution, lotion, tablet, pill, or other unit described above or utilized in drug delivery). When the compound is to be delivered with periodic discontinuation, a package or kit can include placebos during periods when the compound is not delivered. When varying concentrations of a composition, of the components of the composition, or of relative ratios of the compound or other agents within a composition over time is desired, a package or kit may contain a sequence of dosage units, so varying.

A number of packages or kits are known in the art for the use in dispensing pharmaceutical agents for oral use. In some embodiments, the package has indicators for each period. In other embodiments, the package is a labeled blister package, dial dispenser package, or bottle.

The packaging means of a kit may itself be geared for administration, such as an inhalant, syringe, pipette, eye dropper, or other such like apparatus, from which the formulation may be applied to an infected area of the body, such as the lungs, injected into a subject, or even applied to and mixed with the other components of the kit.

The compound or composition of these kits also may be provided in dried or lyophilized forms. When reagents or components are provided as a dried form, reconstitution generally is by the addition of a suitable solvent. It is envisioned that the solvent also may be provided in another packaging means.

The kits may include a means for containing the vials in close confinement for commercial sale such as, e.g., injection or blow-molded plastic containers into which the desired vials are retained.

Irrespective of the number or type of packages, the kits also may include, or be packaged with a separate instrument for assisting with the injection/administration or placement of the ultimate complex composition within the body of an animal. Such an instrument may be an inhalant, syringe, pipette, forceps, measuring spoon, eye dropper or any such medically approved delivery means. Other instrumentation includes devices that permit the reading or monitoring of reactions in vitro.

In some embodiments, pharmaceutical kits are provided and contain a compound of formula (I), (II), or (IA). The compound may be in the presence or absence of one or more of the carriers or pharmaceutically effective excipients described above. The kit may optionally contain instructions for administering the compound to a subject having HIV-1.

The compounds may be prepared as described herein using the procedures set forth below, Schemes 1-11, and skill in the art.

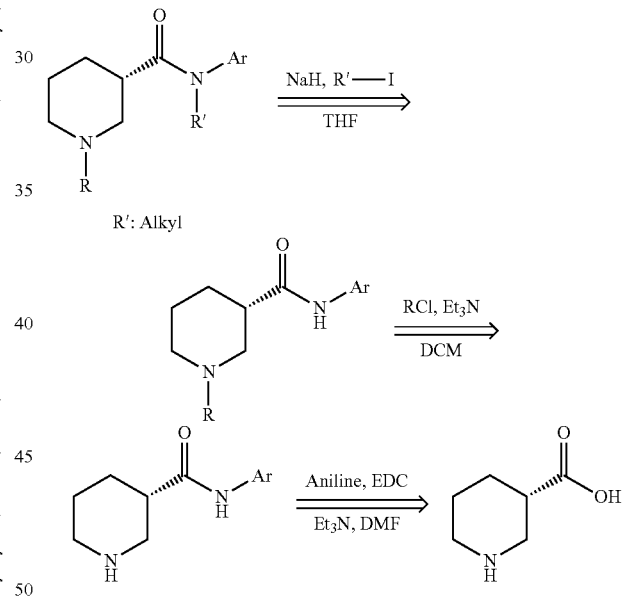

Scheme 1

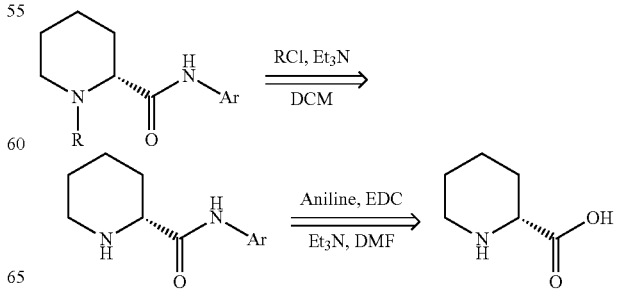

Scheme 2

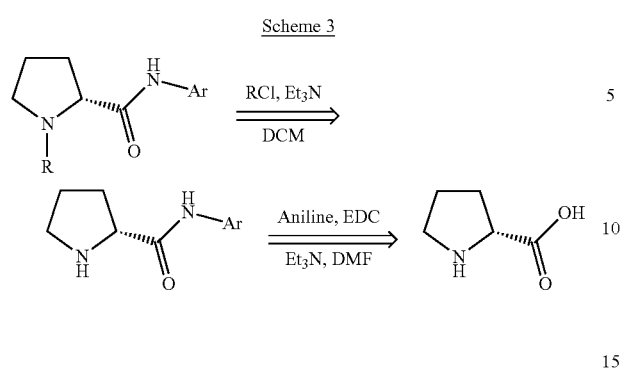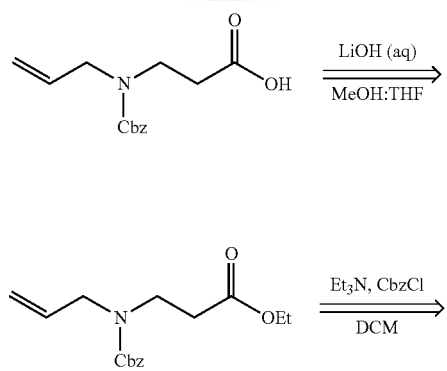

Scheme 7
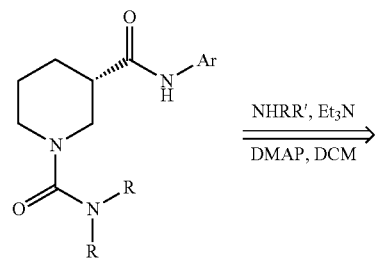
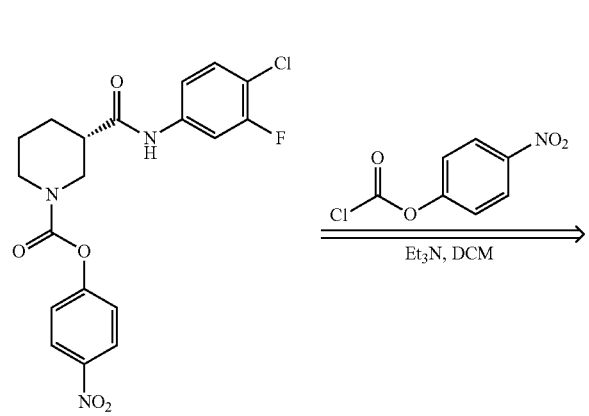
Scheme 8
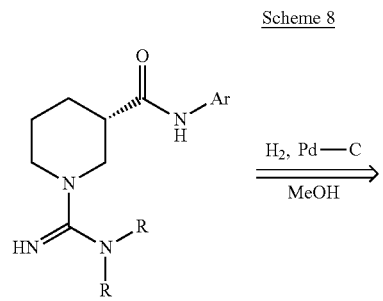
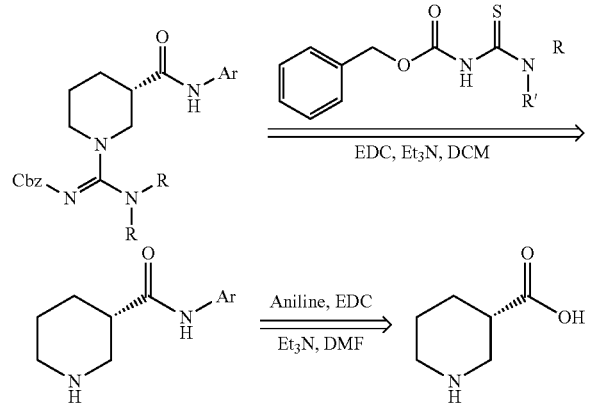
Scheme 9
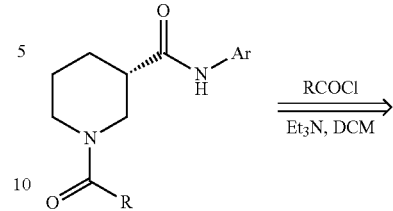
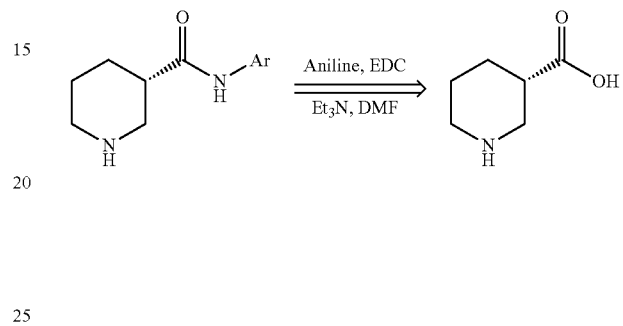
Scheme 10
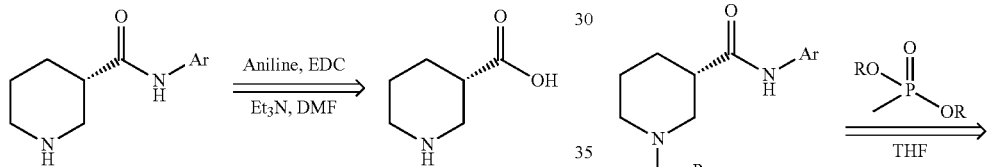
Scheme 11
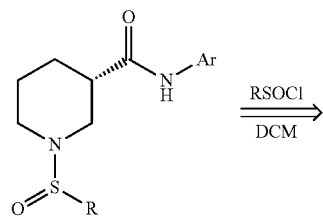

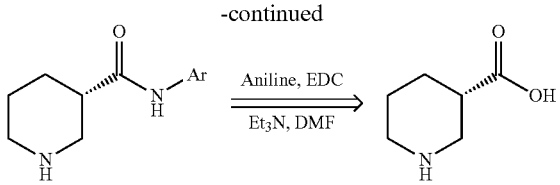

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

EXAMPLES

All reactions were conducted in oven-dried glassware under an inert atmosphere of nitrogen, unless otherwise stated. All solvents were reagent or high-performance liquid chromatography (HPLC) grade. Anhydrous $CH_2Cl_2$, toluene, ether and THF were obtained from the Pure Solve™ PS-400 system under an argon atmosphere. All reagents were purchased from commercially available sources and used as received. Reactions were magnetically stirred under a nitrogen atmosphere, unless otherwise noted and reactions were monitored by either thin layer chromatography (TLC) with 250 μm SiliaPlate™ pre-coated TLC plates or analytical ultra-performance liquid chromatography (UPLC). Yields refer to chromatographically or spectroscopically pure compounds. Optical rotations were measured on a JASCO P-2000 polarimeter. Proton ($^1$H) and carbon ($^{13}$C) NMR spectra were recorded on a Bruker Avance III 500-MHz spectrometer. Chemical shifts (δ) are reported in parts per million (ppm) relative to chloroform (δ 7.26), dimethyl sulfoxide (δ 2.50), acetone (δ 2.05), methanol (δ 3.31), or acetonitrile (δ 1.94) for $^1$H NMR, and chloroform (δ 77.0), dimethyl sulfoxide (δ 39.4), acetone (δ 29.8) or methanol (δ 49.0) for $^{13}$C NMR. Accurate mass measurements (AMM) were recorded at the University of Pennsylvania Mass Spectroscopy Service Center on either a Waters LCT Premier XE LC/MS or a Waters GC-TOF Premier system. Preparative scale UPLC was performed with a Waters AutoPurification system equipped with: a Sunfire C18 OBD column (10 μm packing material, 30×150 mm column dimensions); a 2767 sample manager; a 2545 binary gradient module; a system fluidics organizer; a 2489 UV-Vis dual wavelength (210 and 254 nm) detector; and MassLynx software with the FractionLynx application manager. Solvent systems were comprised of $H_2O$ and acetonitrile containing 0.1% trifluoroacetic acid. Evaporation was performed using a Genevac EZ-2 Plus Evaporating System. SFC analyses were performed with a JASCO system equipped with a PU-280-$CO_2$ plus $CO_2$ Delivery System, a CO-2060 plus Intelligent Column Thermostat/Selector, an HC-2068-01 Heater Controller, a BP-2080 plus Automatic Back Pressure Regulator, an MD-2018 plus Photodiode Array Detector (200-648 nm), and PU 2080 plus Intelligent HPLC Pumps. The purity of new compounds was judged by NMR and LCMS (>95%).

Example 32: Synthesis of (A)-MCG-II-153

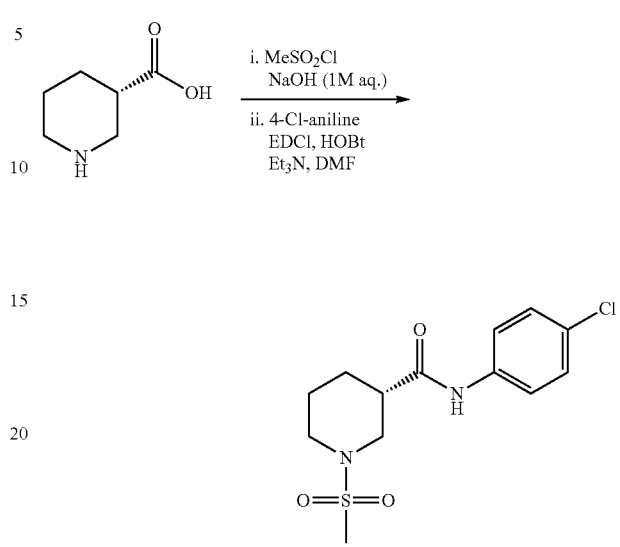

To a precooled (0° C.) solution of (<S)-3-piperidinecarboxylic acid (100. mg, 0.774 mmol) in 1 M aq. NaOH (3.8 mL) under $N_2$ atmosphere was added dropwise methanesulfonyl chloride (0.07 mL, 0.9 mmol). The resulting mixture was stirred at 0° C. for 2 h, then allowed to warm to room temperature and stirred for 2 h. The aqueous solution was washed with ether then acidified with 1 N aq. HCl to pH 3 and diluted with EtOAc. The layers were separated, and the aqueous phase was extracted with EtOAc (3×) then iPrOH:CHCl$_3$ (30:70, 3×). The combined organic layers were dried over MgSO$_4$, and concentrated in vacuo to afford the desired product, which was carried forward without additional purification (30 mg, crude 14% yield).

To a precooled (0° C.) solution of (S)-mesylated piperidine intermediate (16 mg, 0.077 mmol), 4-chloroaniline (9.8 mg, 0.077 mmol), 1-ethyl-3-(3-dimethylaminopropyl)carbodiimide hydrochloride (22 mg, 0.12 mmol) and 1-hydroxybenzotriazole hydrate (10. mg, 0.077 mmol) in DMF (0.8 mL) under $N_2$ atmosphere was added triethylamine (0.01 mL, 0.08 mmol). The resulting solution was allowed to warm to room temperature and stirred for 18 h, then concentrated in vacuo. The resulting residue was taken up in EtOAc and $H_2O$. The layers were separated, and the aqueous phase was extracted with EtOAc (3×). The combined organic layers were washed with brine, dried over MgSO$_4$, and concentrated in vacuo. Flash chromatography (SiO$_2$, 50:50 hexanes:EtOAc) afforded the product as a white solid (15 mg, 70% yield, 89.5% ee). $[\alpha]_D^{22}$+6.75 (c. 0.14, CH$_3$OH); $^1$H NMR (500 MHz, Methanol-d$_4$) δ 7.56 (d, J=8.8 Hz, 1H), 7.29 (d, J=8.7 Hz, 1H), 3.83 (dd, J=11.5, 3.5 Hz, 1H), 3.70 (d, J=12.0 Hz, 1H), 2.91 (t, J=11.3 Hz, 1H), 2.86 (s, 2H), 2.81-2.71 (m, 1H), 2.71-2.59 (m, 1H), 2.10-1.98 (m, 1H), 1.97-1.83 (m, 1H), 1.68 (t, J=10.3 Hz, 2H); NMR (126 MHz, CDCl$_3$) δ 171.07, 136.47, 129.12, 121.21, 100.12, 48.03, 46.40, 43.51, 34.87, 27.38, 24.01; IR (ATR) $v_{max}$ 3296, 1651, 1525, 1322, 1156, 826, 506 cm$^{-1}$; (ESI) m/z 339.0552 [calc for $C_{13}H_{17}ClN_2O_3SNa$ (M+Na)$^+$ 339.0546].

Example 33: Synthesis of (R)-MCG-II-156

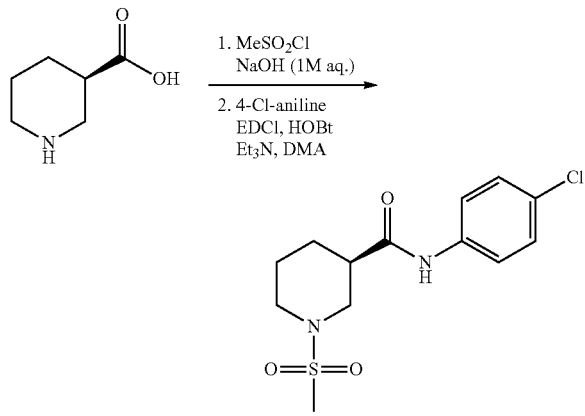

To a precooled (0° C.) solution (R)-3-piperidinecarboxylic acid (100 mg, 0.774 mmol) in 1 M aq. NaOH (3 mL) under $N_2$ atmosphere was added dropwise methanesulfonyl chloride (0.07 mL, 0.9 mmol). The resulting mixture was allowed to warm to room temperature and stirred for 3 h. The aqueous solution was then acidified with 1 N aq. HCl to pH 3 and diluted with iPrOH:CHCl$_3$ (30:70). The layers were separated, and the aqueous phase was extracted with iPrOH:CHCl$_3$ (30:70, 3×). The combined organic layers were dried over MgSO$_4$, and concentrated in vacuo to afford the desired product, which was carried forward without additional purification (62 mg, 30% crude yield).

To a precooled (0° C.) solution (R)-mesylated piperidine intermediate (40. mg, 0.19 mmol), 4-chloroaniline (25 mg, 0.19 mmol), 1-ethyl-3-(3-dimethylaminopropyl)carbodiimide hydrochloride (56 mg, 0.29 mmol) and 1-hydroxybenzotriazole hydrate (26 mg, 0.19 mmol) in dimethylacetamide (1.9 mL) under $N_2$ atmosphere was added triethylamine (0.03 mL, 0.2 mmol). The resulting solution was allowed to warm to room temperature and stirred for 16 h, then quenched with $H_2O$ and diluted with EtOAc. The layers were separated, and the aqueous phase was extracted with EtOAc (3×). The combined organic layers were washed with brine, dried over MgSO$_4$, and concentrated in vacuo. Flash chromatography (SiO$_2$, 50:50 hexanes:EtOAc) afforded the product as a white solid (29 mg, 48% yield, 65.9% ee). $[\alpha]_D^{23}$ −7.25 (c. 0.13, CH$_3$OH); $^1$H NMR (500 MHz, Methanol-d$_4$) δ 7.56 (d, J=8.4 Hz, 1H), 7.29 (d, J=8.4 Hz, 1H), 3.88-3.78 (m, 1H), 3.70 (d, J=11.5 Hz, 1H), 2.91 (t, J=11.3 Hz, 1H), 2.86 (s, 2H), 2.80-2.71 (m, 1H), 2.71-2.61 (m, 1H), 2.09-1.98 (m, 1H), 1.95-1.84 (m, 1H), 1.73-1.58 (m, 1H); $^{13}$C NMR (126 MHz, DMSO) δ 171.33, 137.93, 128.57, 126.78, 120.72, 47.72, 45.42, 42.77, 39.52, 34.36, 26.56, 23.83; IR (ATR) $v_{max}$ 3297, 1656, 1524, 1321, 1141, 984, 826, 499 cm$^{-1}$; AMM (ESI) m/z 339.0563 [calc for C$_{13}$H$_{17}$ClN$_2$O$_3$SNa (M+Na)$^+$ 339.0546]. Enantiomeric excess determined by SFC using a ChiralPak AS-H column; eluent: 15% MeOH in supercritical CO$_2$; flow rate: 4 mL/min; pressure: 12 MPa. Retention times: (+)-(S): 1.8 min, (−)-(R): 2.1 min. (+)-(S)-2.2 er=95:5; (−)-(R)-2.3 er=83:17.

Example 34: Synthesis of Intermediate 2.6

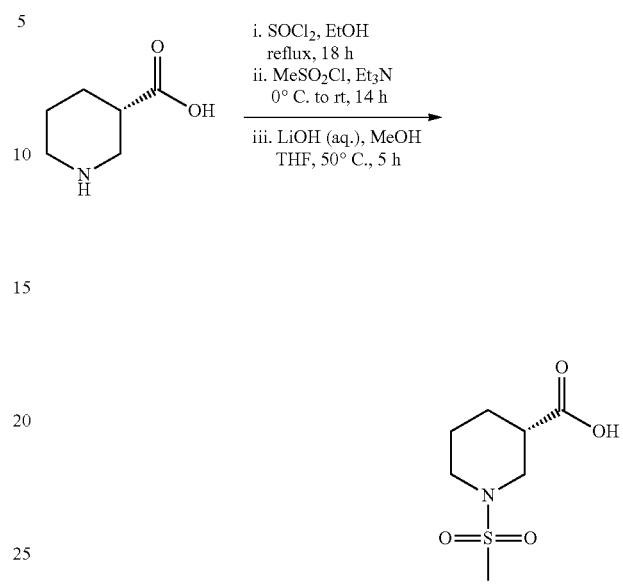

To a precooled (0° C.) solution of (S)-3-piperidinecarboxylic acid (1.5 g, 12 mmol) in ethanol (6 mL) under $N_2$ atmosphere was carefully added dropwise thionyl chloride (3.1 mL, 43 mmol). The resulting mixture was heated to reflux for 18 h, then allowed to cool to room temperature and concentrated in vacuo to afford the product as a pale orange solid and carried forward without further purification.

To a precooled (0° C.) solution of ester intermediate (1.7 g, 8.7 mmol) in CH$_2$Cl$_2$ (87 mL) under $N_2$ atmosphere was added triethylamine (2.4 mL, 17 mmol) and methanesulfonyl chloride (1.0 mL, 13 mmol). The resulting mixture was allowed to warm to room temperature and stirred for 14 h, then diluted with ether and sat. aq. NaHCO$_3$. The biphasic solution was stirred for 30 min, the layers were separated, and the aqueous phase was extracted with CH$_2$Cl$_2$ (3×). The combined organic layers were washed with brine, dried over Na$_2$SO$_4$ and concentrated in vacuo to afford the product as a pale orange oil and carried forward without additional purification.

To a flask charged with mesylated ester intermediate (2.0 g, 8.5 mmol) under ambient atmosphere was added 1 M aq. LiOH (30 mL), MeOH (60 mL) and THF (30 mL). The resulting mixture was heated to 50° C. and stirred for 5 h, then allowed to cool to room temperature, acidified with glacial acetic acid to pH 2, and concentrated in vacuo. The resulting solid was washed with CHCl$_3$ then taken up in toluene and concentrated in vacuo to remove residual acetic acid. The resulting product was carried forward without additional purification (1.0 g, 83% over 3 steps). $[\alpha]_D^{22}$ +20.24 (c. 0.13, CH$_3$OH); $^1$H NMR (500 MHz, Methanol-d$_4$) δ 3.40 (dd, J=13.0, 3.9 Hz, 1H), 3.31 (s, 5H), 3.28-3.15 (m, 2H), 3.10-3.00 (m, 1H), 2.87-2.76 (m, 1H), 2.17-2.07 (m, 1H), 2.00-1.87 (m, 1H), 1.87-1.72 (m, 2H); $^{13}$C NMR (126 MHz, CDCl$_3$) δ 178.03, 77.16, 47.29, 46.11, 40.92, 35.39, 26.55, 24.23; IR (ATR) $v_{max}$ 3245, 2960, 2942, 2860, 1732, 1694, 1317, 1153, 1140, 780, 519 cm$^{-1}$; AMM (ESI) m/z 208.0650 [calc for C$_7$H$_{14}$NO$_4$S (M+H)$^+$ 208.0644].

Example 35: Synthesis of Region I Analogues 2.7-2.18

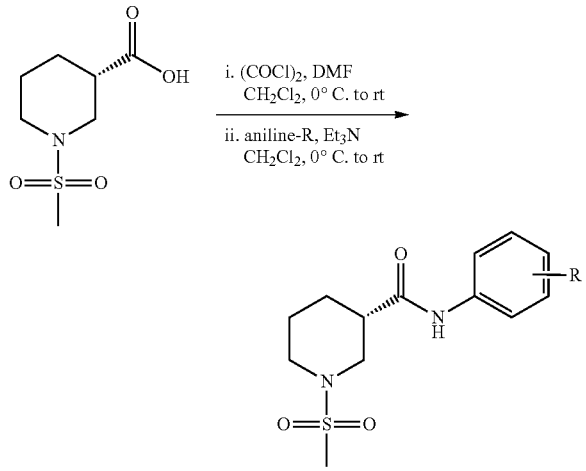

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To separate precooled (0° C.) vials charged with R-aniline (0.20 mmol) was added a solution of acid chloride intermediate (40 mg, 0.18 mmol) and triethylamine (41 µL, 0.35 mmol) in CH$_2$Cl$_2$ (1 mL). The resulting mixtures were allowed to warm to room temperature and stirred for 16 h then quenched with DMSO and H$_2$O. The resulting mixtures were filtered through Celite and purified by mass-directed isolation using ultra-performance liquid chromatography (11-42% yield).

Example 36: Synthesis of (S)-MCG-III-027-A02 (2.7)

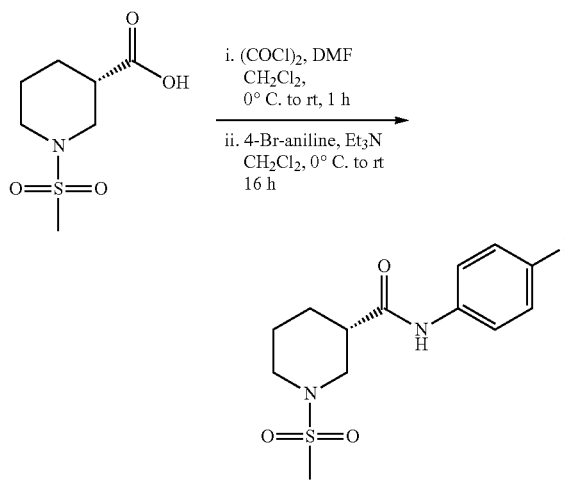

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 4-bromoaniline (34 mg, 0.20 mmol) was added a solution of acid chloride intermediate (40. mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (13 mg, 20% yield). $^1$H NMR (500 MHz, Chloroform-d) δ 8.06 (s, 1H), 7.71 (t, J=2.0 Hz, 1H), 7.39-7.34 (m, 1H), 7.23 (t, J=8.1 Hz, 1H), 7.11-7.04 (m, 1H), 3.75 (dd, J=12.1, 3.7 Hz, 1H), 3.58 (d, J=11.1 Hz, 1H), 3.16 (dd, J=12.1, 9.1 Hz, 1H), 3.00-2.89 (m, 2H), 2.84 (s, 3H), 2.71-2.61 (m, 1H), 2.01-1.95 (m, 1H), 1.92-1.81 (m, 2H); AMM (ESI) m/z 383.0070 [calc for C$_{13}$H$_{17}$BrN$_2$O$_3$SNa (M+Na)$^+$ 383.0041].

Example 37: Synthesis of (S)-MCG-III-027-A03 (2.8)

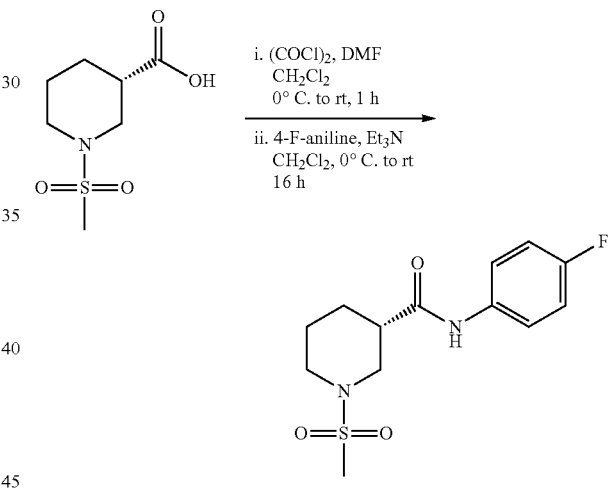

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 4-fluoroaniline (22 mg, 0.20 mmol) was added a solution of acid chloride intermediate (40. mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (15.5 mg, 29% yield). $^1$H NMR (500 MHz, Chloroform-d) δ 7.99 (s, 1H), 7.55-7.44 (m, 2H), 7.00 (t, J=8.6 Hz, 2H), 3.86-3.67 (m, 1H), 3.57 (d, J=11.8 Hz, 1H), 3.17 (dd, J=12.0, 9.0 Hz, 1H), 2.97-2.89 (m, 1H), 2.83 (s, 3H), 2.71-2.60 (m, 1H), 2.00-1.95 (m, 1H), 1.77-1.57 (m, 2H); AMM (ESI) m/z 323.0839 [calc for C$_{13}$H$_{17}$FN$_2$O$_3$SNa (M+Na)$^+$ 323.0842].

Example 38: Synthesis of (S)-MCG-III-027-A04 (2.9)

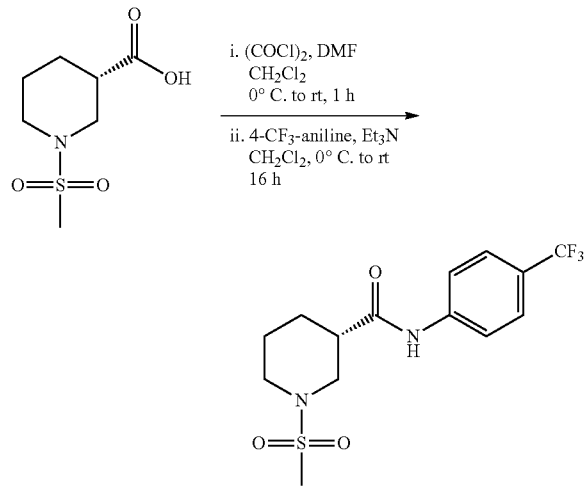

To a precooled (0° C.) solution of intermediate 2.6 (1.2 g, 4.8 mmol) in $CH_2Cl_2$ (9.6 mL) under $N_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 4-trifluoromethylaniline (31 mg, 0.20 mmol) was added a solution of acid chloride intermediate (40. mg, 0.18 mmol) and triethylamine (41 µL, 0.35 mmol) in $CH_2Cl_2$ (1 mL). The resulting mixture was allowed to warm to room temperature and stirred for 16 h then quenched with DMSO and $H_2O$. The resulting mixture was filtered through Celite and purified by mass-directed isolation using ultra-performance liquid chromatography (9.6 mg, 15% yield). $^1$H NMR (500 MHz, Chloroform-d) δ 8.24 (s, 1H), 7.69 (d, J=8.3 Hz, 2H), 7.57 (d, J=8.4 Hz, 2H), 3.74 (dd, J=11.9, 3.7 Hz, 1H), 3.61-3.52 (m, 1H), 3.21 (dd, J=12.1, 8.8 Hz, 1H), 3.03-2.94 (m, 1H), 2.85 (s, 3H), 2.76-2.67 (m, 1H), 2.06-1.97 (m, 1H), 1.94-1.84 (m, 2H); AMM (ESI) m/z 373.0825 [calc for $C_{14}H_{17}F_3N_2O_3SNa$ (M+Na)$^+$ 373.0810].

Example 39: Synthesis of (S)-MCG-III-027-B01 (2.10)

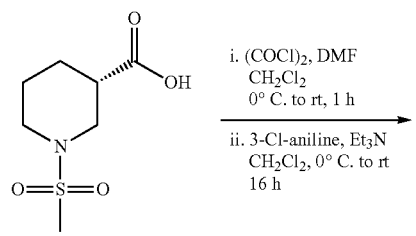

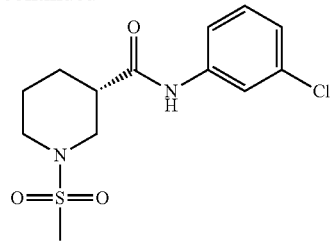

To a precooled (0° C.) solution of intermediate 2.6 (1.2 g, 4.8 mmol) in $CH_2Cl_2$ (9.6 mL) under $N_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 3-chloroaniline (25 mg, 0.20 mmol) was added a solution of acid chloride intermediate (40. mg, 0.18 mmol) and triethylamine (41 µL, 0.35 mmol) in $CH_2Cl_2$ (1 mL). The resulting mixture was allowed to warm to room temperature and stirred for 16 h then quenched with DMSO and $H_2O$. The resulting mixture was filtered through Celite and purified by mass-directed isolation using ultra-performance liquid chromatography (14.7 mg, 26% yield). $^1$H NMR (500 MHz, Chloroform-d) δ 8.06 (s, 1H), 7.71 (t, J=2.0 Hz, 1H), 7.39-7.34 (m, 1H), 7.23 (t, J=8.1 Hz, 1H), 7.11-7.05 (m, 1H), 3.75 (dd, J=12.0, 3.7 Hz, 1H), 3.63-3.53 (m, 1H), 3.16 (dd, J=12.1, 9.1 Hz, 1H), 2.99-2.89 (m, 2H), 2.84 (s, 3H), 2.71-2.63 (m, 1H), 2.01-1.95 (m, 1H), 1.93-1.81 (m, 2H); AMM (ESI) m/z 339.0552 [calc for $C_{13}H_{17}ClN_2O_3SNa$ (M+Na)$^+$ 339.0546].

Example 40: Synthesis of (S)-MCG-III-027-B02 (2.11)

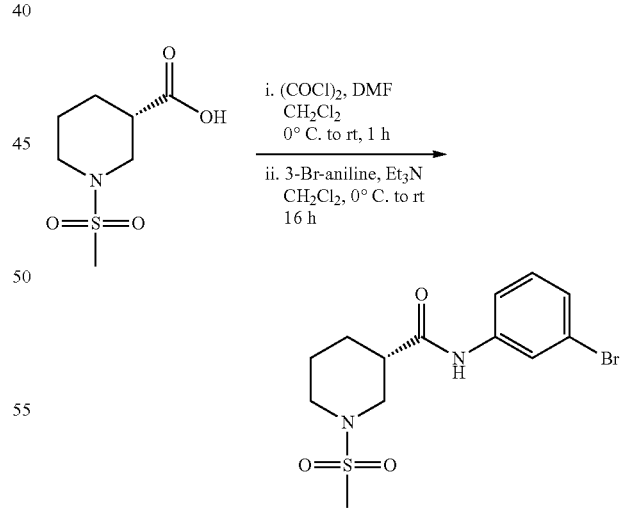

To a precooled (0° C.) solution of intermediate 2.6 (1.2 g, 4.8 mmol) in $CH_2Cl_2$ (9.6 mL) under $N_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 3-bromoaniline (34 mg, 0.20 mmol) was added a solution of acid chloride intermediate (40. mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (16 mg, 24% yield). $^1$H NMR (500 MHz, Chloroform-d) δ 8.00 (s, 1H), 7.86 (t, J=2.0 Hz, 1H), 7.42 (d, J=7.9 Hz, 1H), 7.24 (d, J=8.1 Hz, 1H), 7.17 (t, J=8.0 Hz, 1H), 3.74 (dd, J=12.1, 3.7 Hz, 1H), 3.57 (d, J=11.6 Hz, 1H), 3.17 (dd, J=12.1, 8.9 Hz, 1H), 3.00-2.90 (m, 2H), 2.84 (s, 3H), 2.71-2.61 (m, 1H), 2.01-1.95 (m, 1H), 1.93-1.81 (m, 3H); AMM (ESI) m/z 383.0041 [calc for C$_{13}$H$_{17}$BrN$_2$O$_3$SNa (M+Na)$^+$ 383.0041].

Example 41: Synthesis of (S)-MCG-III-027-B03 (2.12)

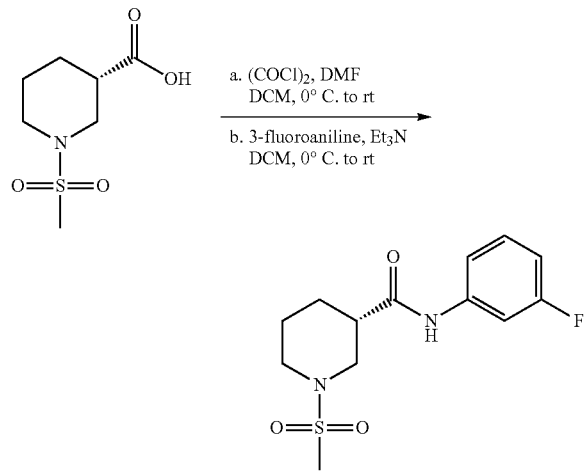

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 3-fluoroaniline (22 mg, 0.20 mmol) was added a solution of acid chloride intermediate (40 mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (17 mg, 32% yield). $^1$H NMR (500 MHz, Chloroform-d) δ 8.13 (s, 1H), 7.53 (dt, J=10.9, 2.3 Hz, 1H), 7.26-7.21 (m, 1H), 7.19 (d, J=8.1 Hz, 1H), 6.80 (td, J=8.2, 2.5 Hz, 1H), 3.76 (dd, J=12.1, 3.8 Hz, 1H), 3.65-3.55 (m, 1H), 3.15 (dd, J=12.0, 9.2 Hz, 1H), 2.99-2.88 (m, 2H), 2.84 (s, 3H), 2.74-2.63 (m, 1H), 2.06-1.97 (m, 1H), 1.95-1.83 (m, 2H); AMM (ESI) m/z 323.0850 [calc for C$_{13}$H$_{17}$FN$_2$O$_3$SNa (M+Na)$^+$ 323.0842].

Example 42: Synthesis of (S)-MCG-III-027-B04 (2.13)

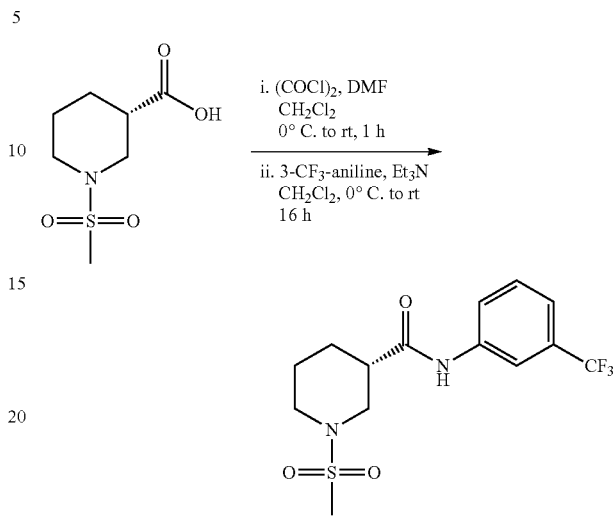

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 3-trifluoromethylaniline (31 mg, 0.20 mmol) was added a solution of acid chloride intermediate (40. mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (19 mg, 30% yield). $^1$H NMR (500 MHz, Chloroform-d) δ 8.15 (s, 1H), 7.95 (s, 1H), 7.68 (d, J=8.0 Hz, 1H), 7.43 (t, J=8.0 Hz, 1H), 7.36 (d, J=7.7 Hz, 1H), 3.75 (d, J=12.6 Hz, 1H), 3.57 (d, J=11.9 Hz, 1H), 3.20 (dd, J=12.1, 8.8 Hz, 1H), 2.97 (m, 1H), 2.84 (s, 3H), 2.70 (m, 1H), 2.00 (m, 1H), 1.95-1.82 (m, 2H); AMM (ESI) m/z 373.0835 [calc for C$_{14}$H$_{17}$F$_3$N$_2$O$_3$SNa (M+Na)$^+$ 373.0810].

Example 43: Synthesis of (S)-MCG-III-027-B05 (2.14)

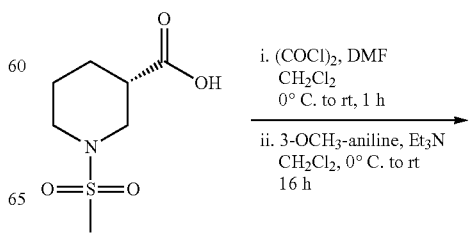

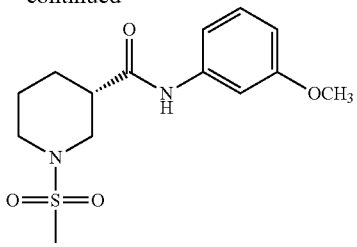

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with meta-anisole (21 mg, 0.20 mmol) was added a solution of acid chloride intermediate (40 mg, 0.18 mmol) and triethylamine (41 μL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (23 mg, 42% yield). $^1$H NMR (500 MHz, Chloroform-d) δ 7.92 (s, 1H), 7.32 (s, 1H), 7.20 (t, J=8.1 Hz, 1H), 7.05-6.97 (m, 1H), 6.66 (dd, J=8.2, 2.5 Hz, 1H), 3.91-3.72 (m, 4H), 3.65-3.56 (m, 1H), 3.10 (dd, J=12.1, 9.4 Hz, 1H), 2.90-2.83 (m, 2H), 2.82 (s, 3H), 2.69-2.58 (m, 1H), 2.06-1.96 (m, 2H), 1.77-1.65 (m, 1H); AMM (ESI) m/z 335.1048 [calc for C$_{14}$H$_{20}$N$_2$O$_4$SNa (M+Na)$^+$ 335.1041].

Example 44: Synthesis of (S)-MCG-III-027-C01 (2.15)

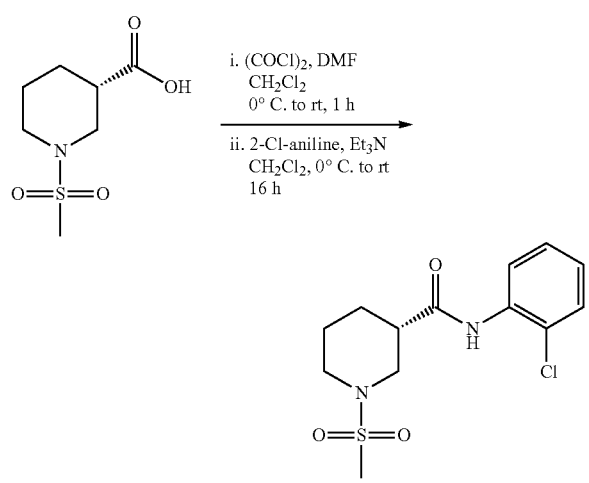

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 2-chloroaniline (25 mg, 0.20 mmol) was added a solution of acid chloride intermediate (40. mg, 0.18 mmol) and triethylamine (41 μL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (16 mg, 29% yield). $^1$H NMR (500 MHz, Chloroform-d) δ 8.28 (d, J=8.3 Hz, 1H), 7.88 (s, 1H), 7.38 (d, J=7.9 Hz, 1H), 7.28 (d, J=8.6 Hz, 1H), 7.07 (t, J=7.6 Hz, 1H), 3.93-3.82 (m, 1H), 3.68 (d, J=11.8 Hz, 1H), 3.08 (dd, J=12.0, 9.6 Hz, 1H), 2.98-2.88 (m, 1H), 2.83 (s, 3H), 2.74-2.64 (m, 1H), 2.15-2.05 (m, 1H), 1.93 (d, J=12.0 Hz, 2H); AMM (ESI) m/z 339.0571 [calc for C$_{13}$H$_{17}$ClN$_2$O$_3$SNa (M+Na)$^+$ 339.0546].

Example 45: Synthesis of (S)-MCG-III-027-C05 (2.16)

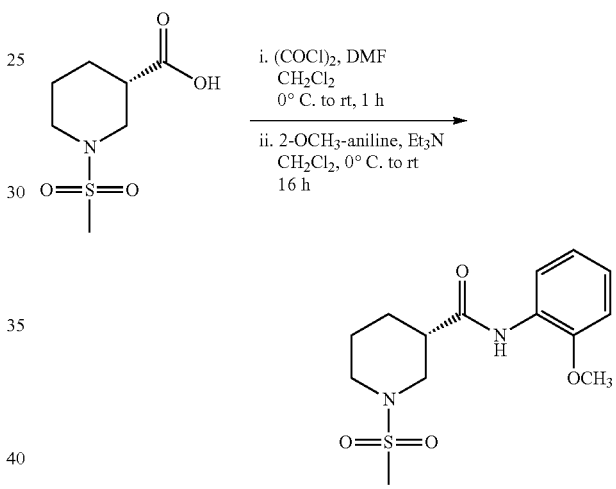

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with ortho-anisole (21 mg, 0.20 mmol) was added a solution of acid chloride intermediate (40. mg, 0.18 mmol) and triethylamine (41 μL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (7.3 mg, 13% yield). $^1$H NMR (500 MHz, Chloroform-d) δ 8.31 (dd, J=8.1, 1.6 Hz, 1H), 8.11 (s, 1H), 7.09-7.03 (m, 1H), 6.98-6.92 (m, 1H), 6.91-6.85 (m, 1H), 3.90 (s, 3H), 3.82 (d, J=11.6 Hz, 1H), 3.64 (d, J=12.0 Hz, 1H), 3.14-3.04 (m, 1H), 2.90-2.82 (m, 1H), 2.81 (s, 3H), 2.71-2.62 (m, 1H), 2.04-1.98 (m, 1H), 1.95-1.86 (m, 1H), 1.86-1.79 (m, 1H), 1.77-1.67 (m, 1H); AMM (ESI) m/z 335.1039 [calc for C$_{14}$H$_{20}$N$_2$O$_4$SNa (M+Na)$^+$ 335.1041].

Example 46: Synthesis of (S)-MCG-III-027-D04 (2.17)

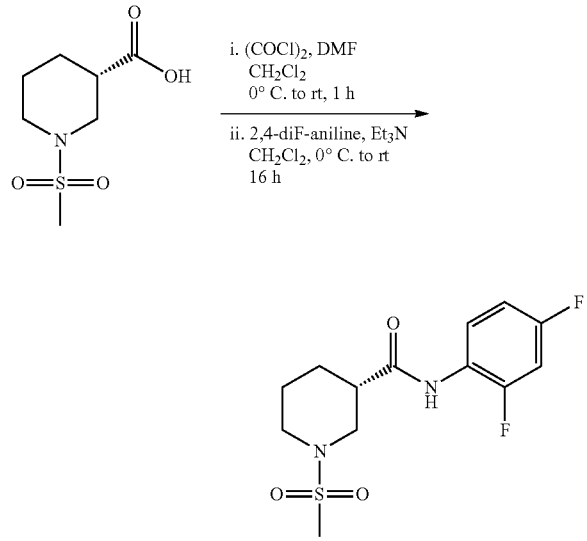

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 2,4-difluoroaniline (25 mg, 0.20 mmol) was added a solution of acid chloride intermediate (40. mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (8.1 mg, 14% yield). $^1$H NMR (500 MHz, Chloroform-d) δ 8.22-8.12 (m, 1H), 7.60 (s, 1H), 6.92-6.83 (m, 2H), 3.81 (d, J=12.1 Hz, 1H), 3.64 (d, J=11.7 Hz, 1H), 3.16-3.06 (m, 1H), 2.88 (t, J=10.8 Hz, 1H), 2.82 (s, 3H), 2.73-2.61 (m, 1H), 2.09-1.99 (m, 1H), 1.96-1.87 (m, 1H), 1.86-1.79 (m, 1H), 1.79-1.69 (m, 1H); AMM (ESI) m/z 341.0762 [calc for C$_{13}$H$_{16}$F$_2$N$_2$O$_3$SNa (M+Na)$^+$ 341.0747].

Example 47: Synthesis of (S)-MCG-III-027-D05 (2.18)

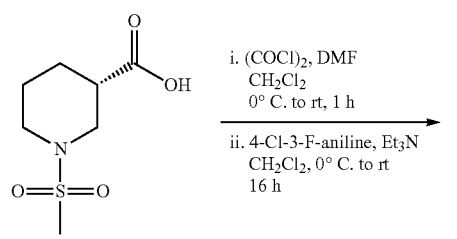

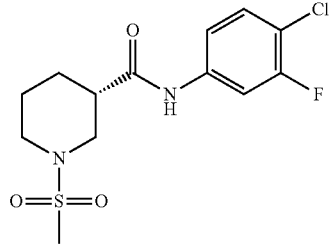

To a precooled (0° C.) solution of intermediate 2.6 (1.2 g, 4.8 mmol) in CH$_2$Cl$_2$ (9.6 mL) under N$_2$ atmosphere was added dropwise oxalyl chloride (0.43 mL, 5.0 mmol) then DMF (several drops). The resulting mixture was stirred at 0° C. for 10 min. then allowed to warm to room temperature and stirred for 1 h. The mixture was concentrated in vacuo and used directly.

To a precooled (0° C.) vial charged with 4-chloro-3-fluoroaniline (28 mg, 0.20 mmol) was added a solution of acid chloride intermediate (40 mg, 0.18 mmol) and triethylamine (41 µL, 0.35 mmol) in CH$_2$Cl$_2$ (1 mL). The resulting mixture was allowed to warm to room temperature and stirred for 16 h then quenched with DMSO and H$_2$O. The resulting mixture was filtered through Celite and purified by mass-directed isolation using ultra-performance liquid chromatography (6.7 mg, 11% yield). [α]$_D^{23}$+4.31 (c. 0.083, CH$_3$OH); $^1$H NMR (500 MHz, Acetonitrile-d$_3$) δ 8.70 (s, 1H), 7.72 (dd, J=11.8, 2.4 Hz, 1H), 7.37 (t, J=8.6 Hz, 1H), 7.24 (ddd, J=8.8, 2.4, 1.1 Hz, 1H), 3.79 (ddt, J=11.8, 3.6, 1.6 Hz, 1H), 3.61 (d, J=11.7 Hz, 1H), 2.87 (dd, J=11.8, 10.7 Hz, 1H), 2.78 (s, 3H), 2.72 (td, J=11.5, 2.9 Hz, 1H), 2.58 (tt, J=10.7, 3.9 Hz, 1H), 2.00 (d, J=7.6 Hz, 1H), 1.89-1.80 (m, 1H), 1.66-1.55 (m, 2H); $^{13}$C NMR (126 MHz, MeOD) δ 174.03, 160.08, 158.13, 140.39, 140.31, 131.53, 117.34, 117.31, 116.09, 115.94, 109.33, 109.12, 47.09, 45.02, 40.40, 34.89, 28.45, 25.53; IR (ATR) ν$_{max}$ 2990, 1665, 1529, 1422, 1322, 1201, 1166, 815, 491 cm$^{-1}$; AMM (ESI) m/z 357.0457 [calc for C$_{13}$H$_{16}$ClFN$_2$O$_3$SNa (M+Na)$^+$ 357.0452].

Example 48: Synthesis of Region I Analogues 2.19-2.23

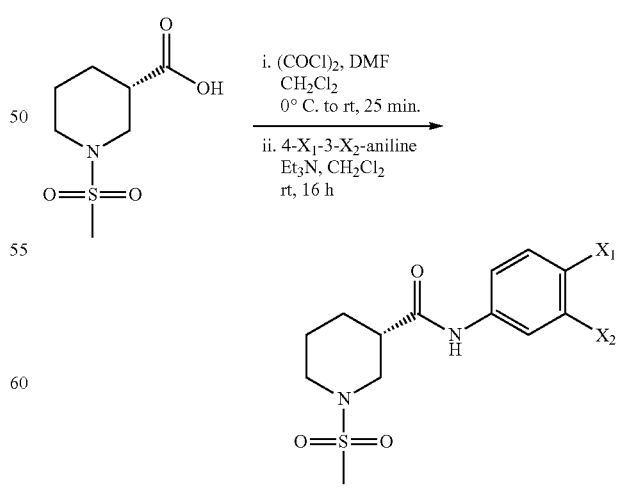

To a precooled (0° C.) solution of intermediate 2.6 (170. Mg, 0.698 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To precooled (0° C.) solutions of 4-$X_1$-3-$X_2$-aniline (15 mg) in $CH_2Cl_2$ (0.5 mL) was added triethylamine (15 µL, 0.11 mmol) then a solution of acid chloride intermediate (1.1 eq.) in $CH_2Cl_2$ (0.5 mL). The resulting mixtures were allowed to warm to room temperature and stirred for 16 h then quenched with DMSO (0.5 mL), filtered through Celite and purified by mass-directed isolation using ultra-performance liquid chromatography (9-24% yield).

Example 49: Synthesis of (S)-MCG-III-085-A02 (2.19)

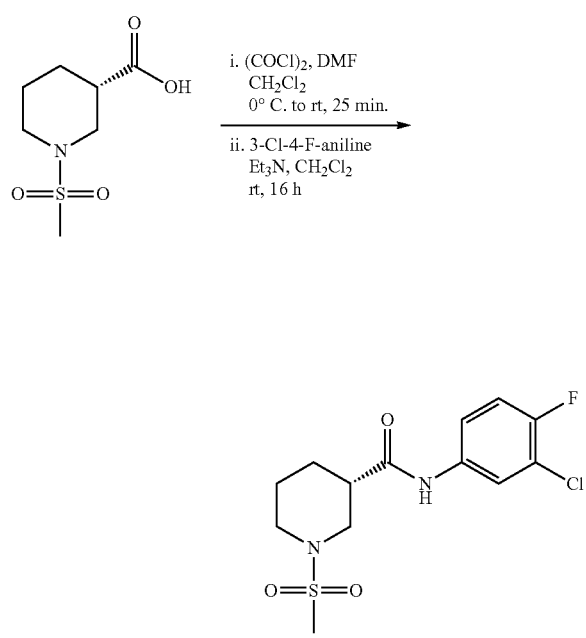 [SMILES: CS(=O)(=O)N1CCC[C@H](C(=O)O)C1 ; CS(=O)(=O)N1CCC[C@H](C(=O)Nc2ccc(Br)cc2)C1]

To a precooled (0° C.) solution of intermediate 2.6 (170. mg, 0.698 mmol) in $CH_2Cl_2$ (3.5 mL) under $N_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3-chloro-4-fluoroaniline (15 mg, 0.10 mmol) in $CH_2Cl_2$ (0.5 mL) was added triethylamine (15 µL, 0.11 mmol) then a solution of acid chloride intermediate (26 mg, 0.11 mmol) in $CH_2Cl_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (5.6 mg, 16% yield). $^1$H NMR (500 MHz, Acetonitrile-$d_3$) δ 8.58 (s, 1H), 7.85-7.79 (m, 1H), 7.45-7.38 (m, 1H), 7.18 (td, J=9.1, 1.0 Hz, 1H), 3.84-3.75 (m, 1H), 3.62 (d, J=11.8 Hz, 1H), 2.87 (t, J=11.2 Hz, 1H), 2.79 (s, 3H), 2.72 (td, J=11.6, 3.1 Hz, 1H), 2.57 (tt, J=10.8, 4.0 Hz, 2H), 2.04-1.98 (m, 1H), 1.89-1.80 (m, 1H), 1.67-1.56 (m, 2H); AMM (ESI) m/z 357.0447 [calc for $C_{13}H_{16}ClFN_2O_3SNa$ (M+Na)$^+$ 357.0452].

Example 50: Synthesis of (S)-MCG-III-085-A03 (2.20)

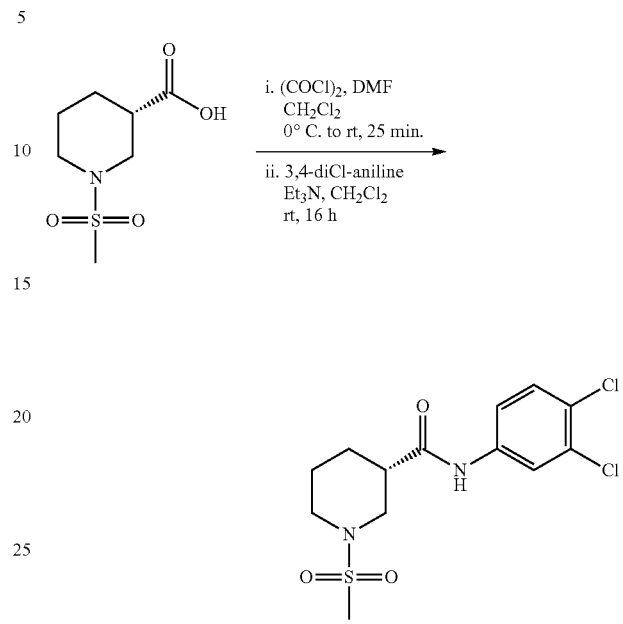

To a precooled (0° C.) solution of intermediate 2.6 (170. mg, 0.698 mmol) in $CH_2Cl_2$ (3.5 mL) under $N_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3,4-dichloroaniline (15 mg, 0.093 mmol) in $CH_2Cl_2$ (0.5 mL) was added triethylamine (15 µL, 0.11 mmol) then a solution of acid chloride intermediate (23 mg, 0.10 mmol) in $CH_2Cl_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (5.0, 15% yield). $^1$H NMR (500 MHz, Acetonitrile-d3) δ 8.67 (s, 1H), 7.89 (dd, J=2.0, 0.9 Hz, 1H), 7.47-7.39 (m, 2H), 3.83-3.74 (m, 1H), 3.66-3.57 (m, 1H), 2.87 (dd, J=11.8, 10.6 Hz, 1H), 2.79 (s, 3H), 2.72 (td, J=11.6, 2.9 Hz, 1H), 2.59 (tt, J=10.8, 3.9 Hz, 1H), 2.05-1.98 (m, 1H), 1.90-1.82 (m, 1H), 1.67-1.56 (m, 2H); AMM (ESI) m/z 373.0159 [calc for $C_{13}H_{16}Cl_2N_2O_3SNa$ (M+Na)$^+$ 373.0156].

Example 51: Synthesis of (S)-MCG-III-085-A04 (2.21)

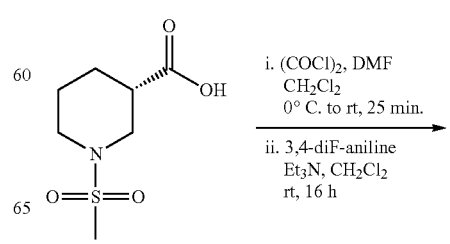

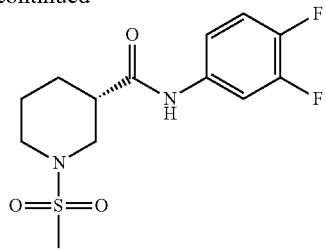

To a precooled (0° C.) solution of intermediate 2.6 (170. mg, 0.698 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3,4-difluoroaniline (15 mg, 0.12 mmol) in CH$_2$Cl$_2$ (0.5 mL) was added triethylamine (15 μL, 0.11 mmol) then a solution of acid chloride intermediate (29 mg, 0.13 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (5.7 mg, 15% yield). $^1$H NMR (500 MHz, Acetonitrile-d$_3$) δ 8.60 (s, 1H), 7.77-7.66 (m, 1H), 7.25-7.14 (m, 2H), 3.83-3.75 (m, 1H), 3.66-3.58 (m, 1H), 2.87 (dd, J=11.8, 10.6 Hz, 1H), 2.78 (s, 3H), 2.72 (td, J=11.6, 2.9 Hz, 1H), 2.57 (tt, J=10.8, 3.9 Hz, 1H), 2.04-1.97 (m, 1H), 1.90-1.82 (m, 1H), 1.67-1.55 (m, 2H); AMM (ESI) m/z 341.0736 [calc for C$_{13}$H$_{16}$F$_2$N$_2$O$_3$SNa (M+Na)$^+$ 341.0747].

Example 52: Synthesis of (S)-MCG-III-085-A05 (2.22)

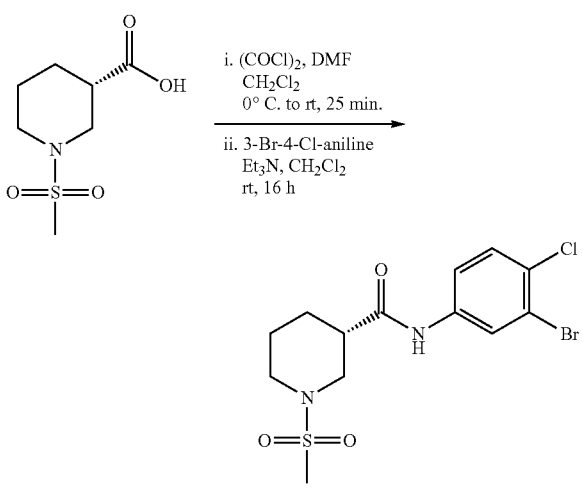

To a precooled (0° C.) solution of intermediate 2.6 (170. mg, 0.698 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3-bromo-4-chloroaniline (15 mg, 0.073 mmol) in CH$_2$Cl$_2$ (0.5 mL) was added triethylamine (15 μL, 0.11 mmol) then a solution of acid chloride intermediate (18 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (2.5 mg 9% yield). $^1$H NMR (500 MHz, Acetonitrile-d$_3$) δ 8.65 (s, 1H), 8.03 (d, J=2.4 Hz, 1H), 7.48 (dd, J=8.8, 2.4 Hz, 1H), 7.43 (d, J=8.7 Hz, 1H), 3.83-3.76 (m, 1H), 3.61 (d, J=11.9 Hz, 1H), 2.87 (dd, J=11.8, 10.6 Hz, 1H), 2.79 (s, 3H), 2.72 (td, J=11.6, 2.9 Hz, 1H), 2.58 (tt, J=10.7, 3.8 Hz, 1H), 2.03-1.98 (m, 1H), 1.90-1.82 (m, 1H), 1.67-1.55 (m, 2H); AMM (ESI) m/z 416.9674 [calc for C$_{13}$H$_{16}$BrClN$_2$O$_3$SNa (M+Na)$^+$ 416.9651].

Example 53: Synthesis of (S)-MCG-III-085-A06 (2.23)

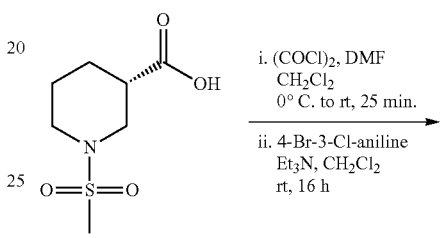

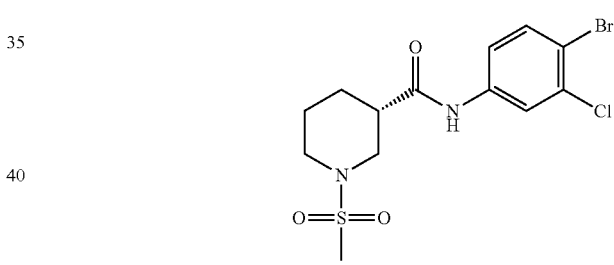

To a precooled (0° C.) solution of intermediate 2.6 (170. mg, 0.698 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 4-bromo-3-chloroaniline (15 mg, 0.073 mmol) in CH$_2$Cl$_2$ (0.5 mL) was added triethylamine (15 μL, 0.11 mmol) then a solution of acid chloride intermediate (18 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (7.0 mg, 24% yield). $^1$H NMR (500 MHz, Acetonitrile-d$_3$) δ 8.66 (s, 1H), 7.90 (d, J=2.5 Hz, 1H), 7.58 (d, J=8.7 Hz, 1H), 7.35 (dd, J=8.8, 2.5 Hz, 1H), 3.79 (ddt, J=11.7, 3.7, 1.7 Hz, 1H), 3.65-3.57 (m, 1H), 2.87 (dd, J=11.8, 10.6 Hz, 1H), 2.79 (s, 3H), 2.77-2.68 (m, 1H), 2.58 (tt, J=10.8, 3.9 Hz, 1H), 2.05-1.98 (m, 1H), 1.90-1.81 (m, 1H), 1.67-1.53 (m, 2H); AMM (ESI) m/z 416.9650 [calc for C$_{13}$H$_{16}$BrClN$_2$O$_3$SNa (M+Na)$^+$ 416.9651].

Example 54: Synthesis of Intermediate 2.24

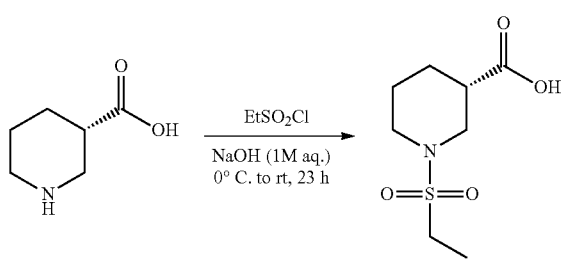

To a precooled (0° C.) solution of (S)-3-piperidinecarboxylic acid (350. mg, 2.71 mmol) in 1 M aq. NaOH (5.4 mL) under $N_2$ atmosphere was added dropwise ethanesulfonyl chloride (0.31 mL, 3.3 mmol). The resulting mixture was allowed to warm to room temperature and stirred for 23 h, then diluted with ether. The aqueous layer was washed with ether (1×) then acidified to pH 1 with 1 M aq. HCl. The layers were separated, and the aqueous phase was extracted with $CH_2Cl_2$ (3×). The combined organic layers were washed with brine, dried over $Na_2SO_4$ and concentrated in vacuo to afford the product as a white solid (206 mg, 34% yield). $[\alpha]_D^{22}$ +21.69 (c. 0.24, $CH_3OH$); $^1H$ NMR (500 MHz, Chloroform-d) δ 3.86 (dd, J=12.4, 3.8 Hz, 1H), 3.66-3.58 (m, 1H), 3.06 (dd, J=12.5, 9.7 Hz, 1H), 2.98 (q, J=7.4 Hz, 2H), 2.89 (ddd, J=12.4, 10.3, 3.2 Hz, 1H), 2.72-2.60 (m, 1H), 2.15-2.05 (m, 1H), 1.89-1.78 (m, 1H), 1.72-1.58 (m, 2H), 1.35 (t, J=7.4 Hz, 3H); $^{13}C$ NMR (126 MHz, $CDCl_3$) δ 178.53, 77.16, 47.24, 46.12, 44.67, 41.18, 26.66, 24.56, 8.00; IR (ATR) $\nu_{max}$ 2945, 2863, 1708, 1452, 1130, 967, 750, 573, 509 $cm^{-1}$; AMM (ESI) m/z 222.0810 [calc for $C_8H_{16}NO_4S$ (M+H)$^+$ 222.0800].

Example 55: Synthesis of Region I Analogues 2.25-2.30

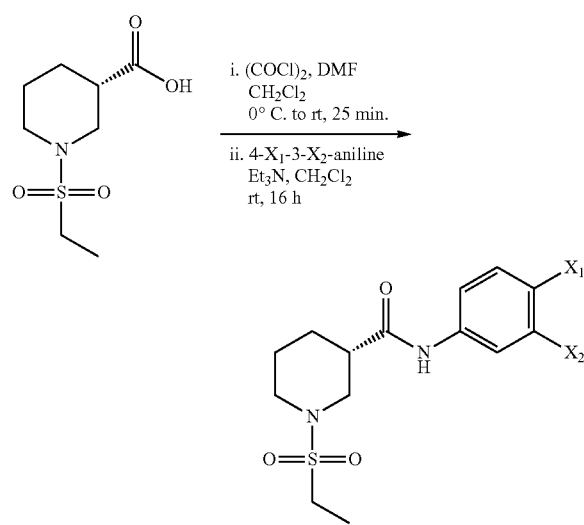

To a precooled (0° C.) solution of intermediate 2.24 (155 mg, 0.701 mmol) in $CH_2Cl_2$ (3.5 mL) under $N_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To precooled (0° C.) solutions of 4-$X_1$-3-$X_2$-aniline (15 mg) in $CH_2Cl_2$ (0.5 mL) was added triethylamine (15 μL, 0.11 mmol) then a solution of acid chloride intermediate (1.1 eq.) in $CH_2Cl_2$ (0.5 mL). The resulting mixtures were allowed to warm to room temperature and stirred for 16 h then quenched with DMSO (0.5 mL), filtered through Celite and purified by mass-directed isolation using ultra-performance liquid chromatography (11-24% yield).

Example 56: Synthesis of (S)-MCG-III-085-C01 (2.25)

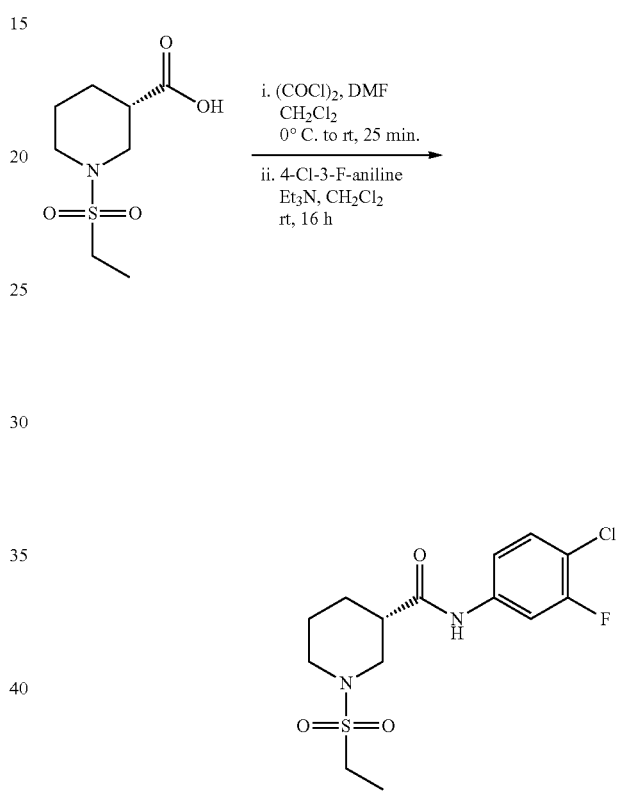

To a precooled (0° C.) solution of intermediate 2.24 (155 mg, 0.701 mmol) in $CH_2Cl_2$ (3.5 mL) under $N_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To precooled (0° C.) solutions of 4-chloro-3-fluoro-aniline (15 mg, 0.10 mmol) in $CH_2Cl_2$ (0.5 mL) was added triethylamine (15 μL, 0.11 mmol) then a solution of acid chloride intermediate (27 mg, 0.11 mmol) in $CH_2Cl_2$ (0.5 mL). The resulting mixtures were allowed to warm to room temperature and stirred for 16 h then quenched with DMSO (0.5 mL), filtered through Celite and purified by mass-directed isolation using ultra-performance liquid chromatography (6.6 mg, 18% yield). $^1H$ NMR (500 MHz, Acetonitrile-$d_3$) δ 8.69 (s, 1H), 7.72 (dd, J=11.9, 2.4 Hz, 1H), 7.37 (t, J=8.6 Hz, 1H), 7.28-7.20 (m, 1H), 3.86-3.74 (m, 1H), 3.64 (dd, J=12.6, 4.2 Hz, 1H), 3.06-2.93 (m, 3H), 2.83 (td, J=11.8, 2.9 Hz, 1H), 2.61-2.49 (m, 2H), 2.04-1.97 (m, 1H), 1.86-1.77 (m, 1H), 1.71-1.50 (m, 2H), 1.27 (t, J=7.4 Hz, 3H); AMM (ESI) m/z 371.0599 [calc for $C_{14}H_{18}ClFN_2O_3SNa$ (M+Na)$^+$ 371.0608].

Example 57: Synthesis of (S)-MCG-III-085-C02 (2.26)

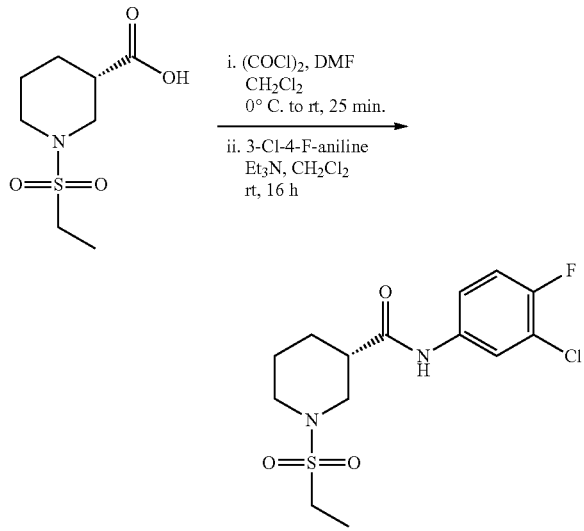

To a precooled (0° C.) solution of intermediate 2.24 (155 mg, 0.701 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To precooled (0° C.) solutions of 3-chloro-4-fluoro-aniline (15 mg, 0.10 mmol) in CH$_2$Cl$_2$ (0.5 mL) was added triethylamine (15 µL, 0.11 mmol) then a solution of acid chloride intermediate (27 mg, 0.11 mmol) in CH$_2$Cl$_2$ (0.5 mL). The resulting mixtures were allowed to warm to room temperature and stirred for 16 h then quenched with DMSO (0.5 mL), filtered through Celite and purified by mass-directed isolation using ultra-performance liquid chromatography (7.6 mg, 21% yield). $^1$H NMR (500 MHz, Acetonitrile-d$_3$) δ 8.57 (s, 1H), 7.81 (dd, J=6.8, 2.6 Hz, 1H), 7.45-7.36 (m, 1H), 7.17 (t, J=9.0 Hz, 1H), 3.81 (ddt, J=12.2, 3.7, 1.7 Hz, 1H), 3.68-3.58 (m, 1H), 3.04-2.92 (m, 3H), 2.83 (td, J=11.7, 2.8 Hz, 1H), 2.59-2.49 (m, 1H), 2.03-1.96 (m, 1H), 1.87-1.76 (m, 1H), 1.70-1.50 (m, 2H), 1.27 (t, J=7.4 Hz, 3H); AMM (ESI) m/z 371.0618 [calc for C$_{14}$H$_{18}$ClFN$_2$O$_3$SNa (M+Na)$^+$ 371.0608].

Example 58: Synthesis of (S)-MCG-III-085-C03 (2.27)

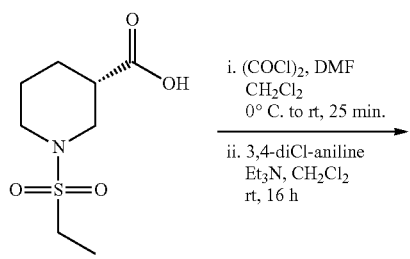

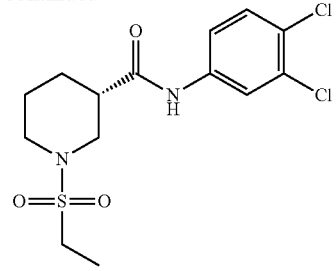

To a precooled (0° C.) solution of intermediate 2.24 (155 mg, 0.701 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3,4-dichloroaniline (15 mg, 0.093 mmol) in CH$_2$Cl$_2$ (0.5 mL) was added triethylamine (15 µL, 0.11 mmol) then a solution of acid chloride intermediate (24 mg, 0.10 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (6.7 mg, 20% yield). $^1$H NMR (500 MHz, Acetonitrile-d$_3$) δ 8.65 (s, 1H), 7.89 (dd, J=1.8, 0.9 Hz, 1H), 7.47-7.38 (m, 2H), 3.81 (ddt, J=12.2, 3.7, 1.7 Hz, 1H), 3.68-3.59 (m, 1H), 3.05-2.92 (m, 3H), 2.83 (td, J=11.7, 2.9 Hz, 1H), 2.61-2.49 (m, 1H), 2.04-1.97 (m, 1H), 1.89-1.78 (m, 1H), 1.70-1.50 (m, 2H), 1.27 (t, J=7.4 Hz, 3H); AMM (ESI) m/z 387.0302 [calc for C$_{14}$H$_{18}$Cl$_2$N$_2$O$_3$SNa (M+Na)$^+$ 387.0313].

Example 59: Synthesis of (S)-MCG-III-085-C04 (2.28)

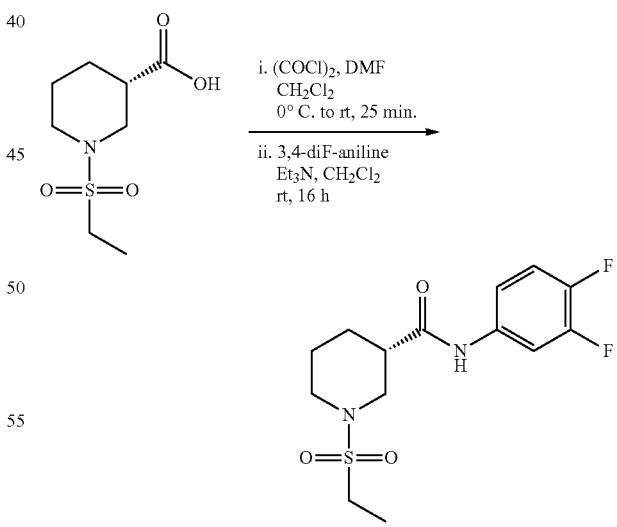

To a precooled (0° C.) solution of intermediate 2.24 (155 mg, 0.701 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3,4-difluoroaniline (15 mg, 0.12 mmol) in CH$_2$Cl$_2$ (0.5 mL) was added triethylamine (15 μL, 0.11 mmol) then a solution of acid chloride intermediate (31 mg, 0.13 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (9.0 mg, 23% yield). $^1$H NMR (500 MHz, Acetonitrile-d$_3$) δ 8.58 (s, 1H), 7.75-7.66 (m, 1H), 7.24-7.13 (m, 2H), 3.85-3.76 (m, 1H), 3.68-3.58 (m, 1H), 3.04-2.93 (m, 3H), 2.83 (td, J=11.7, 2.8 Hz, 1H), 2.59-2.47 (m, 1H), 2.04-1.96 (m, 1H), 1.87-1.78 (m, 1H), 1.70-1.51 (m, 2H), 1.27 (t, J=7.4 Hz, 3H); AMM (ESI) m/z 355.0882 [calc for C$_{14}$H$_{18}$F$_2$N$_2$O$_3$SNa (M+Na)$^+$ 355.0904].

Example 60: Synthesis of (S)-MCG-III-085-C05 (2.29)

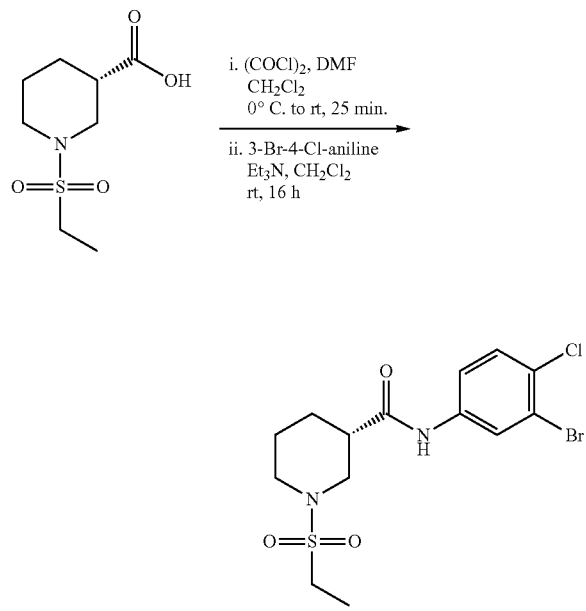 [SMILES: CCS(=O)(=O)N1CCC[C@H](C(=O)O)C1 ; CCS(=O)(=O)N1CCC[C@H](C(=O)Nc2ccc(Cl)c(Br)c2)C1]

To a precooled (0° C.) solution of intermediate 2.24 (155 mg, 0.701 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solution of 3-bromo-4-chloroaniline (15 mg, 0.073 mmol) in CH$_2$Cl$_2$ (0.5 mL) was added triethylamine (15 μL, 0.11 mmol) then a solution of acid chloride intermediate (19 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (3.4 mg, 11% yield). $^1$H NMR (500 MHz, Acetonitrile-d$_3$) δ 8.66 (s, 1H), 8.03 (d, J=2.4 Hz, 1H), 7.48 (dd, J=8.8, 2.4 Hz, 1H), 7.43 (d, J=8.7 Hz, 1H), 3.85-3.75 (m, 1H), 3.63 (d, J=12.4 Hz, 1H), 3.05-2.93 (m, 3H), 2.83 (td, J=11.7, 2.8 Hz, 1H), 2.60-2.52 (m, 1H), 2.04-1.97 (m, 1H), 1.88-1.78 (m, 2H), 1.70-1.50 (m, 3H), 1.27 (t, J=7.4 Hz, 3H); AMM (ESI) m/z 430.9807 [calc for C$_{14}$H$_{18}$BrClN$_2$O$_3$SNa (M+Na)$^+$ 430.9808].

Example 61: Synthesis of (S)-MCG-III-085-C06 (2.30)

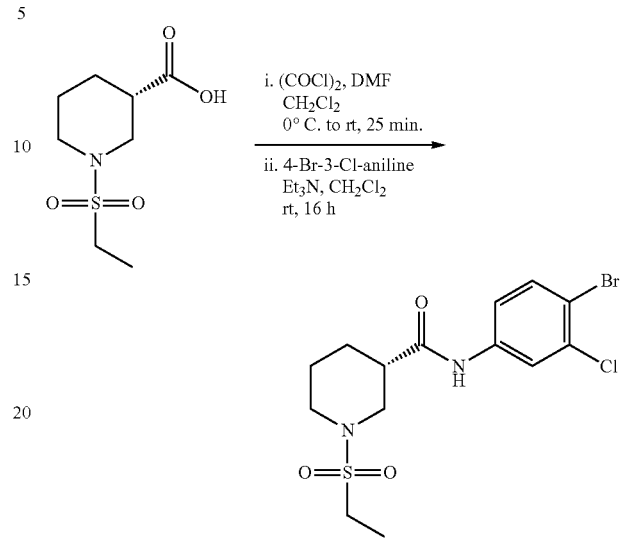

To a precooled (0° C.) solution of intermediate 2.24 (155 mg, 0.701 mmol) in CH$_2$Cl$_2$ (3.5 mL) under N$_2$ atmosphere was added dropwise oxalyl chloride (0.06 mL, 0.7 mmol) then DMF (2 drops). The resulting mixture was stirred at 0° C. for 25 min. then concentrated in vacuo and used directly.

To a precooled (0° C.) solutions of 4-bromo-3-chloroaniline (15 mg, 0.073 mmol) in CH$_2$Cl$_2$ (0.5 mL) was added triethylamine (15 μL, 0.11 mmol) then a solution of acid chloride intermediate (19 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (7.2 mg, 24% yield). $^1$H NMR (500 MHz, Acetonitrile-d$_3$) δ 8.67 (s, 1H), 7.90 (d, J=2.5 Hz, 1H), 7.58 (d, J=8.7 Hz, 1H), 7.35 (dd, J=8.7, 2.5 Hz, 1H), 3.85-3.76 (m, 1H), 3.67-3.58 (m, 1H), 3.04-2.93 (m, 3H), 2.83 (td, J=11.7, 2.8 Hz, 1H), 2.61-2.50 (m, 1H), 2.04-1.97 (m, 1H), 1.86-1.78 (m, 1H), 1.71-1.49 (m, 2H), 1.27 (t, J=7.4 Hz, 3H); AMM (ESI) m/z 430.9834 [calc for C$_{14}$H$_{18}$BrClN$_2$O$_3$SNa (M+Na)$^+$ 430.9808].

Example 62: Synthesis of Intermediate 2.31

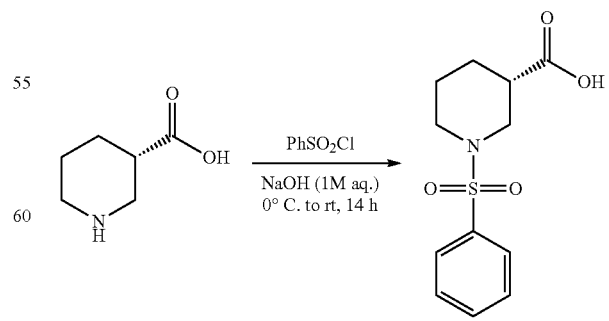

To a precooled (0° C.) solution of (S)-3-piperidinecarboxylic acid (400. mg, 3.10 mmol) in 1 M aq. NaOH (6.2 mL) under N₂ atmosphere was added dropwise benzenesulfonyl chloride (0.48 mL, 3.7 mmol). The resulting mixture was allowed to warm to room temperature and stirred for 14 h, then diluted with Et₂O and acidified to pH 1 with 1 M aq. HCl. The layers were separated, and the aqueous phase was extracted with Et₂O (1×) then CH₂Cl₂ (2×). The combined organic layers were washed with brine, dried over Na₂SO₄ and concentrated in vacuo to afford the product as a white solid (803 mg, 96% yield). $[\alpha]_D^{22}$ −11.7 (c. 0.13, CH₃OH); ¹H NMR (500 MHz, Chloroform-d) δ 7.81-7.74 (m, 2H), 7.65-7.58 (m, 1H), 7.58-7.50 (m, 2H), 3.81 (dd, J=11.6, 3.7 Hz, 1H), 3.64-3.52 (m, 1H), 2.73-2.62 (m, 1H), 2.57 (t, J=10.8 Hz, 1H), 2.41 (td, J=11.3, 3.0 Hz, 1H), 2.05-1.94 (m, 1H), 1.86-1.75 (m, 1H), 1.73-1.58 (m, 1H), 1.49-1.33 (m, 1H); ¹³C NMR (126 MHz, CDCl₃) δ 178.51, 136.00, 132.98, 129.19, 127.59, 77.16, 47.38, 46.28, 40.76, 26.17, 23.86; IR (ATR) $v_{max}$ 2950, 1733, 1197, 1167, 737, 571 cm⁻¹; AMM (ESI) m/z 270.0805 [calc for C₁₂H₁₆NO₄S (M+H)⁺ 270.0800].

Example 63: Synthesis of Region I Analogues 2.32-2.37

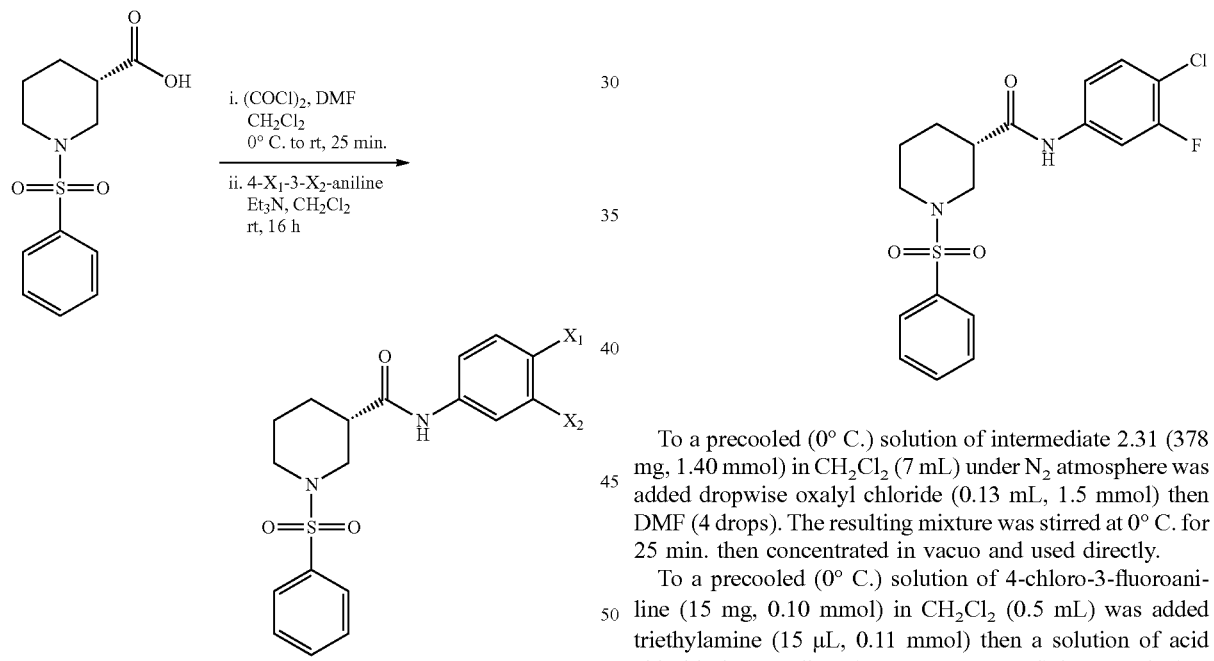

To a precooled (0° C.) solution of intermediate 2.31 (378 mg, 1.40 mmol) in CH₂Cl₂ (7 mL) under N₂ atmosphere was added dropwise oxalyl chloride (0.13 mL, 1.5 mmol) then DMF (4 drops). The resulting mixture was stirred at 0° C. for 25 min. then concentrated in vacuo and used directly.

To precooled (0° C.) solutions of 4-X₁-3-X₂-aniline (15 mg) in CH₂Cl₂ (0.5 mL) was added triethylamine (15 µL, 0.11 mmol) then a solution of acid chloride (1.1 eq.) in CH₂Cl₂ (0.5 mL). The resulting mixtures were allowed to warm to room temperature and stirred for 16 h then quenched with DMSO (0.5 mL), filtered through Celite and purified by mass-directed isolation using ultra-performance liquid chromatography (7-21% yield).

Example 64: Synthesis of (S)-MCG-III-085-D01 (2.32)

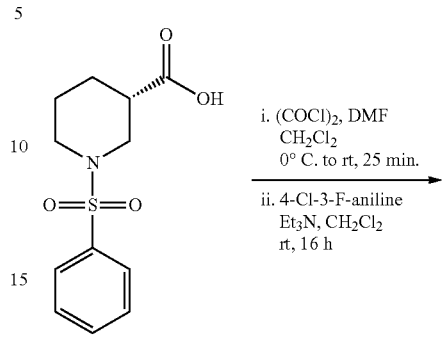

To a precooled (0° C.) solution of intermediate 2.31 (378 mg, 1.40 mmol) in CH₂Cl₂ (7 mL) under N₂ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 4-chloro-3-fluoroaniline (15 mg, 0.10 mmol) in CH₂Cl₂ (0.5 mL) was added triethylamine (15 µL, 0.11 mmol) then a solution of acid chloride intermediate (33 mg, 0.11 mmol) in CH₂Cl₂ (0.5 mL). The resulting mixture was allowed to warm to room temperature and stirred for 16 h then quenched with DMSO (0.5 mL), filtered through Celite and purified by mass-directed isolation using ultra-performance liquid chromatography (6.7 mg 16% yield). ¹H NMR (500 MHz, Acetonitrile-d₃) δ 8.61 (s, 1H), 7.77-7.71 (m, 2H), 7.71-7.63 (m, 2H), 7.63-7.56 (m, 2H), 7.35 (t, J=8.6 Hz, 1H), 7.23-7.15 (m, 1H), 3.85-3.76 (m, 1H), 3.62 (d, J=11.7 Hz, 1H), 2.60-2.52 (m, 2H), 2.38 (t, J=11.1 Hz, 2H), 2.26 (td, J=11.7, 2.9 Hz, 1H), 1.88 (dd, J=13.3, 3.6 Hz, 1H), 1.81-1.73 (m, 1H), 1.65-1.50 (m, 1H), 1.46-1.32 (m, 1H); AMM (ESI) m/z 419.0588 [calc for C₁₈H₁₈ClFN₂O₃SNa (M+Na)⁺ 419.0608].

Example 65: Synthesis of (S)-MCG-III-085-D02 (2.33)

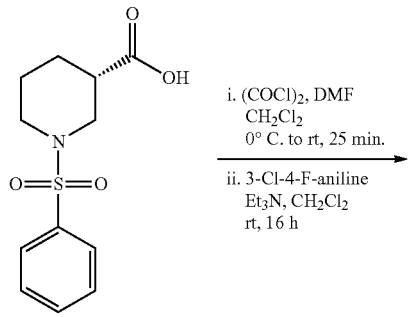

i. (COCl)$_2$, DMF
CH$_2$Cl$_2$
0° C. to rt, 25 min.

ii. 3-Cl-4-F-aniline
Et$_3$N, CH$_2$Cl$_2$
rt, 16 h

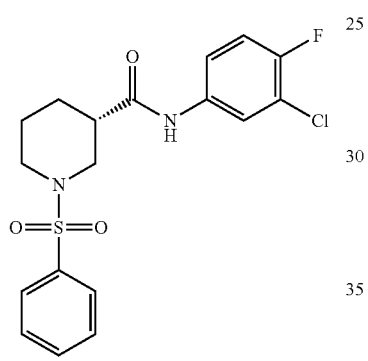

To a precooled (0° C.) solution of intermediate 2.31 (378 mg, 1.40 mmol) in CH$_2$Cl$_2$ (7 mL) under N$_2$ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 3-chloro-4-fluoroaniline (15 mg, 0.10 mmol) in CH$_2$Cl$_2$ (0.5 mL) was added triethylamine (15 μL, 0.11 mmol) then a solution of acid chloride intermediate (33 mg, 0.11 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (8.4 mg, 210% yield). $^1$H NMR (500 MHz, Acetonitrile-d$_3$) δ 8.49 (s, 1H), 7.80-7.70 (m, 3H), 7.70-7.62 (m, 1H), 7.62-7.55 (m, 2H), 7.41-7.32 (m, 1H), 7.15 (t, J=9.1 Hz, 1H), 3.85-3.77 (m, 1H), 3.67-3.58 (m, 1H), 2.54 (tt, J=11.1, 3.8 Hz, 1H), 2.38 (t, J=11.1 Hz, 1H), 2.25 (td, J=11.7, 2.9 Hz, 1H), 1.90-1.82 (m, 1H), 1.82-1.72 (m, 1H), 1.63-1.50 (m, 1H), 1.45-1.34 (m, 1H); AMM (ESI) m/z 419.0610 [calc for C$_{18}$H$_{18}$ClFN$_2$O$_3$SNa (M+Na)$^+$ 419.0608].

Example 66: Synthesis of (S)-MCG-III-085-D03 (2.34)

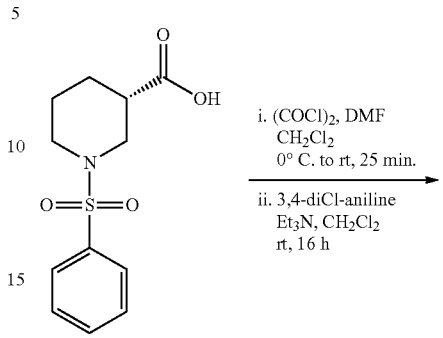

i. (COCl)$_2$, DMF
CH$_2$Cl$_2$
0° C. to rt, 25 min.

ii. 3,4-diCl-aniline
Et$_3$N, CH$_2$Cl$_2$
rt, 16 h

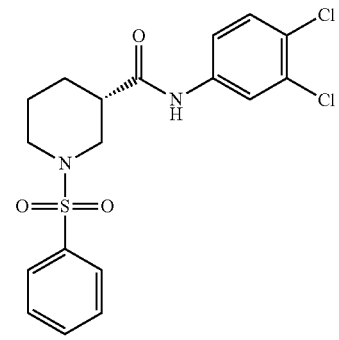

To a precooled (0° C.) solution of intermediate 2.31 (378 mg, 1.40 mmol) in CH$_2$Cl$_2$ (7 mL) under N$_2$ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 3,4-dichloroaniline (15 mg, 0.093 mmol) in CH$_2$Cl$_2$ (0.5 mL) was added triethylamine (15 μL, 0.11 mmol) then a solution of acid chloride intermediate (29 mg, 0.10 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (6.3 mg, 16% yield). $^1$H NMR (500 MHz, Acetonitrile-d$_3$) δ 8.53 (s, 1H), 7.80-7.72 (m, 2H), 7.68 (q, J=6.9 Hz, 2H), 7.61 (t, J=7.6 Hz, 2H), 7.24-7.10 (m, 2H), 3.83 (dd, J=11.8, 4.2 Hz, 1H), 3.64 (d, J=11.5 Hz, 1H), 2.65-2.51 (m, 1H), 2.40 (t, J=11.1 Hz, 1H), 2.28 (td, J=11.7, 3.0 Hz, 1H), 1.92-1.84 (m, 1H), 1.84-1.75 (m, 1H), 1.66-1.52 (m, 1H), 1.42 (qd, J=12.5, 3.9 Hz, 1H); AMM (ESI) m/z 435.0310 [calc for C$_{18}$H$_{18}$Cl$_2$N$_2$O$_3$SNa (M+Na)$^+$ 435.0313].

Example 67: Synthesis of (S)-MCG-III-085-D04 (2.35)

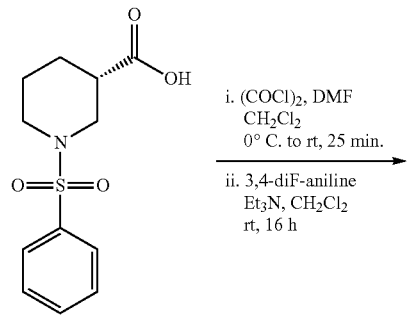

i. (COCl)$_2$, DMF
CH$_2$Cl$_2$
0° C. to rt, 25 min.

ii. 3,4-diF-aniline
Et$_3$N, CH$_2$Cl$_2$
rt, 16 h

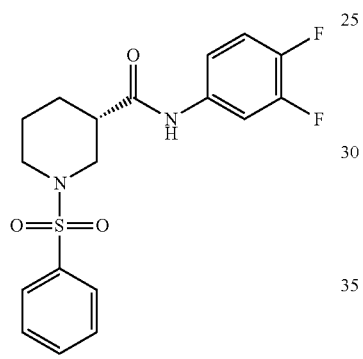

To a precooled (0° C.) solution of intermediate 2.31 (378 mg, 1.40 mmol) in CH$_2$Cl$_2$ (7 mL) under N$_2$ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 3,4-difluoroaniline (15 mg, 0.12 mmol) in CH$_2$Cl$_2$ (0.5 mL) was added triethylamine (15 µL, 0.11 mmol) then a solution of acid chloride intermediate (37 mg, 0.13 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (8.6 mg, 19% yield). $^1$H NMR (500 MHz, Acetonitrile-d$_3$) δ 8.53 (s, 1H), 7.81-7.72 (m, 2H), 7.68 (q, J=6.9 Hz, 2H), 7.61 (t, J=7.6 Hz, 2H), 7.24-7.12 (m, 2H), 3.83 (dd, J=11.8, 4.2 Hz, 1H), 3.64 (d, J=11.5 Hz, 1H), 2.63-2.50 (m, 1H), 2.40 (t, J=11.1 Hz, 1H), 2.28 (td, J=11.7, 3.0 Hz, 1H), 1.92-1.86 (m, 1H), 1.84-1.74 (m, 1H), 1.59 (qt, J=12.3, 4.1 Hz, 1H), 1.42 (qd, J=12.5, 3.9 Hz, 1H); AMM (ESI) m/z 403.0910 [calc for C$_{18}$H$_{18}$F$_2$N$_2$O$_3$SNa (M+Na)$^+$ 403.0904].

Example 68: Synthesis of (S)-MCG-III-085-D05 (2.36)

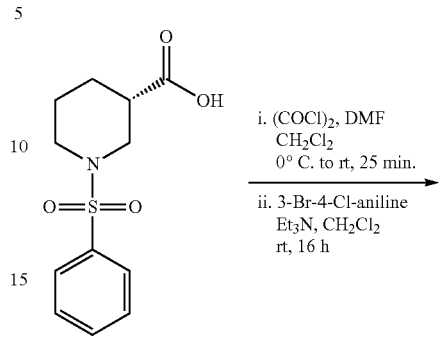

i. (COCl)$_2$, DMF
CH$_2$Cl$_2$
0° C. to rt, 25 min.

ii. 3-Br-4-Cl-aniline
Et$_3$N, CH$_2$Cl$_2$
rt, 16 h

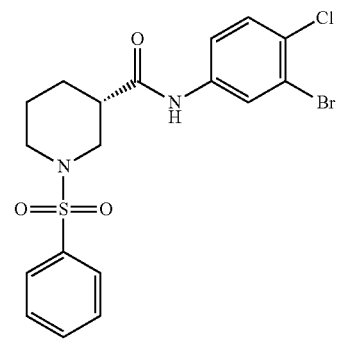

To a precooled (0° C.) solution of intermediate 2.31 (378 mg, 1.40 mmol) in CH$_2$Cl$_2$ (7 mL) under N$_2$ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 3-bromo-4-chloroaniline (15 mg, 0.073 mmol) in CH$_2$Cl$_2$ (0.5 mL) was added triethylamine (15 µL, 0.11 mmol) then a solution of acid chloride intermediate (23 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (2.3 mg, 7% yield). $^1$H NMR (500 MHz, Acetonitrile-d$_3$) δ 8.64 (s, 1H), 8.01 (d, J=2.4 Hz, 1H), 7.81-7.74 (m, 2H), 7.73-7.67 (m, 1H), 7.62 (t, J=7.6 Hz, 2H), 7.51-7.40 (m, 2H), 3.83 (dd, J=11.6, 3.9 Hz, 1H), 3.64 (d, J=12.0 Hz, 1H), 2.64-2.54 (m, 1H), 2.40 (t, J=11.1 Hz, 1H), 2.28 (td, J=11.8, 3.0 Hz, 1H), 1.93-1.87 (m, 1H), 1.83-1.76 (m, 1H), 1.59 (tdd, J=12.7, 8.3, 4.1 Hz, 1H), 1.41 (qd, J=12.6, 3.9 Hz, 1H); AMM (ESI) m/z 478.9834 [calc for C$_{18}$H$_{18}$BrClN$_2$O$_3$SNa (M+Na)$^+$ 478.9808].

Example 69: Synthesis of (S)-MCG-III-085-D06 (2.37)

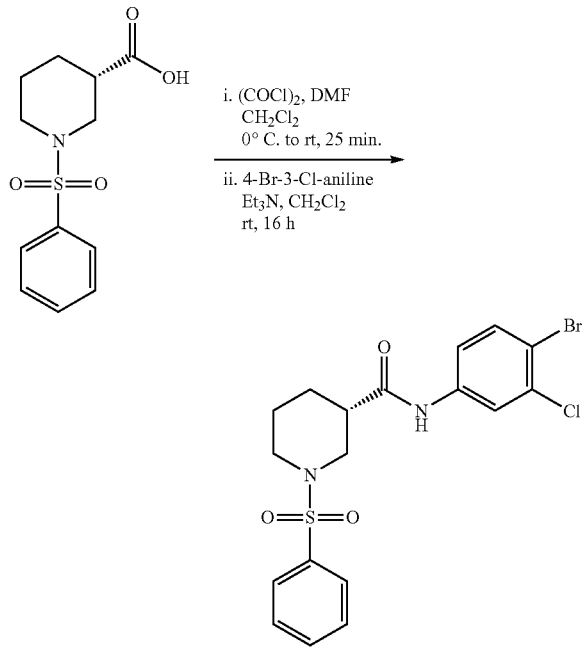

To a precooled (0° C.) solution of intermediate 2.31 (378 mg, 1.40 mmol) in CH$_2$Cl$_2$ (7 mL) under N$_2$ atmosphere was added dropwise oxalyl chloride (0.13 mL, 1.5 mmol) then DMF (4 drops). The resulting mixture was stirred at 0° C. for 25 min. then concentrated in vacuo and used directly.

To a precooled (0° C.) solution of 4-bromo-3-chloroaniline (15 mg, 0.073 mmol) in CH$_2$Cl$_2$ (0.5 mL) was added triethylamine (15 µL, 0.11 mmol) then a solution of acid chloride intermediate (23 mg, 0.080 mmol) in CH$_2$Cl$_2$ (0.5 mL). The resulting mixture was allowed to warm to room temperature and stirred for 16 h then quenched with DMSO (0.5 mL), filtered through Celite and purified by mass-directed isolation using ultra-performance liquid chromatography (3.5 mg, 10% yield). $^1$H NMR (500 MHz, Acetonitrile-d$_3$) δ 8.60 (s, 1H), 7.88 (d, J=2.5 Hz, 1H), 7.80-7.74 (m, 2H), 7.69 (t, J=7.4 Hz, 1H), 7.62 (t, J=7.7 Hz, 2H), 7.58 (d, J=8.7 Hz, 1H), 7.34 (dd, J=8.7, 2.5 Hz, 1H), 3.88-3.79 (m, 1H), 3.64 (d, J=11.5 Hz, 1H), 2.58 (tt, J=11.0, 3.8 Hz, 1H), 2.40 (t, J=11.1 Hz, 1H), 2.28 (td, J=11.8, 3.0 Hz, 1H), 1.92-1.85 (m, 1H), 1.83-1.75 (m, 1H), 1.66-1.53 (m, 1H), 1.47-1.34 (m, 1H); AMM (ESI) m/z 478.9834 [calc for C$_{18}$H$_{18}$BrClN$_2$O$_3$SNa (M+Na)$^+$ 478.9808].

Example 70: Synthesis of Intermediate 2.38

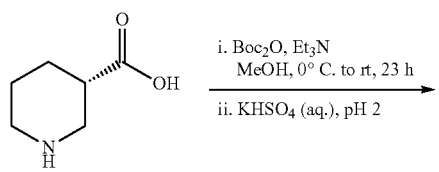

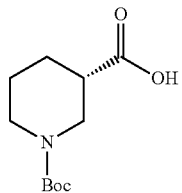

To a precooled (0° C.) solution of (S)-3-piperidinecarboxylic acid (1.00 g, 7.74 mmol) in MeOH (38 mL) under N$_2$ atmosphere was added triethylamine (2.2 mL, 15 mmol) then dropwise Boc anhydride (2.1 mL, 9.3 mmol). The resulting mixture was allowed to warm to room temperature and stirred for 23 h, then concentrated in vacuo. The crude residue was taken up in H$_2$O, cooled to 0° C. and acidified with aq. KHSO$_4$ to pH 2. The aqueous solution was diluted with EtOAc and the biphasic solution was stirred for 10 min. The layers were separated, and the aqueous phase was extracted with EtOAc (3×). The combined organic layers were washed with 1 M aq. HCl then brine, dried over Na$_2$SO$_4$, and concentrated in vacuo to afford the product as a white solid (1.63 g, 92% yield). [α]$_D^{23}$−17.8 (c. 0.64, CH$_3$OH); $^1$H NMR (500 MHz, Chloroform-d) δ 4.11 (s, 1H), 3.88 (d, J=13.4 Hz, 1H), 3.05 (s, 1H), 2.93-2.81 (m, 1H), 2.56-2.42 (m, 1H), 2.13-1.99 (m, 1H), 1.72 (dt, J=13.1, 3.9 Hz, 1H), 1.63-1.68 (m, 1H), 1.46 (s, 9H). $^{13}$C NMR (126 MHz, CDCl$_3$) δ 179.09, 154.87, 80.08, 45.68, 43.87, 41.24, 28.51, 27.30, 24.24; IR (ATR) ν$_{max}$ 3150, 1731, 1657, 1474, 1144, 849 cm$^{-1}$; AMM (ESI) m/z 230.1413 [calc for C$_{11}$H$_{20}$NO$_4$ (M+H)$^+$ 230.1392].

Example 71: Synthesis of Intermediate 2.39

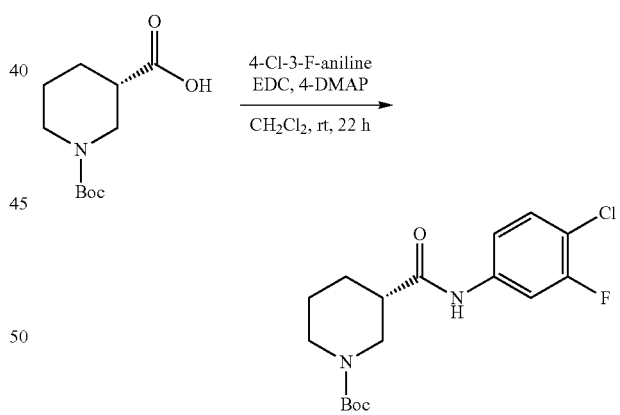

To a flask charged with intermediate 2.38 (2.00, 8.72 mmol), 4-chloro-3-fluoroaniline (1.52 g, 8.72 mmol), 1-ethyl-3-(3-dimethylaminopropyl)carbodiimide (1.84 g, 9.60 mmol) and 4-dimethylaminopyridine (1.17 g, 9.60 mmol) at room temperature under N$_2$ atmosphere was added CH$_2$Cl$_2$ (43 mL). The resulting mixture was stirred at room temperature for 22 h, then quenched with H$_2$O. The biphasic solution was stirred for 30 min, then the layers were separated, and the aqueous phase was extracted with CH$_2$Cl$_2$ (3×). The combined organic layers were washed sequentially with sat. aq. NH$_4$Cl, sat. aq. NaHCO$_3$, and brine, dried over Na$_2$SO$_4$, and concentrated in vacuo. Flash chromatography (SiO$_2$, 95:5 CHCl$_3$:MeOH) afforded the product as a white solid (2.50 g, 80% yield). [α]$_D^{23}$+51.0 (c. 0.42, CH$_3$OH); $^1$H NMR (500 MHz, Chloroform-d) δ 8.91 (s, 1H), 7.70 (dd, J=11.3, 2.3 Hz, 1H), 7.30-7.26 (m, 1H), 7.21 (d, J=8.9 Hz, 1H), 3.85-3.67 (m, 1H), 3.58 (d, J=41.0 Hz, 2H), 3.43-3.21 (m, 1H), 2.58-2.44 (m, 1H), 2.21-2.03 (m, 1H), 1.93-1.80 (m, 1H), 1.69-1.54 (m, 1H), 1.46 (s, 10H); $^{13}$C NMR (126 MHz, CDCl$_3$) δ 171.67, 159.06, 157.10, 155.48, 138.54, 130.43, 115.85, 115.82, 115.54, 108.55, 108.35, 80.71, 77.16, 45.50, 44.92, 43.73, 28.57, 27.73, 24.10; IR (ATR) ν$_{max}$ 3095, 2943, 1656, 1605, 1493, 1147, 857 cm$^{-1}$; AMM (ESI) m/z 357.1396 (ESI) m/z [calc for C$_{17}$H$_{23}$ClFN$_2$O$_3$ (M+H)$^+$ 357.1381].

Example 72: Synthesis of Intermediate 2.40

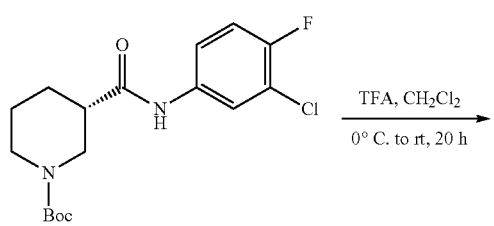

To a precooled (0° C.) solution of intermediate 2.39 (1.07 g, 3.00 mmol) in CH$_2$Cl$_2$ under N$_2$ atmosphere was added dropwise trifluoroacetic acid (1.2 mL, 15 mmol). The resulting mixture was allowed to warm to room temperature and stirred for 20 h, then concentrated in vacuo. The crude residue was taken up in H$_2$O and the resulting mixture was cooled to 0° C. then slowly neutralized with powdered NaHCO$_3$. The aqueous layer was diluted with CH$_2$Cl$_2$, the layers were separated, and the aqueous phase was extracted with CH$_2$Cl$_2$ (3×). The combined organic layers were dried over Na$_2$SO$_4$ and concentrated in vacuo to afford the product as a white solid (722 mg, 94% yield). [α]$_D^{23}$+2.6 (c. 0.72, CH$_3$OH); $^1$H NMR (500 MHz, Chloroform-d) δ 10.87 (s, 1H), 7.67 (dd, J=11.2, 2.4 Hz, 1H), 7.32-7.27 (m, 1H), 7.17 (dd, J=8.7, 2.3 Hz, 1H), 3.28 (d, J=12.2 Hz, 1H), 3.11 (d, J=11.3 Hz, 1H), 2.96 (d, J=12.1 Hz, 1H), 2.83-2.73 (m, 1H), 2.63-2.56 (m, 1H), 2.10-2.01 (m, 1H), 1.83-1.71 (m, 2H), 1.66-1.54 (m, 1H); $^{13}$C NMR (126 MHz, CDCl$_3$) δ 174.00, 159.07, 157.11, 138.67, 138.59, 130.35, 115.92, 115.89, 115.08, 114.94, 108.67, 108.31, 47.79, 46.47, 41.78, 27.52, 22.60; IR (ATR) ν$_{max}$ 3275, 2425, 1670, 1604, 1490, 1201, 857, 719 cm$^{-1}$; AMM (ESI) m/z 257.0842 [calc for C$_{12}$H$_{15}$ClFN$_2$O (M+H)$^+$ 256.0857].

Example 73: Synthesis of Region IV Analogues 2.41-2.48

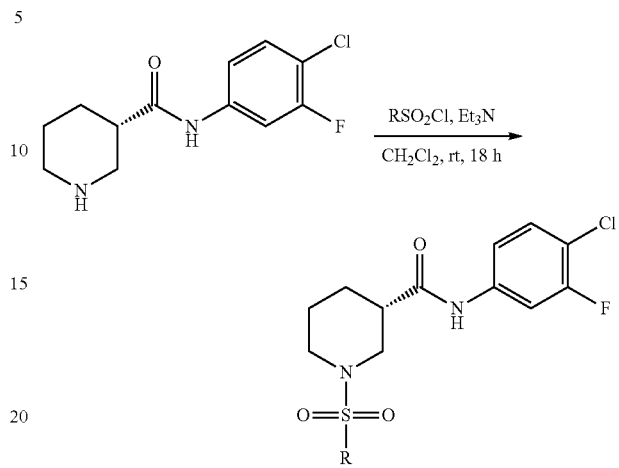

To separate solutions of intermediate 2.40 (20. mg, 0.078 mmol) and triethylamine (30 µL, 0.2 mmol) in CH$_2$Cl$_2$ (0.5 mL) at ambient temperature was added R-sulfonyl chloride (0.12 mmol). The resulting mixtures were stirred for 18-72 h, then diluted with wet dimethyl sulfoxide (0.5 mL), filtered through Celite and purified via mass-directed isolation using ultra-performance liquid chromatography (7-91% yield).

Example 74: Synthesis of (S)-MCG-III-116-A01 (2.41)

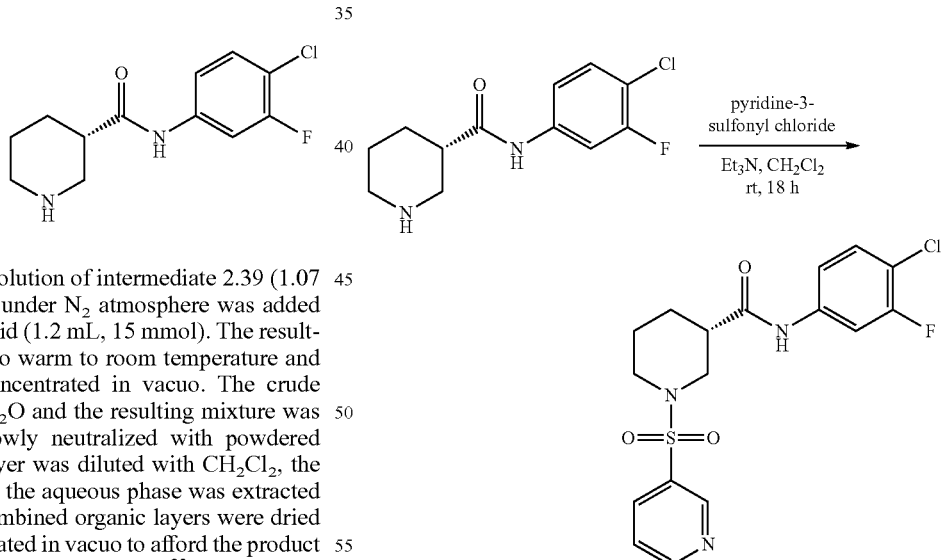

To a solution of intermediate 2.40 (20. mg, 0.078 mmol) and triethylamine (30 µL, 0.2 mmol) in CH$_2$Cl$_2$ (0.5 mL) at ambient temperature was added pyridine-3-sulfonyl chloride (21 mg, 0.12 mmol). The resulting mixture was stirred for 18 h, then diluted with wet dimethyl sulfoxide (0.5 mL), filtered through Celite and purified via mass-directed isolation using ultra-performance liquid chromatography (28 mg, 91% yield). $^1$H NMR (500 MHz, Acetonitrile-d$_3$) δ 8.98 (s, 1H), 8.90-8.79 (m, 1H), 8.61 (s, 1H), 8.20 (d, J=8.4 Hz, 1H), 7.72-7.61 (m, 2H), 7.37 (t, J=8.7 Hz, 1H), 7.25-7.15 (m, 1H), 3.89 (d, J=10.7 Hz, 1H), 3.70 (d, J=11.5 Hz, 1H), 2.67-2.48 (m, 2H), 2.42 (td, J=11.8, 2.9 Hz, 1H), 1.86-1.72 (m, 1H), 1.68-1.52 (m, 1H), 1.52-1.34 (m, 1H); AMM (ESI) m/z 398.0728 [calc for $C_{17}H_{18}ClFN_3O_3S$ $(M+H)^+$ 398.0741].

Example 75: Synthesis of (S)-MCG-III-116-A02 (2.42)

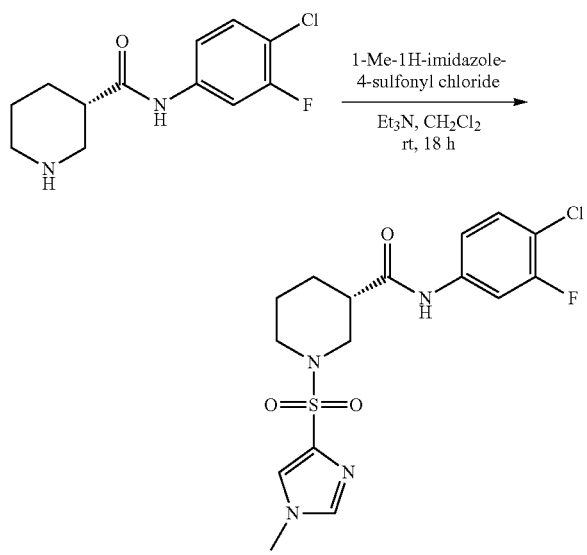

To a solution of intermediate 2.40 (20. mg, 0.078 mmol) and triethylamine (30 μL, 0.2 mmol) in dichloromethane (0.5 mL) at ambient temperature was added 1-methyl-1H-imidazole-4-sulfonyl chloride (21 mg, 0.12 mmol). The resulting mixture was stirred for 18 h, then diluted with wet dimethyl sulfoxide (0.5 mL), filtered through Celite and purified via mass-directed isolation using ultra-performance liquid chromatography (21 mg, 68% yield). $^1$H NMR (500 MHz, Acetonitrile-d$_3$) δ 8.64 (s, 1H), 7.70 (dd, J=11.8, 2.4 Hz, 1H), 7.62 (d, J=1.4 Hz, 1H), 7.54 (d, J=1.4 Hz, 1H), 7.37 (t, J=8.6 Hz, 1H), 7.22 (ddd, J=8.8, 2.4, 1.2 Hz, 1H), 3.80 (ddd, J=11.7, 3.7, 1.9 Hz, 1H), 3.71 (s, 3H), 3.63 (d, J=12.1 Hz, 1H), 2.65 (t, J=11.1 Hz, 1H), 2.58 (ddt, J=10.8, 7.2, 3.5 Hz, 1H), 2.52 (td, J=11.9, 3.0 Hz, 1H), 1.93-1.89 (m, 1H), 1.85-1.74 (m, 1H), 1.65-1.52 (m, 1H), 1.52-1.39 (m, 1H); AMM (ESI) m/z 401.0858 [calc for $C_{16}H_{19}ClFN_4O_3S$ $(M+H)^+$ 401.0850].

Example 76: Synthesis of (S)-MCG-III-116-A03 (2.43)

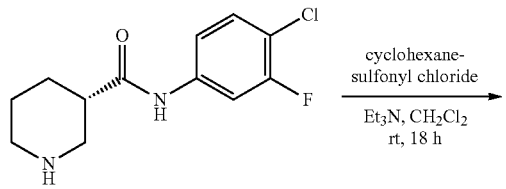

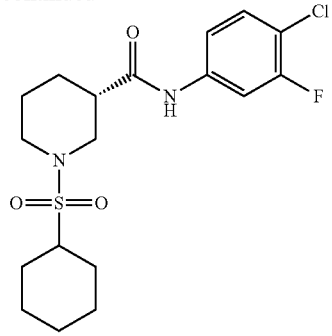

To a solution of intermediate 2.40 (20. mg, 0.078 mmol) and triethylamine (30 μL, 0.2 mmol) in dichloromethane (0.5 mL) at ambient temperature was added cyclohexanesulfonyl chloride (21 mg, 0.12 mmol). The resulting mixture was stirred for 18 h, then diluted with wet dimethyl sulfoxide (0.5 mL), filtered through Celite and purified via mass-directed isolation using ultra-performance liquid chromatography (5.9 mg, 19% yield). $^1$H NMR (500 MHz, Acetonitrile-d$_3$) δ 8.71 (s, 1H), 7.72 (dd, J=11.8, 2.4 Hz, 1H), 7.37 (t, J=8.6 Hz, 1H), 7.28-7.20 (m, 1H), 3.86-3.76 (m, 1H), 3.63 (dt, J=12.6, 3.9 Hz, 1H), 3.09 (dd, J=12.6, 10.3 Hz, 1H), 3.02 (tt, J=12.0, 3.5 Hz, 1H), 2.98-2.89 (m, 1H), 2.52 (tt, J=10.6, 3.9 Hz, 1H), 2.09-1.97 (m, 3H), 1.87-1.74 (m, 3H), 1.73-1.61 (m, 2H), 1.60-1.48 (m, 1H), 1.42 (qd, J=12.4, 3.5 Hz, 2H), 1.29 (qt, J=12.7, 3.3 Hz, 2H), 1.18 (qt, J=12.7, 3.2 Hz, 1H); AMM (ESI) m/z 403.1252 [calc for $C_{18}H_{25}ClFN_2O_3S$ $(M+H)^+$ 403.1258].

Example 77: Synthesis of (S)-MCG-III-116-A05 (2.44)

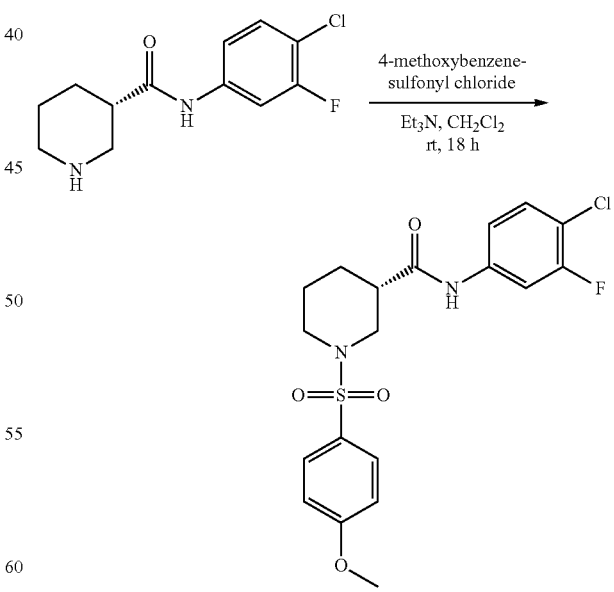

To a solution of intermediate 2.40 (20. mg, 0.078 mmol) and triethylamine (30 μL, 0.2 mmol) in dichloromethane (0.5 mL) at ambient temperature was added 4-methoxybenzenesulfonyl chloride (24 mg, 0.12 mmol). The resulting mixture was stirred for 18 h, then diluted with wet dimethyl sulfoxide (0.5 mL), filtered through Celite and purified via mass-directed isolation using ultra-performance liquid chromatography (13 mg, 38% yield). $^1$H NMR (500 MHz, Acetonitrile-d$_3$) δ 8.69 (s, 1H), 7.75-7.65 (m, 3H), 7.37 (t, J=8.6 Hz, 1H), 7.26-7.19 (m, 1H), 7.13-7.04 (m, 2H), 3.87 (s, 3H), 3.84-3.76 (m, 1H), 3.61 (d, J=11.7 Hz, 1H), 2.58 (tt, J=11.0, 3.8 Hz, 1H), 2.37 (t, J=11.1 Hz, 1H), 2.25 (td, J=11.7, 2.9 Hz, 2H), 1.90 (dd, J=13.2, 3.7 Hz, 1H), 1.84-1.75 (m, 1H), 1.59 (qt, J=12.4, 4.0 Hz, 1H), 1.40 (qd, J=12.5, 3.9 Hz, 1H); AMM (ESI) m/z 427.0902 [calc for C$_{19}$H$_{21}$ClFN$_2$O$_4$S (M+H)$^+$ 427.0895].

Example 78: Synthesis of (S)-MCG-III-116-A06 (2.45)

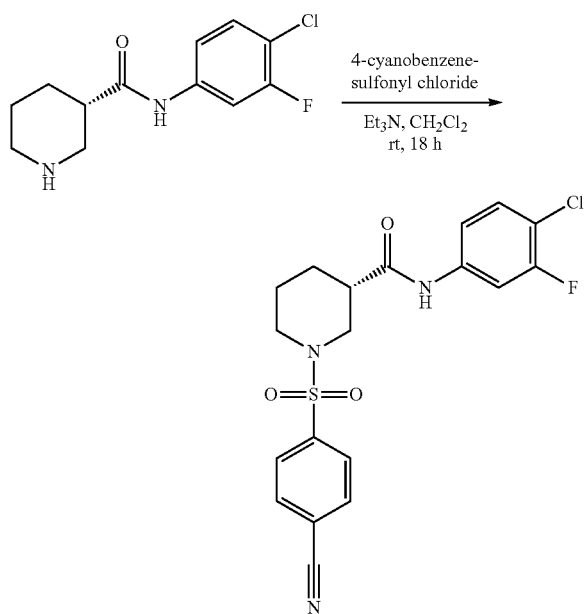

To a solution of intermediate 2.40 (20. mg, 0.078 mmol) and triethylamine (30 µL, 0.2 mmol) in dichloromethane (0.5 mL) at ambient temperature was added 4-cyanobenzenesulfonyl chloride (24 mg, 0.12 mmol). The resulting mixture was stirred for 18 h, then diluted with wet dimethyl sulfoxide (0.5 mL), filtered through Celite and purified via mass-directed isolation using ultra-performance liquid chromatography (2.3 mg, 7% yield). $^1$H NMR (500 MHz, Chloroform-d) δ 7.88 (q, J=5.4, 3.0 Hz, 3H), 7.84 (d, J=18.1 Hz, 1H), 7.65 (d, J=10.8 Hz, 1H), 7.32 (t, J=8.4 Hz, 1H), 7.13 (d, J=8.9 Hz, 1H), 3.67 (d, J=12.3 Hz, 1H), 3.52 (d, J=11.5 Hz, 1H), 2.96-2.84 (m, 1H), 2.78-2.56 (m, 2H), 2.01-1.82 (m, 2H), 1.82-1.69 (m, 2H); AMM (ESI) m/z 422.0743 [calc for C$_{19}$H$_{18}$ClFN$_3$O$_3$S (M+H)$^+$ 422.0741].

Example 79: Synthesis of (S)-MCG-III-117 (2.46)

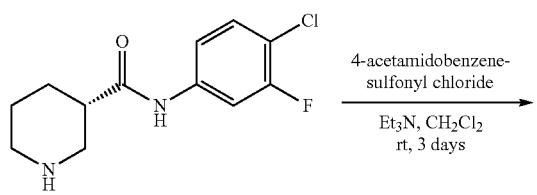

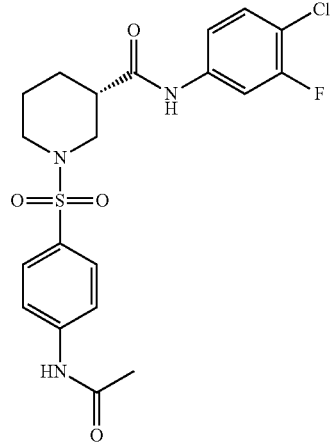

To a solution of intermediate 2.40 (12 mg, 0.048 mmol) and triethylamine (30 µL, 0.2 mmol) in dichloromethane (0.3 mL) at ambient temperature was added 4-acetamidobenzenesulfonyl chloride (17 mg, 0.071 mmol). The resulting mixture was stirred for 3 days, then diluted with wet dimethyl sulfoxide (0.5 mL), filtered through Celite and purified via mass-directed isolation using ultra-performance liquid chromatography (9.0 mg, 42% yield). $^1$H NMR (500 MHz, Acetonitrile-d$_3$) δ 8.66 (s, 1H), 8.60 (s, 1H), 7.80-7.74 (m, 2H), 7.73-7.64 (m, 2H), 7.37 (t, J=8.6 Hz, 1H), 7.25-7.17 (m, 1H), 3.83-3.76 (m, 1H), 3.60 (d, J=11.5 Hz, 1H), 2.63-2.51 (m, 1H), 2.40 (t, J=11.1 Hz, 1H), 2.29 (td, J=11.6, 2.9 Hz, 1H), 2.10 (s, 3H), 1.92-1.84 (m, 1H), 1.83-1.75 (m, 1H), 1.65-1.52 (m, 1H), 1.48-1.36 (m, 1H); AMM (ESI) m/z 454.1022 [calc for C$_{20}$H$_{22}$ClFN$_3$O$_4$S (M+H)$^+$ 454.1004].

Example 80: Synthesis of (S)-MCG-III-128 (2.47)

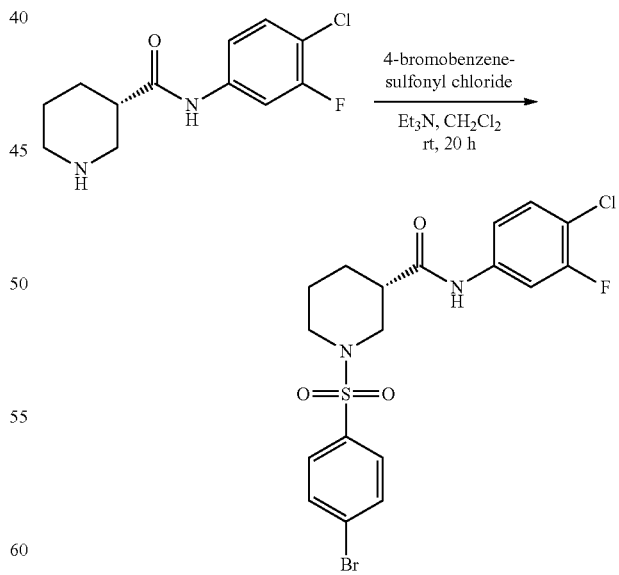

To a precooled solution of intermediate 2.40 (20 mg, 0.078 mmol) and triethylamine (30 µL, 0.2 mmol) in dichloromethane (0.5 mL) at 0° C. was added 4-bromobenzene sulfonyl chloride (30. mg, 0.12 mmol). The resulting mixture was allowed to warm to ambient temperature and stirred for 20 h, then diluted with wet dimethyl sulfoxide (0.5 mL), filtered through Celite and purified via mass-directed isolation using ultra-performance liquid chromatography (18 mg, 49% yield). $^1$H NMR (500 MHz, Acetonitrile-d$_3$) δ 8.64 (s, 1H), 7.81-7.75 (m, 2H), 7.72-7.62 (m, 3H), 7.37 (t, J=8.6 Hz, 1H), 7.23 (dd, J=9.2, 2.4 Hz, 1H), 3.86-3.77 (m, 1H), 3.63 (d, J=11.8 Hz, 1H), 2.58 (tt, J=11.1, 3.8 Hz, 1H), 2.53-2.42 (m, 1H), 2.34 (td, J=11.8, 2.9 Hz, 1H), 1.92-1.87 (m, 1H), 1.81 (dt, J=13.6, 3.5 Hz, 1H), 1.66-1.52 (m, 1H), 1.50-1.37 (m, 1H); AMM 496.9738 (ESI) m/z [calc for C$_{18}$H$_{17}$BrClFN$_2$O$_3$SNa (M+Na)$^+$ 496.9714].

Example 81: Synthesis of (S)-MCG-III-132 (2.48)

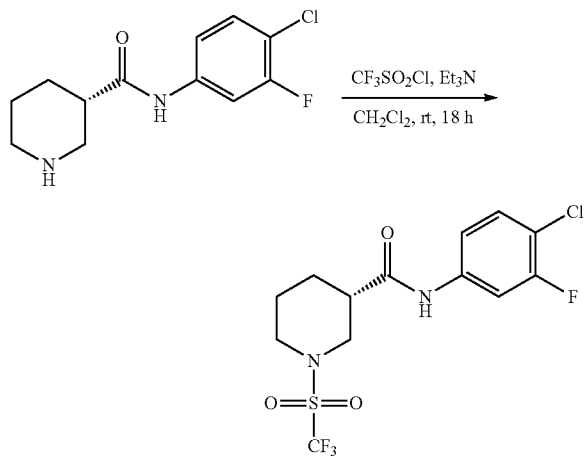

To a precooled solution of intermediate 2.40 (20 mg, 0.078 mmol) and triethylamine (30 μL, 0.2 mmol) in dichloromethane (1 mL) at 0° C. was added trifluoromethanesulfonyl chloride (20. mg, 0.12 mmol). The resulting mixture was allowed to warm to ambient temperature and stirred for 18 h, then diluted with wet dimethyl sulfoxide (0.5 mL), filtered through Celite and purified via mass-directed isolation using ultra-performance liquid chromatography (4.0 mg, 13% yield). $^1$H NMR (500 MHz, Acetonitrile-d$_3$) δ 8.67 (s, 1H), 7.69 (dd, J=11.8, 2.4 Hz, 1H), 7.38 (t, J=8.6 Hz, 1H), 7.29-7.19 (m, 1H), 3.99 (d, J=13.5 Hz, 1H), 3.83 (d, J=13.1 Hz, 1H), 3.38-3.22 (m, 1H), 3.21-3.07 (m, 1H), 2.61 (tt, J=11.1, 3.9 Hz, 1H), 2.40-2.22 (m, 2H), 2.08 (d, J=12.6 Hz, 1H), 1.92-1.83 (m, 1H), 1.79-1.54 (m, 3H); AMM 411.0157 (ESI) m/z [calc for C$_{13}$H$_{13}$ClF$_4$N$_2$O$_3$SNa (M+Na)$^+$ 411.0169].

Example 82: Synthesis of Intermediate 2.50

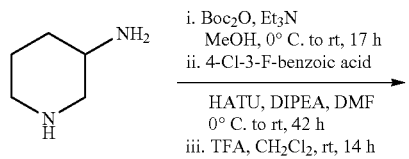

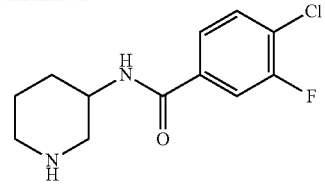

To a precooled (0° C.) solution of 3-aminopiperidine (300. mg, 3.00 mmol) in MeOH (15 mL) under N$_2$ atmosphere was added triethylamine (0.83 mL, 6.0 mmol) then Boc anhydride (0.68 mL, 3.0 mmol). The resulting mixture was allowed to warm to room temperature and stirred for 17 h, then concentrated in vacuo. The resulting residue was taken up in CH$_2$Cl$_2$ and quenched with sat. aq. NaHCO$_3$. The layers were separated, and the aqueous phase was extracted with CH$_2$Cl$_2$ (3×). The combined organic layers were washed with brine, dried over Na$_2$SO$_4$, and concentrated in vacuo to afford the product as a white solid (573 mg), which was carried forward without additional purification.

To a precooled (0° C.) solution of intermediate (350. mg, 1.75 mmol), 4-chloro-3-fluorobenzoic acid (366 mg, 2.10 mmol) and HATU (731 mg, 1.92 mmol) in DMF (5.8 mL) under N$_2$ atmosphere was added diisopropylethylamine (0.9 mL, 5 mmol). The resulting mixture was allowed to warm to room temperature and stirred for 42 h, then concentrated in vacuo. The resulting residue was taken up in CH$_2$Cl$_2$ and the organic layer was washed with sat. aq. NaHCO$_3$. The aqueous phase was then extracted with CH$_2$Cl$_2$ (1×). The combined organic layers were washed with H$_2$O and brine, dried over Na$_2$SO$_4$, and concentrated in vacuo to afford the product as a white solid (528 mg), which was carried forward without additional purification.

To a solution of intermediate (526 mg, 1.47 mmol) in CH$_2$Cl$_2$ (7.4 mL) at room temperature under N$_2$ atmosphere was added trifluoroacetic acid (0.34 mL, 4.4 mmol). The resulting mixture was stirred at room temperature for 14 h, followed by addition of trifluoroacetic acid (0.1 mL, 1.3 mmol). The resulting mixture was stirred for an additional 24 h, then concentrated in vacuo. The resulting residue was taken up in CH$_2$Cl$_2$ and diluted with H$_2$O. The layers were separated, and the organic layer was extracted with H$_2$O (3×). The combined aqueous layers were basified with powdered NaHCO$_3$ to pH 8 then diluted with CH$_2$Cl$_2$. The layers were separated, and the aqueous phase was extracted with CH$_2$Cl$_2$ (3×). The combined organic layers were dried over Na$_2$SO$_4$ and concentrated in vacuo to afford the product as a white solid (122 mg, 64% yield over 3 steps). $^1$H NMR (500 MHz, Chloroform-d) δ 7.71-7.57 (m, 1H), 7.57-7.33 (m, 2H), 7.24-7.00 (m, 1H), 4.44-4.08 (m, 2H), 4.08-3.89 (m, 1H), 3.87-3.66 (m, 1H), 3.62-3.34 (m, 2H), 2.25-2.04 (m, 1H), 1.99-1.83 (m, 1H), 1.83-1.43 (m, 2H); $^{13}$C NMR (126 MHz, CDCl$_3$) δ 165.28, 159.24, 159.10, 157.25, 157.10, 131.23, 131.12, 124.03, 123.23, 123.20, 115.90, 115.72, 49.29, 47.55, 42.96, 28.90, 23.28; IR (ATR) ν$_{max}$ 3209, 1674, 1440, 1190, 1133, 801, 724 cm$^{-1}$; AMM 257.0861 (ESI) m/z [calc for C$_{12}$H$_{15}$ClFN$_2$O (M+H)$^+$ 257.0857].

Example 83: Synthesis of Region II Analogues 2.51-2.53

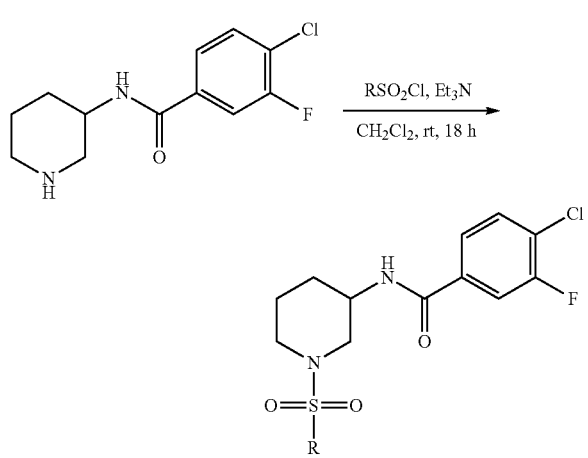

To separate solutions of intermediate 2.50 (24 mg, 0.093 mmol) and triethylamine (40 µL, 0.3 mmol) in dichloromethane (0.6 mL) at 0° C. was added R-sulfonyl chloride (0.14 mmol). The resulting mixtures were stirred for 18 h, then diluted with wet DMSO (1 mL), filtered through Celite and purified via mass-directed isolation using ultra-performance liquid chromatography (45-57% yield).

Example 84: Synthesis of MCG-III-157-C01 (2.51)

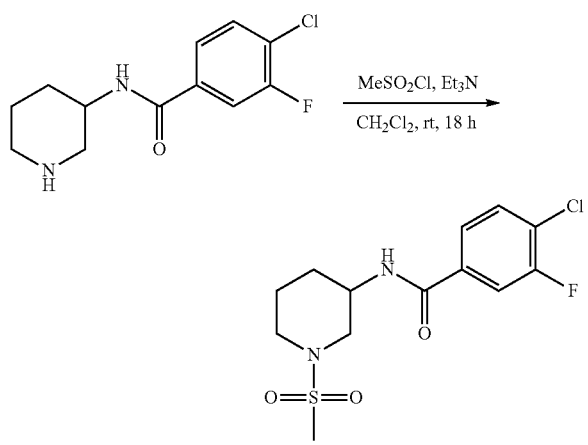

To a solution of intermediate 2.50 (24 mg, 0.093 mmol) and triethylamine (40 µL, 0.3 mmol) in dichloromethane (0.6 mL) at 0° C. was added methanesulfonyl chloride (11 µL, 0.14 mmol). The resulting mixture was stirred for 18 h, then diluted with wet DMSO (1 mL), filtered through Celite and purified via mass-directed isolation using ultra-performance liquid chromatography (12 mg, 45% yield). $^1$H NMR (500 MHz, Acetonitrile-$d_3$) δ 7.67 (dd, J=10.0, 1.9 Hz, 1H), 7.62-7.53 (m, 2H), 7.02 (s, 1H), 4.10-3.97 (m, 1H), 3.66 (dd, J=11.7, 3.8 Hz, 1H), 3.50-3.34 (m, 1H), 2.98-2.86 (m, 1H), 2.78 (s, 3H), 1.92-1.82 (m, 1H), 1.75-1.63 (m, 1H), 1.63-1.53 (m, 1H); AMM 357.0455 (ESI) m/z [calc for $C_{13}H_{16}ClFN_2O_3SNa$ (M+Na)$^+$ 357.0452].

Example 85: Synthesis of MCG-III-157-C02 (2.52)

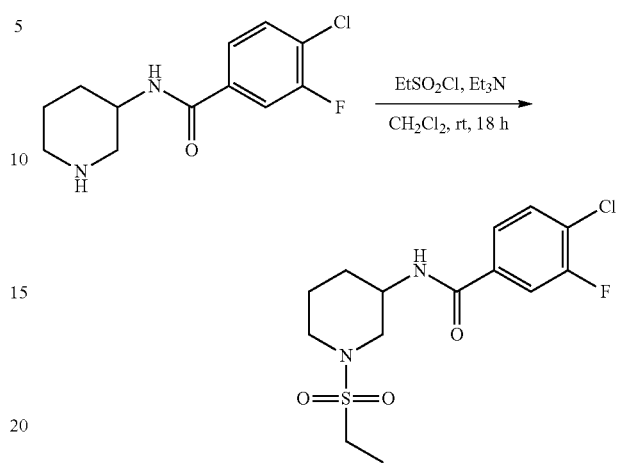

To a solution of intermediate 2.50 (24 mg, 0.093 mmol) and triethylamine (40 µL, 0.3 mmol) in dichloromethane (0.6 mL) at 0° C. was added ethanesulfonyl chloride (13 µL, 0.14 mmol). The resulting mixture was stirred for 18 h, then diluted with wet DMSO (1 mL), filtered through Celite and purified via mass-directed isolation using ultra-performance liquid chromatography (12 mg, 43% yield). $^1$H NMR (500 MHz, Acetonitrile-$d_3$) δ 7.67 (dd, J=10.1, 1.9 Hz, 1H), 7.62-7.52 (m, 2H), 7.01 (s, 1H), 4.07-3.92 (m, 1H), 3.70 (dd, J=12.0, 3.9 Hz, 1H), 3.53-3.40 (m, 1H), 3.07-2.94 (m, 3H), 2.90 (dd, J=11.9, 8.5 Hz, 1H), 1.90-1.79 (m, 1H), 1.72-1.53 (m, 2H), 1.27 (t, J=7.4 Hz, 3H); AMM 371.0603 (ESI) m/z [calc for $C_{14}H_{18}ClFN_2O_3SNa$ (M+Na)$^+$ 371.0608].

Example 86: Synthesis of MCG-III-157-C04 (2.53)

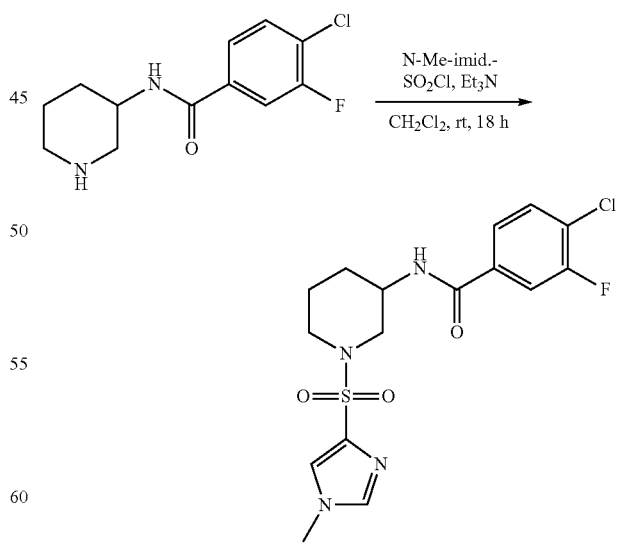

To a solution of intermediate 2.50 (24 mg, 0.093 mmol) and triethylamine (40 µL, 0.3 mmol) in dichloromethane (0.6 mL) at 0° C. was added 1-methyl-1H-imidazole-4-sulfonyl chloride (25 mg, 0.14 mmol). The resulting mixture was stirred for 18 h, then diluted with wet DMSO (1 mL), filtered through Celite and purified via mass-directed isolation using ultra-performance liquid chromatography (17 mg, 55% yield). $^1$H NMR (500 MHz, Acetonitrile-d$_3$) δ 7.70 (dd, J=10.1, 1.9 Hz, 1H), 7.65-7.60 (m, 2H), 7.60-7.53 (m, 2H), 7.40 (s, 1H), 4.07 (tt, J=7.9, 4.1 Hz, 1H), 3.70 (s, 3H), 3.59 (dd, J=12.2, 3.7 Hz, 1H), 3.40-3.30 (m, 1H), 2.96-2.85 (m, 2H), 1.88-1.80 (m, 1H), 1.80-1.71 (m, 1H), 1.67-1.47 (m, 2H); AMM 423.0685 (ESI) m/z [calc for C$_{16}$H$_{18}$ClFN$_4$O$_3$SNa (M+Na)$^+$ 423.0670].

Example 87: Synthesis of Intermediate 2.54

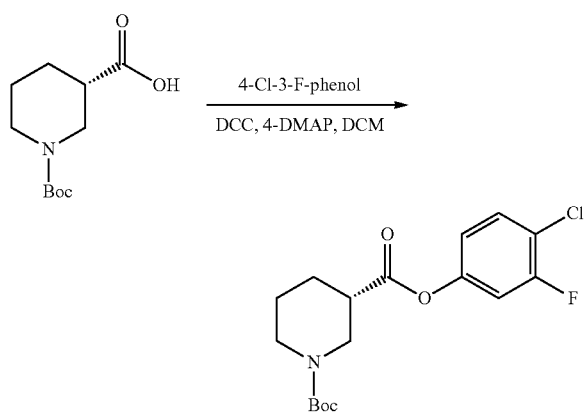

To a solution of intermediate 2.38 (877 mg, 3.83 mmol), 4-chloro-3-fluorophenol (510 mg, 3.48 mmol), and 4-dimethylaminopyridine (128 mg, 1.04 mmol) in CH$_2$Cl$_2$ (24 mL) at room temperature under N$_2$ atmosphere was added dropwise a solution of ',N'-dicyclohexylcarbodiimide (DCC, 1.2 g, 5.7 mmol) in CH$_2$Cl$_2$ (14 mL). The resulting mixture was stirred for 14 h, then filtered and rinsed with minimal CH$_2$Cl$_2$. The filtrate was concentrated in vacuo. Flash column chromatography (SiO$_2$, 90:10 hexanes:ethyl acetate, dry loaded Celite) afforded the desired product as a white solid (1.08 g, 87% yield). $[α]_D^{22}$ −22.1 (c. 0.22, CH$_3$OH); $^1$H NMR (500 MHz, Chloroform-d) δ 7.38 (t, J=8.5 Hz, 1H), 6.97 (dd, J=9.4, 2.6 Hz, 1H), 6.89-6.82 (m, 1H), 4.12 (s, 1H), 3.81 (s, 1H), 3.29 (dd, J=13.3, 9.3 Hz, 1H), 3.10-2.92 (m, 1H), 2.71 (s, 1H), 2.12 (d, J=12.4 Hz, 1H), 1.87-1.73 (m, 2H), 1.60-1.49 (m, 1H), 1.46 (s, 9H); $^{13}$C NMR (126 MHz, CDCl$_3$) δ 171.45, 159.07, 157.08, 154.75, 149.84, 149.77, 130.75, 118.49, 118.31, 118.28, 111.12, 110.93, 80.10, 45.64, 41.34, 34.11, 28.55, 27.18, 24.04; IR (ATR) $v_{max}$ 2948, 1759, 1673, 1426, 1175, 1144, 1127, 997 cm$^{-1}$; AMM 358.1240 (ESI) m/z [calc for C$_{17}$H$_{22}$ClFNO$_4$ (M+H)$^+$ 358.1221].

Example 88: Synthesis of Intermediate 2.55

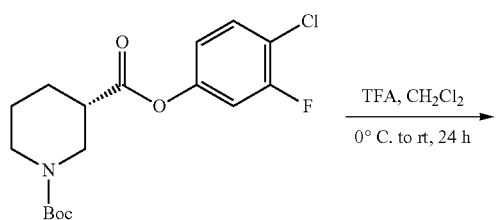

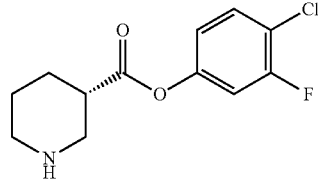

To a precooled (0° C.) solution of intermediate 2.54 (1.04 g, 2.91 mmol) in CH$_2$Cl$_2$ (15 mL) under N$_2$ atmosphere was added dropwise trifluoroacetic acid (0.66 mL, 8.7 mmol). The resulting mixture was allowed to warm to room temperature and stirred for 24 h, then concentrated in vacuo. The resulting residue was taken up in CH$_2$Cl$_2$ and diluted with H$_2$O. The layers were separated, and the organic layer was extracted with H$_2$O (3×). The combined aqueous layers were basified with powdered NaHCO$_3$ to pH 8 then diluted with CH$_2$Cl$_2$. The layers were separated, and the aqueous phase was extracted with CH$_2$Cl$_2$ (3×). The combined organic layers were washed with brine, dried over Na$_2$SO$_4$, and concentrated in vacuo to afford the product as a colorless oil (418 mg, 84% yield). $[α]_D^{24}$+0.67 (c. 0.21, CH$_3$OH); $^1$H NMR (500 MHz, Acetonitrile-d$_3$) δ 8.71 (s, 1H), 7.97 (s, 1H), 7.53 (t, J=8.6 Hz, 1H), 7.15 (dd, J=9.9, 2.6 Hz, 1H), 7.05-6.95 (m, 1H), 3.55 (dd, J=12.5, 3.3 Hz, 1H), 3.36-3.23 (m, 2H), 3.23-3.12 (m, 2H), 3.08-2.94 (m, 1H), 2.26-2.14 (m, 1H), 1.92-1.81 (m, 2H); $^{13}$C NMR (126 MHz, MeOD) δ 171.25, 160.08, 158.10, 151.17, 151.09, 131.88, 119.76, 119.73, 119.32, 119.18, 112.12, 111.93, 49.00, 45.26, 45.02, 44.92, 39.60, 34.68, 26.01, 25.92, 22.29; IR (ATR) $v_{max}$ 1753, 1661, 1492, 1427, 1196, 1173, 1149, 1068, 1048, 835, 795, 722 cm$^{-1}$; AMM 258.0695 (ESI) m/z [calc for C$_{12}$H$_{14}$ClFNO$_2$ (M+H)$^+$ 258.0697].

Example 89: Synthesis of Region II Analogues 2.56-2.59

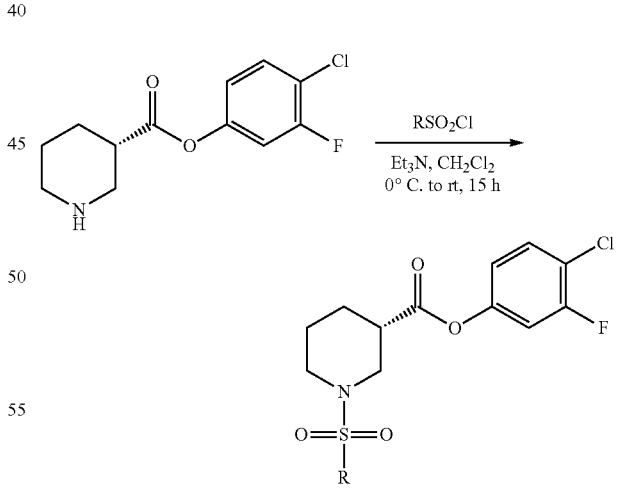

To separate precooled (0° C.) solutions of intermediate 2.55 (20. mg, 0.078 mmol) in dichloromethane (0.5 mL) was added triethylamine (30 μL, 0.2 mmol) and R-sulfonyl chloride (0.12 mmol). The resulting mixtures were allowed to warm to room temperature and stirred for 15 h, then diluted with wet DMSO (0.5 mL), filtered through Celite and purified via mass-directed isolation using ultra-performance liquid chromatography (9-45% yield).

Example 90: Synthesis of (S)-MCG-III-213-A01 (2.56)

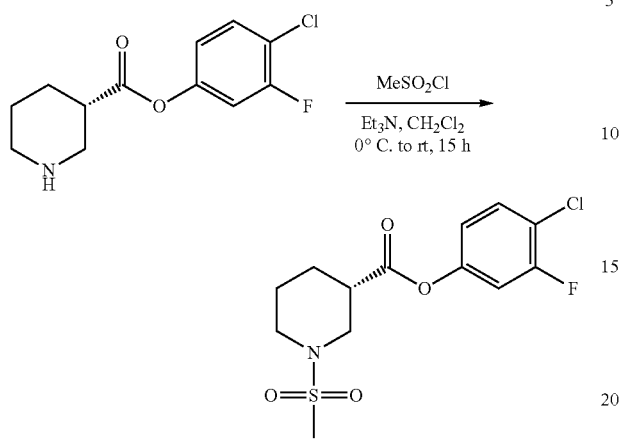

To a precooled (0° C.) solution of intermediate 2.55 (20. mg, 0.078 mmol) in dichloromethane (0.5 mL) was added triethylamine (30 μL, 0.2 mmol) and methanesulfonyl chloride (9.0 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (2.3 mg, 9% yield). $^1$H NMR (500 MHz, Acetonitrile-$d_3$) δ 7.52 (t, J=8.6 Hz, 1H), 7.11 (dd, J=9.9, 2.6 Hz, 1H), 7.02-6.95 (m, 1H), 3.72 (dd, J=12.0, 3.9 Hz, 1H), 3.41 (dt, J=10.7, 4.7 Hz, 1H), 3.25 (dd, J=11.9, 8.7 Hz, 1H), 3.00-2.96 (m, 1H), 2.96-2.88 (m, 1H), 2.80 (s, 3H), 2.11-2.02 (m, 1H), 1.91-1.83 (m, 1H), 1.83-1.72 (m, 1H), 1.72-1.62 (m, 1H); AMM 336.0464 (ESI) m/z [calc for $C_{13}H_{16}ClFNO_4S$ (M+H)$^+$ 336.0473].

Example 91: Synthesis of (S)-MCG-III-213-A02 (2.57)

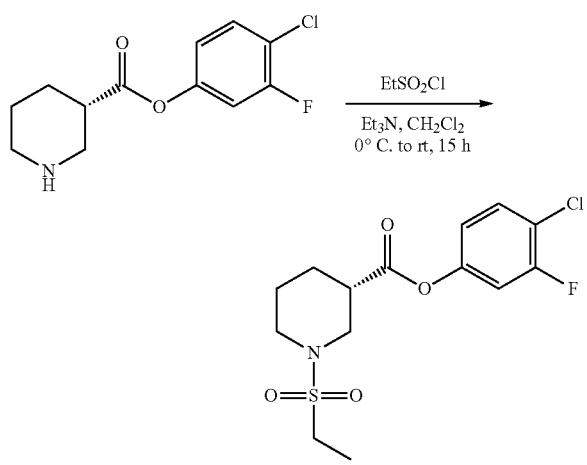

To a precooled (0° C.) solution of intermediate 2.55 (20. mg, 0.078 mmol) in dichloromethane (0.5 mL) was added triethylamine (30 μL, 0.2 mmol) and ethanesulfonyl chloride (11 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (2.7 mg, 10% yield). $^1$H NMR (500 MHz, Acetonitrile-$d_3$) δ 7.51 (t, J=8.6 Hz, 1H), 7.11 (dd, J=9.9, 2.6 Hz, 1H), 7.01-6.96 (m, 1H), 3.76 (dd, J=12.4, 3.9 Hz, 1H), 3.49-3.41 (m, 1H), 3.33 (dd, J=12.4, 8.6 Hz, 1H), 3.10-3.03 (m, 1H), 3.00 (q, J=7.4 Hz, 2H), 2.89 (tt, J=8.3, 3.9 Hz, 1H), 2.10-2.03 (m, 1H), 1.89-1.75 (m, 2H), 1.70-1.58 (m, 1H), 1.28 (t, J=7.4 Hz, 3H); AMM 350.0648 (ESI) m/z [calc for $C_{14}H_{18}ClFNO_4S$ (M+H)$^+$ 350.0629].

Example 92: Synthesis of (S)-MCG-III-213-A03 (2.58)

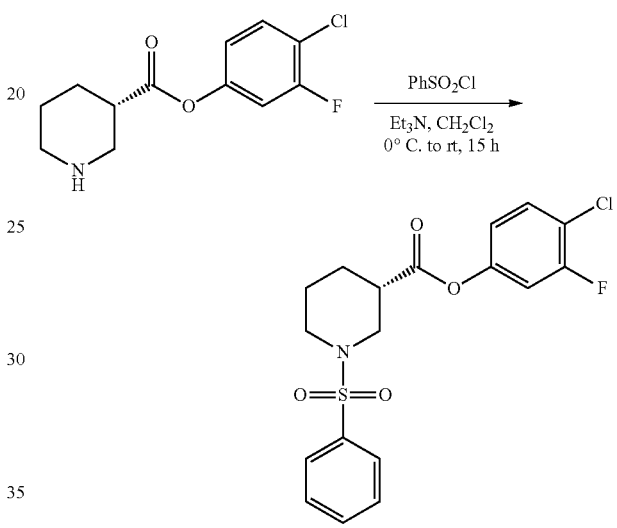

To a precooled (0° C.) solution of intermediate 2.55 (20. mg, 0.078 mmol) in dichloromethane (0.5 mL) was added triethylamine (30 μL, 0.2 mmol) and benzenesulfonyl chloride (15 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (2.9 mg, 9% yield). $^1$H NMR (500 MHz, Acetonitrile-$d_3$) δ 7.82-7.76 (m, 2H), 7.72-7.66 (m, 1H), 7.65-7.58 (m, 2H), 7.52 (t, J=8.6 Hz, 1H), 7.10 (dd, J=9.9, 2.6 Hz, 1H), 7.01-6.95 (m, 1H), 3.60 (d, J=11.2 Hz, 1H), 3.35-3.26 (m, 1H), 3.01-2.94 (m, 1H), 2.91 (tt, J=8.7, 3.9 Hz, 1H), 2.74-2.65 (m, 1H), 1.89-1.77 (m, 1H), 1.70-1.57 (m, 2H); AMM 398.0639 (ESI) m/z [calc for $C_{18}H_{18}ClFNO_4S$ (M+H)$^+$ 398.0629].

Example 93: Synthesis of (S)-MCG-III-213-A04 (2.59)

-continued

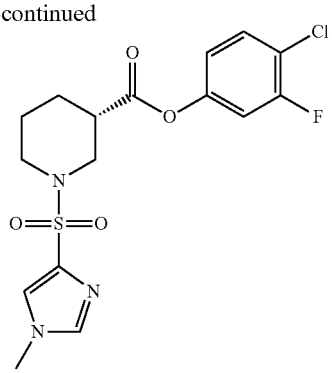

To a precooled (0° C.) solution of intermediate 2.55 (20. mg, 0.078 mmol) in dichloromethane (0.5 mL) was added triethylamine (30 μL, 0.2 mmol) and 1-methyl-1H-imidazole-4-sulfonyl chloride (21 mg, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (14 mg, 45% yield). $^1$H NMR (500 MHz, Acetonitrile-$d_3$) δ 7.63 (d, J=1.4 Hz, 1H), 7.56 (d, J=1.4 Hz, 1H), 7.51 (t, J=8.6 Hz, 1H), 7.11 (dd, J=9.9, 2.6 Hz, 1H), 7.01-6.95 (m, 1H), 3.75-3.72 (m, 1H), 3.71 (s, 3H), 3.40 (dd, J=12.3, 5.1 Hz, 1H), 3.10 (dd, J=12.1, 9.1 Hz, 1H), 2.92 (tt, J=9.0, 4.0 Hz, 1H), 2.81 (ddd, J=12.9, 9.6, 3.4 Hz, 1H), 2.05-1.97 (m, 1H), 1.87-1.78 (m, 1H), 1.70-1.56 (m, 2H); AMM 402.0697 (ESI) m/z [calc for $C_{16}H_{18}ClFN_3O_4S$ (M+H)$^+$ 402.0691].

Example 94: Synthesis of Intermediate 2.61

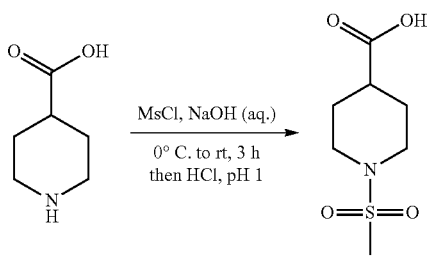

To a precooled (0° C.) solution of 4-piperidine carboxylic acid (1.0 g, 7.7 mmol) in 1M aq. NaOH (15 mL) was added methanesulfonyl chloride (0.72 mL, 9.3 mmol). The resulting mixture was stirred at 0° C. to room temperature for 3 h, then quenched slowly with 6 M aq. HCl and diluted with EtOAc. The layers were separated, and the aqueous phase was extracted with EtOAc (3×). The combined organic layers were dried over Na$_2$SO$_4$ and concentrated in vacuo to afford the product as a white solid (264 mg, 16% yield). $^1$H NMR (500 MHz, Chloroform-d) δ 3.73-3.62 (m, 2H), 2.94-2.83 (m, 2H), 2.79 (s, 3H), 2.11-2.01 (m, 2H), 1.94-1.77 (m, 3H); $^{13}$C NMR (126 MHz, CDCl$_3$) δ 179.40, 45.14, 39.85, 35.23, 27.51; IR (ATR) ν$_{max}$ 2936, 1697, 1320, 1141, 920, 776, 518 cm$^{-1}$; AMM (ESI) m/z 208.0641 [calc for $C_7H_{14}NO_4S$ (M+H)$^+$ 208.0644].

Example 95: Synthesis of Regioisomeric Analogue MCG-III-101 (2.62)

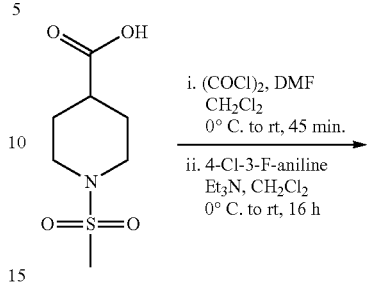

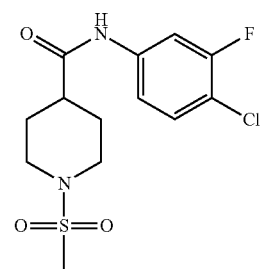

To a precooled (0° C.) solution of intermediate 2.61 (100. mg, 0.41 mmol) in CH$_2$Cl$_2$ (2 mL) under N$_2$ atmosphere was added dropwise oxalyl chloride (0.04 mL, 0.4 mmol) then DMF (1 drop). The resulting mixture was allowed to warm to room temperature and stirred for 45 min. then concentrated in vacuo and carried forward without additional purification.

To a precooled (0° C.) solution of 4-chloro-3-fluoroaniline (60. mg, 0.41 mmol) and triethylamine (0.1 mL, 0.8 mmol) in CH$_2$Cl$_2$ (1 mL) was added a precooled (0° C.) solution of acid chloride intermediate (93 mg, 0.41 mmol) in CH$_2$Cl$_2$ (3 mL). The resulting mixture was allowed to warm to room temperature and stirred for 16 h, then quenched with H$_2$O. The layers were separated and the aqueous phase was extracted with CH$_2$Cl$_2$ (3×). The combined organic layers were washed with brine, dried over Na$_2$SO4, and concentrated in vacuo. Flash chromatography (SiO$_2$, 50:50 ethyl acetate:hexanes) afforded the product as a white solid (91 mg, 66% yield). $^1$H NMR (500 MHz, Acetonitrile-$d_3$) δ 8.52 (s, 1H), 7.73 (dd, J=11.9, 2.7 Hz, 1H), 7.37 (dd, J=10.1, 7.3 Hz, 1H), 7.24 (d, J=8.6 Hz, 1H), 3.75-3.63 (m, 2H), 2.84-2.68 (m, 5H), 2.50-2.36 (m, 1H), 1.83-1.68 (m, 2H); AMM (ESI) m/z 335.0640 [calc for $C_{13}H_{17}ClFN_2O_3S$ (M+H)$^+$ 335.0632].

Example 96: Synthesis of Intermediate 2.64

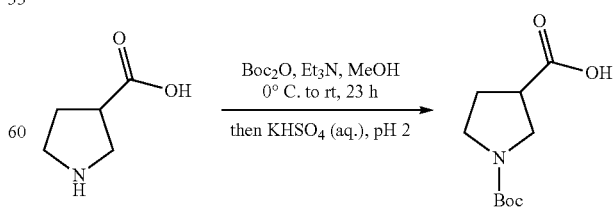

To a precooled (0° C.) solution of pyrrolidine-3-carboxylic acid (300. mg, 2.61 mmol) in MeOH (13 mL) under N$_2$ atmosphere was added triethylamine (0.7 mL, 3 mmol) then Boc anhydride (0.7 mL, 3 mmol). The resulting mixture was allowed to warm to room temperature and stirred for 23 h then concentrated in vacuo. The resulting residue was taken up in $CH_2Cl_2$ and the solution acidified with sat. aq. $KHSO_4$ to pH 2. The layers were separated, and the aqueous phase was extracted with $CH_2Cl_2$ (3×). The combined organic layers were dried over $Na_2SO_4$ and concentrated in vacuo to afford the product as a white solid (556 mg, 99% yield). $^1$H NMR (500 MHz, Chloroform-d) δ 3.87 (dt, J=13.4, 4.1 Hz, 1H), 3.21-2.94 (m, 1H), 2.85 (t, J=12.5 Hz, 1H), 2.53-2.39 (m, 1H), 2.12-2.00 (m, 1H), 1.77-1.67 (m, 1H), 1.67-1.55 (m, 1H), 1.45 (d, J=2.0 Hz, 9H); $^{13}$C NMR (126 MHz, DMSO) δ 174.32, 153.75, 78.65, 40.54, 39.52, 28.13, 28.03, 26.59, 23.80; IR (ATR) $v_{max}$ 2975, 1732, 1660, 1435, 1271, 1144, 849, 767, 640 cm$^{-1}$; AMM (ESI) m/z 216.1224 [calc for $C_{10}H_{18}NO_4$ (M+H)$^+$ 216.1236].

Example 97: Synthesis of Intermediate 2.65

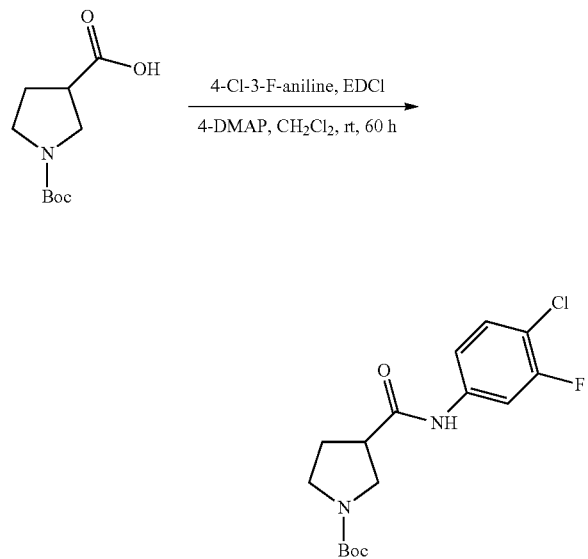

To a precooled (0° C.) solution of 4-chloro-3-fluoroaniline (262 mg, 1.50 mmol), 1-ethyl-3-(3-dimethylaminopropyl)-carbodiimide hydrochloride (316 mg, 1.65 mmol) and 4-dimethylaminopyridine (202 mg, 1.65 mmol) in $CH_2Cl_2$ (7.5 mL) under $N_2$ atmosphere was added a solution of intermediate 2.64 (323 mg, 1.50 mmol) in $CH_2Cl_2$ (7.5 mL). The resulting mixture was allowed to warm to room temperature and stirred for 60 h, then quenched with $H_2O$. The layers were separated, and the aqueous phase was extracted with $CH_2Cl_2$ (3×). The combined organic layers were washed with brine, dried over $Na_2SO_4$ and concentrated in vacuo. Flash chromatography ($SiO_2$, 60:40 hexanes:EtOAc) afforded the product as a white solid (417 mg, 81% yield). $^1$H NMR (500 MHz, Chloroform-d) δ 9.22 (d, J=8.9 Hz, 1H), 7.58 (dd, J=11.2, 2.4 Hz, 1H), 7.24-7.06 (m, 2H), 3.65-3.45 (m, 3H), 3.38-3.19 (m, 1H), 3.15-2.96 (m, 1H), 2.26-2.00 (m, 2H), 1.41 (s, 9H); $^{13}$C NMR (126 MHz, CDCl$_3$) δ 171.52, 158.74, 156.78, 154.64, 138.28, 138.20, 130.29, 116.12, 116.09, 115.53, 115.39, 108.68, 108.47, 79.97, 77.16, 48.79, 48.64, 45.76, 45.47, 45.11, 44.31, 29.53, 29.04, 28.43. AMM (ESI) m/z 343.1228 [calc for $C_{16}H_{21}ClFN_2O_3$ (M+H)$^+$ 343.1225].

Example 98: Synthesis of Intermediate 2.66

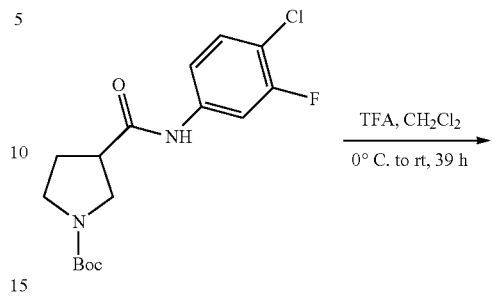

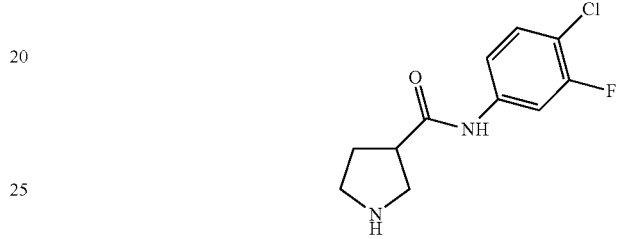

To a precooled (0° C.) solution of intermediate 2.65 (139 mg, 0.405 mmol) in $CH_2Cl_2$ (2 mL) under $N_2$ atmosphere was added dropwise trifluoroacetic acid (0.2 mL, 2 mmol). The resulting mixture was allowed to warm to room temperature and stirred for 39 h then concentrated in vacuo. The resulting residue was taken up in $H_2O$ and the aqueous solution was neutralized with powdered $NaHCO_3$ then diluted with $CHCl_3$. The layers were separated, and the aqueous phase was extracted with $CHCl_3$ (3×). The combined organic layers were dried over $Na_2SO_4$ and concentrated in vacuo to afford the product as a white solid (35 mg, 36% yield). $^1$H NMR (500 MHz, Chloroform-d) δ 9.17 (s, 1H), 7.61 (dd, J=11.2, 2.5 Hz, 1H), 7.31-7.22 (m, 1H), 7.10 (dd, J=8.9, 2.4 Hz, 1H), 3.28 (dd, J=10.3, 2.3 Hz, 1H), 3.19 (ddd, J=10.0, 8.5, 4.2 Hz, 1H), 2.99-2.82 (m, 3H), 2.39 (s, 1H), 2.25-2.11 (m, 1H), 2.09-1.95 (m, 1H); $^{13}$C NMR (126 MHz, CDCl$_3$) δ 174.59, 130.49, 115.76, 108.50, 108.29, 53.57, 50.81, 45.73, 45.66, 29.86, 29.74; IR (ATR) $v_{max}$ 3243, 3187, 3111, 2926, 1674, 1604, 1538, 1492, 1422, 1213, 1061, 863, 814 cm$^{-1}$; AMM (ESI) m/z 243.0692 [calc for $C_{11}H_{13}ClFN_2O$ (M+H)$^+$ 243.0700].

Example 99: Synthesis of Region III Analogues 2.67-2.70

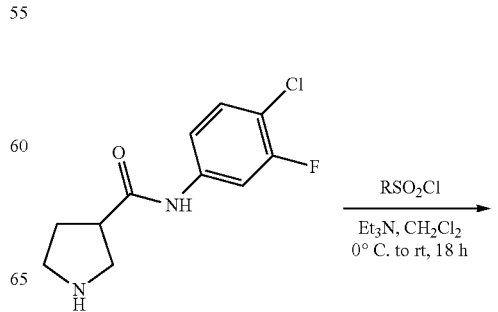

-continued

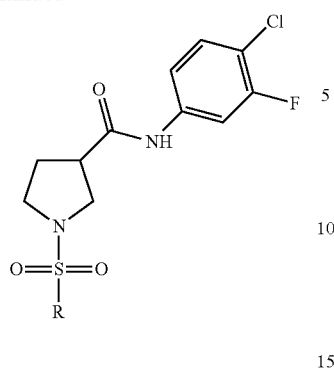

To separate precooled (0° C.) solutions of intermediate 2.66 (18 mg, 0.074 mmol) and triethylamine (30 μL, 0.2 mmol) in dichloromethane (0.5 mL) was added R-sulfonyl chloride (0.11 mmol). The resulting mixtures were allowed to warm to room temperature and stirred for 18 h, then diluted with wet DMSO (1 mL), filtered through Celite and purified via mass-directed isolation using ultra-performance liquid chromatography (22-29% yield).

Example 100: Synthesis of MCG-III-157-A01
(2.67)

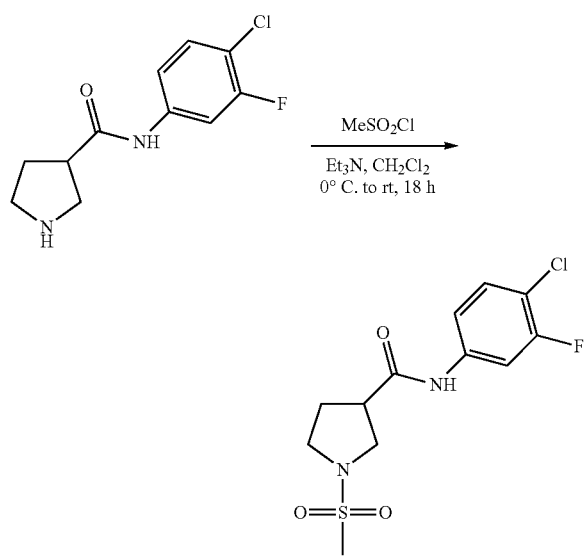

To a precooled (0° C.) solution of intermediate 2.66 (18 mg, 0.074 mmol) and triethylamine (30 μL, 0.2 mmol) in dichloromethane (0.5 mL) was added methanesulfonyl chloride (8.6 μL, 0.11 mmol). The resulting mixture was allowed to warm to room temperature and stirred for 18 h, then diluted with wet DMSO (1 mL), filtered through Celite and purified via mass-directed isolation using ultra-performance liquid chromatography (6.9 mg, 29% yield). $^1$H NMR (500 MHz, Acetonitrile-$d_3$) δ 8.71 (s, 1H), 7.71 (dd, J=11.8, 2.4 Hz, 1H), 7.39 (t, J=8.6 Hz, 1H), 7.26 (ddd, J=8.8, 2.5, 1.2 Hz, 1H), 3.55 (dd, J=10.4, 7.8 Hz, 1H), 3.49 (dd, J=10.4, 6.2 Hz, 1H), 3.44-3.30 (m, 2H), 3.17 (p, J=7.2 Hz, 1H), 2.84 (s, 3H), 2.31-2.12 (m, 2H); AMM 343.0306 (ESI) m/z [calc for $C_{12}H_{14}ClFN_2O_3SNa$ (M+Na)$^+$] 343.0295].

Example 101: Synthesis of MCG-III-157-A02
(2.68)

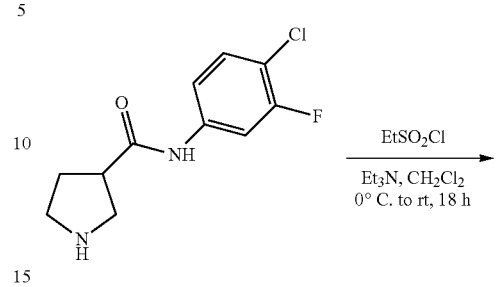

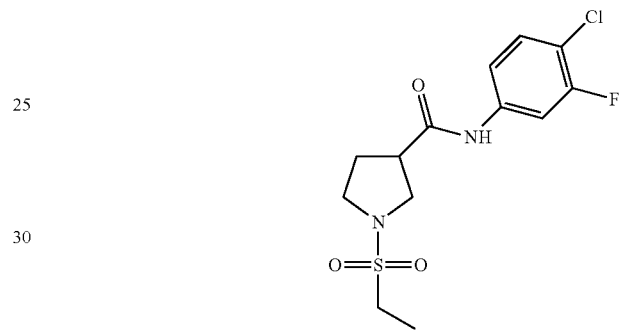

To a precooled (0° C.) solution of intermediate 2.66 (18 mg, 0.074 mmol) and triethylamine (30 μL, 0.2 mmol) in dichloromethane (0.5 mL) was added ethanesulfonyl chloride (11 μL, 0.11 mmol). The resulting mixture was allowed to warm to room temperature and stirred for 18 h, then diluted with wet DMSO (1 mL), filtered through Celite and purified via mass-directed isolation using ultra-performance liquid chromatography (5.6 mg, 23% yield). $^1$H NMR (500 MHz, Acetonitrile-$d_3$) δ 8.68 (s, 1H), 7.71 (dd, J=11.8, 2.4 Hz, 1H), 7.39 (t, J=8.6 Hz, 1H), 7.31-7.21 (m, 1H), 3.59 (dd, J=10.1, 7.8 Hz, 1H), 3.51 (dd, J=10.1, 6.4 Hz, 1H), 3.48-3.34 (m, 2H), 3.16 (p, J=7.3 Hz, 1H), 3.05 (qd, J=7.3, 2.4 Hz, 2H), 2.30-2.11 (m, 2H), 1.30 (t, J=7.4 Hz, 3H); AMM 357.0447 (ESI) m/z [calc for $C_{13}H_{16}ClFN_2O_3SNa$ (M+Na)$^+$] 357.0452].

Example 102: Synthesis of MCG-III-157-A03
(2.69)

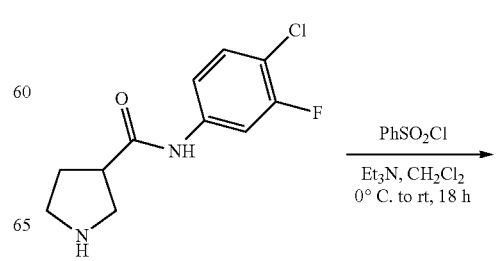

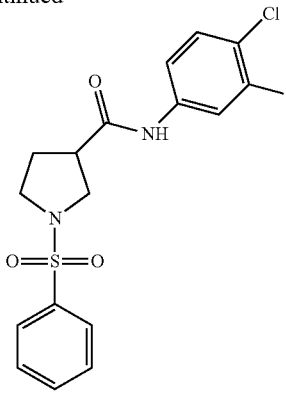

To a precooled (0° C.) solution of intermediate 2.66 (18 mg, 0.074 mmol) and triethylamine (30 µL, 0.2 mmol) in dichloromethane (0.5 mL) was added benzenesulfonyl chloride (14 µL, 0.11 mmol). The resulting mixture was allowed to warm to room temperature and stirred for 18 h, then diluted with wet DMSO (1 mL), filtered through Celite and purified via mass-directed isolation using ultra-performance liquid chromatography (7.3 mg, 26% yield). $^1$H NMR (500 MHz, Acetonitrile-$d_3$) δ 8.58 (s, 1H), 7.88-7.80 (m, 2H), 7.71-7.64 (m, 1H), 7.64-7.56 (m, 3H), 7.36 (t, J=8.6 Hz, 1H), 7.21-7.13 (m, 1H), 3.54 (dd, J=10.3, 8.0 Hz, 1H), 3.39-3.24 (m, 3H), 2.97 (p, J=7.5 Hz, 1H), 2.10-2.00 (m, 1H); AMM 405.0446 (ESI) m/z [calc for $C_{17}H_{16}ClFN_2O_3SNa$ (M+Na)$^+$]405.0452].

Example 103: Synthesis of MCG-III-157-A04 (2.70)

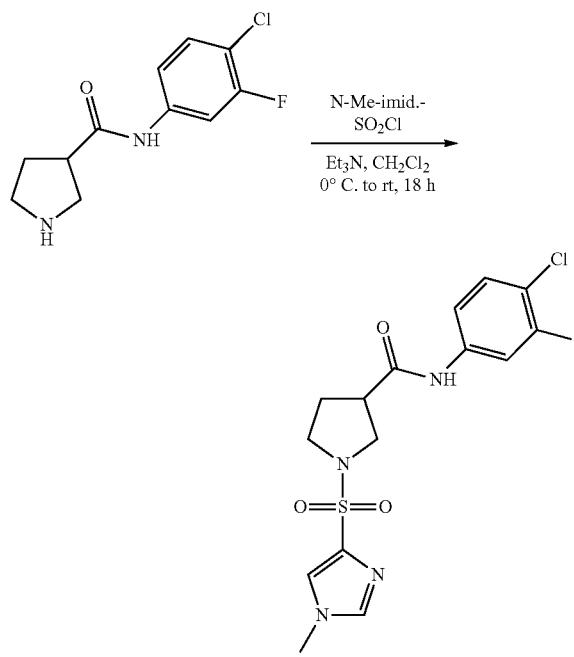

To a precooled (0° C.) solution of intermediate 2.66 (18 mg, 0.074 mmol) and triethylamine (30 µL, 0.2 mmol) in dichloromethane (0.5 mL) was added 1-methyl-1H-imidazole-4-sulfonyl chloride (20. mg, 0.11 mmol). The resulting mixture was allowed to warm to room temperature and stirred for 18 h, then diluted with wet DMSO (1 mL), filtered through Celite and purified via mass-directed isolation using ultra-performance liquid chromatography (6.3 mg, 22% yield). $^1$H NMR (500 MHz, Acetonitrile-$d_3$) δ 8.56 (s, 1H), 7.69 (s, 1H), 7.66 (dd, J=11.8, 2.4 Hz, 1H), 7.59 (d, J=1.4 Hz, 1H), 7.37 (t, J=8.6 Hz, 1H), 7.21 (dd, J=8.7, 2.1 Hz, 1H), 3.72 (s, 3H), 3.63 (dd, J=10.4, 7.9 Hz, 1H), 3.50-3.40 (m, 2H), 3.40-3.32 (m, 1H), 3.00 (p, J=7.6 Hz, 1H), 2.14-1.96 (m, 2H); AMM 409.0521 (ESI) m/z [calc for $C_{15}H_{16}ClFN_4O_3SNa$ (M+Na)$^+$ 409.0513].

Example 104: Synthesis of Intermediate 2.72

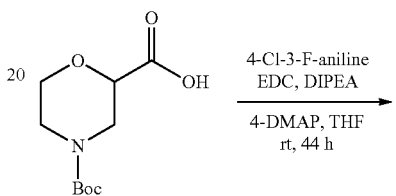

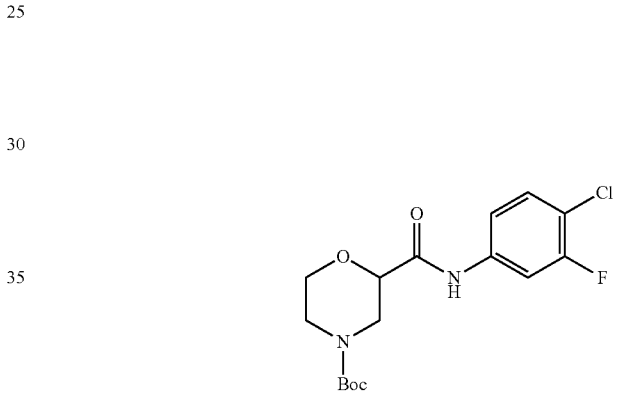

To a precooled (0° C.) solution of 4-Boc-morpholine-2-carboxylic acid (400. mg, 1.73 mmol), 4-chloro-3-fluoroaniline (378 mg, 2.60 mmol), 1-ethyl-3-(3-dimethylaminopropyl)-carbodiimide hydrochloride (EDCI, 269 mg, 1.73 mmol) and 4-dimethylaminopyridine (42 mg, 0.35 mmol) in tetrahydrofuran (17 mL) under $N_2$ atmosphere was added diisopropylethylamine (0.75 mL, 4.3 mmol). The resulting mixture was allowed to warm to room temperature and stirred for 44 h then quenched with sat. aq. $NaHCO_3$ and diluted with EtOAc. The layers were separated, and the aqueous phase was extracted with ethyl acetate (3×). The combined organic layers were washed with brine, dried over $Na_2SO_4$, and concentrated in vacuo. Flash column chromatography ($SiO_2$, 70:30 hexanes:ethyl acetate) afforded the product as a white solid (330 mg, 53% yield). $^1$H NMR (500 MHz, Chloroform-d) δ 8.34 (s, 1H), 7.66 (dd, J=10.9, 2.4 Hz, 1H), 7.32 (t, J=8.3 Hz, 1H), 7.21-7.13 (m, 1H), 4.41 (s, 1H), 4.11-3.92 (m, 3H), 3.64 (td, J=11.8, 2.8 Hz, 1H), 3.02-2.74 (m, 2H), 1.48 (s, 9H); $^{13}$C NMR (126 MHz, CDCl$_3$) δ 167.04, 159.18, 157.21, 154.61, 137.10, 137.02, 130.70, 116.40, 116.26, 115.88, 115.85, 108.64, 108.44, 80.88, 75.12, 66.88, 46.17, 28.50; IR (ATR) $v_{max}$ 3398, 2925, 1691, 1527, 1416, 1127, 868, 809, 605 cm$^{-1}$; AMM 359.1197 (ESI) m/z [calc for $C_{16}H_{21}ClFN_2O_4$ (M+H)$^+$ 359.1174].

Example 105: Synthesis of Intermediate 2.73

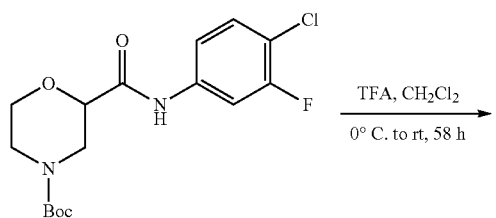

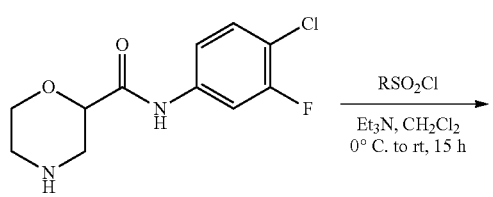

To a precooled (0° C.) solution of intermediate 2.72 (300. mg, 0.836 mmol) in CH$_2$Cl$_2$ (8.4 mL) under N$_2$ atmosphere was added dropwise trifluoroacetic acid (0.2 mL, 3 mmol). The resulting mixture was allowed to warm to room temperature and stirred for 22 h, then cooled to 0° C. before addition of trifluoroacetic acid (0.2 mL, 3 mmol). The resulting mixture was allowed to warm to room temperature and stirred for 36 h, then concentrated in vacuo. The resulting residue was taken up in CH$_2$Cl$_2$ and the solution was quenched with sat. aq. NaHCO$_3$. The layers were separated, and the aqueous phase was extracted with CH$_2$Cl$_2$ (3×). The combined organic layers were dried over Na$_2$SO$_4$ and concentrated in vacuo to afford the product as a white solid (233 mg, 98% yield). $^1$H NMR (500 MHz, Acetonitrile-d$_3$) δ 8.92 (s, 1H), 7.70 (dd, J=11.6, 2.4 Hz, 1H), 7.41 (t, J=8.5 Hz, 1H), 7.37-7.31 (m, 1H), 4.53 (dd, J=10.7, 2.8 Hz, 1H), 4.19-4.10 (m, 1H), 3.99 (ddd, J=13.1, 11.4, 2.6 Hz, 1H), 3.67-3.59 (m, 1H), 3.31 (d, J=13.1 Hz, 1H), 3.20-3.09 (m, 2H); $^{13}$C NMR (126 MHz, CDCl$_3$) δ 159.16, 157.19, 137.30, 137.23, 130.65, 116.19, 116.05, 115.86, 115.83, 108.59, 108.39, 100.12, 34.26; IR (ATR) ν$_{max}$ 3380, 2500, 1708, 1663, 1522, 1426, 1196, 1171, 1130, 1066, 836, 792, 725 cm$^{-1}$; AMM 259.0669 (ESI) m/z [calc for C$_{11}$H$_{13}$ClFN$_2$O$_2$ (M+H)$^+$ 259.0650].

Example 106: Synthesis of Region III Analogues 2.74-2.77

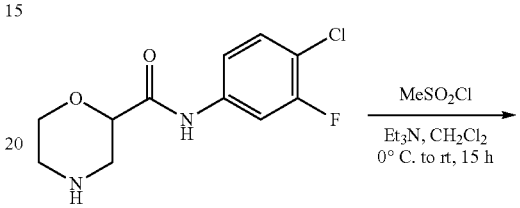

To separate precooled (0° C.) solutions of intermediate 2.73 (20. mg, 0.077 mmol) in dichloromethane (0.5 mL) was added triethylamine (30 μL, 0.2 mmol) and R-sulfonyl chloride (0.12 mmol). The resulting mixtures were allowed to warm to room temperature and stirred for 15 h, then diluted with wet DMSO (0.5 mL), filtered through Celite and purified via mass-directed isolation using ultra-performance liquid chromatography (41-91% yield).

Example 107: Synthesis of MCG-III-211-A01 (2.74)

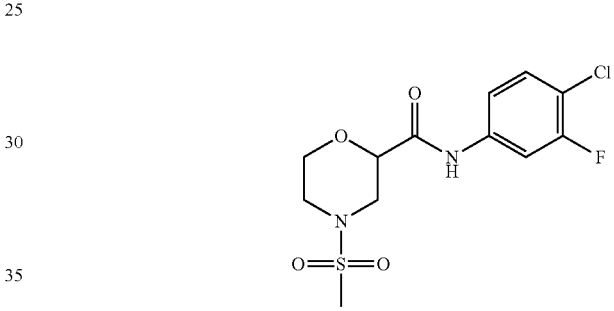

To a precooled (0° C.) solution of intermediate 2.73 (20. mg, 0.077 mmol) in dichloromethane (0.5 mL) was added triethylamine (30 μL, 0.2 mmol) and methanesulfonyl chloride (9.0 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (11 mg, 41% yield). $^1$H NMR (500 MHz, Acetonitrile-d$_3$) δ 8.84 (s, 1H), 7.72 (dd, J=11.6, 2.3 Hz, 1H), 7.41 (t, J=8.4 Hz, 1H), 7.39-7.33 (m, 1H), 4.19 (dd, J=10.0, 3.1 Hz, 1H), 4.15-4.07 (m, 1H), 3.84-3.78 (m, 1H), 3.74 (td, J=11.3, 2.8 Hz, 1H), 3.48 (dq, J=12.1, 2.2 Hz, 1H), 2.98-2.85 (m, 2H), 2.82 (s, 3H); AMM 337.0448 (ESI) m/z [calc for C$_{12}$H$_{15}$ClFN$_2$O$_4$S (M+H)$^+$ 337.0425].

Example 108: Synthesis of MCG-III-211-A02 (2.75)

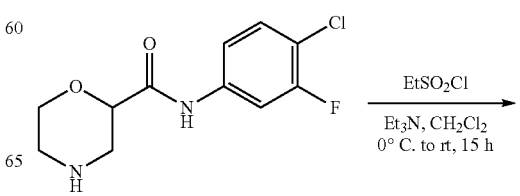

-continued

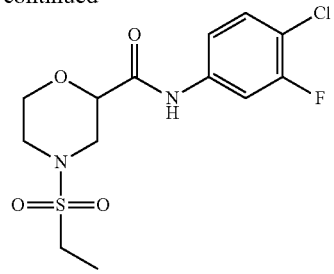

To a precooled (0° C.) solution of intermediate 2.73 (20. mg, 0.077 mmol) in dichloromethane (0.5 mL) was added triethylamine (30 μL, 0.2 mmol) and ethanesulfonyl chloride (11 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (14 mg, 51% yield). $^1$H NMR (500 MHz, Acetonitrile-d$_3$) δ 8.83 (s, 1H), 7.72 (dd, J=11.7, 2.4 Hz, 1H), 7.41 (t, J=8.4 Hz, 1H), 7.39-7.33 (m, 1H), 4.16 (dd, J=10.0, 3.1 Hz, 1H), 4.07 (ddd, J=11.6, 3.3, 2.1 Hz, 1H), 3.83 (ddd, J=12.3, 3.1, 1.8 Hz, 1H), 3.71 (ddd, J=11.7, 10.9, 2.8 Hz, 1H), 3.51 (dq, J=12.4, 2.2 Hz, 1H), 3.09-2.93 (m, 4H), 1.29 (t, J=7.4 Hz, 3H); AMM 351.0597 (ESI) m/z [calc for C$_{13}$H$_{17}$ClFN$_2$O$_4$S (M+H)$^+$ 351.0582].

Example 109: Synthesis of MCG-III-211-A03 (2.76)

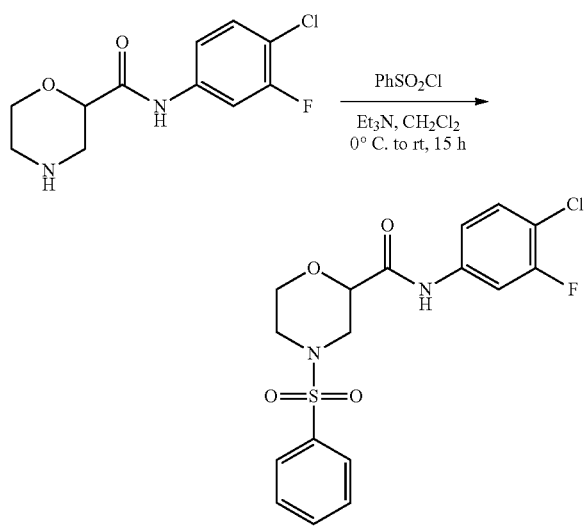

To a precooled (0° C.) solution of intermediate 2.73 (20. mg, 0.077 mmol) in dichloromethane (0.5 mL) was added triethylamine (30 μL, 0.2 mmol) and benzenesulfonyl chloride (15 μL, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (17 mg, 55% yield). $^1$H NMR (500 MHz, Acetonitrile-d$_3$) δ 8.73 (s, 1H), 7.82-7.76 (m, 2H), 7.73-7.65 (m, 2H), 7.65-7.59 (m, 2H), 7.39 (t, J=8.5 Hz, 1H), 7.34-7.28 (m, 1H), 4.19 (dd, J=10.1, 3.0 Hz, 1H), 4.03 (ddd, J=11.7, 3.4, 2.1 Hz, 1H), 3.81 (ddd, J=11.8, 3.1, 1.8 Hz, 1H), 3.74 (td, J=11.3, 2.8 Hz, 1H), 3.50 (dq, J=12.0, 2.2 Hz, 1H), 2.53-2.40 (m, 3H); AMM 399.0594 (ESI) m/z [calc for C$_{17}$H$_{17}$ClFN$_2$O$_4$S (M+H)$^+$ 399.0582].

Example 110: Synthesis of MCG-III-211-A04 (2.77)

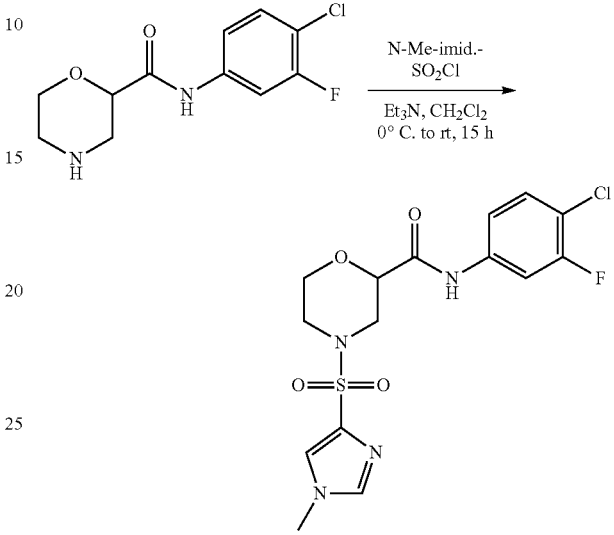

To a precooled (0° C.) solution of intermediate 2.73 (20. mg, 0.077 mmol) in dichloromethane (0.5 mL) was added triethylamine (30 μL, 0.2 mmol) and 1-methyl-1H-imidazole-4-sulfonyl chloride (21 mg, 0.12 mmol). The resulting mixture was allowed to warm to room temperature and stirred for 15 h, then diluted with wet DMSO (0.5 mL), filtered through Celite and purified via mass-directed isolation using ultra-performance liquid chromatography (28 mg, 91% yield). $^1$H NMR (500 MHz, Acetonitrile-d$_3$) δ 8.77 (s, 1H), 7.76 (d, J=1.4 Hz, 1H), 7.69 (dd, J=11.6, 2.4 Hz, 1H), 7.63 (d, J=1.4 Hz, 1H), 7.39 (t, J=8.5 Hz, 1H), 7.35-7.29 (m, 1H), 4.19 (dd, J=10.3, 3.1 Hz, 1H), 4.05 (ddd, J=11.7, 3.5, 2.0 Hz, 1H), 3.81 (ddd, J=12.1, 3.1, 1.8 Hz, 1H), 3.72 (s, 5H), 3.52 (dt, J=12.4, 2.2 Hz, 1H), 2.75 (ddd, J=12.3, 11.1, 3.4 Hz, 1H), 2.69-2.59 (m, 1H); AMM 403.0655 (ESI) m/z [calc for C$_{15}$H$_{17}$ClFN$_4$O$_4$S (M+H)$^+$ 403.0643].

Example 111: Synthesis of Intermediate 2.79

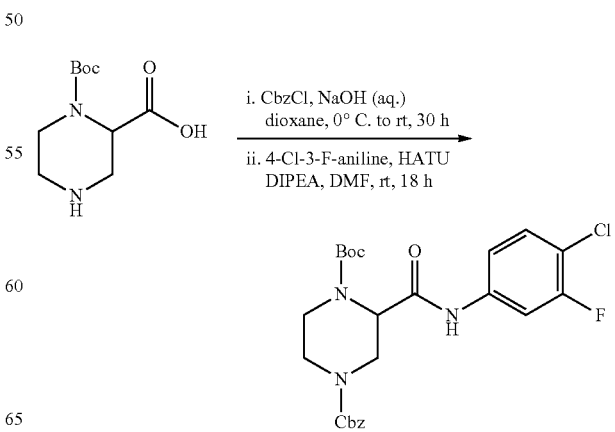

To a precooled (0° C.) solution of 1-Boc-piperazine-2-carboxylic acid (500. mg, 2.17 mmol) in 1,4-dioxane (11 mL) under $N_2$ atmosphere was added 1 M aq. NaOH until pH 11 achieved. To the resulting mixture was then added dropwise benzyl chloroformate (0.31 mL, 2.17 mmol) followed by additional 1 M aq. NaOH to maintain pH 11. The resulting mixture was allowed to warm to room temperature and stirred for 3 h, then cooled to 0° C. before addition of benzyl chloroformate (0.31 mL, 2.17 mmol) and 1 M aq. NaOH to maintain pH 11. The resulting mixture was allowed to warm to room temperature and stirred for 28 h, then cooled to 0° C. and acidified slowly with 1 M aq. HCl to pH 2. The aqueous layer was diluted with EtOAc and the layers were separated then the aqueous phase was extracted with EtOAc (3×). The combined organic layers were washed with brine, dried over $Na_2SO_4$, and concentrated in vacuo to afford the product, which was carried forward.

To a solution of intermediate (586 mg, 1.61 mmol), 4-chloro-3-fluoroaniline (281 mg, 1.93 mmol), and HATU (673 mg, 1.77 mmol) in DMF (8.0 mL) at room temperature under $N_2$ atmosphere was added diisopropylethylamine (0.84 mL, 4.8 mmol). The resulting mixture was stirred at room temperature for 18 h then concentrated in vacuo. The resulting residue was taken up in EtOAc and quenched with $H_2O$. The layers were separated, and the aqueous phase was extracted with EtOAc (3×). The combined organic layers were washed with brine, dried over $Na_2SO_4$ and concentrated in vacuo. Flash chromatography ($SiO_2$, 50:50 hexanes:EtOAc) afforded the product as a white solid (216 mg, 20% yield over 2 steps). $^1$H NMR (500 MHz, Chloroform-d) δ 8.76 (s, 1H), 7.61 (d, J=10.5 Hz, 1H), 7.30 (t, J=8.4 Hz, 1H), 7.11-7.04 (m, 1H), 4.59 (d, J=4.2 Hz, 1H), 3.91 (s, 1H), 3.56 (d, J=13.2 Hz, 1H), 3.05-2.92 (m, 2H), 2.88 (dd, J=13.4, 4.3 Hz, 1H), 2.78 (td, J=12.4, 3.5 Hz, 1H), 1.52 (s, 9H); $^{13}$C NMR (126 MHz, $CDCl_3$) δ 174.33, 147.70, 143.90, 139.16, 129.72, 127.25, 125.47, 119.69, 117.66, 114.46, 52.08, 43.73, 38.55, 29.84; IR (ATR) $v_{max}$ 3285, 2925, 2850, 1653, 1525, 1321, 1154, 983, 948, 826, 790, 506 cm$^{-1}$; AMM 492.1708 (ESI) m/z [calc for $C_{24}H_{28}ClFN_3O_5$ (M+H)$^+$ 492.1702].

Example 112: Synthesis of Intermediate 2.80

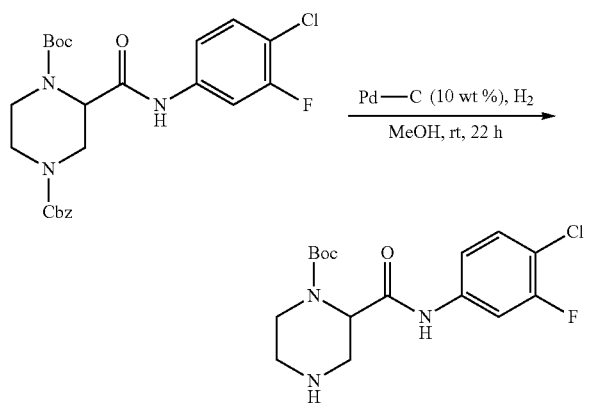

To a solution of palladium on carbon (10 wt. %, 17 mg, 0.16 mmol) in MeOH (3 mL) at room temperature under $N_2$ atmosphere was added a solution of intermediate 2.79 (389 mg, 0.791 mmol) in MeOH (5 mL). The resulting mixture was then backfilled with $H_2$ (3×) then stirred at room temperature under $H_2$ atmosphere for 22 h. The resulting mixture was filtered through a bed of Celite and rinsed with MeOH. The filtrate was concentrated in vacuo. Flash chromatography ($SiO_2$, 95:5 $CH_2Cl_2$:MeOH) afforded the product as a white solid (152 mg, 53% yield). $^1$H NMR (500 MHz, Acetonitrile-d$_3$) δ 9.47 (s, 1H), 7.74 (dd, J=11.6, 2.4 Hz, 1H), 7.45 (t, J=8.5 Hz, 1H), 7.35 (d, J=8.8 Hz, 1H), 4.01 (s, 1H), 3.51-3.43 (m, 1H), 3.37 (dd, J=12.9, 7.5 Hz, 1H), 3.24-3.09 (m, 3H), 2.54 (s, 1H), 1.95 (s, 9H); IR (ATR) $v_{max}$ 2456, 1660, 1607, 1533, 1429, 1182, 1137, 867, 797, 724, 596 cm$^{-1}$; AMM 358.1334 (ESI) m/z [calc for $C_{16}H_{22}ClFN_3O_3$ (M+H)$^+$ 358.1334].

Example 113: Synthesis of Region III Analogues 2.81-2.83

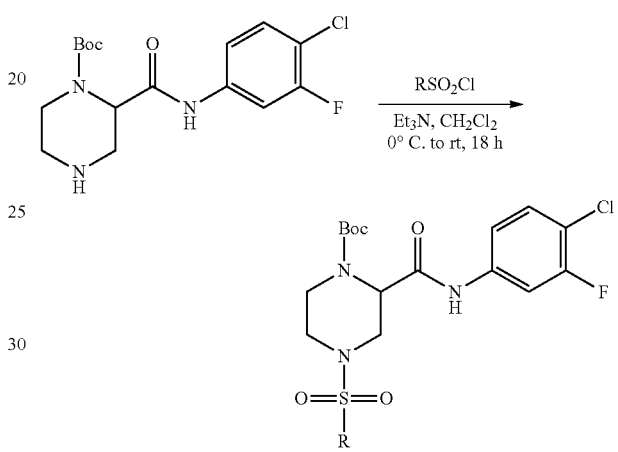

To separate precooled (0° C.) solutions of intermediate 2.80 (20. mg, 0.056 mmol) in dichloromethane (0.5 mL) was added triethylamine (20 µL, 0.1 mmol) and R-sulfonyl chloride (0.084 mmol). The resulting mixtures were allowed to warm to room temperature and stirred for 15 h, then diluted with wet DMSO (0.5 mL), filtered through Celite and purified via mass-directed isolation using ultra-performance liquid chromatography (40-78% yield).

Example 114: Synthesis of MCG-III-212-A01 (2.81)

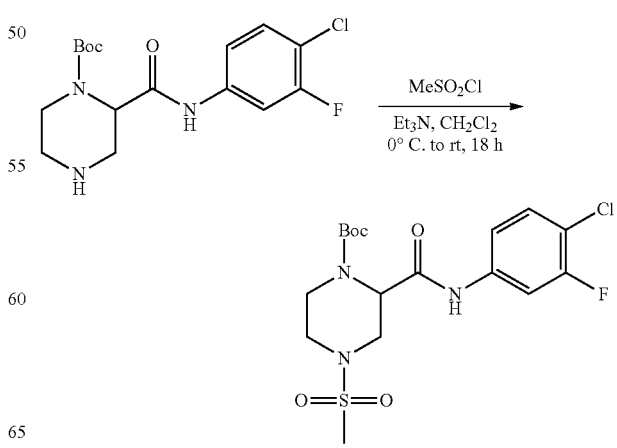

To a precooled (0° C.) solution of intermediate 2.80 (20. mg, 0.056 mmol) in dichloromethane (0.5 mL) was added triethylamine (20 µL, 0.1 mmol) and methanesulfonyl chloride (9.1 µL, 0.084 mmol). The resulting mixtures were allowed to warm to room temperature and stirred for 15 h, then diluted with wet DMSO (0.5 mL), filtered through Celite and purified via mass-directed isolation using ultra-performance liquid chromatography (10 mg, 40% yield). $^1$H NMR (500 MHz, Acetonitrile-d$_3$) δ 8.81 (s, 1H), 7.69 (dd, J=11.7, 2.4 Hz, 1H), 7.40 (t, J=8.5 Hz, 1H), 7.32 (d, J=8.9 Hz, 1H), 4.83 (s, 1H), 4.13 (d, J=12.6 Hz, 1H), 4.02 (d, J=13.6 Hz, 1H), 3.55 (d, J=11.8 Hz, 1H), 3.30 (s, 1H), 3.03 (dd, J=12.6, 4.3 Hz, 1H), 2.83 (dd, J=14.9, 3.1 Hz, 1H), 2.79 (s, 3H), 1.45 (s, 9H); AMM 436.1121 (ESI) m/z [calc for C$_{17}$H$_{24}$ClFN$_3$O$_5$S (M+H)$^+$ 436.1109].

Example 115: Synthesis of MCG-III-212-A03 (2.82)

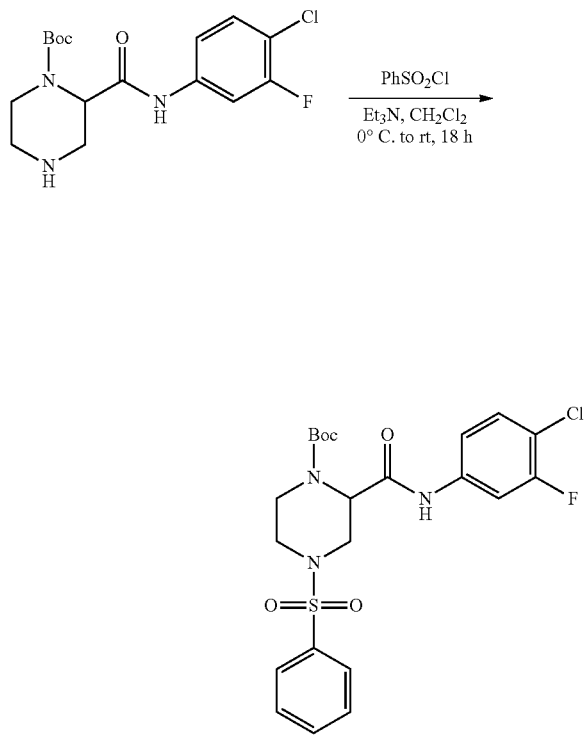

To a precooled (0° C.) solution of intermediate 2.80 (20. mg, 0.056 mmol) in dichloromethane (0.5 mL) was added triethylamine (20 µL, 0.1 mmol) and benzenesulfonyl chloride (20 µL, 0.084 mmol). The resulting mixtures were allowed to warm to room temperature and stirred for 15 h, then diluted with wet DMSO (0.5 mL), filtered through Celite and purified via mass-directed isolation using ultra-performance liquid chromatography (18 mg, 65% yield). $^1$H NMR (500 MHz, Acetonitrile-d$_3$) δ 8.82 (s, 1H), 7.77-7.73 (m, 2H), 7.72-7.65 (m, 2H), 7.59 (dd, J=8.4, 7.0 Hz, 2H), 7.41 (t, J=8.5 Hz, 1H), 7.32 (d, J=8.1 Hz, 1H), 4.76 (s, 1H), 4.17 (d, J=12.4 Hz, 1H), 3.96 (d, J=13.9 Hz, 1H), 3.60 (d, J=11.8 Hz, 1H), 2.60 (dd, J=12.4, 4.4 Hz, 1H), 2.39 (d, J=11.7 Hz, 2H), 1.39 (s, 9H); AMM 498.1280 (ESI) m/z [calc for C$_{22}$H$_{26}$ClFN$_3$O$_5$S (M+H)$^+$ 498.1266].

Example 116: Synthesis of MCG-III-212-A04 (2.83)

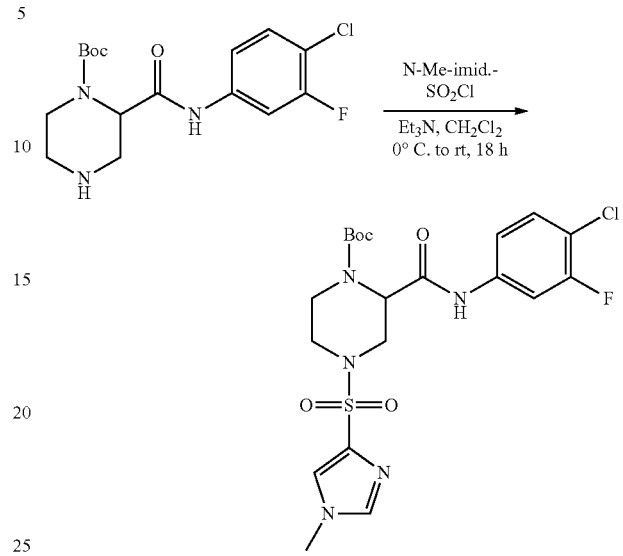

To a precooled (0° C.) solution of intermediate 2.80 (20. mg, 0.056 mmol) in dichloromethane (0.5 mL) was added triethylamine (20 µL, 0.1 mmol) and 1-methyl-1H-imidazole-4-sulfonyl chloride (25 mg, 0.084 mmol). The resulting mixtures were allowed to warm to room temperature and stirred for 15 h, then diluted with wet DMSO (0.5 mL), filtered through Celite and purified via mass-directed isolation using ultra-performance liquid chromatography (12 mg, 42% yield). $^1$H NMR (500 MHz, Acetonitrile-d$_3$) δ 8.69 (s, 1H), 7.69 (dd, J=11.7, 2.4 Hz, 1H), 7.54 (s, 2H), 7.41 (t, J=8.6 Hz, 1H), 7.36-7.28 (m, 1H), 4.76 (s, 1H), 4.15 (d, J=12.7 Hz, 1H), 3.96 (d, J=13.6 Hz, 1H), 3.67 (s, 3H), 3.61-3.53 (m, 1H), 2.85 (d, J=12.7 Hz, 1H), 2.58 (td, J=11.9, 3.6 Hz, 1H), 1.41 (s, 9H); AMM 502.1324 (ESI) m/z [calc for C$_{20}$H$_{26}$ClFN$_5$O$_5$S (M+H)$^+$ 502.1327].

Example 117: Synthesis of Region III Analogues 2.84-2.88

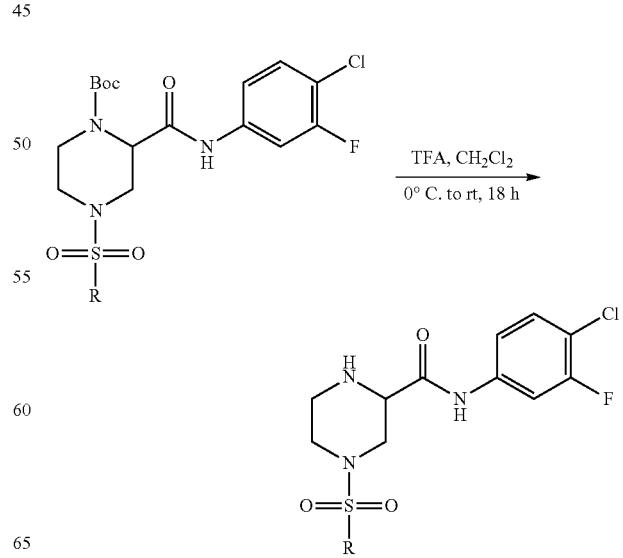

To separate precooled (0° C.) solutions of 2.80-2.83 (10. mg) in dichloromethane (0.5 mL) was added trifluoroacetic acid (10 µL, 0.1 mmol). The resulting mixtures were allowed to warm to room temperature and stirred for 18 h, then diluted with wet DMSO (0.5 mL), filtered through Celite and purified via mass-directed isolation using ultra-performance liquid chromatography (60-92% yield).

Example 118: Synthesis of MCG-III-216-A02 (2.84)

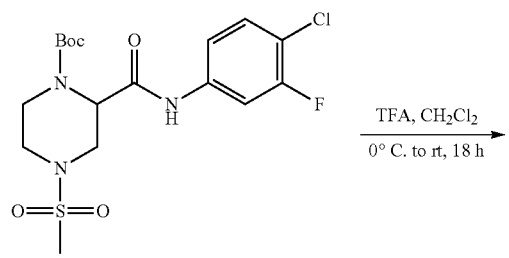

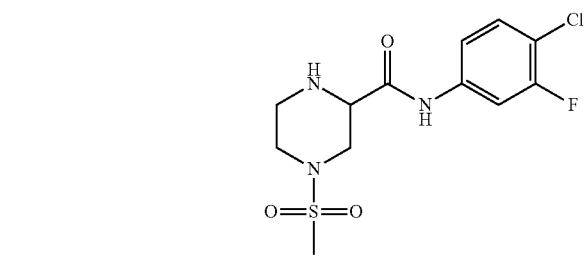

To a precooled (0° C.) solution of 2.81 (10. mg, 0.023 mmol) in dichloromethane (0.5 mL) was added trifluoroacetic acid (10 µL, 0.1 mmol). The resulting mixtures were allowed to warm to room temperature and stirred for 18 h, then diluted with wet DMSO (0.5 mL), filtered through Celite and purified via mass-directed isolation using ultra-performance liquid chromatography (4.6 mg, 60% yield). $^1$H NMR (500 MHz, Acetonitrile-d$_3$) δ 9.50 (s, 1H), 7.62 (dd, J=11.3, 2.5 Hz, 1H), 7.43 (t, J=8.5 Hz, 1H), 7.33-7.24 (m, 1H), 4.26 (dd, J=10.4, 3.9 Hz, 1H), 4.19-4.11 (m, 1H), 3.81-3.71 (m, 1H), 3.63-3.53 (m, 1H), 3.40-3.22 (m, 3H), 2.91 (s, 3H); AMM 336.0599 (ESI) m/z [calc for C$_{12}$H$_{16}$ClFN$_3$O$_3$S (M+H)$^+$ 336.0585].

Example 119: Synthesis of MCG-III-212-A02 (2.85)

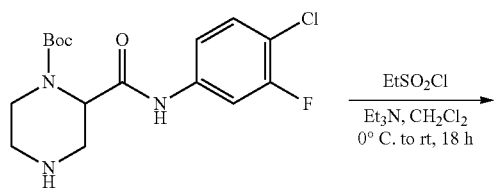

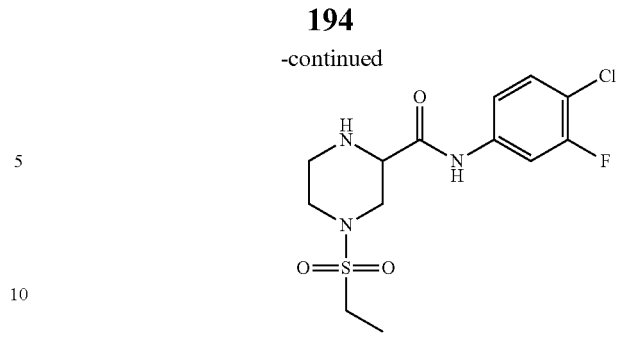

To a precooled (0° C.) solution of intermediate 2.80 (20. mg, 0.056 mmol) in dichloromethane (0.5 mL) was added triethylamine (20 µL, 0.1 mmol) and ethanesulfonyl chloride (7.9 µL, 0.084 mmol). The resulting mixtures were allowed to warm to room temperature and stirred for 15 h, then diluted with wet DMSO (0.5 mL), filtered through Celite and purified via mass-directed isolation using ultra-performance liquid chromatography (15 mg, 78% yield). *Note: Boc deprotection. $^1$H NMR (500 MHz, Acetonitrile-d$_3$) δ 8.82 (s, 1H), 7.72 (dd, J=11.6, 2.4 Hz, 1H), 7.41 (t, J=8.4 Hz, 1H), 7.36 (ddd, J=8.8, 2.4, 0.9 Hz, 1H), 4.16 (dd, J=10.0, 3.1 Hz, 1H), 4.07 (ddd, J=11.7, 3.3, 2.1 Hz, 1H), 3.83 (ddd, J=12.3, 3.2, 1.8 Hz, 1H), 3.72 (td, J=11.3, 2.8 Hz, 1H), 3.51 (dq, J=12.5, 2.2 Hz, 1H), 3.07-2.94 (m, 4H), 1.29 (t, J=7.4 Hz, 3H); AMM 350.0765 (ESI) m/z [calc for C$_{13}$H$_{18}$ClFN$_3$O$_3$S (M+H)$^+$ 350.0741].

Example 120: Synthesis of MCG-III-216-A03 (2.86)

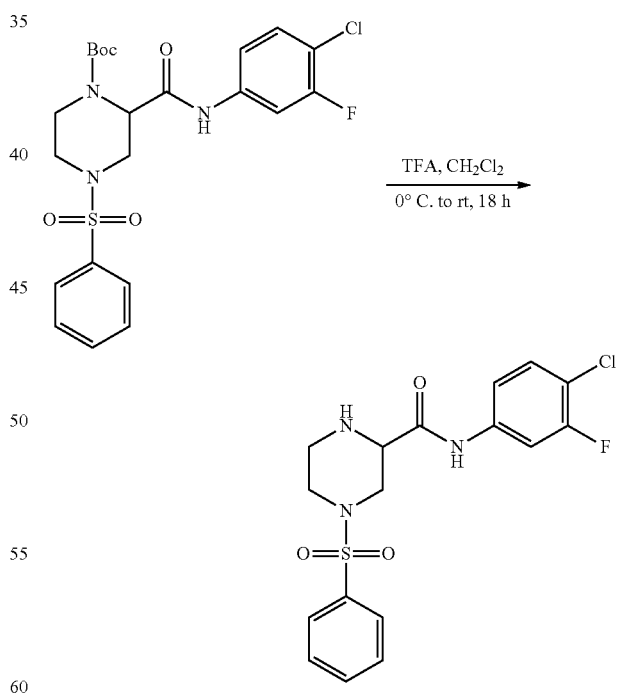

To a precooled (0° C.) solution of 2.82 (10. mg, 0.020 mmol) in dichloromethane (0.5 mL) was added trifluoroacetic acid (10 µL, 0.1 mmol). The resulting mixtures were allowed to warm to room temperature and stirred for 18 h, then diluted with wet DMSO (0.5 mL), filtered through Celite and purified via mass-directed isolation using ultra-performance liquid chromatography (6.6 mg, 83% yield). $^1$H NMR (500 MHz, Acetonitrile-$d_3$) δ 9.54 (d, J=7.5 Hz, 1H), 7.83-7.76 (m, 2H), 7.76-7.69 (m, 1H), 7.67-7.56 (m, 3H), 7.42 (t, J=8.5 Hz, 1H), 7.29-7.23 (m, 1H), 4.28-4.22 (m, 1H), 4.13-4.05 (m, 1H), 3.68 (d, J=13.1 Hz, 1H), 3.51 (dt, J=13.2, 3.3 Hz, 1H), 3.33-3.22 (m, 1H), 2.91-2.75 (m, 2H); AMM 398.0737 (ESI) m/z [calc for $C_{17}H_{18}ClFN_3O_3S$ (M+H)$^+$ 398.0741].

Example 121: Synthesis of MCG-III-216-A04 (2.87)

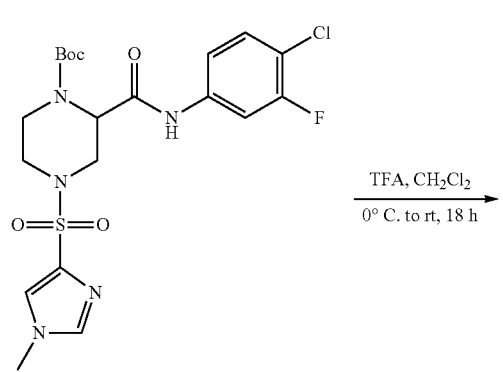

To a precooled (0° C.) solution of 2.83 (10. mg, 0.020 mmol) in dichloromethane (0.5 mL) was added trifluoroacetic acid (10 μL, 0.1 mmol). The resulting mixtures were allowed to warm to room temperature and stirred for 18 h, then diluted with wet DMSO (0.5 mL), filtered through Celite and purified via mass-directed isolation using ultra-performance liquid chromatography (7.4 mg, 92% yield). $^1$H NMR (500 MHz, Acetonitrile-$d_3$) δ 9.38 (s, 1H), 7.64 (dd, J=14.0, 1.3 Hz, 2H), 7.60 (dd, J=11.3, 2.4 Hz, 1H), 7.43 (t, J=8.5 Hz, 1H), 7.29-7.24 (m, 1H), 4.27 (dd, J=10.6, 3.8 Hz, 1H), 4.25-4.20 (m, 1H), 3.76 (d, J=13.6 Hz, 1H), 3.72 (s, 3H), 3.53 (dt, J=13.1, 3.1 Hz, 1H), 3.27 (td, J=12.9, 12.3, 3.8 Hz, 1H), 3.16-3.03 (m, 2H); AMM 402.0795 (ESI) m/z [calc for $C_{15}H_{18}ClFN_5O_3S$ (M+H)$^+$ 402.0803].

Example 122: Synthesis of MCG-III-216-A01 (2.88)

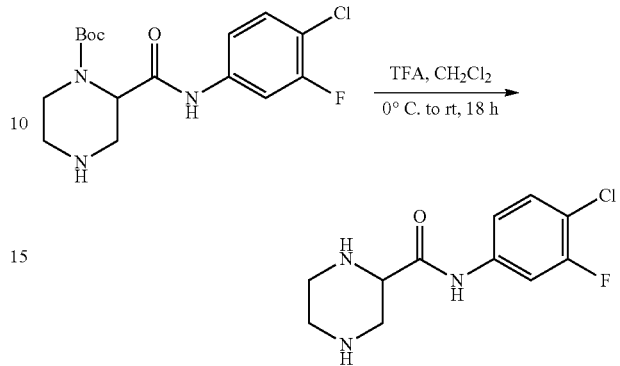

To a precooled (0° C.) solution of 2.80 (10. mg, 0.028 mmol) in dichloromethane (0.5 mL) was added trifluoroacetic acid (10 μL, 0.1 mmol). The resulting mixtures were allowed to warm to room temperature and stirred for 18 h, then diluted with wet DMSO (0.5 mL), filtered through Celite and purified via mass-directed isolation using ultra-performance liquid chromatography (13.2 mg, 85% yield). $^1$H NMR (500 MHz, Acetonitrile-$d_3$) δ 9.73 (s, 1H), 7.67 (dd, J=11.3, 2.6 Hz, 1H), 7.44 (t, J=8.4 Hz, 1H), 7.35-7.24 (m, 1H), 4.34 (s, 1H), 3.67 (s, 1H), 3.47 (dd, J=13.4, 9.1 Hz, 1H), 3.43-3.22 (m, 4H), 2.10-2.03 (m, 1H); AMM 258.0818 (ESI) m/z [calc for $C_{11}H_{14}ClFN_3O$ (M+H)$^+$ 258.0809].

Example 123: Synthesis of Intermediate 2.90

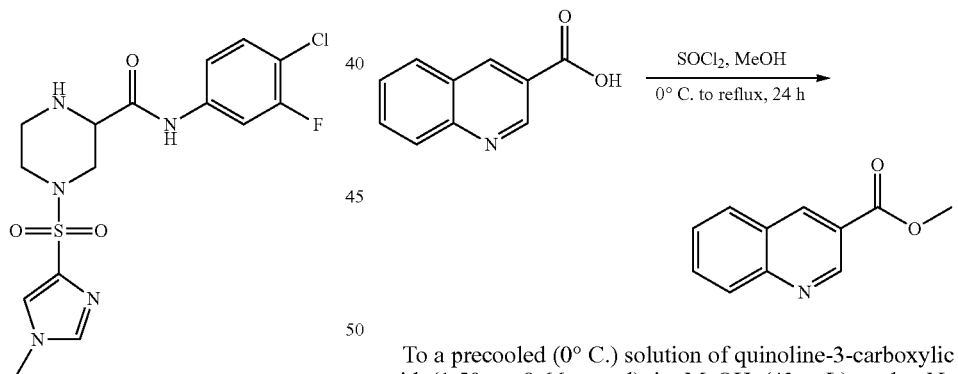

To a precooled (0° C.) solution of quinoline-3-carboxylic acid (1.50 g, 8.66 mmol) in MeOH (43 mL) under $N_2$ atmosphere was added dropwise thionyl chloride (1.3 mL, 17 mmol). The resulting mixture was heated to reflux and stirred for 24 h, then allowed to cool to room temperature and concentrated in vacuo. The resulting residue was taken up in $CH_2Cl_2$ and quenched with sat. aq. $NaHCO_3$. The layers were separated, and the aqueous phase was extracted with $CH_2Cl_2$ (3×). The combined organic layers were washed with brine, dried over $Na_2SO_4$ and concentrated in vacuo to afford the product as an off-white solid (1.58 g, 97% yield). See, Chen, Org. Biomol. Chem. 2016, 14 (24), 5505-5510. $^1$H NMR (500 MHz, Chloroform-d) δ 9.43 (s, 1H), 8.82 (d, J=2.0 Hz, 1H), 8.16 (d, J=8.5 Hz, 1H), 7.94-7.86 (m, 1H), 7.81 (ddd, J=8.4, 6.9, 1.4 Hz, 1H), 7.60 (t, J=7.5 Hz, 1H), 3.99 (s, 3H); $^{13}$C NMR (126 MHz, $CDCl_3$) δ 165.78, 149.83, 149.57, 139.07, 132.08, 129.33, 129.20, 127.64, 126.95, 123.12, 77.16, 52.59; IR (ATR) $v_{max}$ 3509, 2994, 1714, 1618, 1572, 1497, 1434, 1367, 1290, 1241, 1192, 1100 cm$^{-1}$; AMM 188.0704 (ESI) m/z [calc for C$_{11}$H$_{10}$NO$_2$ (M+H)$^+$ 188.0712].

Example 124: Synthesis of Intermediate 2.91 and Side Product 2.92

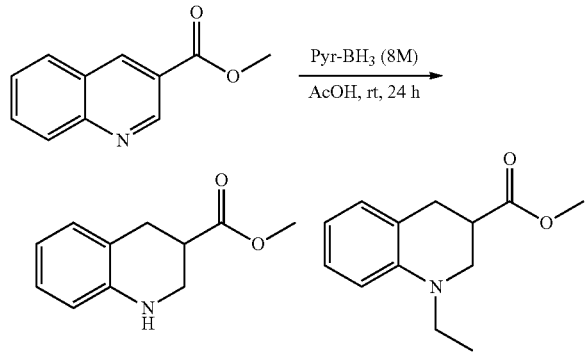

To a precooled (0° C.) solution of intermediate 2.90 (1.50 g, 8.01 mmol) in glacial acetic acid (40 mL) under N$_2$ atmosphere was added 8 M borane pyridine complex (2.0 mL, 16 mmol). The resulting mixture was allowed to warm to room temperature and stirred for 24 h, then concentrated in vacuo. The resulting residue was taken up in EtOAc and the solution was cooled to 0° C. and neutralized with sat. aq. NaHCO$_3$. The layers were separated, and the aqueous phase was extracted with EtOAc (3×). The combined organic layers were washed with brined, dried over Na$_2$SO$_4$, and concentrated in vacuo. Flash chromatography (SiO$_2$, 80:20 hexanes:EtOAc) afforded the product 2.91 (874 mg, 57% yield) and side product 2.92 (464 mg, 26% yield).

2.91: The experimental data agreed with that described in Chen, L.; Wilder, P. T.; Drennen, B.; Tran, J.; Roth, B. M.; Chesko, K.; Shapiro, P.; Fletcher, S. Structure-Based Design of 3-Carboxy-Substituted 1,2,3,4-Tetrahydroquinolines as Inhibitors of Myeloid Cell Leukemia-1 (Mcl-1). Org. Biomol. Chem. 2016, 14 (24), 5505-5510. $^1$H NMR (500 MHz, Chloroform-d) δ 6.99 (t, J=7.3 Hz, 2H), 6.65 (td, J=7.4, 1.2 Hz, 1H), 6.51 (dd, J=8.4, 1.5 Hz, 1H), 3.74 (s, 3H), 3.55 (ddd, J=11.6, 3.4, 1.3 Hz, 1H), 3.37 (dd, J=11.4, 9.4 Hz, 1H), 3.06-2.99 (m, 2H), 2.98-2.87 (m, 1H); AMM 192.1023 (ESI) m/z [calc for C$_{11}$H$_{14}$NO$_2$ (M+H)$^+$ 192.1025].

2.92: $^1$H NMR (500 MHz, Chloroform-d) δ 7.12-7.04 (m, 1H), 7.00 (d, J=7.1 Hz, 1H), 6.67-6.56 (m, 2H), 3.74 (s, 3H), 3.53-3.42 (m, 2H), 3.42-3.35 (m, 1H), 3.34-3.24 (m, 1H), 3.04-2.89 (m, 3H), 1.15 (t, J=7.0 Hz, 3H); $^{13}$C NMR (126 MHz, CDCl$_3$) δ 173.92, 144.09, 129.30, 127.31, 120.43, 115.99, 110.76, 51.76, 49.61, 45.30, 38.29, 30.63, 10.79; AMM 220.1351 (ESI) m/z [calc for C$_{13}$H$_{18}$NO$_2$ (M+H)$^+$ 220.1338].

Example 125: Synthesis of Intermediate 2.93

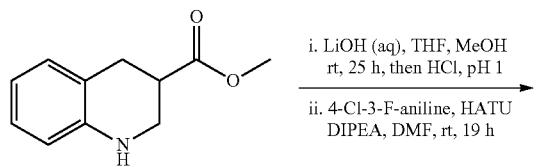

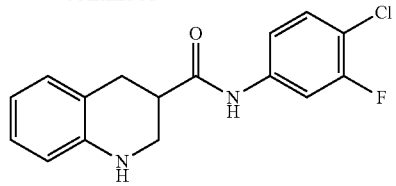

To a flask charged with intermediate 2.91 (786 mg, 4.11 mmol) at room temperature under N$_2$ atmosphere was added 1 M aq. LiOH (8 mL), THF (24 mL) and MeOH (8 mL). The resulting mixture was stirred at room temperature for 25 h, then concentrated in vacuo to remove volatiles. The remaining mixture was quenched with 1 M aq. NaOH and the aqueous phase was washed with Et$_2$O then cooled to 0° C. and acidified with 1 M aq. HCl to pH 2 and diluted with CH$_2$Cl$_2$. The layers were separated, and the aqueous phase was extracted with CH$_2$Cl$_2$ (3×). The combined organic layers were washed with brine, dried over Na$_2$SO$_4$, and concentrated in vacuo to afford the product, which was carried forward without additional purification.

To a solution of intermediate (129 mg, 0.727 mmol), 4-chloro-3-fluoroaniline (128 mg, 0.872 mmol), and HATU (304 mg, 0.800 mmol) in DMF (3.6 mL) at room temperature under N$_2$ atmosphere was added diisopropylethylamine (0.38 mL, 2.18 mmol). The resulting mixture was stirred at room temperature for 19 h, then concentrated in vacuo. The resulting residue was taken up in EtOAc and quenched with H$_2$O. The layers were separated, and the aqueous phase was extracted with EtOAc (3×). The combined organic layers were washed with brine, dried over Na$_2$SO$_4$ and concentrated in vacuo. Flash chromatography (SiO$_2$, 80:20 hexanes:EtOAc) afforded the product as a white solid (195 mg, 17% yield over 2 steps). $^1$H NMR (500 MHz, Acetonitrile-d$_3$) δ 9.01 (s, 1H), 7.69 (dd, J=11.7, 2.4 Hz, 1H), 7.40 (t, J=8.5 Hz, 1H), 7.30-7.19 (m, 3H), 7.17-7.10 (m, 1H), 7.07 (d, J=8.0 Hz, 1H), 3.65-3.52 (m, 2H), 3.21-3.05 (m, 3H); $^{13}$C NMR (126 MHz, CDCl$_3$) δ 172.78, 159.06, 157.10, 143.11, 138.18, 138.10, 130.46, 129.98, 127.50, 119.74, 118.99, 116.08, 115.16, 108.84, 108.63, 77.16, 43.51, 40.19, 38.75, 30.11; IR (ATR) $v_{max}$ 3400, 2928, 1667, 1604, 1531, 1493, 1423, 1385, 840, 747, 556 cm$^{-1}$; AMM 305.0869 (ESI) m/z [calc for C$_{16}$H$_{15}$ClFN$_2$O (M+H)$^+$ 305.0857].

Example 126: Synthesis of Region III Analogues 2.94-2.97

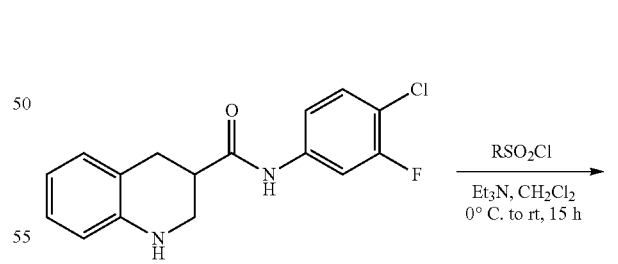

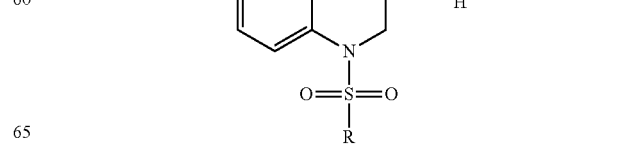

To separate precooled (0° C.) solutions of intermediate 2.93 (20. mg, 0.066 mmol) in dichloromethane (0.5 mL) was added triethylamine (30 µL, 0.2 mmol) and R-sulfonyl chloride (0.098 mmol). The resulting mixtures were allowed to warm to room temperature and stirred for 15 h, then diluted with wet DMSO (0.5 mL), filtered through Celite and purified via mass-directed isolation using ultra-performance liquid chromatography (4-52% yield).

Example 127: Synthesis of MCG-III-214-A01
(2.94)

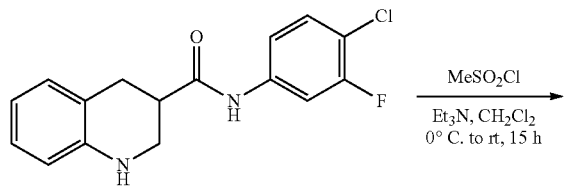

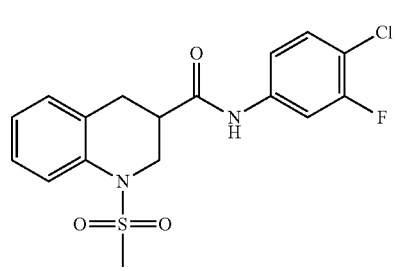

To a precooled (0° C.) solution of intermediate 2.93 (20. mg, 0.066 mmol) in dichloromethane (0.5 mL) was added triethylamine (30 µL, 0.2 mmol) and methanesulfonyl chloride (7.6 µL, 0.098 mmol). The resulting mixture was allowed to warm to room temperature and stirred for 15 h, then diluted with wet DMSO (0.5 mL), filtered through Celite and purified via mass-directed isolation using ultra-performance liquid chromatography (7.0 mg, 28% yield). $^1$H NMR (500 MHz, Acetonitrile-$d_3$) δ 8.81 (s, 1H), 7.76-7.69 (m, 1H), 7.62 (dd, J=8.2, 1.2 Hz, 1H), 7.40 (t, J=8.6 Hz, 1H), 7.31-7.26 (m, 1H), 7.26-7.18 (m, 2H), 7.12 (td, J=7.4, 1.2 Hz, 1H), 4.19 (dd, J=13.4, 4.3 Hz, 1H), 3.65 (dd, J=13.3, 9.5 Hz, 1H), 3.10 (d, J=7.8 Hz, 2H), 3.06-3.00 (m, 1H), 3.00 (s, 3H); AMM 383.0619 (ESI) m/z [calc for $C_{17}H_{17}ClFN_2O_3S$ (M+H)$^+$ 383.0632].

Example 128: Synthesis of MCG-III-214-A03
(2.96)

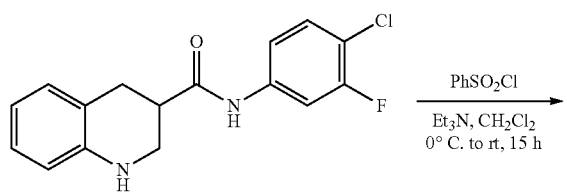

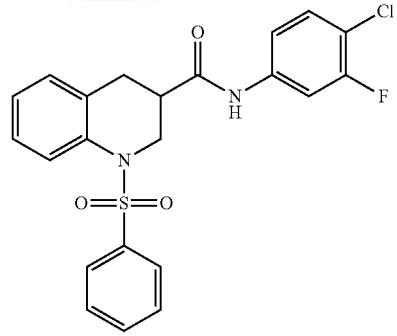

To a precooled (0° C.) solution of intermediate 2.93 (20. mg, 0.066 mmol) in dichloromethane (0.5 mL) was added triethylamine (30 µL, 0.2 mmol) and benzenesulfonyl chloride (13 µL, 0.098 mmol). The resulting mixture was allowed to warm to room temperature and stirred for 15 h, then diluted with wet DMSO (0.5 mL), filtered through Celite and purified via mass-directed isolation using ultra-performance liquid chromatography (13 mg, 43% yield). $^1$H NMR (500 MHz, Acetonitrile-$d_3$) δ 8.62 (s, 1H), 7.72-7.58 (m, 5H), 7.53-7.44 (m, 2H), 7.36 (t, J=8.6 Hz, 1H), 7.26-7.15 (m, 2H), 7.12-7.05 (m, 2H), 4.28 (ddd, J=13.4, 4.8, 1.6 Hz, 1H), 3.69 (ddd, J=11.6, 8.2, 1.9 Hz, 1H), 2.79-2.65 (m, 2H), 2.64-2.52 (m, 1H); AMM 445.0809 (ESI) m/z [calc for $C_{22}H_{19}ClFN_2O_3S$ (M+H)$^+$ 445.0789].

Example 129: Synthesis of MCG-III-214-A04
(2.97)

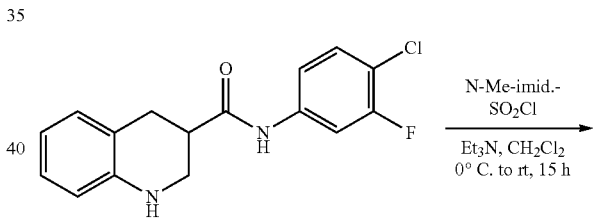

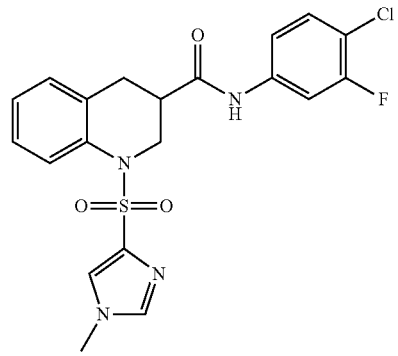

To a precooled (0° C.) solution of intermediate 2.93 (20. mg, 0.066 mmol) in dichloromethane (0.5 mL) was added triethylamine (30 µL, 0.2 mmol) and 1-methyl-1H-imidazole-4-sulfonyl chloride (18 mg, 0.098 mmol). The resulting mixture was allowed to warm to room temperature and stirred for 15 h, then diluted with wet DMSO (0.5 mL), filtered through Celite and purified via mass-directed isolation using ultra-performance liquid chromatography (15 mg, 52% yield). $^1$H NMR (500 MHz, Acetonitrile-$d_3$) δ 8.85 (s, 1H), 7.77-7.65 (m, 2H), 7.53 (dd, J=12.3, 1.5 Hz, 2H), 7.39

(t, J=8.5 Hz, 1H), 7.32-7.24 (m, 1H), 7.21-7.10 (m, 2H), 7.10-7.02 (m, 1H), 4.36 (dd, J=13.3, 4.3 Hz, 1H), 3.68-3.58 (m, 4H), 3.06-2.94 (m, 1H), 2.94-2.86 (m, 2H); AMM 449.0869 (ESI) m/z [calc for $C_{20}H_{19}ClFN_4O_3S$ (M+H)$^+$ 449.0850].

Example 130: Synthesis of Analogue 2.98

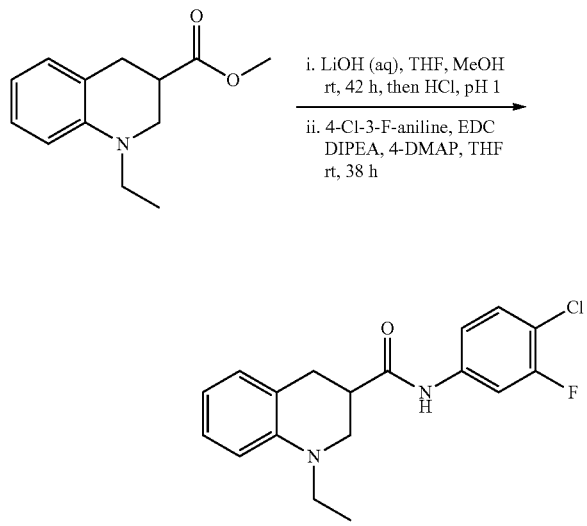 [SMILES: CCN1CC(C(=O)OC)Cc2ccccc21 ; CCN1CC(C(=O)Nc2ccc(Cl)c(F)c2)Cc2ccccc21]

To a flask charged with side product 2.92 (293 mg, 1.34 mmol) at room temperature under $N_2$ was added 1 M aq. LiOH (2.6 mL), THF (8.0 mL), and MeOH (2.6 mL). The resulting mixture was stirred at room temperature for 42 h, then concentrated in vacuo to remove volatiles. The remaining mixture was washed with $Et_2O$ then cooled to 0° C. and acidified with 6 M aq. HCl to pH 1 and diluted with $CH_2Cl_2$. The layers were separated, and the aqueous phase was extracted with $CH_2Cl_2$ (3×). The combined organic layers were dried over $Na_2SO_4$ and concentrated in vacuo to afford the product, which was carried forward without additional purification.

To a precooled (0° C.) solution of intermediate (50 mg, 0.25 mmol), 4-Cl-3-F-aniline (53 mg, 0.37 mmol), 1-ethyl-3-(3-dimethylaminopropyl)carbodiimide hydrochloride (38 mg, 0.25 mmol) and 4-DMAP (6 mg, 0.05 mmol) in THF (2.5 mL) under $N_2$ atmosphere was added diisopropylethylamine (0.11 mL, 0.61 mmol). The resulting mixture was allowed to warm to room temperature and stirred for 38 h, then quenched with sat. aq. $NaHCO_3$ and diluted with EtOAc. The layers were separated, and the aqueous phase was extracted with EtOAc (3×). The combined organic layers were washed with brine, dried over $Na_2SO_4$ and concentrated in vacuo. Flash chromatography ($SiO_2$, 90:10 hexanes:EtOAc) afforded the product as a white solid (55 mg, 43% yield over 2 steps). $^1H$ NMR (500 MHz, Acetonitrile-$d_3$) δ 8.76 (s, 1H), 7.74 (dd, J=11.8, 2.4 Hz, 1H), 7.39 (t, J=8.6 Hz, 1H), 7.26 (ddd, J=8.8, 2.4, 1.2 Hz, 1H), 7.11 (t, J=7.8 Hz, 1H), 7.07 (d, J=7.5 Hz, 1H), 6.85 (d, J=8.3 Hz, 1H), 6.74 (t, J=7.4 Hz, 1H), 3.57-3.46 (m, 2H), 3.46-3.33 (m, 2H), 3.08-2.98 (m, 2H), 2.98-2.86 (m, 1H), 1.16 (t, J=7.1 Hz, 3H); AMM 333.1180 (ESI) m/z [calc for $C_{18}H_{19}ClFN_2O$ (M+H)$^+$ 333.1170].

Example 131: Synthesis of Analogue 2.99

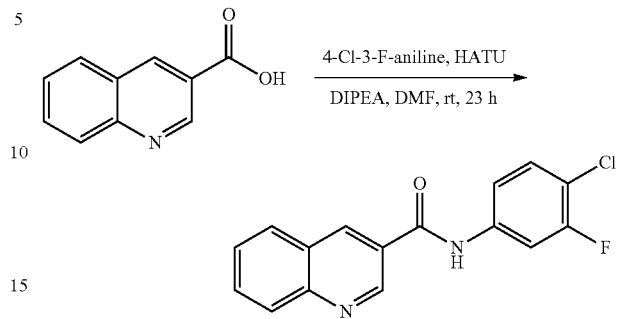

To a solution of quinoline-3-carboxylic acid (200. mg, 1.16 mmol), 4-chloro-3-fluoroaniline (252 mg, 1.73 mmol) and HATU (439 mg, 1.16 mmol) in DMF (5.8 mL) at room temperature under $N_2$ atmosphere was added diisopropylethylamine (0.6 mL, 3 mmol). The resulting mixture was stirred at room temperature for 23 h, then concentrated in vacuo. The resulting residue was taken up in EtOAc and quenched with $H_2O$. The layers were separated, and the aqueous phase was extracted with EtOAc (3×). The combined organic layers were washed with brine, dried over $Na_2SO_4$ and concentrated in vacuo. Flash chromatography ($SiO_2$, 50:50 hexanes:EtOAc, dry loaded Celite) afforded the product as a white solid (206 mg, 59% yield). $^1H$ NMR (500 MHz, Acetonitrile-$d_3$) δ 9.41 (d, J=2.2 Hz, 1H), 9.27 (s, 1H), 9.03 (d, J=2.2 Hz, 1H), 8.24 (d, J=8.5 Hz, 1H), 8.17 (d, J=8.1 Hz, 1H), 7.99 (ddd, J=8.4, 6.9, 1.4 Hz, 1H), 7.94-7.87 (m, 1H), 7.81 (ddd, J=8.1, 6.9, 1.1 Hz, 1H), 7.54-7.45 (m, 2H); AMM 301.0541 (ESI) m/z [calc for $C_{16}H_{11}ClFN_2O$ (M+H)$^+$ 301.0544].

Example 132: Synthesis of Intermediate 2.101

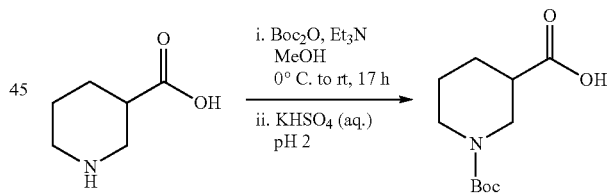

To a precooled (0° C.) solution of piperidine-3-carboxylic acid (300. mg, 2.32 mmol) in MeOH (12 mL) under $N_2$ atmosphere was added triethylamine (0.65 mL, 4.6 mmol) then dropwise Boc anhydride (0.64 mL, 2.8 mmol). The resulting mixture was allowed to warm to room temperature and stirred for 17 h, then concentrated in vacuo. The crude residue was taken up in $CH_2Cl_2$ and acidified with aq. $KHSO_4$ to pH 2. The layers were separated, and the aqueous phase was extracted with $CH_2Cl_2$ (3×). The combined organic layers were washed with 1 M aq. HCl then brine, dried over $Na_2SO_4$, and concentrated in vacuo to afford the product as a white solid (357 mg, 67% yield). $^1H$ NMR (500 MHz, Chloroform-d) δ 4.10 (s, 1H), 3.88 (dt, J=13.4, 4.1 Hz, 1H), 3.23-2.93 (m, 1H), 2.93-2.80 (m, 1H), 2.56-2.42 (m, 1H), 2.14-2.01 (m, 1H), 1.80-1.56 (m, 2H), 1.46 (d, J=6.8 Hz, 9H); $^{13}C$ NMR (126 MHz, $CDCl_3$) δ 177.93, 154.65, 79.98, 48.08, 45.48, 45.20, 43.21, 42.39, 31.11, 28.58; IR (ATR) $v_{max}$ 3177, 2972, 1741, 1665, 1424, 1165, 1131, 868, 831, 765, 648, 581 cm$^{-1}$; AMM 230.1406 (ESI) m/z [calc for $C_{11}H_{20}NO_4$ (M+H)$^+$ 230.1392].

Example 133: Synthesis of Intermediate 2.102

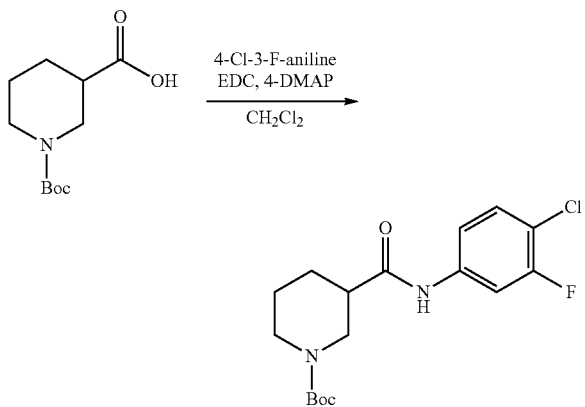

To a precooled (0° C.) solution of intermediate 2.101 (357 mg, 1.56 mmol), hexafluorophosphate azabenzotriazole tetramethyl uranium (HATU, 652 mg, 1.71 mmol), and 4-chloro-3-fluoroaniline (327 mg, 1.87 mmol) in dimethylformamide (5.2 mL) under $N_2$ atmosphere was added diisopropylethylamine (0.81 mL, 4.7 mmol). The resulting mixture was stirred at room temperature for 45 h, then concentrated in vacuo. The crude residue was taken up in $CH_2Cl_2$. The organic layer was washed sequentially with sat. aq. $NaHCO_3$, and brine, dried over $Na_2SO_4$, and concentrated in vacuo. Flash chromatography ($SiO_2$, 60:40 hexanes:EtOAc) afforded the product as a white solid (247 mg, 44% yield). $^1$H NMR (500 MHz, Chloroform-d) δ 9.19 (s, 1H), 7.81-7.58 (m, 1H), 7.37-7.05 (m, 2H), 4.00-3.79 (m, 1H), 3.68 (s, 1H), 3.45 (s, 1H), 3.19 (s, 1H), 2.62-2.42 (m, 1H), 2.16-1.98 (m, 1H), 1.98-1.82 (m, 1H), 1.74-1.58 (m, 1H), 1.47 (s, 10H); $^{13}$C NMR (126 MHz, CDCl$_3$) δ 171.79, 158.98, 157.02, 155.41, 138.61, 130.38, 115.84, 115.81, 115.44, 115.30, 108.50, 108.29, 80.64, 45.60, 44.85, 43.78, 28.52, 24.15; IR (ATR) $v_{max}$ 3150, 1731, 1657, 1474, 1144, 849 cm$^{-1}$; AMM (ESI) m/z 357.1393 [calc for $C_{17}H_{23}ClFN_2O_3$ (M+H)$^+$ 357.1381].

Example 134: Synthesis of Intermediate 2.103

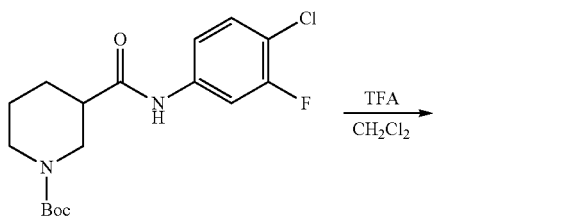

To a solution of intermediate 2.102 (247 mg, 0.692 mmol) in $CH_2Cl_2$ (3.5 mL) at room temperature under $N_2$ atmosphere was added trifluoroacetic acid (0.16 mL, 2.1 mmol). The resulting mixture was stirred for 38 h, then concentrated in vacuo. The crude residue was taken up in $CH_2Cl_2$ and diluted with water. The layers were separated, and the organic phase was washed with water (3×). The combined aqueous layers were basified to pH 8 with powdered $NaHCO_3$. The aqueous phase was then extracted with $CH_2Cl_2$ (3×), then the combined organic layers were dried over $Na_2SO_4$, and concentrated in vacuo to afford the product as a white solid (66 mg, 37% yield). $^1$H NMR (500 MHz, Chloroform-d) δ 11.01 (s, 1H), 7.69 (dd, J=11.3, 2.3 Hz, 1H), 7.32-7.23 (m, 1H), 7.17 (dd, J=8.9, 2.3 Hz, 1H), 3.26 (dd, J=12.1, 3.2 Hz, 1H), 3.16-3.02 (m, 1H), 2.93 (dd, J=12.0, 3.1 Hz, 1H), 2.75 (td, J=10.9, 3.2 Hz, 1H), 2.60-2.51 (m, 1H), 2.35-2.17 (m, 1H), 2.11-1.99 (m, 1H), 1.85-1.66 (m, 2H), 1.65-1.51 (m, 1H); $^{13}$C NMR (126 MHz, CDCl$_3$) δ 174.27, 159.08, 157.12, 138.66, 138.58, 130.35, 115.89, 115.86, 115.03, 114.88, 108.50, 108.30, 47.92, 46.67, 41.79, 29.82, 27.62, 22.61; IR (ATR) $v_{max}$ 3075, 2920, 2850, 1673, 1604, 1545, 1490, 1420, 1337, 1202, 857, 805, 717 cm$^{-1}$; AMM (ESI) m/z 257.0877 [calc for $C_{12}H_{15}ClFN_2O$ (M+H)$^+$ 257.0857].

Example 135: Synthesis of Analogues 2.104-2.107

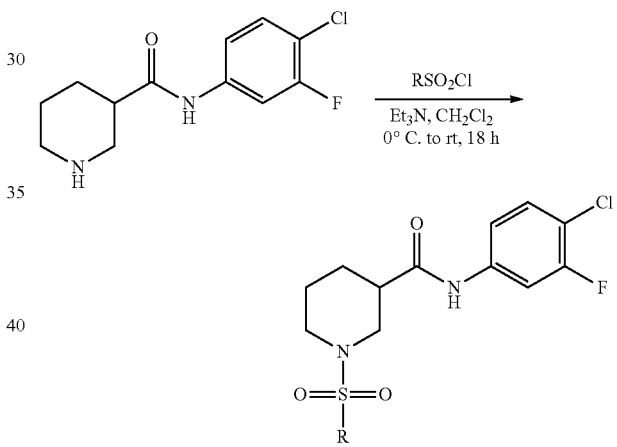

To separate precooled (0° C.) solutions of intermediate 2.103 (20. mg, 0.078 mmol) and triethylamine (30 µL, 0.2 mmol) in dichloromethane (0.5 mL) was added R-sulfonyl chloride (0.12 mmol). The resulting mixtures were allowed to warm to room temperature and stirred for 18 h, then diluted with wet DMSO (0.5 mL), filtered through Celite and purified via mass-directed isolation using ultra-performance liquid chromatography (43-57% yield).

Example 136: Synthesis of MCG-III-157-B01 (2.104)

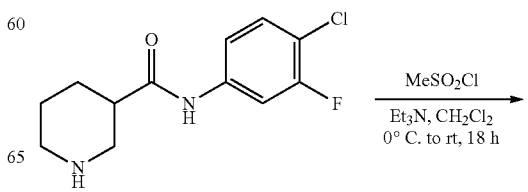

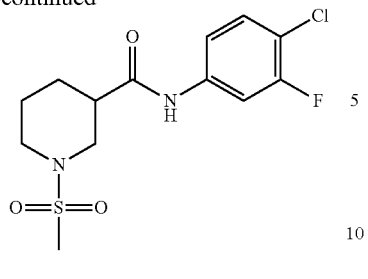

To a solution of intermediate 2.103 (20. mg, 0.078 mmol) and triethylamine (30 µL, 0.2 mmol) in dichloromethane (0.5 mL) at 0° C. was added methanesulfonyl chloride (9.0 µL, 0.12 mmol). The resulting mixture was stirred for 18 h, then diluted with wet DMSO (1 mL), filtered through Celite and purified via mass-directed isolation using ultra-performance liquid chromatography (12 mg, 45% yield). $^1$H NMR (500 MHz, Acetonitrile-$d_3$) δ 8.65 (s, 1H), 7.71 (dd, J=11.8, 2.4 Hz, 1H), 7.37 (t, J=8.6 Hz, 1H), 7.28-7.19 (m, 1H), 3.84-3.74 (m, 1H), 3.65-3.56 (m, 1H), 2.88 (dd, J=11.8, 10.6 Hz, 1H), 2.79 (s, 3H), 2.77-2.68 (m, 1H), 2.63-2.53 (m, 1H), 2.05-1.97 (m, 1H), 1.90-1.80 (m, 1H), 1.68-1.51 (m, 2H); AMM 357.0471 (ESI) m/z [calc for $C_{13}H_{16}ClFN_2O_3SNa$ (M+Na)$^+$ 357.0452].

Example 137: Synthesis of MCG-III-157-B02 (2.105)

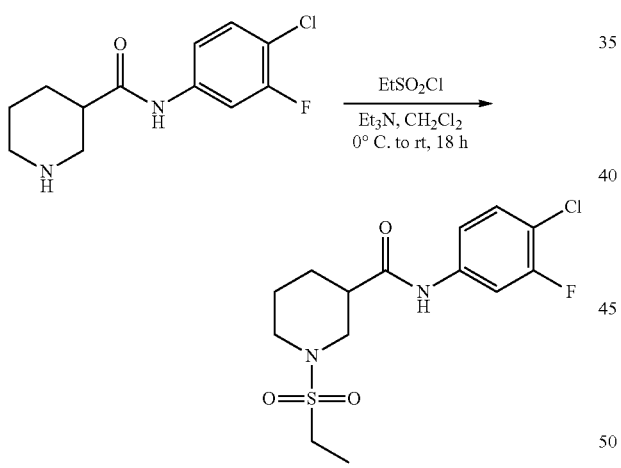

To a solution of intermediate 2.103 (20. mg, 0.078 mmol) and triethylamine (30 µL, 0.2 mmol) in dichloromethane (0.5 mL) at 0° C. was added ethanesulfonyl chloride (11 µL, 0.12 mmol). The resulting mixture was stirred for 18 h, then diluted with wet DMSO (1 mL), filtered through Celite and purified via mass-directed isolation using ultra-performance liquid chromatography (12 mg, 43% yield). $^1$H NMR (500 MHz, Acetonitrile-$d_3$) δ 8.65 (s, 1H), 7.71 (dd, J=11.8, 2.4 Hz, 1H), 7.37 (t, J=8.6 Hz, 1H), 7.27-7.19 (m, 1H), 3.86-3.75 (m, 1H), 3.68-3.57 (m, 1H), 3.04-2.91 (m, 3H), 2.84 (td, J=11.7, 2.9 Hz, 1H), 2.61-2.49 (m, 1H), 2.05-1.96 (m, 1H), 1.87-1.77 (m, 1H), 1.71-1.50 (m, 2H), 1.27 (t, J=7.4 Hz, 3H); AMM 349.0814 (ESI) m/z [calc for $C_{14}H_{19}ClFN_2O_3S$ (M+H)$^+$ 349.0789].

Example 138: Synthesis of MCG-III-157-B03 (2.106)

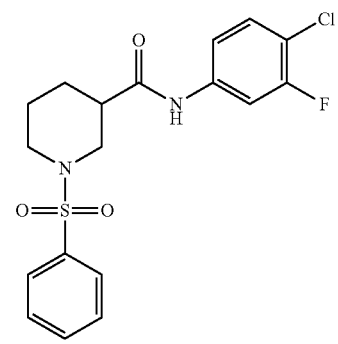

To a solution of intermediate 2.103 (20. mg, 0.078 mmol) and triethylamine (30 µL, 0.2 mmol) in dichloromethane (0.5 mL) at 0° C. was added benzenesulfonyl chloride (15 µL, 0.12 mmol). The resulting mixture was stirred for 18 h, then diluted with wet DMSO (1 mL), filtered through Celite and purified via mass-directed isolation using ultra-performance liquid chromatography (14 mg, 45% yield). $^1$H NMR (500 MHz, Acetonitrile-$d_3$) δ 8.59 (s, 1H), 7.80-7.73 (m, 2H), 7.72-7.65 (m, 2H), 7.65-7.58 (m, 2H), 7.37 (t, J=8.6 Hz, 1H), 7.26-7.17 (m, 1H), 3.87-3.78 (m, 1H), 3.64 (d, J=11.7 Hz, 1H), 2.63-2.54 (m, 1H), 2.42 (t, J=11.1 Hz, 1H), 2.30 (td, J=11.7, 2.9 Hz, 1H), 1.92-1.86 (m, 1H), 1.84-1.74 (m, 1H), 1.67-1.52 (m, 1H), 1.42 (qd, J=12.6, 3.9 Hz, 1H); AMM 419.0621 (ESI) m/z [calc for $C_{18}H_{18}ClFN_2O_3SNa$ (M+Na)$^+$ 419.0608].

Example 139: Synthesis of MCG-III-157-B04 (2.107)

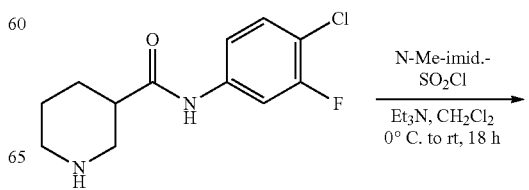

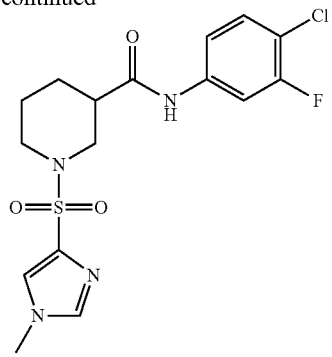

To a solution of intermediate 2.103 (20. mg, 0.078 mmol) and triethylamine (30 µL, 0.2 mmol) in dichloromethane (0.5 mL) at 0° C. was added 1-methyl-1H-imidazole-4-sulfonyl chloride (21 mg, 0.12 mmol). The resulting mixture was stirred for 18 h, then diluted with wet DMSO (1 mL), filtered through Celite and purified via mass-directed isolation using ultra-performance liquid chromatography (18 mg, 57% yield). $^1$H NMR (500 MHz, Acetonitrile-$d_3$) δ 8.61 (s, 1H), 7.73 (s, 1H), 7.69 (dd, J=11.8, 2.4 Hz, 1H), 7.57 (d, J=1.4 Hz, 1H), 7.37 (t, J=8.6 Hz, 1H), 7.26-7.18 (m, 1H), 3.85-3.77 (m, 1H), 3.73 (s, 3H), 3.64 (d, J=12.0 Hz, 1H), 2.67 (t, J=11.2 Hz, 1H), 2.62-2.47 (m, 2H), 1.85-1.76 (m, 1H), 1.59 (qt, J=12.5, 4.0 Hz, 1H), 1.53-1.41 (m, 1H); AMM 423.0678 (ESI) m/z [calc for $C_{16}H_{18}ClFN_4O_3SNa$ (M+Na)$^+$ 423.0670].

Example 140: Synthesis of MCG-III-207 (2.109)

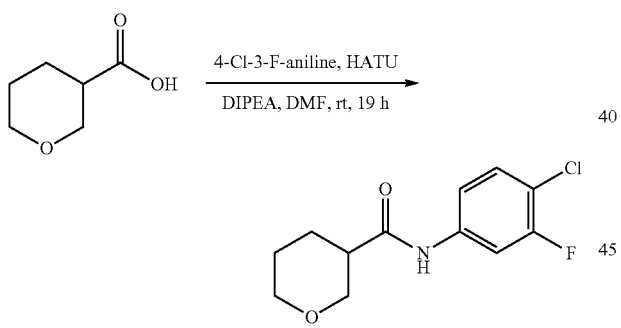

To a precooled (0° C.) solution of 4-chloro-3-fluoroaniline (336 mg, 2.31 mmol) and HATU (584 mg, 1.54 mmol) in DMF (8 mL) under $N_2$ atmosphere was added tetrahydro-2H-pyran-3-carboxylic acid (200. mg, 1.54 mmol) then diisopropylethylamine (0.80 mL, 4.61 mmol). The resulting mixture was allowed to warm to room temperature and stirred for 19 h, then concentrated in vacuo. The resulting residue was taken up in EtOAc and quenched with $H_2O$. The layers were separated, and the aqueous phase was extracted with EtOAc (3×). The combined organic layers were washed with brine, dried over $Na_2SO_4$, and concentrated in vacuo. Flash chromatography ($SiO_2$, 80:30 hexanes:EtOAc) afforded the product as a white solid (345 mg, 87% yield). $^1$H NMR (500 MHz, Acetonitrile-$d_3$) δ 8.56 (s, 1H), 7.72 (dd, J=11.9, 2.4 Hz, 1H), 7.37 (t, J=8.6 Hz, 1H), 7.27-7.19 (m, 1H), 4.00-3.91 (m, 1H), 3.82 (dt, J=11.1, 3.6 Hz, 1H), 3.49 (dd, J=11.3, 9.8 Hz, 1H), 3.40 (td, J=11.1, 3.0 Hz, 1H), 2.62-2.51 (m, 1H), 2.03-1.96 (m, 1H), 1.84-1.71 (m, 1H), 1.71-1.53 (m, 2H); $^{13}$C NMR (126 MHz, CDCl$_3$) δ 172.36, 159.14, 157.17, 137.94, 137.87, 130.56, 116.01, 115.98, 108.83, 108.62, 68.98, 68.67, 43.60, 38.79, 26.45, 23.77; AMM 258.0711 (ESI) m/z [calc for $C_{12}H_{14}ClFNO_2$ (M+H)$^+$ 258.0697].

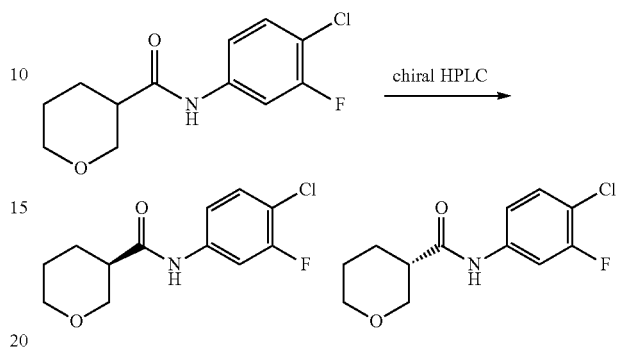

Chiral HPLC purification was performed using a Shimadzu HPLC (5 to 30% reagent alcohol in hexanes, 30 min.) with a chiral normal phase column (ChiralPak AD-H, 5 µM pore size, column dimensions 21 mm×250 mm).

(−)-2.109 (MCG-III-207-P1): Retention time=21 min. $[α]_D^{22}$−36.12 (c. 0.083, CH$_3$OH)

(+)-2.109 (MCG-III-207-P2): Retention time=28 min. $[α]_D^{22}$+27.80 (c. 0.11, CH$_3$OH)

Example 141: Synthesis of Analogues 2.110-2.114

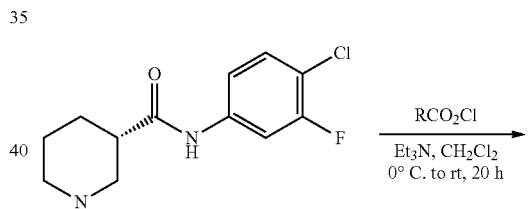

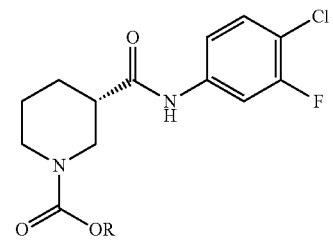

To separate precooled (0° C.) solutions of intermediate 2.41 (20. mg, 0.078 mmol) in dichloromethane (0.5 mL) was added triethylamine (30 µL, 0.2 mmol) and R-chloroformate (0.12 mmol). The resulting mixtures were allowed to warm to room temperature and stirred for 20 h, then diluted with wet DMSO (0.5 mL), filtered through Celite and purified via mass-directed isolation using ultra-performance liquid chromatography (23-61% yield).

Example 142: Synthesis of (S)-MCG-III-188-A01 (2.110)

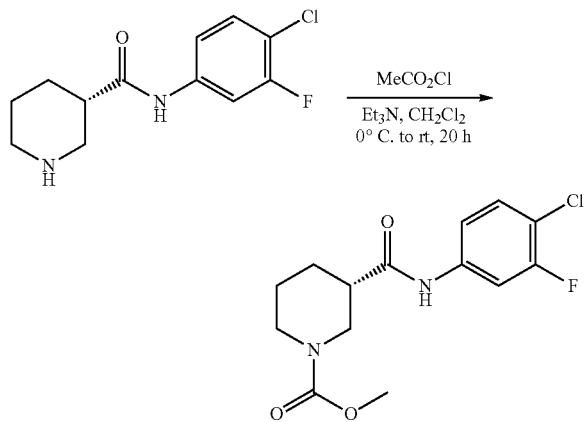

To a precooled (0° C.) solution of intermediate 2.41 (20. mg, 0.078 mmol) in dichloromethane (0.5 mL) was added triethylamine (30 μL, 0.2 mmol) and methylchloroformate (10. μL, 0.12 mmol). The resulting mixture was allowed to warm to room temperature and stirred for 20 h, then diluted with wet DMSO (0.5 mL), filtered through Celite and purified via mass-directed isolation using ultra-performance liquid chromatography (5.7 mg, 23% yield). $[\alpha]_D^{22}$+45.6 (c. 0.045, CH$_3$OH); $^1$H NMR (500 MHz, Acetonitrile-d$_3$) δ 8.61 (s, 1H), 7.71 (dd, J=11.9, 2.4 Hz, 1H), 7.37 (t, J=8.6 Hz, 1H), 7.28-7.20 (m, 1H), 4.11 (d, J=13.2 Hz, 1H), 4.00-3.85 (m, 1H), 3.63 (s, 3H), 3.02 (t, J=12.0 Hz, 1H), 2.86 (s, 1H), 2.49-2.38 (m, 1H), 1.99 (d, J=12.5 Hz, 1H), 1.78-1.62 (m, 2H), 1.53-1.37 (m, 1H); $^{13}$C NMR (126 MHz, MeOD) δ 174.42, 160.08, 158.13, 140.41, 140.33, 131.52, 117.33, 117.30, 116.05, 115.91, 109.32, 109.11, 53.38, 47.34, 45.28, 44.95, 40.40, 28.92, 25.41; IR (ATR) $\nu_{max}$ 3260, 1714, 1695, 1660, 1597, 1532, 1469, 1235, 1207, 1165 cm$^{-1}$; AMM 315.0932 (ESI) m/z [calc for C$_{14}$H$_{17}$ClFN$_2$O$_3$ (M+H)$^+$ 315.0912].

Example 143: Synthesis of (S)-MCG-III-188-A02 (2.111)

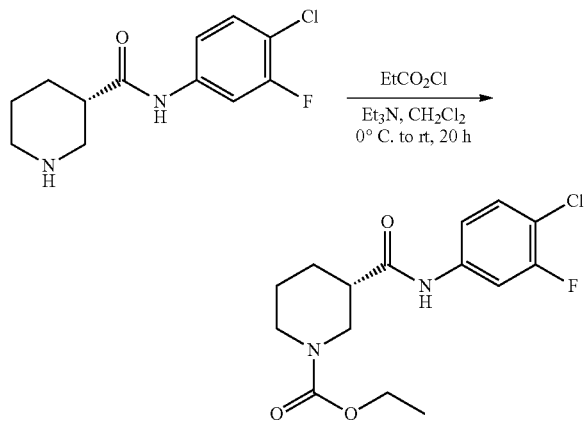

To a precooled (0° C.) solution of intermediate 2.41 (20. mg, 0.078 mmol) in dichloromethane (0.5 mL) was added triethylamine (30 μL, 0.2 mmol) and ethylchloroformate (11 μL, 0.12 mmol). The resulting mixture was allowed to warm to room temperature and stirred for 20 h, then diluted with wet DMSO (0.5 mL), filtered through Celite and purified via mass-directed isolation using ultra-performance liquid chromatography (9.5 mg, 37% yield). $[\alpha]_D^{22}$+36.24 (c. 0.057, CH$_3$OH); $^1$H NMR (500 MHz, Acetonitrile-d$_3$) δ 8.59 (s, 1H), 7.68 (dd, J=11.9, 2.4 Hz, 1H), 7.33 (t, J=8.6 Hz, 1H), 7.24-7.16 (m, 1H), 4.11-3.98 (m, 3H), 3.89 (d, J=13.3 Hz, 1H), 2.99 (t, J=12.0 Hz, 1H), 2.83 (s, 1H), 2.44-2.33 (m, 1H), 1.99-1.92 (m, 1H), 1.74-1.59 (m, 2H), 1.48-1.33 (m, 1H), 1.17 (t, J=7.1 Hz, 3H); $^{13}$C NMR (126 MHz, MeOD) δ 174.44, 160.09, 158.14, 157.20, 140.43, 140.35, 131.53, 117.31, 117.29, 116.03, 115.89, 109.30, 109.10, 62.82, 47.25, 44.94, 40.40, 28.95, 25.41, 14.93; IR (ATR) $\nu_{max}$ 3313, 1669, 1536, 1496, 1437, 1198, 1136, 852 cm$^{-1}$; AMM 329.1082 (ESI) m/z [calc for C$_{15}$H$_{19}$ClFN$_2$O$_3$ (M+H)$^+$ 329.1068].

Example 144: Synthesis of (S)-MCG-III-188-A03 (2.112)

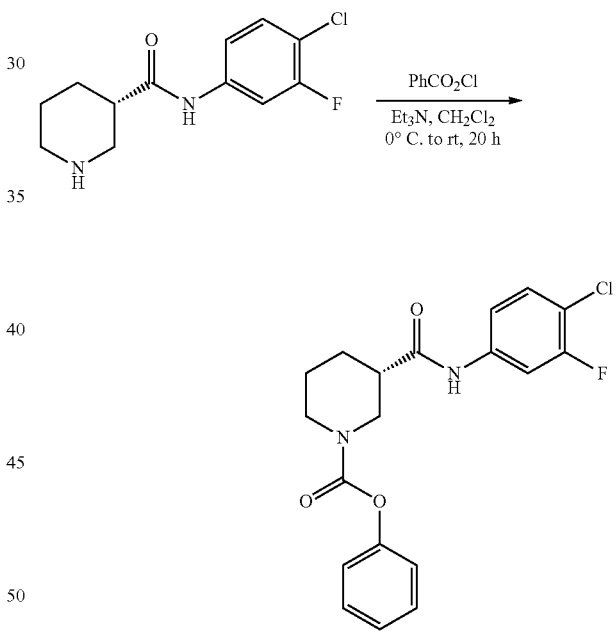

To a precooled (0° C.) solution of intermediate 2.41 (20. mg, 0.078 mmol) in dichloromethane (0.5 mL) was added triethylamine (30 μL, 0.2 mmol) and phenylchloroformate (15 μL, 0.12 mmol). The resulting mixture was allowed to warm to room temperature and stirred for 20 h, then diluted with wet DMSO (0.5 mL), filtered through Celite and purified via mass-directed isolation using ultra-performance liquid chromatography (18 mg, 61% yield). $^1$H NMR (500 MHz, Acetonitrile-d$_3$) δ 8.58 (s, 1H), 7.68 (dd, J=11.9, 2.4 Hz, 1H), 7.38-7.30 (m, 3H), 7.25-7.14 (m, 2H), 7.07 (d, J=7.9 Hz, 2H), 4.29-4.02 (m, 2H), 3.92 (s, 1H), 3.35-3.18 (m, 1H), 3.18-2.90 (m, 2H), 2.61-2.42 (m, 2H), 2.06-1.96 (m, 1H), 1.84-1.66 (m, 2H), 1.55 (s, 1H); AMM 377.1087 (ESI) m/z [calc for C$_{19}$H$_{19}$ClFN$_2$O$_3$ (M+H)$^+$ 377.1068].

Example 145: Synthesis of (S)-MCG-IV-058 (2.113)

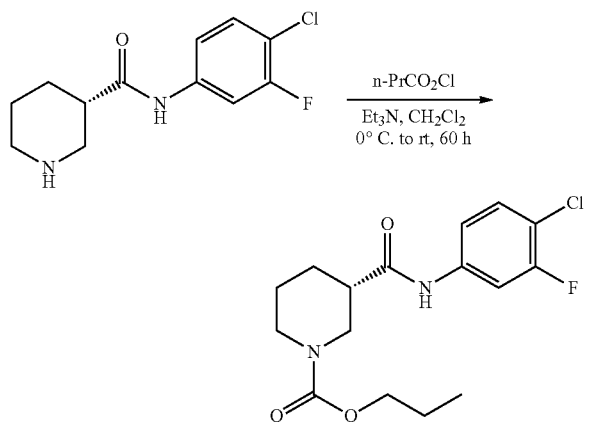

To a precooled (0° C.) solution of intermediate 2.41 (20. mg, 0.078 mmol) in dichloromethane (0.6 mL) was added triethylamine (30 µL, 0.2 mmol) and n-propylchloroformate (10 µL, 0.12 mmol). The resulting mixture was allowed to warm to room temperature and stirred for 60 h, then diluted with wet DMSO (0.5 mL), filtered through Celite and purified via mass-directed isolation using ultra-performance liquid chromatography (10 mg, 36% yield). $^1$H NMR (500 MHz, Acetonitrile-d3) δ 8.63 (s, 1H), 7.68 (dd, J=11.9, 2.5 Hz, 1H), 7.33 (t, J=8.6 Hz, 1H), 7.25-7.17 (m, 1H), 4.07 (d, J=13.3 Hz, 1H), 4.01-3.84 (m, 3H), 3.00 (s, 1H), 2.84 (s, 1H), 2.46-2.34 (m, 3H), 1.77-1.62 (m, 2H), 1.62-1.50 (m, 2H), 1.50-1.33 (m, 1H), 0.88 (t, J=7.4 Hz, 3H); AMM (ESI) m/z 406.1303 [calc for $C_{18}H_{23}ClFN_3O_3$ (M+Na)$^+$ (ACN) 406.1210].

Example 146: Synthesis of (S)-MCG-IV-061 (2.114)

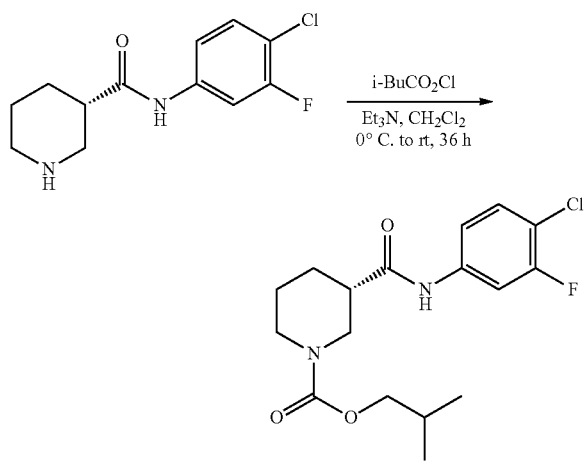

To a precooled (0° C.) solution of intermediate 2.41 (20. mg, 0.078 mmol) in dichloromethane (0.6 mL) was added triethylamine (30 µL, 0.2 mmol) and i-butylchloroformate (20 µL, 0.12 mmol). The resulting mixture was allowed to warm to room temperature and stirred for 60 h, then diluted with wet DMSO (0.5 mL), filtered through Celite and purified via mass-directed isolation using ultra-performance liquid chromatography (13 mg, 46% yield). $^1$H NMR (500 MHz, Acetonitrile-d$_3$) δ 8.57 (s, 1H), 7.68 (dd, J=11.9, 2.5 Hz, 1H), 7.33 (t, J=8.6 Hz, 1H), 7.23-7.16 (m, 1H), 4.12-4.03 (m, 1H), 3.94-3.85 (m, 1H), 3.78 (d, J=6.6 Hz, 2H), 3.01 (s, 1H), 2.86 (s, 1H), 2.45-2.32 (m, 1H), 1.98-1.92 (m, 1H), 1.88-1.80 (m, 1H), 1.77-1.59 (m, 2H), 1.49-1.33 (m, 1H), 0.87 (d, J=6.8 Hz, 6H); AMM 379.1212 (ESI) m/z [calc for $C_{17}H_{22}ClFN_2O_3Na$ (M+Na)$^+$ 379.1201].

Example 147: Synthesis of Intermediate 2.115

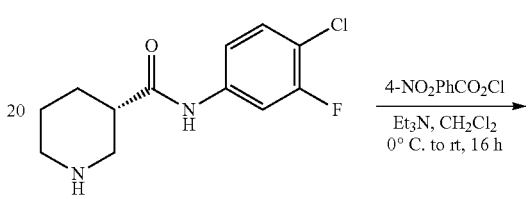

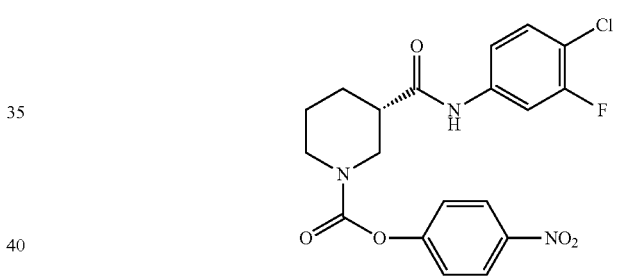

To a precooled (0° C.) solution of intermediate 2.41 (300. mg, 1.17 mmol) and para-nitrophenylchloroformate (236 mg, 1.17 mmol) in CH$_2$Cl$_2$ (6 mL) under N$_2$ atmosphere was added dropwise triethylamine (0.33 mL, 2.3 mmol). The resulting mixture was allowed to warm to room temperature and stirred for 16 h, then quenched with sat. aq. NaHCO$_3$. The layers were separated, and the aqueous phase was extracted with CH$_2$Cl$_2$ (3×). The combined organic layers were washed with brine, dried over Na$_2$SO$_4$, and concentrated in vacuo. Flash chromatography (SiO$_2$, 50:50 hexanes:EtOAc) to afford the product as a white solid (125 mg, 48% yield). $[α]_D^{23}$+72.7 (c. 0.63, CH$_3$OH); $^1$H NMR (500 MHz, DMSO-d$_6$) δ 10.35 (t, J=4.7 Hz, 1H), 8.34-8.20 (m, 2H), 7.77 (t, J=9.5 Hz, 1H), 7.55-7.46 (m, 1H), 7.46-7.37 (m, 2H), 7.33 (d, J=8.9 Hz, 1H), 4.26-4.00 (m, 2H), 3.25-3.01 (m, 2H), 2.73-2.56 (m, 1H), 2.12-1.94 (m, 1H), 1.91-1.79 (m, 1H), 1.79-1.63 (m, 1H), 1.63-1.43 (m, 1H); $^{13}$C NMR (126 MHz, DMSO) δ 172.16, 171.99, 157.91, 156.31, 155.98, 151.79, 144.45, 139.58, 139.50, 130.52, 126.22, 125.09, 122.77, 122.68, 116.17, 115.84, 113.02, 112.89, 107.51, 107.31, 46.45, 46.10, 44.67, 44.15, 42.76, 42.58, 27.16, 24.15, 23.46; IR (ATR) $ν_{max}$ 3075, 1715, 1656, 1606, 1519, 1423, 1344, 1212, 857, 748 cm$^{-1}$; AMM (ESI) m/z 422.0936 [calc for $C_{19}H_{18}ClFN_3O_5$ (M+H)$^+$ 422.0919].

Example 148: Synthesis of Analogues 2.116-2.120

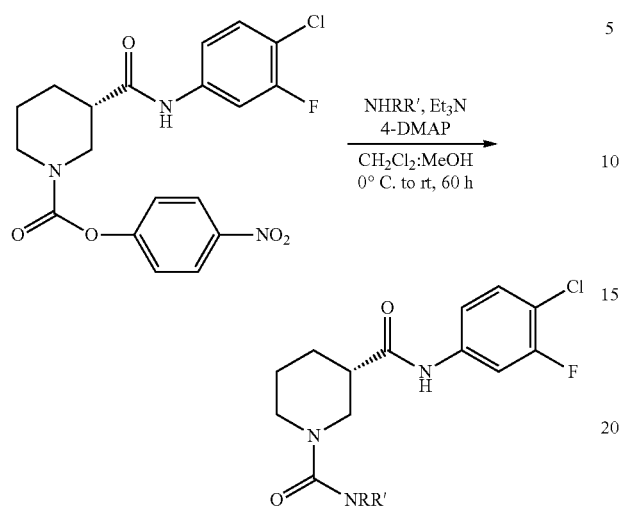

To separated precooled (0° C.) vials charged with NHRR' (0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (13-98%).

Example 149: Synthesis of (S)-MCG-IV-031-A02 (2.116)

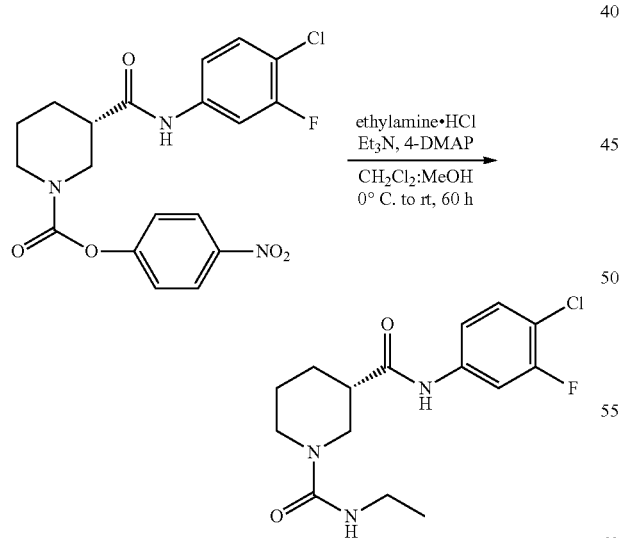

To a precooled (0° C.) vial charged with ethylamine HCl (13 mg, 0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (3.6 mg, 13%). $^1$H NMR (500 MHz, Acetonitrile-$d_3$) δ 8.90 (s, 1H), 7.71 (dd, J=11.9, 2.4 Hz, 1H), 7.33 (t, J=8.6 Hz, 1H), 7.22 (dd, J=9.3, 2.2 Hz, 1H), 4.02 (q, J=7.1 Hz, 1H), 3.82 (d, J=14.5 Hz, 1H), 3.64 (d, J=13.9 Hz, 1H), 3.17-3.07 (m, 5H), 2.90-2.82 (m, 2H), 2.44-2.33 (m, 1H), 1.80-1.67 (m, 1H), 1.64-1.53 (m, 1H), 1.47-1.34 (m, 1H), 1.31-1.19 (m, 2H), 1.16 (t, J=7.1 Hz, 1H), 1.02 (t, J=7.2 Hz, 2H), 0.89-0.79 (m, 2H); AMM (ESI) m/z 328.1248 [calc for $C_{15}H_{20}ClFN_3O_2$ (M+H)$^+$ 328.1228].

Example 150: Synthesis of (S)-MCG-IV-031-A03 (2.117)

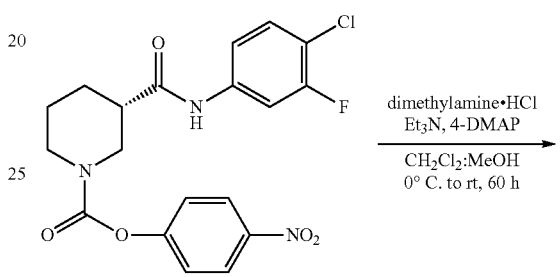

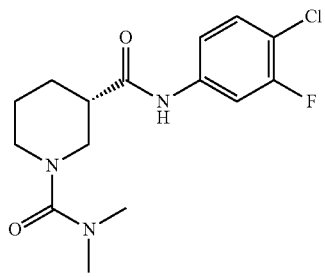

To a precooled (0° C.) vial charged with dimethylamine·HCl (16 mg, 0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (10 mg, 32%). $^1$H NMR (500 MHz, Acetonitrile-$d_3$) δ 9.19 (s, 1H), 7.75 (d, J=12.1 Hz, 1H), 7.42-7.32 (m, 1H), 7.28 (d, J=9.1 Hz, 1H), 3.60 (d, J=13.6 Hz, 1H), 3.47 (d, J=13.1 Hz, 1H), 3.17 (t, J=11.4 Hz, 1H), 2.94 (t, J=11.9 Hz, 1H), 2.79 (d, J=3.4 Hz, 6H), 2.57-2.48 (m, 1H), 1.87-1.73 (m, 1H), 1.69-1.58 (m, 1H), 1.58-1.45 (m, 1H), 1.36-1.16 (m, 1H); AMM (ESI) m/z 328.1239 [calc for $C_{15}H_{20}ClFN_3O_2$ (M+H)$^+$ 328.1228].

Example 151: Synthesis of (S)-MCG-IV-031-A04 (2.118)

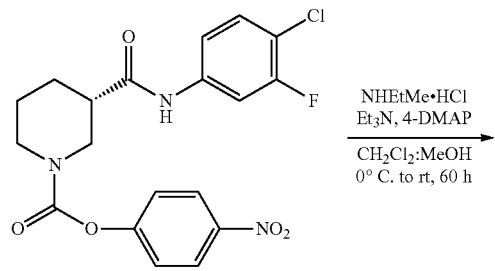

NHEtMe·HCl
Et₃N, 4-DMAP
―――――――――→
CH₂Cl₂:MeOH
0° C. to rt, 60 h

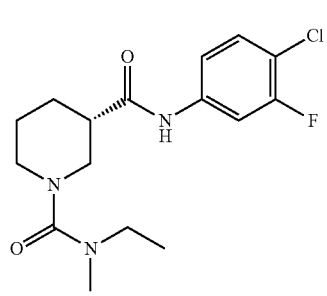

To a precooled (0° C.) vial charged with N-ethylmethylamine (10 µL, 0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (10 mg, 62%). $^1$H NMR (500 MHz, Acetonitrile-d₃) δ 9.13 (s, 1H), 7.70 (dd, J=11.9, 2.4 Hz, 1H), 7.33 (t, J=8.5 Hz, 1H), 7.27-7.20 (m, 1H), 3.54 (dd, J=13.6, 3.8 Hz, 1H), 3.48-3.34 (m, 1H), 3.15 (q, J=7.0 Hz, 2H), 2.99-2.87 (m, 1H), 2.75 (s, 3H), 2.56-2.46 (m, 1H), 1.82-1.72 (m, 1H), 1.72-1.55 (m, 2H), 1.55-1.43 (m, 1H), 1.07 (t, J=7.1 Hz, 3H); AMM (ESI) m/z 342.1380 [calc for C₁₆H₂₂ClFN₃O₂ (M+H)⁺ 342.1385].

Example 152: Synthesis of (S)-MCG-IV-031-A05 (2.119)

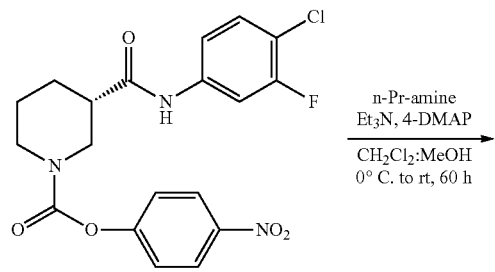

n-Pr-amine
Et₃N, 4-DMAP
―――――――――→
CH₂Cl₂:MeOH
0° C. to rt, 60 h

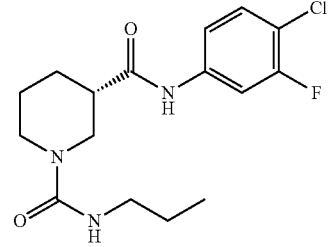

To a precooled (0° C.) vial charged with n-propylamine (10 µL, 0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (16 mg, 98%). [α]$_D^{23}$+18.5 (c. 0.033, CH₃OH); $^1$H NMR (500 MHz, Acetonitrile-d₃) δ 8.95 (s, 1H), 7.74 (dd, J=11.9, 2.4 Hz, 1H), 7.37 (t, J=8.5 Hz, 1H), 7.31-7.21 (m, 1H), 3.93-3.84 (m, 1H), 3.70 (d, J=13.4 Hz, 1H), 3.25-3.12 (m, 1H), 3.09 (t, J=7.1 Hz, 2H), 2.92 (ddd, J=13.7, 10.7, 3.2 Hz, 1H), 2.51-2.38 (m, 1H), 1.85-1.71 (m, 1H), 1.71-1.57 (m, 1H), 1.56-1.39 (m, 3H), 0.94-0.79 (m, 3H); $^{13}$C NMR (126 MHz, MeOD) δ 174.69, 160.08, 160.00, 158.13, 140.46, 140.38, 131.52, 117.27, 117.24, 115.99, 115.85, 109.25, 109.05, 47.43, 45.49, 45.06, 43.62, 40.40, 29.15, 25.45, 24.44, 11.64; IR (ATR) ν$_{max}$ 3209, 1680, 1426, 1189, 1136, 801, 723 cm⁻¹; AMM (ESI) m/z 342.1392 [calc for C₁₆H₂₂ClFN₃O₂ (M+H)⁺ 342.1385].

Example 153: Synthesis of (S)-MCG-IV-031-A06 (2.120)

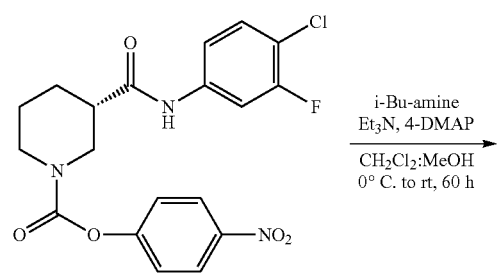

i-Bu-amine
Et₃N, 4-DMAP
―――――――――→
CH₂Cl₂:MeOH
0° C. to rt, 60 h

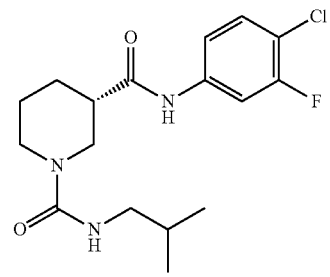

To a precooled (0° C.) vial charged with i-butylamine (10 µL, 0.17 mmol) was added a solution of intermediate 2.115 (36 mg, 0.085 mmol), triethylamine (20 µL, 0.2 mmol), and 4-dimethylaminopyridine (2 mg, 0.002 mmol) in dichloromethane (0.5 mL) and methanol (0.3 mL). The resulting mixtures were allowed to warm to room temperature and stirred for 60 h, then diluted with wet DMSO (0.5 mL), filtered through Celite, and purified via mass-directed isolation using ultra-performance liquid chromatography (11 mg, 67%). $^1$H NMR (500 MHz, Acetonitrile-$d_3$) δ 8.97 (d, J=18.4 Hz, 1H), 7.74 (dd, J=12.0, 2.8 Hz, 1H), 7.37 (t, J=8.7 Hz, 1H), 7.26 (d, J=9.2 Hz, 1H), 3.94-3.84 (m, 1H), 3.70 (d, J=13.7 Hz, 1H), 3.18 (dd, J=13.5, 9.7 Hz, 1H), 3.04-2.86 (m, 3H), 2.45 (dt, J=13.7, 6.2 Hz, 1H), 1.86-1.56 (m, 3H), 1.46 (t, J=12.4 Hz, 1H), 1.36-1.08 (m, 1H), 0.85 (d, J=6.6 Hz, 6H); AMM (ESI) m/z 356.1551 [calc for $C_{17}H_{24}ClFN_3O_2$ (M+H)$^+$ 356.1541].

Example 154: Synthesis of Crude Intermediates S1-S3

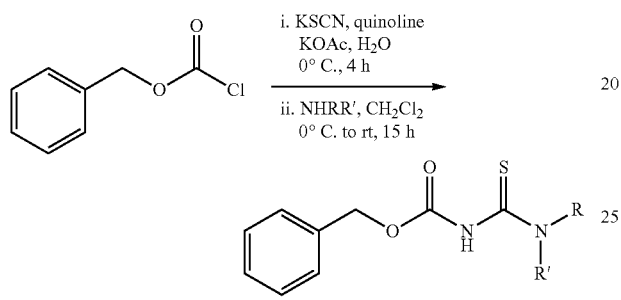

To a solution of potassium thiocyanate (6.38 g, 31.7 mmol) in water (3 mL) was added potassium acetate (53 mg, 0.054 mmol) and quinoline (46 μL, 0.039 mmol). The resulting mixture was cooled to 0° C. before dropwise addition of benzyl chloroformate (1.6 mL, 12 mmol). The resulting mixture was stirred at 0° C. for 4 h, then diluted with CH$_2$Cl$_2$ and water. The layers were separated, then the aqueous phase was extracted with CH$_2$Cl$_2$ (3×). The combined organic layers were dried over Na$_2$SO$_4$ and concentrated in vacuo. Flash chromatography (SiO$_2$, 85:15 hexanes:CH$_2$Cl$_2$) afforded the product as a clear, colorless oil (1.85 g, 82% yield).

To precooled (0° C.) vials charged with NHRR' (0.52 mmol) was added a solution of intermediate (50. mg, 0.26 mmol) in CH$_2$Cl$_2$ (0.5 mL). The resulting mixtures were allowed to warm to room temperature and stirred for 15 h, then concentrated in vacuo. The crude residues were taken up in CH$_2$Cl$_2$ and the organic phase was washed with water, dried over Na$_2$SO$_4$, and concentrated in vacuo to afford the products, which were carried forward without additional purification.

Example 155: Synthesis of S1

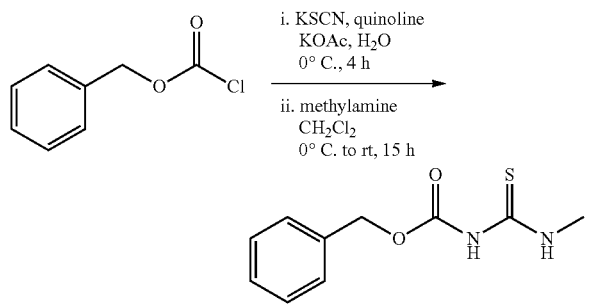

To a solution of potassium thiocyanate (6.38 g, 31.7 mmol) in water (3 mL) was added potassium acetate (53 mg, 0.054 mmol) and quinoline (46 μL, 0.039 mmol). The resulting mixture was cooled to 0° C. before dropwise addition of benzyl chloroformate (1.6 mL, 12 mmol). The resulting mixture was stirred at 0° C. for 4 h, then diluted with CH$_2$Cl$_2$ and water. The layers were separated, then the aqueous phase was extracted with CH$_2$Cl$_2$ (3×). The combined organic layers were dried over Na$_2$SO$_4$ and concentrated in vacuo. Flash chromatography (SiO$_2$, 85:15 hexanes:CH$_2$Cl$_2$) afforded the product as a clear, colorless oil (1.85 g, 82% yield).

To a precooled (0° C.) vial charged with methylamine (0.26 mL, 0.52 mmol) was added a solution of intermediate (50. mg, 0.26 mmol) in CH$_2$Cl$_2$ (0.5 mL). The resulting mixture was allowed to warm to room temperature and stirred for 15 h, then concentrated in vacuo. The crude residue was taken up in CH$_2$Cl$_2$ and the organic phase was washed with water, dried over Na$_2$SO$_4$, and concentrated in vacuo to afford the product, which was carried forward without additional purification.

Example 156: Synthesis of S2

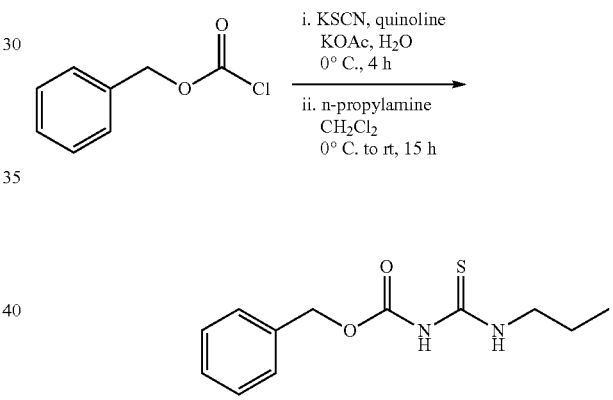

To a solution of potassium thiocyanate (6.38 g, 31.7 mmol) in water (3 mL) was added potassium acetate (53 mg, 0.054 mmol) and quinoline (46 μL, 0.039 mmol). The resulting mixture was cooled to 0° C. before dropwise addition of benzyl chloroformate (1.6 mL, 12 mmol). The resulting mixture was stirred at 0° C. for 4 h, then diluted with CH$_2$Cl$_2$ and water. The layers were separated, then the aqueous phase was extracted with CH$_2$Cl$_2$ (3×). The combined organic layers were dried over Na$_2$SO$_4$ and concentrated in vacuo. Flash chromatography (SiO$_2$, 85:15 hexanes:CH$_2$Cl$_2$) afforded the product as a clear, colorless oil (1.85 g, 82% yield).

To a precooled (0° C.) vial charged with n-propylamine (31 mg, 0.52 mmol) was added a solution of intermediate (50. mg, 0.26 mmol) in CH$_2$Cl$_2$ (0.5 mL). The resulting mixture was allowed to warm to room temperature and stirred for 15 h, then concentrated in vacuo. The crude residue was taken up in CH$_2$Cl$_2$ and the organic phase was washed with water, dried over Na$_2$SO$_4$, and concentrated in vacuo to afford the product, which was carried forward without additional purification.

Example 157: Synthesis of S3

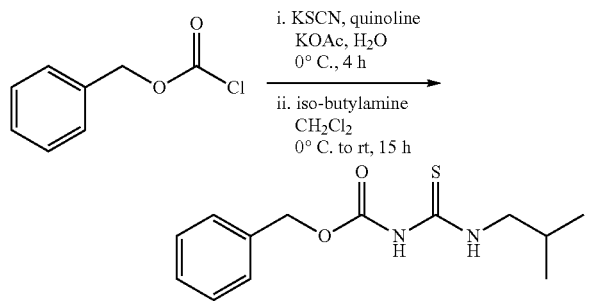

To a solution of potassium thiocyanate (6.38 g, 31.7 mmol) in water (3 mL) was added potassium acetate (53 mg, 0.054 mmol) and quinoline (46 µL, 0.039 mmol). The resulting mixture was cooled to 0° C. before dropwise addition of benzyl chloroformate (1.6 mL, 12 mmol). The resulting mixture was stirred at 0° C. for 4 h, then diluted with $CH_2Cl_2$ and water. The layers were separated, then the aqueous phase was extracted with $CH_2Cl_2$ (3×). The combined organic layers were dried over $Na_2SO_4$ and concentrated in vacuo. Flash chromatography ($SiO_2$, 85:15 hexanes:$CH_2Cl_2$) afforded the product as a clear, colorless oil (1.85 g, 82% yield).

To a precooled (0° C.) vial charged with iso-butylamine (31 mg, 0.52 mmol) was added a solution of intermediate (50. mg, 0.26 mmol) in $CH_2Cl_2$ (0.5 mL). The resulting mixture was allowed to warm to room temperature and stirred for 15 h, then concentrated in vacuo. The crude residue was taken up in $CH_2Cl_2$ and the organic phase was washed with water, dried over $Na_2SO_4$, and concentrated in vacuo to afford the product, which was carried forward without additional purification.

Example 158: Synthesis of 2.121-2.123

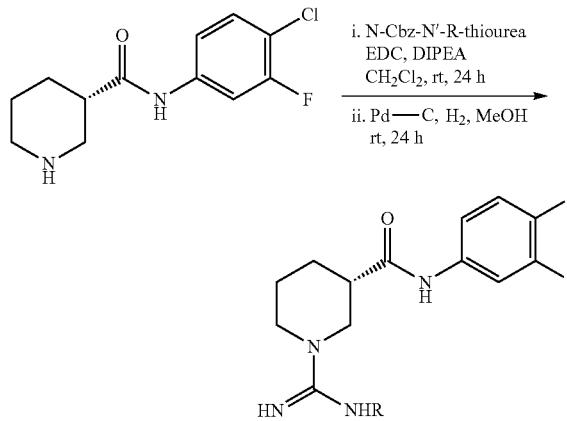

To separate vials charged with N-Cbz-N'—R-thiourea (S1-S3, 0.12 mmol) was added a solution of intermediate 2.41 (30. mg, 0.12 mmol), 1-ethyl-3-(3-dimethylaminopropyl)-carbodiimide hydrochloride (EDCI, 34 mg, 0.18 mmol) and diisopropylethylamine (40 µL, 0.3 mmol) in $CH_2Cl_2$ (0.5 mL). The resulting mixtures were stirred at room temperature for 24 h, then diluted with wet DMSO (0.5 mL), filtered through Celite, and purified via mass-directed isolation via ultra-performance liquid chromatography (24-70% yield).

Example 159: Synthesis of (S)-MCG-IV-053-A01 (2.121)

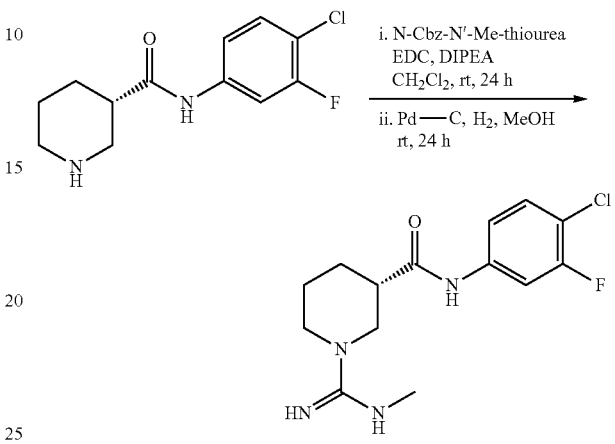

To a vial charged with N-Cbz-N'-methyl-thiourea (S1, 26 mg, 0.12 mmol) was added a solution of intermediate 2.41 (30. mg, 0.12 mmol), 1-ethyl-3-(3-dimethylaminopropyl)-carbodiimide hydrochloride (EDCI, 34 mg, 0.18 mmol) and diisopropylethylamine (40 µL, 0.3 mmol) in $CH_2Cl_2$ (0.5 mL). The resulting mixture was stirred at room temperature for 24 h, then diluted with wet DMSO (0.5 mL), filtered through Celite, and purified via mass-directed isolation via ultra-performance liquid chromatography to afford the product as a white solid (37 mg, 70% yield). $^1$H NMR (500 MHz, Acetonitrile-$d_3$) δ 10.02 (s, 1H), 7.84-7.74 (m, 1H), 7.43-7.32 (m, 1H), 7.06 (s, 1H), 6.55 (s, 1H), 3.92 (d, J=14.0 Hz, 1H), 3.60 (d, J=13.5 Hz, 1H), 3.26 (dd, J=13.9, 10.0 Hz, 1H), 3.11 (ddd, J=13.8, 11.0, 3.4 Hz, 1H), 2.83 (d, J=4.7 Hz, 3H), 2.81-2.71 (m, 1H), 2.04-1.97 (m, 1H), 1.91-1.80 (m, 1H), 1.80-1.71 (m, 1H), 1.63-1.48 (m, 1H); AMM 313.1245 (ESI) m/z [calc for $C_{14}H_{19}ClFN_4O$ (M+H)$^+$ 313.1231].

Example 160: Synthesis of (S)-MCG-IV-053-A05 (2.122)

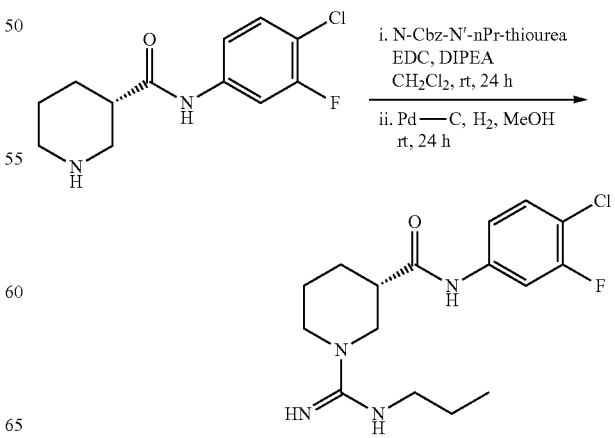

To a vial charged with N-Cbz-N'-n-propyl-thiourea (S2, 30 mg, 0.12 mmol) was added a solution of intermediate 2.41 (30. mg, 0.12 mmol), 1-ethyl-3-(3-dimethylaminopropyl)-carbodiimide hydrochloride (EDCI, 34 mg, 0.18 mmol) and diisopropylethylamine (40 μL, 0.3 mmol) in CH$_2$Cl$_2$ (0.5 mL). The resulting mixture was stirred at room temperature for 24 h, then diluted with wet DMSO (0.5 mL), filtered through Celite, and purified via mass-directed isolation via ultra-performance liquid chromatography to afford the product as a white solid (13 mg, 24% yield). $^1$H NMR (500 MHz, Acetonitrile-d$_3$) δ 9.92 (s, 1H), 7.79 (d, J=11.2 Hz, 1H), 7.37 (d, J=5.9 Hz, 1H), 6.90 (s, 1H), 6.55 (s, 2H), 3.88 (d, J=13.9 Hz, 1H), 3.57 (d, J=12.6 Hz, 1H), 3.32 (dd, J=13.8, 9.5 Hz, 1H), 3.21-3.09 (m, 1H), 2.83-2.71 (m, 1H), 1.90-1.80 (m, 2H), 1.80-1.68 (m, 2H), 1.66-1.48 (m, 3H), 0.99-0.87 (m, 3H); AMM 341.1557 (ESI) m/z [calc for C$_{16}$H$_{23}$ClFN$_4$O (M+H)$^+$ 341.1544].

Example 161: Synthesis of (S)-MCG-IV-053-A06 (2.123)

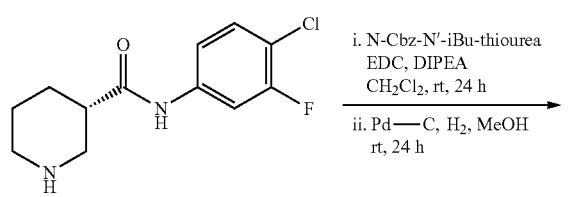

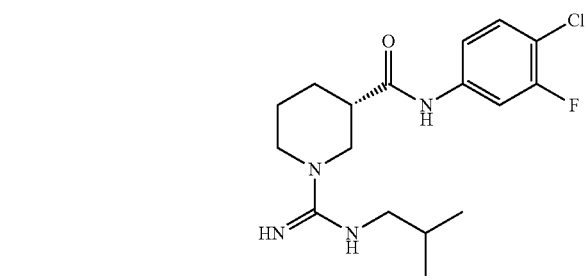

To a vial charged with N-Cbz-N'-i-butyl-thiourea (S3, 31 mg, 0.12 mmol) was added a solution of intermediate 2.41 (30. mg, 0.12 mmol), 1-ethyl-3-(3-dimethylaminopropyl)-carbodiimide hydrochloride (EDCI, 34 mg, 0.18 mmol) and diisopropylethylamine (40 μL, 0.3 mmol) in CH$_2$Cl$_2$ (0.5 mL). The resulting mixture was stirred at room temperature for 24 h, then diluted with wet DMSO (0.5 mL), filtered through Celite, and purified via mass-directed isolation via ultra-performance liquid chromatography to afford the product as a white solid (18 mg, 32% yield). $^1$H NMR (500 MHz, Acetonitrile-d$_3$) δ 9.95 (s, 1H), 7.84-7.72 (m, 1H), 7.42-7.33 (m, 1H), 6.96 (s, 1H), 6.60 (s, 1H), 3.87 (dd, J=13.7, 3.8 Hz, 1H), 3.64-3.52 (m, 1H), 3.35 (dd, J=13.9, 9.3 Hz, 1H), 3.17 (ddd, J=13.5, 10.4, 3.4 Hz, 1H), 3.01 (dd, J=7.2, 5.7 Hz, 2H), 2.79 (tt, J=9.1, 4.1 Hz, 2H), 2.05-1.97 (m, 1H), 1.92-1.83 (m, 2H), 1.80-1.70 (m, 1H), 1.62-1.51 (m, 1H), 0.93 (d, J=6.7 Hz, 6H); AMM 355.1712 (ESI) m/z [calc for C$_{17}$H$_{25}$ClFN$_4$O (M+H)$^+$ 355.1701].

Example 162: Synthesis of Intermediate 2.124

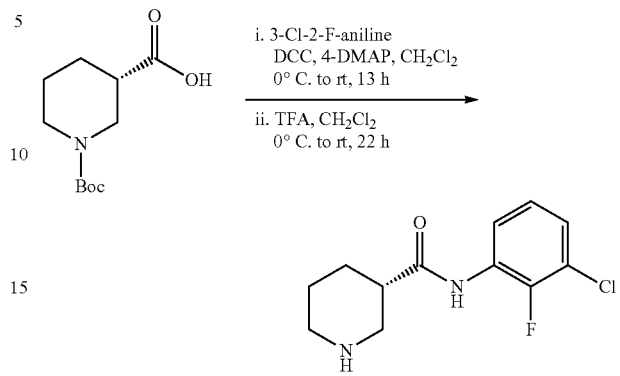

To a precooled (0° C.) solution of intermediate 2.38 (150. mg, 0.654 mmol), N,N'-dicyclohexylcarbodiimide (202 mg, 0.981 mmol) and 4-dimethylaminopyridine (24 mg, 0.20 mmol) in CH$_2$Cl$_2$ (5 mL) under N$_2$ atmosphere was added 3-chloro-2-fluoroaniline (0.1 mL). The resulting mixture was allowed to warm to room temperature and stirred for 13 h, then concentrated in vacuo. The crude residue was diluted with ether and filtered. The filtrate was washed sequentially with sat. aq. NH$_4$Cl, sat. aq. NaHCO$_3$, and brine, dried over Na$_2$SO$_4$, and concentrated in vacuo to afford the product.

To a precooled (0° C.) solution of intermediate (136 mg, 0.381 mmol) in CH$_2$Cl$_2$ (1.9 mL) under N$_2$ atmosphere was added dropwise trifluoroacetic acid (0.15 mL, 1.9 mmol). The resulting mixture was allowed to warm to room temperature and stirred for 22 h, then concentrated in vacuo. The crude residue was taken up in CH$_2$Cl$_2$ and diluted with H$_2$O. The layers were separated, and the organic phase was extracted with H$_2$O (3×). The combined aqueous layers were cooled to 0° C. and neutralized with powdered NaHCO$_3$. The aqueous phase was extracted with CH$_2$Cl$_2$ (3×), dried over Na$_2$SO$_4$, and concentrated in vacuo to afford the desired product as a clear colorless oil (83 mg, 85% yield). [α]$_D^{23}$ −0.72 (c. 0.12, CH$_3$OH); $^1$H NMR (500 MHz, Chloroform-d) δ 9.68 (s, 1H), 8.80 (s, 1H), 8.20 (s, 1H), 8.00 (t, J=7.6 Hz, 1H), 7.15 (t, J=7.4 Hz, 1H), 7.05 (t, J=8.3 Hz, 1H), 3.52 (d, J=12.2 Hz, 1H), 3.34 (s, 1H), 3.27 (s, 1H), 3.08 (s, 2H), 2.14 (s, 1H), 1.97 (d, J=40.1 Hz, 3H); $^{13}$C NMR (126 MHz, CDCl$_3$) δ 174.31, 149.59, 147.64, 128.28, 128.20, 124.50, 124.46, 124.16, 120.41, 120.28, 120.11, 77.00, 47.79, 46.46, 41.87, 27.47, 22.34; IR (ATR) ν$_{max}$ 3025, 2924, 2850, 2809, 1668, 1606, 1542, 1457, 1102, 782, 653, 485 cm$^{-1}$; AMM 257.0869 (ESI) m/z [calc for C$_{12}$H$_{15}$ClFN$_2$O (M+H)$^+$ 257.0857].

Example 163: Synthesis of 2.125-2.126

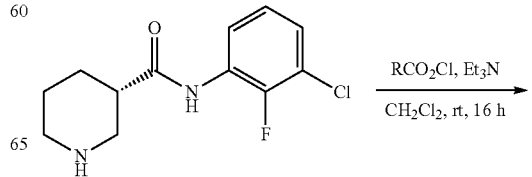

-continued

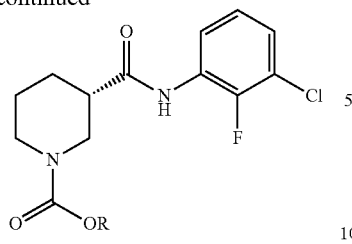

To separate precooled (0° C.) solutions of intermediate 2.124 (16 mg, 0.062 mmol) in $CH_2Cl_2$ (0.4 mL) was added triethylamine (30 μL, 0.2 mmol) then alkylchloroformate (0.093 mmol). The resulting reaction mixtures were allowed to warm to room temperature and stirred for 16 h, then diluted with wet DMSO (0.5 mL), filtered through Celite, and purified via mass-directed isolation using ultra-performance liquid chromatography (32-51% yield).

Example 164: Synthesis of (S)-MCG-IV-026-A03 (2.125)

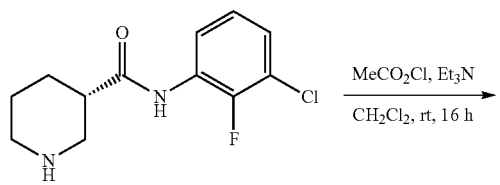

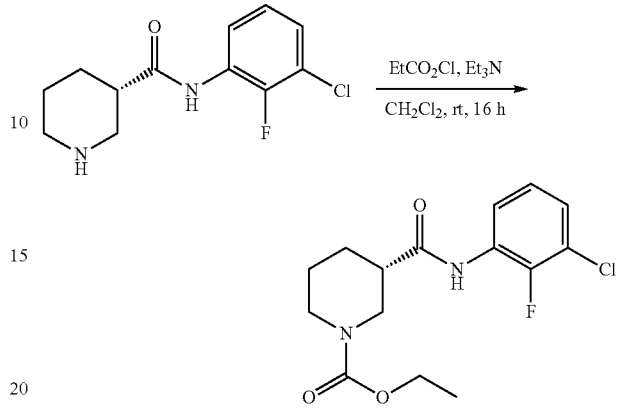

To a precooled (0° C.) solution of intermediate 2.124 (16 mg, 0.062 mmol) in $CH_2Cl_2$ (0.4 mL) was added triethylamine (30 μL, 0.2 mmol) then methylchloroformate (7.2 μL, 0.093 mmol). The resulting reaction mixture was allowed to warm to room temperature and stirred for 16 h, then diluted with wet DMSO (0.5 mL), filtered through Celite, and purified via mass-directed isolation using ultra-performance liquid chromatography to afford the product as a white solid (8.1 mg, 51% yield). $^1$H NMR (500 MHz, Acetonitrile-$d_3$) δ 8.19 (s, 1H), 7.86 (d, J=8.2 Hz, 1H), 7.36-7.26 (m, 1H), 7.09-7.00 (m, 1H), 4.23-4.02 (m, 1H), 3.91 (d, J=13.2 Hz, 1H), 3.64 (s, 3H), 3.18-2.99 (m, 1H), 2.90 (t, J=12.3 Hz, 1H), 2.68-2.54 (m, 1H), 2.10-1.99 (m, 1H), 1.81-1.64 (m, 2H), 1.56-1.41 (m, 1H); AMM (ESI) m/z 329.1092 [calc for $C_{15}H_{19}ClFN_2O_3$ (M+H)$^+$ 329.1068].

Example 165: Synthesis of (S)-MCG-IV-026-A04 (2.126)

To a precooled (0° C.) solution of intermediate 2.124 (16 mg, 0.062 mmol) in $CH_2Cl_2$ (0.4 mL) was added triethylamine (30 μL, 0.2 mmol) then ethylchloroformate (8.2 μL, 0.093 mmol). The resulting reaction mixture was allowed to warm to room temperature and stirred for 16 h, then diluted with wet DMSO (0.5 mL), filtered through Celite, and purified via mass-directed isolation using ultra-performance liquid chromatography to afford the product as a white solid (8.6 mg, 32% yield). $^1$H NMR (500 MHz, Acetonitrile-$d_3$) δ 8.33 (s, 1H), 7.99 (t, J=7.6 Hz, 1H), 7.21 (td, J=7.4, 6.8, 1.6 Hz, 1H), 7.12 (td, J=8.2, 1.5 Hz, 1H), 4.19-4.02 (m, 3H), 3.94 (dt, J=13.3, 3.7 Hz, 1H), 3.04 (s, 1H), 2.94-2.78 (m, 1H), 2.63-2.49 (m, 1H), 2.08-1.98 (m, 1H), 1.81-1.62 (m, 2H), 1.55-1.39 (m, 1H), 1.21 (t, J=7.1 Hz, 3H); AMM (ESI) m/z 329.1092 [calc for $C_{15}H_{19}ClFN_2O_3$ (M+H)$^+$ 329.1068].

Example 166: Synthesis of Intermediate 2.127

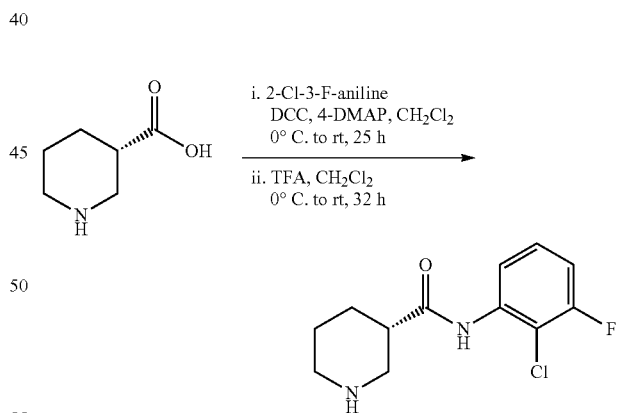

To a precooled (0° C.) solution of intermediate 2.38 (200. mg, 0.872 mmol), N,N'-dicyclohexylcarbodiimide (270 mg, 1.31 mmol) and 4-dimethylaminopyridine (32 mg, 0.26 mmol) in $CH_2Cl_2$ (7 mL) under $N_2$ atmosphere was added 2-chloro-3-fluoroaniline (0.1 mL). The resulting mixture was allowed to warm to room temperature and stirred for 25 h, then concentrated in vacuo. The crude residue was diluted with ether and filtered. The filtrate was washed sequentially with sat. aq. $NH_4Cl$, sat. aq. $NaHCO_3$, and brine, dried over $Na_2SO_4$, and concentrated in vacuo to afford the product which was carried forward.

To a precooled (0° C.) solution of intermediate (97 mg, 0.27 mmol) in CH₂Cl₂ (1.4 mL) under N₂ atmosphere was added dropwise trifluoroacetic acid (0.1 mL, 1 mmol). The resulting mixture was allowed to warm to room temperature and stirred for 32 h, then concentrated in vacuo. The crude residue was taken up in CH₂Cl₂ and diluted with H₂O. The layers were separated, and the organic phase was extracted with H₂O (3×). The combined aqueous layers were cooled to 0° C. and neutralized with powdered NaHCO₃. The aqueous phase was extracted with CH₂Cl₂ (3×), dried over Na₂SO₄, and concentrated in vacuo to afford the desired product as a clear colorless oil (33 mg, 47% yield, 2 steps). $[\alpha]_D^{23}$ +0.95 (c. 0.078, CH₃OH); ¹H NMR (500 MHz, Chloroform-d) δ 11.21 (s, 1H), 8.21 (d, J=8.4 Hz, 1H), 7.21 (td, J=8.3, 6.1 Hz, 1H), 6.87 (td, J=8.6, 1.4 Hz, 1H), 3.35-3.23 (m, 1H), 3.11 (dt, J=11.4, 3.9 Hz, 1H), 2.93 (dd, J=11.9, 3.1 Hz, 1H), 2.75 (td, J=11.1, 3.0 Hz, 1H), 2.61 (dq, J=6.6, 3.5 Hz, 1H), 2.17 (s, 1H), 2.05 (dd, J=13.5, 3.9 Hz, 1H), 1.93-1.70 (m, 2H), 1.57 (dp, J=10.6, 3.5 Hz, 1H); ¹³C NMR (126 MHz, CDCl₃) δ 174.52, 159.36, 157.40, 137.59, 127.81, 127.74, 117.40, 117.37, 110.99, 110.82, 47.89, 46.63, 42.30, 29.82, 27.71, 22.58; IR (ATR) $v_{max}$ 2937, 2859, 1668, 1590, 1538, 1470, 1434, 1251, 1199, 777, 642 cm⁻¹; AMM (ESI) m/z 257.0869 [calc for C₁₂H₁₅ClFN₂O (M+H)⁺ 257.0857].

Example 167: Synthesis of 2.128-2.129

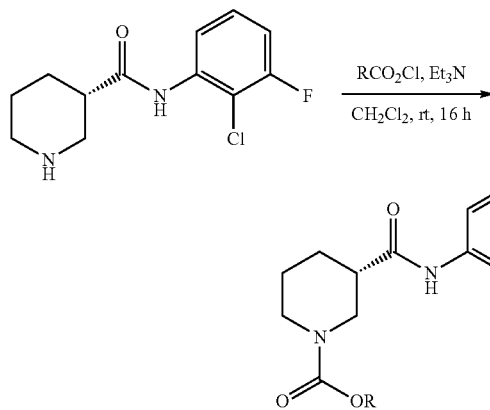

To separate precooled (0° C.) solutions of intermediate 2.127 (13 mg, 0.051 mmol) in CH₂Cl₂ (0.4 mL) was added triethylamine (20 µL, 0.1 mmol) then alkylchloroformate (0.076 mmol). The resulting reaction mixtures were allowed to warm to room temperature and stirred for 16 h, then diluted with wet DMSO (0.5 mL), filtered through Celite, and purified via mass-directed isolation using ultra-performance liquid chromatography (34-81% yield).

Example 168: Synthesis of (S)-MCG-IV-026-A01 (2.128)

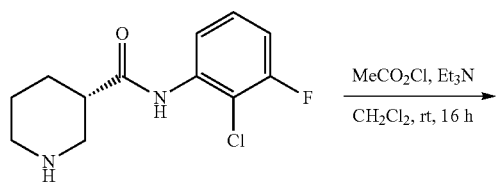

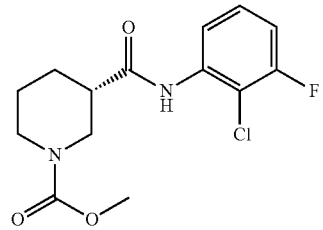

To a precooled (0° C.) solution of intermediate 2.127 (13 mg, 0.051 mmol) in CH₂Cl₂ (0.4 mL) was added triethylamine (20 µL, 0.1 mmol) then methylchloroformate (5.9 µL, 0.076 mmol). The resulting reaction mixture was allowed to warm to room temperature and stirred for 16 h, then diluted with wet DMSO (0.5 mL), filtered through Celite, and purified via mass-directed isolation using ultra-performance liquid chromatography to afford the product as a white solid (13 mg, 81% yield). ¹H NMR (500 MHz, Acetonitrile-d₃) δ 8.19 (s, 1H), 7.86 (d, J=8.3 Hz, 1H), 7.35-7.25 (m, 1H), 7.04 (t, J=8.7 Hz, 1H), 4.11 (s, 1H), 3.91 (d, J=13.3 Hz, 1H), 3.64 (d, J=2.2 Hz, 3H), 3.18-2.99 (m, 1H), 2.90 (t, J=12.6 Hz, 1H), 2.67-2.54 (m, 1H), 2.04 (d, J=12.8 Hz, 1H), 1.80-1.65 (m, 2H), 1.56-1.39 (m, 1H); AMM (ESI) m/z 329.1071 [calc for C₁₅H₁₉ClFN₂O₃ (M+H)⁺ 329.1068].

Example 169: Synthesis of (S)-MCG-IV-026-A02 (2.129)

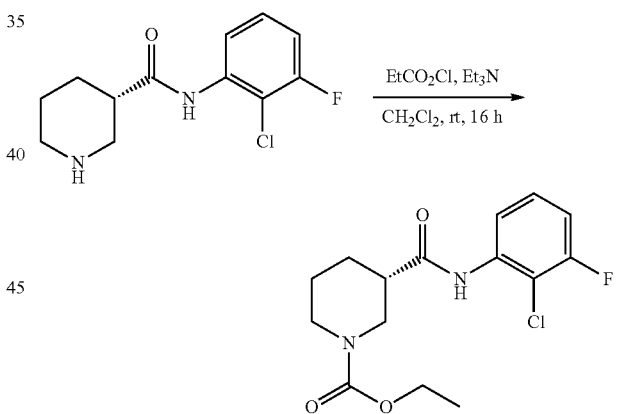

To a precooled (0° C.) solution of intermediate 2.127 (13 mg, 0.051 mmol) in CH₂Cl₂ (0.4 mL) was added triethylamine (20 µL, 0.1 mmol) then ethylchloroformate (6.8 µL, 0.076 mmol). The resulting reaction mixture was allowed to warm to room temperature and stirred for 16 h, then diluted with wet DMSO (0.5 mL), filtered through Celite, and purified via mass-directed isolation using ultra-performance liquid chromatography to afford the product as a white solid (7.0 mg, 34% yield). ¹H NMR (500 MHz, Acetonitrile-d₃) δ 8.33 (s, 1H), 8.04-7.94 (m, 1H), 7.26-7.17 (m, 1H), 7.12 (td, J=8.2, 1.6 Hz, 1H), 4.19-4.02 (m, 3H), 3.94 (dt, J=13.3, 3.7 Hz, 1H), 3.04 (s, 1H), 2.96-2.79 (m, 1H), 2.61-2.48 (m, 1H), 2.06-1.98 (m, 1H), 1.81-1.63 (m, 2H), 1.53-1.39 (m, 1H), 1.21 (t, J=7.1 Hz, 3H); AMM (ESI) m/z 329.1067 [calc for C₁₅H₁₉ClFN₂O₃ (M+H)⁺ 329.1068].

Example 170: Synthesis of MCG-IV-024-A01 (2.130)

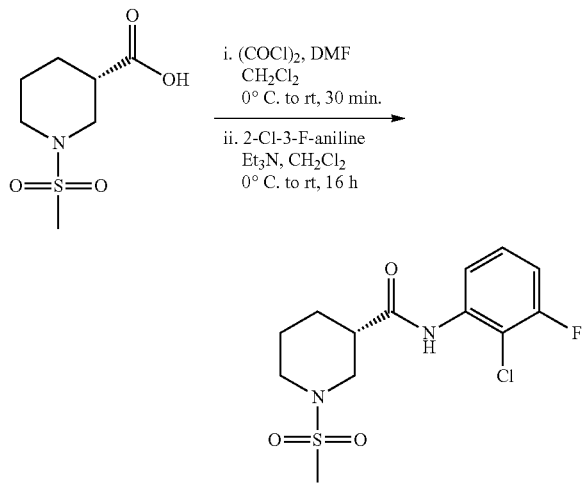

i. (COCl)₂, DMF
CH₂Cl₂
0° C. to rt, 30 min.

ii. 2-Cl-3-F-aniline
Et₃N, CH₂Cl₂
0° C. to rt, 16 h

To a precooled (0° C.) solution of 2.6 (64 mg, 0.31 mmol) in dichloromethane (1.5 mL) was added oxalyl chloride (30 µL, 0.3 mmol) and dimethylformamide (1 drop). The resulting reaction mixture was allowed to warm to room temperature and stirred for 30 min. then concentrated in vacuo and used directly.

To a precooled (0° C.) solution of 2-chloro-3-fluoroaniline (15 mg, 0.10 mmol) in dichloromethane (0.5 mL) was added triethylamine (10 µL, 0.1 mmol) then dropwise a solution of intermediate acid chloride (26 mg, 0.11 mmol) in dichloromethane (0.5 mL). The resulting mixture was allowed to warm to room temperature and stirred for 16 h, then diluted with wet DMSO (0.5 mL), filtered through Celite, and purified via mass-directed isolation using ultra-performance liquid chromatography to afford the product as a white solid (19 mg, 54% yield). $^1$H NMR (500 MHz, Acetonitrile-d₃) δ 8.29 (s, 1H), 7.87 (dt, J=8.3, 1.4 Hz, 1H), 7.31 (td, J=8.4, 6.2 Hz, 1H), 7.05 (ddd, J=9.6, 8.4, 1.4 Hz, 1H), 3.82-3.74 (m, 1H), 3.58 (d, J=11.8 Hz, 1H), 2.97 (dd, J=11.8, 10.1 Hz, 1H), 2.80 (s, 4H), 2.78-2.71 (m, 2H), 2.10-1.99 (m, 2H), 1.91-1.82 (m, 2H), 1.70-1.59 (m, 3H); AMM (ESI) m/z 335.0646 [calc for C₁₃H₁₇ClFN₂O₃S (M+H)⁺ 335.0632].

Example 171: Synthesis of MCG-IV-024-B01 (2.131)

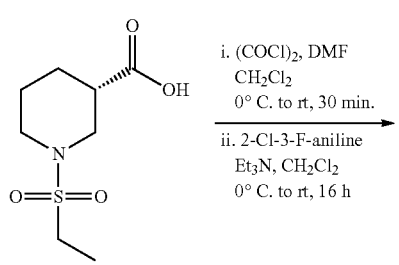

i. (COCl)₂, DMF
CH₂Cl₂
0° C. to rt, 30 min.

ii. 2-Cl-3-F-aniline
Et₃N, CH₂Cl₂
0° C. to rt, 16 h

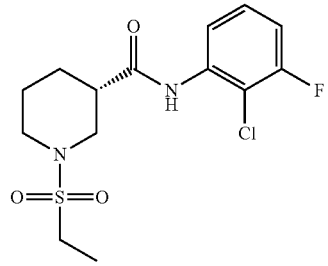

To a precooled (0° C.) solution of 2.24 (150 mg, 0.68 mmol) in dichloromethane (3.4 mL) was added oxalyl chloride (60 µL, 0.7 mmol) and dimethylformamide (1 drop). The resulting reaction mixture was allowed to warm to room temperature and stirred for 30 min. then concentrated in vacuo and used directly.

To a precooled (0° C.) solution of 2-chloro-3-fluoroaniline (15 mg, 0.10 mmol) in dichloromethane (0.5 mL) was added triethylamine (10 µL, 0.1 mmol) then dropwise a solution of intermediate acid chloride (26 mg, 0.11 mmol) in dichloromethane (0.5 mL). The resulting mixture was allowed to warm to room temperature and stirred for 16 h, then diluted with wet DMSO (0.5 mL), filtered through Celite, and purified via mass-directed isolation using ultra-performance liquid chromatography to afford the product as a white solid (21 mg, 57% yield). $^1$H NMR (500 MHz, Acetonitrile-d₃) δ 8.26 (s, 1H), 7.86 (d, J=8.2 Hz, 1H), 7.31 (td, J=8.4, 6.2 Hz, 1H), 7.09-7.00 (m, 1H), 3.86-3.75 (m, 1H), 3.62 (d, J=12.4 Hz, 1H), 3.11-2.93 (m, 3H), 2.88 (td, J=11.6, 3.0 Hz, 1H), 2.80-2.67 (m, 1H), 2.10-2.02 (m, 1H), 1.88-1.79 (m, 1H), 1.72-1.54 (m, 2H), 1.28 (t, J=7.4 Hz, 3H); AMM (ESI) m/z 349.0807[calc for C₁₄H₁₉ClFN₂O₃S (M+H)⁺ 349.0789].

Example 172: Synthesis of Intermediate 2.132

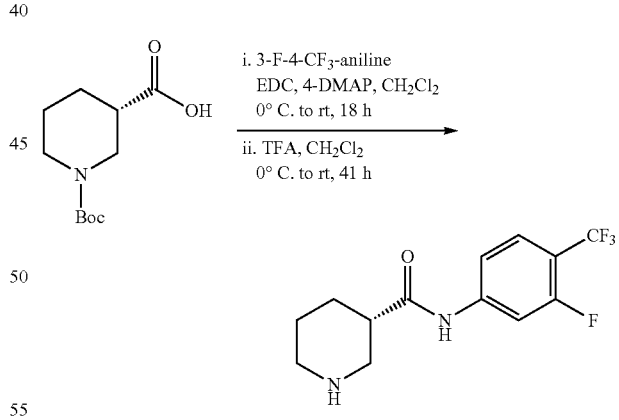

i. 3-F-4-CF₃-aniline
EDC, 4-DMAP, CH₂Cl₂
0° C. to rt, 18 h ii. TFA, CH₂Cl₂
0° C. to rt, 41 h To a solution of intermediate 2.38 (591 mg, 2.58 mmol), 3-fluoro-4-trifluoromethylaniline (462 mg, 2.58 mmol) and 1-ethyl-3-(3-dimethylaminopropyl)-carbodiimide hydrochloride (EDCI, 544 mg, 2.84 mmol) in CH₂Cl₂ (13 mL) at room temperature under N₂ atmosphere was added 4-dimethylaminopyridine (346 mg, 2.84 mmol). The resulting mixture was stirred for 18 h, then quenched with water. The layers were separated, and the aqueous phase was extracted with CH₂Cl₂ (3×). The combined organic layers were washed sequentially with sat. aq. NH₄Cl, sat. aq. NaHCO₃, and brine, dried over Na₂SO₄, and concentrated in vacuo.

Flash chromatography (SiO$_2$, 80:20 hexanes:ethyl acetate) afforded the product as a white solid (1.00 g).

To a precooled (0° C.) solution of intermediate (1.00 g, 2.56 mmol) in CH$_2$Cl$_2$ (12 mL) under N$_2$ atmosphere was added dropwise trifluoroacetic acid (0.59 mL, 7.7 mmol). The resulting mixture was allowed to warm to room temperature and stirred for 41 h, then concentrated in vacuo. The crude residue was taken up in water, cooled to 0° C., then slowly neutralized with powdered NaHCO$_3$. The aqueous phase was diluted with CH$_2$Cl$_2$. The layers were separated, and the aqueous phase was extracted with CH$_2$Cl$_2$ (3×). The combined organic layers were dried over Na$_2$SO$_4$ and concentrated in vacuo to afford the desired product as a white solid (678 mg, 68% yield). [α]$_D^{23}$ −5.0 (c. 0.31, CH$_3$OH); $^1$H NMR (500 MHz, Chloroform-d) δ 11.21 (s, 1H), 7.71 (d, J=12.9 Hz, 1H), 7.53-7.38 (m, 1H), 7.26 (s, 1H), 3.37 (d, J=37.4 Hz, 1H), 3.28-3.18 (m, 1H), 3.14-3.01 (m, 1H), 3.01-2.92 (m, 1H), 2.78 (t, J=11.2 Hz, 1H), 2.66-2.56 (m, 1H), 2.08-1.95 (m, 1H), 1.86-1.67 (m, 2H), 1.67-1.51 (m, 1H), 1.44 (d, J=3.8 Hz, 1H); $^{13}$C NMR (126 MHz, CDCl$_3$) δ 174.52, 161.20, 159.18, 143.56, 143.47, 127.38, 123.87, 121.72, 114.51, 114.48, 107.93, 107.73, 77.16, 47.58, 46.32, 46.28, 41.72, 28.42, 28.40, 27.41, 22.45; IR (ATR) ν$_{max}$ 3280, 2927, 1679, 1610, 1416, 1319, 1118, 1049, 863, 637 cm$^{-1}$; AMM (ESI) m/z 291.1139 [calc for C$_{13}$H$_{15}$N$_2$F$_4$O (M+H)$^+$ 291.1121].

Example 173: Synthesis of 2.133-2.134

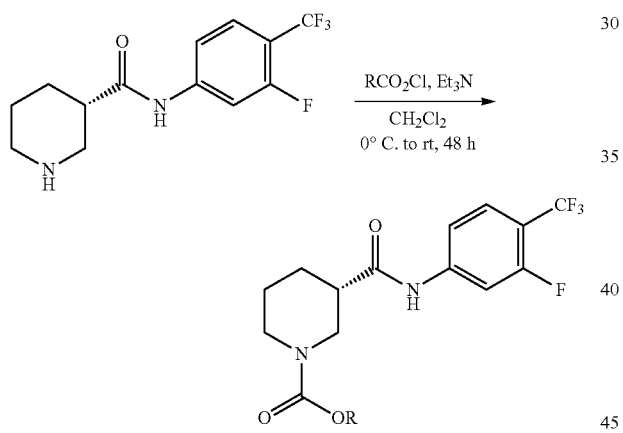

To separated precooled (0° C.) solutions of 2.132 (20. mg, 0.069 mmol) in CH$_2$Cl$_2$ (1 mL) was added triethylamine (30 μL, 0.2 mmol) then alkylchloroformate (0.10 mmol). The resulting mixtures were allowed to warm to room temperature and stirred for 48 h, then diluted with wet DMSO (0.5 mL), filtered through Celite, and purified via mass-directed isolation via ultra-performance liquid chromatography (33-36% yield).

Example 174: Synthesis of (S)-MCG-IV-050-A01 (2.133)

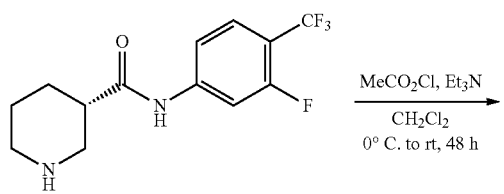

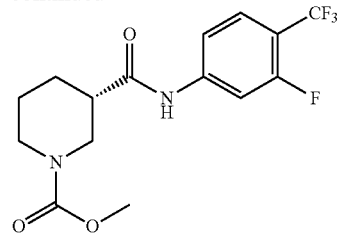

To a precooled (0° C.) solution of 2.132 (20. mg, 0.069 mmol) in CH$_2$Cl$_2$ (1 mL) was added triethylamine (30 μL, 0.2 mmol) then methylchloroformate (8.0 μL, 0.10 mmol). The resulting mixtures were allowed to warm to room temperature and stirred for 48 h, then diluted with wet DMSO (0.5 mL), filtered through Celite, and purified via mass-directed isolation via ultra-performance liquid chromatography (8.6 mg, 36% yield). $^1$H NMR (500 MHz, Acetonitrile-d$_3$) δ 8.87 (s, 1H), 7.78 (dt, J=13.3, 1.5 Hz, 1H), 7.59 (t, J=8.5 Hz, 1H), 7.42-7.32 (m, 1H), 4.12 (s, 1H), 3.92 (s, 1H), 3.63 (s, 3H), 3.03 (t, J=11.9 Hz, 1H), 2.87 (s, 1H), 2.54-2.42 (m, 1H), 2.06-1.97 (m, 1H), 1.78-1.62 (m, 2H), 1.54-1.39 (m, 1H); AMM 371.0986 (ESI) m/z [calc for C$_{15}$H$_{16}$F$_4$N$_2$O$_3$Na (M+Na)$^+$ 371.0995].

Example 175: Synthesis of (S)-MCG-IV-050-A02 (2.134)

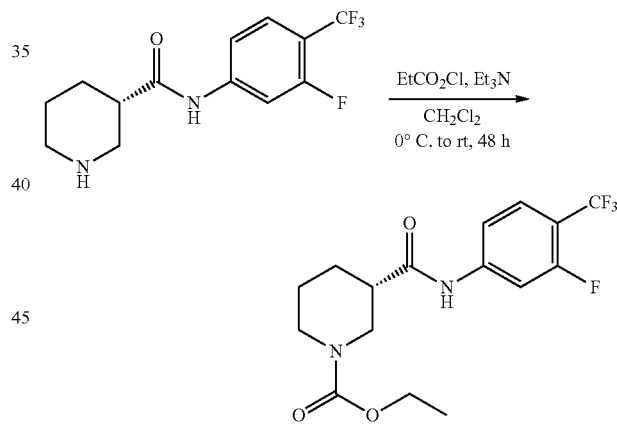

To a precooled (0° C.) solution of 2.132 (20. mg, 0.069 mmol) in CH$_2$Cl$_2$ (1 mL) was added triethylamine (30 μL, 0.2 mmol) then ethylchloroformate (9.8 μL, 0.10 mmol). The resulting mixtures were allowed to warm to room temperature and stirred for 48 h, then diluted with wet DMSO (0.5 mL), filtered through Celite, and purified via mass-directed isolation via ultra-performance liquid chromatography (8.3 mg, 33% yield). $^1$H NMR (500 MHz, Acetonitrile-d$_3$) δ 8.90 (s, 1H), 7.83-7.73 (m, 1H), 7.59 (t, J=8.5 Hz, 1H), 7.42-7.34 (m, 1H), 4.18-4.00 (m, 3H), 3.93 (d, J=13.5 Hz, 1H), 3.15-2.96 (m, 1H), 2.88 (s, 1H), 2.54-2.41 (m, 1H), 2.05-1.97 (m, 1H), 1.80-1.64 (m, 2H), 1.54-1.39 (m, 1H), 1.21 (t, J=7.1 Hz, 3H); AMM 385.1149 (ESI) m/z [calc for C$_{16}$H$_{18}$F$_4$N$_2$O$_3$Na (M+Na)$^+$ 385.1151].

Example 176: Synthesis of 2.135-2.140

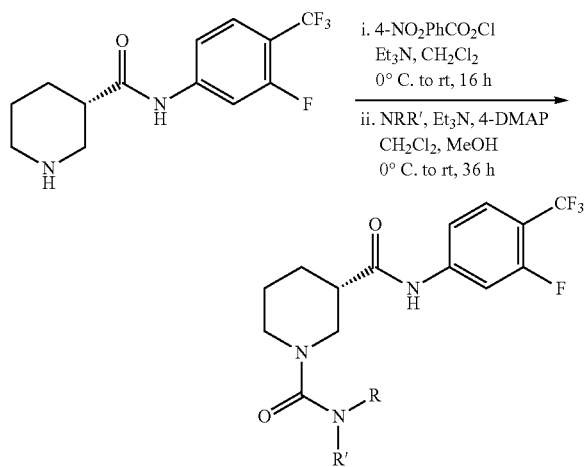

To a precooled (0° C.) solution of intermediate 2.132 (150 mg, 0.571 mmol) and p-nitrophenylchloroformate (156 mg, 0.775 mmol) in CH$_2$Cl$_2$ (4 mL) under N$_2$ atmosphere was added dropwise triethylamine (22 µL, 1.6 mmol). The reaction mixture was allowed to warm to room temperature and stirred for 16 h, then quenched with NaHCO$_3$ (sat. aq.). The layers were separated, and the aqueous phase was extracted with CH$_2$Cl$_2$ (3×). The combined organic layers were washed with brine, dried over Na$_2$SO$_4$ and concentrated in vacuo. Flash chromatography (SiO$_2$, 70:30 hexanes:ethyl acetate) afforded the product, which was carried forward.

To separated precooled (0° C.) vials charged with amine (0.13 mmol) was added a solution of intermediate (30. mg, 0.066 mmol), triethylamine (20 µL, 0.1 mmol) and 4-dimethylaminopyridine (2 mg, 0.002 mmol) in CH$_2$Cl$_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (16-19% yield).

Example 177: Synthesis of (S)-MCG-IV-063-A01 (2.135)

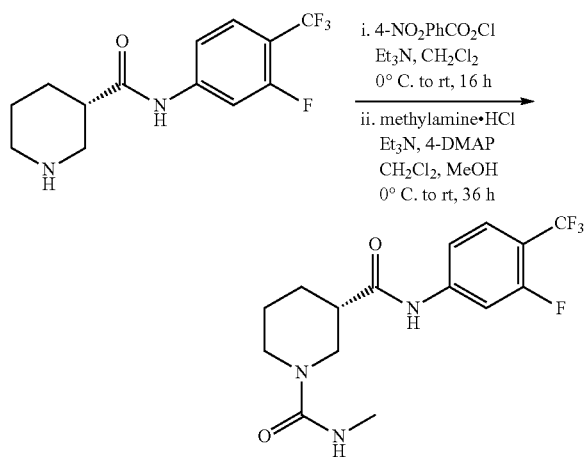

To a precooled (0° C.) solution of intermediate 2.132 (150 mg, 0.571 mmol) and p-nitrophenylchloroformate (156 mg, 0.775 mmol) in CH$_2$Cl$_2$ (4 mL) under N$_2$ atmosphere was added dropwise triethylamine (22 µL, 1.6 mmol). The reaction mixture was allowed to warm to room temperature and stirred for 16 h, then quenched with NaHCO$_3$ (sat. aq.). The layers were separated, and the aqueous phase was extracted with CH$_2$Cl$_2$ (3×). The combined organic layers were washed with brine, dried over Na$_2$SO$_4$ and concentrated in vacuo. Flash chromatography (SiO$_2$, 70:30 hexanes:ethyl acetate) afforded the product, which was carried forward.

To a precooled (0° C.) vial charged with methylamine HCl (8.9 mg, 0.13 mmol) was added a solution of intermediate (30. mg, 0.066 mmol), triethylamine (20 µL, 0.1 mmol) and 4-dimethylaminopyridine (2 mg, 0.002 mmol) in CH$_2$Cl$_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (4.3 mg, 19% yield). $^1$H NMR (500 MHz, Acetonitrile-d$_3$) δ 9.28 (s, 1H), 7.81 (d, J=12.7 Hz, 1H), 7.59 (t, J=8.5 Hz, 1H), 7.40 (d, J=9.0 Hz, 1H), 3.91 (d, J=14.0 Hz, 1H), 3.73-3.63 (m, 1H), 3.14 (dd, J=13.6, 9.5 Hz, 1H), 2.90 (ddd, J=13.7, 10.7, 3.2 Hz, 2H), 2.67 (s, 3H), 1.86-1.72 (m, 2H), 1.69-1.59 (m, 1H), 1.51-1.38 (m, 1H); AMM 348.1348 (ESI) m/z [calc for C$_{15}$H$_{18}$F$_4$N$_3$O$_2$ (M+H)$^+$ 348.1335].

Example 178: Synthesis of (S)-MCG-IV-063-A02 (2.136)

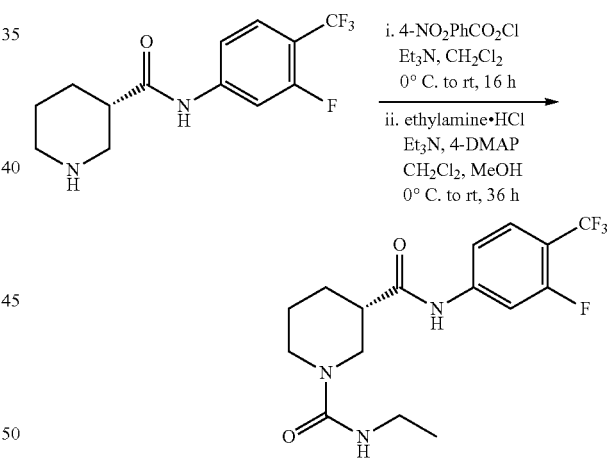

To a precooled (0° C.) solution of intermediate 2.132 (150 mg, 0.571 mmol) and p-nitrophenylchloroformate (156 mg, 0.775 mmol) in CH$_2$Cl$_2$ (4 mL) under N$_2$ atmosphere was added dropwise triethylamine (22 µL, 1.6 mmol). The reaction mixture was allowed to warm to room temperature and stirred for 16 h, then quenched with NaHCO$_3$ (sat. aq.). The layers were separated, and the aqueous phase was extracted with CH$_2$Cl$_2$ (3×). The combined organic layers were washed with brine, dried over Na$_2$SO$_4$ and concentrated in vacuo. Flash chromatography (SiO$_2$, 70:30 hexanes:ethyl acetate) afforded the product, which was carried forward.

To a precooled (0° C.) vial charged with ethylamine HCl (11 mg, 0.13 mmol) was added a solution of intermediate (30. mg, 0.066 mmol), triethylamine (20 µL, 0.1 mmol) and 4-dimethylaminopyridine (2 mg, 0.002 mmol) in CH$_2$Cl$_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (4.5 mg, 19% yield). $^1$H NMR (500 MHz, Acetonitrile-$d_3$) δ 9.31 (s, 1H), 7.81 (d, J=13.8 Hz, 1H), 7.59 (t, J=8.4 Hz, 1H), 7.41 (d, J=8.5 Hz, 1H), 3.89 (d, J=13.5 Hz, 1H), 3.71-3.62 (m, 1H), 3.24-3.10 (m, 3H), 2.97-2.86 (m, 1H), 1.89-1.72 (m, 2H), 1.69-1.57 (m, 1H), 1.51-1.39 (m, 1H), 1.06 (t, J=7.2 Hz, 3H); AMM 362.1483 (ESI) m/z [calc for $C_{16}H_{20}F_4N_3O_2$ (M+H)$^+$ 362.1492].

Example 179: Synthesis of (S)-MCG-IV-063-A03 (2.137)

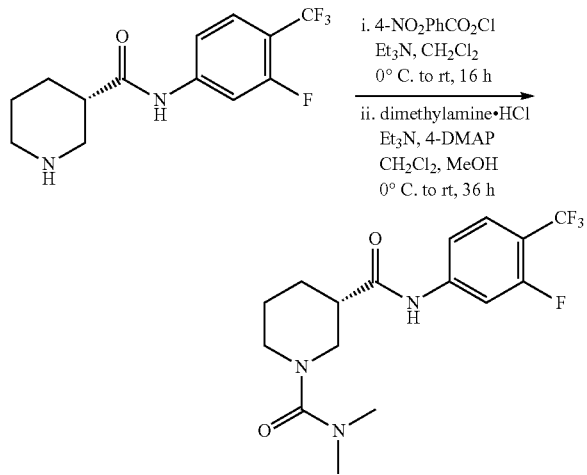

To a precooled (0° C.) solution of intermediate 2.132 (150 mg, 0.571 mmol) and p-nitrophenylchloroformate (156 mg, 0.775 mmol) in $CH_2Cl_2$ (4 mL) under $N_2$ atmosphere was added dropwise triethylamine (22 μL, 1.6 mmol). The reaction mixture was allowed to warm to room temperature and stirred for 16 h, then quenched with NaHCO$_3$ (sat. aq.). The layers were separated, and the aqueous phase was extracted with $CH_2Cl_2$ (3×). The combined organic layers were washed with brine, dried over $Na_2SO_4$ and concentrated in vacuo. Flash chromatography (SiO$_2$, 70:30 hexanes:ethyl acetate) afforded the product, which was carried forward.

To a precooled (0° C.) vial charged with dimethylamine HCl (11 mg, 0.13 mmol) was added a solution of intermediate (30. mg, 0.066 mmol), triethylamine (20 μL, 0.1 mmol) and 4-dimethylaminopyridine (2 mg, 0.002 mmol) in $CH_2Cl_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (3.9 mg, 16% yield). $^1$H NMR (500 MHz, Acetonitrile-$d_3$) δ 9.51 (s, 1H), 7.81 (dd, J=13.5, 1.9 Hz, 1H), 7.59 (t, J=8.5 Hz, 1H), 7.41 (d, J=8.3 Hz, 1H), 3.61 (dd, J=13.4, 3.8 Hz, 1H), 3.52-3.41 (m, 1H), 3.18 (dd, J=13.5, 8.9 Hz, 1H), 2.79 (s, 6H), 2.61-2.52 (m, 1H), 1.81 (dtd, J=13.6, 10.1, 3.9 Hz, 1H), 1.69-1.58 (m, 1H), 1.57-1.45 (m, 1H); AMM 362.1494 (ESI) m/z [calc for $C_{16}H_{20}F_4N_3O_2$ (M+H)$^+$ 362.1492].

Example 180: Synthesis of (S)-MCG-IV-063-A05 (2.139)

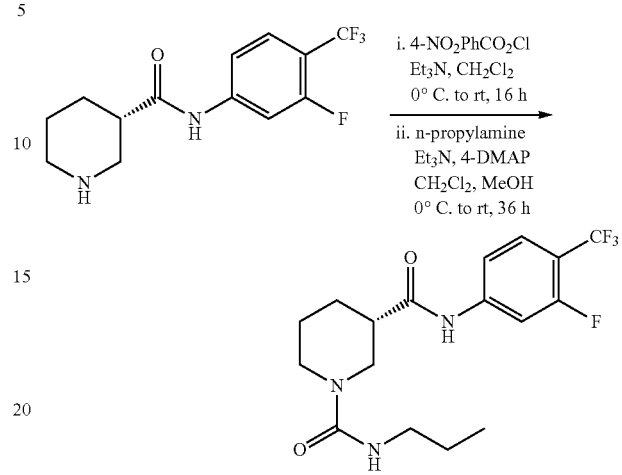

To a precooled (0° C.) solution of intermediate 2.132 (150 mg, 0.571 mmol) and p-nitrophenylchloroformate (156 mg, 0.775 mmol) in $CH_2Cl_2$ (4 mL) under $N_2$ atmosphere was added dropwise triethylamine (22 μL, 1.6 mmol). The reaction mixture was allowed to warm to room temperature and stirred for 16 h, then quenched with NaHCO$_3$ (sat. aq.). The layers were separated, and the aqueous phase was extracted with $CH_2Cl_2$ (3×). The combined organic layers were washed with brine, dried over $Na_2SO_4$ and concentrated in vacuo. Flash chromatography (SiO$_2$, 70:30 hexanes:ethyl acetate) afforded the product, which was carried forward.

To a precooled (0° C.) vial charged with iso-butylamine HCl (11 μL, 0.13 mmol) was added a solution of intermediate (30. mg, 0.066 mmol), triethylamine (20 μL, 0.1 mmol) and 4-dimethylaminopyridine (2 mg, 0.002 mmol) in $CH_2Cl_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (4.2 mg, 17% yield). $^1$H NMR (500 MHz, Acetonitrile-$d_3$) δ 9.19 (d, J=14.1 Hz, 1H), 7.78 (dd, J=13.4, 1.9 Hz, 1H), 7.56 (t, J=8.4 Hz, 1H), 7.42-7.32 (m, 1H), 3.88 (dd, J=13.4, 4.1 Hz, 1H), 3.66 (d, J=13.3 Hz, 2H), 3.21-3.11 (m, 2H), 3.07 (t, J=7.1 Hz, 3H), 2.91 (ddd, J=13.3, 10.4, 3.1 Hz, 1H), 2.51-2.39 (m, 1H), 1.77 (dtd, J=13.7, 10.5, 3.9 Hz, 1H), 1.68-1.55 (m, 1H), 1.51-1.36 (m, 3H), 0.84 (t, J=7.4 Hz, 3H); AMM 376.1641 (ESI) m/z [calc for $C_{17}H_{22}F_4N_3O_2$ (M+H)$^+$ 376.1648].

Example 181: Synthesis of (S)-MCG-IV-063-A06 (2.140)

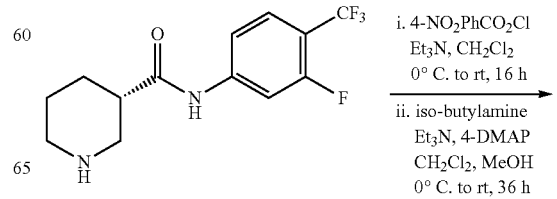

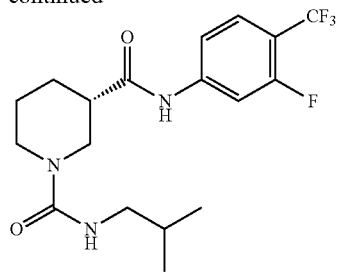

To a precooled (0° C.) solution of intermediate 2.132 (150 mg, 0.571 mmol) and p-nitrophenylchloroformate (156 mg, 0.775 mmol) in CH$_2$Cl$_2$ (4 mL) under N$_2$ atmosphere was added dropwise triethylamine (22 μL, 1.6 mmol). The reaction mixture was allowed to warm to room temperature and stirred for 16 h, then quenched with NaHCO$_3$ (sat. aq.). The layers were separated, and the aqueous phase was extracted with CH$_2$Cl$_2$ (3×). The combined organic layers were washed with brine, dried over Na$_2$SO$_4$ and concentrated in vacuo. Flash chromatography (SiO$_2$, 70:30 hexanes:ethyl acetate) afforded the product, which was carried forward.

To a precooled (0° C.) vial charged with iso-butylamine HCl (13 μL, 0.13 mmol) was added a solution of intermediate (30. mg, 0.066 mmol), triethylamine (20 μL, 0.1 mmol) and 4-dimethylaminopyridine (2 mg, 0.002 mmol) in CH$_2$Cl$_2$ (0.5 mL) and MeOH (0.5 mL). The resulting mixtures were allowed to warm to room temperature and stirred for 36 h, then diluted with wet DMSO (0.5 mL), filtered through Celite, and purified via mass-directed isolation using ultra-performance liquid chromatography (4.6 mg, 18% yield). $^1$H NMR (500 MHz, Acetonitrile-d$_3$) δ 9.29 (s, 1H), 7.81 (d, J=13.5 Hz, 1H), 7.59 (t, J=8.3 Hz, 1H), 7.40 (d, J=9.2 Hz, 1H), 5.37 (s, 1H), 3.85 (d, J=13.8 Hz, 1H), 3.71-3.55 (m, 1H), 3.26 (dd, J=13.7, 8.9 Hz, 1H), 3.03-2.85 (m, 2H), 2.52-2.42 (m, 2H), 1.88-1.76 (m, 1H), 1.76-1.66 (m, 1H), 1.61 (t, J=8.9 Hz, 1H), 1.54-1.37 (m, 1H), 0.92-0.74 (m, 3H); AMM 412.1631 (ESI) m/z [calc for C$_{18}$H$_{23}$F$_4$N$_3$O$_2$Na (M+Na)$^+$ 412.1624].

Example 182: Synthesis of MCG-IV-024-A02 (2.141)

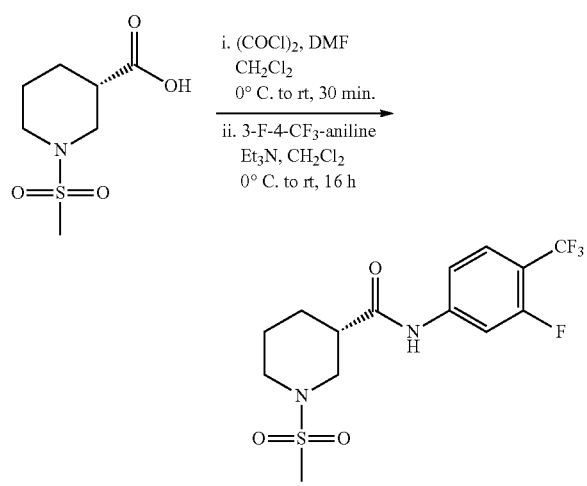

To a precooled (0° C.) solution of 2.6 (64 mg, 0.31 mmol) in dichloromethane (1.5 mL) was added oxalyl chloride (30 μL, 0.3 mmol) and dimethylformamide (1 drop). The resulting reaction mixture was allowed to warm to room temperature and stirred for 30 min. then concentrated in vacuo and used directly.

To a precooled (0° C.) solution of 3-fluoro-4-trifluoromethylaniline (15 mg, 0.084 mmol) in dichloromethane (0.5 mL) was added triethylamine (10 μL, 0.1 mmol) then dropwise a solution of intermediate acid chloride (26 mg, 0.11 mmol) in dichloromethane (0.5 mL). The resulting mixture was allowed to warm to room temperature and stirred for 16 h, then diluted with wet DMSO (0.5 mL), filtered through Celite, and purified via mass-directed isolation using ultra-performance liquid chromatography to afford the product as a white solid (21 mg, 69% yield). $^1$H NMR (500 MHz, Acetonitrile-d$_3$) δ 8.91 (s, 1H), 7.81-7.74 (m, 1H), 7.59 (t, J=8.4 Hz, 1H), 7.37 (d, J=8.6 Hz, 1H), 3.85-3.76 (m, 1H), 3.62 (d, J=11.7 Hz, 1H), 2.89 (dd, J=11.8, 10.6 Hz, 1H), 2.79 (s, 3H), 2.74 (td, J=11.6, 2.8 Hz, 1H), 2.68-2.57 (m, 1H), 2.08-1.98 (m, 1H), 1.90-1.81 (m, 1H), 1.68-1.56 (m, 2H); AMM 369.0875 (ESI) m/z [calc for C$_{14}$H$_{17}$F$_4$N$_2$O$_3$S (M+H)$^+$ 369.0896].

Example 183: Synthesis of MCG-IV-024-B02 (2.142)

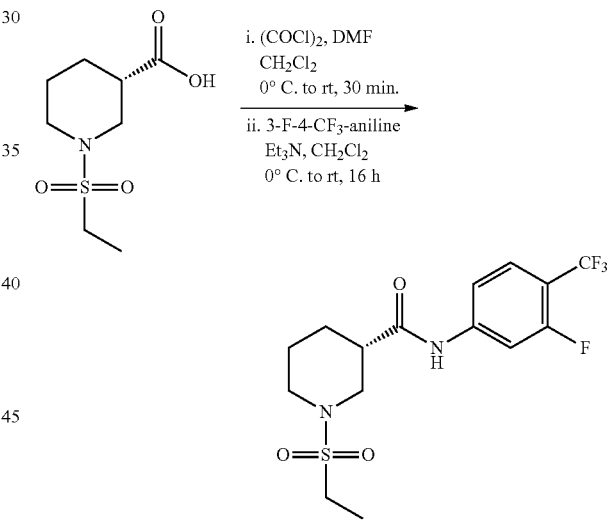

To a precooled (0° C.) solution of 2.24 (150 mg, 0.68 mmol) in dichloromethane (3.4 mL) was added oxalyl chloride (60 μL, 0.7 mmol) and dimethylformamide (1 drop). The resulting reaction mixture was allowed to warm to room temperature and stirred for 30 min. then concentrated in vacuo and used directly.

To a precooled (0° C.) solution of 3-fluoro-4-trifluoromethylaniline (15 mg, 0.084 mmol) in dichloromethane (0.5 mL) was added triethylamine (10 μL, 0.1 mmol) then dropwise a solution of intermediate acid chloride (26 mg, 0.11 mmol) in dichloromethane (0.5 mL). The resulting mixture was allowed to warm to room temperature and stirred for 16 h, then diluted with wet DMSO (0.5 mL), filtered through Celite, and purified via mass-directed isolation using ultra-performance liquid chromatography to afford the product as a white solid (24 mg, 73% yield). $^1$H NMR (500 MHz, Acetonitrile-d$_3$) δ 8.93-8.77 (m, 1H), 7.77

(dd, J=13.5, 1.9 Hz, 1H), 7.59 (t, J=8.4 Hz, 1H), 7.37 (d, J=8.6 Hz, 1H), 3.87-3.78 (m, 1H), 3.67-3.59 (m, 1H), 3.05-2.93 (m, 3H), 2.84 (td, J=11.8, 2.9 Hz, 1H), 2.63-2.54 (m, 1H), 2.07-1.98 (m, 1H), 1.87-1.78 (m, 1H), 1.71-1.51 (m, 2H), 1.27 (t, J=7.4 Hz, 3H); AMM (ESI) m/z 383.1073 [calc for $C_{15}H_{19}F_4N_2O_3S$ (M+H)$^+$ 383.1053].

Example 184: Synthesis of (S)-MCG-IV-210 (2.143)

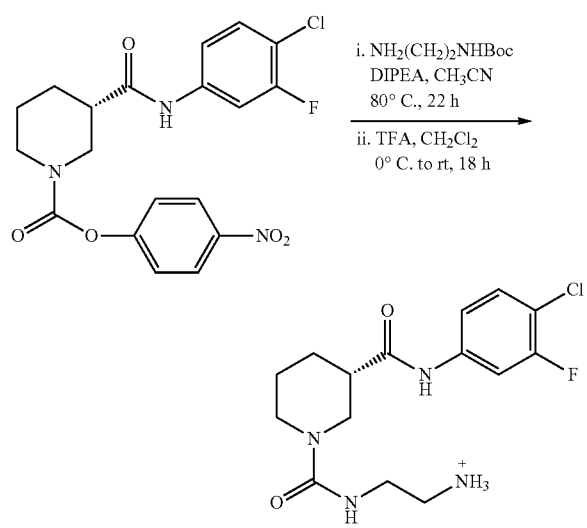

To a microwave reactor vial charged with intermediate 2.115 (50. mg, 0.12 mmol) and $NH_2(CH_2)_2NHBoc$ (57 mg, 0.36 mmol) was added acetonitrile (1 mL) then diisopropylethylamine (40 µL, 0.2 mmol). The vial was sealed and heated to 80° C. for 22 h, then allowed to cool to room temperature and diluted with $CHCl_3$ and $H_2O$. The layers were separated, and the aqueous phase was extracted with $CHCl_3$ (3×). The combined organic layers were washed with sat. aq. $NaHCO_3$ and $H_2O$, dried over $Na_2SO_4$ and concentrated in vacuo to afford the product, which was carried forward without additional purification.

To a precooled (0° C.) solution of intermediate (53 mg, 0.12 mmol) in $CH_2Cl_2$ (1.2 mL) under $N_2$ atmosphere was added dropwise trifluoroacetic acid (0.1 mL, 1 mmol). The resulting mixture was allowed to warm to room temperature and stirred for 18 h, then concentrated in vacuo. The crude residue was diluted with wet DMSO (0.5 mL) and purified via mass-directed isolation using ultra-performance liquid chromatography to afford the product as a white solid (6.0 mg, 15% yield). $[\alpha]_D^{23}$+18.9 (c. 0.056, $CH_3OH$); $^1H$ NMR (500 MHz, Methanol-$d_4$) δ 7.71 (dd, J=11.5, 2.4 Hz, 1H), 7.40 (t, J=8.4 Hz, 1H), 7.31-7.25 (m, 1H), 4.10-4.02 (m, 1H), 3.86 (d, J=13.4 Hz, 1H), 3.44 (t, J=5.8 Hz, 2H), 3.17 (dd, J=13.4, 9.9 Hz, 1H), 3.10-2.97 (m, 3H), 2.59-2.49 (m, 1H), 2.11-2.01 (m, 1H), 1.89-1.76 (m, 2H), 1.62-1.49 (m, 1H); $^{13}C$ NMR (126 MHz, MeOD) δ 174.68, 160.27, 160.09, 158.14, 140.38, 140.30, 131.56, 117.34, 117.31, 116.10, 115.96, 109.33, 109.12, 47.18, 45.40, 44.60, 41.91, 40.40, 39.55, 29.03, 25.24; IR (ATR) $v_{max}$ 3260, 1663, 1596, 1531, 1493, 1203, 1185, 1130, 701 cm$^{-1}$; AMM 343.1328 (ESI) m/z [calc for $C_{15}H_{21}ClFN_4O_2$ (M)$^+$ 343.1337].

Example 185: Synthesis of (S)-MCG-IV-211 (2.144)

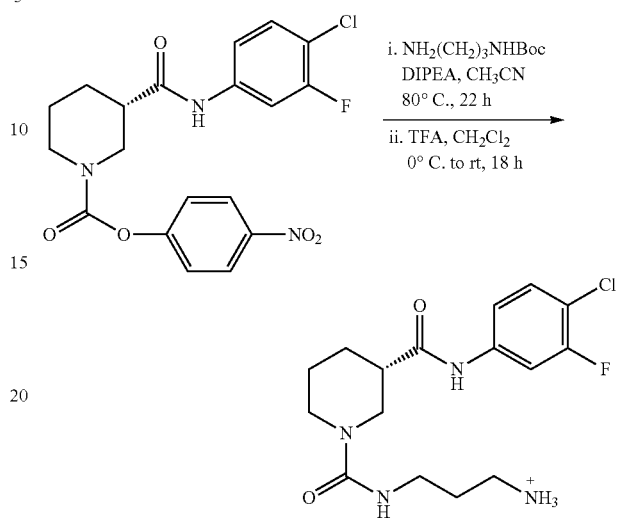

To a microwave reactor vial charged with intermediate 2.115 (50. mg, 0.12 mmol) and $NH_2(CH_2)_3NHBoc$ (62 mg, 0.36 mmol) was added acetonitrile (1 mL) then diisopropylethylamine (40 µL, 0.2 mmol). The vial was sealed and heated to 80° C. for 22 h, then allowed to cool to room temperature and diluted with $CHCl_3$ and $H_2O$. The layers were separated, and the aqueous phase was extracted with $CHCl_3$ (3×). The combined organic layers were washed with sat. aq. $NaHCO_3$ and $H_2O$, dried over $Na_2SO_4$ and concentrated in vacuo to afford the product, which was carried forward without additional purification.

To a precooled (0° C.) solution of intermediate (54 mg, 0.12 mmol) in $CH_2Cl_2$ (1.2 mL) under $N_2$ atmosphere was added dropwise trifluoroacetic acid (0.1 mL, 1 mmol). The resulting mixture was allowed to warm to room temperature and stirred for 18 h, then concentrated in vacuo. The crude residue was diluted with wet DMSO (0.5 mL) and purified via mass-directed isolation using ultra-performance liquid chromatography to afford the product as a white solid (2.9 mg, 7% yield). $^1H$ NMR (500 MHz, Methanol-$d_4$) δ 7.70 (dd, J=11.6, 2.3 Hz, 1H), 7.38 (t, J=8.5 Hz, 1H), 7.25 (dd, J=8.2, 2.2 Hz, 1H), 4.05 (d, J=13.6 Hz, 1H), 3.87 (d, J=13.3 Hz, 1H), 3.30-3.26 (m, 2H), 3.10 (dd, J=13.4, 10.3 Hz, 1H), 2.94 (q, J=10.3, 8.7 Hz, 2H), 2.56-2.45 (m, 1H), 2.05 (d, J=12.2 Hz, 1H), 1.88-1.73 (m, 3H), 1.52 (d, J=12.7 Hz, 1H); AMM 357.1518 (ESI) m/z [calc for $C_{16}H_{23}ClFN_4O_2$ (M)$^+$ 357.1494].

Example 186: Synthesis of (S)-MCG-IV-267 (2.145)

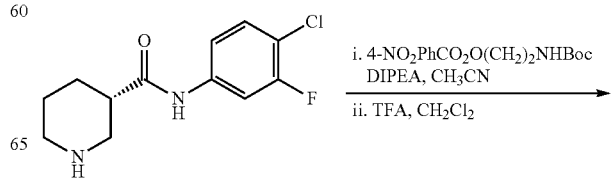

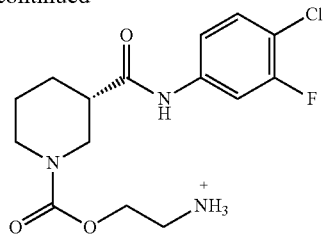

To a solution of intermediate 2.41 (30. mg, 0.12 mmol) and tert-butyl (2-(((4-nitrophenoxy)-carbonyl)oxy)ethyl)carbamate (76 mg, 0.23 mmol) in acetonitrile (1.2 mL) at room temperature was added diisopropylethylamine (60 µL, 0.4 mmol). The resulting mixture was heated to 80° C. in a sealed microwave reaction vessel for 66 h, then concentrated in vacuo. The crude residue was taken up in EtOAc and diluted with H$_2$O. The layers were separated, and the aqueous phase was extracted with EtOAc (3×). The combined organic layers were dried over Na$_2$SO$_4$, filtered, and concentrated in vacuo to afford the product, which was carried forward without purification.

To a precooled (0° C.) solution of intermediate (32 mg, 0.071 mmol) in dichloromethane (0.7 mL) under N$_2$ atmosphere was added dropwise trifluoroacetic acid (0.1 mL, 1 mmol). The resulting mixture was allowed to warm to room temperature and stirred for 18 h, then concentrated in vacuo. The crude residue was diluted with wet DMSO (0.5 mL) and purified via mass-directed isolation using ultra-performance liquid chromatography to afford the product as a white solid (26 mg, 77% yield). $^1$H NMR (500 MHz, Methanol-d$_4$) δ 7.69 (dd, J=11.6, 2.3 Hz, 1H), 7.38 (t, J=8.3 Hz, 1H), 7.29-7.23 (m, 1H), 4.42 (s, 1H), 4.23 (s, 1H), 4.16-3.99 (m, 1H), 3.24 (s, 1H), 3.14-2.97 (m, 1H), 2.61-2.48 (m, 1H), 2.17-1.98 (m, 2H), 1.88-1.73 (m, 2H), 1.54 (d, J=12.4 Hz, 1H); AMM 344.1190 (ESI) m/z [calc for C$_{15}$H$_{20}$ClFN$_3$O$_3$ (M)$^+$ 344.1177].

Example 187: Synthesis of Intermediate 2.147

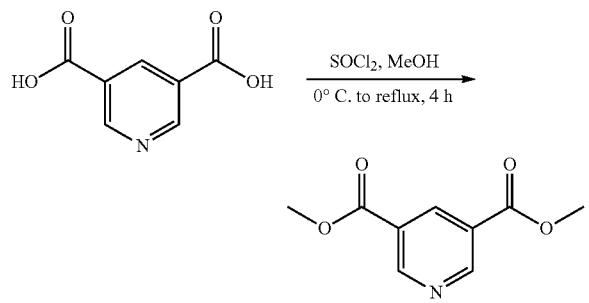

To a precooled (0° C.) solution of pyridine-3,5-dicarboxylic acid (10.0 g, 59.8 mmol) in MeOH (100 mL) under N$_2$ atmosphere was slowly added thionyl chloride (13 mL, 180 mmol). The resulting mixture was allowed to warm to room temperature then heated to reflux and stirred for 4 h. The mixture was then allowed to cool to room temperature and concentrated in vacuo. The resulting white solid was taken up in H$_2$O and the aqueous solution was cooled (0° C.) then neutralized with 10 M aq. NaOH (white ppt formed). The heterogenous mixture was diluted with EtOAc and the bisphasic solution was stirred for 5 min. The layers were separated, and the aqueous phase was extracted with EtOAc (3×). The combined organic layers were washed with brine, dried over Na$_2$SO$_4$ and concentrated in vacuo to afford the product as a white solid (10.4 g, 89% yield). $^1$H NMR (500 MHz, Chloroform-d) δ 9.35 (d, J=2.1 Hz, 2H), 8.85 (t, J=2.1 Hz, 1H), 3.98 (s, 6H); $^{13}$C NMR (126 MHz, CDCl$_3$) δ 165.05, 154.37, 138.19, 126.15, 52.85; IR (ATR) $v_{max}$ 3074, 2966, 1713, 1445, 1312, 1256, 1108, 979, 745 cm$^{-1}$; AMM (ESI) m/z 196.0600 [calc for C$_9$H$_{10}$NO$_4$ (M+H)$^+$ 196.0610].

Example 188: Synthesis of Intermediate 2.148

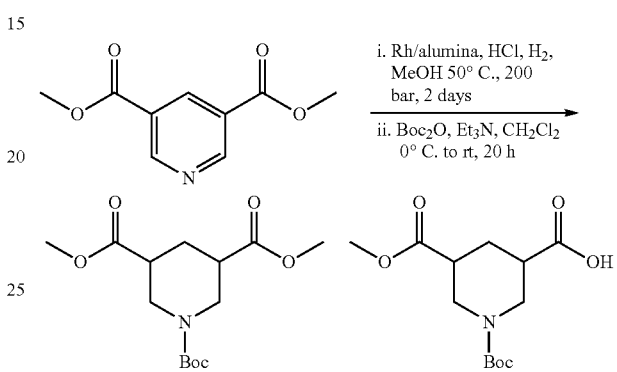

To a solution of intermediate 2.147 (11.4 g, 58.3 mmol) in MeOH (58 mL) and 6 M aq. HCl (15 mL) was added rhodium on alumina (5%, 1.1 g). The resulting mixture was hydrogenated at 50° C. while stirring under 200 bar pressure in a Parr reactor for 2 days. The reactor was then allowed to cool to room temperature and depressurized to ambient atmosphere. The crude heterogeneous resulting mixture was filtered through a bed of Celite and rinsed with MeOH. The filtrate was concentrated in vacuo, and the resulting product was carried forward without additional purification.

To a precooled (0° C.) solution of crude intermediate (11.7 g, 58.3 mmol assumed) in CH$_2$Cl$_2$ (60 mL) under N$_2$ atmosphere was added triethylamine (33 mL, 230 mmol) then Boc anhydride (20 mL, 87 mmol). The resulting mixture was then allowed to warm to room temperature and stirred for 16 h, then quenched with H$_2$O. The layers were separated, and the aqueous phase was extracted with CH$_2$Cl$_2$ (3×). The combined organic layers were washed with brine, dried over Na$_2$SO4, and concentrated in vacuo. Flash chromatography (SiO$_2$, 75:25 hexanes:EtOAc, dry loaded Celite) afforded the product mixture as a clear colorless oil (3.08 g, 21% yield over 2 steps). The experimental data agreed with that in Imaeda, ACS Med. Chem. Lett. 2016, 7 (10), 933-938.

Example 189: Synthesis of Intermediate 2.149

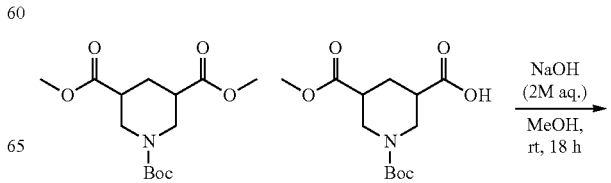

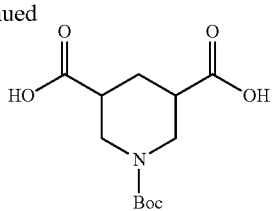

To a solution of intermediate 2.148 (3.00 g, 9.96 mmol) in MeOH (20 mL) at room temperature under $N_2$ atmosphere was added 2 M aq. NaOH (10 mL, 20 mmol). The resulting mixture was stirred at room temperature for 18 h then concentrated in vacuo. The resulting residue was taken up in sat. aq. $NaHCO_3$ and the aqueous layer was washed with ether (1×) then cooled to 0° C. and acidified with 6 M aq. HCl to pH 2. The solid precipitate was collected by vacuum filtrated and dried to afford the product as a white solid (1.21 g, 45% yield). The experimental data agreed with that described in Imaeda, ACS Med. Chem. Lett. 2016, 7 (10), 933-938. AMM 296.1117 (ESI) m/z [calc for $C_{12}H_{19}NO_6Na$ $(M+Na)^+ 296.1110$].

Example 190: Synthesis of Intermediate 2.151

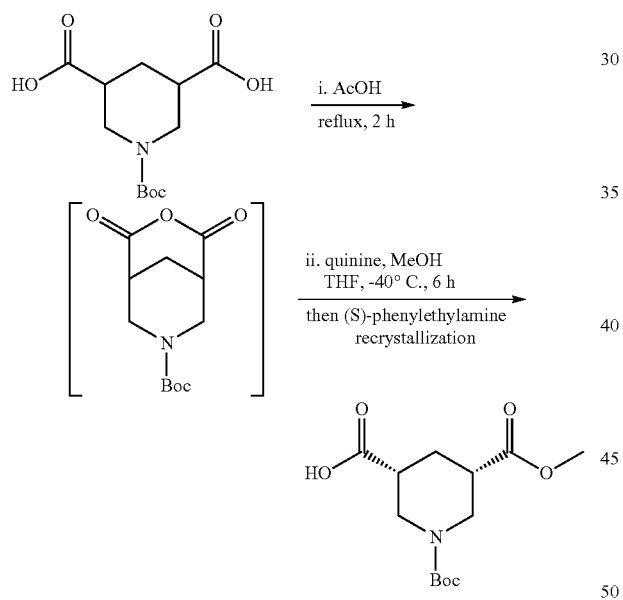

To a flask charged with intermediate 2.149 (800. mg, 2.93 mmol) and equipped with a reflux condenser at room temperature under $N_2$ atmosphere was added acetic anhydride (7 mL). The resulting mixture was heated to reflux for 2 h, then allowed to cool to room temperature and concentrated in vacuo. The crude residue was taken up in toluene and concentrated in vacuo (3×) then the resulting solid was used directly.

To a precooled (−40° C.) solution of intermediate 2.150 (1.04 g, 2.91 mmol assumed) and quinine (1.42 g, 4.37 mmol) in THF (16 mL) was slowly added dropwise a solution of MeOH (1.6 mL, 41 mmol) in THF (2 mL). The resulting mixture was stirred at −40° C. for 6 h then allowed to warm to 0° C. and quenched with 1 M aq. HCl and diluted with EtOAc. The layers were separated, and the aqueous phase was extracted with EtOAc (3×). The combined organic layers were washed with 1 M aq. HCl then brine, dried over $Na_2SO_4$, and concentrated in vacuo to afford the crude product (780 mg, 66% ee). The resulting solid was suspended in EtOH (3 mL) and warmed to 80° C. followed by addition of (S)-phenylethylamine (3 mg, 3 mmol). The resulting mixture was allowed to cool to room temperature and stood still for 19 h. The precipitated solid was collected by vacuum filtration, rinsed with hexanes and dried. The obtained solid was taken up in $H_2O$ and treated with sat. aq. $KHSO_4$ and diluted with EtOAc. The layers were separated, and the aqueous phase was extracted with EtOAc (3×). The combined organic layers were washed with brine, dried over $Na_2SO_4$ and concentrated in vacuo to afford the product as a white solid (509 mg, 43% yield over 2 steps, 96% ee). The absolute stereochemistry was determined by comparison with that described in Tokuhara, Bioorg. Med. Chem. 2018, 26 (12), 3261-3286. $[\alpha]_D^{23}$+3.25 (c. 0.09, $CH_3OH$); $^1H$ NMR (500 MHz, Methanol-$d_4$) δ 4.30 (d, J=13.0 Hz, 2H), 3.70 (d, J=2.6 Hz, 3H), 2.73 (s, 2H), 2.59-2.34 (m, 3H), 1.75-1.56 (m, 1H), 1.47 (d, J=2.6 Hz, 9H).

*Compound (−)-2.151 was prepared using the same synthesis employing quinidine instead of quinine. $[\alpha]_D^{23}$−4.53 (c. 0.26, $CH_3OH$).

Enantiomeric excess determined by SFC using the following conditions: column: ChiralPak AD-H; eluent: 10% MeOH in supercritical $CO_2$; flow rate: 4 mL/min; pressure: 12 MPa. Retention times: (+)-2.151: 1.4 min, (−)-2.151: 1.6 min. (−)-2.151*: er=16:84; (+)-2.151: er=83:17; (+)-2.151 er=98:2

Example 191: Synthesis of Intermediate 2.152

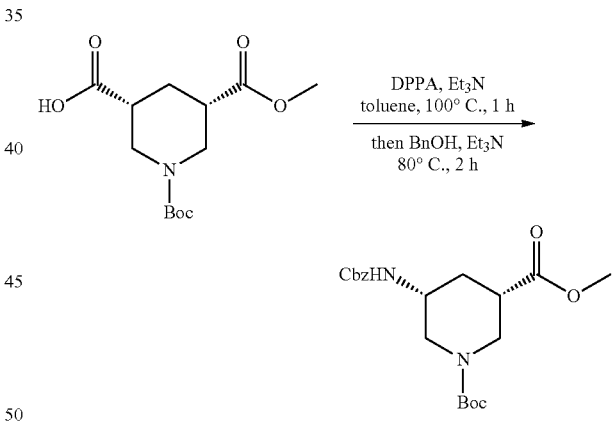

To a solution of intermediate 2.151 (550 mg, 1.91 mmol) in toluene (9.6 mL) at room temperature under $N_2$ atmosphere was added triethylamine (0.32 mL, 2.3 mmol) then diphenyl phosphoryl azide (0.50 mL, 2.3 mmol). The resulting mixture was heated to 100° C. and stirred for 1 h, then allowed to cool to room temperature. To the mixture was then added triethylamine (0.32 mL, 2.3 mmol) and benzyl alcohol (0.5 mL, 4.8 mmol). The resulting mixture was heated to 80° C. and stirred for 2 h, then allowed to cool to room temperature and quenched with $H_2O$. The layers were separated, and the aqueous phase was extracted with toluene (3×). The combined organic layers were washed with sat. aq. citric acid, sat. aq. $NaHCO_3$, then brine, dried over $Na_2SO_4$ and concentrated in vacuo. Flash chromatography ($SiO_2$, 60:40 hexanes:EtOAc) afforded the product as a white solid (727 mg, 28% yield). The experimental data agreed with that described in Imaeda, ACS Med. Chem. Lett. 2016, 7 (10), 933-938. $[\alpha]_D^{23}$ -3.15 (c. 0.10, $CH_3OH$);

Example 192: Synthesis of Intermediate 2.153

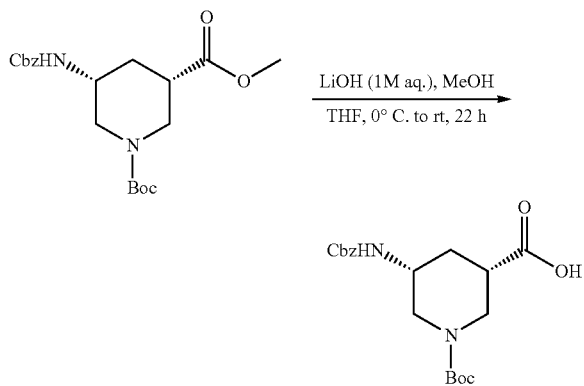

To a precooled (0° C.) solution of intermediate 2.152 (727 mg, 1.85 mmol) in MeOH (6 mL) under $N_2$ atmosphere was added THF (3 mL) then 1 M aq. LiOH (3 mL). The resulting mixture was allowed to warm to room temperature and stirred vigorously for 22 h, then concentrated in vacuo. The resulting residue was taken up in sat. aq. citric acid (white ppt formed) then diluted with $CH_2Cl_2$. The layers were separated, and the aqueous phase was extracted with $CH_2Cl_2$ (3×). The combined organic layers were dried over $Na_2SO_4$ and concentrated in vacuo to afford the product as a white solid (663 mg, 95% yield). The experimental data agreed with that described in Tokuhara, Bioorg. Med. Chem. 2018, 26 (12), 3261-3286. $[\alpha]_D^{23}$ +5.91 (c. 0.05, $CH_3OH$); AMM 379.1867 (ESI) m/z [calc for $C_{19}H_{27}N_2O_6$ $(M+H)^+$ 379.1869].

Example 193: Synthesis of Intermediate 2.154

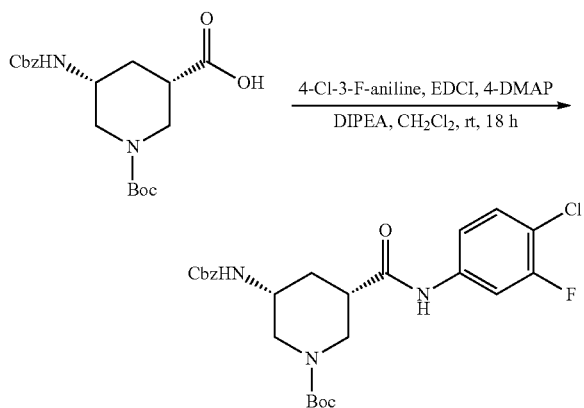

To a precooled (0° C.) solution of intermediate 2.153 (663 mg, 1.75 mmol), 1-ethyl-3-(3-dimethylaminopropyl)carbodiimide hydrochloride (272 mg, 1.75 mmol), and 4-chloro-3-fluoroaniline (383 mg, 2.63 mmol) in $CH_2Cl_2$ under $N_2$ atmosphere was added 4-dimethylaminopyridine (43 mg, 0.35 mmol) then diisopropylethylamine (0.8 mL, 4 mmol). The resulting mixture was allowed to warm to room temperature and stirred for 18 h, then quenched with $H_2O$. The layers were separated, and the aqueous phase was extracted with $CH_2Cl_2$ (3×). The combined organic layers were washed sequentially with sat. aq. $NH_4Cl$, sat. aq. $NaHCO_3$, and brine, dried over $Na_2SO_4$, and concentrated in vacuo. Flash chromatography ($SiO_2$, 50:50 hexanes:EtOAc) afforded the product as a white solid (541 mg, 61% yield). $[\alpha]_D^{24}$ -4.02 (c. 0.091, $CH_3OH$); $^1H$ NMR (500 MHz, Methanol-$d_4$) δ 7.64 (dd, J=11.5, 2.4 Hz, 1H), 7.38-7.15 (m, 8H), 5.03 (s, 2H), 4.18-3.98 (m, 2H), 3.59-3.45 (m, 1H), 3.05-2.73 (m, 1H), 2.70-2.48 (m, 2H), 2.14 (d, J=12.8 Hz, 1H), 1.72-1.53 (m, 1H), 1.41 (s, 9H); $^{13}C$ NMR (126 MHz, MeOD) δ 173.32, 160.02, 158.07, 158.00, 156.19, 140.26, 140.18, 138.16, 131.48, 130.44, 129.42, 128.97, 128.79, 127.02, 122.55, 117.27, 117.25, 116.10, 115.96, 109.31, 109.10, 81.67, 67.49, 49.00, 46.63, 44.14, 34.62, 28.58; IR (ATR) $v_{max}$ 3315, 2935, 1662, 1531, 1421, 1147, 696 $cm^{-1}$; AMM 506.1854 (ESI) m/z [calc for $C_{25}H_{30}ClFN_3O_5$ $(M+H)^+$ 506.1858].

Example 194: Synthesis of Intermediate 2.155

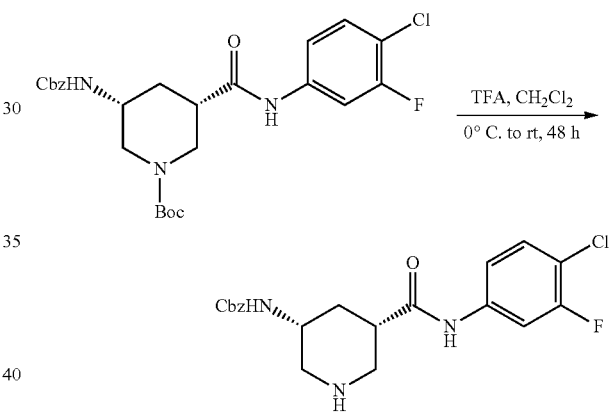

To a precooled (0° C.) solution of intermediate 2.154 (1.14 g, 2.25 mmol) in $CH_2Cl_2$ (23 mL) under $N_2$ atmosphere was added dropwise trifluoroacetic acid (1.04 mL, 13.5 mmol). The resulting mixture was allowed to warm to room temperature and stirred for 18 h, then cooled to 0° C. before addition of trifluoroacetic acid (1.0 mL, 13 mmol). The resulting mixture was allowed to warm to room temperature and stirred for 48 h, then concentrated in vacuo. The resulting residue was suspended in $H_2O$ and the resulting aqueous solution was cooled to 0° C. and neutralized with powdered $NaHCO_3$ then diluted with $CH_2Cl_2$. The layers were separated, and the aqueous phase was extracted with $CH_2Cl_2$ (3×). The combined organic layers were dried over $Na_2SO_4$ and concentrated in vacuo to afford the product as a white solid (739 mg, 81% yield). $[\alpha]_D^{23}$ -31.3 (c. 0.13, $CH_3OH$); $^1H$ NMR (500 MHz, Chloroform-d) δ 8.30 (s, 1H), 7.64 (d, J=10.9 Hz, 1H), 7.43-7.22 (m, 6H), 7.12 (d, J=8.9 Hz, 1H), 5.08 (s, 1H), 5.00 (s, 1H), 3.88-3.60 (m, 2H), 3.29-3.10 (m, 2H), 3.01 (s, 1H), 2.68 (s, 1H), 2.58 (s, 1H), 1.89 (s, 1H), 1.42-1.17 (m, 2H), 0.86 (s, 1H); IR (ATR) $v_{max}$ 3286, 1679, 1654, 1545, 1491, 1284, 1062, 693, 618 $cm^{-1}$; AMM 406.1307 (ESI) m/z [calc for $C_{20}H_{22}ClFN_3O_3$ $(M+H)^+$ 406.1334].

Example 195: Synthesis of Intermediate 2.156

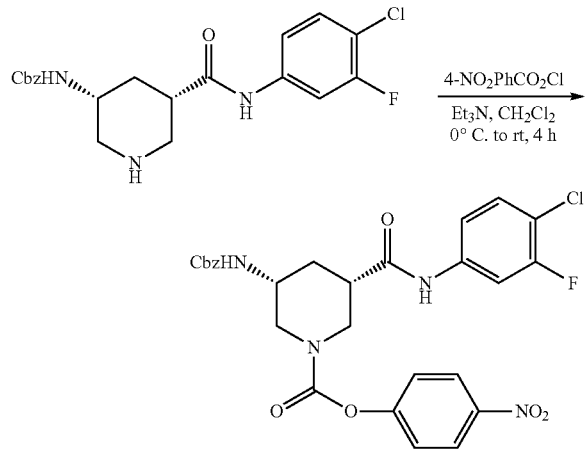

To a precooled (0° C.) solution of intermediate (99 mg, 0.39 mmol) and para-nitrophenyl chloroformate (79 mg, 0.39 mmol) in CH$_2$Cl$_2$ under N$_2$ atmosphere was added dropwise triethylamine (0.1 mL, 0.8 mmol). The resulting mixture was allowed to warm to room temperature and stirred for 4 h, then quenched with sat. aq. NaHCO$_3$. The layers were separated, and the aqueous phase was extracted with CH$_2$Cl$_2$ (3×). The combined organic layers were washed with brine, dried over Na$_2$SO$_4$ and concentrated in vacuo. Flash chromatography 10:90 hexanes:EtOAc) afforded the desired product as a white solid (93 mg, 57% yield). [α]$_D^{23}$+8.79 (c. 0.029, CH$_3$OH); $^1$H NMR (500 MHz, DMSO-d$_6$) δ 10.43 (s, 1H), 8.29 (d, J=8.6 Hz, 2H), 7.82-7.74 (m, 1H), 7.61-7.41 (m, 4H), 7.41-7.24 (m, 5H), 5.04 (s, 2H), 4.39-4.21 (m, 1H), 4.14 (d, J=5.4 Hz, 2H), 3.71-3.47 (m, 3H), 3.19-3.03 (m, 1H), 3.03-2.89 (m, 1H), 2.89-2.69 (m, 2H), 2.26-2.11 (m, 1H), 1.76-1.56 (m, 2H), 1.26 (d, J=22.8 Hz, 2H), 0.94-0.77 (m, 1H). $^{13}$C NMR (126 MHz, DMSO) δ 170.93, 168.77, 157.87, 156.06, 155.93, 155.48, 151.73, 144.48, 139.86, 139.41, 136.93, 131.49, 130.45, 130.37, 128.62, 128.33, 127.81, 126.11, 125.05, 122.75, 116.16, 115.73, 112.97, 112.44, 107.53, 107.32, 107.08, 106.87, 67.38, 65.49, 51.37, 48.51, 45.77, 42.35, 42.06, 38.10, 29.80, 28.35, 23.98, 23.24, 22.38, 13.83, 10.74. IR (ATR) ν$_{max}$ 3296, 1729, 1677, 1533, 1423, 1344, 1215, 866, 742 cm$^{-1}$; AMM 593.1230 (ESI) m/z [calc for C$_{27}$H$_{24}$ClFN$_4$O$_7$Na (M)$^+$ 593.1215].

Example 196: Synthesis of (S)-MCG-IV-226 (2.157)

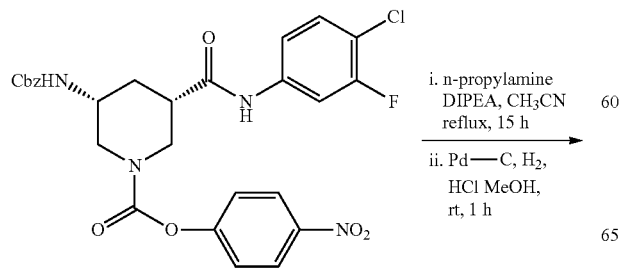

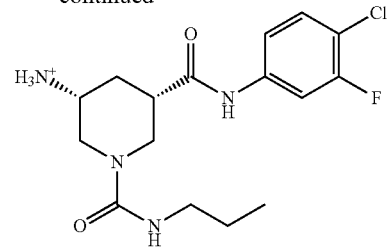

To a solution of intermediate 2.156 (43 mg, 0.076 mmol) in acetonitrile (1 mL) at room temperature was added triethylamine (30 µL, 0.2 mmol) and n-propylamine (20 µL, 0.2 mmol). The reaction mixture was heated to reflux and stirred for 15 h, then concentrated in vacuo. The crude residue was taken up in chloroform and diluted with water. The layers were separated, and the aqueous phase was extracted with chloroform (3×). The combined organic layers were washed with brine, dried over NaSO$_4$, and concentrated in vacuo to afford the product, which was carried forward.

To a solution of intermediate (25 mg, 0.051 mmol) and palladium on carbon (10 wt %, 5 mg, 0.05 mmol) in methanol (1 mL) at room temperature under N$_2$ atmosphere was added concentrated HCl (few drops). The reaction flask was backfilled with H$_2$ (3×) and the resulting mixture was stirred under H$_2$ atmosphere (balloon) for 1 h, then backfilled with N$_2$, and filtered through Celite and rinsed with MeOH. The filtrate was concentrated in vacuo and the crude residue was diluted with wet DMSO (0.5 mL) and purified via mass-directed isolation using ultra-performance liquid chromatography to afford the product as a white solid (4.7 mg, 28% yield). $^1$H NMR (500 MHz, Methanol-d$_4$) δ 7.72 (dd, J=11.6, 2.4 Hz, 1H), 7.41 (t, J=8.5 Hz, 1H), 7.26 (d, J=8.7 Hz, 1H), 4.17-4.05 (m, 1H), 3.93 (dd, J=13.8, 4.0 Hz, 1H), 3.21-3.01 (m, 2H), 2.80-2.69 (m, 1H), 2.30 (d, J=14.0 Hz, 1H), 1.99-1.87 (m, 1H), 1.57-1.39 (m, 2H), 1.00-0.80 (m, 3H); AMM 357.1517 (ESI) m/z [calc for C$_{16}$H$_{23}$ClFN$_4$O$_2$ (M+H)$^+$ 357.1494].

Example 197: Synthesis of (S)-MCG-IV-273 (2.158)

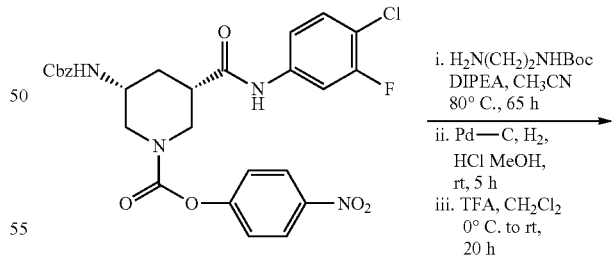

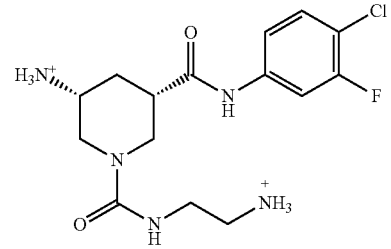

To a solution of intermediate 2.156 (40 mg, 0.070 mmol) and H$_2$N(CH$_2$)$_2$NHBoc (22 mg, 0.14 mmol) in acetonitrile (1 mL) at room temperature was added diisopropylethylamine (20 μL, 0.1 mmol). The reaction mixture was heated to 80° C. and stirred for 65 h, then concentrated in vacuo. The crude residue was taken up in EtOAc and diluted with water. The layers were separated, and the aqueous phase was extracted with EtOAc (3×). The combined organic layers were dried over NaSO$_4$ and concentrated in vacuo to afford the product, which was carried forward.

To a solution of intermediate (35 mg, 0.060 mmol) and palladium on carbon (10 wt %, 6.4 mg, 0.060 mmol) in methanol (1.2 mL) at room temperature under N$_2$ atmosphere was added concentrated HCl (few drops). The reaction flask was backfilled with H$_2$ (3×) and the resulting mixture was stirred under H$_2$ atmosphere (balloon) for 5 h, then backfilled with N$_2$, and filtered through Celite and rinsed with MeOH. The filtrate was concentrated in vacuo and the crude product was carried forward without additional purification.

To a precooled (0° C.) solution of intermediate (28 mg, 0.060 mmol) in CH$_2$Cl$_2$ (1.2 mL) under N$_2$ atmosphere was added trifluoroacetic acid (50 μL, 0.6 mmol). The resulting mixture was allowed to warm to room temperature and stirred for 20 h, then concentrated in vacuo. The crude residue was taken up in wet DMSO (0.8 mL), filtered through Celite, and purified via mass-directed isolation using ultra-performance liquid chromatography to afford the product as a white solid (12 mg, 29% yield over 3 steps). $^1$H NMR (500 MHz, Methanol-d$_4$) δ 7.76-7.68 (m, 1H), 7.41 (t, J=8.5 Hz, 1H), 7.27 (d, J=8.7 Hz, 1H), 4.19-4.07 (m, 1H), 3.98-3.89 (m, 1H), 3.48-3.37 (m, 1H), 3.24-3.13 (m, 1H), 3.03 (t, J=5.8 Hz, 1H), 2.85-2.75 (m, 1H), 2.33 (d, J=13.7 Hz, 1H), 1.99-1.87 (m, 1H).

Example 198: Synthesis of (S)-MCG-IV-274 (2.159)

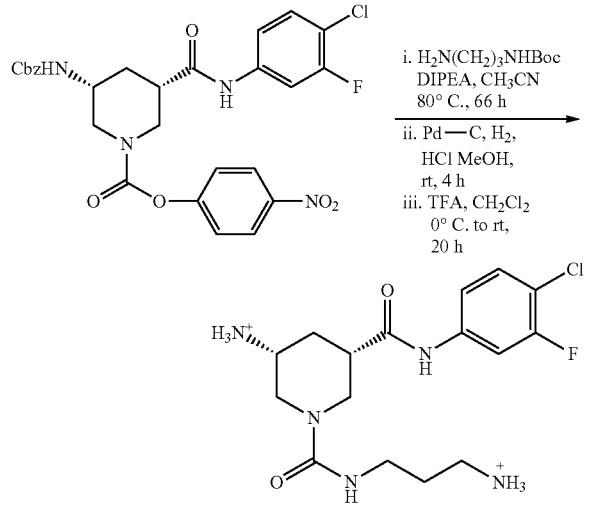

To a solution of intermediate 2.156 (40 mg, 0.070 mmol) and H$_2$N(CH$_2$)$_3$NHBoc (24 mg, 0.14 mmol) in acetonitrile (1 mL) at room temperature was added diisopropylethylamine (20 μL, 0.1 mmol). The reaction mixture was heated to 80° C. and stirred for 66 h, then concentrated in vacuo. The crude residue was taken up in EtOAc and diluted with water. The layers were separated, and the aqueous phase was extracted with EtOAc (3×). The combined organic layers were dried over NaSO$_4$ and concentrated in vacuo to afford the product, which was carried forward.

To a solution of intermediate (23 mg, 0.037 mmol) and palladium on carbon (10 wt %, 4.0 mg, 0.037 mmol) in methanol (0.8 mL) at room temperature under N$_2$ atmosphere was added concentrated HCl (few drops). The reaction flask was backfilled with H$_2$ (3×) and the resulting mixture was stirred under H$_2$ atmosphere (balloon) for 4 h, then backfilled with N$_2$, and filtered through Celite and rinsed with MeOH. The filtrate was concentrated in vacuo and the crude product was carried forward without additional purification.

To a precooled (0° C.) solution of intermediate (18 mg, 0.037 mmol) in CH$_2$Cl$_2$ (0.8 mL) under N$_2$ atmosphere was added trifluoroacetic acid (30 μL, 0.4 mmol). The resulting mixture was allowed to warm to room temperature and stirred for 20 h, then concentrated in vacuo. The crude residue was taken up in wet DMSO (1 mL), filtered through Celite, and purified via mass-directed isolation using ultra-performance liquid chromatography to afford the product as a white solid (13 mg, 32% yield over 3 steps). $^1$H NMR (500 MHz, Methanol-d$_4$) δ 7.75-7.68 (m, 1H), 7.41 (t, J=8.6 Hz, 1H), 7.27 (d, J=8.6 Hz, 1H), 4.08 (d, J=14.0 Hz, 1H), 3.90 (d, J=14.3 Hz, 1H), 3.39 (dd, J=14.0, 8.4 Hz, 1H), 3.26 (dd, J=14.9, 7.6 Hz, 1H), 2.94 (s, 1H), 2.78 (d, J=9.9 Hz, 1H), 2.33 (d, J=14.2 Hz, 1H), 1.94 (d, J=8.6 Hz, 1H), 1.86-1.72 (m, 2H); AMM (ESI) m/z 372.1593 [calc for C$_{16}$H$_{24}$ClFN$_5$O$_2$ (free base+H)$^+$ 372.1603].

Example 199: Synthesis of (S)-MCG-IV-272 (2.160)

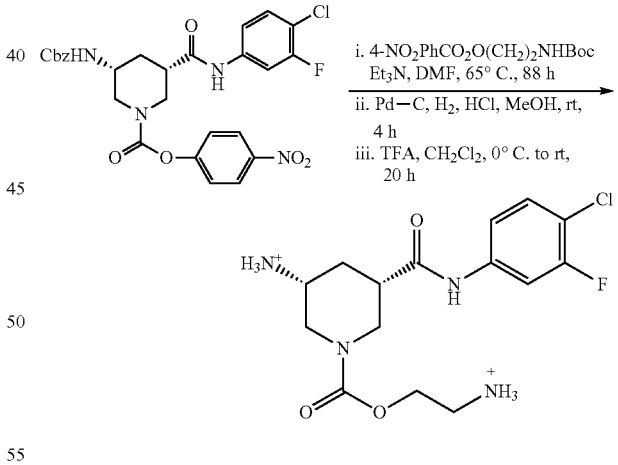

To a solution of intermediate 2.155 (30. mg, 0.074 mmol) and 4-NO$_2$PhCO$_2$—O(CH$_2$)$_2$NHBoc (24 mg, 0.074 mmol) in dimethylformamide (0.7 mL) at room temperature was added triethylamime (30 μL, 0.2 mmol). The microwave reaction vessel was sealed, and the resulting mixture was heated to 65° C. and stirred for 88 h, then allowed to cool to room temperature and diluted with EtOAc and H$_2$O. The layers were separated, and the aqueous phase was extracted with EtOAc (3×). The combined organic layers were dried over Na$_2$SO$_4$ and concentrated in vacuo to afford the product, which was carried forward without additional purification.

To a solution of intermediate (32 mg, 0.074 mmol) and palladium on carbon (10 wt %, 8 mg, 0.07 mmol) in methanol (2 mL) at room temperature under $N_2$ atmosphere was added concentrated HCl (few drops). The reaction flask was backfilled with $H_2$ (3×) and the resulting mixture was stirred under $H_2$ atmosphere (balloon) for 4 h, then backfilled with $N_2$, and filtered through Celite and rinsed with MeOH. The filtrate was concentrated in vacuo and the crude product was carried forward without additional purification.

To a precooled (0° C.) solution of intermediate (25 mg, 0.054 mmol) in $CH_2Cl_2$ (0.8 mL) under $N_2$ atmosphere was added trifluoroacetic acid (30 µL, 0.4 mmol). The resulting mixture was allowed to warm to room temperature and stirred for 20 h, then concentrated in vacuo. The crude residue was taken up in wet DMSO (1 mL), filtered through Celite, and purified via mass-directed isolation using ultra-performance liquid chromatography to afford the product as a white solid (13 mg, 51% yield over 3 steps). $^1$H NMR (500 MHz, Methanol-$d_4$) δ 7.72 (d, J=11.6 Hz, 1H), 7.42 (t, J=8.5 Hz, 1H), 7.22-7.34 (m, 1H), 4.24-4.44 (m, 2H), 4.02-4.22 (m, 1H) 3.37-3.57 (m, 3H), 2.89-2.77 (m, 1H), 2.24-2.40 (m, 1H), 1.88-2.04 (m, 1H); AMM (ESI) m/z 359.1268 [calc for $C_{15}H_{21}ClFN_4O_3$ (free base+H)$^+$ 359.1286].

Example 200: Synthesis of MCG-IV-177 (2.161)

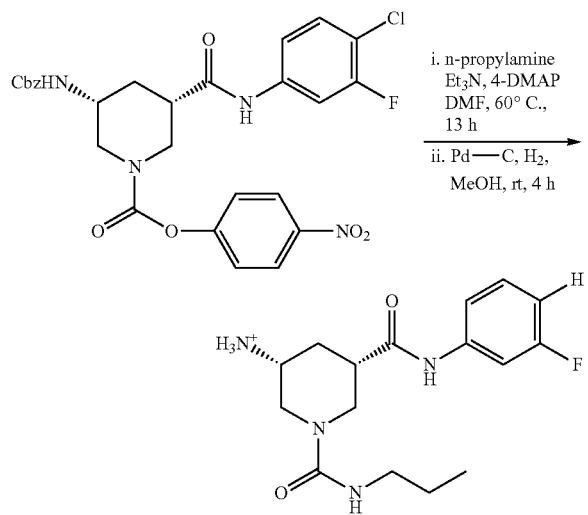

To a solution of intermediate 2.156 (90 mg, 0.16 mmol) in dimethylformamide (3 mL) at room temperature was added triethylamine (40 µL, 0.3 mmol), 4-dimethylaminopyridine (4 mg, 0.03 mmol) and n-propylamine (26 µL, 0.32 mmol). The microwave reaction vessel was sealed and the resulting mixture was heated to 60° C. and stirred for 13 h, then allowed to cool to room temperature and quenched with $H_2O$ and diluted with EtOAc. The layers were separated, and the aqueous phase was extracted with EtOAc (3×). The combined organic layers were washed with fresh $H_2O$ then brine, dried over $NaSO_4$, and concentrated in vacuo to afford the product, which was carried forward.

To a flask charged with palladium on carbon (10 wt %, 3.5 mg, 0.16 mmol) in EtOAc (0.5 mL) at room temperature under $N_2$ atmosphere was added a solution of intermediate (77 mg, 0.16 mmol) in methanol (3 mL). The reaction flask was backfilled with $H_2$ (3×) and the resulting mixture was stirred under $H_2$ atmosphere (balloon) for 4 h, then backfilled with $N_2$, and filtered through Celite and rinsed with MeOH. The filtrate was concentrated in vacuo and the crude residue was diluted with wet DMSO (0.5 mL) and purified via mass-directed isolation using ultra-performance liquid chromatography to afford the product as a white solid (10 mg, 18% yield over 2 steps). $^1$H NMR (500 MHz, Acetonitrile-$d_3$) δ 9.06 (s, 1H), 7.64-7.41 (m, 3H), 7.41-7.29 (m, 1H), 7.23 (dd, J=8.1, 1.9 Hz, 1H), 6.90 (td, J=8.5, 2.6 Hz, 1H), 4.10-3.98 (m, 1H), 3.87 (d, J=14.6 Hz, 1H), 3.50 (dd, J=14.7, 4.4 Hz, 2H), 3.34 (dd, J=14.6, 3.2 Hz, 1H), 2.98 (t, J=7.1 Hz, 2H), 2.90-2.79 (m, 1H), 2.26-2.14 (m, 1H), 2.14-2.02 (m, 1H), 1.41-1.28 (m, 2H), 0.76 (t, J=7.4 Hz, 3H); AMM (ESI) m/z 323.1896 [calc for $C_{16}H_{24}FN_4O_2$ (M+H)$^+$ 323.1883].

Example 201: Cell-Based ELISA

Detection of trimeric HIV-1 Env at the surface of HOS cells was performed by cell-based ELISA, as described in Desormeaux, "The highly conserved layer-3 component of the HIV-1 gp120 inner domain is critical for CD4-required conformational transitions," J. Virol. 87:2549-2562; Alsahafi, "Effects of the I559P gp41 change on the conformation and function of the human immunodeficiency virus (HIV-1) membrane envelope glycoprotein trimer," 2015, PLoS One 10:e0122111; and Veillette, "Conformational evaluation of HIV-1 trimeric envelope glycoproteins using a cell-based ELISA assay," 2014, J. Vis. Exp., 91:51995. To enhance cell-surface expression of HIV-1 EnvRF a stop codon was introduced to replace the codon for Gly 711, truncating the cytoplasmic tail (ACT). Briefly, HOS cells were seeded in T-75 flasks (3×10$^6$ cells per flask) and transfected the next day with 22.5 µg of Env-expressing plasmids (wild-type and mutants S375W, S375T, H66A, A582T/L587A, etc) using the standard polyethylenimine (PEI, Polyscience Inc, PA, USA) transfection method. Twenty-four hours after transfection, cells were plated in 384-wells plates (2×10$^4$ cells per well). One day later, cells were washed twice with blocking buffer (10 mg/mL non-fat dry milk, 1.8 mM $CaCl_2$), 1 mM $MgCl_2$, 25 mM Tris, pH 7.5 and 140 mM NaCl) and then incubated for 30 minutes at room temperature with different concentrations of MCG analogs or equivalent volume of vehicle (DMSO). Cells were then incubated for an additional 1 h at room temperature with anti-HIV-1 Env monoclonal antibodies recognizing CD4-induced gp120 epitopes (17b, A32), CD4-binding site gp120 epitopes (VRC03, VRC01, F105, and b12), gp120 V3 glycans (19b, PGT126, PGT122, and 10.1074), gp120 outer domain (2G12), and gp120-gp41 interface (PGT151 and VRC34) epitopes. All ligands were diluted in blocking buffer. A horseradish peroxidase-conjugated antibody specific for the Fc region of human or mouse IgG (Pierce) was then incubated with the samples for 45 minutes at room temperature. For all conditions, cells were washed 5 times with blocking buffer and 5 times with washing buffer (1.8 mM $CaCl_2$), 1 mM $MgCl_2$, 25 mM Tris, pH 7.5 and 140 mM NaCl). HRP enzyme activity was determined after the addition of 20 µl per well of a 1:1 mix of Western Lightning oxidizing and luminol reagents (Perkin Elmer Life Sciences). Light emission was measured with an LB 941 TriStar luminometer (Berthold Technologies) and analysis with Graph Pad software.

Flow Cytometry of Transfected Cells

To assess Env conformation of wild-type HIV-1 Env by flow cytometric analysis, 3×10$^5$ 293T cells were transfected by the calcium phosphate method with the HIV-1 Env expressing plasmid along with a pIRES-GFP vector, at a ratio of 2 µg of pcDNA3.1 HIV-1 Env to 0.5 µg of green fluorescence protein (GFP). Sixteen hours post-transfection, cells were washed with fresh medium (DMEM) and epitope exposure was evaluated 24 h later. Alternatively, transfected 293T cells were incubated for 1 h at room temperature with increasing concentrations of MCG analogs (0-200 μM) or equivalent volume of the vehicle (DMSO) before detection with anti-HIV-1 Env monoclonal antibodies (1 μg/mL) (17b, A32, PG9, HIV+ sera, etc). The conformation independent anti-gp120 outer domain 2G12 antibody was used to normalize Env expression on the cell surface. Antibody binding was detected by gating on GFP-positive cells with an LSRII cytometer (BD Biosciences, Mississauga, ON, Canada). Data analysis was performed using FlowJo vX0.7 (Tree Star, Ashland, OR, USA).

Flow Cytometry Analysis of CD4+ T Cell-Surface Staining

Cell-surface staining of primary CD4+ T cells from healthy HIV uninfected individuals or CEM-NKr cells is performed, as described in Prevost, "Influence of the Envelope gp120 Phe 43 Cavity on HIV-1 Sensitivity to Antibody-Dependent Cell-Mediated Cytotoxicity Responses," 2017, J. Virol 91; Richard, "CD4 mimetics sensitize HIV-1-infected cells to ADCC," 2015, Proc. Natl. Acad. Sci. USA, 112: E2687-2694; Richard, "Small CD4 Mimetics Prevent HIV-1 Uninfected Bystander CD4+ T Cell Killing Mediated by Antibody-dependent Cell-mediated Cytotoxicity," 2016, EBioMedicine 3:122-134; Veillette, "The HIV-1 gp120 CD4-Bound Conformation Is Preferentially Targeted by Antibody-Dependent Cellular Cytotoxicity-Mediating Antibodies in Sera from HIV-1-Infected Individuals," 2015, J. Virol., 89:545-551; Veillette, "Interaction with cellular CD4 exposes HIV-1 envelope epitopes targeted by antibody-dependent cell-mediated cytotoxicity," 2014, J. Virol., 88:2633-2644; Richard, "Uninfected Bystander Cells Impact the Measurement of HIV-Specific Antibody-Dependent Cellular Cytotoxicity Responses," 2018, MBio. 9(2): e00358-18; Richard, "BST-2 Expression Modulates Small CD4-Mimetic Sensitization of HIV-1-Infected Cells to Antibody-Dependent Cellular Cytotoxicity," 2017, J. Virol. 91(11):e00219-17. Binding of HIV-1 infected cells by HIV+ sera (1:1000 dilution) or anti-Env Abs (such as 17b) is performed 48 after in vitro infection at 37° C. in presence of different concentrations of the MCG analogs or with equivalent volume of vehicle (DMSO). Cells infected with HIV-1 primary isolates are stained intracellularly for HIV-1 p24 using the Cytofix/Cytoperm Fixation/Permeabilization Kit (BD Biosciences, Mississauga, ON, Canada) and then fluorescent anti-p24 mAb (PE-anti-p24, clone KC57; Beckman Coulter/Immunotech, Hialeah, FL) (1:100 final concentration). The percentage of infected cells (p24+ or GFP+ cells) is determined by gating the living cell population based on the viability dye staining. Samples are analyzed on an LSRII cytometer (BD Biosciences, Mississauga, ON, Canada) and data analysis is performed using FlowJo vX0.7 (Tree Star, Ashland, OR, USA).

Flow Cytometry Analysis of ADCC

Measurement of antibody or serum-mediated ADCC is performed with a FACS-based assay as described in Prevost, "Influence of the Envelope gp120 Phe 43 Cavity on HIV-1 Sensitivity to Antibody-Dependent Cell-Mediated Cytotoxicity Responses," 2017, J. Virol 91; Richard, "CD4 mimetics sensitize HIV-1-infected cells to ADCC," 2015, Proc. Natl. Acad. Sci. USA, 112:E2687-2694; Richard, "Small CD4 Mimetics Prevent HIV-1 Uninfected Bystander CD4+ T Cell Killing Mediated by Antibody-dependent Cell-mediated Cytotoxicity," 2016, EBioMedicine 3:122-134; Veillette, "The HIV-1 gp120 CD4-Bound Conformation Is Preferentially Targeted by Antibody-Dependent Cellular Cytotoxic-ity-Mediating Antibodies in Sera from HIV-1-Infected Individuals," 2015, J. Virol., 89:545-551; Veillette, "Interaction with cellular CD4 exposes HIV-1 envelope epitopes targeted by antibody-dependent cell-mediated cytotoxicity," 2014, J. Virol., 88:2633-2644; Richard, "Uninfected Bystander Cells Impact the Measurement of HIV-Specific Antibody-Dependent Cellular Cytotoxicity Responses," 2018, MBio. 9(2): e00358-18; Richard, "BST-2 Expression Modulates Small CD4-Mimetic Sensitization of HIV-1-Infected Cells to Antibody-Dependent Cellular Cytotoxicity," 2017, J. Virol. 91(11):e00219-17. This assay specifically measures ADCC activity against productively infected cells and is not affected by the confounding effect of uninfected bystander cells. See, Richard, "Uninfected Bystander Cells Impact the Measurement of HIV-Specific Antibody-Dependent Cellular Cytotoxicity Responses," 2018, MBio., 9(2): e00358-18.

Briefly, primary CD4+ T cells isolated from healthy HIV-1-negative individuals or CEM-NKr cells are infected with HIV viruses. Forty-eight hours post-infection, cells are incubated with autologous PBMC (effector:target cell ratio of 10:1) in the presence of 1:1000 HIV+ sera dilution or anti-Env Abs (5 μg/mL) alone or in combination with increasing concentration of MCG analogs. Infected cells are identified by intracellular staining for HIV-1 p24 or GFP expression (for GFP expressing infectious molecular clones) and the percentage of cytotoxicity is calculated the following formula as described.

$$\frac{(\text{relative count of } GFP^+ \text{ cells in Targets plus Effectors}) - \left(\begin{array}{c}\text{relative count of } GFP^+ \text{ cells in Targets plus} \\ \text{Effectors plus serum or antibodies}\end{array}\right)}{(\text{relative count of } GFP^+ \text{ cells in Targets})}$$

For cells infected with HIV-1 primary isolates, infected cells are identified by intracellular staining for HIV-1 p24. In that context, the percentage of cytotoxicity is calculated with the following formula by gating infected lived target cells:

$$\frac{(\% \text{ of } p24^+ \text{ cells in Targets plus Effectors}) - \left(\begin{array}{c}\% \text{ of } p24^+ \text{ cells in Targets plus Effectors} \\ \text{plus serum or antibodies}\end{array}\right)}{(\% \text{ of } p24^+ \text{ cells in Targets})}$$

Samples are analyzed on an LSRII cytometer (BD Biosciences, Mississauga, ON, Canada) and data analysis is performed using FlowJo vX0.7 (Tree Star, Ashland, OR, USA).

Recombinant Luciferase Viruses and Infection

Neutralization assays are performed, as described in Desormeaux, "The highly conserved layer-3 component of the HIV-1 gp120 inner domain is critical for CD4-required conformational transitions," 2013, J. Virol., 87:2549-2562; Finzi, "Topological layers in the HIV-1 gp120 inner domain regulate gp41 interaction and CD4-triggered conformational transitions," 2010, Mol. Cell 37:656-667; and Ding, "A Highly Conserved gp120 Inner Domain Residue Modulates Env Conformation and Trimer Stability," 2016, J. Virol., 90(19):8395-409. Briefly, recombinant viruses containing the firefly luciferase gene are produced by calcium phosphate transfection of 293T cells with the HIV-1 proviral vector pNL4.3 Env-Luc and plasmids expressing the wild-type or mutant HIV-1 envelope glycoproteins (AMLV Env is used as a negative control) at a ratio of 2:1. Two days after transfection, the cell supernatants are harvested; the reverse transcriptase activities of all viruses are measured, as described in Rho, "Characterization of the reverse transcriptase from anew retrovirus (HTLV) produced by a human cutaneous T-cell lymphoma cell line," 1981, Virology, 112:355-360. The virus-containing supernatants are then stored in aliquots at −80° C.

Cf2Th-CD4-CCR5 target cells are seeded at a density of $5 \times 10^3$ cells/well in 96-well luminometer-compatible tissue culture plates (Perkin Elmer) 24 h before infection. Recombinant are incubated for 1 h at 37° C. with increasing concentration of MCG analogs before adding them to the target cells followed by incubation for 48 h at 37° C.; the medium is then removed from each well, and the cells are lysed by the addition of 30 μL of passive lysis buffer (Promega) and three freeze-thaw cycles. An LB 941 TriStar luminometer (Berthold Technologies) is used to measure the luciferase activity of each well after the addition of 100 μl of luciferin buffer (15 mM $MgSO_4$, 15 mM $KPO_4$ [pH 7.8], 1 mM ATP, and 1 mM dithiothreitol) and 50 μl of 1 mM D-luciferin potassium salt (Prolume). See, Tables 1A and 1B.

TABLE 1A

|  | Fold Over DMSO (patient sera, n = 3) | Fold Over DMSO (17b, n = 1) | Fold over DMSO (% ADCC with ps, n = 3) | Solubility (in PBS) |
| --- | --- | --- | --- | --- |
| DMSO (50 μM) | 1 | 1 | 1 |  |
| (S)-MCG-III-027-A01 | 1.825005333 | 1.368031902 | 0.373884356 | Yes |
| (S)-MCG-III-027-A02 | 2.077222667 | 1.651007939 | 0.290825542 | Yes |
| (S)-MCG-III-027-A03 | 1.523065 | 1.120773066 | 0.968700391 | Yes |
| (S)-MCG-III-027-A04 | 1.3964 | 1.072702818 | −0.32013358 | Yes |
| (S)-MCG-III-027-B01 | 1.371531667 | 1.042321674 | 0.870248286 | Yes |
| (S)-MCG-III-027-B02 | 1.618784333 | 1.063734027 | 0.740093705 | Yes |
| (S)-MCG-III-027-B03 | 1.440950333 | 1.048199526 | 1.173398338 | Yes |
| (S)-MCG-III-027-B04 | 1.474656667 | 1.012405812 | 0.129421522 | Yes |
| (S)-MCG-III-027-B05 | 1.713523667 | 1.025634838 | 0.360811473 | Yes |
| (S)-MCG-III-027-C01 | 1.0614591 | 1.138601288 | 0.722276612 | Yes |
| (S)-MCG-III-027-C05 | 1.755845667 | 1.495987199 | 0.460008125 | Yes |
| (S)-MCG-III-027-D04 | 1.2411943 | 1.169164507 | 1.373017337 | Yes |
| (S)-MCG-III-027-D05 | 2.830632333 | 2.220293149 | 1.01257053 | Yes |
| (S)-MCG-III-085-A01* | 3.838757 | 4.3170441 | 1.591492698 | Yes |
| (S)-MCG-III-085-A02 | 1.129914 | 2.150178784 | NA | Yes |
| (S)-MCG-III-085-A03 | 1.463822 | 3.340882002 | NA | Yes |
| (S)-MCG-III-085-A04 | 1.310037333 | 2.998808105 | NA | Yes |
| (S)-MCG-III-085-A05 | 1.114798333 | 2.15375447 | NA | Yes |
| (S)-MCG-III-085-A06 | 1.609657333 | 3.297973778 | NA | Yes |
| (S)-MCG-III-085-C01 | 3.281544333 | 5.698450536 | 0.487075659 | Yes |
| (S)-MCG-III-085-C02 | 1.194762667 | 2.152562574 | NA | Yes |
| (S)-MCG-III-085-C03 | 1.654687 | 3.833134684 | NA | Yes |
| (S)-MCG-III-085-C04 | 1.675857333 | 3.94874851 | NA | Yes |
| (S)-MCG-III-085-C05 | 1.035824467 | 1.772348033 | NA | Yes |
| (S)-MCG-III-085-C06 | 1.279895333 | 3.103694875 | NA | NO |
| (S)-MCG-III-085-D01 | 5.952359333 | 6.396901073 | NA | NO |
| (S)-MCG-III-085-D02 | 1.365632667 | 2.539928486 | NA | NO |
| (S)-MCG-III-085-D03 | 2.034836333 | 4.867699642 | NA | NO |
| (S)-MCG-III-085-D04 | 1.840546 | 3.150178784 | NA | NO |
| (S)-MCG-III-085-D05 | 1.548206333 | 5.57568534 | NA | NO |
| (S)-MCG-III-085-D06 | 2.002674 | 6.458879619 | NA | NO |
| (S)-MCG-III-116-A01 | 2.153085333 | NA | NA | NO |
| (S)-MCG-III-116-A02 | 1.970415667 | NA | 1.861167092 | NO |
| (S)-MCG-III-116-A03 | 1.562711 | NA | NA | NO |
| (S)-MCG-III-116-A05 | 1.097831767 | NA | NA | NO |
| (S)-MCG-III-116-A06 | 1.149892667 | NA | NA | NO |
| MCG-III-101 | 1.1394174 | NA | NA | NO |
| (S)-MCG-III-115 | 1.847331667 | NA | NA | Yes |
| (S)-MCG-III-117 | 1.885978 | NA | NA | NO |
| MCG-III-157-A01 | 1.850942333 | NA | NA | Yes |
| MCG-III-157-A02 | 1.639329667 | NA | NA | Yes |
| MCG-III-157-A03 | 1.565856 | NA | NA | NO |
| MCG-III-157-A04 | 1.282933733 | NA | NA | Yes |
| MCG-III-157-B01 | 1.482047667 | NA | NA | Yes |
| MCG-III-157-B02 | 2.624921667 | NA | NA | NO |
| MCG-III-157-B03 | 3.728364 | NA | 1.937106786 | NO |
| MCG-III-157-B04 | 2.398155667 | NA | 1.731722322 | Yes |
| MCG-III-157-C01 | 1.040678133 | NA | NA | NO |
| MCG-III-157-C02 | 1.0455777 | NA | NA | Yes |
| MCG-III-157-C04 | 0.8970854 | NA | NA | Yes |
| (S)-MCG-III-132 | 1.579617333 | NA | NA | Yes |
| (S)-MCG-III-128 | 1.0702113 | NA | NA | NO |
| MCG-III-211-A01 | 1.469887 | 2.629570747 | NA | Yes |
| MCG-III-211-A02 | 1.812215667 | 3.640699523 | NA | Yes |
| MCG-III-211-A03 | 1.701009333 | 2.637519873 | NA | NO |
| MCG-III-211-A04 | 1.633989667 | 3.60572337 | NA | Yes |
| MCG-III-212-A01 | 0.981731067 | 0.968203498 | NA | Yes |
| MCG-III-212-A02 | 1.846007 | 3.950715421 | NA | Yes |
| MCG-III-212-A03 | 1.236253667 | 1.098569157 | NA | NO |

TABLE 1A-continued

| | Fold Over DMSO (patient sera, n = 3) | Fold Over DMSO (17b, n = 1) | Fold over DMSO (% ADCC with ps, n = 3) | Solubility (in PBS) |
|---|---|---|---|---|
| MCG-III-212-A04 | 0.924049033 | 1.041335453 | NA | Yes |
| (S)-MCG-III-213-A01 | 1.081624033 | 1.081081081 | NA | Yes |
| (S)-MCG-III-213-A02 | 1.030842333 | 1.06836248 | NA | Yes |
| (S)-MCG-III-213-A03 | 1.080718433 | 0.92845787 | NA | NO |
| (S)-MCG-III-213-A04 | 1.068656 | 1.058823529 | NA | Yes |
| MCG-III-214-A01 | 1.293235333 | 1.387917329 | NA | Yes |
| MCG-III-214-A02 | 3.251645667 | 5.163751987 | NA | Yes** |
| MCG-III-214-A03 | 1.050124333 | 0.910969793 | NA | NO |
| MCG-III-214-A04 | 0.923961 | 1.149443561 | NA | NO |
| MCG-III-196 | 1.498782 | 2.594594595 | NA | Yes |
| MCG-III-210 | 1.121543333 | 1.721780604 | NA | Yes |
| (S)-MCG-III-189 | 0.947801533 | 1.012718601 | NA | Yes |
| MCG-III-209 | 1.823014667 | 3.232114467 | NA | Yes |
| MCG-III-207 | 1.9198725 | 3.693123901 | 1.591385445 | Yes |
| MCG-III-204 | 0.981101533 | 1.031796502 | NA | NO |
| MCG-III-201 | 0.988966867 | 1.386327504 | NA | Yes |
| MCG-III-216-A01 | 0.999102567 | 1.734499205 | NA | Yes |
| MCG-III-216-A02 | 1.025732933 | 1.303656598 | NA | Yes |
| MCG-III-216-A03 | 1.050439667 | 1.46899841 | NA | Yes |
| MCG-III-216-A04 | 0.844827667 | 1.236883943 | NA | Yes |
| (S)-MCG-III-188-A01 | 2.689711 | 7.110311421 | 2.270296855 | Yes |
| (S)-MCG-III-188-A02 | 3.826625167 | 6.354473323 | 0.866542152 | Yes |
| (S)-MCG-III-188-A03 | 4.6088345 | 3.106499406 | NA | NO |

*(S)-MCG-III-027-D05 (batch: (S)-MCG-III-085-A01)
**Non-specific binding

HIV+ Patient Sera (n=3) Recognition of CH58TF Infected Primary CD4+ T-Cells

Staining with patient sera and 50 µM of compounds given as a fold change over DMSO (vehicle).

The data of Table 2 is given as the fold over BNM-III-170 (5 µM) of Cell-Based ELISA with MCG Analogs (50 µM)—17b readout, 2G12 and DMSO normalized.

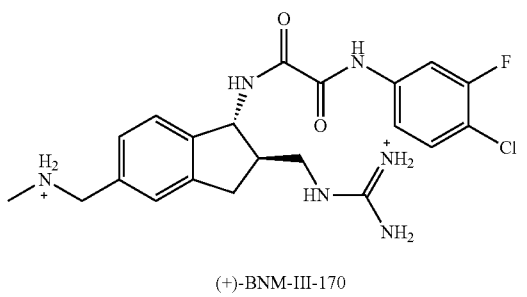

(+)-BNM-III-170

TABLE 1B

| Compound Name | Fold over BNM-III-170 - 17b binding (±0.05) |
|---|---|
| (S)-MCG-II-153 | 0.20/0.31 |
| (R)-MCG-II-156 | 0.08 |
| (S)-MCG-III-027-A02 | 0.36 |
| (S)-MCG-III-027-A03 | 0.12 |
| (S)-MCG-III-027-A04 | 0.17 |
| (S)-MCG-III-027-B01 | 0.10 |
| (S)-MCG-III-027-B02 | 0.10 |
| (S)-MCG-III-027-B03 | 0.13 |
| (S)-MCG-III-027-B04 | 0.07 |
| (S)-MCG-III-027-B05 | 0.06 |
| (S)-MCG-III-027-C01 | 0.06 |
| (S)-MCG-III-027-C02 | 0.14 |
| (S)-MCG-III-027-D04 | 0.07 |
| (S)-MCG-III-027-D05 | 0.46/0.58 |

TABLE 1B-continued

| Compound Name | Fold over BNM-III-170 - 17b binding (±0.05) |
|---|---|
| (S)-MCG-III-085-A02 | 0.22 |
| (S)-MCG-III-085-A03 | 0.19 |
| (S)-MCG-III-085-A04 | 0.10 |
| (S)-MCG-III-085-A05 | 0.16 |
| (S)-MCG-III-085-A06 | 0.14 |
| (S)-MCG-III-085-C01 | 0.35 |
| (S)-MCG-III-085-C02 | 0.20 |
| (S)-MCG-III-085-C03 | 0.25 |
| (S)-MCG-III-085-C04 | 0.26 |
| (S)-MCG-III-085-C05 | 0.26 |
| (S)-MCG-III-085-C06 | 0.34 |
| (S)-MCG-III-085-D01 | 0.45 |
| (S)-MCG-III-085-D02 | 0.18 |
| (S)-MCG-III-085-D03 | 0.20 |
| (S)-MCG-III-085-D04 | 0.28 |
| (S)-MCG-III-085-D05 | 0.10 |
| (S)-MCG-III-085-D06 | 0.19 |
| (S)-MCG-III-116-A01 | 0.41 |
| (S)-MCG-III-116-A02 | 0.24 |
| (S)-MCG-III-116-A03 | 0.36 |
| (S)-MCG-III-116-A05 | 0.29 |
| (S)-MCG-III-116-A06 | 0.31 |
| (S)-MCG-III-117 | 0.21 |
| (S)-MCG-III-132 | 0.27 |
| (S)-MCG-III-128 | 0.21 |
| (±)-MCG-III-157-C01 | 0.08 |
| (±)-MCG-III-157-C02 | 0.07 |
| (±)-MCG-III-157-C04 | 0.04 |
| (S)-MCG-III-213-A01 | 0.07 |
| (S)-MCG-III-213-A02 | 0.07 |
| (S)-MCG-III-213-A03 | 0.05 |
| (S)-MCG-III-213-A04 | 0.10 |
| MCG-III-101 | 0.21 |
| (±)-MCG-III-196 | 0.34 |
| (±)-MCG-III-210 | 0.22 |
| (±)-MCG-III-216-A01 | 0.21 |
| (±)-MCG-III-209 | 0.42 |
| (±)-MCG-III-157-A01 | 0.36 |
| (±)-MCG-III-157-A02 | 0.27 |
| (±)-MCG-III-157-A03 | 0.33 |
| (±)-MCG-III-157-A04 | 0.34 |

TABLE 1B-continued

| Compound Name | Fold over BNM-III-170 - 17b binding (±0.05) |
|---|---|
| (±)-MCG-III-211-A01 | 0.28 |
| (±)-MCG-III-211-A02 | 0.33 |
| (±)-MCG-III-211-A03 | 0.28 |
| (±)-MCG-III-211-A04 | 0.35 |
| (±)-MCG-III-212-A01 | 0.06 |
| (±)-MCG-III-212-A03 | 0.06 |
| (±)-MCG-III-212-A04 | 0.06 |
| (±)-MCG-III-216-A02 | 0.10 |
| (±)-MCG-III-212-A02 | 0.36 |
| (±)-MCG-III-216-A03 | 0.11 |
| (±)-MCG-III-216-A04 | 0.10 |
| (±)-MCG-III-214-A01 | 0.24 |
| (±)-MCG-III-214-A03 | 0.09 |
| (±)-MCG-III-214-A04 | 0.18 |
| (±)-MCG-III-157-B01 | 0.42 |
| (±)-MCG-III-157-B02 | 0.68 |
| (±)-MCG-III-157-B03 | 0.43 |
| (±)-MCG-III-157-B04 | 0.69 |
| (±)-MCG-III-207 | 0.48 |
| (+)-MCG-III-207 | 0.58 |
| (−)-MCG-III-207 | 0.28 |
| (S)-MCG-III-115 | 0.39 |
| (S)-MCG-III-188-A01 | 0.50 |
| (S)-MCG-III-188-A02 | 0.53 |
| (S)-MCG-III-188-A03 | 0.47 |
| (S)-MCG-IV-058 | 0.51 |
| (S)-MCG-IV-061 | 0.62 |
| (S)-MCG-IV-267 | 0.30 |
| (S)-MCG-IV-031-A02 | 0.37 |
| (S)-MCG-IV-031-A03 | 0.71 |
| (S)-MCG-IV-031-A04 | 0.54 |
| (S)-MCG-IV-031-A05 | 0.55 |
| (S)-MCG-IV-031-A06 | 0.42 |
| (S)-MCG-IV-210 | 0.58 |
| (S)-MCG-IV-211 | 0.25 |
| (S)-MCG-IV-053-A01 | 0.42 |
| (S)-MCG-IV-053-A05 | 0.85 |
| (S)-MCG-IV-053-A06 | 0.60 |
| (3R,5S)-MCG-IV-272 | 0.07 |
| (3R,5S)-MCG-IV-226 | 0.11 |
| (3R,5S)-MCG-IV-273 | 0.06 |
| (3R,5S)-MCG-IV-274 | 0.06 |
| (S)-MCG-IV-024-A02 | 0.38 |
| (S)-MCG-IV-024-B02 | 0.36 |
| (S)-MCG-IV-050-A01 | 0.44 |
| (S)-MCG-IV-050-A02 | 0.49 |
| (S)-MCG-IV-063-A01 | 0.33 |
| (S)-MCG-IV-063-A02 | 0.35 |
| (S)-MCG-IV-063-A03 | 0.48 |
| (S)-MCG-IV-063-A05 | 0.45 |
| (S)-MCG-IV-063-A06 | 0.36 |

Example 202

To identify molecules able to expose vulnerable Env epitopes, a cell-based ELISA (CBE) assay was adapted, capable of measuring conformational changes of membrane-bound trimeric Env as described in Veillette, 2014, J. Vis. Exp. doi:10.3791/51995:51995; Haim, 2011, PLoS Pathog 7:e1002101, into a high-throughput screening (HTS) platform (FIG. 10A). Briefly, the cytoplasmic-tail deleted HIV-$1_{JR-FL}$ Tier-2/3 Env was expressed on the surface of HOS cells in a 384-well-plate format. The cytoplasmic tail of Env was deleted to enhance Env expression at the cell surface and therefore enhance the sensitivity of the CBE assay. See, Veilette and Haim, 2009, PLoS Pathog 5:e100036. Small molecules or, as a positive control, soluble (sCD4) were added to expose the HIV-$1_{JR-FL}$ EnvΔCT epitope that can be recognized by the CD4i antibody 17b. See, Wyatt, 1995, J. Virol. 69:5723-5733; Rizzuto, 1998, Science 280:1949-1953.

17b binding was detected by a horseradish peroxidase-conjugated (HRP) second antibody, and HRP enzyme activity was measured by Western Lightning oxidizing and luminal reagents. 17b binding in the presence of sCD4 was set as the control (FIG. 10B, blue dots), small molecules that enhanced 17b binding above 25% of the one induced by sCD4 were retested in quadruplicate and only one molecule (UM0059920) was deemed a true positive (FIG. 10B, red dots). Adding (S)-MCG-II-153 but not (R)-MCG-II-156 enhanced 17b binding to similar levels as UM0059920 in the CBE assay.

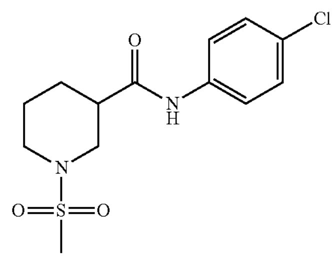

UM0059920

Synthesis of the individual enantiomers and testing by CBE revealed the active enantiomer to be (S)-MCG-II-153 (FIG. 10C). (S)-MCG-II-153 shared the halogenated aromatic ring attached via an amide (or oxalamide) linker to a piperidine (later indane) core. However, NBD-556 lacked the methyl sulfonamide substituent on the piperidine nitrogen. The straightforward access to (S)-MCG-II-153 via a two-step synthesis made this lead structure. A fluorine atom was added ortho to the chlorine atom on the aromatic ring and compared its ability to expose the CoRBS to early (NBD-556), and late [(+)-BNM-III-170] generations of CD4mc.

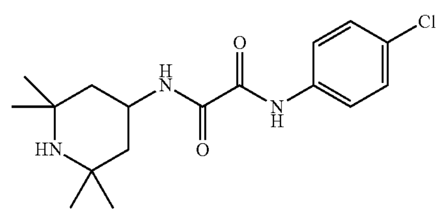

NBD-556

The CBE was used to evaluate 17b binding to HIV-$1_{JR-FL}$ EnvΔCT expressed at the surface of HOS cells in the presence of the different compounds (50 μM), sCD4 (10 μg/m) or the compounds' vehicle (DMSO). These data illustrated that addition of the fluorine enhanced the capacity of (S)-MCG-III-027-D05 to expose the CoRBS, compared with (S)-MCG-II-153 (FIG. 11). Importantly, (S)-MCG-III-027-D05 exposed CoRBS at levels similar levels to those reached by NBD-556. Interestingly, it was found that analogs sharing replacement of the sulfonamide substituent presented higher activity [(S)-MCG-III-188-A01, (S)-MCG-III-188-A02, (S)-MCG-IV-031-A05, and (S)-MCG-IV-210]. See, FIG. 12.

To gain a better understanding of their mode of action, certain analogs were co-crystallized in complex with a gp120 core (LM/HT $gp120_{CRF01\_A}$ $core_e$) stabilized in the gp120 in the CD4-bound conformation. See, Zoubchenok, J.

Figure 6:
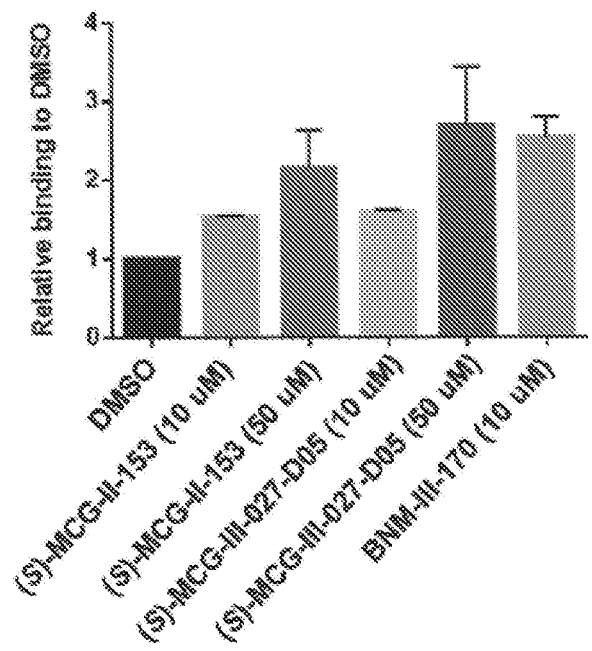
FIG. 6 is a bar graph showing the effect of compounds of the disclosure shown in Example 2 on monomeric gp120 conformational changes as described in Example 32.
Figure 7:
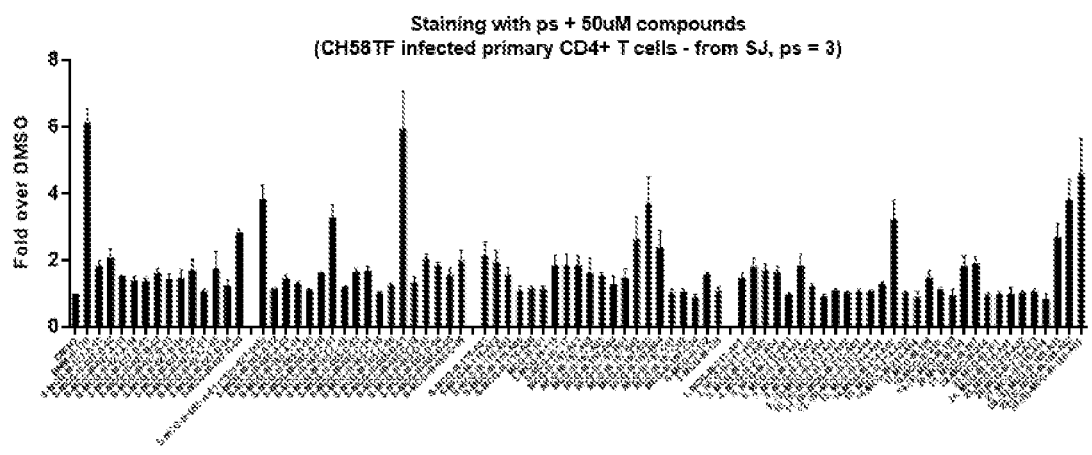
FIG. 7 is a bar graph showing the recognition of primary CD4+ T cells infected with the transmitted/founder CH58 virus by HIV+ sera described in Example 32 of compounds disclosed herein shown in Examples 1-31. Compounds labeled with red did not dissolve well in PBS. Compounds labeled in blue had non-specific binding to mock cells.
Figure 8:
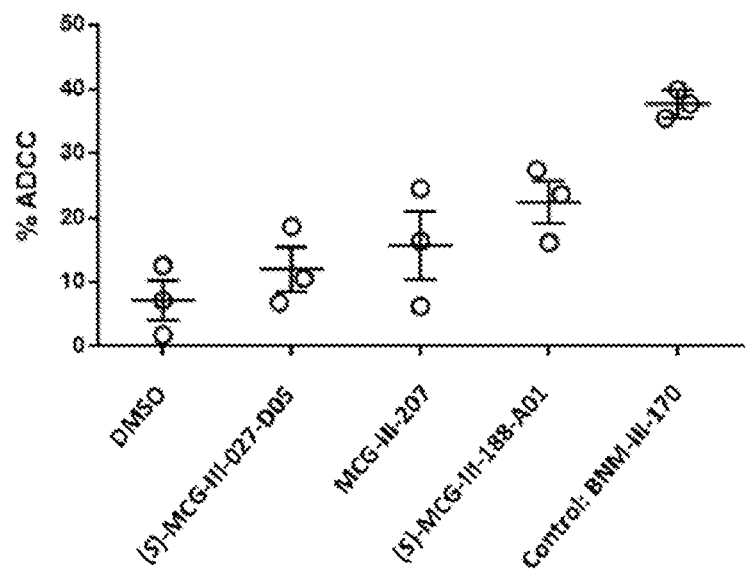
FIG. 8 is a plot showing the effect of (S)-MCG-III-027-D05, MCG-III-207 and (S)-MCG-III-188-A01 shown in Examples 1, 29 and 31 on ADCC as described in Example 32.
Figure 9:
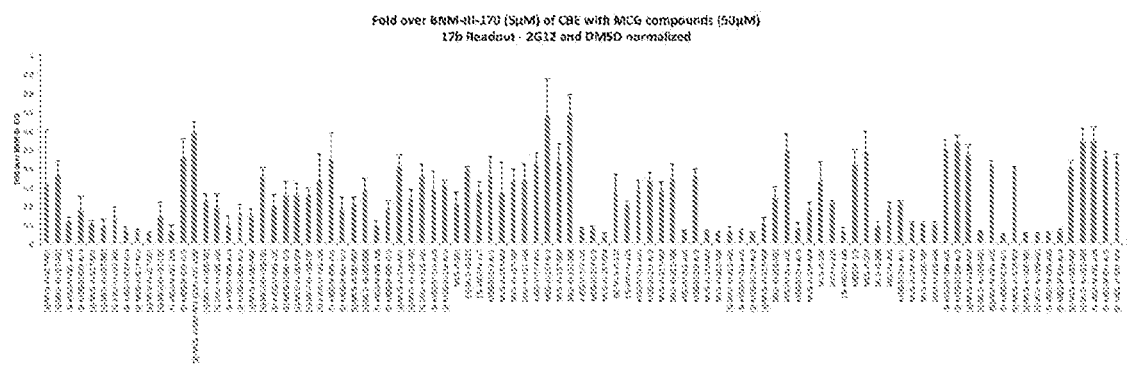
FIG. 9 is a bar graph showing the effect of compounds of the disclosure on the recognition of HIV-1 infected cells by 17b as described in Example 32 using examples shown in Examples 1-31.
Figure 10A:
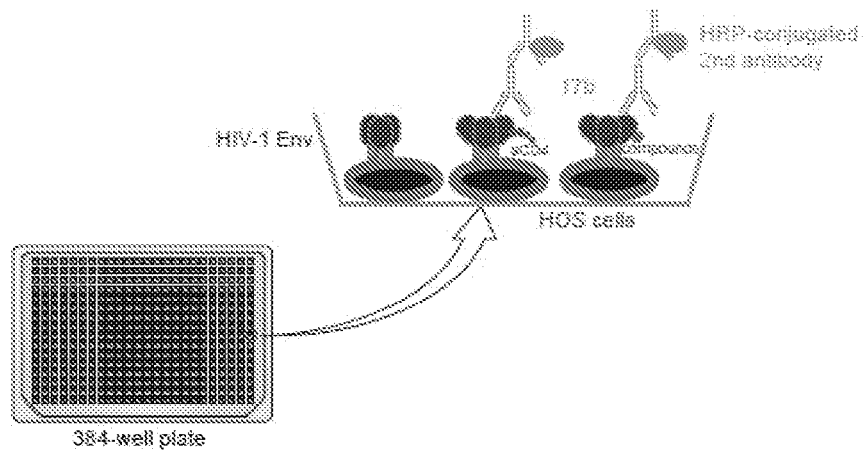
FIG. 10A is a schematic of a high-throughput screening of small molecules for their ability to exp cance was evaluated using a paired t test (*, P<0.05; ****, P<0.0001; ns, not significant).
Figure 10B:
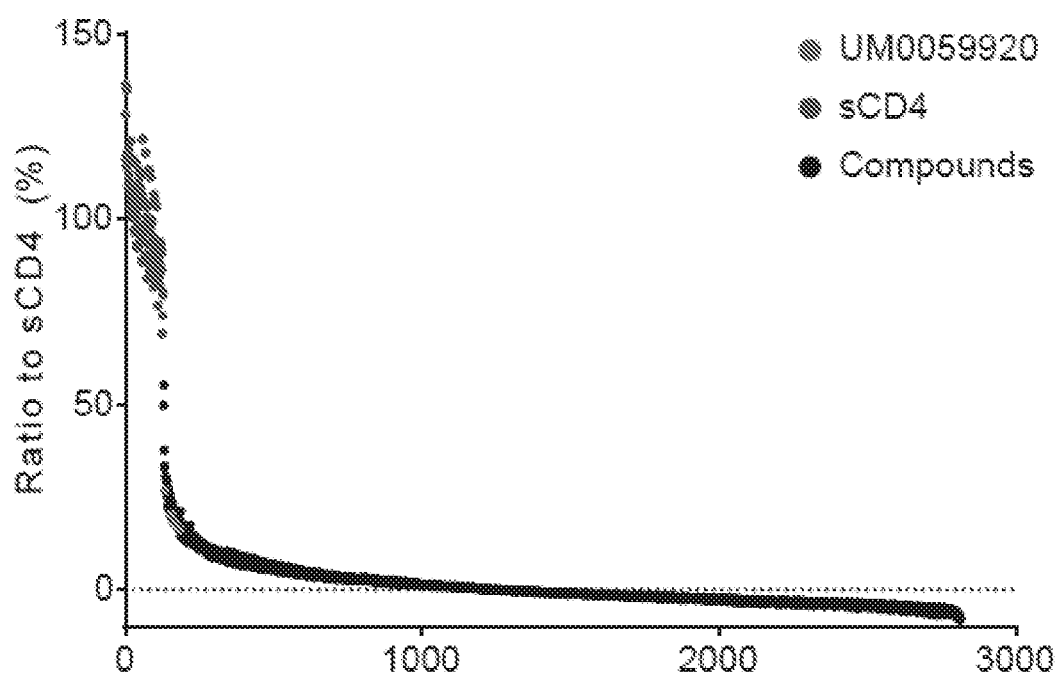
Figure 10C:
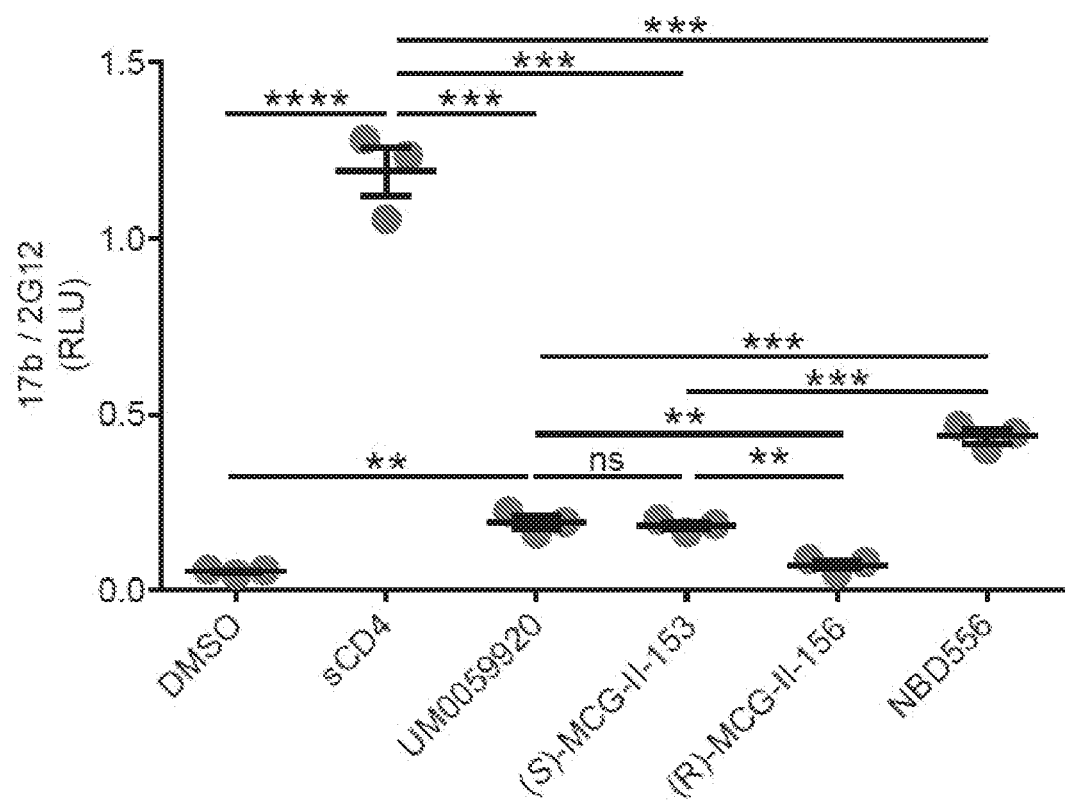
Figure 11:
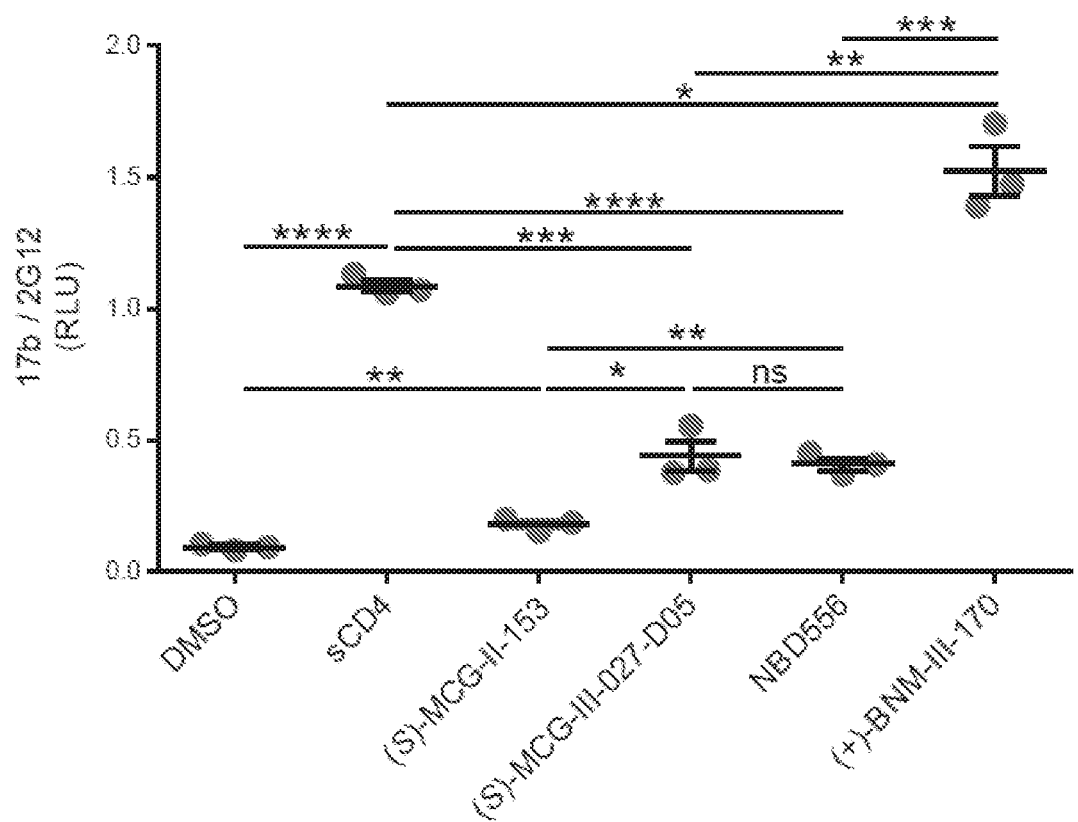
Figure 12:
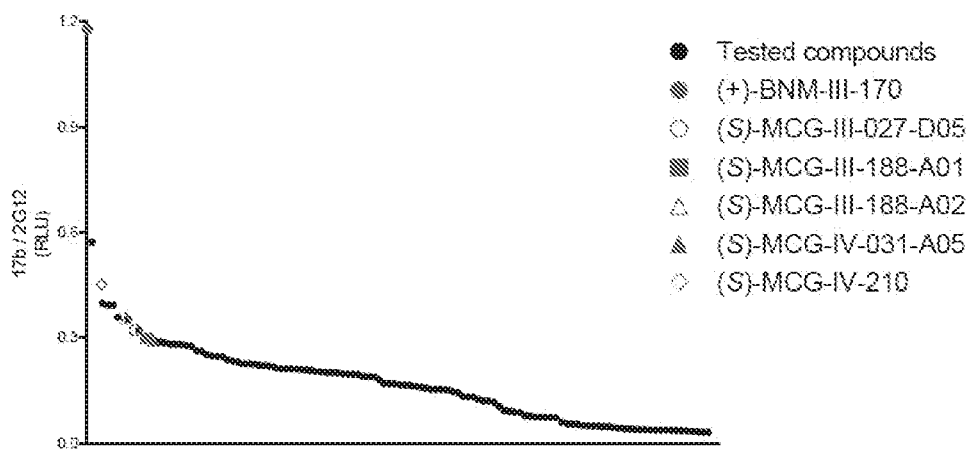
Figures 1, 13A:
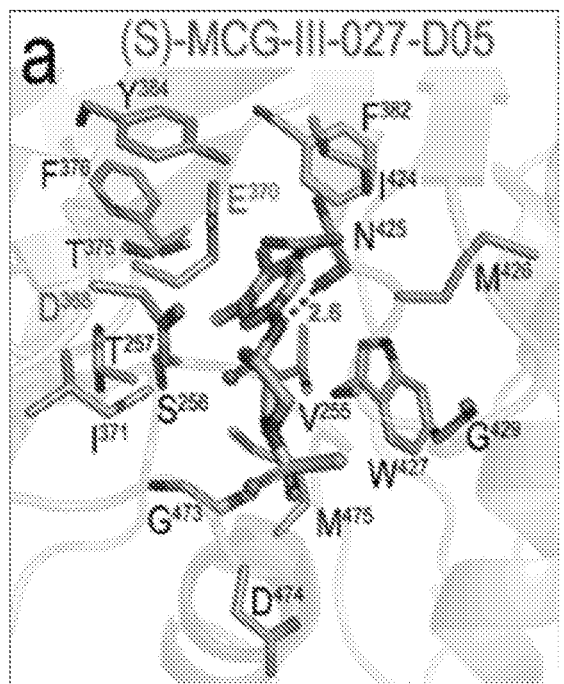
Figures 2, 13A:
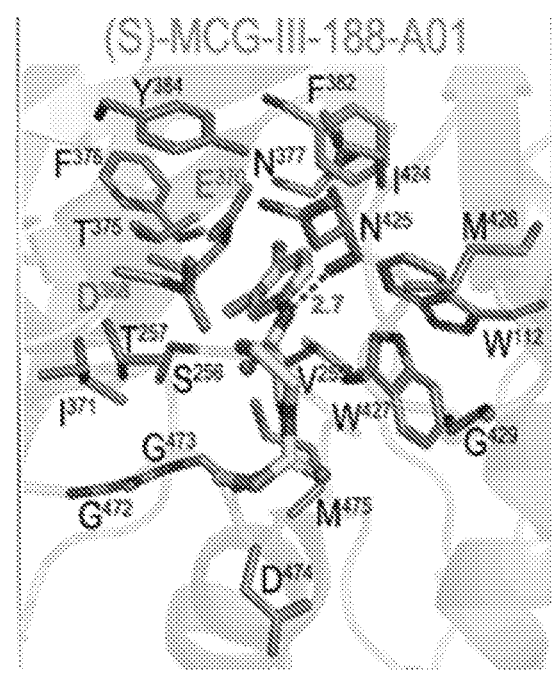
Figures 3, 13A:
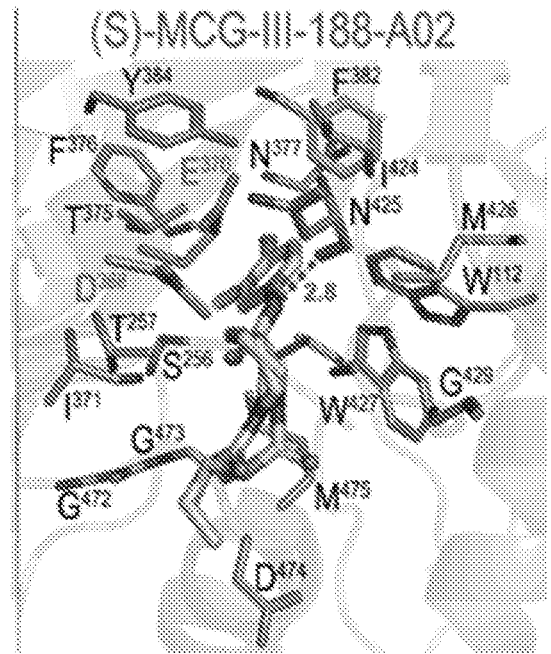
Figures 4, 13A:
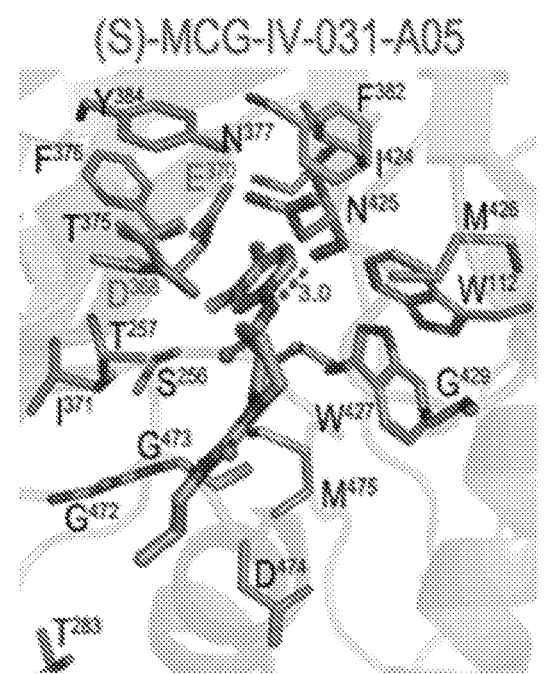
Figures 5, 13A:
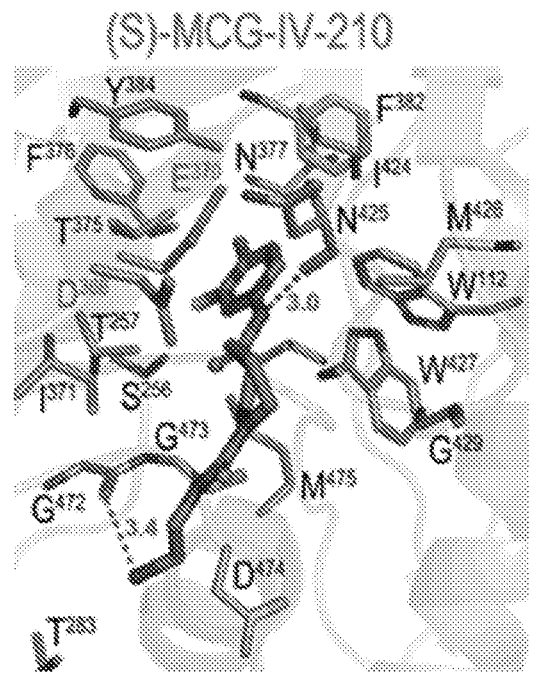
Figures 6, 13A:
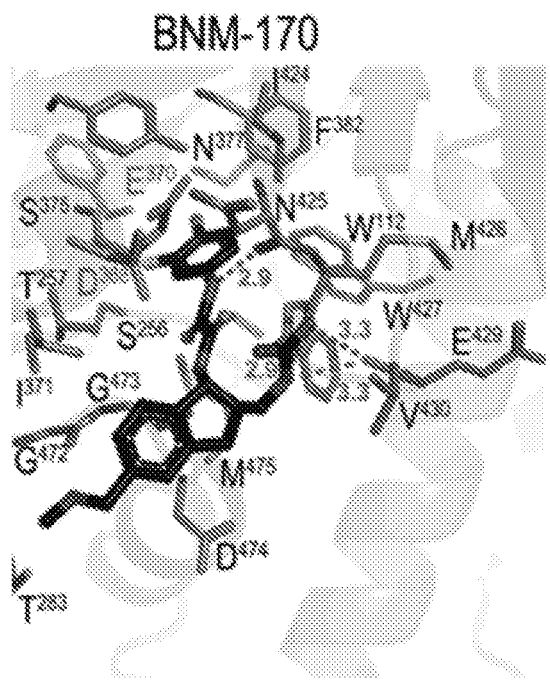

Virol. 91. Complex structures of a gp120$_{CRF01\_A}$ core$_e$ with (S)-MCG-III-027-D05, (S)-MCG-III-188-A01, (S)-MCG-III-188-A02, (S)-MCG-IV-031-A05, and (S)-MCG-IV-210 were solved in the same P2$_1$2$_1$2$_1$ orthorhombic space group (Table 2) at 3.25-Å, 2.2-Å, 1.84-Å, 2.24-Å, and 2.65-Å resolution, respectively. As shown in FIG. 13A-1 to 13A-6, the tested MCG analogs bind within the CD4 binding site, with the aromatic ring anchoring deeply in the Phe43 cavity; the entrance to this cavity is occupied by Phe43 of CD4 in the gp120-CD4 receptor complex. See, Kwong, 1998, Nature 393:648-659. Interestingly, the chloride group of the 4-chloro-3-fluoro substituted aromatic ring packs against Cβ atom of Thr$^{375}$, contributing significantly to the binding through hydrophobic forces (FIG. 13A-1 to 13A-6). The compounds largely overlap when bound to the CD4 binding cavity (FIG. 13C). Also, they involve almost the same set of gp120 residues for binding that include: Val$^{255}$, Ser$^{265}$, Thr$^{257}$, Asp$^{368}$, Glu$^{370}$, Ile$^{371}$, Thr$^{37}$, Phe$^{376}$, Phe$^{382}$, Tyr$^{384}$, Ile$^{424}$, Asn$^{425}$, Gly$^{429}$, Gly$^{473}$, Asp$^{474}$ and Met$^{475}$. In addition, analogs sharing replacement of the sulfonamide substituent, e.g. (S)-MCG-III-188-A01, (S)-MCG-III-188-A02, (S)-MCG-IV-031-A05, and (S)-MCG-IV-210, reach deep into the Phe43 cavity and are within van der Waals contact distance to Trp$^{112}$ and the Gly$^{472}$Gly$^{473}$ stretch immediately preceding the α5 helix of gp120 (FIG. 13A-1 to 13A-6). The contribution of residues lining the Phe43 cavity to the binding of each compound is shown in FIG. 13D. Interestingly, all but (S)-MCG-III-188-A01 contact Asp$^{474}$, with the highest buried surface area for this residue observed for the most potent compound in this group: (S)-MCG-IV-210 (FIG. 13D). Overall, (S)-MCG-IV-210 stands out among the compounds tested. (S)-MCG-IV-210 establishes the most contacts with gp120 with: a) the highest total area buried at the interface, 687 Å$^2$ (as compared to: 641 Å$^2$ for (S)-MCG-III-188-A01 >614 Å$^2$ for (S)-MCG-III-027-D05 >604 Å$^2$ for (S)-MCG-IV-031-A05 >592 Å$^2$ for (S)-MCG-III-188-A02); b) the addition of a hydrogen bond with the main chain oxygen of Gly$^{472}$; c) the highest buried surface area of Gly$^{473}$ (FIG. 13C); and d) the furthest reach toward Thr$^{283}$ (FIGS. 13A and 13C). Overall the binding mode of (S)-MCG-IV-210 is reminiscent of the binding mode of BNM-III-170 (see, Melillo, 2016, ACS Med Chem Lett 7:330-334), with improved contacts in (S)-MCG-IV-210 to the highly conserved gp120 residue Asp$^{368}$ (FIG. 13B-1 to B-6).

Figures 1, 13B:
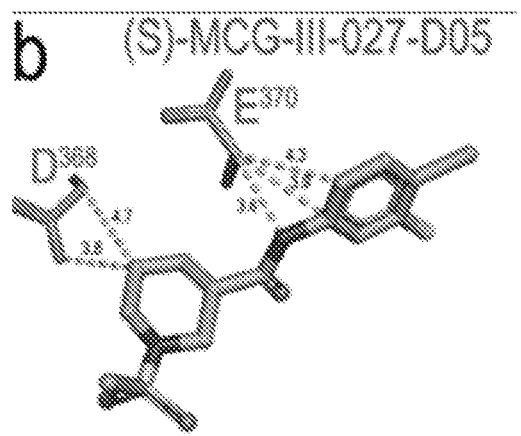
Figures 2, 13B:
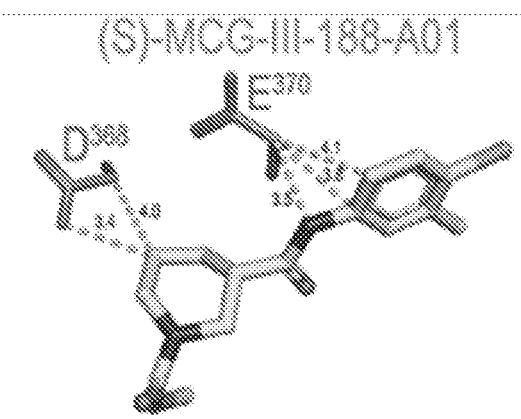
Figures 3, 13B:
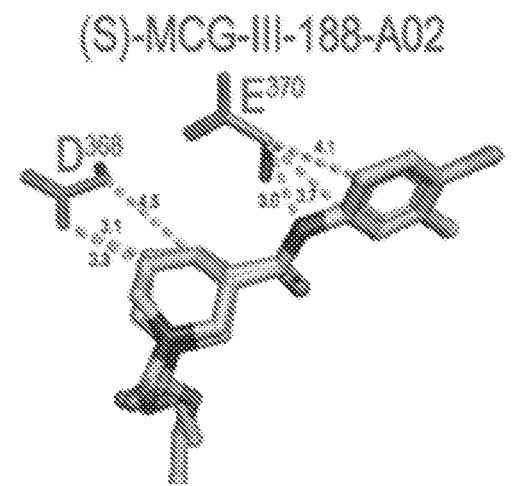
Figures 4, 13B:
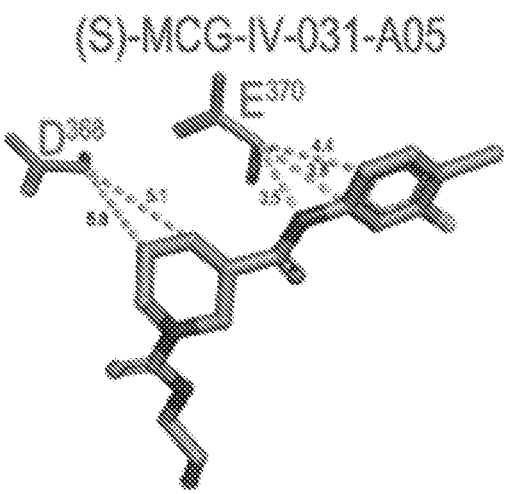
Figures 5, 13B:
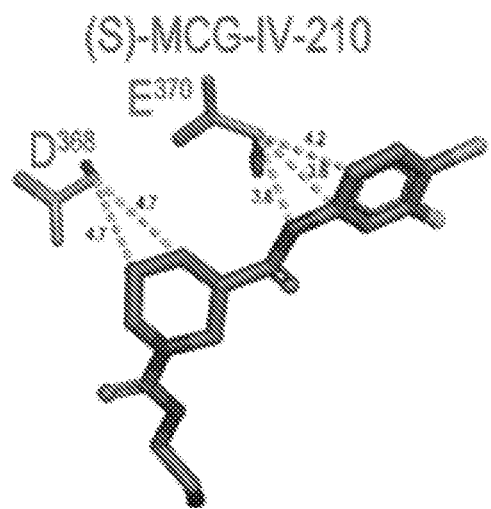
Figures 6, 13B:
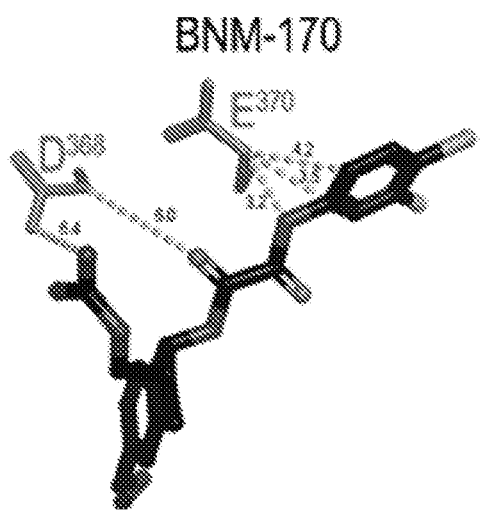
Figure 13C:
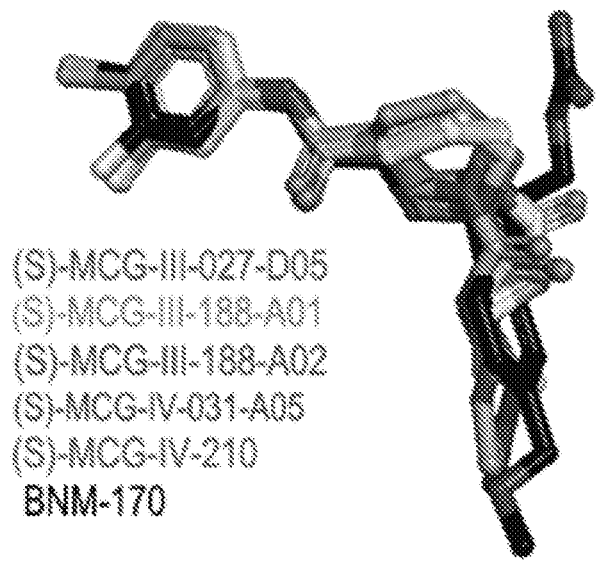
Figure 13D:
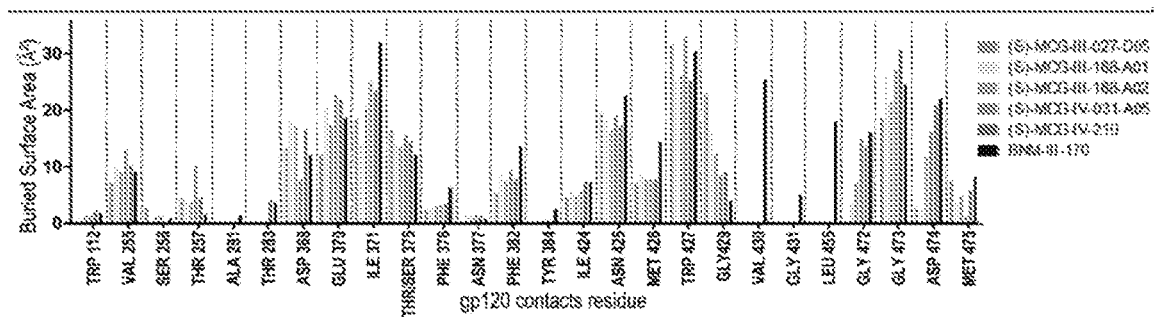
Figure 16:
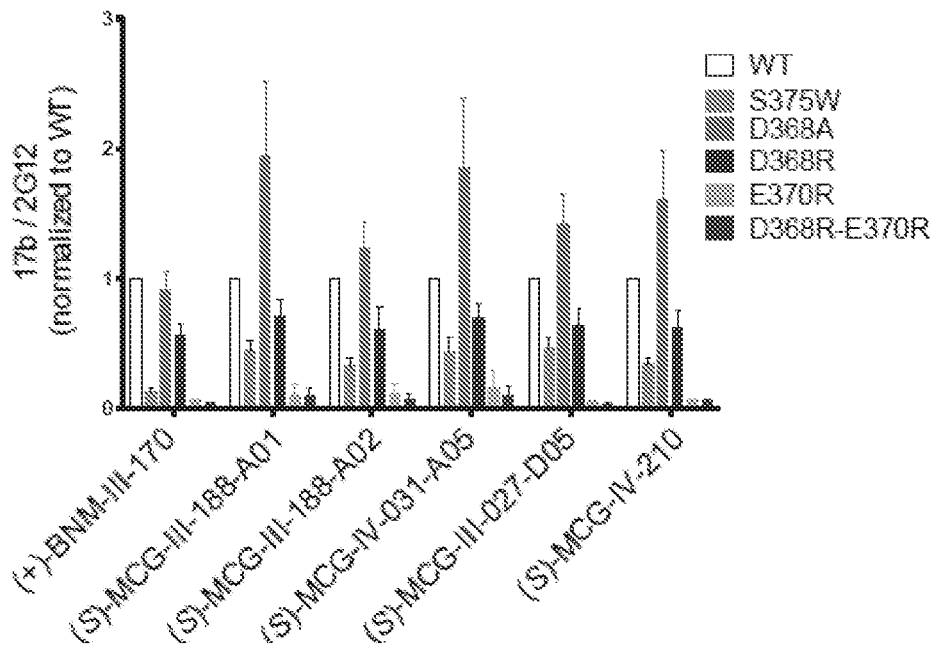

FIG. 13B-1 to 13B-6 shows the network of interactions of these CD4mc with the side chain atoms of Asp$^{368}$ and Glu$^{370}$, two highly-conserved CD4-binding site residues. In all cases, there are extensive contacts mediated by C atoms of the 4-chloro-3-fluoro substituted aromatic ring and piperidine ring to the Cβ atom or carboxyl oxygen of Asp$^{368}$ and Glu$^{370}$ (as measured by distances below 5 Å). To test the contribution of Asp$^{368}$ and Glu$^{370}$ to CD4mc binding, these residues were altered alone and in combination, then evaluated the ability of the CD4mc to expose the CoRBS of these mutant Envs. Of note, none of the altered gp120 residues are part of the 17b epitope. See, Rizzuto 1998 cited above. In addition, residue 375 was altered, which lines the Phe43 cavity. As expected, and as shown in FIG. 16, filling the Phe43 cavity with a tryptophan (S375W) almost completely abrogated the capacity of all CD4mc tested to expose the 17b epitope as measured by CBE. Interestingly, it was found that substitution of aspartic acid (D368) with alanine (A368) in HIV-1$_{JR-FL}$ EnvΔCT enhanced the ability of the MCG analogs to expose the CoRBS compared to wt; this result was in contrast to that observed for late generation CD4mc [(+)-BNM-III-170)], which exhibited no impact of D368A relative to the unmodified EnvΔCT. This indicates a hydrophobic interaction mediated by a Cβ atom of the residue at position 368 is sufficient to stabilize CD4mc in the Phe43 cavity, and the interactions mediated by the carboxyl group of Asp368 may have a potentially disrupting effect. Additionally, substitution of the D368 residue with an arginine (D368R) reduced the ability of all compounds to induce exposure of the CoRBS for all compounds to the same extent. Moreover, substitution of E370 with an arginine (E370R) or addition of the D368R to the E370R abrogated the activity of all CD4mc tested.

(S)-MCG-IV-210 Stabilizes State 2A

HIV-1 Env is a flexible molecule known to sample three different conformational states (States 1-3). By exploring the Env conformational landscape in association with the epitopes recognized by different classes of CD4i Abs, it was found that Env is able to sample a fourth conformation, State 2A, in the presence of the CD4mc (+)-BNM-III-170 and sera from HIV-1-infected individuals. The hallmark of State 2A is the exposure of otherwise occluded cluster A gp120 epitopes which are exposed upon a sequential opening of the trimer. This opening requires the initial triggering by CD4mc, followed by interaction of CoRBS Abs, which then exposes the cluster A region.

Figure 14A:
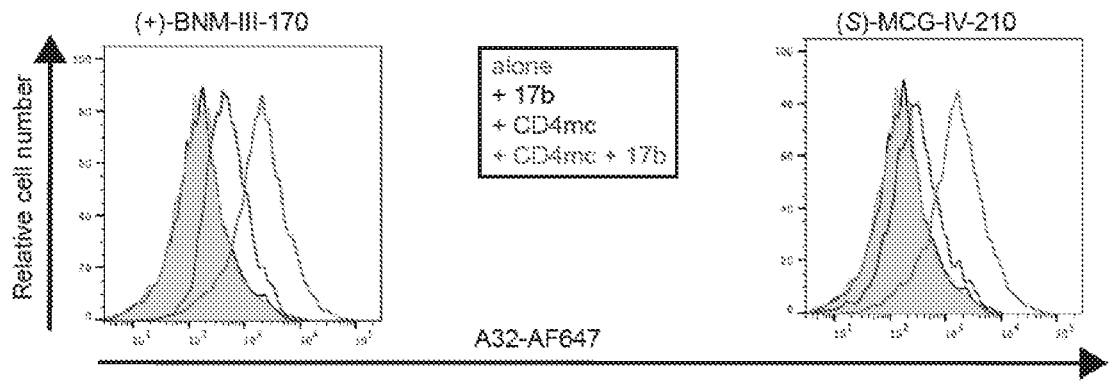
Figure 14B:
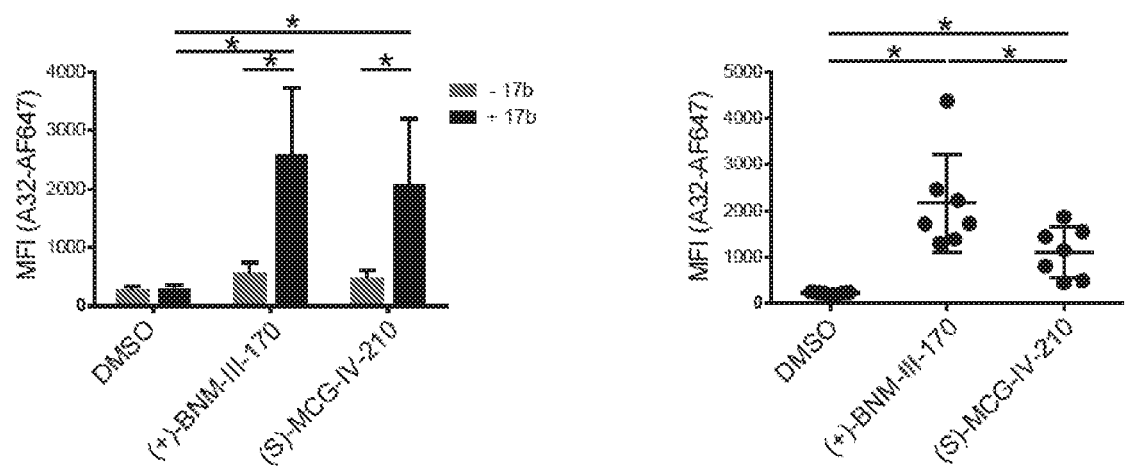
Figure 14C:
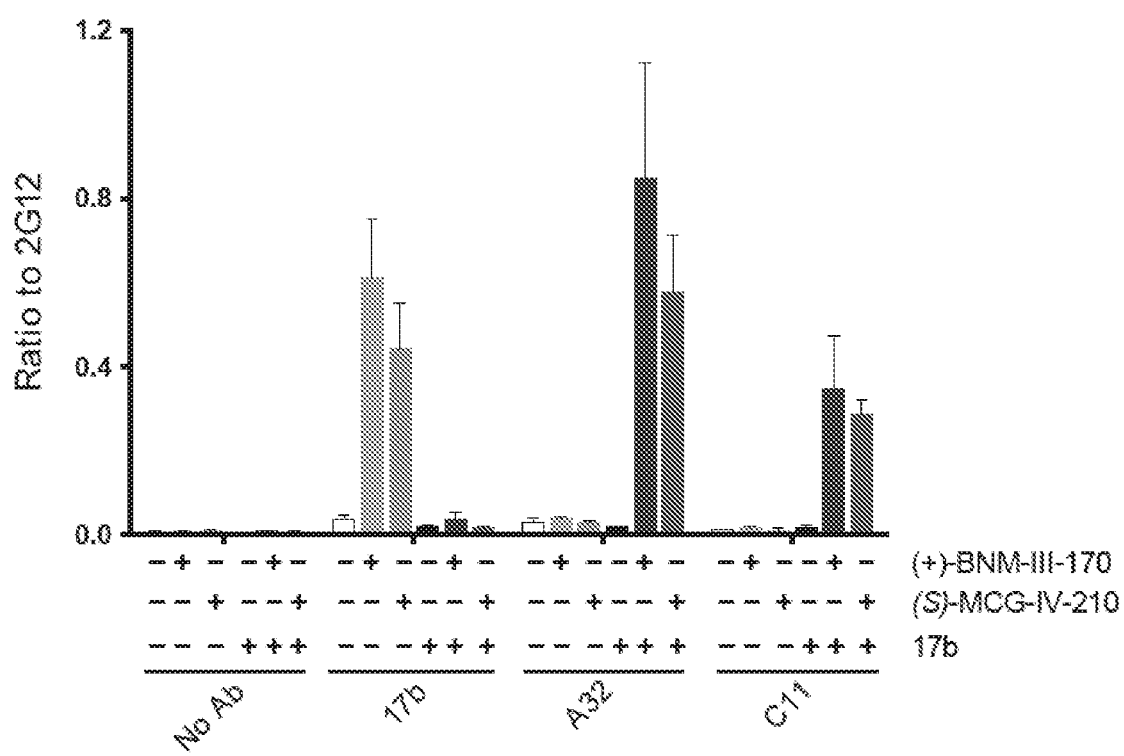

To evaluate whether (S)-MCG-IV-210 was able to stabilize State 2A, primary CD4+ T cells were infected with the primary CH58 transmitted/founder (CH58 TF) virus and evaluated the exposure of the cluster A region with an Alexa-Fluor 647-conjugated A32 (A32-AF647) antibody in the presence or absence of CD4mc and the CoRBS 17b Ab, as reported. See, Richard, 2016, EbioMedicine doi:10.1016/j.ebiom.2016.09.004. Specifically, gor cell surface staining with A32-AF647, primary CD4 T cells isolated from PBMC were infected with HIV-1$_{CH58TF}$ for 48 hours. Cells were then incubated with A32-AF647 together with 5 µg/ml 17b (a, b, c) or 1:1000 diluted HIV+ plasma from infected individuals (d) in the presence of DMSO, 50 µM (+)-BNM-III-170 or 50 µM (S)-MCG-IV-210 at 37° C. Mean fluorescence intensity (MFI) of A32-AF647 was measured by flow cytometry. As a positive control, the CD4mc (+)-BNM-III-170 was used and previously shown to stabilize State 2A and expose the A32 epitope in the presence of 17b. See, Alsahafi, 2019, Cell Host Microbe 25:578-587 e575. A32-AF647 failed to bind infected cells in the absence of CD4mc. Addition of 17b significantly enhanced the recognition of infected cells by A32-647 in the presence of (+)-BNM-III-170 or (S)-MCG-IV-210 (FIGS. 14A-C). Since anti-cluster A and CoRBS Abs are present in a majority of HIV-1-infected individuals (Veillette, 2015, J. Virol. 89:545-551; Decker, 2005, J. Exp. Med. 201:1407-1419), HIV+ plasma was evaluated to determined if it facilitated the exposure of the A32 epitope in presence of (+)-BNM-III-170 and (S)-MCG-IV-210. Although (+)-BNM-III-170 exhibited higher activity, both CD4mc significantly enhanced binding of infected cells by A32-AF647 in the presence of HIV+ plasma (FIG. 14D); thus, both CD4mc apparently stabilize State 2A at the surface of HIV-1-infected cells.

To verify that (S)-MCG-IV-210 also stabilizes State 2A at the surface of viral particles, a virus capture assay was adapted to evaluate Env conformation on virions. See, Moore, 2006, J. Virol. 80:2515-2528 and Kassa, 2009, J. Virol. This virus-based ELISA (VBE) assay relies on the capture of HIV-1 virions by anti-Env Abs immobilized on ELISA plates. The viral particles used in this assay were generated by co-transfecting the pNL4.3 Luc Env-construct (Kassa, 2009, J. Virol.; Desormeaux, 2013, Mol. Cell 37:656-667; Pacheco, 2017, J. Virol. 91) with a plasmid encoding the Env of the transmitted/founder virus CH58

(Ochsenbauer, 2012, J. Virol. 86:2715-2728; Bar, 2012, PLoS Pathog 8:e1002721; Parrish, 2013, Proc Natl Acad Sci USA 110:6626-6633; Fenton-May, 2013, Retrovirology 10:146) and a plasmid encoding the G glycoprotein from vesicular stomatitis virus (VSV-G), resulting in a virus capable of a single round of infection. Specifically, virus produced from 293T cells co-transfected with plasmids pNL4.3 Luc Env-, HIV-1$_{CH58TF}$ and VSV-G was incubated with or without 5 µg/ml 17b in the presence of DMSO, 50 µM (+)-BNM-III-170 or 50 µM (S)-MCG-IV-210 at 37° C. for one hour. Virus was then applied to ELISA plates coated with Abs 2G12, 17b, A32 or C11 overnight at 4° C. Free virions were washed away and HEK293T cells were added to the well. After 48 hours, cells were lysed and luciferase activity was measured. To compare the binding capacity of different Abs, the relative ratio of the luciferase activity to the luciferase activity of 2G12 was calculated. Infection was mediated by VSV-G and measured by luciferase activity 2 days after incubation with the HEK293T cells. In agreement with the occluded nature of CD4i epitopes, CoRBS 17b and anti-cluster A A32 and C11 Abs failed to capture viral particles. Addition of both CD4mc exposed the CoRBS region as shown by a dramatic increase in 17b-mediated capture of virions (FIG. 14E). In agreement with a sequential opening of the trimer required to expose the cluster A region, addition of CD4mc in combination with 17b was required to permit virion capture by the A32 and C11 Cluster A antibodies. Altogether, these results indicate that (S)-MCG-IV-210 is able to stabilize State 2A at the surface of infected cells and viral particles.

(S)-MCG-IV-210 Sensitizes HIV-1-Infected Cells to ADCC and Prevents Killing of Uninfected Bystander CD4+ T Cells The ADCC susceptibility of primary CD4+ T cells infected with CH58 TF mediated by HIV+ plasma+/−MCG analogs also was evaluated using a FACS-based assay as previously reported. See, Ding, 2016, J Virol., 90:2127-2134; and Richard, 2018, MBio 9.

Briefly, Primary CD4 T cells isolated from PBMC were infected with HIV-1$_{CH58TF}$ for 48 hours. For cell surface staining, 5 µg/ml 17b (FIG. 15A) or 1:1000 diluted HIV+ plasma (n=15) (FIG. 15B) were used in the presence of the different MCG analogs (50 µM), (+)-BNM-III-170 or with an equivalent volume of vehicle (DMSO). An Alexa Fluor 647-conjugated anti-human IgG secondary Ab was then used for fluorescent labeling. For ADCC (FIG. 15C), infected cells were used as target cells in a FACS-based ADCC assay that measures the killing of infected (p24+ cells). See, Madani, 2016, J. Virol., 90:5031-5046. The assay determines susceptibility to ADCC mediated by a 1/1,000 dilution of plasma from 15 HIV-1-infected individuals in the presence of the different MCG analogs (50 µM), (+)-BNM-III-170 (50 µM) or with an equivalent volume of vehicle (DMSO). Correlation between cell-surface staining with HIV+ plasma and ADCC was calculated using the Spearman rank correlation (FIG. 15D).

Figure 15A:
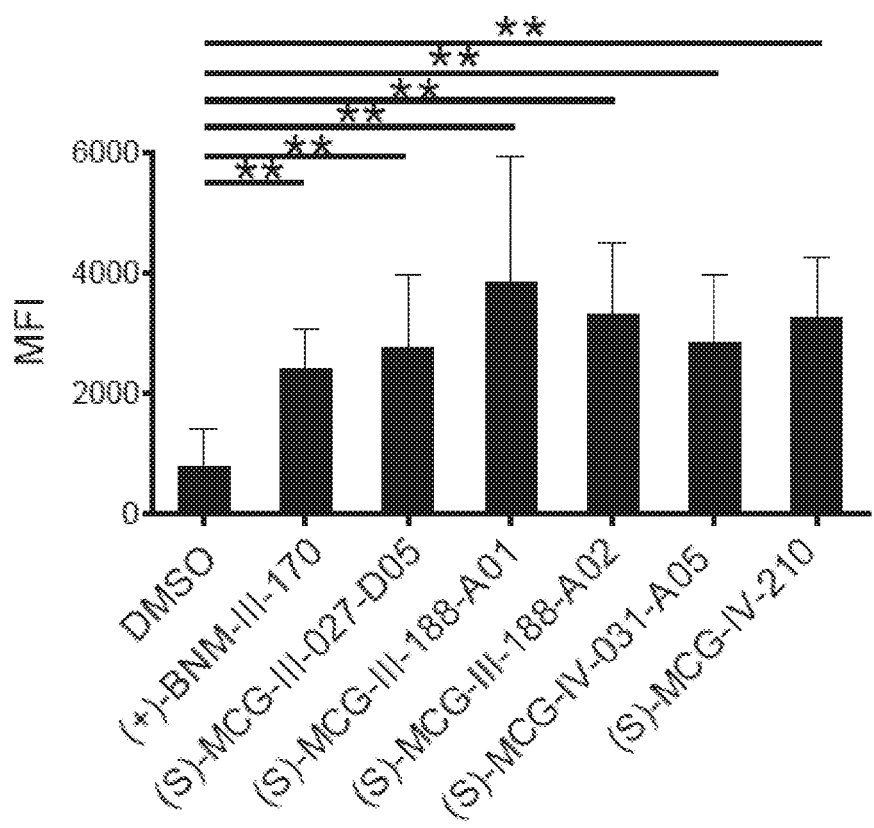
Figure 15B:
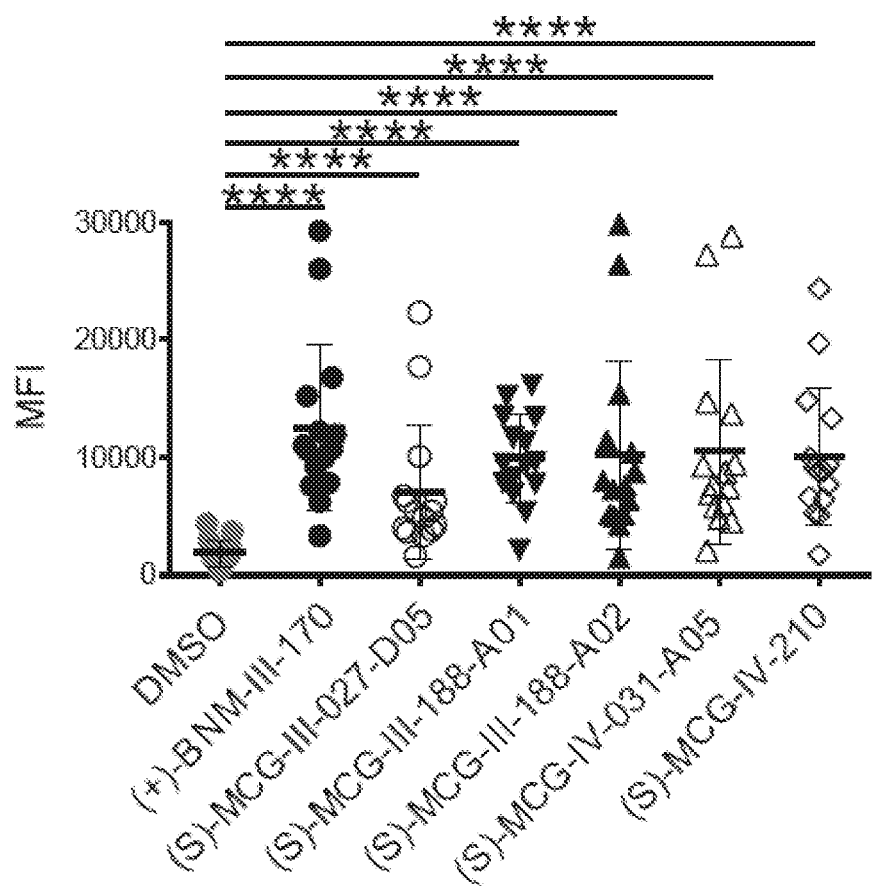
Figure 15C:
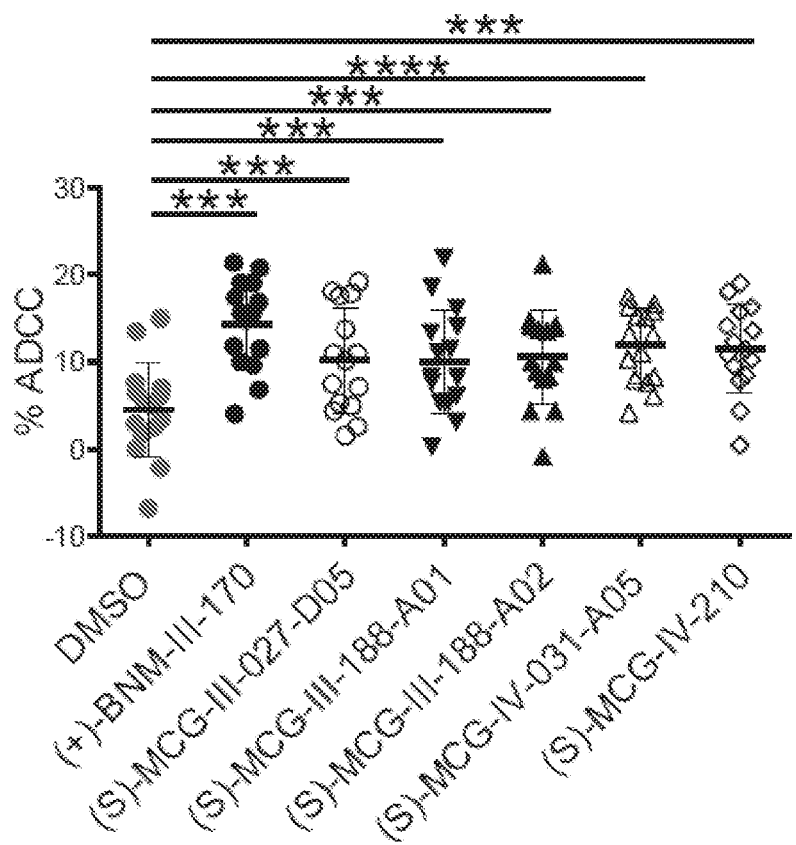
Figure 15D:
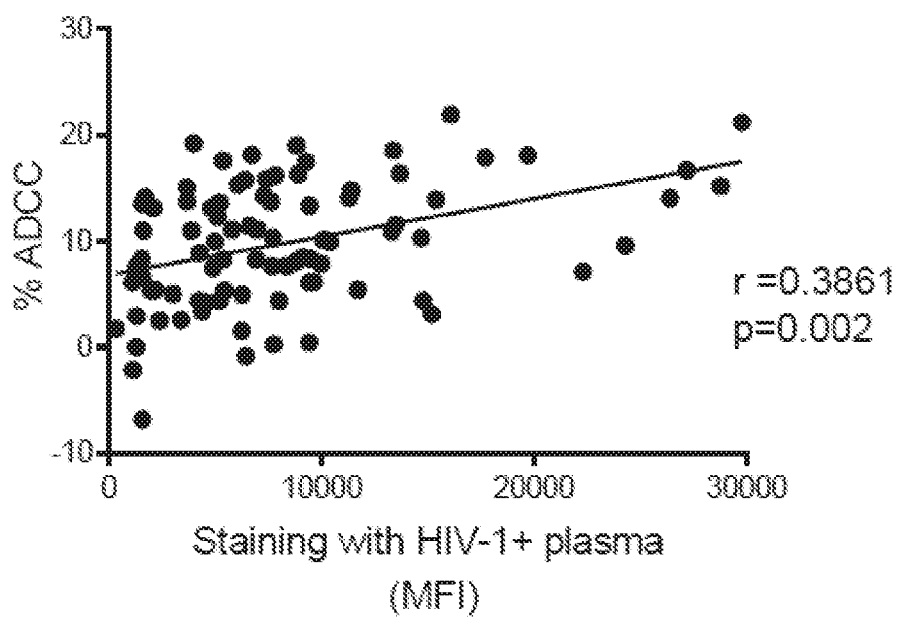

As shown in FIGS. 15A and 15B, all tested MCG CD4mc [(S)-MCG-III-027-D05, (S)-MCG-III-188-A01, (S)-MCG-III-188-A02, (S)-MCG-IV-031-A05, and (S)-MCG-IV-210] enhanced the recognition of infected cells by the anti-CoRBS 17b antibody and by plasma from 15 HIV-1-infected individuals. Importantly, enhanced recognition of infected cells was translated into enhanced ADCC responses, supporting the positive correlation expected for these two activities (FIGS. 15C and 15D).

To evaluate the direct virus-neutralizing ability of the analogs, I, HIV-1$_{CH58TF}$ was incubated with indicated amounts of different compounds or DMSO for 1 hour at 37° C., then added to TZM-bl cells. After incubation for 48 h at 37° C., luciferase activity was measured. Relative infectivity was calculated as the percentage of the value seen in the absence of compound. To measure the ability of (S)-MCG-IV-210 to sensitize viral particles to neutralization by otherwise non-neutralizing 17b (FIG. 15F), HIV-1$_{CH58TF}$ was incubated with the indicated amounts of 17b in the presence of 0.5 µM (+)-BNM-III-170, 20 µM (S)-MCG-IV-210 or DMSO for 1 hour at 37° C., then added to TZM-bl cells. After incubation for 48 h at 37° C., luciferase activity was measured.

Figure 17A:
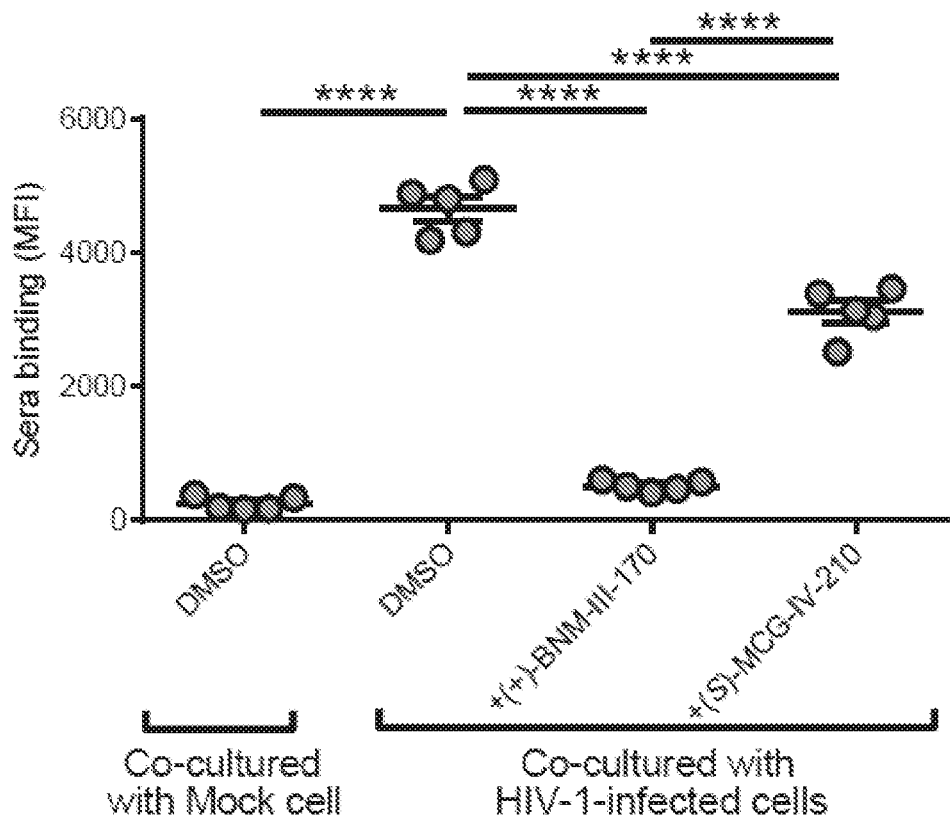

The capacity of (S)-MCG-IV-210 to protect uninfected bystander CD4+ T cells from ADCC responses was evaluated. Briefly, primary CD4+ T cells were infected with the NL4-3.ADA.GFP WT virus. The cell proliferation dye eFluor-450 was used to stain uninfected autologous CD4+ T cells, which were then added to the infected cells (eFluor-450-cells) and co-cultured for 72 h. The ability of HIV+ plasma to recognize uninfected bystander cells in the presence of 50 µM (+)-BNM-III-170 or (S)-MCG-IV-210 was evaluated by FACS (FIG. 17A). These uninfected eFluor 450+ cells were also used as target cells for ADCC with autologous PBMC and 5 HIV+ plasma in the presence of 50 µM (+)-BNM-III-170 or (S)-MCG-IV-210 (FIG. 17B).

Figure 17B:
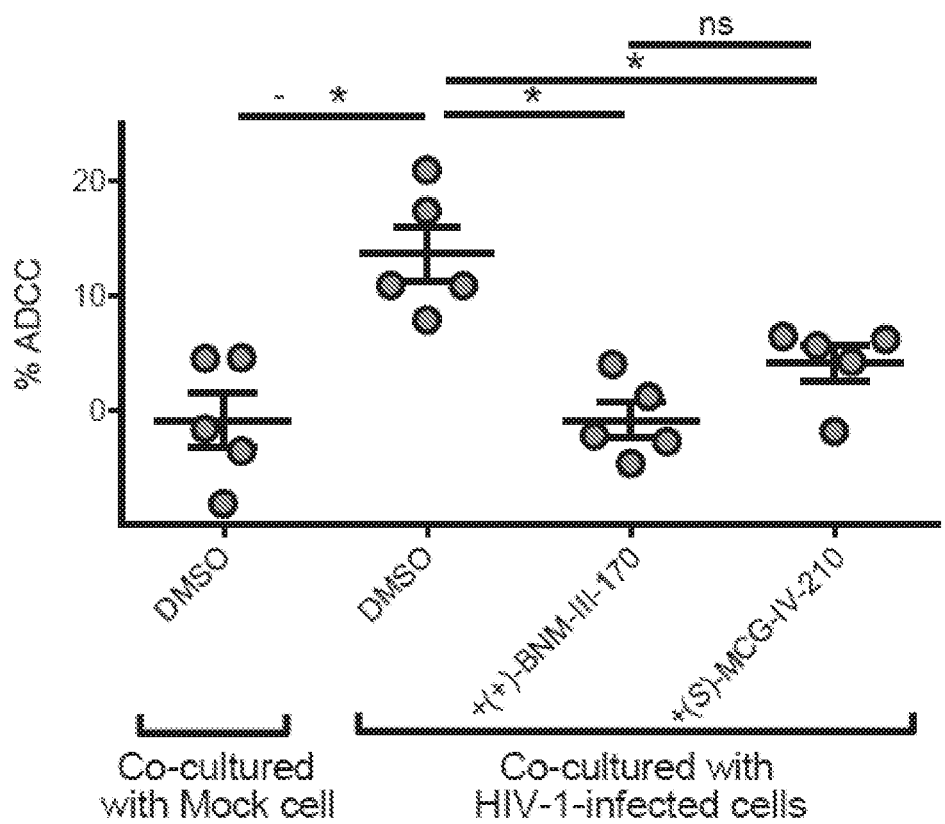

When (+)-BNM-III-170 or (S)-MCG-IV-210 were added at the time of co-culture between infected and eFluor-450-stained bystander cells, recognition of bystander cells by HIV+ plasma was significantly decreased, thereby protecting uninfected bystander CD4+ T cells from ADCC-mediating killing (FIG. 17B). This observation suggests that, besides sensitizing HIV-1-infected cells to ADCC, (S)-MCG-IV-210 analogs might have therapeutic utility by preventing the death of uninfected CD4+ T cells.

Figure 15E:
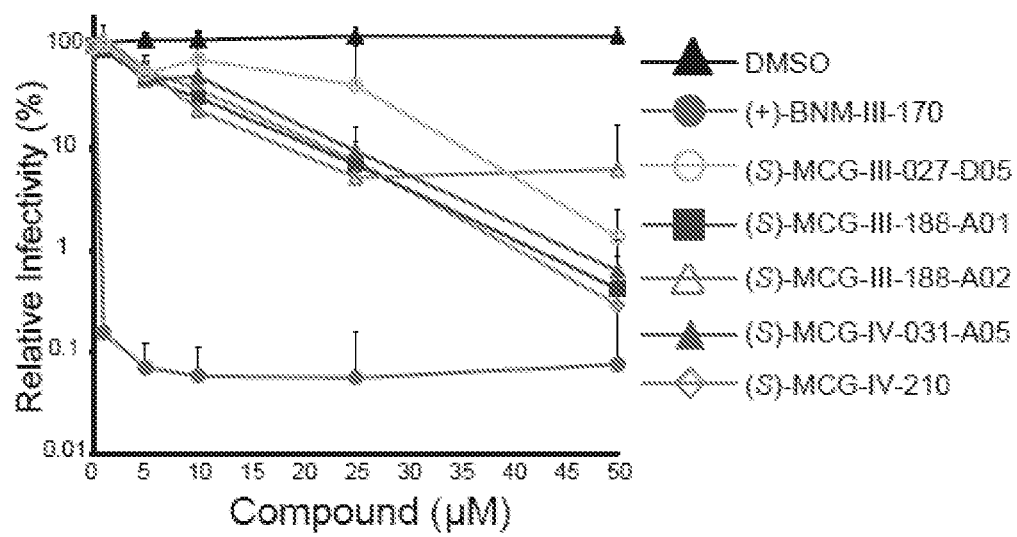

(S)-MCG-IV-210 Both Neutralizes Viral Particles and Sensitizes Viral Particles to Neutralization by nnAbs Since (S)-MCG-IV-210 exhibited the highest activity among the different MCG analogs, the capacity of (S)-MCG-IV-210 to neutralize HIV-1 viral particles bearing the primary HIV-1$_{CH58TF}$ Env in a standard TZM-bl assay was evaluated. As a positive control, (+)-BNM-III-170 was used, which has been reported to inhibit HIV-1 infection at low micromolar concentrations. See, Melillo, ACS Med Chem Lett 7:330-334. (+)-BNM-III-170 neutralized HIV-1$_{CH58TF}$ with an IC$_{50}$ of 0.11 uM. While all tested MCG analogs also neutralized HIV-1$_{CH58TF}$, they did so with only modest potency (FIG. 15E). For example, MCG-IV-210 inhibited HIV-1$_{CH58TF}$ infection with an IC$_{50}$ of 6.97 µM.

Figure 15F:
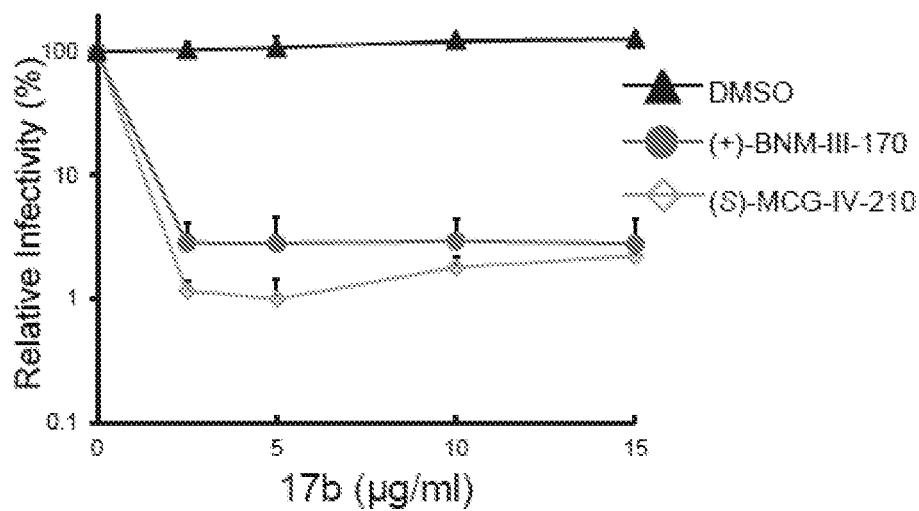

Another well-documented antiviral property of CD4mc is their capacity to sensitize viral particles to neutralization by otherwise non-neutralizing antibodies. See, Madani, 2018, Nat. Commun. 9:2363; Madani, 2014, J. Virol. 88:6542-6555; and Madani, 2016, J. Virol., 90:5031-5046. (S)-MCG-IV-210 was tested to determine if this compound shared this property. It was found that the anti-CoRBS 17b Ab did not neutralize infectious viral particles bearing the primary HIV-1$_{CH58}$ Env, but potently neutralized these same viral particles when they were sensitized with sub-inhibitory concentrations of (S)-MCG-IV-210 (FIG. 15F).

Summary: In combination with CoRBS Abs or HIV+ plasma, these new small molecule CD4mc stabilized the antibody-vulnerable State-2A conformation and sensitized HIV-1-infected cells to ADCC. Although these CD4mc have low direct neutralization capacities, they sensitize viral particles to neutralization by otherwise non-neutralizing antibodies. This family of CD4mc thus has some unique features that warrant additional efforts to improve their potency. The 3-substituted piperidine core is readily accessible from commercial (S)-3-piperidinecarboxylic acid via amide coupling with 4-chloro-3-fluoroaniline. The piperidine nitrogen can then be reacted with a variety of electrophiles to access N-substituted piperidine analogs. For example, addition of an alkyl urea with a terminal amino group [(S)-MCG-IV-210] further improved the capacity of the compound to "open" Env. Accordingly, (S)-MCG-IV-210 was able to stabilize the vulnerable State-2A conformation at the surface of HIV-1-infected cells and viral particles. Thus the small molecule MCG compounds could serve as a new scaffold to develop more potent CD4mc able to sensitize HIV-1-infected cells to ADCC and viral particles to commonly-elicited non-neutralizing antibodies.

Co-crystal structures of these small-molecule CD4mc with a modified gp120 core confirm that these compounds anchor deeply within the HIV-1 gp120 Phe43 cavity, while also establishing contacts with the residues at the cavity rim. Most importantly, the mode of binding of this class of CD4mc allows contacts to the side chain atoms of $Asp^{368}$ and $Glu^{370}$. These two residues are highly conserved in HIV-1 circulating strains; therefore, targeting these sites by analogs capable of establishing side chain specific contacts to these residues might ensure the breadth of this class of CD4mcs.

TABLE 2

| | LM/HT $gp120_{CRF01\_AE}$ $core_e$ - (S)-MCG-III-027-D05 | LM/HT $gp120_{CRF01\_AE}$ $core_e$ - (S)-MCG-III-188-A01 | LM/HT $gp120_{CRF01\_AE}$ $core_e$ - (S)-MCG-III-188-A02 | LM/HT $gp120_{CRF01\_AE}$ $core_e$ - (S)-MCG-IV-031-A05 | LM/HT $gp120_{CRF01\_AE}$ $core_e$ - (S)-MCG-IV-210 |
|---|---|---|---|---|---|
| Data collection | | | | | |
| Wavelength, Å | 0.979 | 0.920 | 0.920 | 0.979 | 0.979 |
| Space group | $P2_12_12_1$ | $P2_12_12_1$ | $P2_12_12_1$ | $P2_12_12_1$ | $P2_12_12_1$ |
| Cell parameters | | | | | |
| a, b, c, | 66.3, 67.2, 86.4 | 66.3,67.0, 86.9 | 66.6, 66.8, 86.4 | 67.1,66.8, 85.9 | 66.4, 67.9, 86.4 |
| α, β, γ, ° | 90, 90, 90 | 90, 90, 90 | 90, 90, 90 | 90, 90, 90 | 90, 90, 90 |
| Complexes/a.u. | 1 | 1 | 1 | 1 | 1 |
| Resolution, (Å) | 50-3.25 (3.31-3.25) | 50-2.2 (2.32-2.2) | 50-1.84 (1.94-1.84) | 50-2..24 (2.37-2.24) | 50-2.65 (2.79-2.65) |
| # of reflections | | | | | |
| Total | | | | | |
| Unique | 19,162 | 69,146 | 71,541 | 46,804 | 28,961 |
| $R_{merge}^a$, % | 4,355 | 18,550 | 29,710 | 15,219 | 9,603 |
| $R_{pim}^b$, % | 21.3 (86.6) | 11.0 (72.4) | 7.0 (55.4) | 16.5 (55.7) | 35.4 (100) |
| $CC_{1/2}^c$ | 10.8 (51.3) | 6.2 (41.1) | 5.2 (43.5) | 10.7 (36.4) | 23.1 (78.5) |
| I/σ | 0.96 (0.45) | 0.99 (0.72) | 0.99 (0.69) | 0.96 (0.45) | 0.87 (0.51) |
| Completeness, | 12.6 (1.6) | 4.4 (1.0) | 6.9 (1.3) | 5.2 (3.0) | 2.2 (0.8) |
| % | 67.6 (65.9) | 92.3 (95.0) | 88.5 (93.3) | 80.6 (85.5) | 82.4 (83.6) |
| Redundancy | 4.4 (4.1) | 3.7 (3.7) | 2.4 (2.3) | 3.1 (3.0) | 3.0 (3.1) |
| Refinement | | | | | |
| Statistics | 50.0-3.25 | 50.0-2.2 | 50.0-1.84 | 50.0-2.25 | 50.0-2.65 |
| Resolution, Å | 20.8 | 19.8 | 19.2 | 22.0 | 24.9 |
| $R^d$ % | 26.5 | 24.5 | 23.1 | 27.9 | 30.7 |
| $R_{free}^e$, % | | | | | |
| # of atoms | 2,642 | 2,674 | 2,676 | 2,657 | 2,667 |
| Protein | — | 107 | 222 | 131 | 29 |
| Water | 176 | 190 | 199 | 178 | 178 |
| Ligand/Ion | | | | | |
| Overall B value | 100 | 42 | 32 | 25 | 29 |
| $(Å)^2$ | — | 39 | 35 | 25 | 24 |
| Protein | 115 | 60 | 43 | 36 | 39 |
| Water | | | | | |
| Ligand/Ion | | | | | |
| $RMSD^f$ | 0.006 | 0.005 | 0.009 | 0.007 | 0.005 |
| Bond lengths, | 1.0 | 0.7 | 0.9 | 1.0 | 0.8 |
| Å | | | | | |
| Bond angles, ° | | | | | |
| $Ramachandran^g$ | 90.3 | 95.8 | 96.7 | 96.4 | 94.9 |
| favored, % | 8.2 | 3.6 | 3.3 | 3.0 | 4.2 |
| allowed, % | 1.5 | 0.6 | 0.0 | 0.6 | 0.9 |
| outliers, % | 6ONV | 6ONE | 6ONF | 6ONH | 6P9N |
| PDB ID | | | | | |

Values in parentheses are for highest-resolution shell.

$^aR_{merge}$ = Σ | I − <I> |/Σ I, where I is the observed intensity and <I> is the average intensity obtained from multiple observations of symmetry-related reflections after rejections.

$^bR_{pim}$ = as defined in Weiss, 2001, Global indicators of X-ray data quality. J. Appl. Cryst. 34, 130-135.

$^cCC_{1/2}$ = as defined by Karplus and Diederichs, 2012, Linking crystallographic model and data quality, Science, 336, 1030-1033.

$^dR = \Sigma||F_o| - |F_c||/\Sigma|F_o|$, where $F_o$ and $F_c$ are the observed and calculated structure factors, respectively.

$^eR_{free}$ = as defined by Brünger, 1997, Free R value: Cross-validation in crystallography. In Methods in Enzymology, Academic Press, pp. 366-396.

$^f$RMSD = Root mean square deviation.

$^g$Calculated with MolProbity.

It is to be understood that while the invention has been described in conjunction with the preferred specific embodiments thereof, that the foregoing description and the examples that follow are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains. In addition to the embodiments described herein, the present invention contemplates and claims those inventions resulting from the combination of features of the invention cited herein and those of the cited prior art references which complement the features of the present invention. Similarly, it will be appreciated that any described material, feature, or article may be used in combination with any other material, feature, or article, and such combinations are considered within the scope of this invention.

The disclosures of each patent, patent application, and publication cited or described in this document are hereby incorporated herein by reference, each in its entirety, for all purposes.

What is claimed:

1. A method of treating HIV-1 in a human infected with HIV-1 or preventing HIV-1 infection in a human susceptible to infection with HIV-1 comprising administering to the human a therapeutically effective amount of a compound of formula (I):

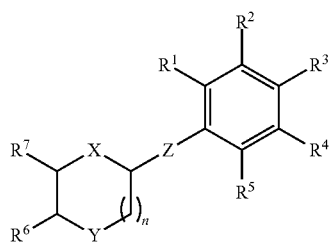

wherein:
n is 1;
X is —$CH_2$—;
Y is —N(C(O)O$C_{1-6}$alk)-, —N($SO_2R^9$)—, —N(C(O)$R^8$)—, —N(C(O)N$R^9R^{10}$)—, or —N(C(=NH)N$R^9R^{10}$)—;
Z is C(O)NH—;
$R^1$ is H;
$R^2$ is H;
(i) $R^3$ is H, halogen, $C_{1-6}$alkyl, —O$C_{1-6}$alkyl, or $C_{1-6}$haloalkyl; and $R^4$ is halogen; or (ii) $R^3$ is halo or $C_{1-6}$haloalkyl; and $R^4$ is H;
$R^5$ is H, halogen, $C_{1-6}$alkyl, —O$C_{1-6}$alkyl, or $C_{1-6}$haloalkyl;
$R^6$ and $R^7$ are each H or $NH_2$;
$R^8$ is —O$C_{1-6}$alkyl, —O—$C_{1-6}$alk-$NH_2$, —NH($C_{1-6}$alkyl), —N($C_{1-6}$alkyl)($C_{1-6}$alkyl), —NH—$C_{1-6}$alk-$NH_2$, phenyl, or heteroaryl; and
$R^9$ and $R^{10}$ are, independently, H, $C_{1-6}$alkyl, —C(O)O$C_{1-6}$alkyl, halogenated $C_{1-6}$alkyl, $C_{3-8}$cycloalkyl, aryl, or heteroaryl;

wherein $R^8$, $R^9$, and $R^{10}$ are, independently, optionally substituted by halo, CN, O$C_{1-6}$alkyl, —NHC(O)($C_{1-6}$alkyl), or unsubstituted $C_{1-6}$alkyl;
or a pharmaceutically acceptable salt thereof.

2. The method of claim 1, wherein Y is —N($SO_2R^9$).
3. The method of claim 1, wherein Y is —N(C(O)$R^8$)—.
4. The method of claim 3, wherein Y is —N(C(O)O$C_{1-6}$alkyl).
5. The method of claim 1, wherein Y is —N(C(O)N$R^9R^{10}$)—.
6. The method of claim 1, wherein Y is —N(C(=NH)N$R^9R^{10}$)—.
7. The method of claim 1, wherein:
$R^3$ is Cl and $R^5$ is H;
$R^3$ is F and $R^5$ is H;
$R^3$ is Br and $R^5$ is H;
$R^3$ is $CF_3$ and $R^5$ is H;
$R^4$ is Cl and $R^3$ and $R^5$ is H;
$R^4$ is Br and $R^3$ and $R^5$ is H;
$R^4$ is F and $R^3$ and $R^5$ is H;
$R^5$ is H;
$R^5$ is H, $R^3$ is Cl and $R^4$ is F;
$R^5$ is H, $R^3$ is F and $R^4$ is Cl;
$R^5$ is H, $R^3$ is Cl are $R^4$ is Br;
$R^5$ is H, $R^3$ is Br are $R^4$ is Cl;
$R^5$ is H, $R^3$ and $R^4$ are Cl;
$R^5$ is H, $R^3$ and $R^4$ are F;
$R^5$ is H, $R^3$ is $CF_3$ and $R^4$ is F;
$R^3$ is H, $R^4$ is F and $R^5$ is Cl; or
$R^3$ is H, $R^4$ is Cl and $R^5$ is F.
8. The method of claim 1, wherein Y is —N($SO_2R^9$)—.
9. The method of claim 1, wherein the compound is of formula (III), (V), (VI), (VII), (VIII), (IX), or (X):

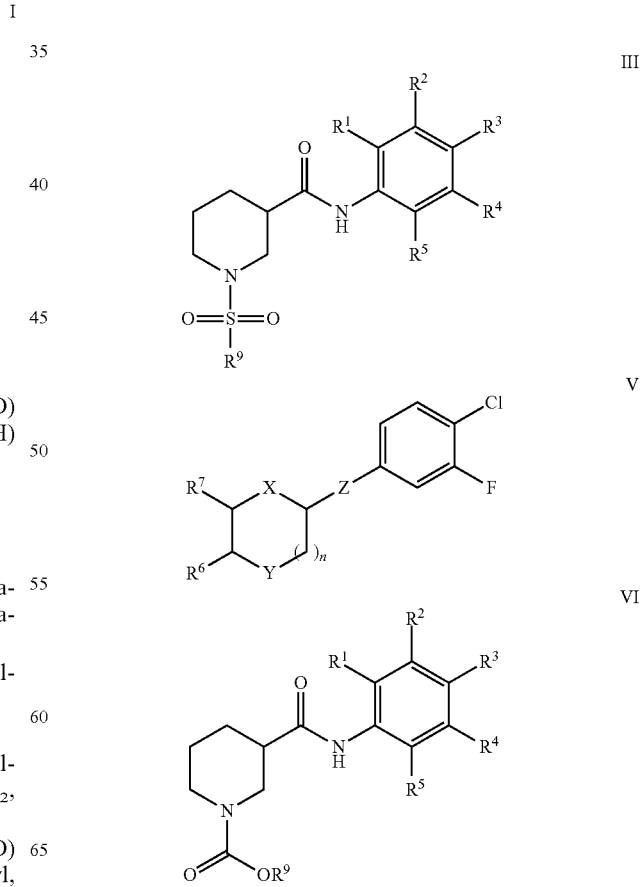

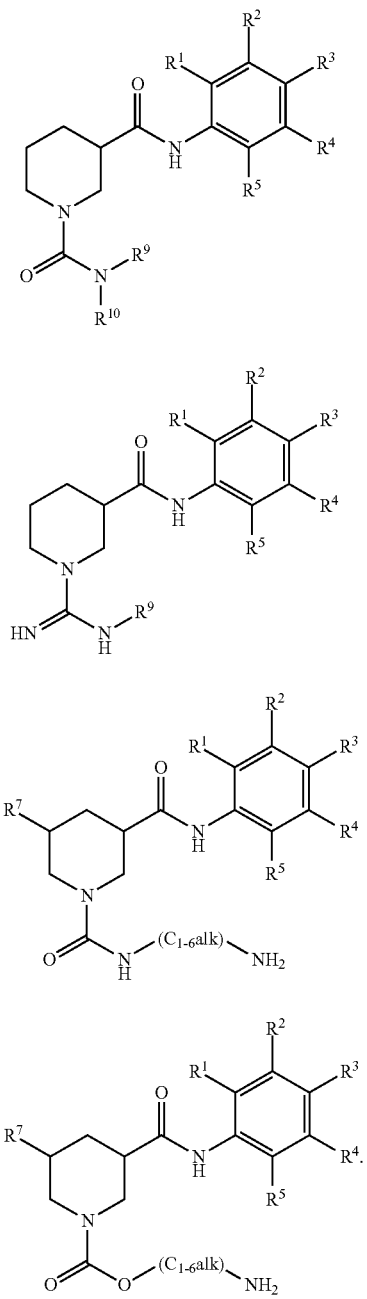
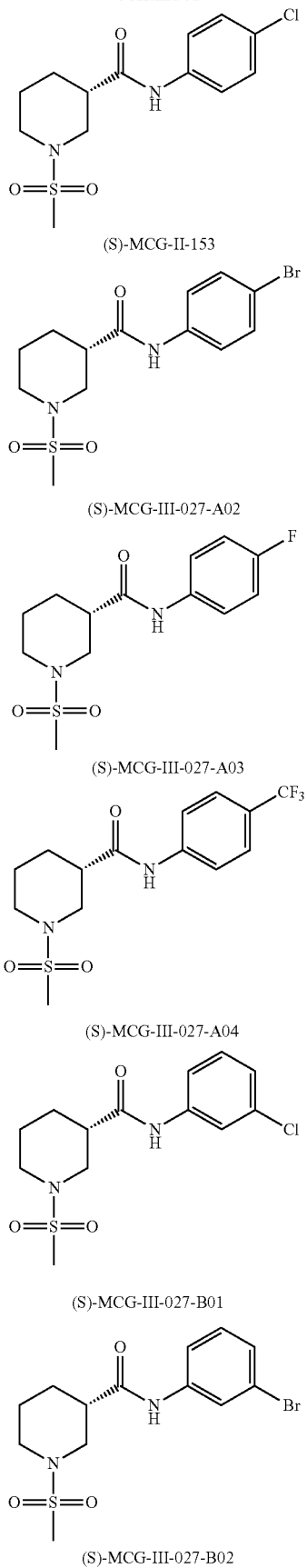
10. The method of claim 1, wherein the compound is:
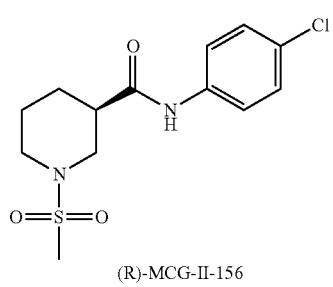

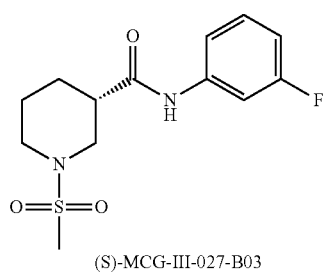
(S)-MCG-III-027-B03
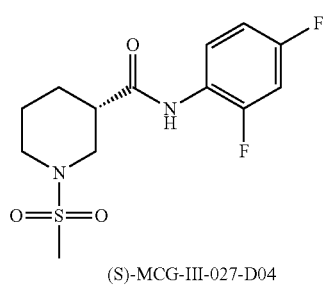
(S)-MCG-III-027-D04
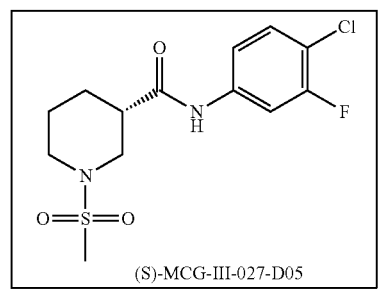
(S)-MCG-III-027-D05
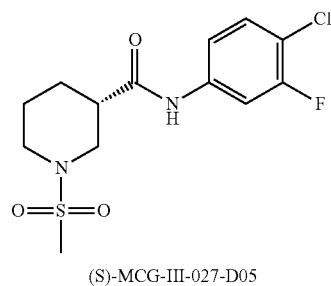
(S)-MCG-III-027-D05
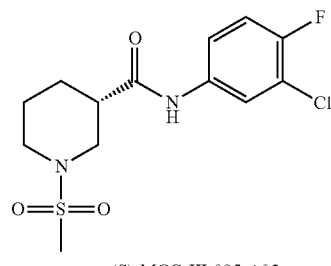
(S)-MCG-III-085-A02
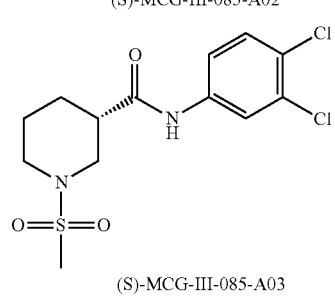
(S)-MCG-III-085-A03
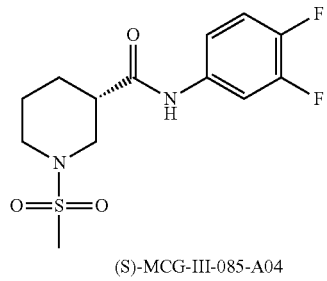
(S)-MCG-III-085-A04
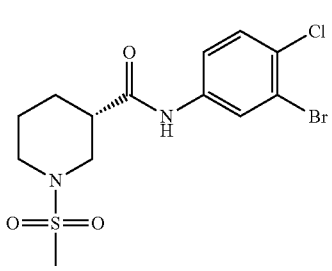
(S)-MCG-III-085-A05
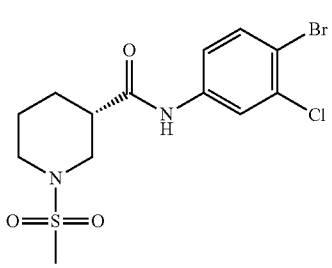
(S)-MCG-III-085-A05
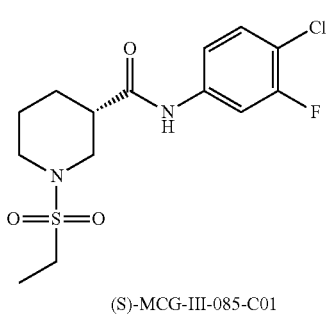
(S)-MCG-III-085-C01
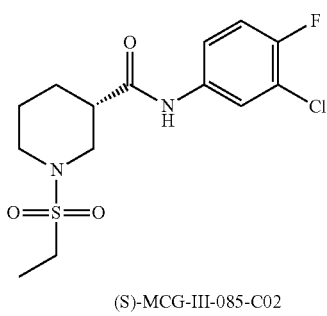
(S)-MCG-III-085-C02

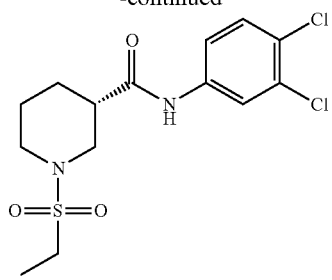
(S)-MCG-III-085-C03
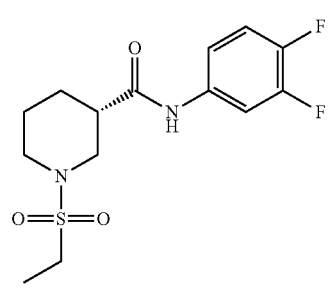
(S)-MCG-III-085-C04
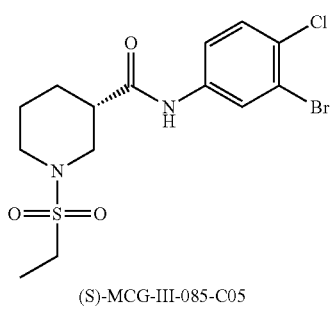
(S)-MCG-III-085-C05
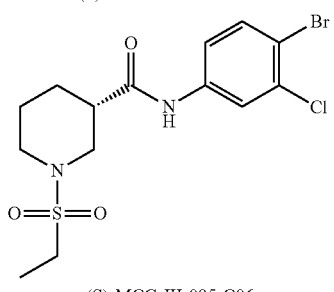
(S)-MCG-III-085-C06
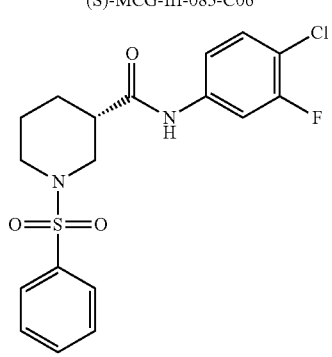
(S)-MCG-III-085-D01
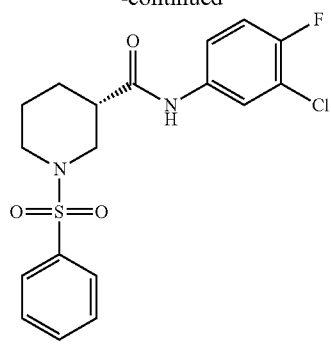
(S)-MCG-III-085-D02
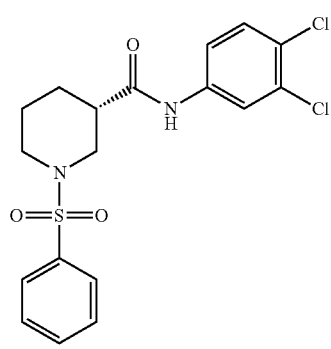
(S)-MCG-III-085-D03
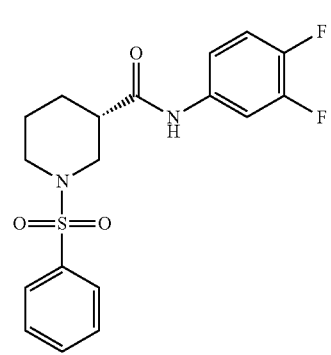
(S)-MCG-III-085-D04
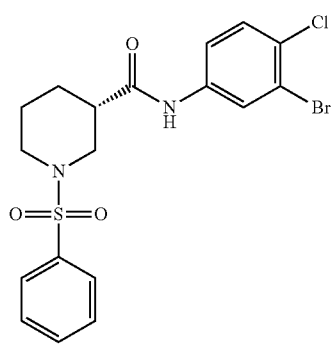
(S)-MCG-III-085-D05

-continued
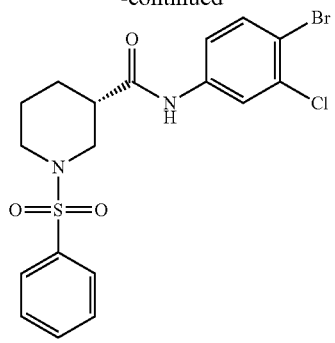
(S)-MCG-III-085-D06
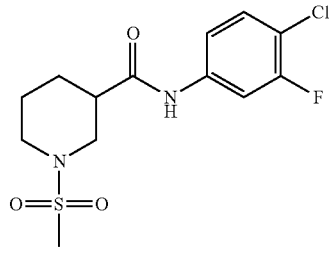
MCG-III-157-B01
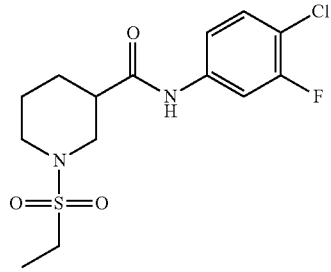
MCG-III-157-B02
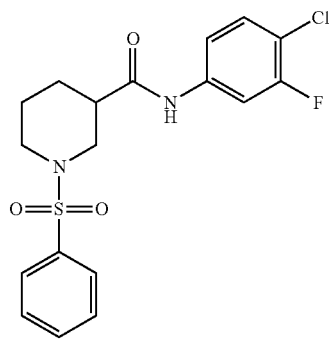
MCG-III-157-B03
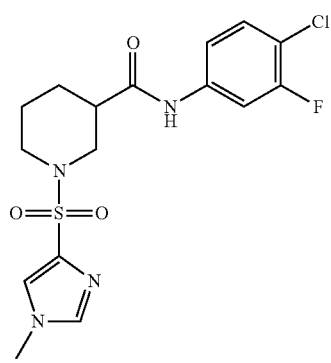
MCG-III-157-B04
-continued
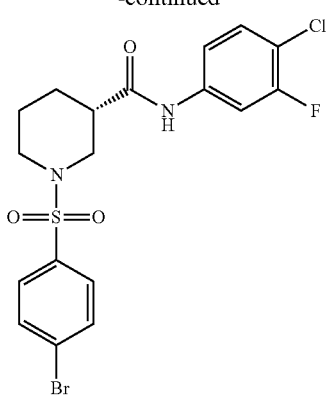
(S)-MCG-III-128
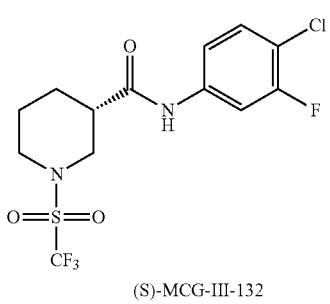 [SMILES: O=C(Nc1ccc(Cl)c(F)c1)[C@H]1CCCN(S(=O)(=O)C(F)(F)F)C1]
(S)-MCG-III-132
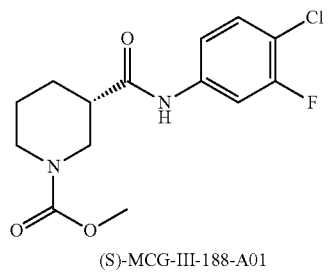
(S)-MCG-III-188-A01
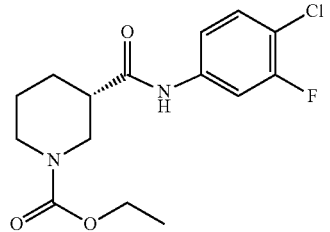
(S)-MCG-III-188-A02
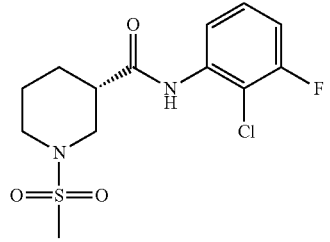
MCG-IV-024-A01

-continued
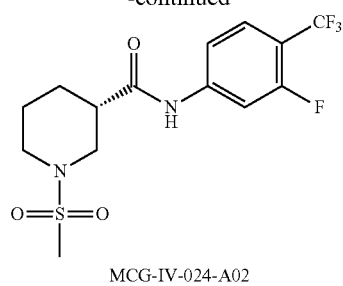
MCG-IV-024-A02
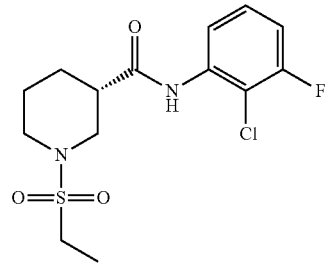
MCG-IV-024-B01
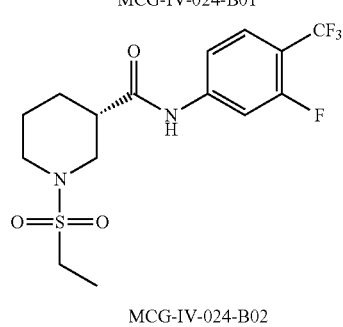
MCG-IV-024-B02
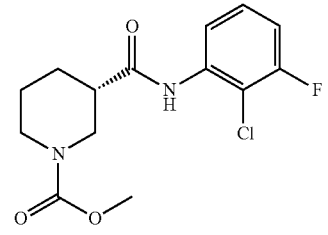
MCG-IV-026-A01
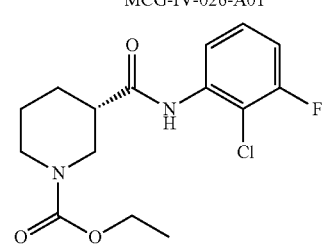
MCG-IV-026-A02
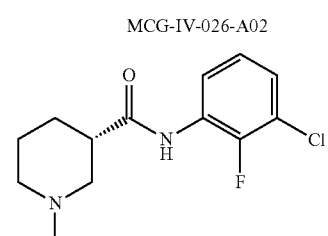
MCG-IV-026-A03
-continued
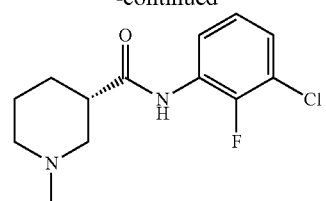
MCG-IV-026-A04
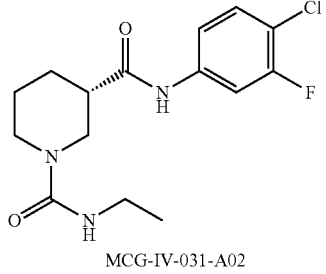
MCG-IV-031-A02
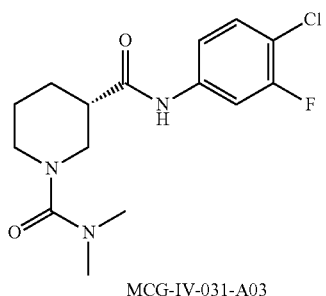
MCG-IV-031-A03
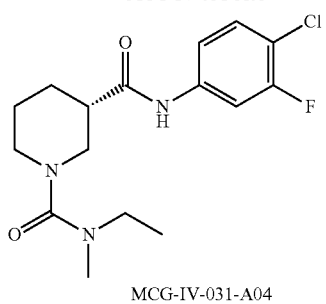
MCG-IV-031-A04
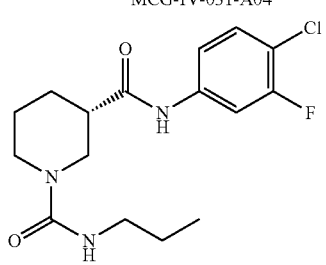
MCG-IV-031-A05
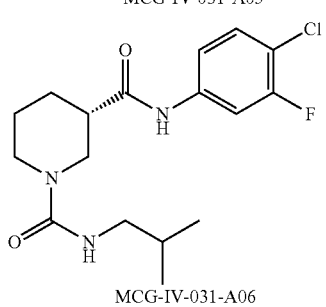
MCG-IV-031-A06

-continued
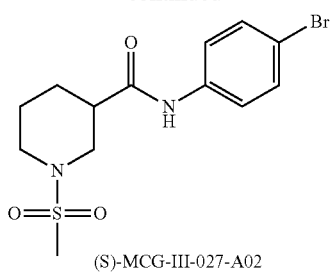
(S)-MCG-III-027-A02
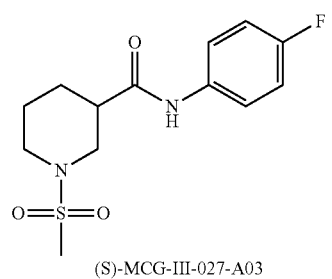
(S)-MCG-III-027-A03
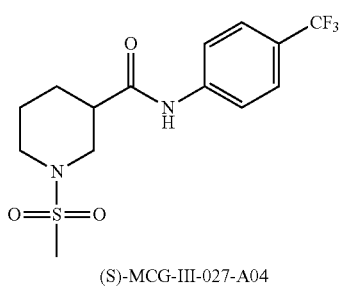
(S)-MCG-III-027-A04
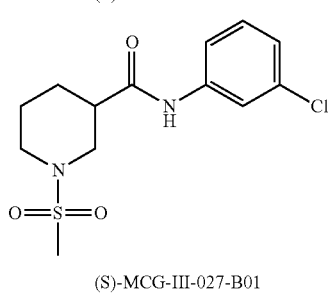
(S)-MCG-III-027-B01
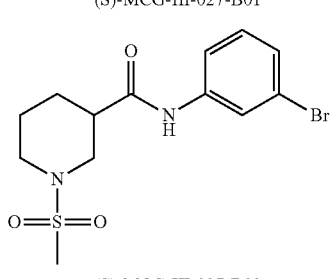
(S)-MCG-III-027-B02
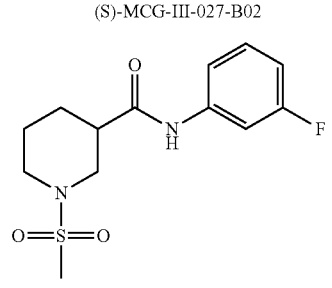
(S)-MCG-III-027-B03
-continued
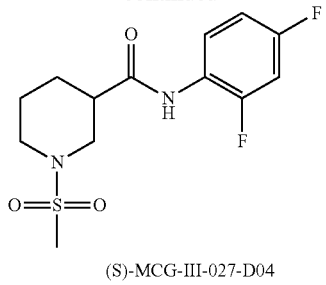
(S)-MCG-III-027-D04
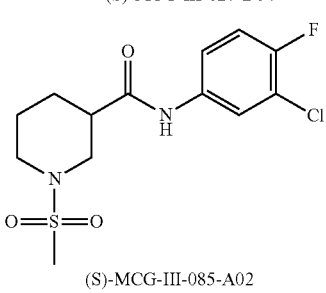
(S)-MCG-III-085-A02
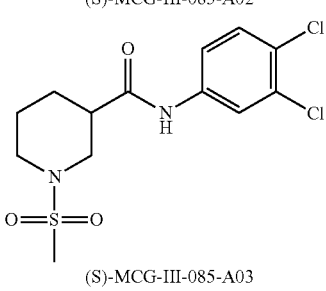
(S)-MCG-III-085-A03
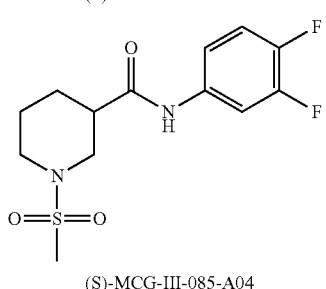
(S)-MCG-III-085-A04
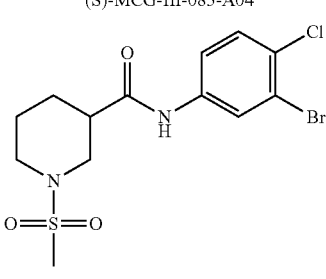
(S)-MCG-III-085-A05
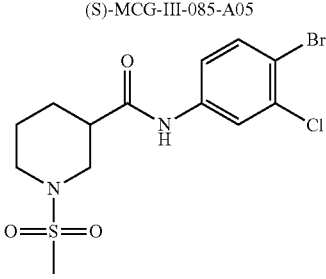
(S)-MCG-III-085-A06

-continued
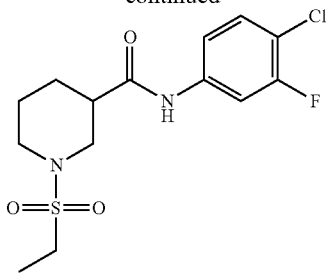
(S)-MCG-III-085-C01
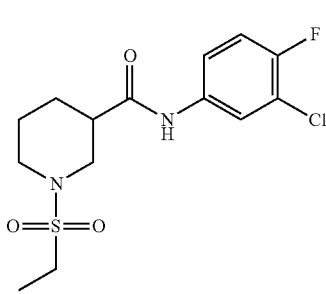
(S)-MCG-III-085-C02
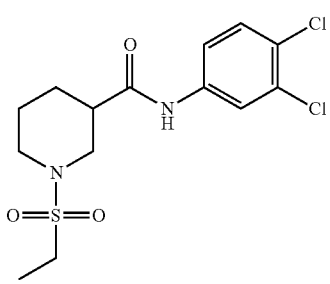
(S)-MCG-III-085-C03
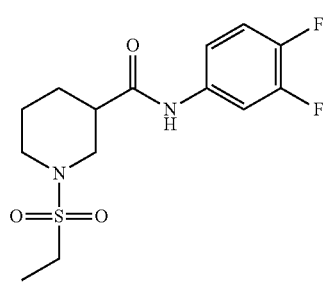
(S)-MCG-III-085-C04
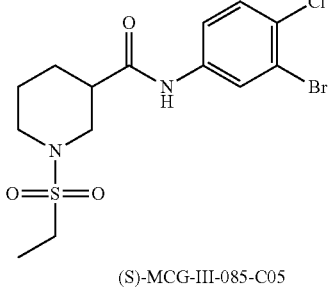
(S)-MCG-III-085-C05
-continued
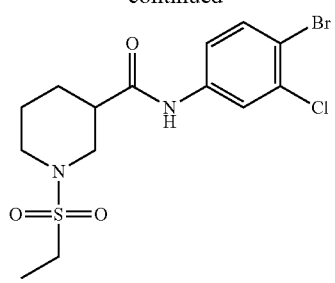
(S)-MCG-III-085-C06
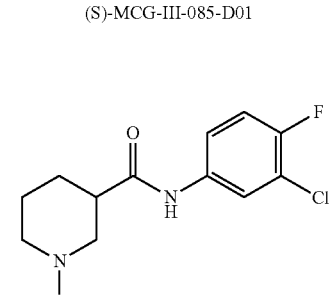
(S)-MCG-III-085-D01
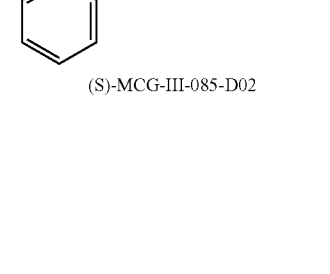
(S)-MCG-III-085-D02
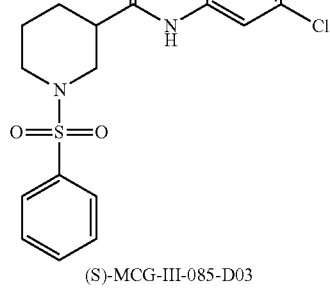
(S)-MCG-III-085-D03

-continued
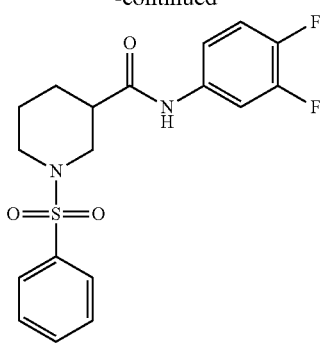
(S)-MCG-III-085-D04
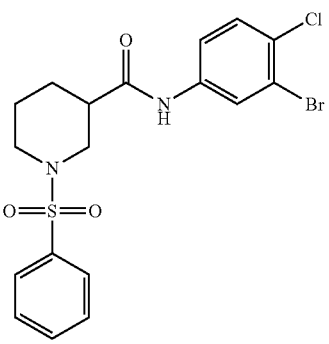
(S)-MCG-III-085-D05
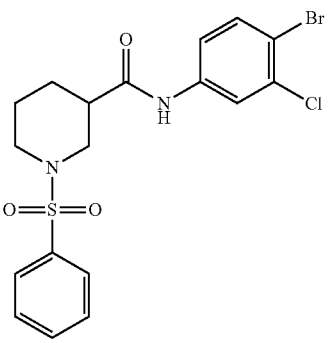
(S)-MCG-III-085-D06
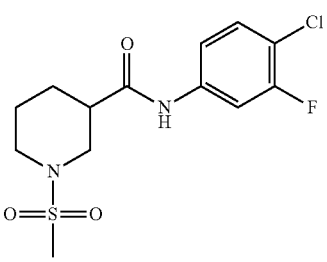
MCG-III-157-B01
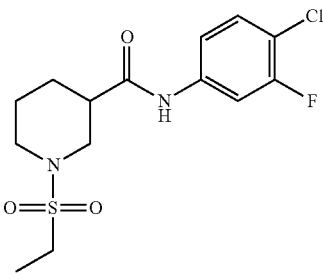
MCG-III-157-B02
-continued
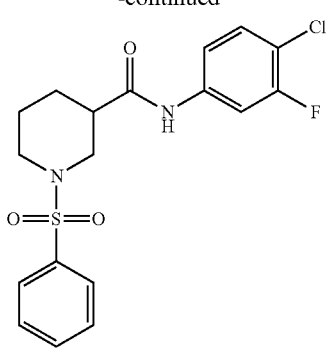
MCG-III-157-B03
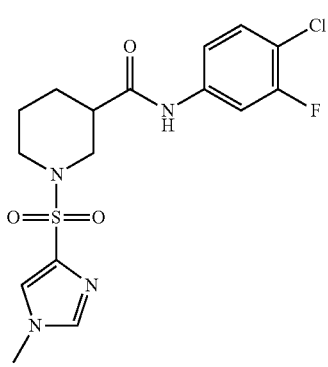
MCG-III-157-B04
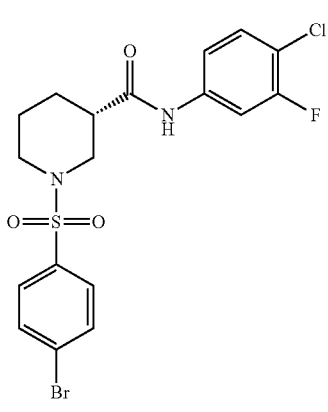
(S)-MCG-III-128
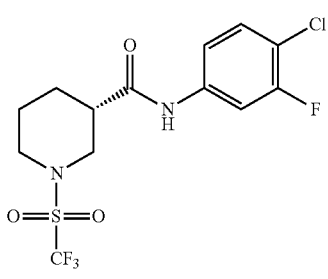
(S)-MCG-III-132

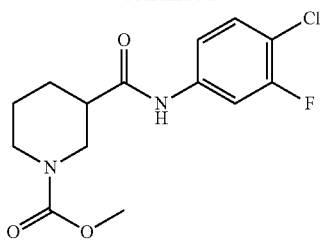
(S)-MCG-III-188-A01
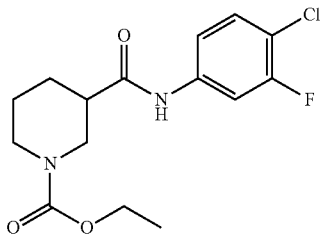
(S)-MCG-III-188-A02
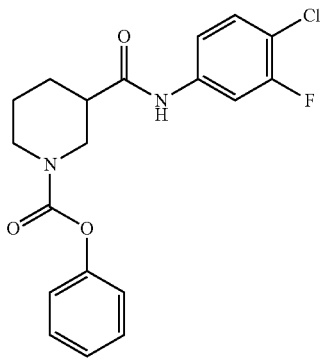
(S)-MCG-III-188-A03
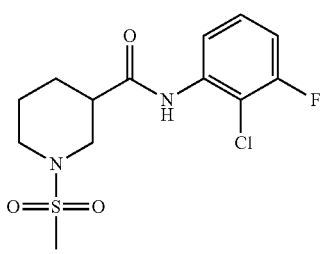
(S)-MCG-IV-024-A01
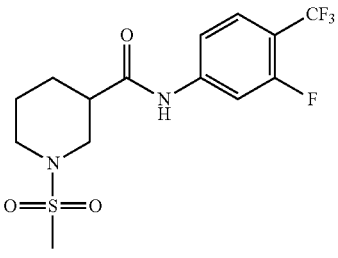
(S)-MCG-IV-024-A02
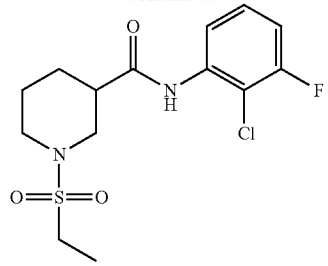
(S)-MCG-IV-024-B01
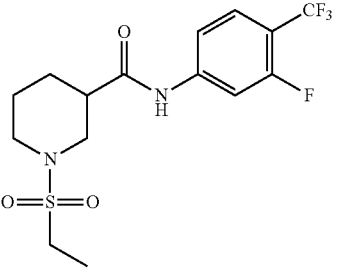
(S)-MCG-IV-024-B02
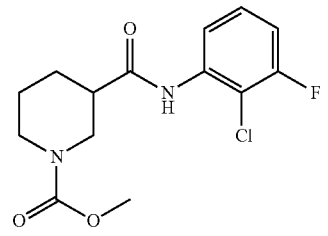
(S)-MCG-IV-026-A01
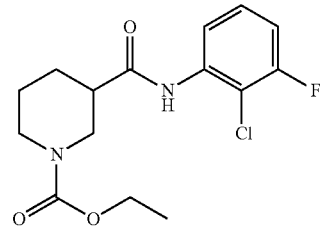
(S)-MCG-IV-026-A02
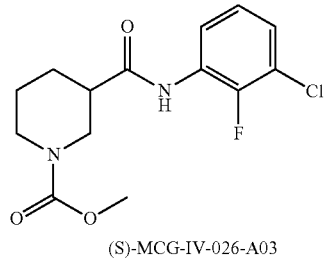
(S)-MCG-IV-026-A03
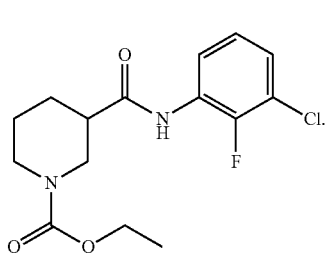
(S)-MCG-IV-026-A04

11. The method of claim 1, wherein the compound is:
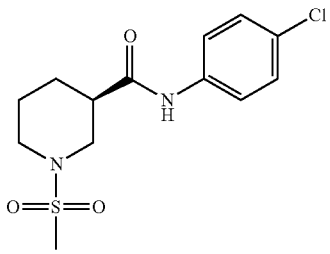
(R)-MCG-II-156
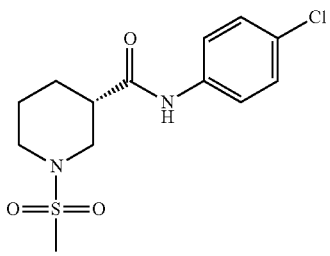
(S)-MCG-II-153
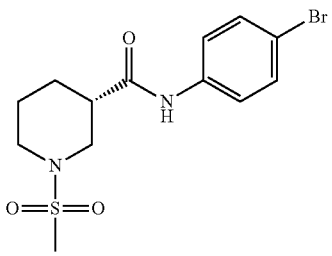
(S)-MCG-III-027-A02
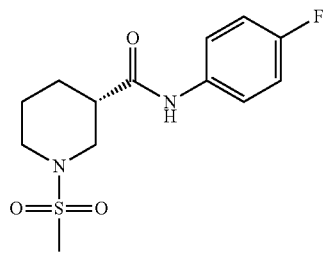
(S)-MCG-III-027-A03
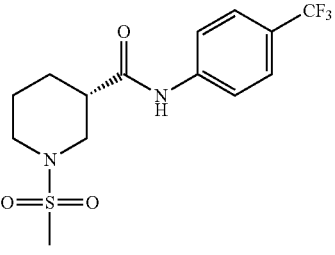
(S)-MCG-III-027-A04
-continued
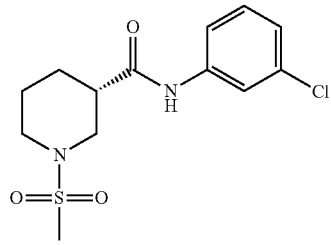
(S)-MCG-III-027-B01
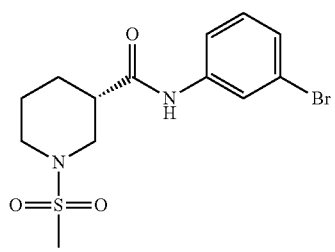
(S)-MCG-III-027-B02
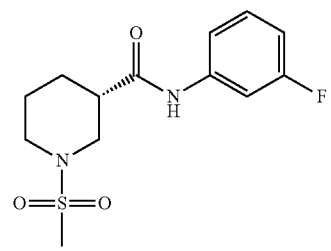
(S)-MCG-III-027-B03
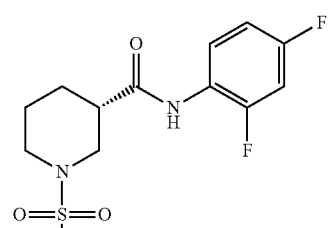
(S)-MCG-III-027-D04
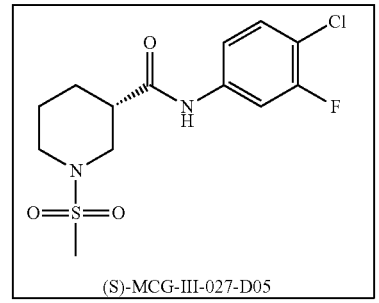
(S)-MCG-III-027-D05

-continued (S)-MCG-III-027-D05

(S)-MCG-III-085-A02

(S)-MCG-III-085-A03

(S)-MCG-III-085-A04

(S)-MCG-III-085-A05

-continued (S)-MCG-III-085-A06

(S)-MCG-III-085-C01

(S)-MCG-III-085-C02

(S)-MCG-III-085-C03

(S)-MCG-III-085-C04

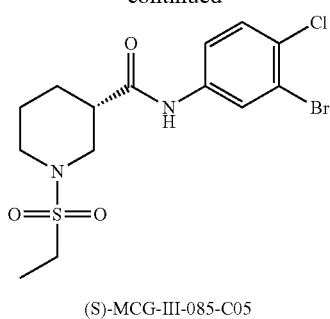
(S)-MCG-III-085-C05
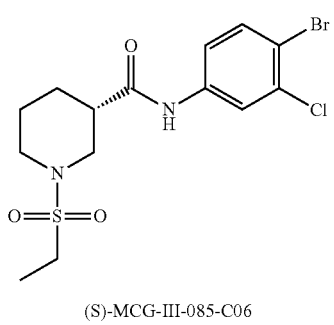
(S)-MCG-III-085-C06
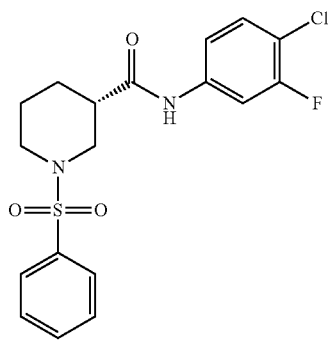
(S)-MCG-III-085-D01
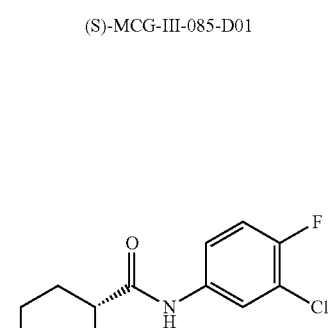
(S)-MCG-III-085-D02
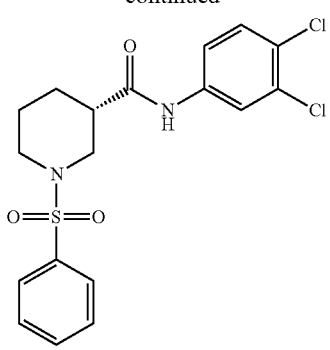
(S)-MCG-III-085-D03
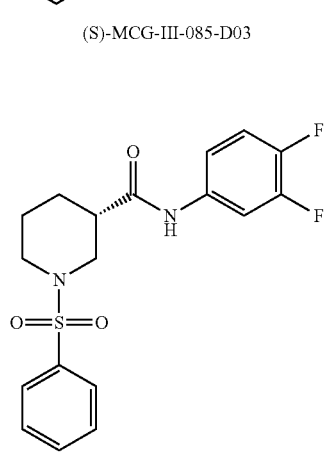
(S)-MCG-III-085-D04
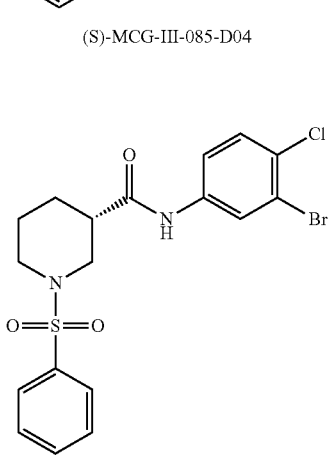
(S)-MCG-III-085-D05
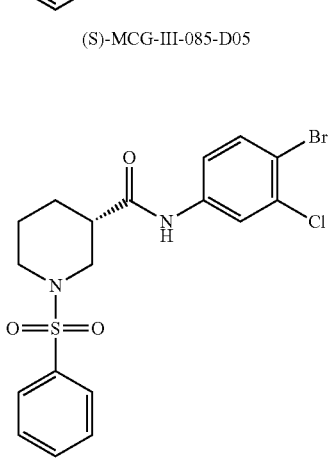
(S)-MCG-III-085-D06

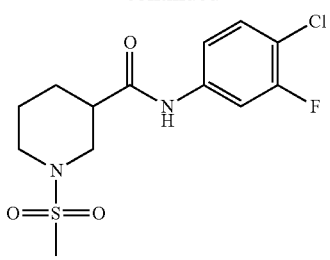
MCG-III-157-B01
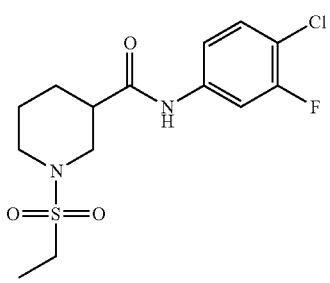
MCG-III-157-B02
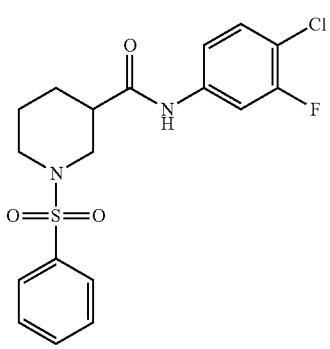
MCG-III-157-B03
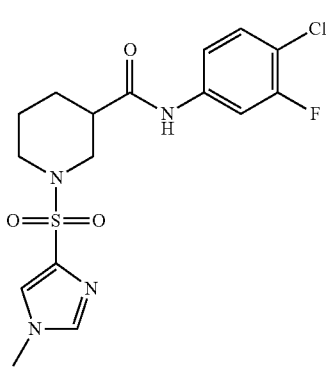
MCG-III-157-B04
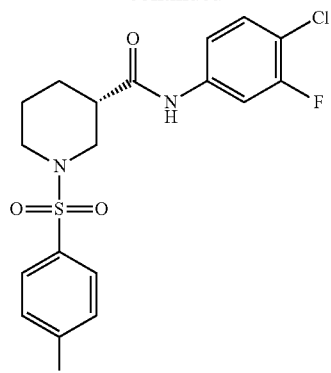
(S)-MCG-III-128
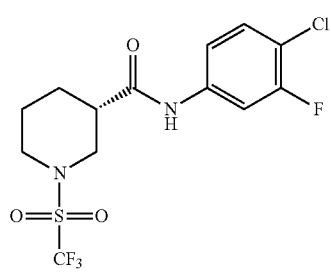
(S)-MCG-III-132
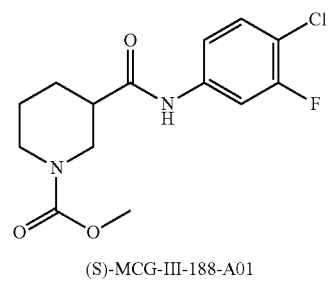
(S)-MCG-III-188-A01
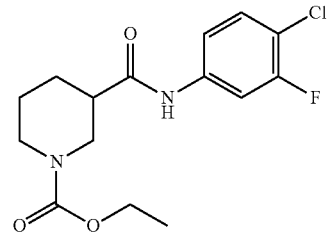
(S)-MCG-III-188-A02
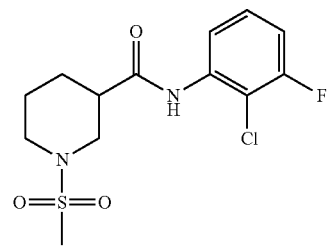
(S)-MCG-IV-024-A01

293
-continued
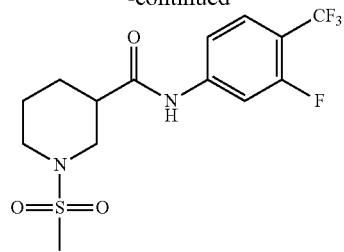
(S)-MCG-IV-024-A02
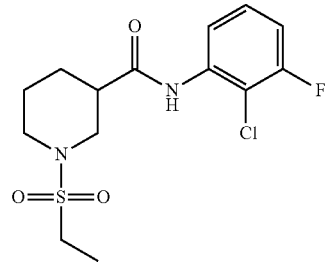
(S)-MCG-IV-024-B01
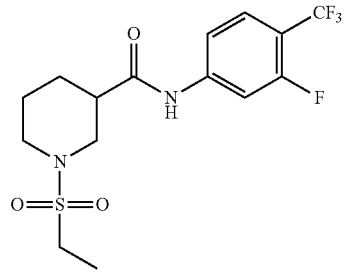
(S)-MCG-IV-024-B02
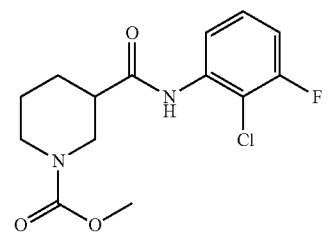
(S)-MCG-IV-026-A01
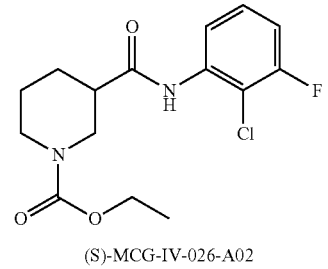
(S)-MCG-IV-026-A02
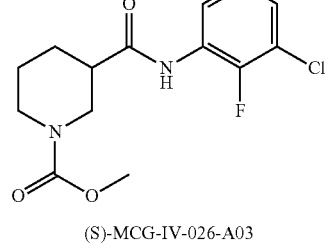
(S)-MCG-IV-026-A03
294
-continued
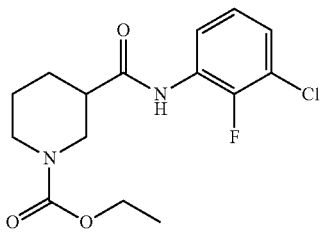
(S)-MCG-IV-026-A04
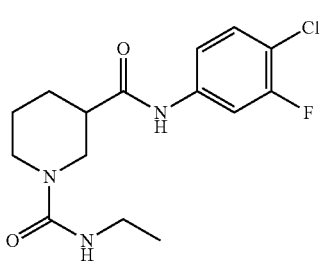
(S)-MCG-IV-031-A02
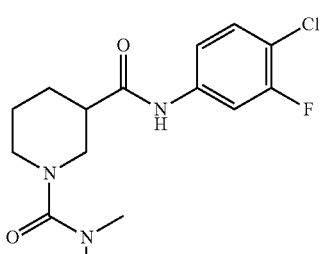
(S)-MCG-IV-031-A03
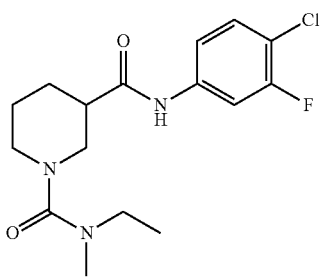
(S)-MCG-IV-031-A04
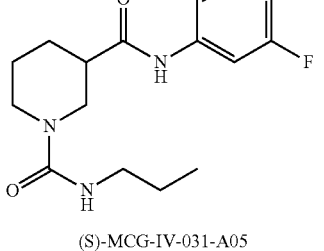
(S)-MCG-IV-031-A05

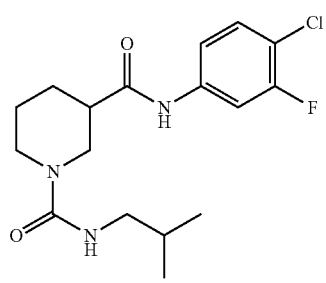
(S)-MCG-IV-031-A06
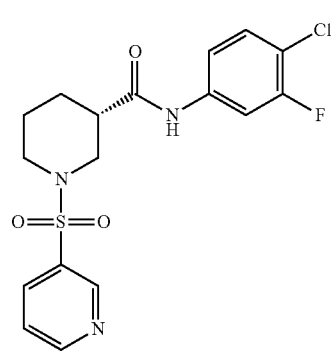
(S)-MCG-III-116-A01
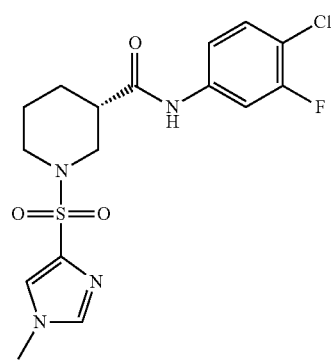
(S)-MCG-III-116-A02
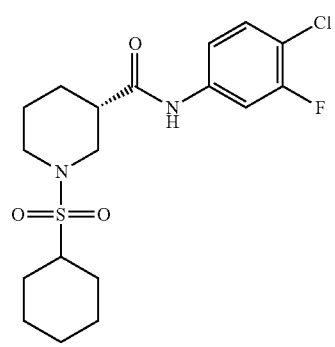
(S)-MCG-III-116-A03
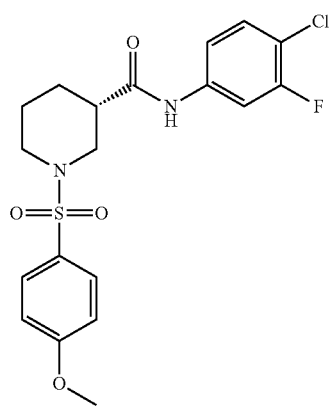
(S)-MCG-III-116-A05
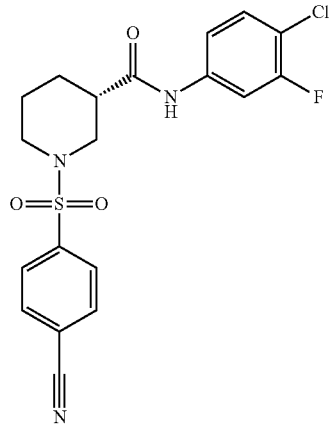
(S)-MCG-III-116-A06
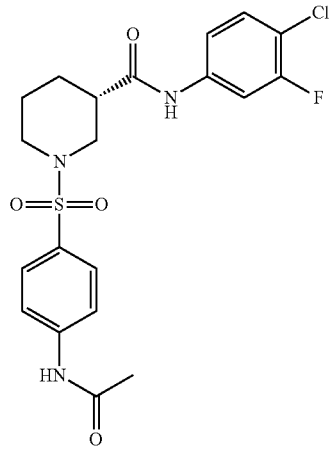
(S)-MCG-III-117
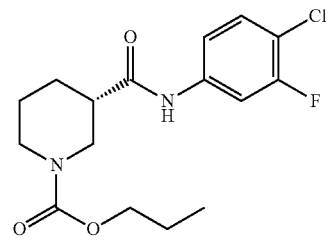
(S)-MCG-IV-058

-continued
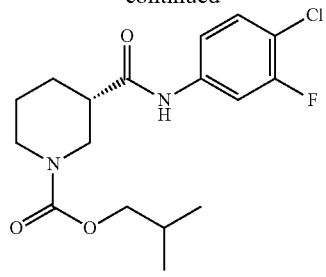
(S)-MCG-IV-061
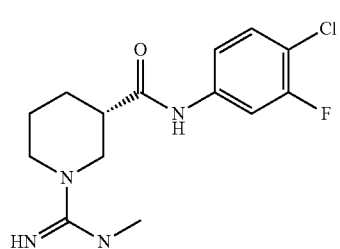
(S)-MCG-IV-053-A01
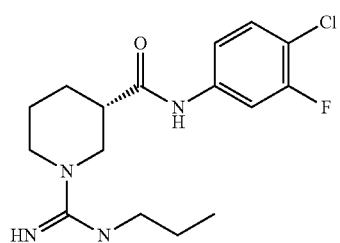
(S)-MCG-IV-053-A05
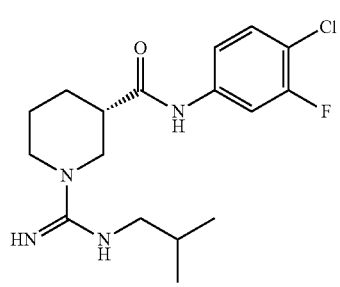
(S)-MCG-IV-053-A06
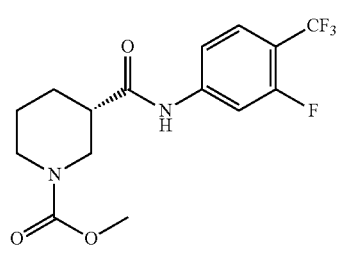
(S)-MCG-IV-050-A02
-continued
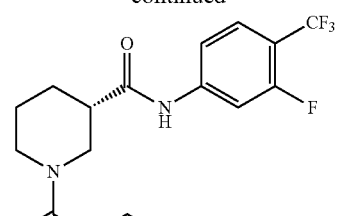
(S)-MCG-IV-050-A02
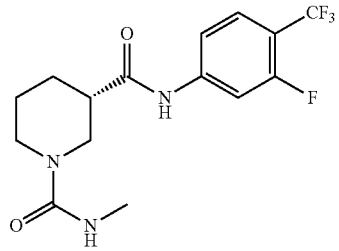
(S)-MCG-IV-063-A01
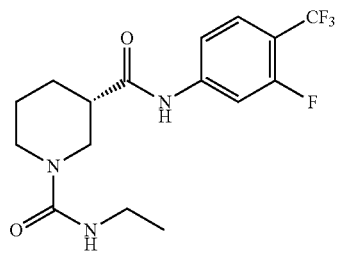
(S)-MCG-IV-063-A02
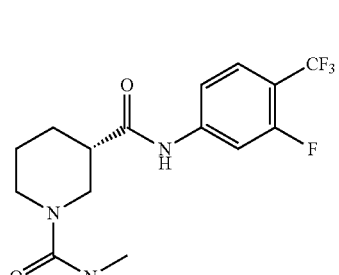
(S)-MCG-IV-063-A03
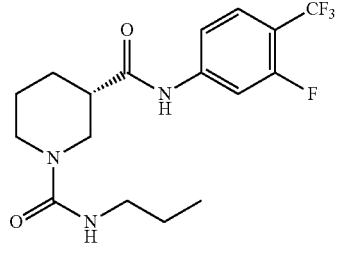
(S)-MCG-IV-063-A05

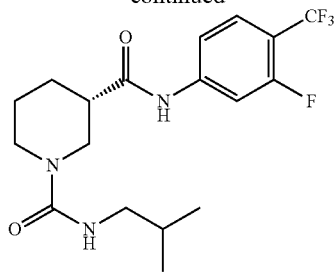
(S)-MCG-IV-063-A06
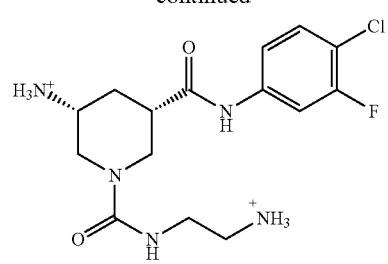
(S)-MCG-IV-273
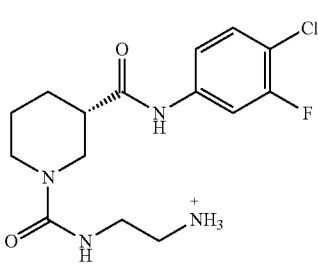
(S)-MCG-IV-210
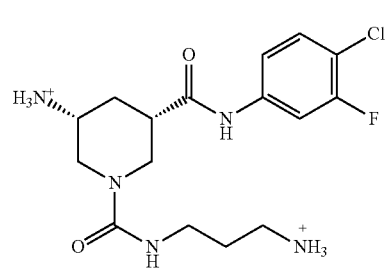
(S)-MCG-IV-274
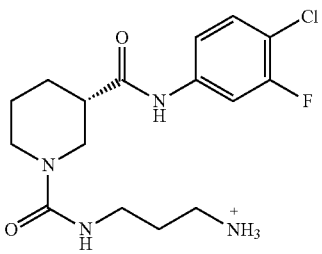
(S)-MCG-IV-211
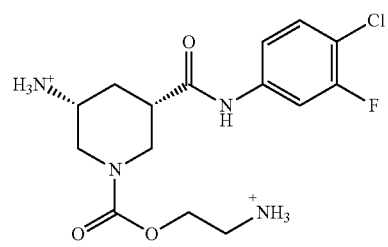
(S)-MCG-IV-272
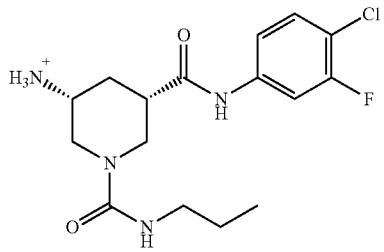
(S)-MCG-IV-226
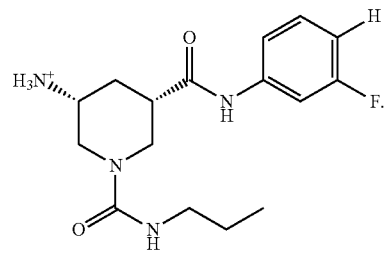
MCG-IV-177
12. The method of claim 11, wherein the compound is:
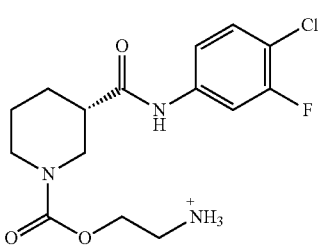
(S)-MCG-IV-267
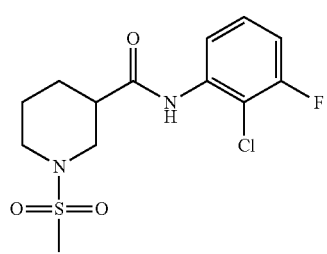
MCG-IV-024-A01

301
-continued
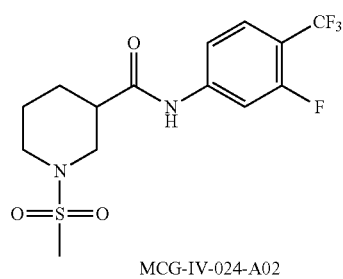
MCG-IV-024-A02
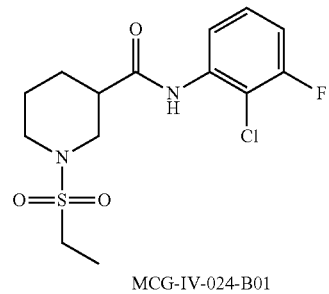
MCG-IV-024-B01
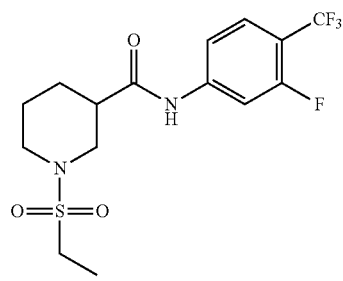
MCG-IV-024-B02
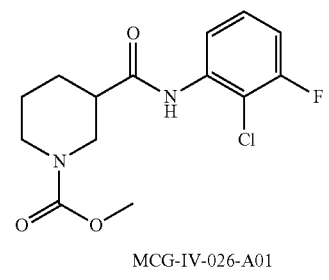
MCG-IV-026-A01
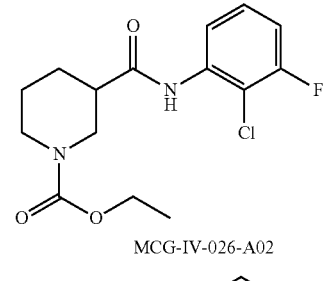
MCG-IV-026-A02
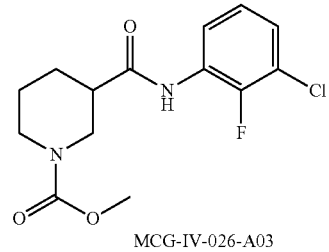
MCG-IV-026-A03
302
-continued
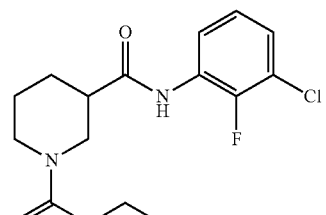
MCG-IV-026-A04
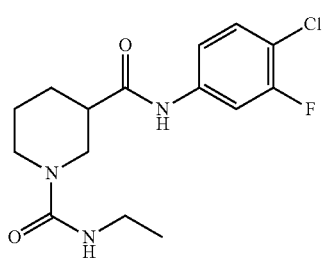
MCG-IV-031-A02
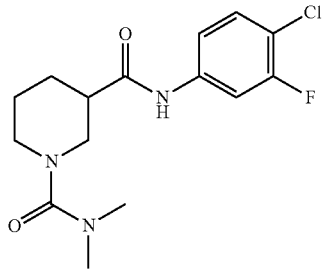
MCG-IV-031-A03
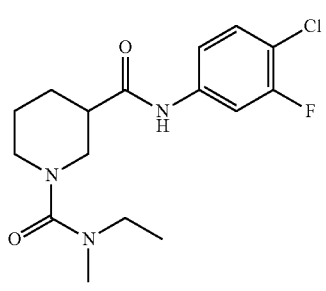
MCG-IV-031-A04
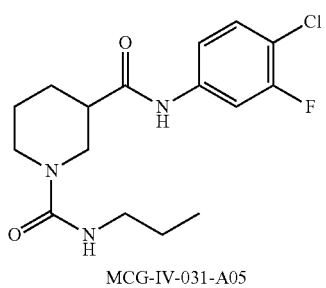
MCG-IV-031-A05

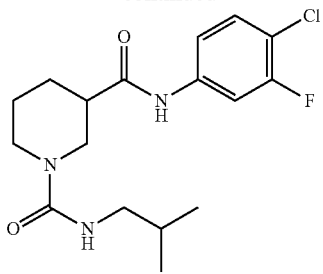
MCG-IV-031-A06
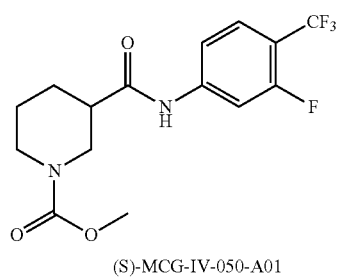
(S)-MCG-IV-050-A01
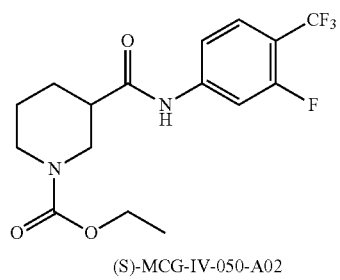
(S)-MCG-IV-050-A02
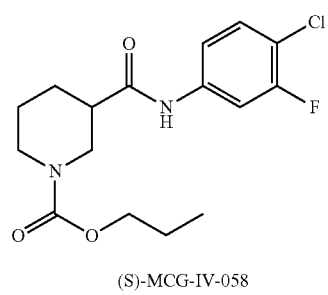
(S)-MCG-IV-058
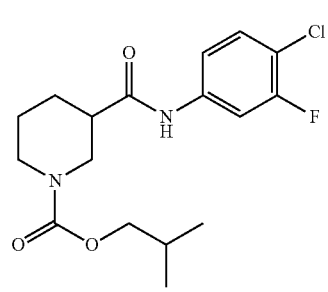
(S)-MCG-IV-061
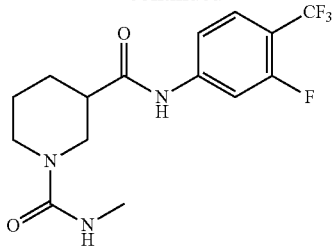
(S)-MCG-IV-063-A01
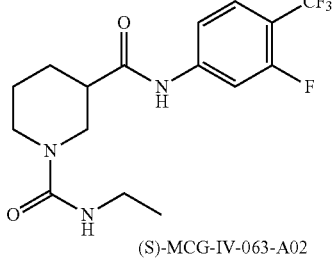
(S)-MCG-IV-063-A02
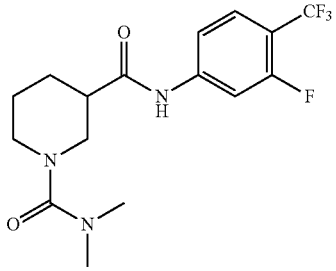
(S)-MCG-IV-063-A03
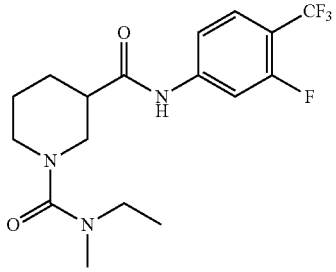
(S)-MCG-IV-063-A04
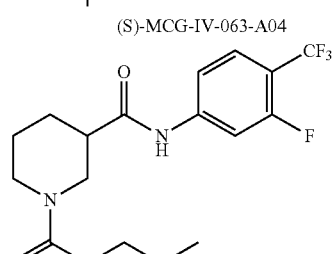
(S)-MCG-IV-063-A05
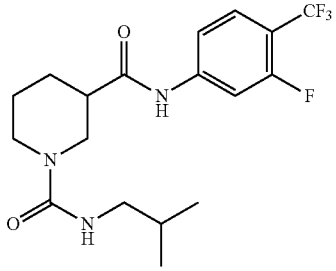
(S)-MCG-IV-063-A06

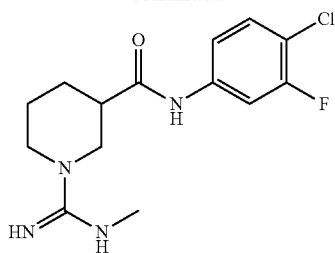
(S)-MCG-IV-053-A01
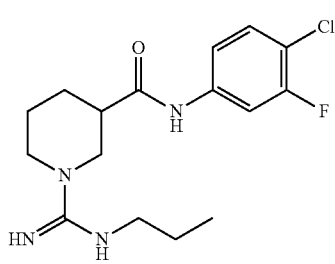
(S)-MCG-IV-053-A05
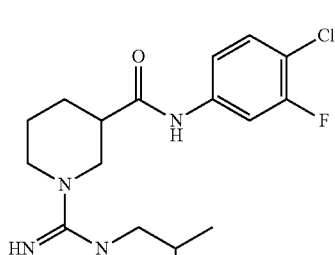
(S)-MCG-IV-053-A06
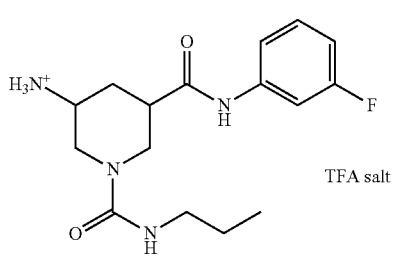
TFA salt
MCG-IV-177
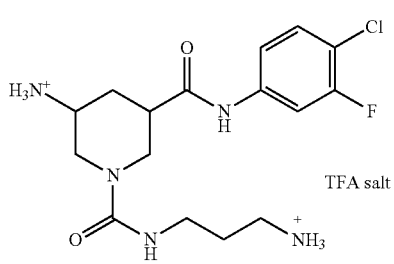
TFA salt
MCG-IV-274
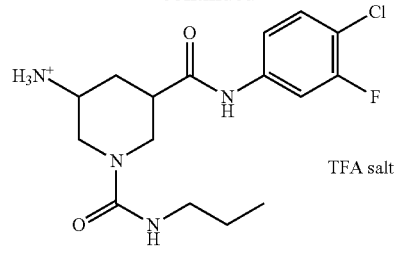
TFA salt
MCG-IV-226
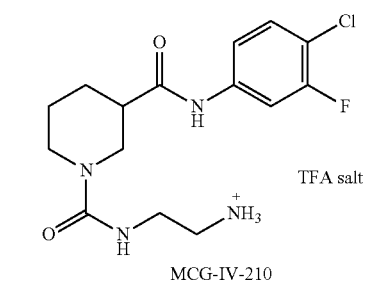
TFA salt
MCG-IV-210
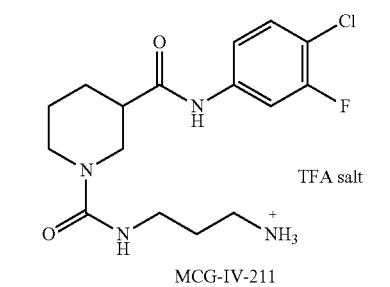
TFA salt
MCG-IV-211
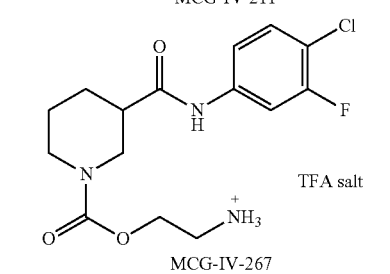
TFA salt
MCG-IV-267
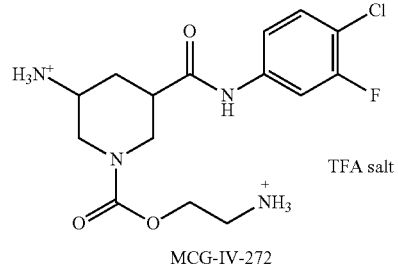
TFA salt
MCG-IV-272
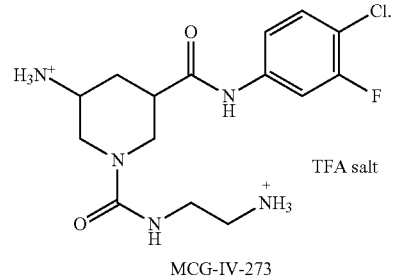
TFA salt
MCG-IV-273

13. The method of claim 1, wherein the compound is:
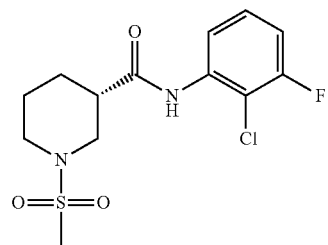
MCG-IV-024-A01
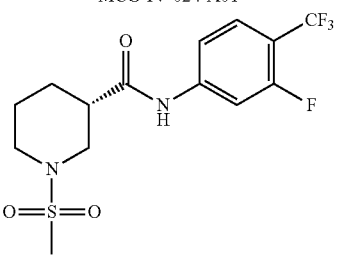
MCG-IV-024-A02
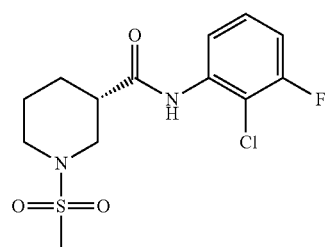
MCG-IV-024-B01
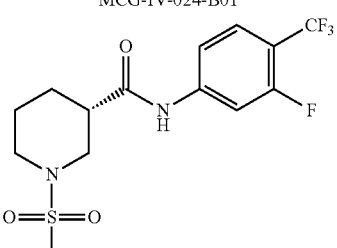
MCG-IV-024-B02
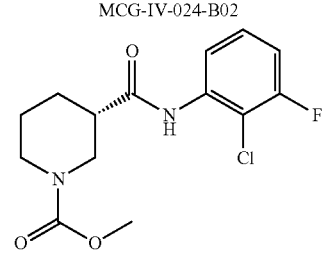
MCG-IV-026-A01
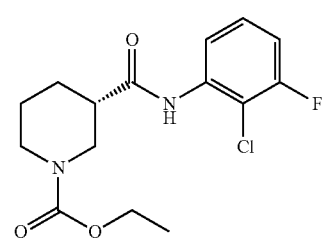
MCG-IV-026-A02
-continued
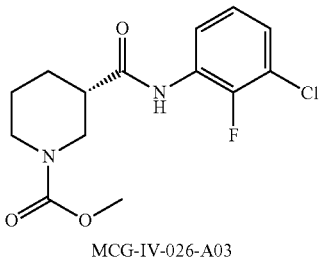
MCG-IV-026-A03
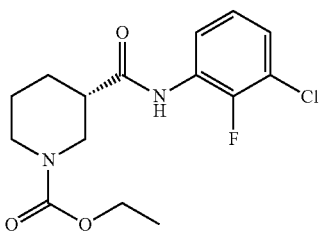
MCG-IV-026-A04
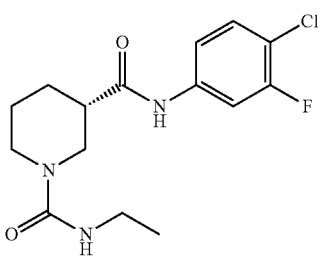
MCG-IV-031-A02
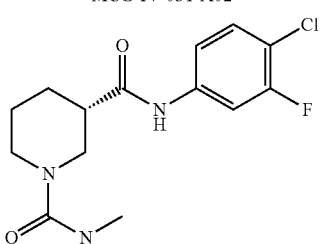
MCG-IV-031-A03
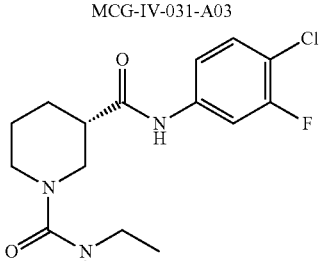
MCG-IV-031-A04
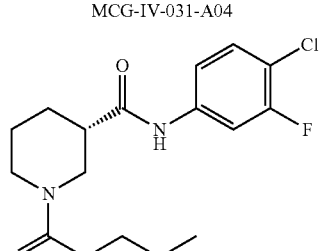
MCG-IV-031-A05

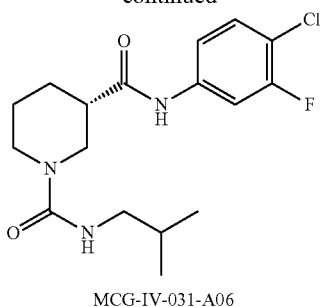
MCG-IV-031-A06
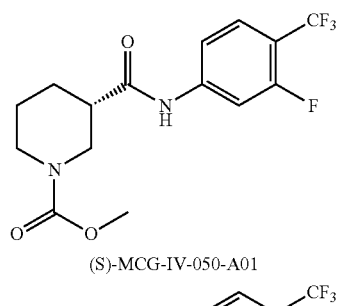
(S)-MCG-IV-050-A01
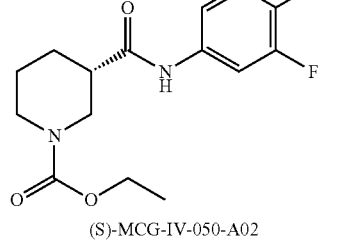
(S)-MCG-IV-050-A02
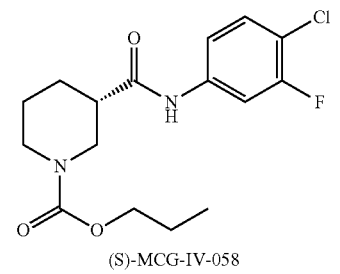
(S)-MCG-IV-058
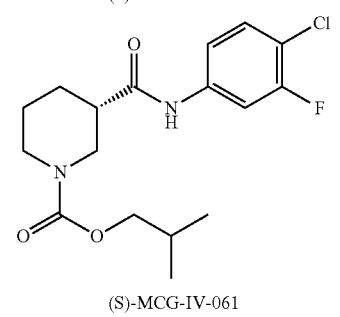
(S)-MCG-IV-061
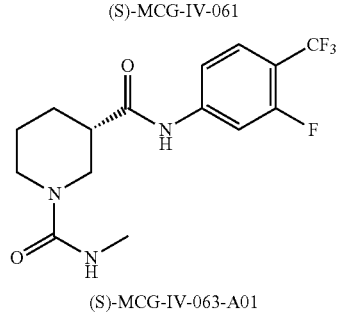
(S)-MCG-IV-063-A01
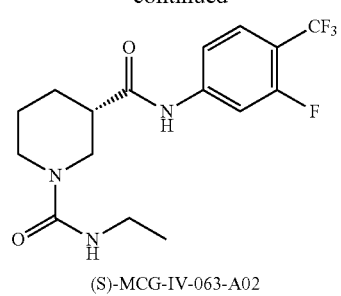
(S)-MCG-IV-063-A02
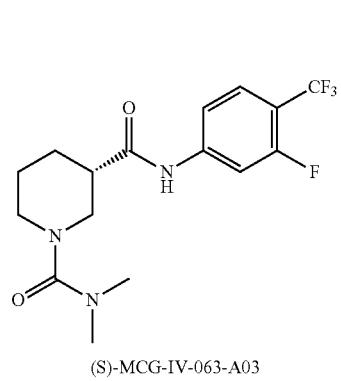
(S)-MCG-IV-063-A03
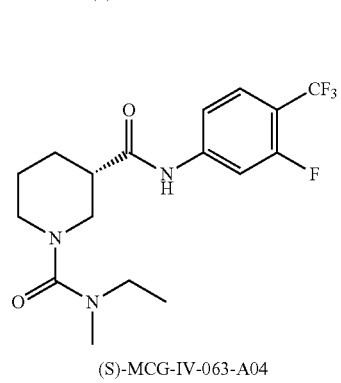
(S)-MCG-IV-063-A04
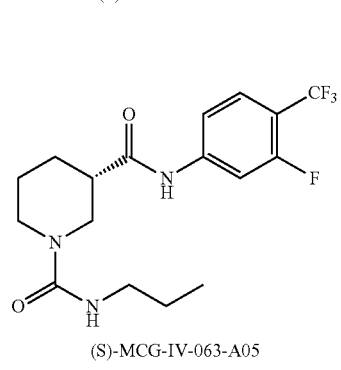
(S)-MCG-IV-063-A05
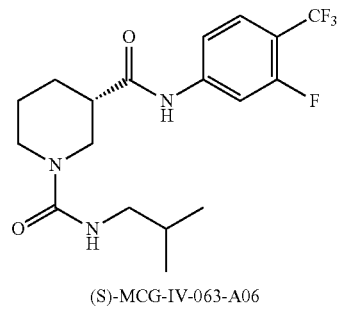
(S)-MCG-IV-063-A06

311
-continued
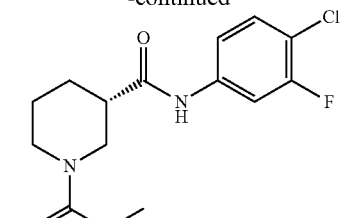
(S)-MCG-IV-053-A01
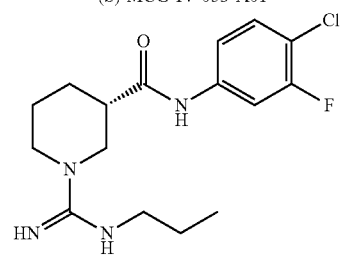
(S)-MCG-IV-053-A05
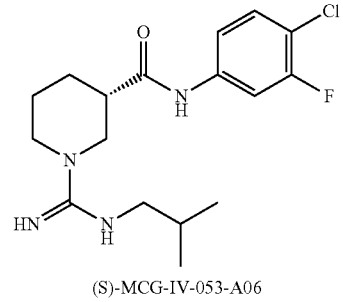
(S)-MCG-IV-053-A06
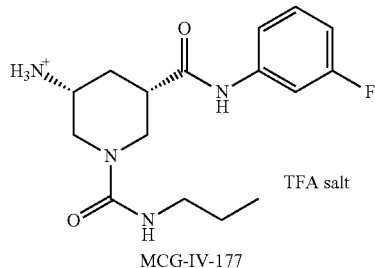
MCG-IV-177
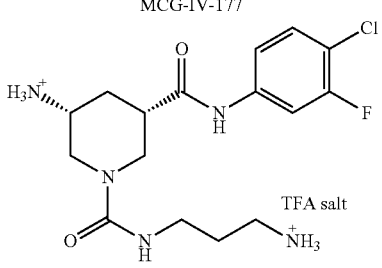
MCG-IV-274
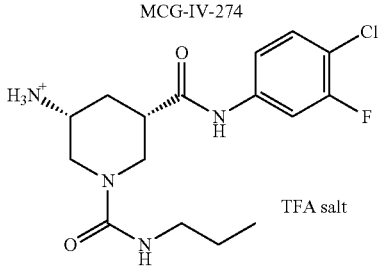
MCG-IV-226
312
-continued
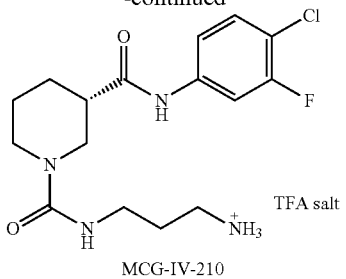
MCG-IV-210
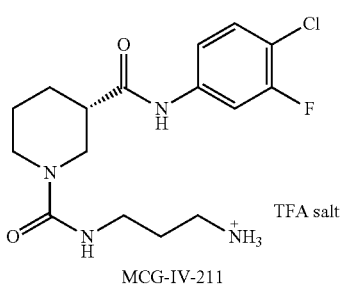
MCG-IV-211
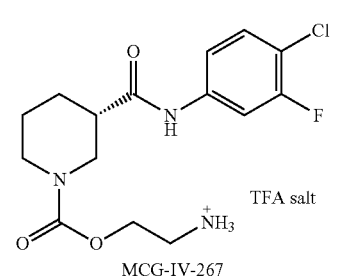
MCG-IV-267
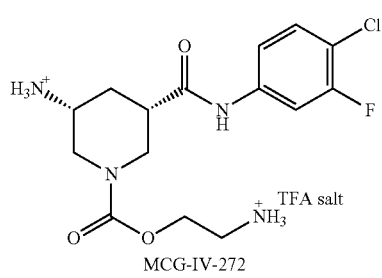
MCG-IV-272
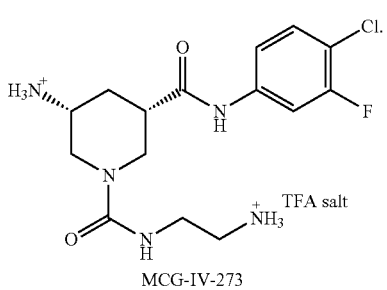
MCG-IV-273
14. The method of claim 2, wherein Y is —N(SO$_2$-aryl)- or —N(SO$_2$-heteroaryl)-.
* * * * *

UNITED STATES PATENT AND TRADEMARK OFFICE
CERTIFICATE OF CORRECTION

PATENT NO.         : 12,286,401 B2                                Page 1 of 1
APPLICATION NO.    : 17/263590
DATED              : April 29, 2025
INVENTOR(S)        : Melissa Carey Davies et al.

It is certified that error appears in the above-identified patent and that said Letters Patent is hereby corrected as shown below:

In the Claims

Under Column no. 40, Lines nos. 56-65, Replace, " 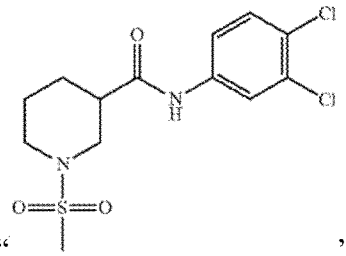 " with

-- 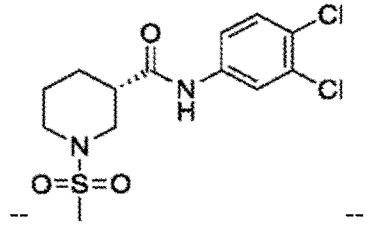 --

Signed and Sealed this
Fifteenth Day of July, 2025

Coke Morgan Stewart
*Acting Director of the United States Patent and Trademark Office*